US011643400B2

(12) United States Patent
Chu et al.

(10) Patent No.: US 11,643,400 B2
(45) Date of Patent: *May 9, 2023

(54) MCL-1 INHIBITORS

(71) Applicant: Gilead Sciences, Inc., Foster City, CA (US)

(72) Inventors: Hang Chu, San Mateo, CA (US); Juan A. Guerrero, Clayton, CA (US); Anna E. Hurtley, San Mateo, CA (US); Tae H. Hwang, Glenview, IL (US); Lan Jiang, Foster City, CA (US); Darryl Kato, San Francisco, CA (US); Tetsuya Kobayashi, Pleasanton, CA (US); John E. Knox, Emerald Hills, CA (US); Scott E. Lazerwith, Burlingame, CA (US); Xiaofen Li, Thousand Oaks, CA (US); David W. Lin, Berkeley, CA (US); Jonathan W. Medley, San Mateo, CA (US); Michael L. Mitchell, Castro Valley, CA (US); Devan Naduthambi, San Bruno, CA (US); Zachary Newby, San Francisco, CA (US); Neil H. Squires, San Francisco, CA (US); Vickie H. Tsui, Burlingame, CA (US); Chandrasekar Venkataramani, San Carlos, CA (US); William J. Watkins, Saratoga, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 159 days.

This patent is subject to a terminal disclaimer.

(21) Appl. No.: 17/171,201

(22) Filed: Feb. 9, 2021

(65) Prior Publication Data

US 2022/0340535 A1 Oct. 27, 2022

Related U.S. Application Data

(63) Continuation of application No. 16/857,021, filed on Apr. 23, 2020, now Pat. No. 10,988,451, which is a continuation of application No. 16/410,457, filed on May 13, 2019, now Pat. No. 10,703,733.

(60) Provisional application No. 62/749,918, filed on Oct. 24, 2018, provisional application No. 62/671,306, filed on May 14, 2018.

(51) Int. Cl.
| | |
|---|---|
| *C07D 513/08* | (2006.01) |
| *A61K 31/553* | (2006.01) |
| *C07D 267/20* | (2006.01) |
| *C07D 413/12* | (2006.01) |
| *C07D 413/14* | (2006.01) |
| *C07D 417/12* | (2006.01) |
| *C07D 471/04* | (2006.01) |
| *C07D 487/04* | (2006.01) |
| *C07D 498/04* | (2006.01) |
| *A61K 45/06* | (2006.01) |

(52) U.S. Cl.
CPC ......... *C07D 267/20* (2013.01); *C07D 413/12* (2013.01); *C07D 413/14* (2013.01); *C07D 417/12* (2013.01); *C07D 471/04* (2013.01); *C07D 487/04* (2013.01); *C07D 498/04* (2013.01); *A61K 45/06* (2013.01)

(58) Field of Classification Search
CPC ........................... C07D 513/08; A61K 31/553
See application file for complete search history.

(56) References Cited

U.S. PATENT DOCUMENTS

| | | | |
|---|---|---|---|
| 10,703,733 | B2 | 7/2020 | Chu et al. |
| 10,988,451 | B2 | 4/2021 | Chu et al. |
| 11,325,891 | B2 | 5/2022 | Brak et al. |
| 2016/0068545 | A1 | 3/2016 | Brown et al. |
| 2017/0088560 | A1 | 3/2017 | Brown et al. |
| 2018/0289720 | A1 | 10/2018 | Harrington et al. |
| 2019/0352271 | A1 | 11/2019 | Chu et al. |
| 2020/0331870 | A1 | 10/2020 | Chu et al. |
| 2021/0171543 | A1 | 6/2021 | Chu et al. |
| 2021/0179570 | A1 | 6/2021 | Brak et al. |
| 2022/0177409 | A1 | 6/2022 | Dixon et al. |

FOREIGN PATENT DOCUMENTS

| | | |
|---|---|---|
| WO | WO-2016/033486 A1 | 3/2016 |
| WO | WO-2017/147410 A1 | 8/2017 |
| WO | WO-2018/183418 A1 | 10/2018 |
| WO | WO-2019/036575 A1 | 2/2019 |
| WO | WO-2019/046150 A1 | 3/2019 |
| WO | WO-2019/079578 A1 | 4/2019 |
| WO | WO-2019/173181 A1 | 9/2019 |
| WO | WO-2019/222112 A1 | 11/2019 |
| WO | WO-2019/222266 A1 | 11/2019 |
| WO | WO-2019/222269 A1 | 11/2019 |
| WO | WO-2020/023657 A1 | 1/2020 |
| WO | WO-2020/097577 A1 | 5/2020 |
| WO | WO-2020/147802 A1 | 7/2020 |
| WO | WO-2021/096860 A1 | 5/2021 |
| WO | WO-2021/108254 A1 | 6/2021 |
| WO | WO-2021/202452 A1 | 10/2021 |

(Continued)

OTHER PUBLICATIONS

Examination Report dated Mar. 3, 2021 for Indian Appl. No. 202017053224.
Office Action dated Apr. 12, 2021 for Japanese Appl. No. 2020-564228.
Office Action dated Apr. 16, 2021 for European Appl. No. 19728793.1.

(Continued)

*Primary Examiner* — Bruck Kifle

(57) ABSTRACT

The present disclosure generally relates to compounds and pharmaceutical compositions that may be used in methods of treating cancer.

20 Claims, No Drawings

(56) References Cited

FOREIGN PATENT DOCUMENTS

| WO | WO-2021/225823 A1 | 11/2021 |
| WO | WO-2021/226168 A1 | 11/2021 |
| WO | WO-2021/250102 A1 | 12/2021 |
| WO | WO-2022/008674 A1 | 1/2022 |
| WO | WO-2022/108984 A1 | 5/2022 |

OTHER PUBLICATIONS

Examination Report dated May 29, 2020 for GC Appl. No. 2019-37562.
Final Office Action dated Feb. 27, 2020 for U.S. Appl. No. 16/410,457.
International Preliminary Report on Patentability dated Nov. 26, 2020 for Intl. Appl. No. PCT/US2019/032053.
Intl. Search Report—Written Opinion dated Aug. 1, 2019 for Intl. Appl. No. PCT/US2019/032053.
Non-Final Office Action dated Dec. 23, 2019 for U.S. Appl. No. 16/410,457.
Non-Final Office Action dated Aug. 20, 2020 for U.S. Appl. No. 16/857,021.
Notice of Allowance dated Mar. 26, 2020 for U.S. Appl. No. 16/410,457.
Notice of Allowance dated Nov. 25, 2020 for U.S. Appl. No. 16/857,021.
Notice of Allowability dated Dec. 14, 2020 for U.S. Appl. No. 16/857,021.
Office Action dated Sep. 7, 2020 for TW Appl. No. 108116508.
Notice of Allowance dated Dec. 1, 2020 for Taiwanese Appl. No. 108116508.
Examination Report dated Jan. 20, 2021 for Gulf Cooperation Council Appl. No. 2019-37562.
Notice of Allowance dated Feb. 16, 2021 for Australian Appl. No. 2019269391.
Notice of Allowance dated Mar. 22, 2021 for U.S. Appl. No. 16/857,021.
Office Action dated Sep. 27, 2021 for Dominican Republic Appl. No. P2020-0206.
Office Action dated Oct. 4, 2021 for Israeli Appl. No. 278336.
Office Action dated Dec. 6, 2021 for Chilean Appl. No. 202002919.
Examination Report dated Dec. 30, 2021 for Canadian Appl. No. 3,099,152.
Notice of Allowance dated Feb. 6, 2022 for Israeli Appl. No. 278336.
Notice of Allowance dated Mar. 2, 2022 for Dominican Republic Appl. No. P2020-0206.
Examination Report dated Mar. 22, 2022 for Canadian Appl. No. 3,099,152.
Office Action dated May 17, 2022 for Chilean Appl. No. 202002919.
Extended European Search Report dated May 27, 2022 for European Appl. No. 21218221.6.
Office Action dated Aug. 12, 2022 for Eurasian Appl. No. 202092239.
Examination Report dated Aug. 18, 2022 for Canadian Appl. No. 3,099,152.
Notice of Allowance dated Aug. 25, 2022 for ARIPO Appl. No. AP/P/2020/012770.
Examination Report dated Sep. 1, 2022 for Australian Appl. No. 2021203373.
Office Action dated Sep. 1, 2022 for Uzbekistan Appl. No. IAP 2020 0534.
Office Action dated Oct. 19, 2022 for Israeli Appl. No. 291430.
Office Action dated Oct. 25, 2022 for Korean Appl. No. 10-2020-7035485.
Office Action dated Oct. 27, 2022 for Indonesian Appl. No. P00202009763.
Office Action dated Nov. 9, 2022 for Colombian Appl. No. NC2020/0014009.
Office Action dated Jan. 3, 2023 for Chinese Appl. No. 201980032695.2.
Morita, Y. (2012) "Application of Bioisosteres in Drug Design" Literature Seminar, May 7, 2012.

MCL-1 INHIBITORS

CROSS-REFERENCES TO RELATED APPLICATIONS

This Application is a Continuation of application Ser. No. 16/857,021 filed on Apr. 23, 2020 which is a Continuation of application Ser. No. 16/410,457 filed on May 13, 2019. Application Ser. No. 16/410,457 claims the benefit of U.S. Provisional Application 62/749,918 filed on Oct. 24, 2018 and U.S. Provisional Application 62/671,306 filed on May 14, 2018. The entire contents of these applications are incorporated herein by reference in their entirety.

FIELD

This application generally relates to certain compounds that inhibit MCL-1, pharmaceutical compositions comprising the compounds, use of the compounds to treat cancers, and methods of making the compounds.

BACKGROUND

Apoptosis (programmed cell death) is a process for elimination of unwanted or potentially dangerous cells from an organism. Avoidance of apoptosis is critical for the development and sustained growth of tumors. Myeloid cell leukemia 1 protein (MCL-1, also abbreviated Mcl-1 or MCL1) is an antiapoptotic member of the Bcl-2 family of proteins. MCL-1 is overexpressed in many cancers. Overexpression of MCL-1 prevents cancer cells from undergoing apoptosis. Research has shown that MCL-1 inhibitors can be used to treat cancers. Thus, a need exists for new compounds that inhibit MCL-1.

BRIEF SUMMARY

The foregoing need is addressed by the present disclosure. In particular, inhibitors of MCL-1 are provided herein.

In one embodiment, the present disclosure provides a compound according to Formula (I):

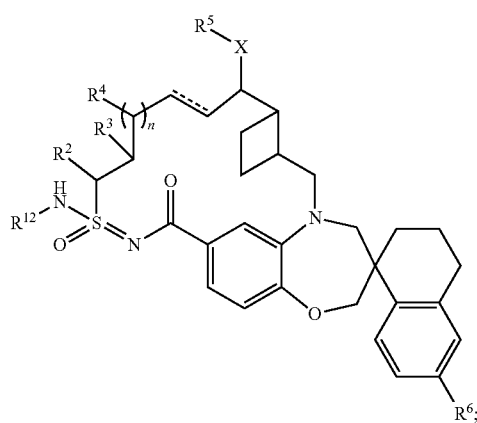

(I)

wherein ═ is a single or double bond;

X is O or $NR^7$;

$R^{12}$ is hydrogen or $—C(O)R^1$;

$R^1$ is $C_{1-6}$alkyl, $C_{1-6}$haloalkyl, $C_{2-6}$alkenyl, $C_{2-6}$alkynyl, $C_{3-10}$cycloalkyl, $C_{6-10}$aryl, 3-12 membered heterocyclyl, 5-10 membered heteroaryl, $—OR^7$, or $—NR^8R^9$, wherein said $C_{1-6}$alkyl, $C_{1-6}$heteroalkyl, $C_{2-6}$alkynyl, $C_{3-10}$cycloalkyl, $C_{6-10}$aryl, 3-12 membered heterocyclyl, and 5-10 membered heteroaryl are optionally substituted with 1-5 $R^{10}$ groups;

$R^2$ is hydrogen, $C_{1-6}$alkyl, $C_{1-6}$heteroalkyl, $C_{3-10}$cycloalkyl, or 3-12 membered heterocyclyl, wherein said $C_{1-6}$alkyl, $C_{1-6}$heteroalkyl, $C_{3-10}$cycloalkyl, and 3-12 membered heterocyclyl are optionally substituted with 1-5 $R^{10}$ groups;

$R^3$ and $R^4$ are independently hydrogen, $C_{1-6}$alkyl, $—OR^7$, $C_{1-6}$heteroalkyl, $—NR^8R^9$, $NR^8C(O)R^9$, $—NR^8C(O)OR^9$, $C_{6-10}$aryl, $C_{3-10}$cycloalkyl, 5-10 membered heteroaryl, 3-12 membered heterocyclyl, $—C(O)R^7$, $—C(O)OR^7$, $—C(O)NR^8R^9$, $—OC(O)NR^8R^9$, $—CN$, or $—SO_2R^7$, wherein said $C_{1-6}$alkyl, $C_{1-6}$heteroalkyl, $C_{6-10}$aryl, $C_{3-10}$cycloalkyl, 5-10 membered heteroaryl, and 3-12 membered heterocyclyl are optionally substituted with 1-5 $R^{10}$ groups;

$R^5$ is hydrogen, $C_{1-6}$alkyl, $—(CH_2CH_2O)_pR^7$, $C_{1-6}$heteroalkyl, $C_{6-10}$aryl, $C_{3-10}$cycloalkyl, 5-10 membered heteroaryl, or 3-12 membered heterocyclyl, wherein said $C_{1-6}$alkyl, $C_{1-6}$heteroalkyl, $C_{6-10}$aryl, $C_{3-10}$cycloalkyl, 5-10 membered heteroaryl, and 3-12 membered heterocyclyl are optionally substituted with 1-5 $R^{10}$ groups;

$R^6$ is hydrogen or halo;

each $R^7$ is independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, wherein said $C_{1-6}$alkyl, $C_{3-10}$cycloalkyl, $C_{1-6}$heteroalkyl, 3-12 membered heterocyclyl, $C_{6-10}$ aryl, and 5-10 membered heteroaryl are optionally substituted with from 1-5 $R^{10}$;

each $R^8$ and $R^9$ are independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$heteroalkyl, 3-12 membered heterocyclyl, $C_{6-10}$ aryl, and 5-10 membered heteroaryl are optionally substituted with 1-5 $R^{10}$;

each $R^{10}$ is independently $C_{1-6}$alkyl, $C_{3-10}$cycloalkyl, $C_{1-6}$heteroalkyl, 3-12 membered heterocyclyl, $C_{6-10}$aryl, 5-10 membered heteroaryl, halo, oxo, $—OR^a$, $—C(O)R^a$, $—C(O)OR^a$, $—C(O)NR^aR^b$, $—OC(O)NR^aR^b$, $—NR^aR^b$, $—NR^aC(O)R^b$, $—NR^aC(O)OR^b$, $—S(O)_qR^a$, $—S(O)_2NR^aR^b$, $—NR^aS(O)_2R^b$, $—N_3$, $—CN$, or $—NO_2$, or two $R^{10}$ groups form a fused, spiro, or bridged $C_{3-10}$ cycloalkyl or 3-12 membered heterocyclyl, wherein each $C_{1-6}$alkyl, $C_{1-6}$ heteroalkyl, $C_{2-6}$alkynyl, $C_{3-10}$cycloalkyl, $C_{6-10}$aryl, 3-12 membered heterocycle, and 5-10 membered heteroaryl is optionally substituted with 1-5 $R^{20}$ groups;

each $R^a$ and $R^b$ is independently hydrogen, $C_{1-6}$alkyl, $C_{2-6}$alkenyl, $C_{3-10}$cycloalkyl, $C_{1-6}$heteroalkyl, 3-12 membered heterocyclyl, $C_{6-10}$aryl, 5-10 membered heteroaryl, or $R^a$ and $R^b$ together with the atoms to which they are attached form a 3-12 membered heterocyclyl wherein said $C_{1-6}$alkyl, $C_{2-6}$ alkenyl, $C_{3-10}$cycloalkyl, $C_{1-6}$heteroalkyl, 3-12 membered heterocyclyl, $C_{6-10}$aryl, 5-10 membered heteroaryl is optionally substituted with 1-5 $R^{20}$ groups;

each $R^{20}$ is independently $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, or halogen;

n is 0, 1, or 2;

p is 0, 1, or 2; and q is 0, 1, or 2;

or a tautomer or pharmaceutically acceptable salt thereof.

In some embodiments, a pharmaceutical composition comprising a compound according to Formula (I), or a tautomer or pharmaceutically acceptable salt thereof, and a pharmaceutically acceptable excipient is provided herein.

In some embodiments, a method of inhibiting MCL-1 in a patient comprising administering a compound according to Formula (I), or a tautomer or pharmaceutically acceptable salt thereof, to the patient is provided herein.

In some embodiments, a method of treating cancer in a patient, comprising administering a compound according to Formula (I), or a tautomer or pharmaceutically acceptable salt thereof, to the patient is provided herein.

DETAILED DESCRIPTION

Unless the context requires otherwise, throughout the present specification and claims, the word "comprise" and variations thereof, such as, "comprises" and "comprising" are to be construed in an open, inclusive sense, that is as "including, but not limited to".

A prefix such as "$C_{u\text{-}v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The term "substituted" means that one or more hydrogen atoms on a hydrocarbon is replaced with one or more atoms or groups other than hydrogen, provided that the designated carbon atom's or atoms' normal valence is not exceeded. A "substituent" is an atom or group that replaces a hydrogen atom on a hydrocarbon when it is "substituted." Unless specified otherwise, where a group is described as optionally substituted, any substituents of the group are themselves unsubstituted.

The term "about" refers to a value or parameter ±10% the indicated amount.

As used herein, "alkyl" is a linear or branched saturated monovalent hydrocarbon. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, n-propyl, —CH(CH$_3$)$_2$), 1-butyl (n-Bu, n-butyl, —CH$_2$CH$_2$CH$_2$CH$_3$), 2-methyl-1-propyl (t-Bu, t-butyl, —CH$_2$CH(CH$_3$)$_2$), 2-butyl (s-Bu, 5-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), and 2,3-dimethyl-2-butyl (—C(CH$_3$)$_2$CH(CH$_3$)$_2$), 3,3-dimethyl-2-butyl (—CH(CH$_3$)C(CH$_3$)$_3$.

"Alkenyl" refers to an aliphatic group containing at least one carbon-carbon double bond. Examples of alkenyl groups include ethenyl, propenyl, butadienyl (including 1,2-butadienyl, and 1,3-butadienyl).

"Alkoxy" as used herein refers to a radical of the formula —OR$_A$ where R$_A$ is an alkyl radical as defined above. Non-limiting examples of alkoxy include methoxy, ethoxy, propoxy, and butoxy.

"Alkynyl" refers to an aliphatic group containing at least one carbon-carbon triple bond.

"Aryl" refers to a monoradical or diradical aromatic carbocyclic group having a single ring (e.g., monocyclic) or multiple rings (e.g., bicyclic or tricyclic) including fused ring systems wherein one or more fused rings is/are fully or partially unsaturated. Non-limiting examples of aryl groups as used herein include phenyl, naphthyl, fluorenyl, indanyl, tetrahydroindenyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "aryloxy" refers to the group —O-aryl.

"Cycloalkyl" refers to a saturated or partially saturated cyclic alkyl group having a single ring or multiple rings including fused, bridged, and spiro ring systems. Examples of cycloalkyl groups include cyclopropyl, cyclobutyl, cyclopentyl, and cyclohexyl.

"Halo" and "halogen" are used herein to refer to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halogen substituent, which may be the same or different. For example, $C_{1-6}$haloalkyl is a $C_{1-6}$alkyl wherein one or more of the hydrogen atoms of the $C_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms selected from nitrogen, sulfur, phosphorus, and oxygen. The heteroatoms within the "heteroalkyl" may be oxidized, e.g. —N(O)—, —S(O)—, —S(O)$_2$—. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen or alkyl.

"Heteroaryl" refers to a monoradical or diradical aromatic group having a single ring, multiple rings, or multiple fused rings, with one or more ring heteroatoms independently selected from nitrogen, oxygen, and sulfur. The heteroatoms within the "heteroaryl" may be oxidized, e.g., —N(O)—, —S(O)—, —S(O)$_2$—. The term includes fused ring systems wherein one or more fused rings is/are fully or partially unsaturated. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above. Non-limiting examples of heteroaryl groups include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl.

The term "heteroaryloxy" refers to the group —O-heteroaryl.

The term "heterocyclyl," "heterocycle," or "heterocyclic" refers to a monoradical or diradical saturated or unsaturated group having a single ring or multiple condensed rings having one or more heteroatoms selected from nitrogen, sulfur, phosphorus, and/or oxygen within the ring. The heteroatoms within the "heterocyclyl" may be oxidized, e.g. —N(O)—, —S(O)—, —S(O)$_2$—. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Exemplary heterocyclic groups include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxothiomorpholinyl.

The term "cyano" refers to the group —CN.

The term "oxo" refers to a group =O.

The term "carboxy" refers to a group —C(O)—OH.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The symbol "(±)" is used to designate a racemic mixture where appropriate.

"Diastereoisomers" are stereoisomers that have at least two asymmetric atoms, but which are not mirror-images of each other.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "prevention" or "preventing" refers to a regimen that protects against the onset of a disease or disorder such that the clinical symptoms of the disease or disorder do not develop. Thus, "prevention" relates to administration of a therapy to a subject before signs of the disease are detectable in the subject. The subject may be an individual at risk of developing the disease or disorder, such as an individual who has one or more risk factors known to be associated with development or onset of the disease or disorder.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the particular compound, and characteristics of the subject to be treated, such as age, weight, etc. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Also provided herein are pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are suitable for veterinary or human pharmaceutical use.

Compounds described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propyl sulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Non-limiting examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

The term "prodrug" as used herein is a biologically inactive derivative of a drug that upon administration to the human body is converted to the biologically active parent drug according to some chemical or enzymatic pathway.

LIST OF ABBREVIATIONS AND ACRONYMS

Abbreviation Meaning
ACN Acetonitrile
MeTHF 2-methyl tetrahydrofuran
Boc t-Butyloxy carbonyl
BSA Bovine Serum Albumin
calcd or calc'd Calculated
DCM Diehl or om ethane
DIPEA N,N-Diisopropylethylamine
DMAP 4-Dimethylaminopyridine
DMF Dimethylformamide
DMSO Dimethylsulfoxide
Et Ethyl
EDCI 1-Ethyl-3-(3-dimethylaminopropyl)carbodiimide
EDTA Ethylenediaminetetraacetic acid
ESI Electronspray Ionization
EtOAc Ethyl acetate
EtOH Ethanol
h or hr(s) Hour(s)
i-Pr Isopropyl
KHMDS Potassium bis(trimethylsilyl)amide
LCMS or Liquid Chromatography Mass Spectrometry
LC/MS
MeOH Methanol
min Minute(s)
MS Mass Spectrometry
m/z Mass-to-charge ratio
NMR Nuclear Magnetic Resonance spectroscopy
n-BuLi n-Butyllithium
RT or rt Room temperature
STAB Sodium triacetoxyborohydride
SFC Supercritical Fluid Chromatography
TBAF Tetra-n-butylammonium fluoride
TBDMS t-Butyl di methyl silyl
TBDMSCl t-Butyldimethyl silyl chloride
TBSOTf t-Butyldimethylsilyl triflate
TEA Trimethylamine
TFA Trifluoroacetic acid
THF Tetrahydrofuran
TLC Thin Layer Chromatography Compounds In some embodiments, the present disclosure provides a compound according to Formula (I):

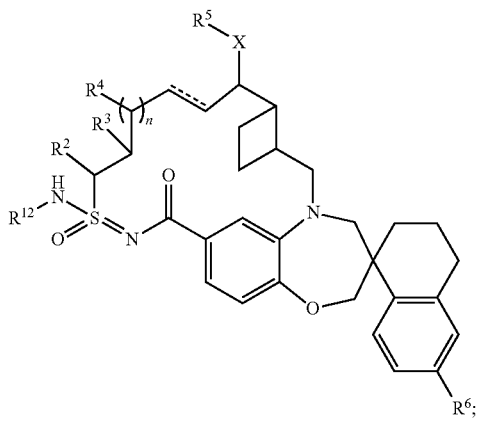

wherein ═ is a single or double bond;
X is O or $NR^7$;
$R^{12}$ is hydrogen or —C(O)$R^1$;
$R^1$ is $C_{1-6}$alkyl, $C_{1-6}$haloalkyl, $C_{2-6}$alkenyl, $C_{2-6}$alkynyl, $C_{3-10}$cycloalkyl, $C_{6-10}$aryl, 3-12 membered heterocyclyl, 5-10 membered heteroaryl, —O$R^7$, or —N$R^8R^9$, wherein
said $C_{1-6}$alkyl, $C_{1-6}$heteroalkyl, $C_{2-6}$alkynyl, $C_{3-10}$cycloalkyl, $C_{6-10}$aryl, 3-12 membered heterocyclyl, and 5-10 membered heteroaryl are optionally substituted with 1-5 $R^{10}$ groups;
$R^2$ is hydrogen, $C_{1-6}$alkyl, $C_{1-6}$heteroalkyl, $C_{3-10}$cycloalkyl, or 3-12 membered heterocyclyl, wherein
said $C_{1-6}$alkyl, $C_{1-6}$heteroalkyl, $C_{3-10}$cycloalkyl, and 3-12 membered heterocyclyl are optionally substituted with 1-5 $R^{10}$ groups;
$R^3$ and $R^4$ are independently hydrogen, $C_{1-6}$alkyl, —O$R^7$, $C_{1-6}$heteroalkyl, —N$R^8R^9$, $NR^8C(O)R^9$, —$NR^8C(O)OR^9$, $C_{6-10}$aryl, $C_{3-10}$cycloalkyl, 5-10 membered heteroaryl, 3-12 membered heterocyclyl, —C(O)$R^7$, —C(O)O$R^7$, —C(O)N$R^8R^9$, —OC(O)N$R^8R^9$, —CN, or —SO$_2R^7$, wherein
said $C_{1-6}$alkyl, $C_{1-6}$heteroalkyl, $C_{6-10}$aryl, $C_{3-10}$cycloalkyl, 5-10 membered heteroaryl, and 3-12 membered heterocyclyl are optionally substituted with 1-5 $R^{10}$ groups;
$R^5$ is hydrogen, $C_{1-6}$alkyl, —(CH$_2$CH$_2$O)$_pR^7$, $C_{1-6}$heteroalkyl, $C_{6-10}$aryl, $C_{3-10}$cycloalkyl, 5-10 membered heteroaryl, or 3-12 membered heterocyclyl, wherein
said $C_{1-6}$alkyl, $C_{1-6}$heteroalkyl, $C_{6-10}$aryl, $C_{3-10}$cycloalkyl, 5-10 membered heteroaryl, and 3-12 membered heterocyclyl are optionally substituted with 1-5 $R^{10}$ groups;
$R^6$ is hydrogen or halo;
each $R^7$ is independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, wherein
said $C_{1-6}$alkyl, $C_{3-10}$cycloalkyl, $C_{1-6}$heteroalkyl, 3-12 membered heterocyclyl, $C_{6-10}$ aryl, and 5-10 membered heteroaryl are optionally substituted with from 1-5 $R^{10}$;
each $R^8$ and $R^9$ are independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, or $R^8$ and $R^9$ together with the atoms to which they are attached form a 3-12 membered heterocycle, wherein
said $C_{1-6}$alkyl, $C_{3-10}$cycloalkyl, $C_{1-6}$heteroalkyl, 3-12 membered heterocyclyl, $C_{6-10}$ aryl, and 5-10 membered heteroaryl are optionally substituted with 1-5 $R^{10}$;
each $R^{10}$ is independently $C_{1-6}$alkyl, $C_{3-10}$cycloalkyl, $C_{1-6}$heteroalkyl, 3-12 membered heterocyclyl, $C_{6-10}$aryl, 5-10 membered heteroaryl, halo, oxo, —O$R^a$, —C(O)$R^a$, —C(O)O$R^a$, —C(O)N$R^aR^b$, —OC(O)N$R^aR^b$, —N$R^aR^b$, —$NR^aC(O)R^b$, —$NR^aC(O)OR^b$, —S(O)$_qR^a$, —S(O)$_2NR^aR^b$, —$NR^aS(O)_2R^b$, —$N_3$, —CN, or —NO$_2$, or two $R^{10}$ groups form a fused, spiro, or bridged $C_{3-10}$ cycloalkyl or 3-12 membered heterocyclyl, wherein
each $C_{1-6}$alkyl, $C_{1-6}$ heteroalkyl, $C_{2-6}$alkynyl, $C_{3-10}$cycloalkyl, $C_{6-10}$aryl, 3-12 membered heterocycle, and 5-10 membered heteroaryl is optionally substituted with 1-5 $R^{20}$ groups;
each $R^a$ and $R^b$ is independently hydrogen, $C_{1-6}$alkyl, $C_{2-6}$alkenyl, $C_{3-10}$cycloalkyl, $C_{1-6}$heteroalkyl, 3-12 membered heterocyclyl, $C_{6-10}$aryl, 5-10 membered heteroaryl, or $R^a$ and $R^b$ together with the atoms to which they are attached form a 3-12 membered heterocyclyl wherein
said $C_{1-6}$alkyl, $C_{2-6}$ alkenyl, $C_{3-10}$cycloalkyl, $C_{1-6}$heteroalkyl, 3-12 membered heterocyclyl, $C_{6-10}$aryl, 5-10 membered heteroaryl is optionally substituted with 1-5 $R^{20}$ groups;
each $R^{20}$ is independently $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $C_{1-6}$ alkoxy, amino, —CN, —C(O)H, —C(O)NH$_2$, —C(O)NH($C_{1-6}$ alkyl), —C(O)N($C_{1-6}$ alkyl)$_2$, —COOH, —C(O)$C_{1-6}$ alkyl, —C(O)O$C_{1-6}$ alkyl, or halogen;
n is 0, 1, or 2;
p is 0, 1, or 2; and
q is 0, 1, or 2;
or a tautomer or pharmaceutically acceptable salt thereof.

In some embodiments, the present disclosure provides a compound of Formula (I) according to Formula (Ia):

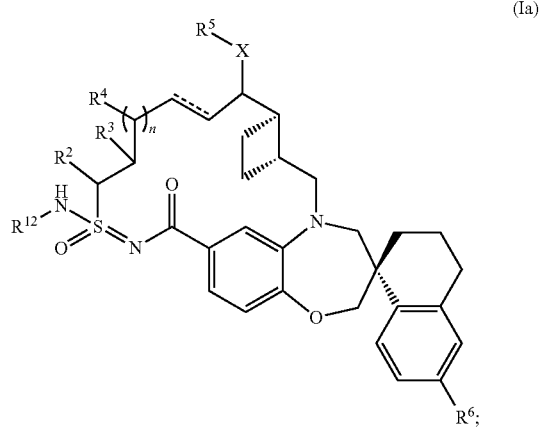

or a tautomer or pharmaceutically acceptable salt thereof.

In some embodiments, the present disclosure provides a compound according to Formula (II):

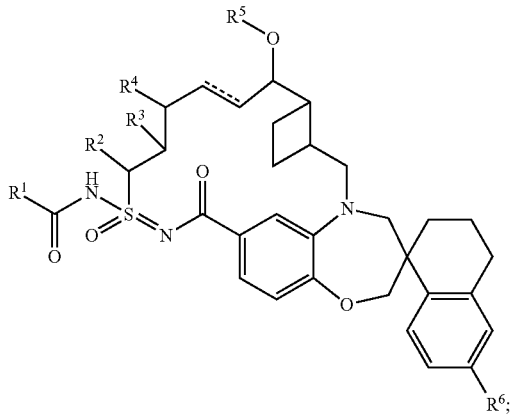

(II)

wherein ⁓ is a single or double bond;
$R^1$ is $C_{1-6}$alkyl, $C_{1-6}$haloalkyl, $C_{2-6}$alkynyl, $C_{3-10}$cycloalkyl, $C_{6-10}$aryl, 5-10 membered heteroaryl, $C_{1-6}$hydroxyalkyl, —$OC_{1-6}$alkyl, —$NHC_{1-6}$alkyl, —$NHC_{1-6}$haloalkyl, 4-6 membered heterocyclyl, $C_{3-6}$cycloalkyl, —$NHC_{3-10}$cycloalkyl, or —$N(C_{1-6}$alkyl$)_2$, wherein
  said $C_{1-6}$alkyl is optionally substituted with $C_{1-6}$alkoxy, —$N(C_{1-6}$alkyl$)_2$, 5-10 membered heteroaryl, $C_{3-6}$cycloalkyl, —$SO_2C_{1-6}$alkyl, phenyl, 5 membered heteroaryloxy, phenoxy, or —O-(4-10 membered heterocyclyl),
  said 5-10 membered heteroaryl is optionally substituted with 1 or 2 substitutents selected from halo, $C_{1-6}$alkyl, and $C_{1-6}$haloalkyl,
    said 5 membered heteroaryloxy is optionally substituted with 1-3 $C_{1-6}$alkyl, and
    said phenyl is optionally substituted with 1-3 halo or $C_{1-6}$haloalkyl;
  said —$NHC_{3-6}$cycloalkyl is optionally substituted with $C_{1-3}$haloalkyl;
  said —$NHC_{1-6}$alkyl is optionally substituted with phenyl, 5-6 membered heteroaryl, or $C_{3-6}$cycloalkyl wherein
    said phenyl is optionally substituted with 1-5 halo,
    said 5 to 6 membered heteroaryl is optionally substituted with 1-3 halo or $C_{1-6}$alkyl, and
  said $C_{1-6}$hydroxyalkyl is optionally substituted with phenyl;
  said $C_{3-6}$cycloalkyl is optionally substituted with 5 membered heteroaryl, wherein
    said 5 membered heteroaryl is optionally substituted with $C_{1-6}$alkyl;
  said —$OC_{1-6}$alkyl is optionally substituted with 5 membered heteroaryl, wherein
    said 5 membered heteroaryl is optionally substituted with $C_{1-6}$alkyl;
  said 5-10 membered heteroaryl is optionally substituted with $C_{1-6}$alkyl;
$R^2$ is hydrogen or $C_{1-6}$alkyl;
$R^3$ is hydrogen or $C_{1-6}$alkyl;
$R^4$ is hydrogen; and
$R^5$ is hydrogen or $C_{1-6}$alkyl, wherein
  said $C_{1-6}$alkyl is optionally substituted with 5-6 membered heterocyclyl;
or a tautomer or pharmaceutically acceptable salt thereof.

In some embodiments, the present disclosure provides a compound of Formula (II) according to Formula (IIa):

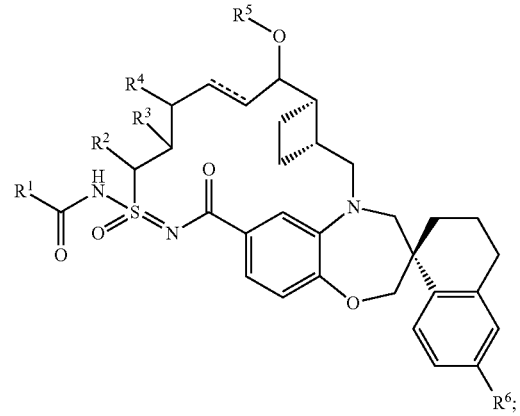

(IIa)

or a tautomer or pharmaceutically acceptable salt thereof.

In some embodiments, the present disclosure provides a compound of Formula (I), Formula (Ia), Formula (II), or Formula (IIa), wherein:
$R^2$ is hydrogen or $C_{1-3}$alkyl;
$R^3$ is hydrogen or $C_{1-3}$alkyl;
$R^4$ is hydrogen; and
$R^5$ is $C_{1-3}$alkyl, wherein
  said $C_{1-3}$alkyl is optionally substituted with a 5-6 membered heterocyclyl;
or a tautomer or pharmaceutically acceptable salt thereof.

In some embodiments, the present disclosure provides a compound of Formula (I), Formula (Ia), Formula (II), or Formula (IIa), wherein:
$R^2$ is hydrogen, methyl, or ethyl;
$R^3$ is hydrogen or methyl;
$R^4$ is hydrogen; and
$R^5$ is hydrogen, methyl,

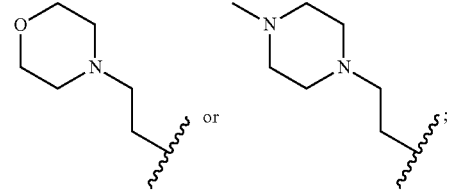

or a tautomer or pharmaceutically acceptable salt thereof.

In some embodiments, the present disclosure provides a compound of Formula (I), Formula (Ia), Formula (II), or Formula (IIa), wherein:
$R^2$ is hydrogen; and
$R^3$ is $C_{1-3}$alkyl;
or a tautomer or pharmaceutically acceptable salt thereof.

In some embodiments, the present disclosure provides a compound of Formula (I), Formula (Ia), Formula (II), or Formula (IIa), wherein:
$R^2$ is $C_{1-3}$alkyl; and
$R^3$ is hydrogen;
or a tautomer or pharmaceutically acceptable salt thereof.

In some embodiments, the present disclosure provides a compound of Formula (I), Formula (Ia), Formula (II), or Formula (IIa), wherein:
$R^2$ is hydrogen; and
$R^3$ is hydrogen;
or a tautomer or pharmaceutically acceptable salt thereof.

In some embodiments, the present disclosure provides a compound of Formula (I), Formula (Ia), Formula (II), or Formula (IIa), wherein:
$R^2$ is $C_{1-3}$alkyl; and
$R^3$ is $C_{1-3}$alkyl;
or a pharmaceutically acceptable salt thereof.

In some embodiments, the present disclosure provides a compound according to Formula (III), or a pharmaceutically acceptable salt thereof:

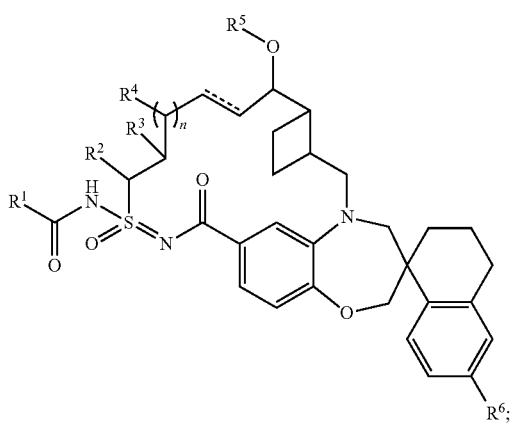

(III)

wherein ⁃ is a single or double bond;
$R^1$ is $C_{1-6}$alkyl, $C_{1-6}$haloalkyl, $C_{2-6}$alkenyl, $C_{2-6}$alkynyl, $C_{3-10}$cycloalkyl, $C_{6-10}$aryl, 3-12 membered heterocyclyl, 5-10 membered heteroaryl, —$OR^7$, or —$NR^8R^9$;
wherein said $C_{1-6}$alkyl, $C_{1-6}$haloalkyl, $C_{2-6}$alkenyl, $C_{2-6}$alkynyl, $C_{3-10}$cycloalkyl, $C_{6-10}$aryl, 3-12 membered heterocyclyl, and 5-10 membered heteroaryl of $R^1$ are independently optionally substituted with 1-5 $R^{10}$ groups;
each $R^2$, $R^3$, $R^4$, and $R^5$ is independently hydrogen or $C_{1-6}$alkyl;
$R^6$ is hydrogen or halo;
each $R^7$ is independently hydrogen, or $C_{1-6}$alkyl, wherein said $C_{1-6}$alkyl is optionally substituted with from 1-5 $R^{10}$;
each $R^8$ and $R^9$ is independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, or $R^8$ and $R^9$ together with the atoms to which they are attached form a 3-12 membered heterocycle, wherein said $C_{1-6}$alkyl, $C_{3-10}$cycloalkyl, $C_{1-6}$heteroalkyl, 3-12 membered heterocyclyl, $C_{6-10}$ aryl, and 5-10 membered heteroaryl of $R^8$ and $R^9$ are independently optionally substituted with 1-5 $R^{10}$;
each $R^{10}$ is independently $C_{1-6}$alkyl, $C_{3-10}$cycloalkyl, $C_{1-6}$heteroalkyl, 3-12 membered heterocyclyl, $C_{6-10}$aryl, 5-10 membered heteroaryl, halo, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_qR^a$, —$S(O)_2NR^aR^b$, —$NR^aS(O)_2R^b$, —$N_3$, —CN, or —$NO_2$, or two $R^{10}$ groups form a fused, spiro, or bridged $C_{3-10}$ cycloalkyl or 3-12 membered heterocyclyl, wherein
each $C_{1-6}$alkyl, $C_{1-6}$ heteroalkyl, $C_{2-6}$alkynyl, $C_{3-10}$cycloalkyl, $C_{6-10}$aryl, 3-12 membered heterocycle, and 5-10 membered heteroaryl of $R^{10}$ is independently optionally substituted with 1-5 $R^{20}$ groups;
each $R^a$ and $R^b$ is independently hydrogen, $C_{1-6}$alkyl, $C_{2-6}$alkenyl, $C_{3-10}$cycloalkyl, $C_{1-6}$heteroalkyl, 3-12 membered heterocyclyl, $C_{6-10}$aryl, or 5-10 membered heteroaryl, or $R^a$ and $R^b$ together with the atoms to which they are attached form a 3-12 membered heterocyclyl wherein
said each $C_{1-6}$alkyl, $C_{2-6}$ alkenyl, $C_{3-10}$cycloalkyl, $C_{1-6}$heteroalkyl, 3-12 membered heterocyclyl, $C_{6-10}$aryl, 5-10 membered heteroaryl of $R^a$ and $R^b$ is independently optionally substituted with 1-5 $R^{20}$ groups;
each $R^{20}$ is independently $C_{1-6}$ alkyl, $C_{3-10}$cycloalkyl, $C_{1-6}$heteroalkyl, 3-12 membered heterocyclyl, $C_{6-10}$aryl, 5-10 membered heteroaryl, hydroxyl, $C_{1-6}$ alkoxy, amino, —CN, —C(O)H, —$C(O)NH_2$, —$C(O)NH(C_{1-6}$ alkyl), —$C(O)N(C_{1-6}$ alkyl$)_2$, —COOH, —$C(O)C_{1-6}$alkyl, —$C(O)OC_{1-6}$alkyl, or halogen;
n is 0, 1, or 2; and
q is 0, 1, or 2.

In some embodiments, the present disclosure provides a compound of Formula (III), according to Formula (IIIa):

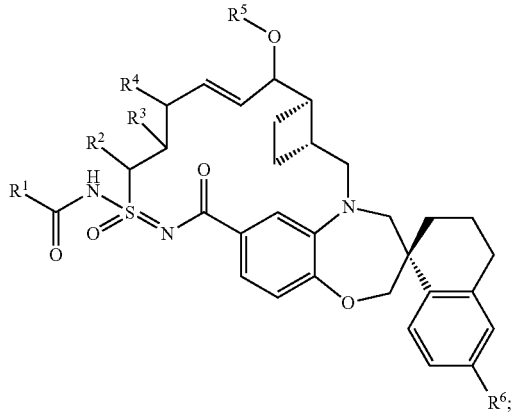

(IIIa)

or pharmaceutically acceptable salt thereof.

In some embodiments, the present disclosure provides a compound of Formula (III), or a pharmaceutically acceptable salt thereof, according to Formula (IIIb):

(IIIb)

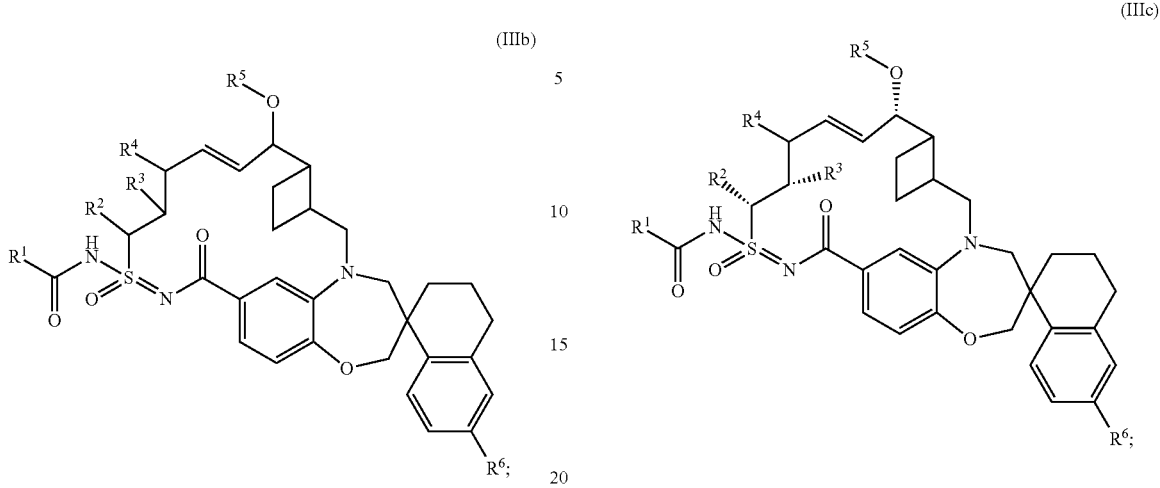

wherein: $R^1$ is $C_{1-6}$alkyl, $C_{3-10}$cycloalkyl, $C_{6-10}$aryl, 5-10 membered heteroaryl, —$NHC_{1-6}$alkyl, —$NHC_{1-6}$haloalkyl, 4-6 membered heterocyclyl, $C_{3-6}$cycloalkyl, —$NHC_{3-10}$cycloalkyl, or —NH(4-6 membered heterocyclyl);

each $C_{1-6}$alkyl and —$NHC_{1-6}$alkyl of $R^1$ is independently optionally substituted with 1-3 substituents independently selected from hydroxyl, $C_{1-6}$alkoxy, 5-10 membered heteroaryl, $C_{3-6}$cycloalkyl, phenyl, or —O-(4-10 membered heterocyclyl);

wherein each 5-10 membered heteroaryl, $C_{3-6}$cycloalkyl, phenyl, and —O-(4-10 membered heterocyclyl) is independently optionally substituted with 1-4 substituents independently selected from halo, $C_{1-6}$alkyl, and $C_{1-6}$haloalkyl;

each $C_{6-10}$aryl and 5-10 membered heteroaryl of $R^1$ is optionally substituted with 1-3 substituents independently selected from halo, hydroxyl, —CN, $C_{1-6}$alkyl, $C_{1-6}$haloalkyl, $C_{1-6}$heteroalkyl, 4-6 membered heterocyclyl, and $C_{3-6}$cycloalkyl; and each 4-6 membered heterocyclyl, $C_{3-6}$cycloalkyl, —$NHC_{3-10}$cycloalkyl, and —NH(4-6 membered heterocyclyl) of $R^1$ is optionally substituted with 1 to 3 substituents independently selected from halo, oxo, hydroxyl, —CN, $C_{1-6}$alkyl, $C_{1-6}$haloalkyl, $C_{1-6}$heteroalkyl, —$C(O)OR^a$, $C_{6-10}$aryl, 5-10 membered heteroaryl, 4-6 membered heterocyclyl, and $C_{3-6}$cycloalkyl;

wherein each $C_{6-10}$aryl, 5-10 membered heteroaryl, 4-6 membered heterocyclyl, and $C_{3-6}$cycloalkyl is independently optionally substituted with 1-3 substituents independently selected from halo, $C_{1-4}$alkyl, and $C_{1-4}$haloalkyl;

each $R^2$, $R^3$, $R^4$, and $R^5$ is independently hydrogen or $C_{1-6}$alkyl; and $R^6$ is hydrogen or halo.

In some embodiments, the present disclosure provides a compound of Formula (IIIc), or a pharmaceutically acceptable salt thereof:

(IIIc)

each $R^1$, $R^2$, $R^3$, $R^4$, $R^5$, and $R^6$ is defined as above, or elsewhere in this disclosure.

In some embodiments, the present disclosure provides a compound of Formula (IIId), or a pharmaceutically acceptable salt thereof:

(IIId)

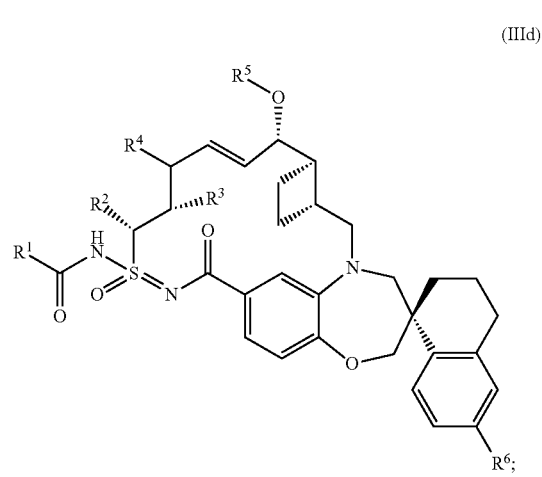

each $R^1$, $R^2$, $R^3$, $R^4$, $R^5$, and $R^6$ is defined as above, or elsewhere in this disclosure.

In some embodiments, the present disclosure provides a compound of Formula (IV), or a pharmaceutically acceptable salt thereof:

(IV)

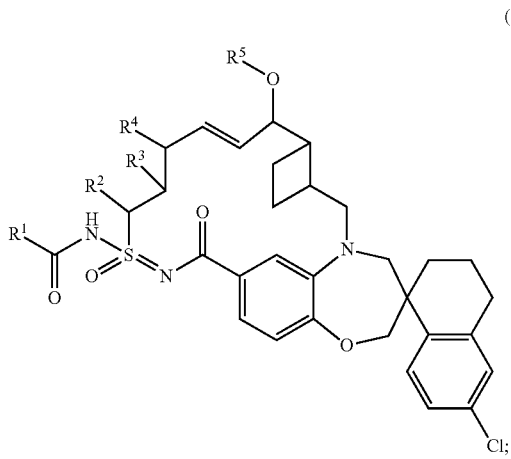

(IVa)

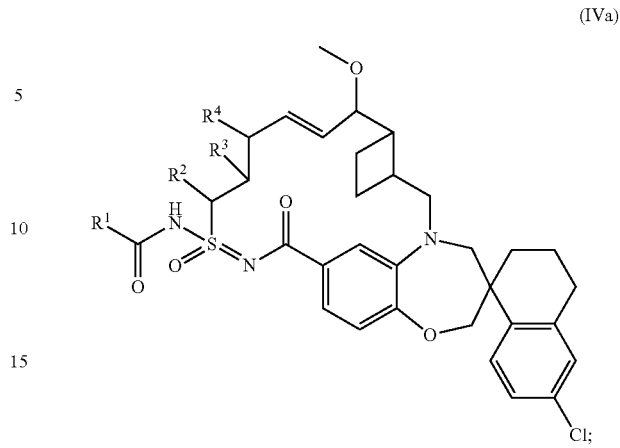

wherein: $R^1$ is $C_{3-10}$cycloalkyl, 3-12 membered heterocyclyl, $C_{6-10}$aryl, or 5-10 membered heteroaryl;
  wherein $R^1$ is independently optionally substituted with 1-4 $R^{10}$;
    wherein each $R^{10}$ is independently selected from halo, hydroxyl, —CN, $C_{1-6}$alkyl, $C_{1-6}$heteroalkyl, $C_{3-10}$cycloalkyl, and 3-12 membered heterocyclyl;
    wherein $C_{1-6}$alkyl, $C_{1-6}$heteroalkyl, $C_{3-10}$cycloalkyl and 3-12 membered heterocyclyl of $R^{10}$ are independently optionally substituted with 1-4 substituents independently selected from halo, $C_{1-4}$alkyl, $C_{1-4}$haloalkyl, and $C_{1-4}$heteroalkyl;
$R^2$ is hydrogen, $C_{1-6}$alkyl, or $C_{1-6}$heteroalkyl;
  wherein $C_{1-6}$alkyl and $C_{1-6}$heteroalkyl of $R^2$ is optionally substituted with 1-3 substituents independently selected from halo, oxo, and hydroxyl;
$R^3$ and $R^4$ are independently hydrogen, $C_{1-6}$alkyl, $C_{1-6}$heteroalkyl, —$OR^7$, or —$SO_2R^7$;
  wherein $C_{1-6}$alkyl and $C_{1-6}$heteroalkyl of $R^3$ and $R^4$ are independently optionally substituted with 1-3 substituents independently selected from halo, oxo, $C_{3-6}$cycloalkyl, 4-6 membered heterocyclyl, $C_{6-10}$aryl, and 5-10 membered heteroaryl;
  wherein $C_{3-6}$cycloalkyl, 4-6 membered heterocyclyl, $C_{6-10}$aryl, and 5-10 membered heteroaryl are independently optionally substituted with 1-3 substituents independently selected from halo, $C_{1-4}$alkyl, and $C_{1-4}$heteroalkyl;
$R^5$ is hydrogen, $C_{1-6}$alkyl, or $C_{1-6}$heteroalkyl;
  wherein $C_{1-6}$alkyl and $C_{1-6}$heteroalkyl of $R^5$ are optionally substituted with 1-3 substituents independently selected from halo, oxo, $C_{3-6}$cycloalkyl, and 4-6 membered heterocyclyl; and
$R^7$ is independently hydrogen, $C_{1-6}$alkyl, $C_{1-6}$heteroalkyl, $C_{3-10}$cycloalkyl, 3-10 membered heterocyclyl, $C_{6-10}$aryl, or 5-10 membered heteroaryl;
  wherein $C_{1-6}$alkyl, $C_{1-6}$heteroalkyl, $C_{3-10}$cycloalkyl, 3-10 membered heterocyclyl, $C_{6-10}$aryl, and 5-10 membered heteroaryl of $R^7$ are optionally substituted with 1-4 substituents independently selected from halo, oxo, $C_{1-4}$alkyl, $C_{1-4}$haloalkyl, and $C_{1-4}$heteroalkyl.

In some embodiments, the present disclosure provides a compound of Formula (IV), or a pharmaceutically acceptable salt thereof, according to Formula (IVa):

wherein: $R^1$ is 3-12 membered heterocyclyl, or 5-10 membered heteroaryl;
  wherein $R^1$ is independently optionally substituted with 1-4 $R^{10}$;
    wherein each $R^{10}$ is independently selected from halo, hydroxyl, —CN, $C_{1-4}$alkyl, $C_{1-4}$alkoxyl, $C_{3-6}$cycloalkyl, and 3-6 membered heterocyclyl;
  each $R^2$, $R^3$, and $R^4$ is independently hydrogen, $C_{1-4}$alkyl, or $C_{1-4}$alkoxyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein heterocyclyl groups are partially unsaturated ring systems containing one or more double bonds. In some embodiments, heterocyclyl groups are fused ring systems with one aromatic ring and one non-aromatic ring, but not fully aromatic ring systems.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^2$ is hydrogen.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^2$ is $C_{1-3}$alkyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^2$ is methyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^3$ is $C_{1-3}$alkyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^3$ is methyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^4$ is hydrogen.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^5$ is $C_{1-3}$alkyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^5$ is methyl.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^6$ is Cl.

In some embodiments, the present disclosure provides a compound of Formula (I), Formula (Ia), Formula (II), or Formula (IIa), wherein —C(O)R$^1$ is selected from the group consisting of

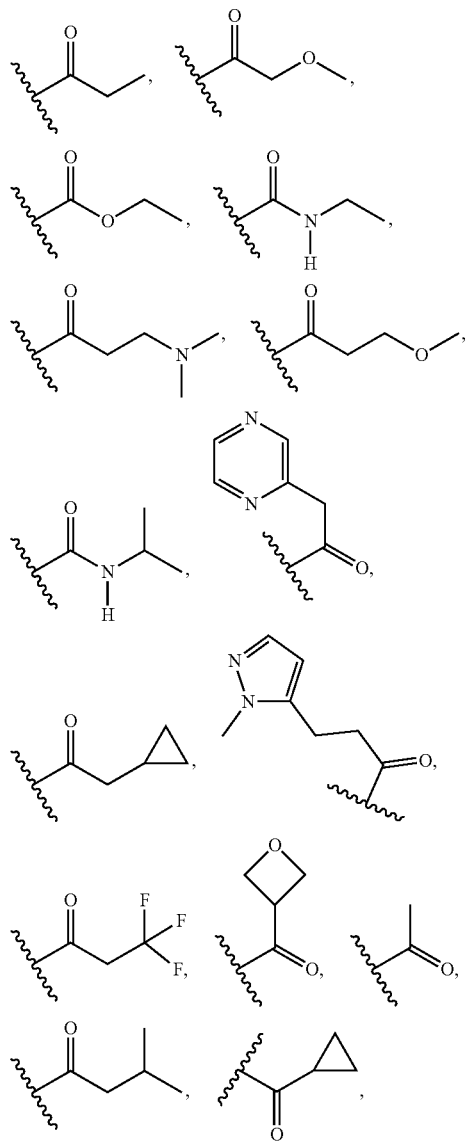

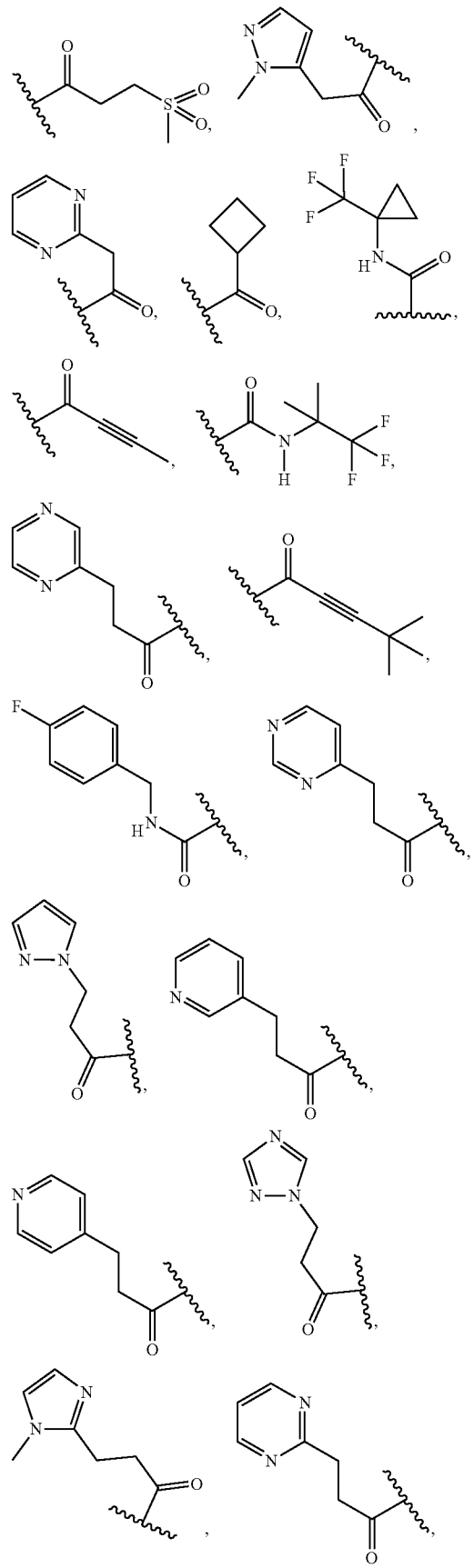

-continued
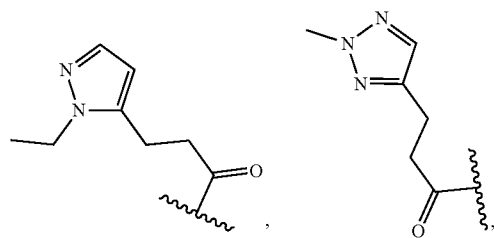
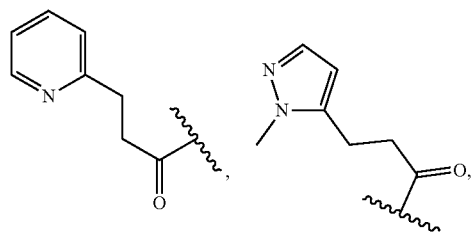
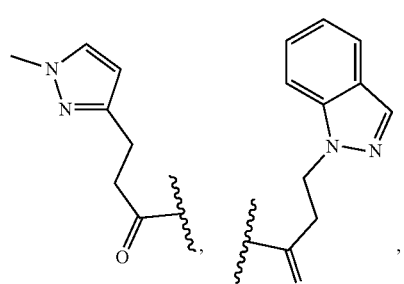
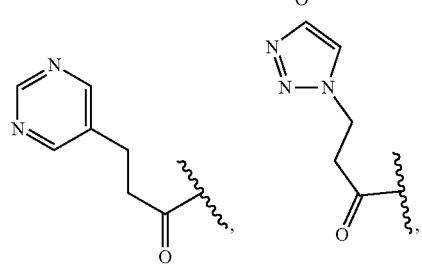
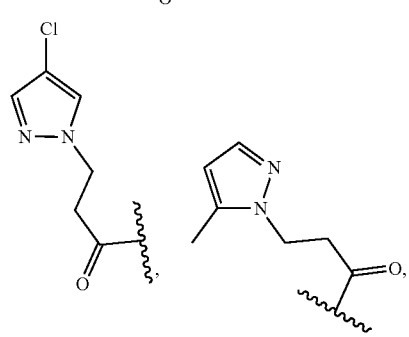
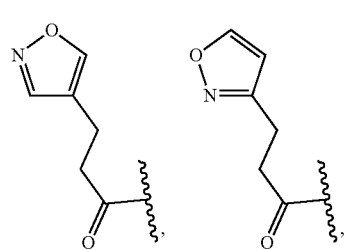
-continued
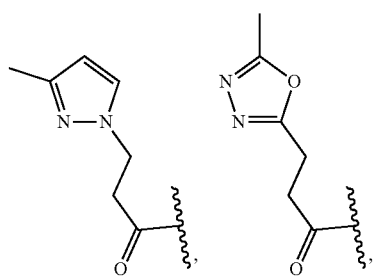
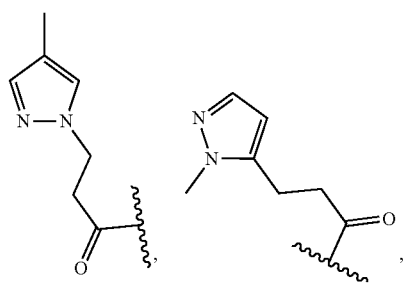
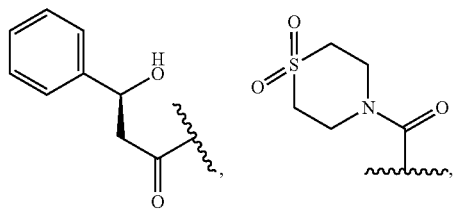
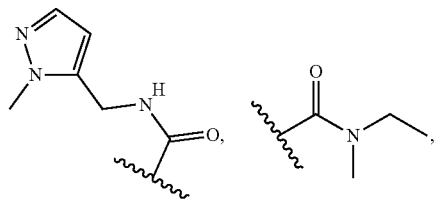
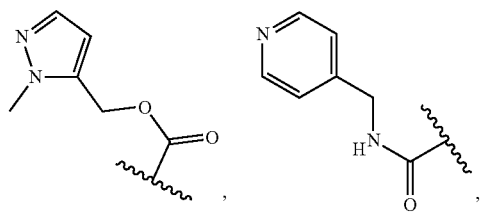
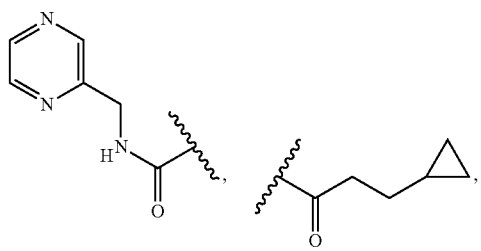
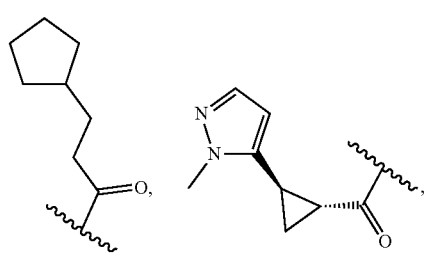

-continued
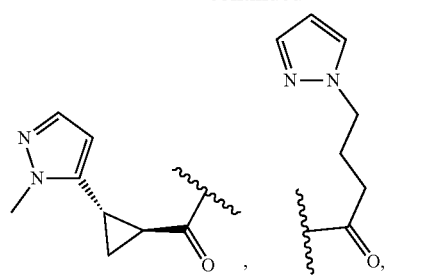
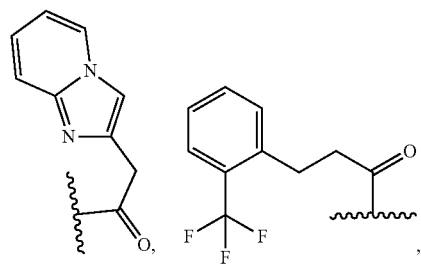
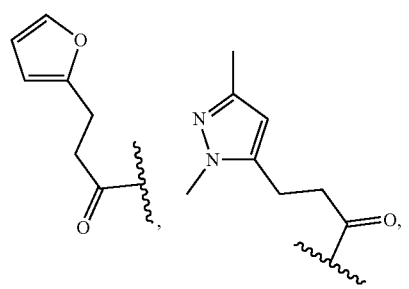
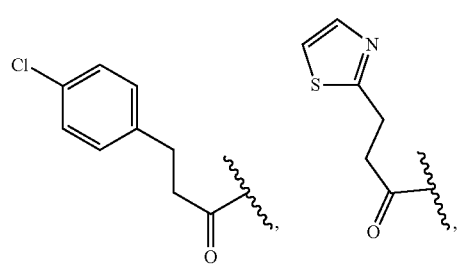
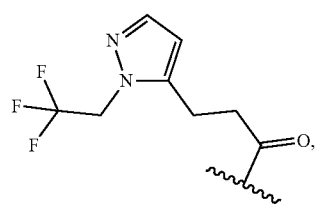
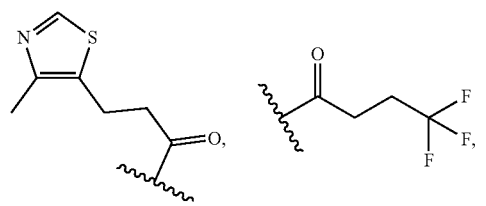
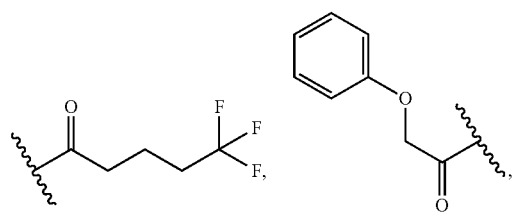
-continued
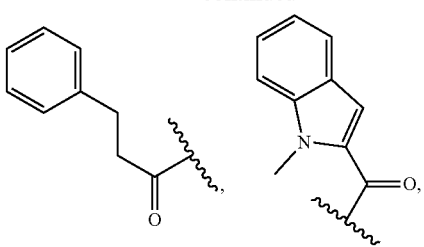
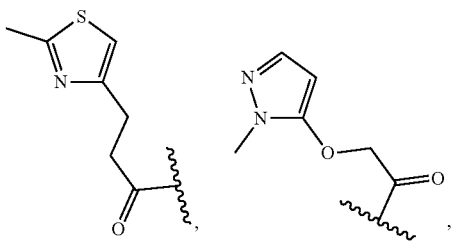
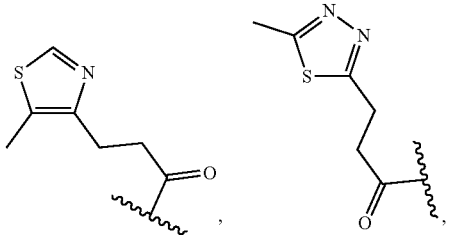
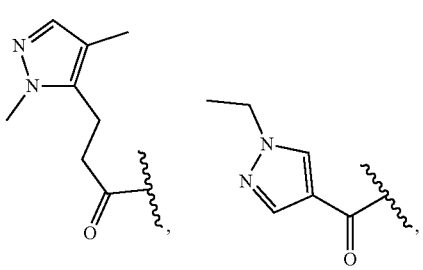
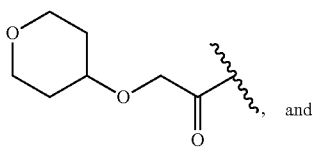
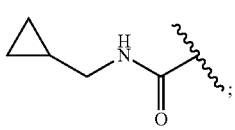
, and
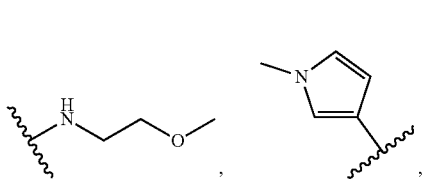
;
or a tautomer or pharmaceutically acceptable salt thereof.
In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^1$ is selected from:

-continued
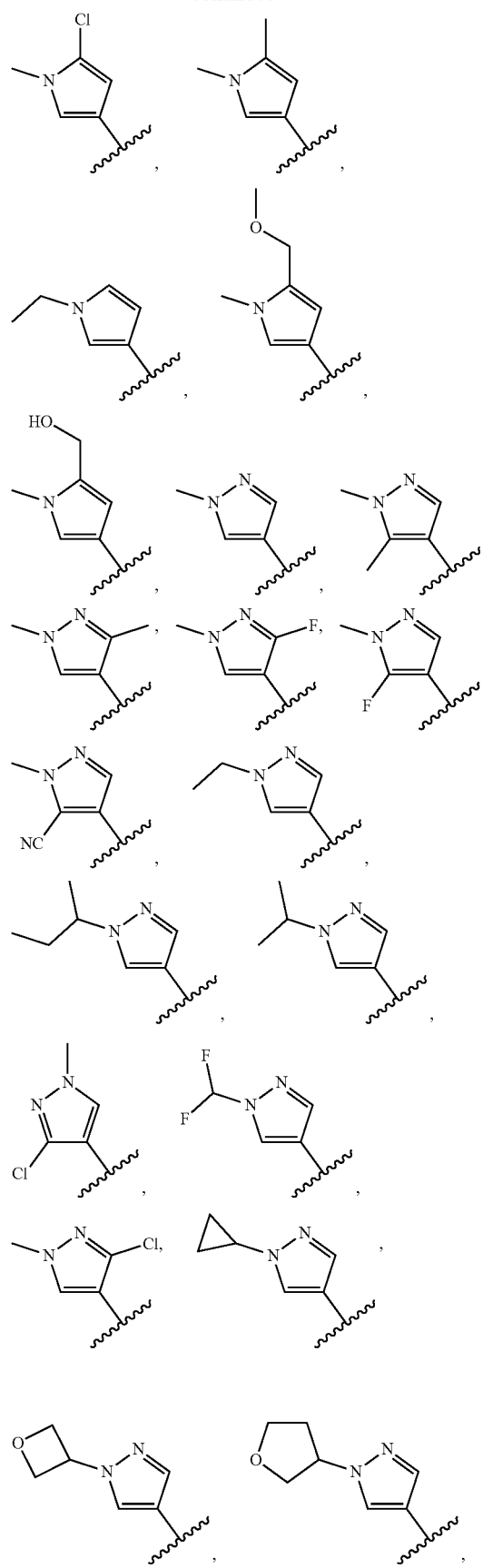
-continued
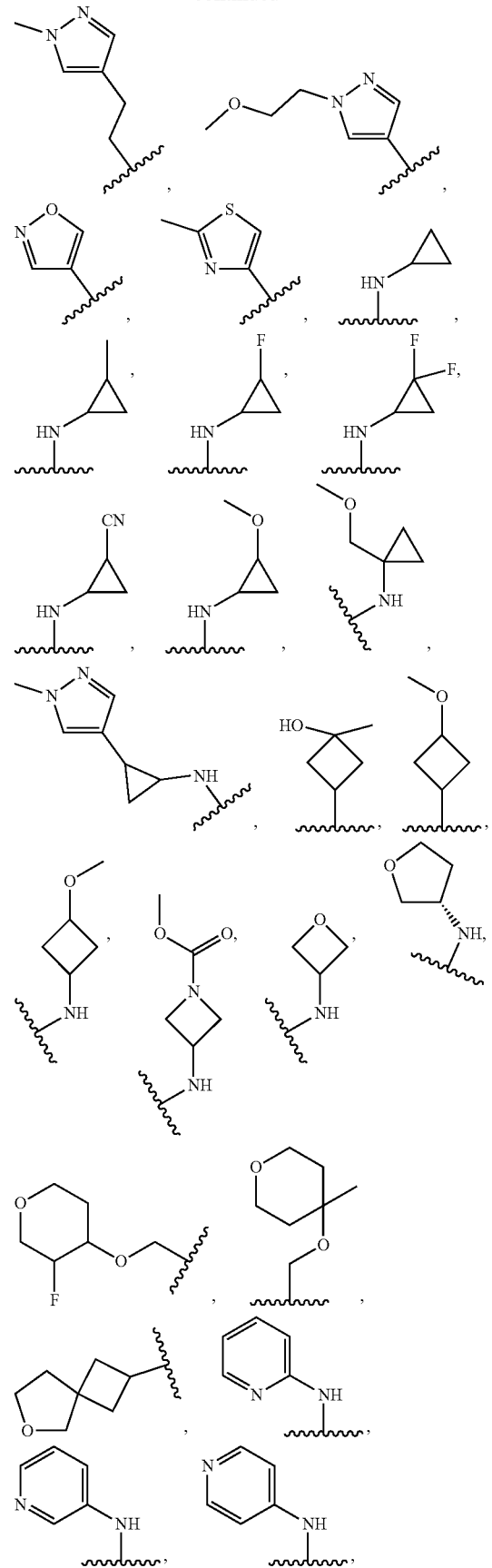

27

-continued

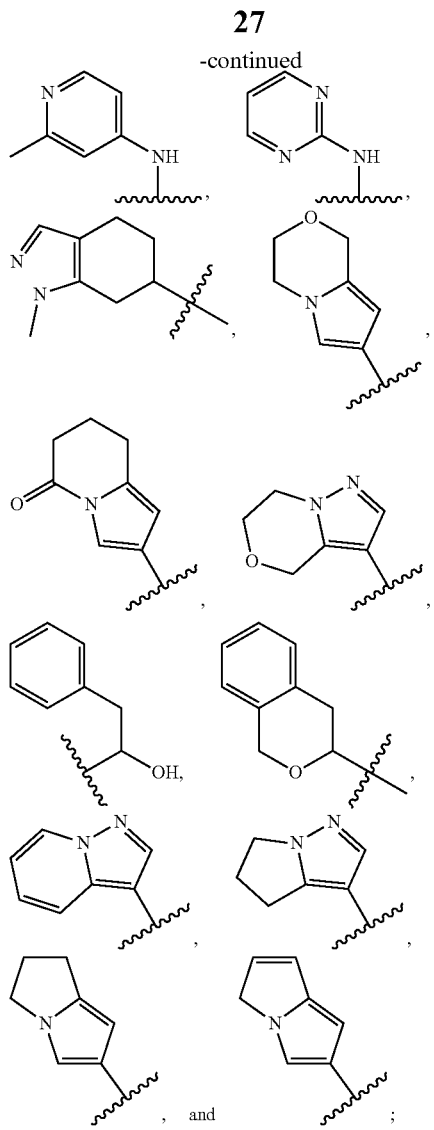

or a pharmaceutically acceptable salt thereof.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^1$ is selected from:

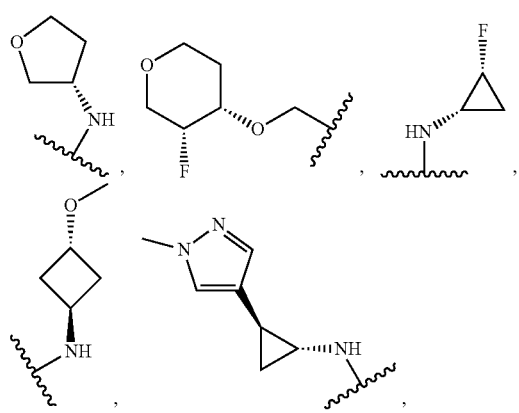

28

-continued

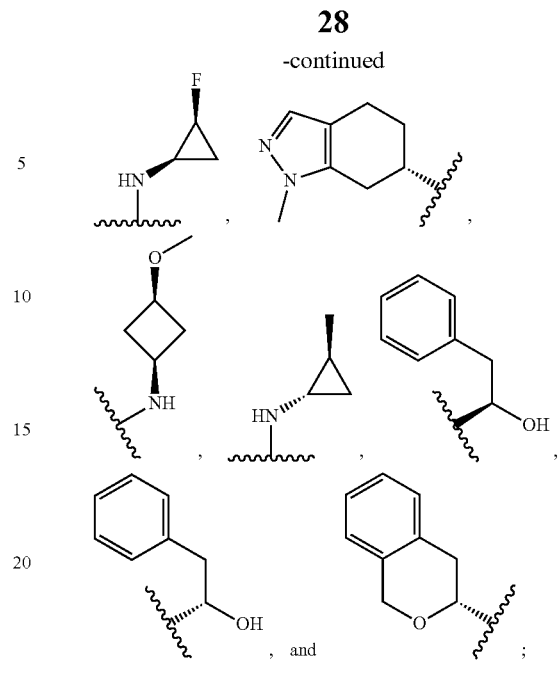

or a pharmaceutically acceptable salt thereof.

In some embodiments, the present disclosure provides a compound of Formula (I), Formula (Ia), Formula (II), Formula (IIa), Formula (III), Formula (IIIa), or Formula (IIIb), or a tautomer or pharmaceutically acceptable salt thereof, wherein $R^1$ is selected from:

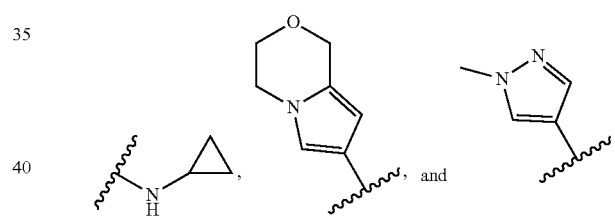

In some embodiments, the present disclosure provides a compound of Formula (II), Formula (IIa), Formula (III), Formula (IIIa), Formula (IIIb), Formula (IIIc), Formula (IIId), Formula (IV), or Formula (IVa), or pharmaceutically acceptable salt thereof, wherein $R^1$ is 3-12 membered heterocyclyl, or 5-10 membered heteroaryl, optionally substituted with 1-2 $R^{10}$.

In some embodiments, the present disclosure provides a compound of Formula (II), Formula (IIa), Formula (III), Formula (IIIa), Formula (IIIb), Formula (IIIc), Formula (IIId), Formula (IV), or Formula (IVa), or pharmaceutically acceptable salt thereof, wherein $R^1$ is selected from:

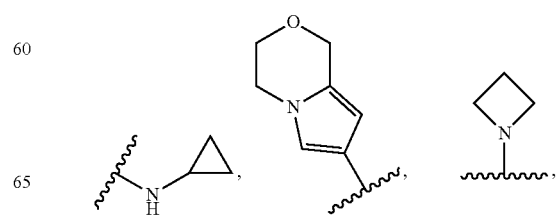

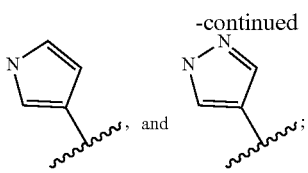

each of which is optionally substituted with 1-2 $R^{10}$. In some embodiments, each $R^{10}$ is independently selected from —$CH_3$, —$CHF_2$, and —$OCH_3$.

In some embodiments, $R^1$ is

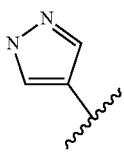

optionally substituted with 1-2 $R^{10}$. In some embodiments, $R^1$ is

optionally substituted with 1-2 $R^{10}$. In some embodiments, $R^{10}$ is independently selected from $C_{1-4}$alkyl, and $C_{1-4}$alkoxyl. In some embodiments, $R^{10}$ is independently selected from —$CH_3$, and —$OCH_3$. In some embodiments, $R^1$ is

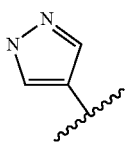

substituted with —$CH_3$, and —$OCH_3$.

In some embodiments, $R^1$ is

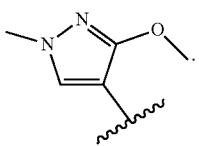

In some embodiments, $R^1$ is

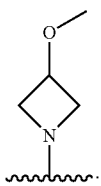 [SMILES: *N1CC(OC)C1]

In some embodiments, the present disclosure provides a compound of Formula (I), Formula (Ia), Formula (II), Formula (IIa), Formula (III), Formula (IIIa), Formula (IIIb), Formula (me), Formula (IIId), Formula (IV), or Formula (IVa), or pharmaceutically acceptable salt thereof, wherein $R^2$ is hydrogen or $C_{1-3}$alkyl. In some embodiments, $R^2$ is selected from hydrogen and methyl. In some embodiments, $R^2$ is hydrogen. In some embodiments, $R^2$ is methyl.

In some embodiments, the present disclosure provides a compound of Formula (I), Formula (Ia), Formula (II), Formula (IIa), Formula (III), Formula (IIIa), Formula (IIIb), Formula (me), Formula (IIId), Formula (IV), or Formula (IVa), or pharmaceutically acceptable salt thereof, wherein $R^3$ is hydrogen or $C_{1-3}$alkyl. In some embodiments, $R^3$ is selected from hydrogen and methyl. In some embodiments, $R^3$ is methyl. In some embodiments, $R^3$ is hydrogen.

In some embodiments, the present disclosure provides a compound of Formula (I), Formula (Ia), Formula (II), Formula (IIa), Formula (III), Formula (IIIa), Formula (IIIb), Formula (me), Formula (IIId), Formula (IV), or Formula (IVa), or pharmaceutically acceptable salt thereof, wherein $R^4$ is hydrogen, $C_{1-3}$alkyl, or $C_{1-3}$alkoxyl. In some embodiments, $R^4$ is selected from hydrogen, methyl, and —$OCH_3$. In some embodiments, $R^4$ is hydrogen. In some embodiments, $R^4$ is —$OCH_3$. In some embodiments, $R^4$ is methyl.

In some embodiments, the present disclosure provides a compound of Formula (I), Formula (Ia), Formula (II), Formula (IIa), Formula (III), Formula (IIIa), Formula (IIIb), Formula (me), Formula (IIId), Formula (IV), or Formula (IVa), or pharmaceutically acceptable salt thereof, wherein $R^2$ and $R^4$ are hydrogen, and $R^3$ is methyl. In some embodiments, $R^2$ and $R^3$ are methyl, and $R^4$ is hydrogen. In some embodiments, $R^2$ is hydrogen, $R^3$ is methyl, and $R^4$ is —$OCH_3$.

In some embodiments, the present disclosure provides a compound of Formula (I), Formula (Ia), Formula (II), Formula (IIa), Formula (III), Formula (IIIa), Formula (IIIb), Formula (me), Formula (IIId), or Formula (IV), or pharmaceutically acceptable salt thereof, wherein $R^5$ is hydrogen or $C_{1-3}$alkyl. In some embodiments, $R^5$ is methyl. In some embodiments, $R^5$ is hydrogen.

In some embodiments, the present disclosure provides a compound selected from examples 1-464.

In some embodiments, the present disclosure provides a compound selected from examples 1-154.

In some embodiments, the present disclosure provides a compound selected from examples 155-464.

In some embodiments, the present disclosure provides a compound selected from the group consisting of:

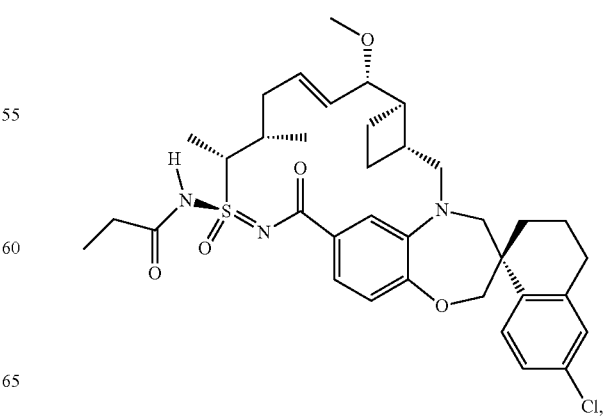

31
-continued
32
-continued
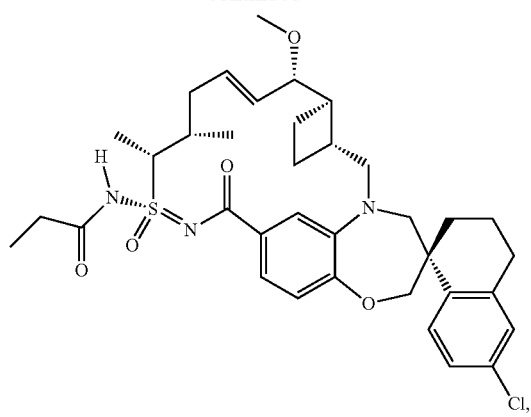
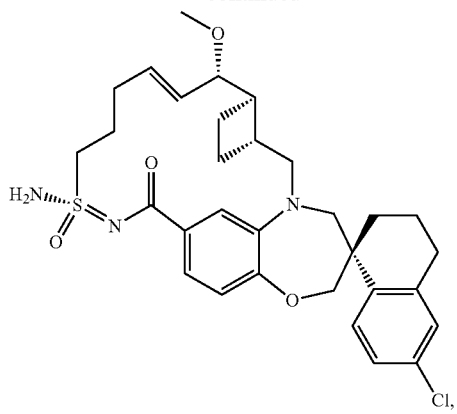

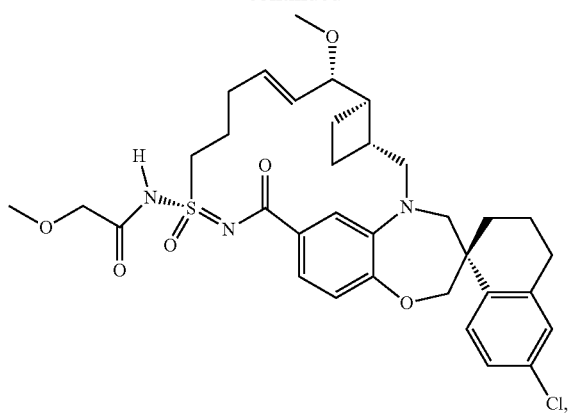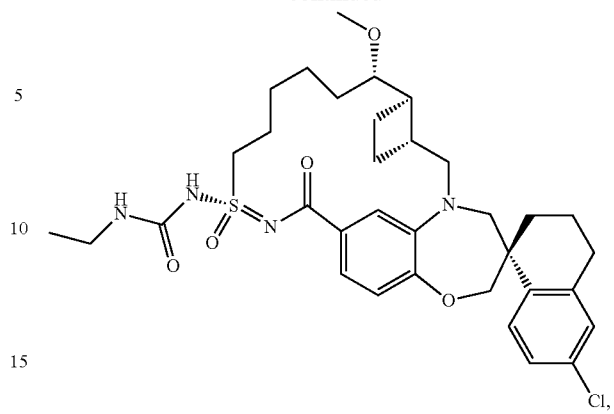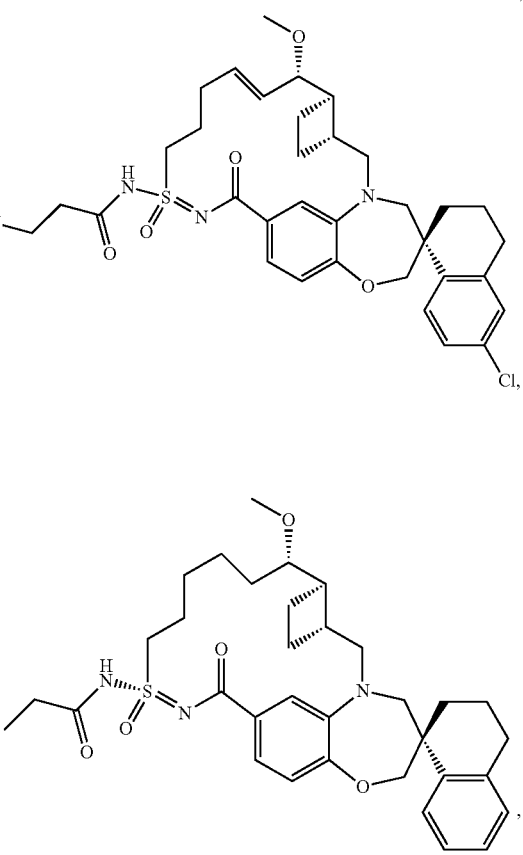

35
-continued
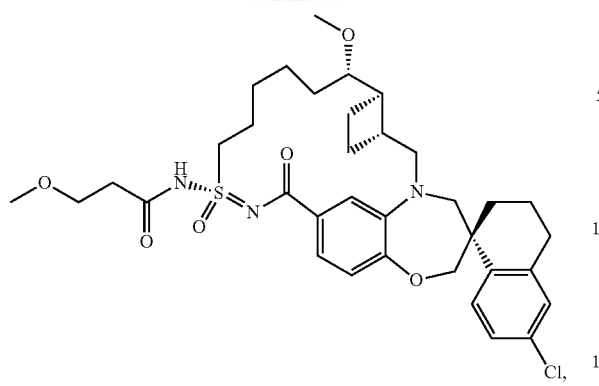
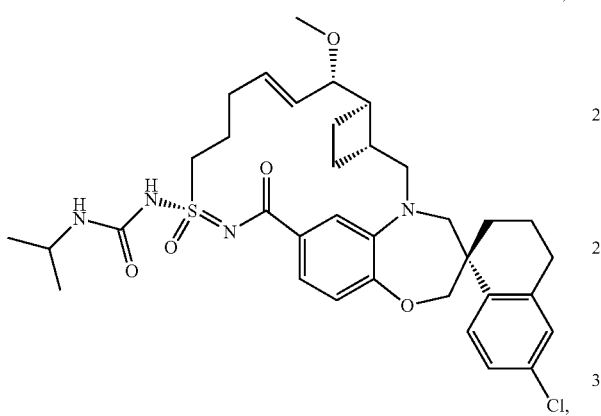
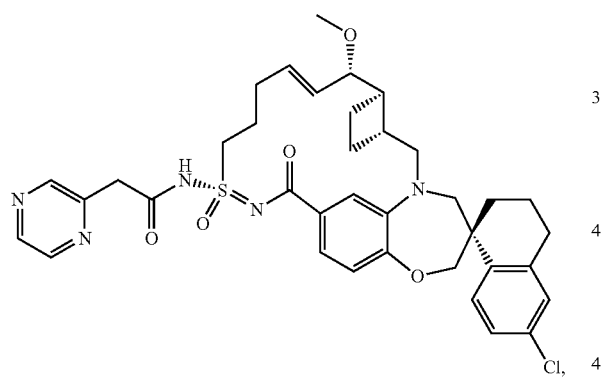
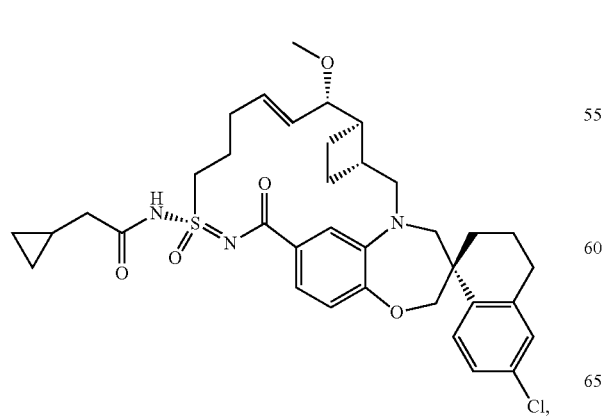
36
-continued
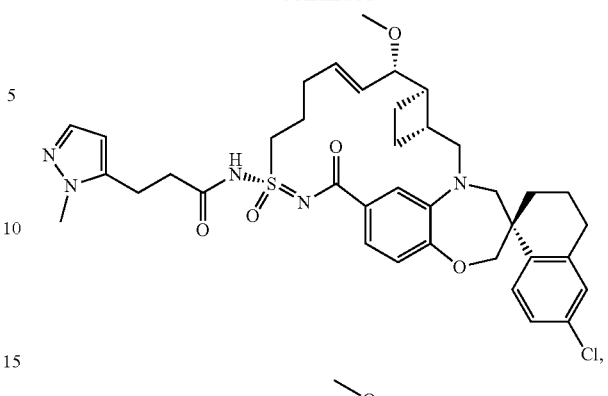
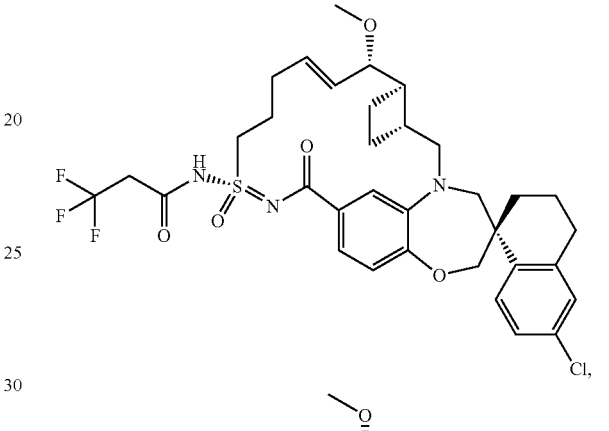
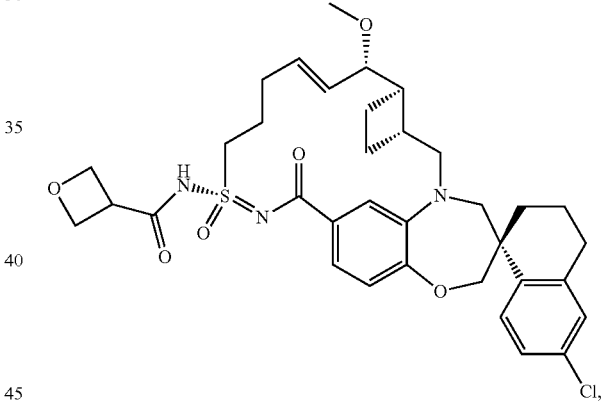
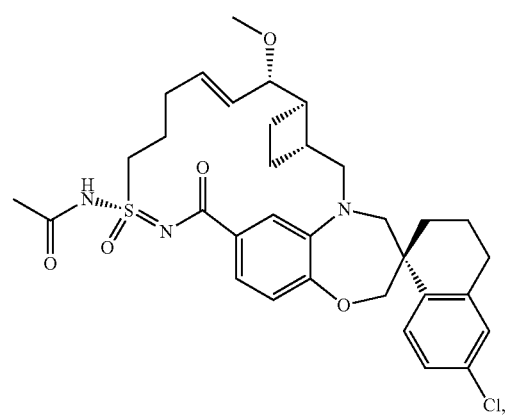

37
-continued
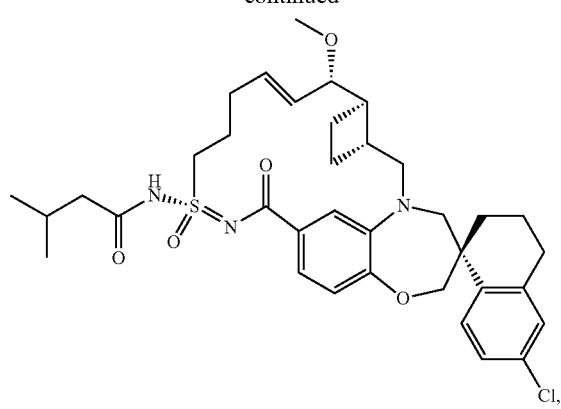
38
-continued
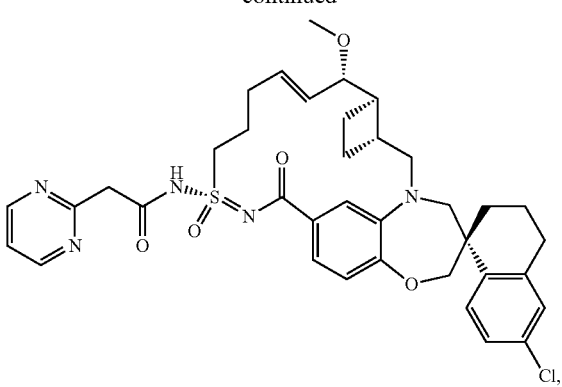
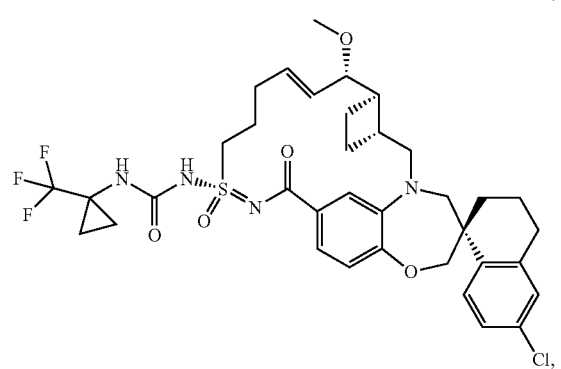
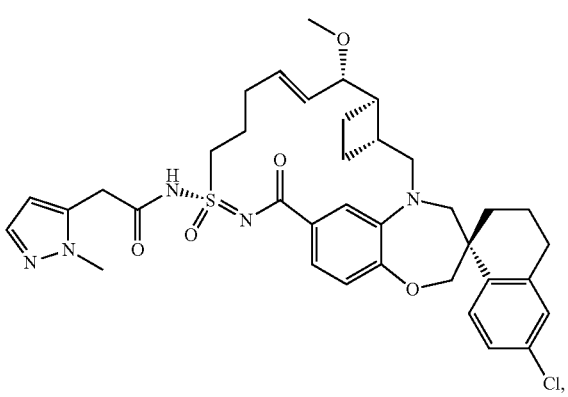

39
-continued
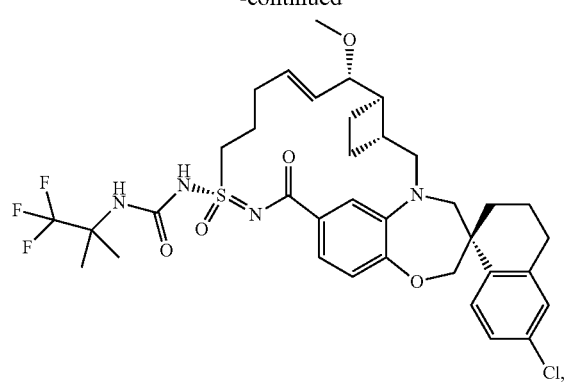
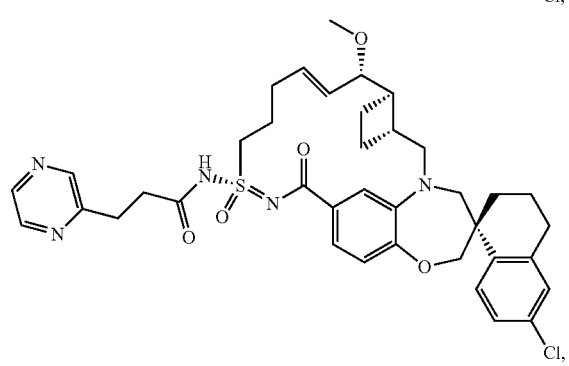
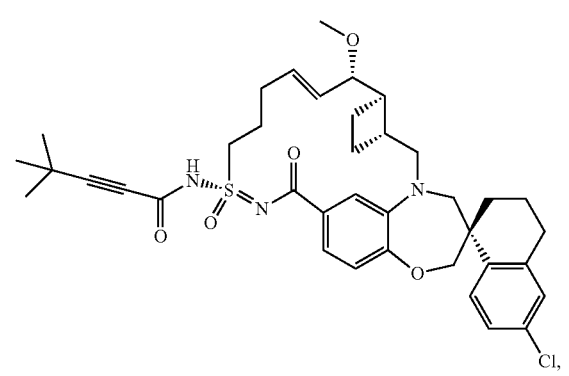
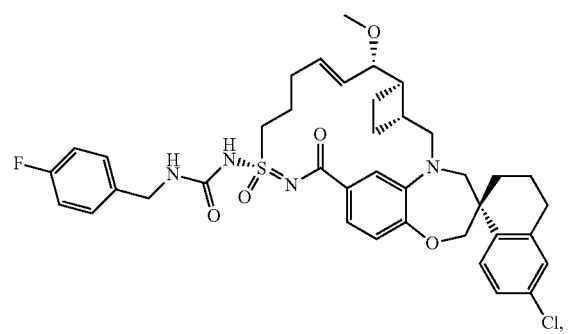
40
-continued
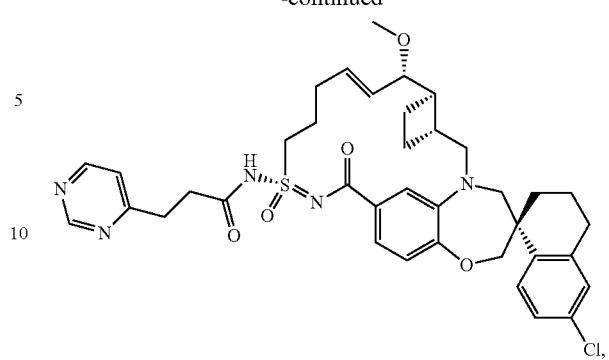
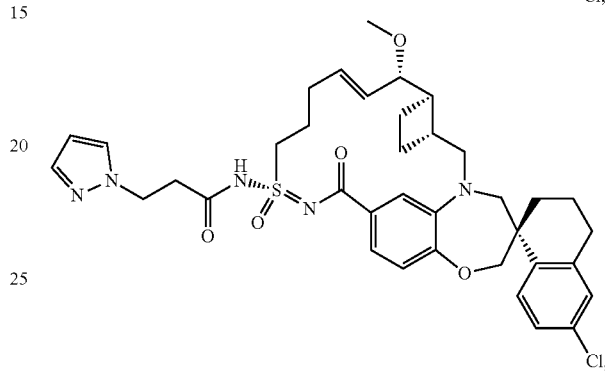
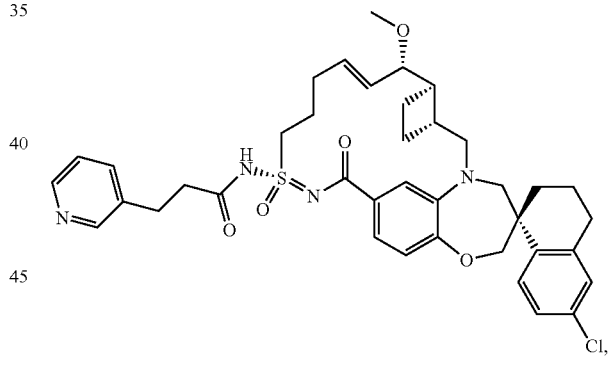
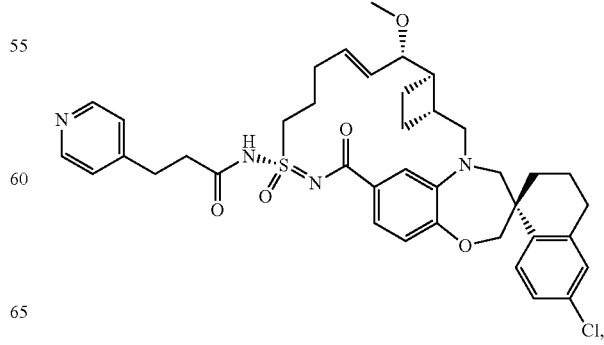

41
-continued
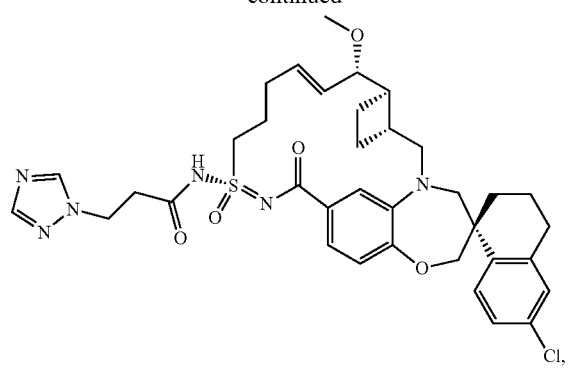
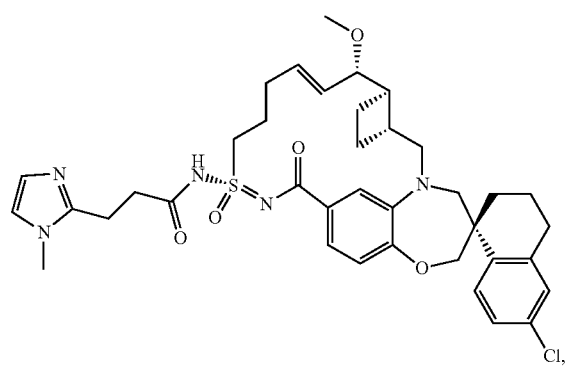
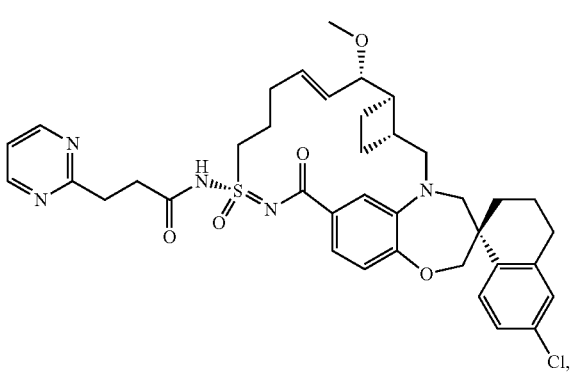
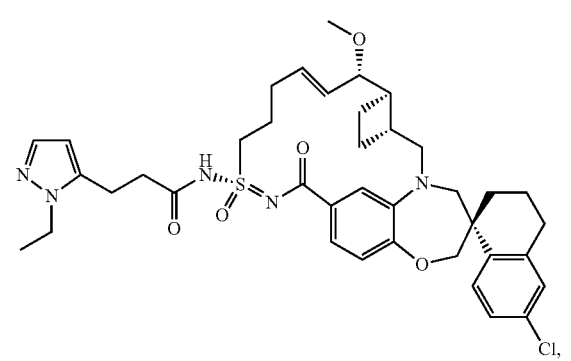
42
-continued
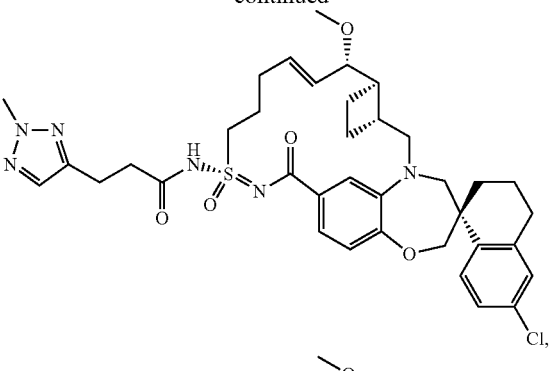

43 44
-continued -continued
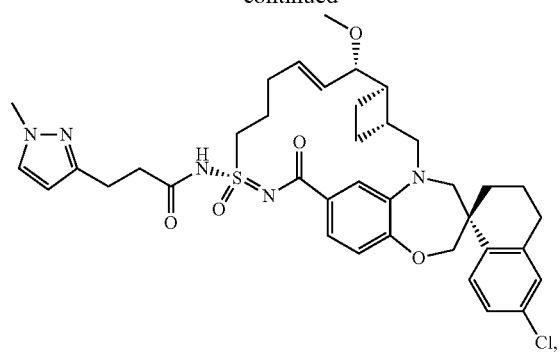
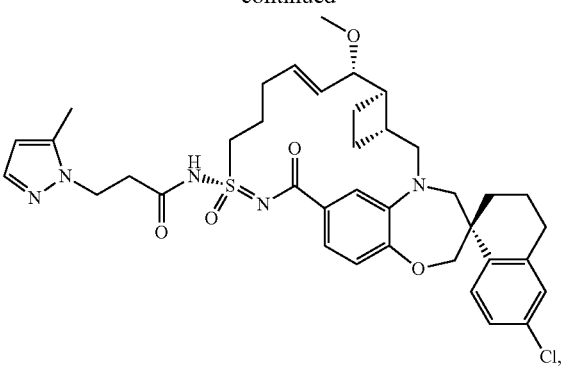

45
-continued
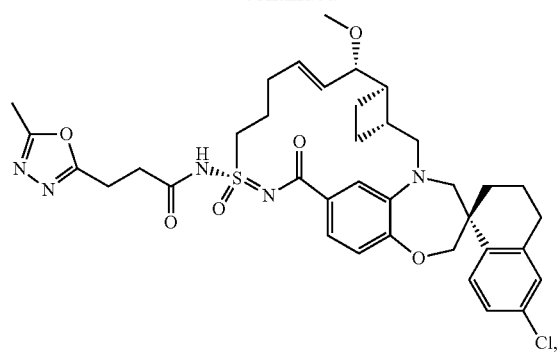
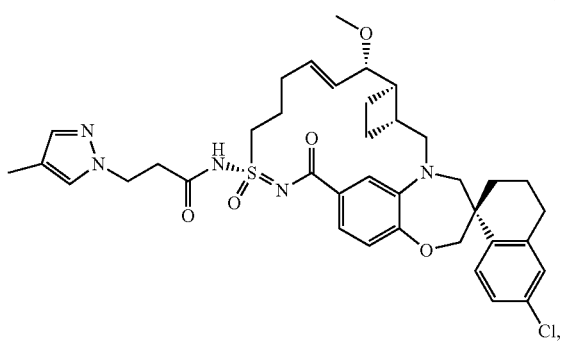
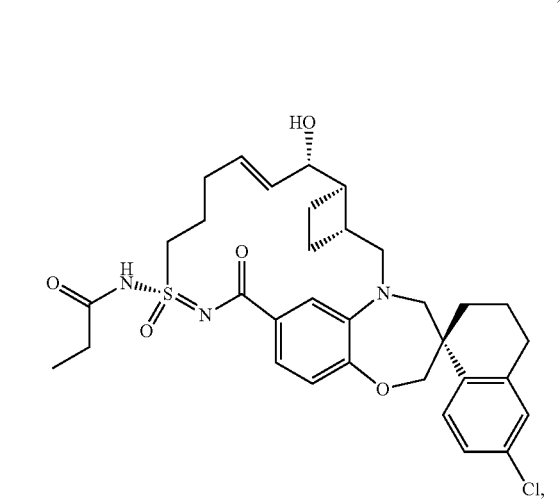
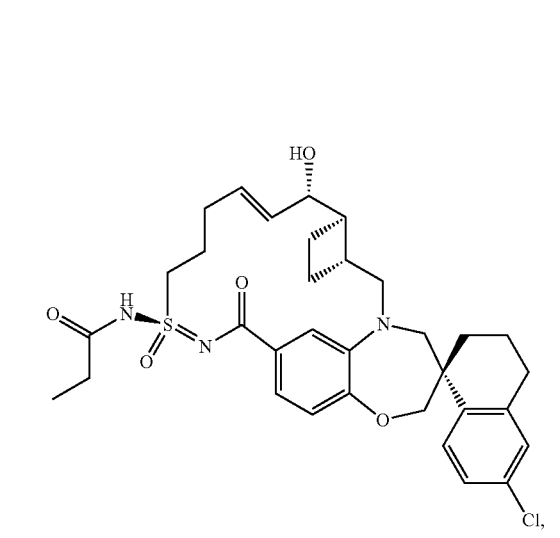
46
-continued
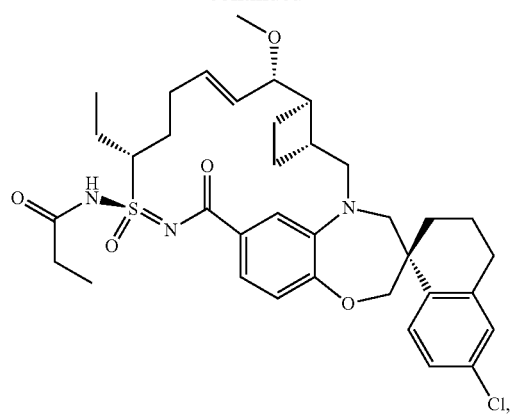
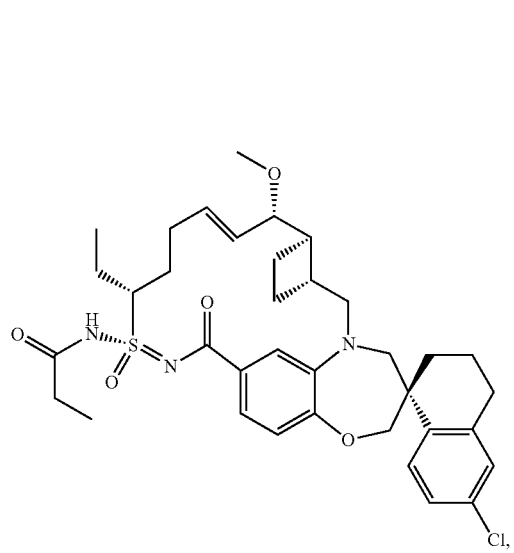
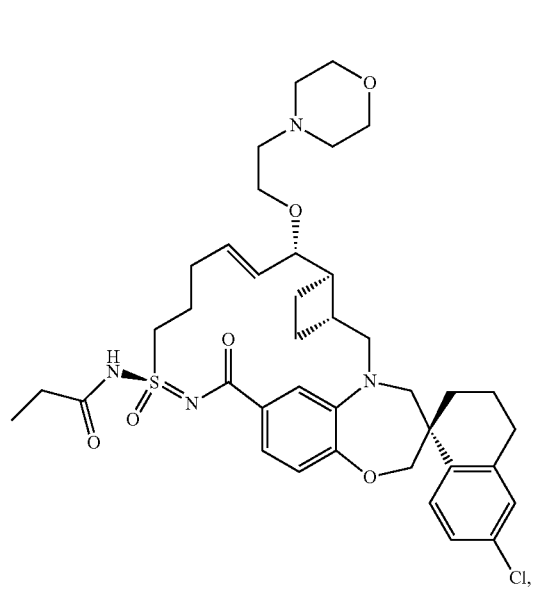

47
-continued
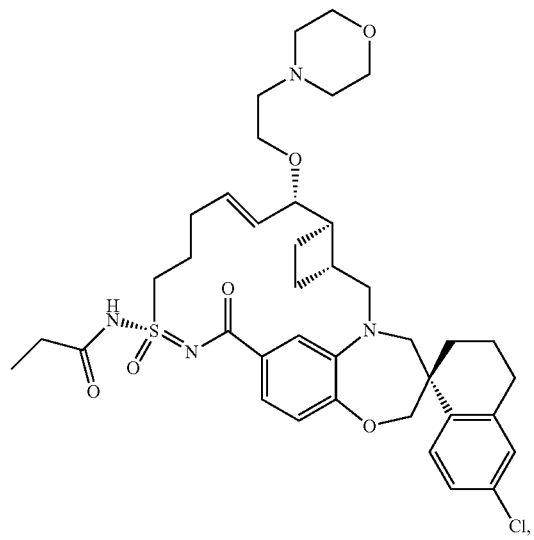
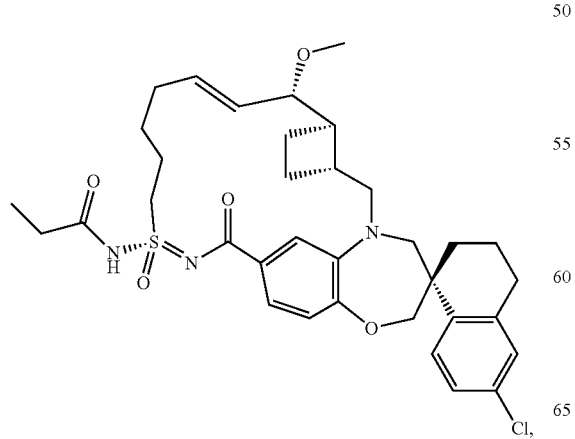
48
-continued
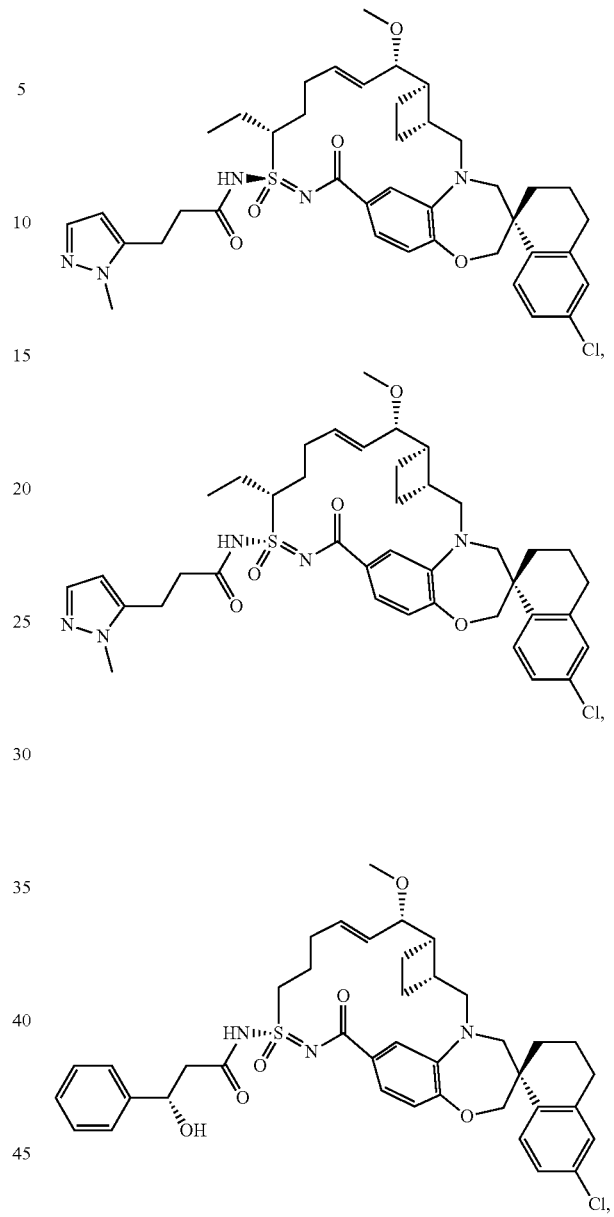

49
-continued
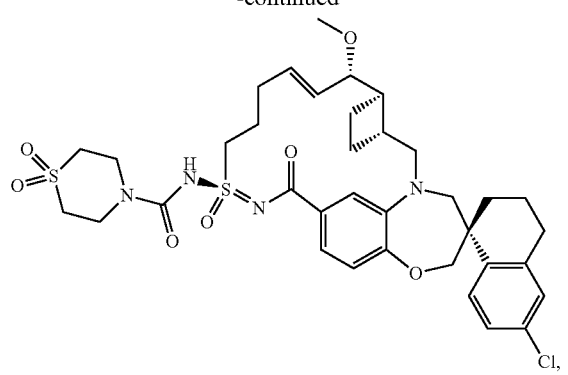
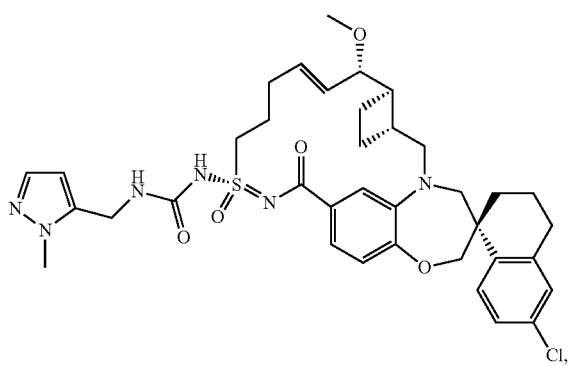
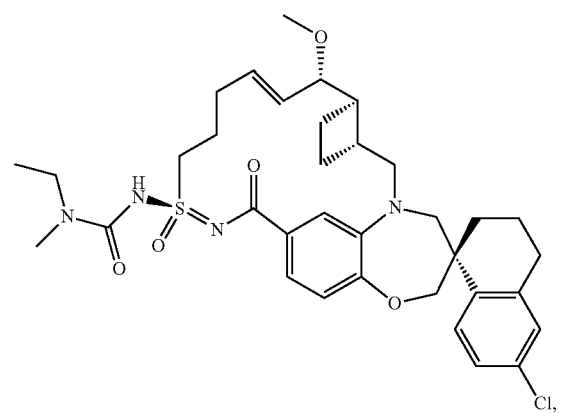
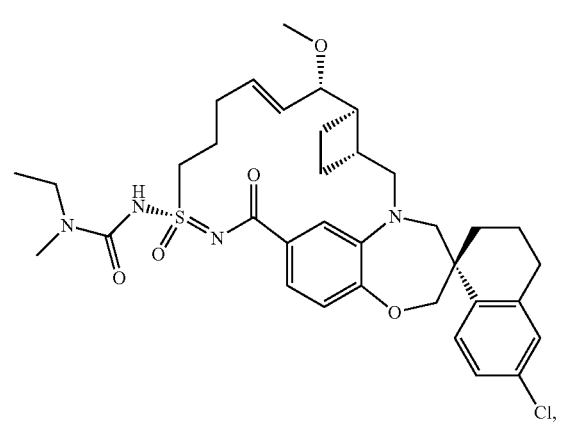
50
-continued
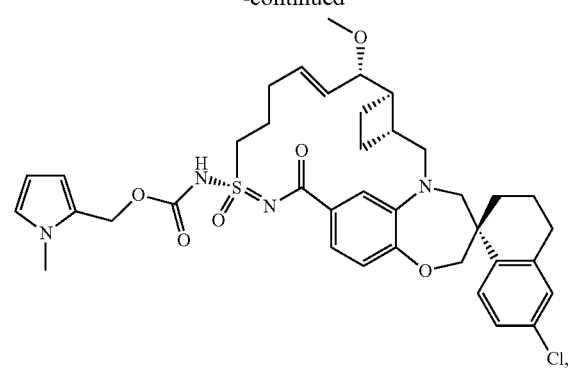
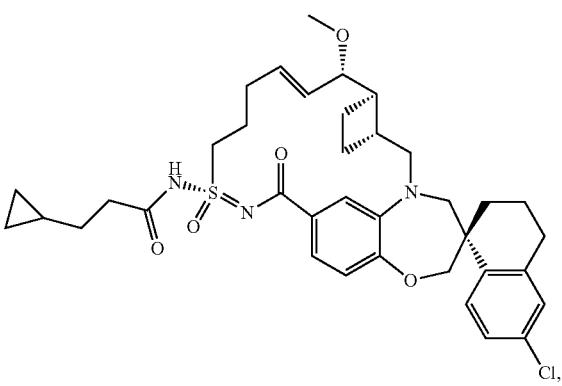

51
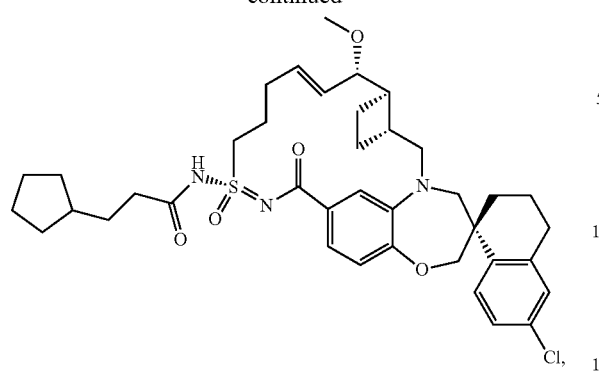
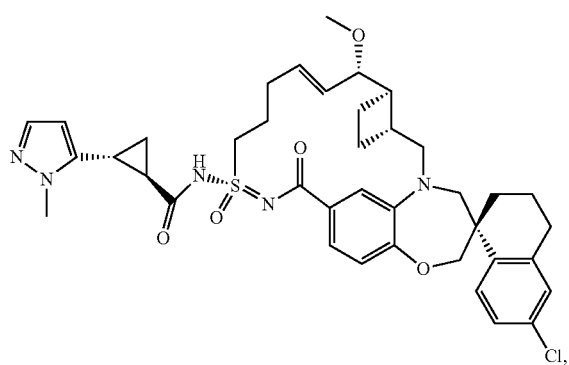
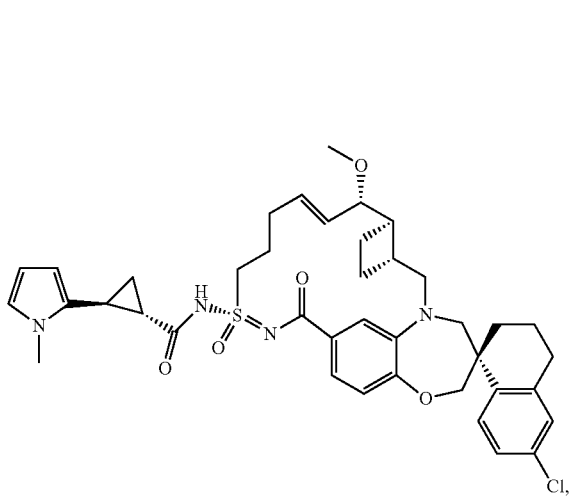
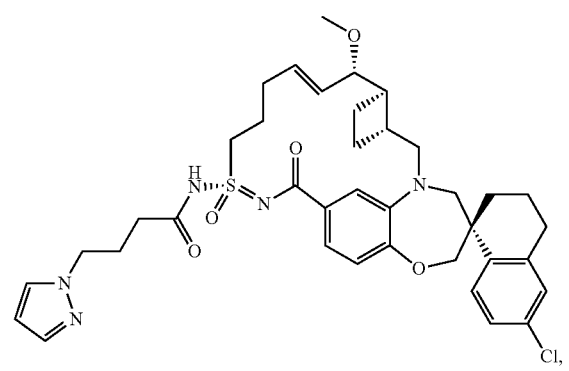
52
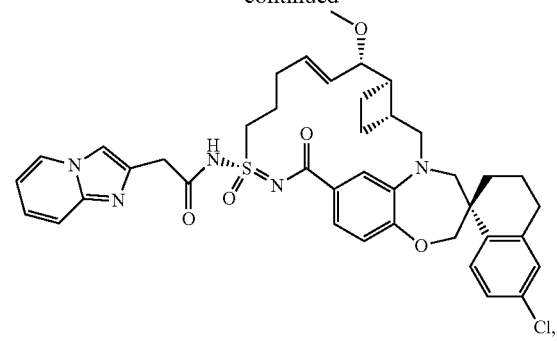
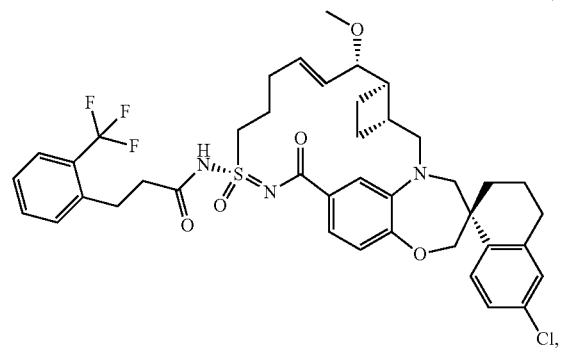
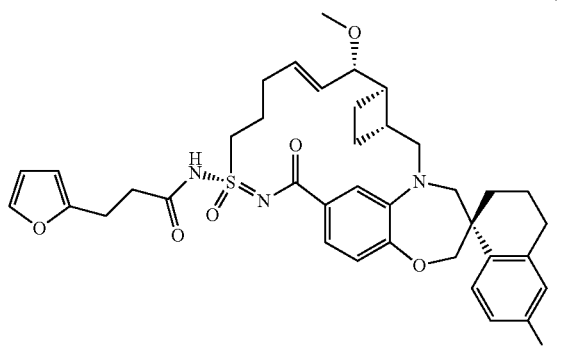
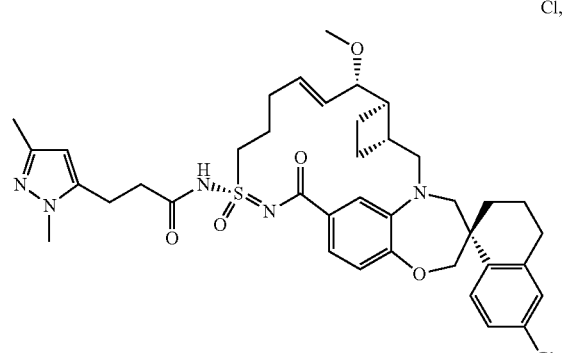
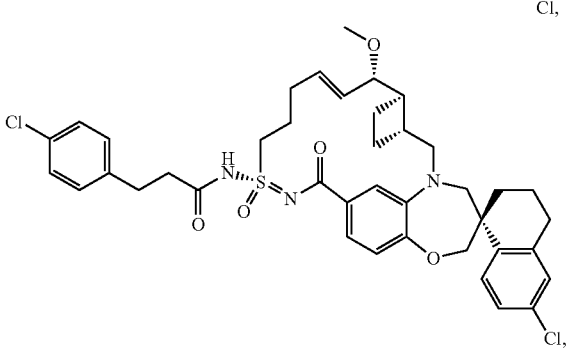

53
-continued
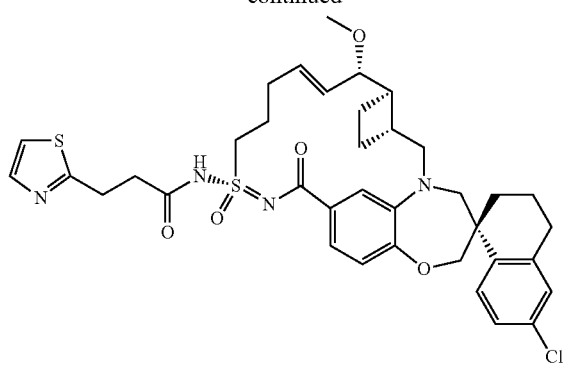
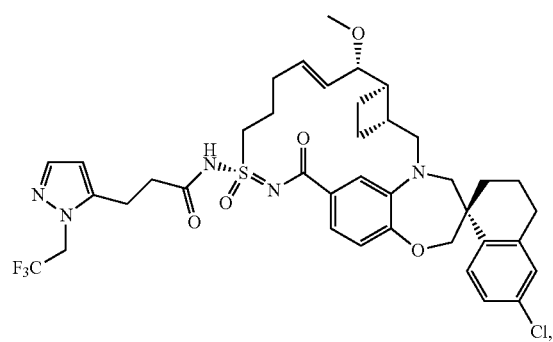
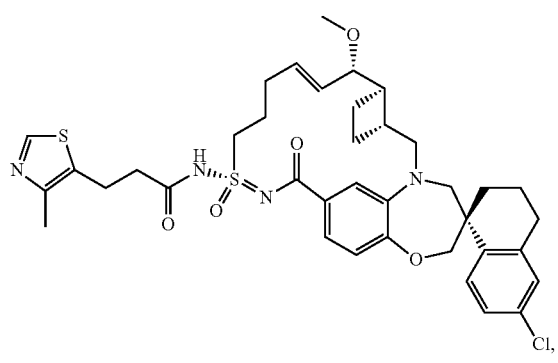
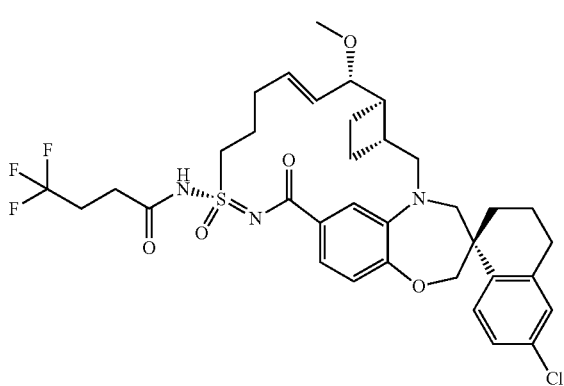
54
-continued
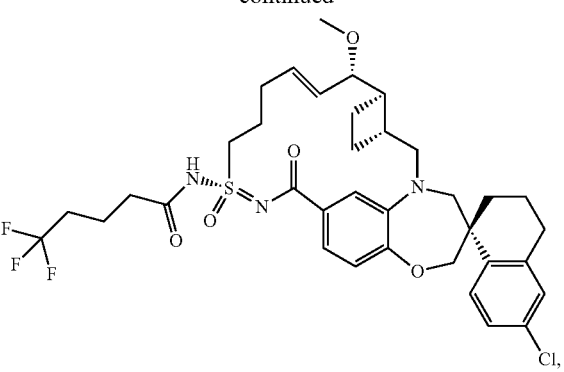
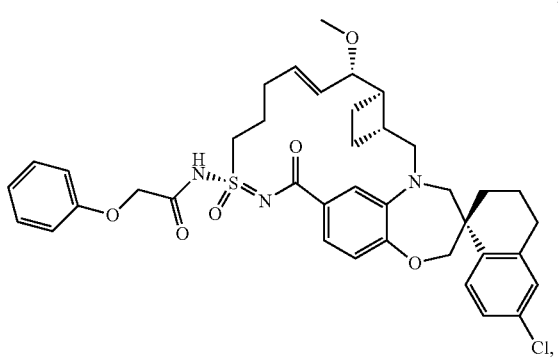
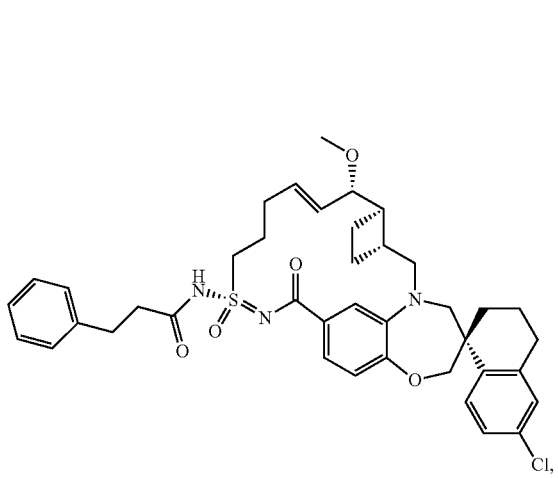
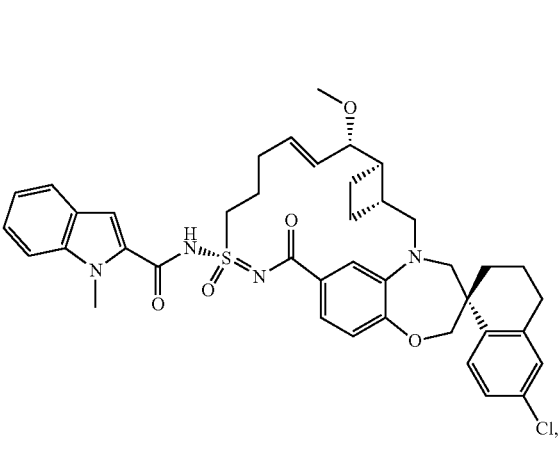

55
-continued
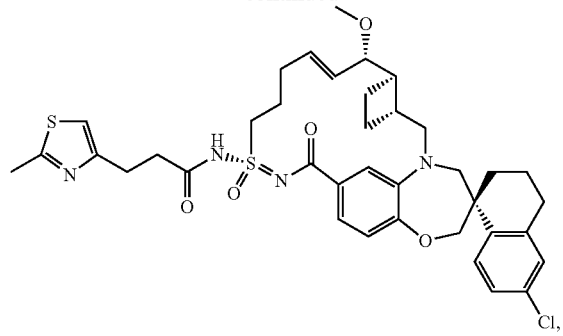
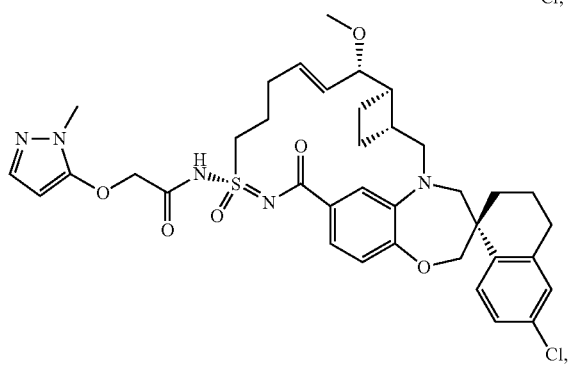
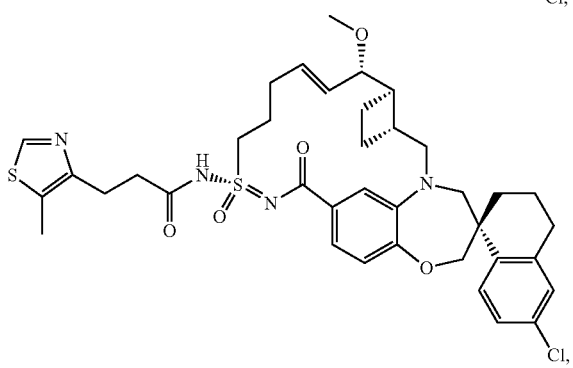
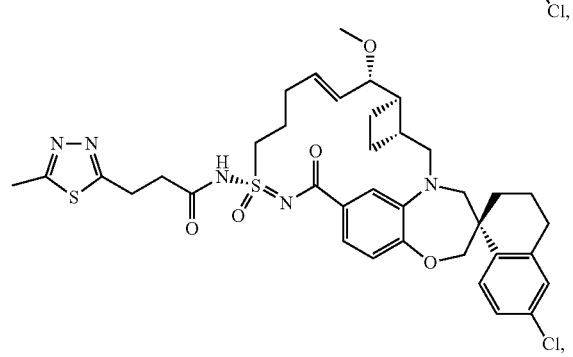
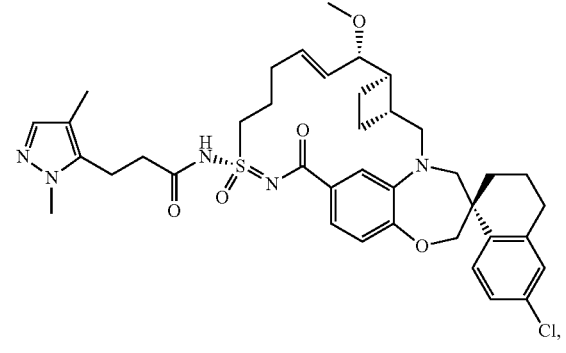
56
-continued
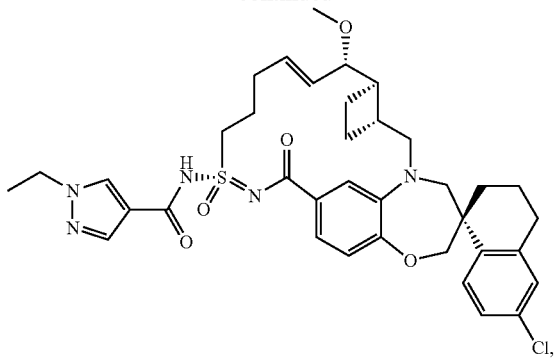
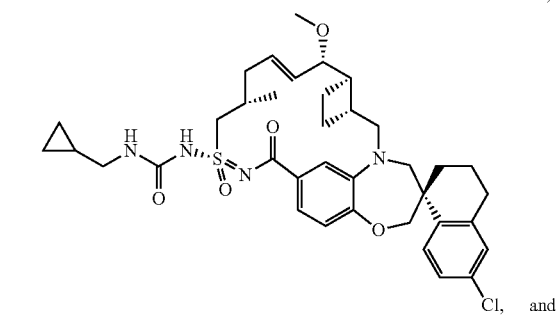
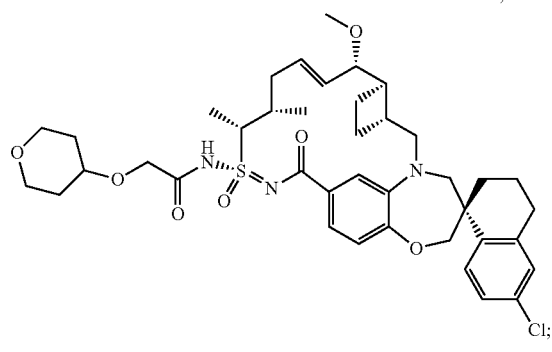
or a pharmaceutically acceptable salt thereof.

In some embodiments, the present disclosure provides a compound selected from:
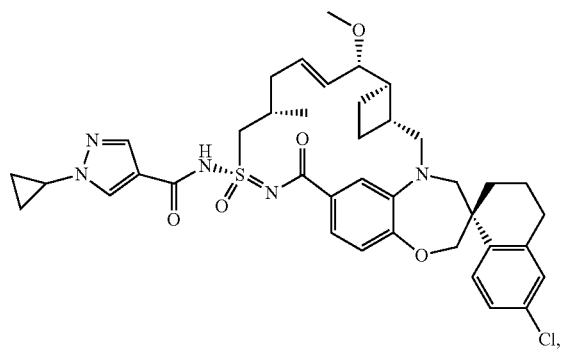
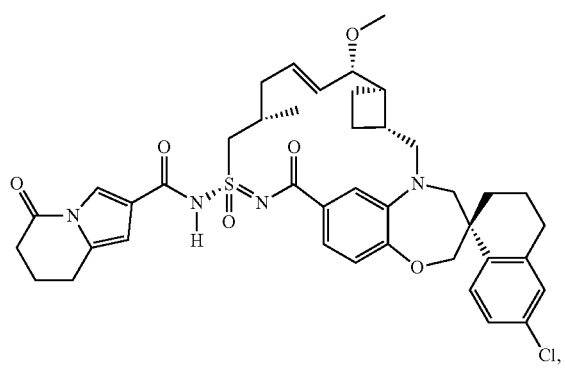
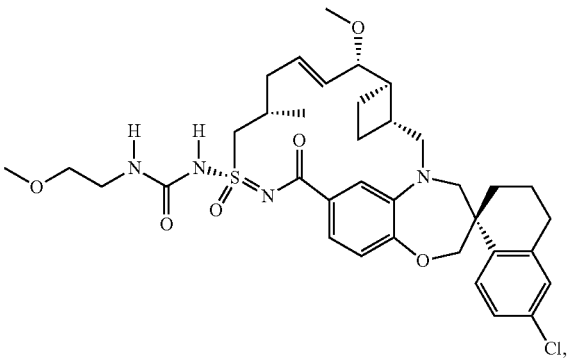
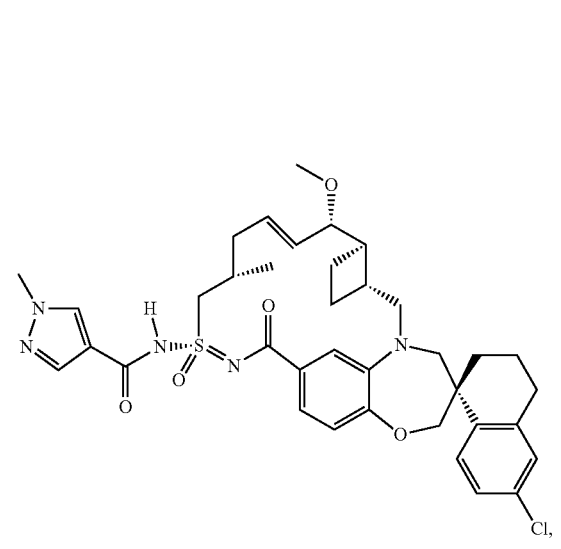
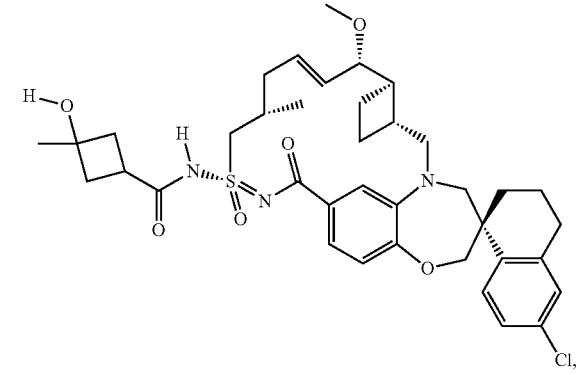
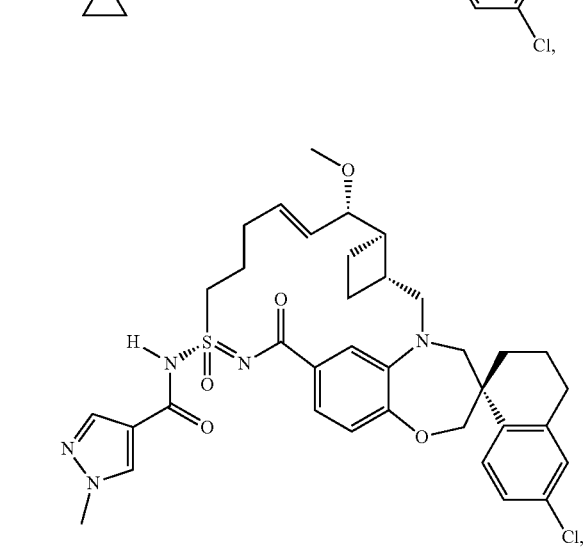
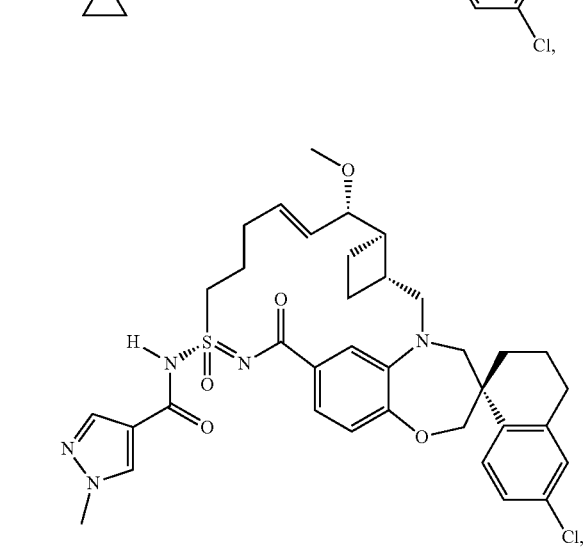

59
-continued
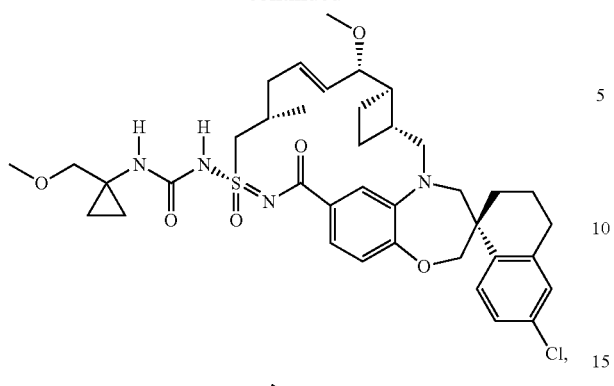
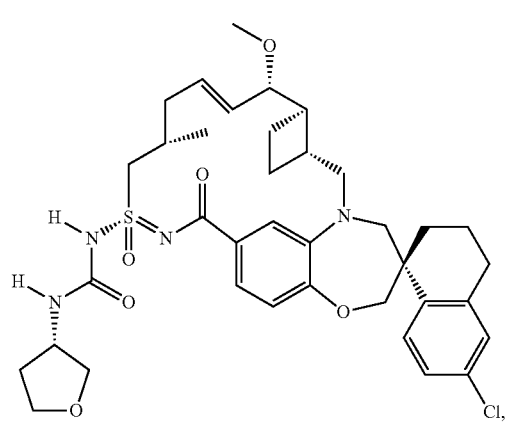
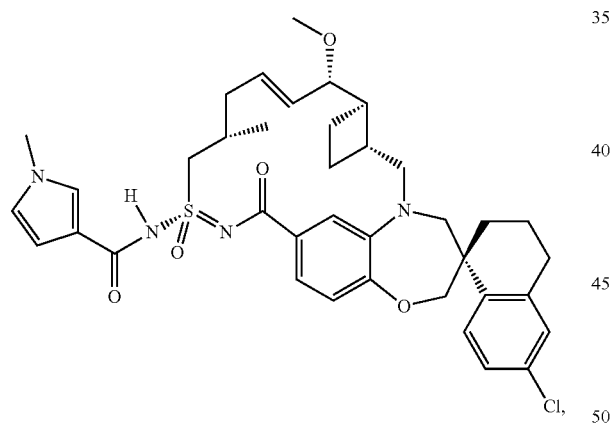
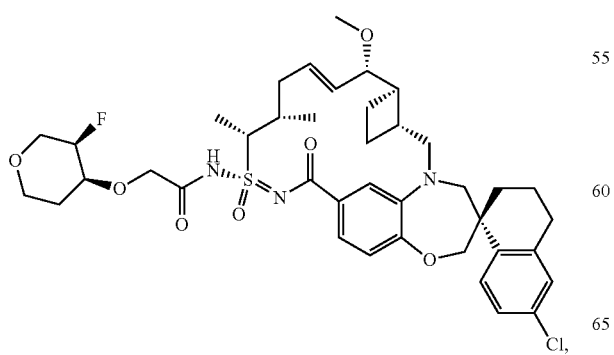
60
-continued
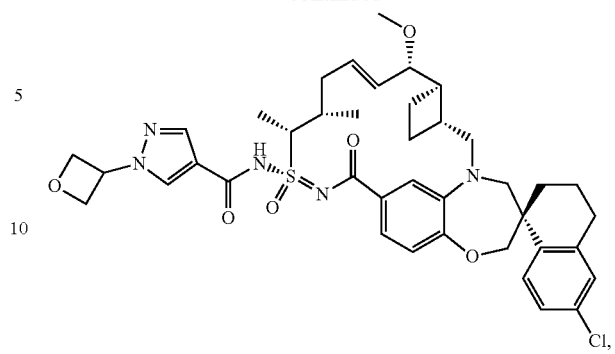
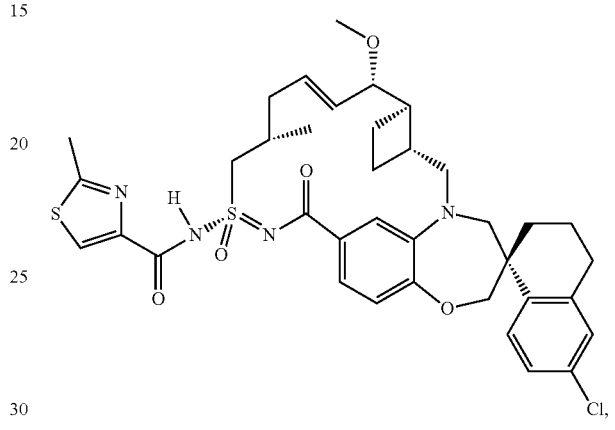
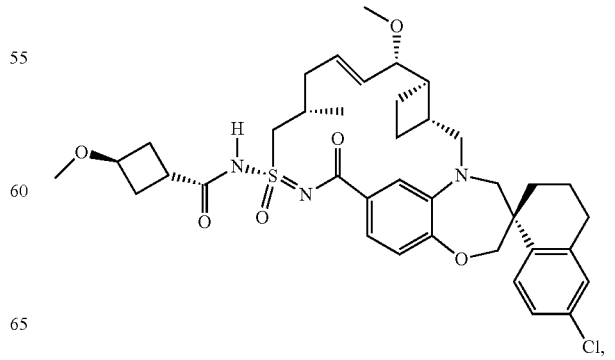

61
-continued
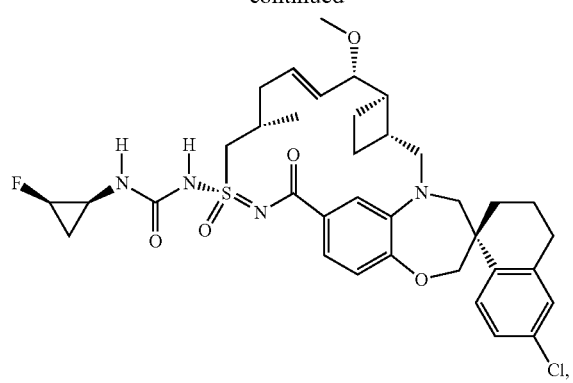
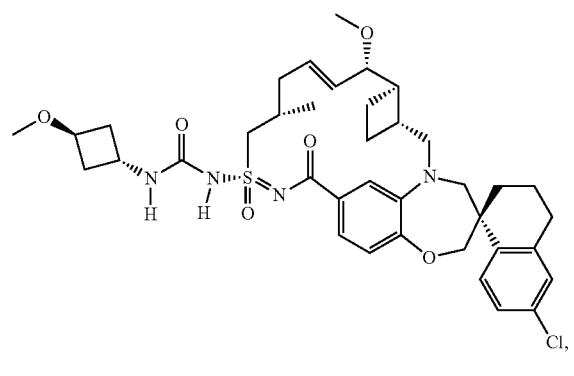
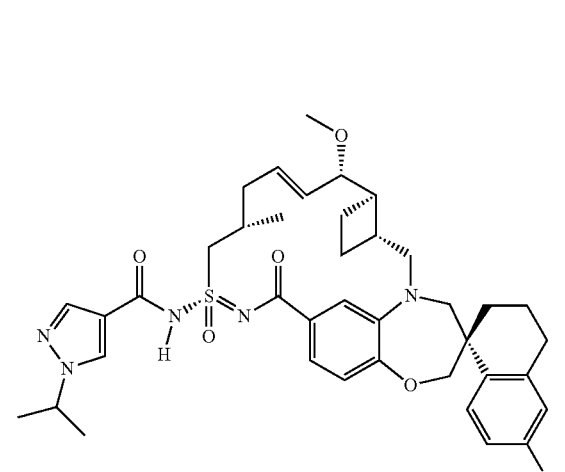
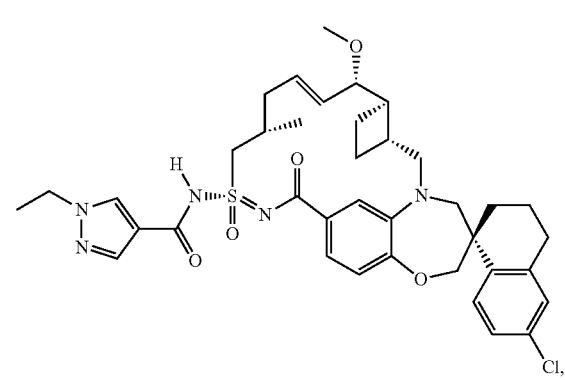
62
-continued
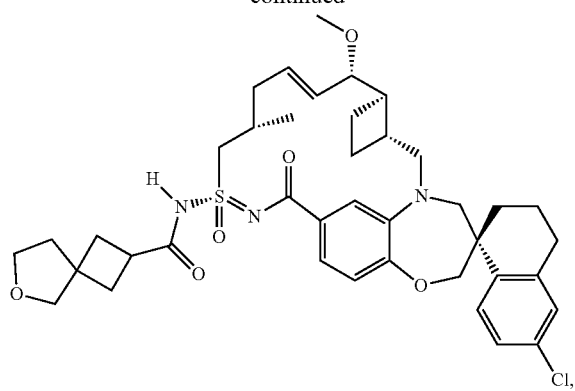
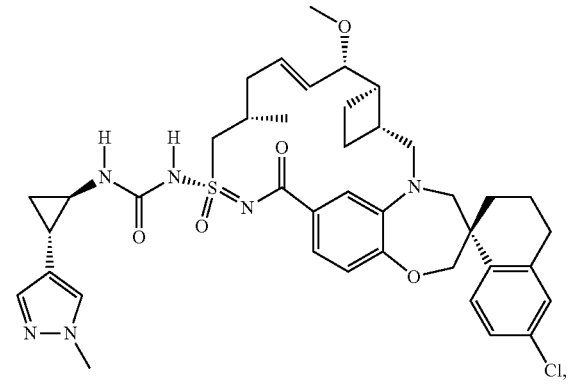
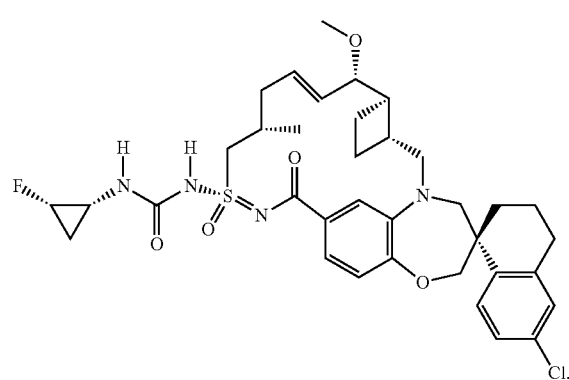
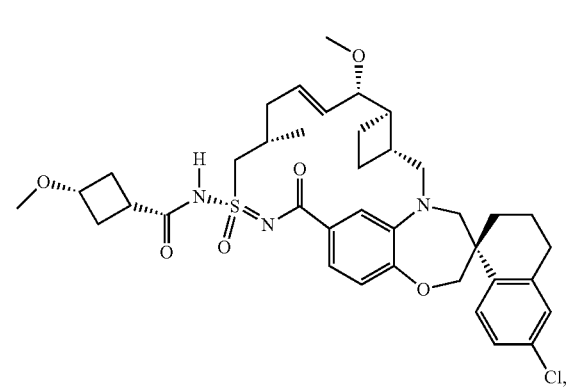

63
-continued
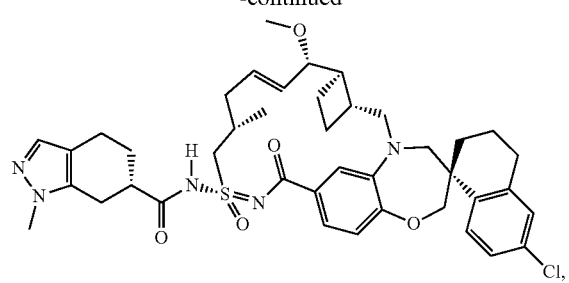
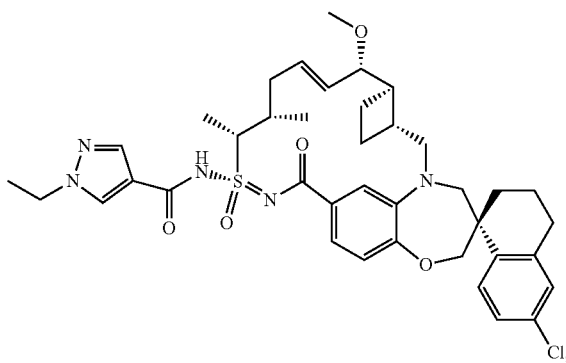
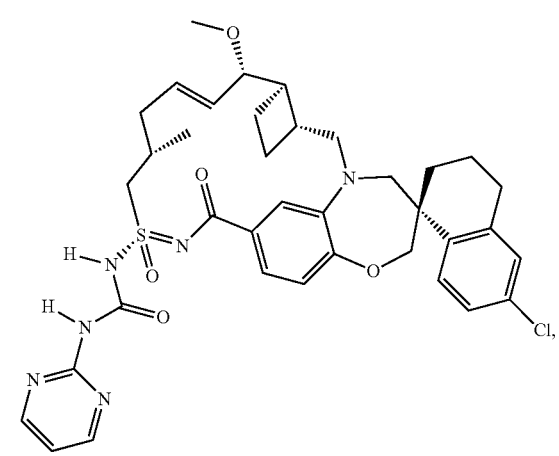
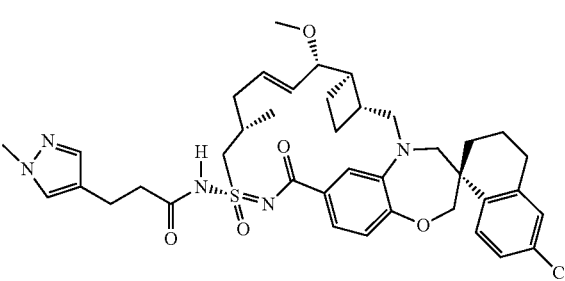
64
-continued
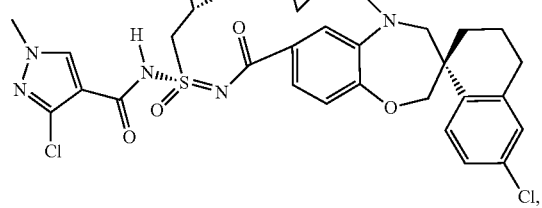
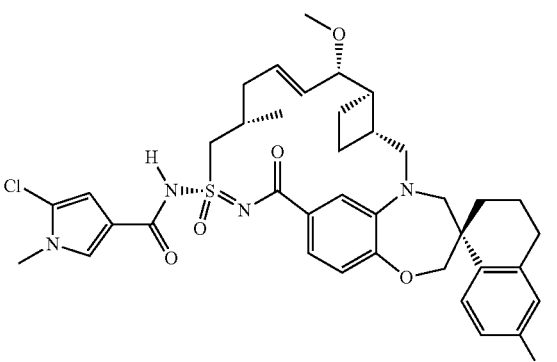
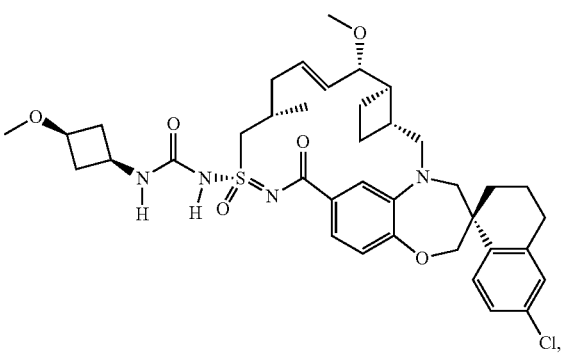
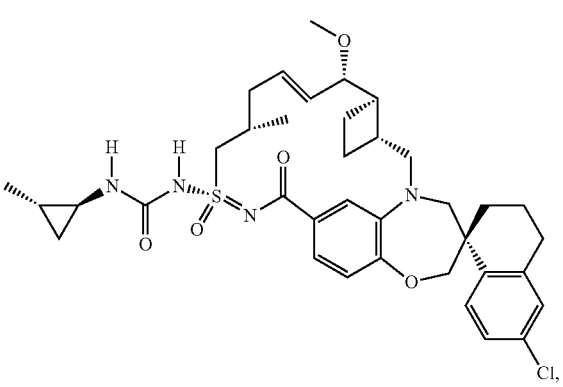

65
-continued
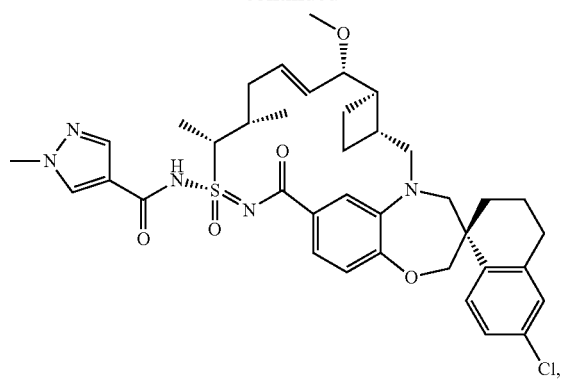
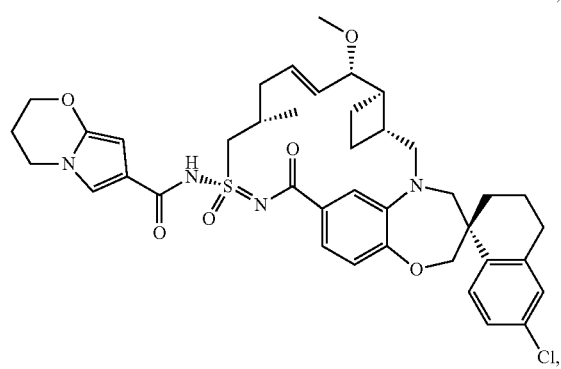
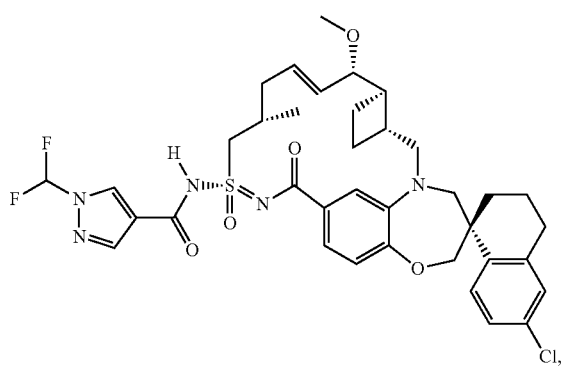
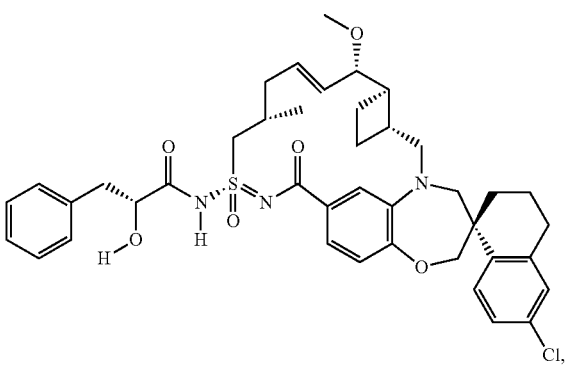
66
-continued
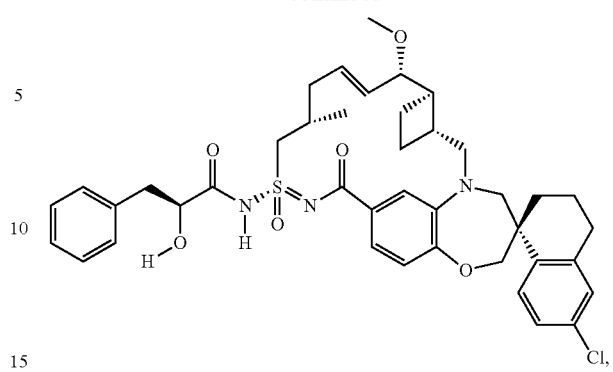
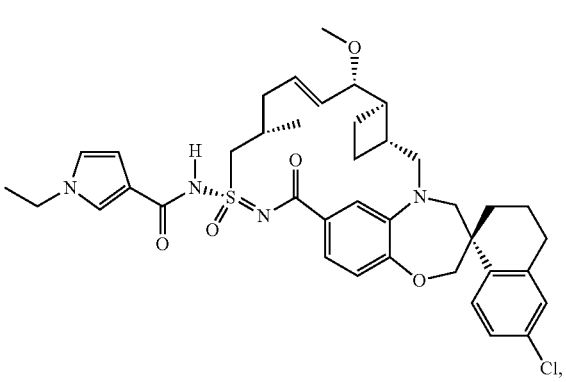

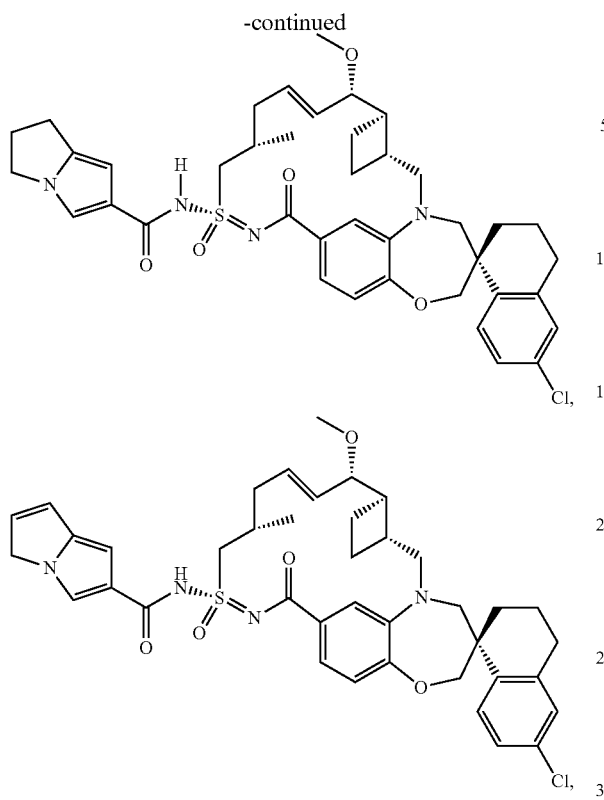
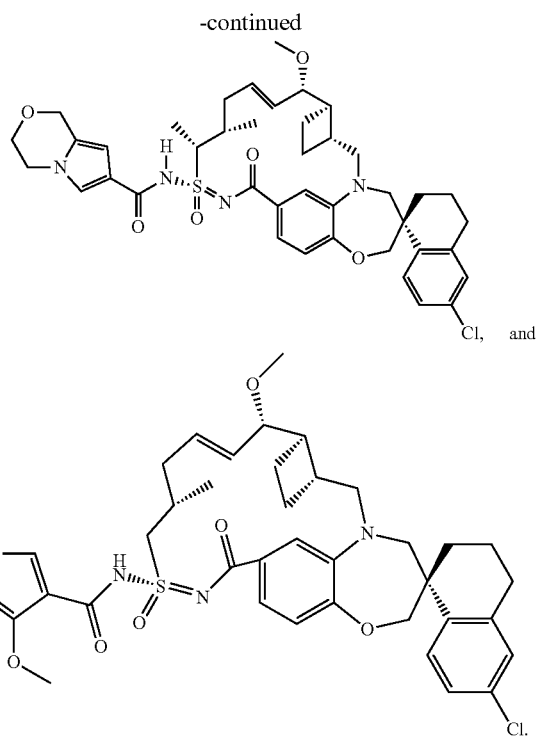
In some embodiments, the present disclosure provides a compound selected from:
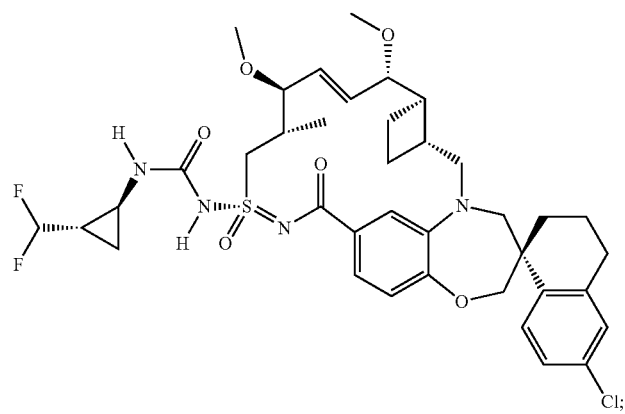
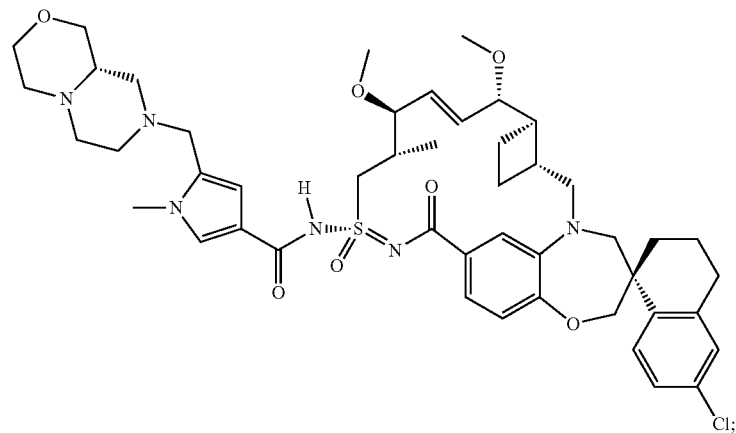

-continued
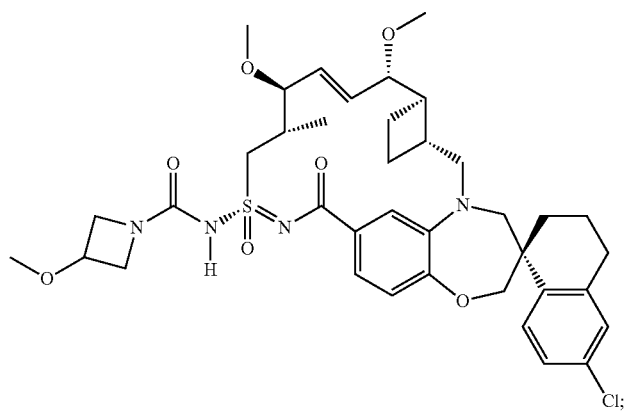
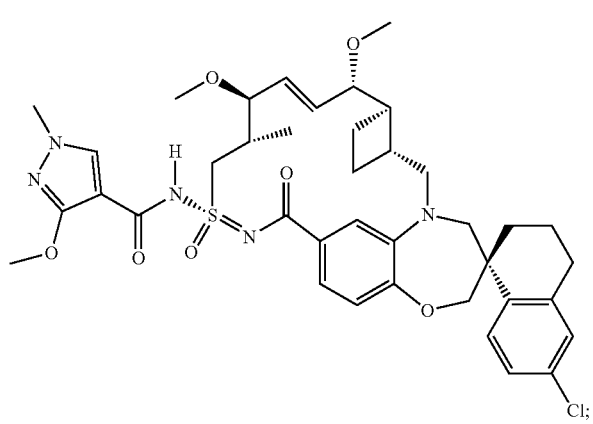
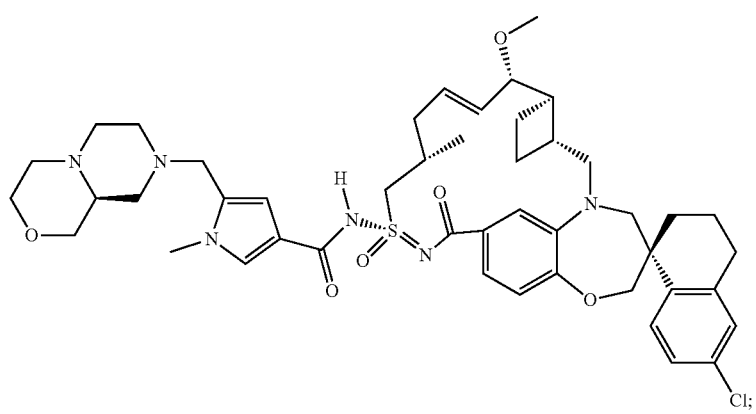
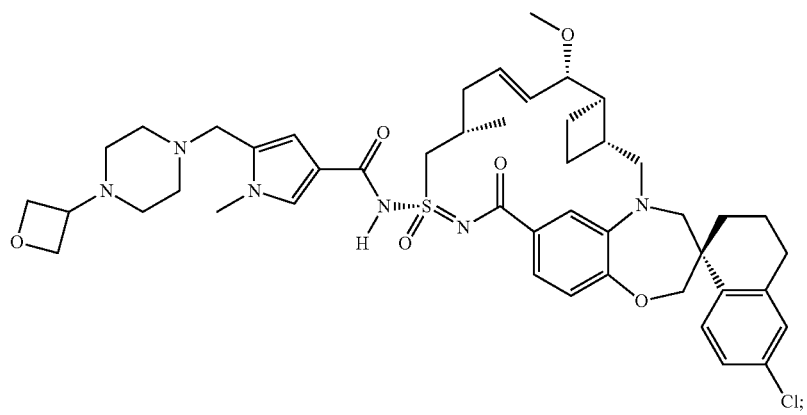

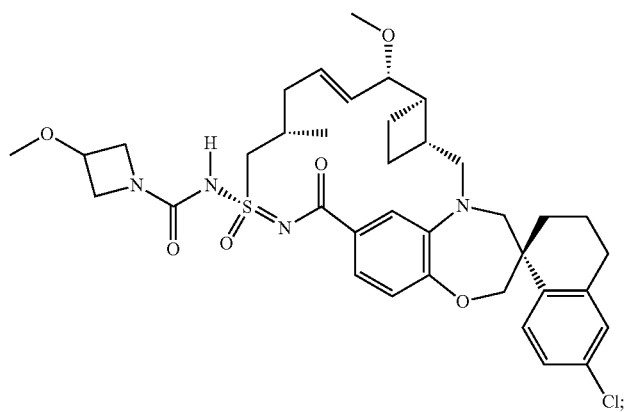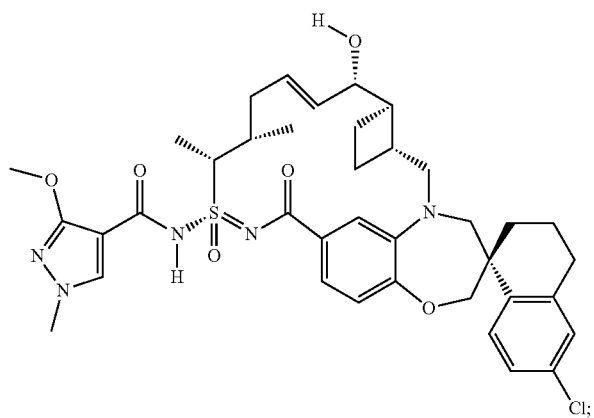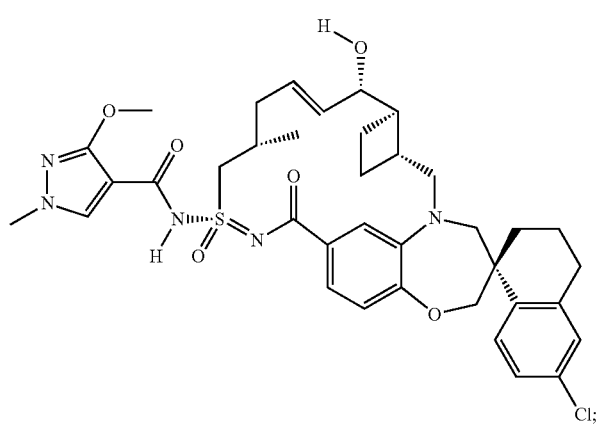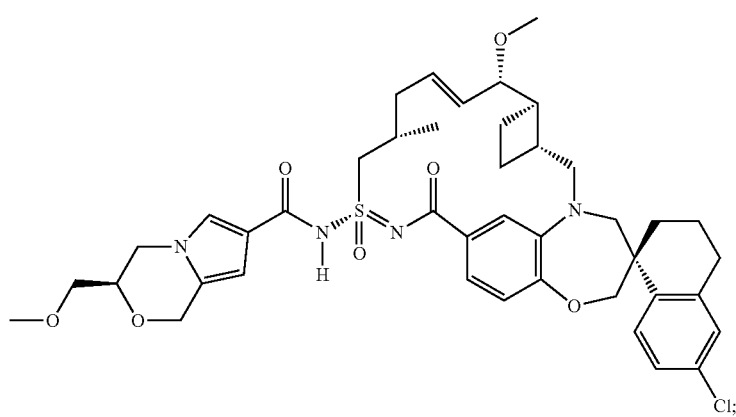

-continued
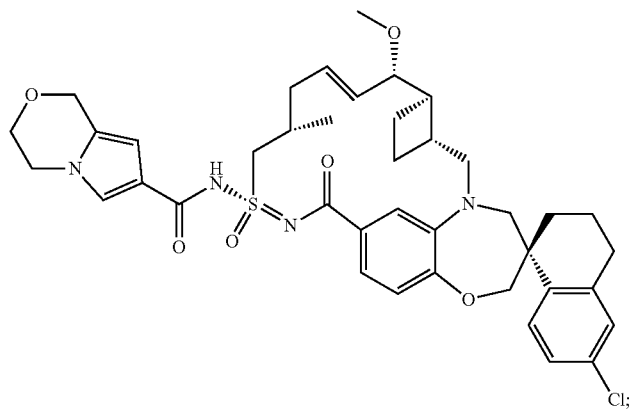
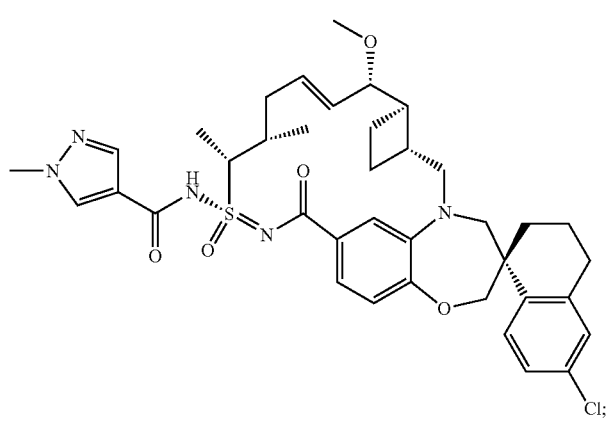
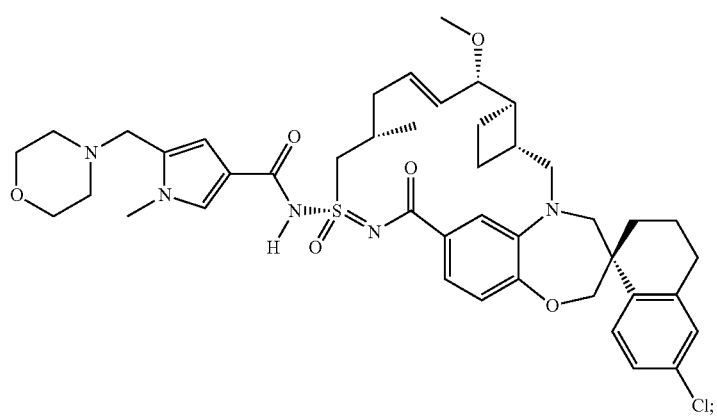
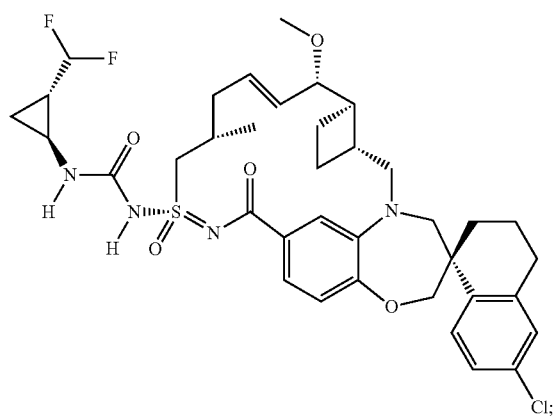

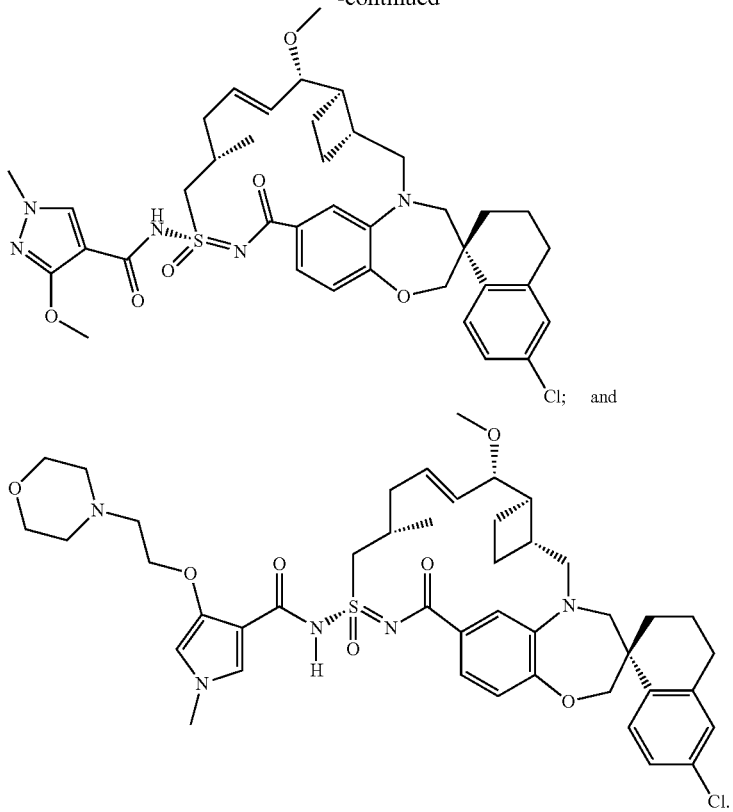

In some embodiments, isotopically labeled forms of the compounds of Formula (I), Formula (Ia), Formula (II), or Formula (IIa) are provided herein. In some embodiments, isotopically labeled forms of the compounds of Formula (I), Formula (Ia), Formula (II), Formula (IIa), Formula (III), Formula (IIIa), Formula (IIIb), Formula (IIIc), Formula (IIId), Formula (IV), or Formula (IVa), are provided herein. Isotopically labeled compounds have structures depicted by the formulas given herein except that one or more atoms are replaced by an isotope having a selected atomic mass or mass number. Isotopically labeled compounds have structures depicted by the formulas given herein except that one or more atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H, $^{13}$C and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The compounds disclosed herein may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Likewise, all tautomeric forms are also intended to be included.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents, as described in more detail below.

Pharmaceutical compositions comprising the compounds disclosed herein, or pharmaceutically acceptable salts thereof, may be prepared with one or more pharmaceutically acceptable excipients which may be selected in accord with ordinary practice. "Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In certain embodiments, pharmaceutical compositions are provided as a solid dosage form, including a solid oral dosage form, such as a tablet. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

Pharmaceutical compositions disclosed herein include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

Methods

In some embodiments, the present disclosure provides a method of inhibiting MCL-1. In some embodiments, the present disclosure provides a method of inhibiting MCL-1 in an individual (e.g., a human) comprising administering a compound of Formula (I), or a tautomer or pharmaceutically acceptable salt thereof, to the individual.

In some embodiments, the present disclosure provides a method of treating or preventing cancer. In certain embodiments, the present disclosure provides a method of treating or preventing cancer comprising administering to a patient a therapeutically effective amount a compound of Formula (I), or a tautomer or pharmaceutically acceptable salt thereof, to the individual. In some embodiments, the cancer is a hematologic malignancy. In some embodiments, the cancer is multiple myeloma. In some embodiments, the cancer is selected from the group consisting of breast cancer, colorectal cancer, skin cancer, melanoma, ovarian cancer, kidney cancer, small cell lung cancer, non-small cell lung cancer, lymphoma, and leukemia.

Compounds disclosed herein can be administered by any route appropriate for use in a method described herein. Suitable routes include oral, rectal, nasal, topical (including buccal and sublingual), transdermal, vaginal and parenteral (including subcutaneous, intramuscular, intravenous, intradermal, intrathecal and epidural), and the like.

Compounds disclosed herein may be administered to an individual in accordance with an effective dosing regimen for a desired period of time or duration, such as at least one week, at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

Therapeutically effective amounts of compounds disclosed herein are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 0.3 µg to about 30 mg per day.

A compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, may be combined with one or more additional therapeutic agents in any dosage amount of the compound of the present disclosure (e.g., from 1 mg to 1000 mg of compound). Therapeutically effective amounts of the compound of Formula (I), Formula (Ia), Formula (II), or Formula (IIa), or a tautomer or pharmaceutically acceptable salt thereof, can range from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I), Formula (Ia), Formula (II), or Formula (IIa) are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I), Formula (Ia), Formula (II), or Formula (IIa) are about 100 mg per dose, or about 125, 150, 175, 200, 225, 250, 275, 300, 350, 400, 450, or about 500 mg per dose.

Therapeutically effective amounts of the compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, can range from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I), Formula (Ia), Formula (II), Formula (IIa), Formula (III), Formula (IIIa), Formula (IIIb), Formula (IIIc), Formula (IIId), Formula (IV), or Formula (IVa), are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I), Formula (Ia), Formula (II), Formula (IIa), Formula (III), Formula (IIIa), Formula (IIIb), Formula (IIIc), Formula (IIId), Formula (IV), or Formula (IVa), are about 100 mg per dose, or about 125, 150, 175, 200, 225, 250, 275, 300, 350, 400, 450, or about 500 mg per dose.

A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of a compound disclosed herein will be determined by the needs of the individual patient and can be, for example, once per day or twice, or more times, per day. Administration of a compound continues for as long as necessary to treat cancer. For example, a compound disclosed herein can be administered to a human having cancer for a period of from 20 days to 180 days or, for example, for a period of from 20 days to 90 days or, for example, for a period of from 30 days to 60 days.

Administration can be intermittent, with a period of several or more days during which a patient receives a daily dose of a compound disclosed herein, followed by a period of several or more days during which a patient does not receive a daily dose of the compound. For example, a patient can receive a dose of a compound every other day, or three times per week. Again by way of non-limiting example, a patient can receive a dose of a compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

Combination Therapy

Also provided are methods of treatment in which a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, is given to a patient in combination with one or more additional active agents or therapy.

Thus in one embodiment, a method of treating cancer and/or diseases or symptoms that co-present or are exacerbated or triggered by the cancer e.g., an allergic disorder and/or an autoimmune and/or inflammatory disease, and/or an acute inflammatory reaction, comprises administering to a patient in need thereof an effective amount of a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, optionally in combination with an additional agent (e.g., a second, third, fourth or fifth active agent) that can be useful for treating a cancer, an allergic disorder and/or an autoimmune and/or inflammatory disease, and/or an acute inflammatory reaction incident to or co-presenting with a cancer. Treatment with the second, third, fourth or fifth active agent may be prior to, concomitant with, or following treatment with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof. In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is combined with another active agent in a single dosage form. Suitable antitumor or anticancer therapeutics that may be used in combination with a compound of Formula (I), Formula (Ia), Formula (II), or Formula (IIa), Formula (III), Formula (IIIa), Formula (IIIb), Formula (IIIc), Formula (IIId), Formula (IV), or Formula (IVa), or a tautomer or pharmaceutically acceptable salt thereof include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

A compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof can be useful as chemo-sensitizing agents, and thus, can be useful in combination with other chemotherapeutic drugs, in particular, drugs that induce apoptosis. Thus, in one embodiment, the present disclosure provides a method for increasing sensitivity of cancer cells to chemotherapy, comprising administering to a patient in need of or undergoing chemotherapy, a chemotherapeutic agent together with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof in an amount sufficient to increase the sensitivity of cancer cells to the chemotherapeutic agent.

Examples of other chemotherapeutic drugs that can be used in combination with compounds of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof include topoisomerase I inhibitors (camptothesin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

In some embodiments, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is used in combination with Rituxan® (Rituximab) and/or other agents that work by selectively depleting CD20+ B-cells.

Included herein are methods of treatment in which a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone. In some embodiments, the anti-inflammatory therapeutic agent is a gold compound such as gold sodium thiomalate or auranofin. In some embodiments, the anti-inflammatory agent is a metabolic inhibitor such as a dihydrofolate reductase inhibitor, such as methotrexate or a dihydroorotate dehydrogenase inhibitor, such as leflunomide.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is used in combination with at least one anti-inflammatory compound that is an anti-C5 monoclonal antibody (such as eculizumab or pexelizumab), a TNF antagonist, such as entanercept, or infliximab, which is an anti-TNF alpha monoclonal antibody.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is used in combination with at least one active agent that is an immunosuppressant compound such as methotrexate, leflunomide, cyclosporine, tacrolimus, azathioprine, or mycophenolate mofetil.

In other embodiments, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is used in combination with one or more phosphatidylinositol 3-kinase (PI3K) inhibitors, including for example, Compounds A, B and C (whose structures are provided below), or a pharmaceutically acceptable salt thereof.

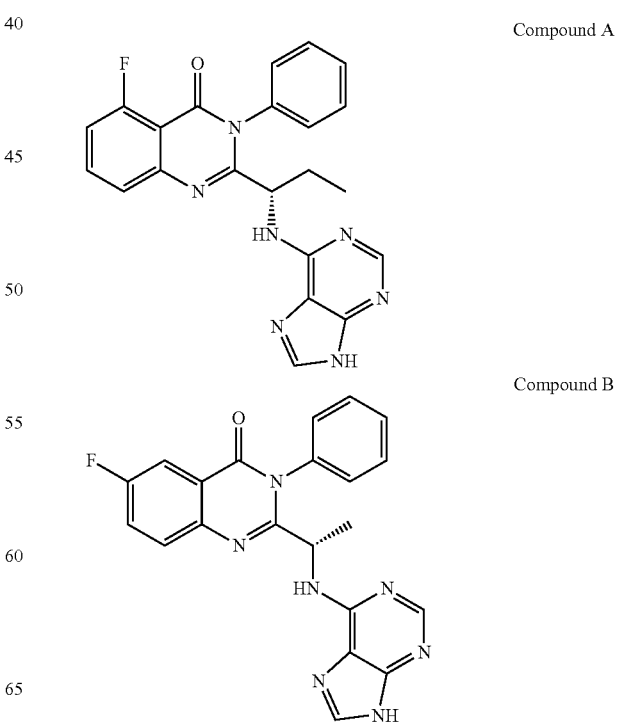

Compound A

Compound B

Compound C

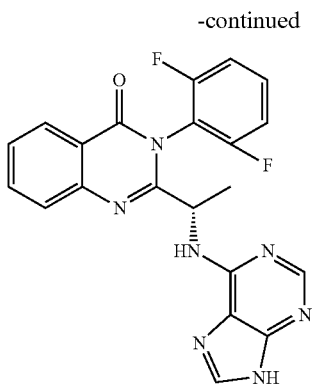

Compounds A, B and C are disclosed in WO2015/017460 and WO2015/100217. Additional examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

In yet another embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be used in combination with Spleen Tyrosine Kinase (SYK) Inhibitors. Examples of SYK inhibitors include, but are not limited to, 6-(1H-indazol-6-yl)-N-(4-morpholinophenyl) imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Connecticut) and those described in U.S. 2015/0175616.

In yet another embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be used in combination with Tyrosine-kinase Inhibitors (TKIs). TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

In yet other embodiments, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be used in combination with one or more inhibitors of lysyl oxidase-like 2 (LOXL) or a substance that binds to LOXL, including for example, a humanized monoclonal antibody (mAb) with an immunoglobulin IgG4 isotype directed against human LOXL2. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologies).

In yet another embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be used in combination with Toll-like receptor 8 (TLR8) inhibitors. Examples of TLR8 inhibitors include, but are not limited to, E-6887, IMO-4200, IMO-8400, IMO-9200, MCT-465, MEDI-9197, motolimod, resiquimod, VTX-1463, and VTX-763.

In yet another embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be used in combination with Toll-like receptor (TLR9) inhibitors. Examples of TLR9 inhibitors include, but are not limited to, IMO-2055, IMO-2125, lefitolimod, litenimod, MGN-1601, and PUL-042.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a BTK (Bruton's Tyrosine kinase) inhibitor. An example of such BTK inhibitor is a compound disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951, tirabrutinib (ONO-4059), PRN-1008, spebrutinib (CC-292), and TAK-020.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a BET inhibitor. An example of such BET inhibitor is a compound disclosed in WO2014/182929, the entire contents of which are incorporated herein by reference.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a TBK (Tank Binding kinase) inhibitor. An example of such TBK inhibitor is a compound disclosed in WO2016/049211.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with an OX40 inhibitor. An example of such OX40 inhibitor is a compound disclosed in U.S. Pat. No. 8,450,460, the entire contents of which are incorporated herein by reference.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD1480, baricitinib, BMS-911543, fedratinib, fdgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with an Indoleamine-pyrrole-2,3-dioxygenase (IDO) inhibitors. An example of such IDO inhibitor is a compound disclosed in WO2016/186967. In one embodiment, the compounds of Formula (I), Formula (Ia), Formula (II), or Formula (IIa) are useful for the treatment of cancer in combination with IDO1 inhibitors including but not limited to BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a Mitogen-activated Protein Kinase (MEK) Inhibitor. MEK inhibitors useful for combination treatment with a compound(s) of Formula (I), Formula (Ia), Formula (II), Formula (IIa), Formula (III), Formula (IIIa), Formula (IIIb), Formula (IIIc), Formula (IIId), Formula (IV), or Formula (IVa), includes antroquinonol, binimetinib, cobimetinib (GDC-0973, XL-518), MT-144, selumetinib (AZD6244), sorafenib, trametinib (GSK1120212), uprosertib and trametinib.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with an Apoptosis Signal-Regulating Kinase (ASK) Inhibitors: ASK inhibitors include but are not limited to those described in WO 2011/008709 (Gilead Sciences) and WO 2013/112741 (Gilead Sciences) including, for example, selonsertib.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be combined with Cluster of Differentiation 47 (CD47) inhibitors. Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be combined with Cyclin-dependent Kinase (CDK) Inhibitors. CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be combined with Discoidin Domain Receptor (DDR) Inhibitors for the treatment of cancer. DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof may be combined with Histone Deacetylase (HDAC) Inhibitors such as those disclosed in U.S. Pat. No. 8,575,353 and equivalents thereof. Additional examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), and vorinostat.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof is useful for the treatment of cancer in combination with a standard of care in the treatment of the respective cancer. One of skill in the art is aware of the standard of care as of a given date in the particular field of cancer therapy or with respect to a given cancer.

Certain embodiments of the present application include or use one or more additional therapeutic agent. The one or more additional therapeutic agent may be an agent useful for the treatment of cancer, inflammation, autoimmune disease and/or related conditions. The one or more additional therapeutic agent may be a chemotherapeutic agent, an anti-angiogenic agent, an antifibrotic agent, an anti-inflammatory agent, an immune modulating agent, an immunotherapeutic agent, a therapeutic antibody, a radiotherapeutic agent, an anti-neoplastic agent, an anti-cancer agent, an anti-proliferation agent, or any combination thereof. In some embodiments, the compound(s) described herein may be used or combined with a chemotherapeutic agent, an anti-angiogenic agent, an anti-fibrotic agent, an anti-inflammatory agent, an immune modulating agent, an immunotherapeutic agent, a therapeutic antibody, a radiotherapeutic agent, an antineoplastic agent or an anti-cancer agent, an anti-proliferation agent, or any combination thereof.

In one embodiment, a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof optionally in combination with an additional anticancer agent described herein, may be used or combined with an anti-neoplastic agent or an anti-cancer agent, anti-fibrotic agent, an anti-anti-inflammatory agent, or an immune modulating agent.

In one embodiment, provided are kits comprising a pharmaceutical composition comprising a compound of Formula (I), Formula (Ia), Formula (II), or Formula (IIa) or a tautomer or pharmaceutically acceptable salt thereof, and at least one additional anticancer agent, or a pharmaceutically acceptable salt thereof, and at least one pharmaceutically acceptable carrier. In one embodiment, provided are kits comprising a pharmaceutical composition comprising a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, and at least one additional anticancer agent, or a pharmaceutically acceptable salt thereof, and at least one pharmaceutically acceptable carrier. In one embodiment, the kit comprises instructions for use in the treatment of cancer. In one embodiment, the instructions in the kit are directed to use of the pharmaceutical composition for the treatment of a hematologic malignancy, multiple myeloma, breast cancer, colorectal cancer, skin cancer, melanoma, ovarian cancer, kidney cancer, small cell lung cancer, non-small cell lung cancer, lymphoma, and/or leukemia.

The application also provides method for treating a subject who is undergoing one or more standard therapies, such as chemotherapy, radiotherapy, immunotherapy, surgery, or combination thereof comprising administering or co-administering a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof to said subject. Accordingly, one or more compound(s) of Formula (I), Formula (Ia), Formula (II), Formula (IIa), Formula (III), Formula (IIIa), Formula (IIIb), Formula (IIIc), Formula (IIId), Formula (IV), or Formula (IVa), or tautomers or pharmaceutically acceptable salts thereof, may be administered before, during, or after administration of a chemotherapy, radiotherapy, immunotherapy, surgery or combination thereof.

In one embodiment, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In one embodiment, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R—CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D.T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States are profiled in Morton, L. M., et al. "Lymphoma Incidence Patterns by WHO Subtype in the United States, 1992-2001" *Blood* 2006, 107(1), p. 265-276.

Examples of immunotherapeutic agents treating lymphoma or leukemia include, but are not limited to, rituximab (such as Rituxan), alemtuzumab (such as Campath, MabCampath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents include using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, fdgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfdgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafd citrate, simvastatin, sirolimus, Styryl sulphones, tacrolimus, tanespimycin, Temsirolimus (CCl-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R—CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC, temozolomide or YERVOY™. Compounds disclosed herein may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using for example, a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) and optionally in combination with a compound of Formula (I), Formula (Ia), Formula (II), Formula (IIa), Formula (III), Formula (IIIa), Formula (IIIb), Formula (IIIc), Formula (IIId), Formula (IV), or Formula (IVa).

The therapeutic treatments can be supplemented or combined with any of the aforementioned therapies with stem cell transplantation or treatment. One example of modified approach is radioimmunotherapy, wherein a monoclonal antibody is combined with a radioisotope particle, such as indium In 111, yttrium Y 90, iodine 1-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures useful in combination with treatment with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the present disclosure provides pharmaceutical compositions comprising a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof in combination with an MMP9 binding protein and/or one or more additional therapeutic agent, and a pharmaceutically acceptable diluent, carrier or excipient. In one embodiment, the pharmaceutical compositions comprise an MMP9 binding protein, one or more additional therapeutic agent, and a pharmaceutically acceptable excipient, carrier or diluent. In some embodiments, the pharmaceutical compositions comprise the compound of formula (I) and anti-MMP9 antibody AB0045.

In one embodiment, the pharmaceutical compositions comprise the compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, anti-MMP9 antibody AB0045, at least one additional therapeutic agent that is an immunomodulating agent, and a pharmaceutically acceptable diluent, carrier or excipient. In certain other embodiments, the pharmaceutical compositions comprise the anti-MMP9 antibody AB0045, at least one additional therapeutic agent that is an anti-inflammatory agent, and a pharmaceutically acceptable diluent, carrier or excipient. In certain other embodiments, the pharmaceutical compositions comprise compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, the anti-MMP9 antibody AB0045, at least one additional therapeutic agent that is an antineoplastic agent or anti-cancer agent, and a pharmaceutically acceptable diluent, carrier or excipient. In one embodiment, MMP9 compounds useful for combination treatment with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, include but are not limited to marimastat (BB-2516), cipemastat (Ro 32-3555), and those described in WO 2012/027721 (Gilead Biologies).

In one embodiment, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti- B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In one embodiment, the immune modulatory agent is an anti-PD-1 or anti-PD-L1 antibody. In some embodiments, immune modulating agents include those agents capable of altering the function of mediators in cytokine mediated signaling pathways.

In some embodiments, the one or more additional therapy or anti-cancer agent is cancer gene therapy or cell therapy. Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019) WO2012079000, WO2017049166, axicabtagene ciloleucel (KTE-C19) U.S. Pat. Nos. 7,741,465, 6,319,494, JCAR-015 U.S. Pat. No. 7,446,190, JCAR-014, JCAR-020, JCAR-024, JCAR-023, JTCR-016, JCAR-018 WO2016090190, JCAR-017, (WO2016196388, WO2016033570, WO2015157386), BPX-501 U.S. Pat. No. 9,089,520, WO2016100236, AU-105, UCART-22, ACTR-087, P-BCMA-101; activated allogeneic natural killer cells CNDO-109-AANK, FATE-NK100, and LFU-835 hematopoietic stem cells.

In one embodiment, the one or more additional therapeutic agent is an immune checkpoint inhibitor. Tumors subvert the immune system by taking advantage of a mechanism known as T-cell exhaustion, which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulator. They act as molecular determinants to influence whether cell cycle progression and other intracellular signaling processes should proceed based upon extracellular information.

In addition to specific antigen recognition through the T-cell receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumor destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., *Int. Immunol.*, 2007; 19: 813-824). The interaction of PD-1 with its ligands, PD-L1 and PD-L2, which are expressed on antigen-presenting, cells (APCs) and dendritic cells (DCs), transmits negative regulatory stimuli to down-modulate the activated T cell immune response. Blockade of PD-1 suppresses this negative signal and amplifies T cell responses. Numerous studies indicate that the cancer microenvironment manipulates the PD-L1/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. This pathway is involved in negative regulation of immune responses of activated T effector cells found in the periphery. PD-L1 is up-regulated in cancer microenvironments, while PD-1 is also up-regulated on activated tumor infiltrating T cells, thus possibly potentiating a vicious cycle of inhibition. This pathway is also intricately involved in both innate and adaptive immune regulation through bi-directional signaling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAh. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAh is a powerful checkpoint inhibitor which removes "the break" from both naive and antigen-experienced cells.

Therapy enhances the antitumor function of CD8+ T cells, increases the ratio of CD8+ T cells to Foxp3+ T regulatory cells, and inhibits the suppressive function of T regulatory cells. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and LAG-3. LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

Thus in one embodiment, the present disclosure provides the use of a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof in combination with one or more additional immune checkpoint inhibitors. In one embodiment, the present disclosure provides the use of a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, with one or more immune checkpoint inhibitors and an anti-MMP9 antibody or antigen binding fragment thereof to treat or prevent cancer. In some embodiments, the immune checkpoint inhibitors may be an anti-PD-1 and/or an anti-PD-L1 antibody or an anti PD-1/PD-L1 interaction inhibitor. In some embodiments, the anti-PD-L1 antibody may be B7-H1 antibody, BMS 936559 antibody, MPDL3280A (atezolizumab) antibody, MEDI-4736 antibody, MSB0010718C antibody or combinations thereof. According to another embodiment, the anti-PD-1 antibody may be nivolumab antibody, pembrolizumab antibody, pidilizumab antibody or combinations thereof.

In addition, PD-1 may also be targeted with AMP-224, which is a PD-L2-IgG recombinant fusion protein. Additional antagonists of inhibitory pathways in the immune response include IMP321, a soluble LAG-3 Ig fusion protein and MHC class II agonist, which is used to increase an immune response to tumors. Lirilumab is an antagonist to the KIR receptor and BMS 986016 is an antagonist of LAG3. The TIM-3-Galectin-9 pathway is another inhibitory checkpoint pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells. Thus, in one embodiment, a compound of Formula (I), or a tautomer or pharmaceutically acceptable salt thereof, is used in combination with IMP321, Lirilumab and/or BMS 986016.

Anti-PD-1 antibodies that may be used in the compositions and methods described herein include but are not limited to: Nivolumab/MDX-1106/BMS-936558/ONO1152, a fully human lgG4 anti-PD-1 monoclonal antibody; pidilizumab (MDV9300/CT-011), a humanized lgG1 monoclonal antibody; pembrolizumab (MK-3475/pembrolizumab/lambrolizumab), a humanized monoclonal IgG4 antibody; durvalumab (MEDI-4736) and atezolizumab. Anti-PD-L1 antibodies that may be used in compositions and methods described herein include but are not limited to: avelumab; BMS-936559, a fully human IgG4 antibody; atezolizumab (MPDL3280A/RG-7446), a human monoclonal antibody; MEDI4736; MSB0010718C, and MDX1105-01.

In one embodiment, the compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, is administered in combination with the anti-PD-1 antibody nivolumab, pembrolizumab, and/or pidilizumab to a patient in need thereof. In one embodiment, the anti-PD-L1 antibody useful for combination treatment with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, is BMS-936559, atezolizumab, or avelumab. In one embodiment, the immune modulating agent inhibits an immune checkpoint pathway. In another embodiment, the immune checkpoint pathway is selected from CTLA-4, LAG-3, B7-H3, B7-H4, Tim3, BTLA, KIR, A2aR, CD200 and PD-1. Additional antibodies that may be used in combination with a compound of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof, in compositions and methods described herein include the anti-PD-1 and anti-PD-L1 antibodies disclosed in U.S. Pat. Nos. 8,008,449 and 7,943,743, respectively.

In one embodiment, the one or more additional therapeutic agent is an anti-inflammatory agent. In certain other embodiments, the anti-inflammatory agent is a tumor necrosis factor alpha (TNF-α) inhibitor. As used herein, the terms "TNF alpha," "TNF-α," and "TNFα," are interchangeable. TNF-α is a pro-inflammatory cytokine secreted primarily by macrophages but also by a variety of other cell types including lymphoid cells, mast cells, endothelial cells, cardiac myocytes, adipose tissue, fibroblasts, and neuronal tissue. TNF-α is also known as endotoxin-induced factor in serum, cachectin, and differentiation inducing factor. The tumor necrosis factor (TNF) family includes TNF alpha, TNF beta, CD40 ligand (CD40L), Fas ligand (FasL), TNF-related apoptosis inducing ligand (TRAIL), and LIGHT (homologous to lymphotoxins, exhibits inducible expression, and competes with HSV glycoprotein D for HVEM, a receptor expressed by T lymphocytes), some of the most important cytokines involved in, among other physiological processes, systematic inflammation, tumor lysis, apoptosis and initiation of the acute phase reaction.

The above therapeutic agents when employed in combination with a compound(s) disclosed herein, may be used, for example, in those amounts indicated in the referenced manuals e.g., Physicians Desk Reference or in amounts generally known to a qualified care giver, i.e., one of ordinary skill in the art. In the methods of the present disclosure, such other therapeutic agent(s) may be administered prior to, simultaneously with, or following the administration of the compound(s) of Formula (I), Formula (Ia), Formula (II), Formula (IIa), Formula (III), Formula (IIIa), Formula (IIIb), Formula (IIIc), Formula (IIId), Formula (IV), or Formula (IVa), or a tautomer or pharmaceutically acceptable salt thereof. Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Compound Preparation

Some embodiments of the instant disclosure are directed to processes and intermediates useful for preparing the subject compounds or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

General Synthetic Schemes
Scheme 1: Preparation of Optically Pure Compounds of Formula (I)
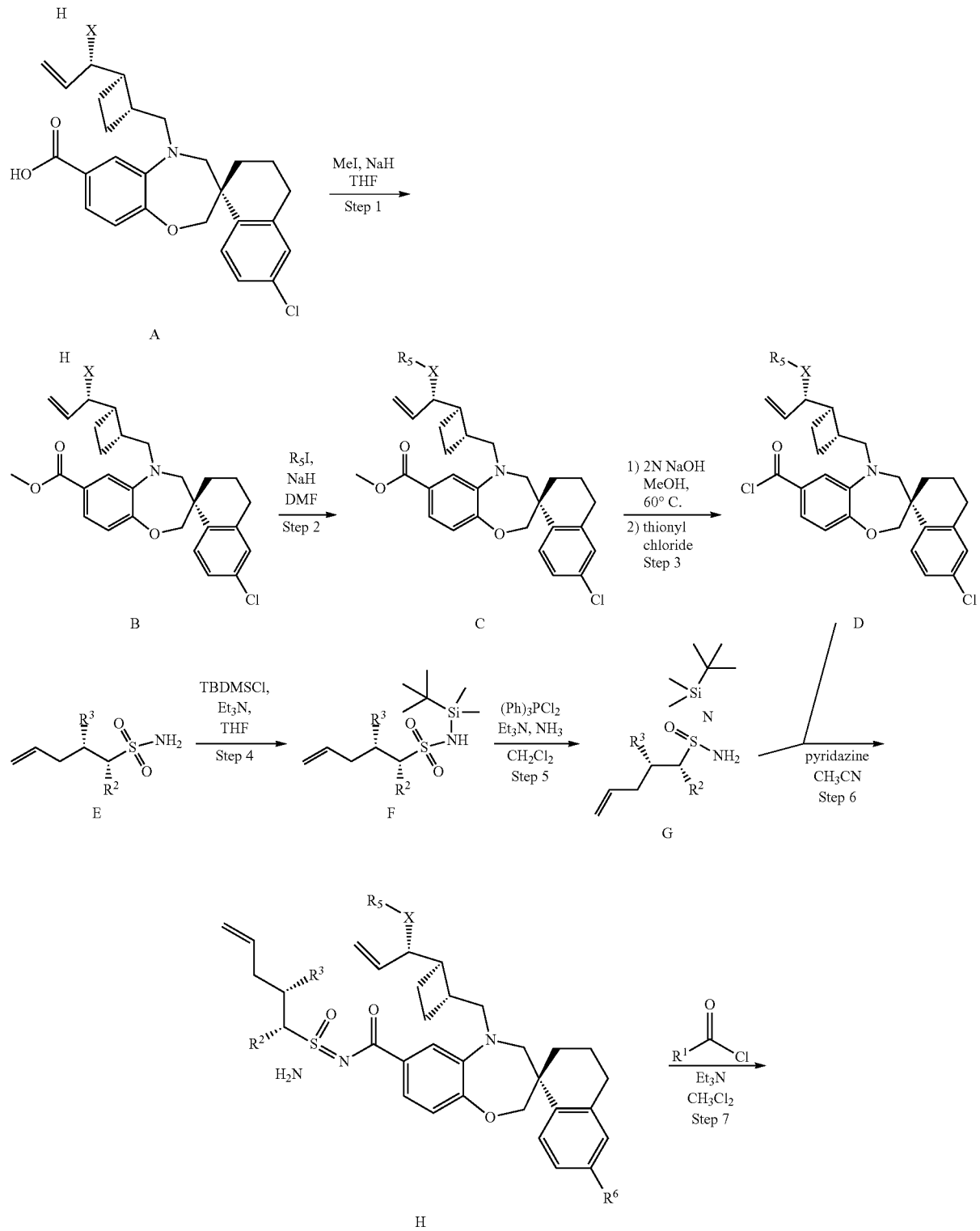

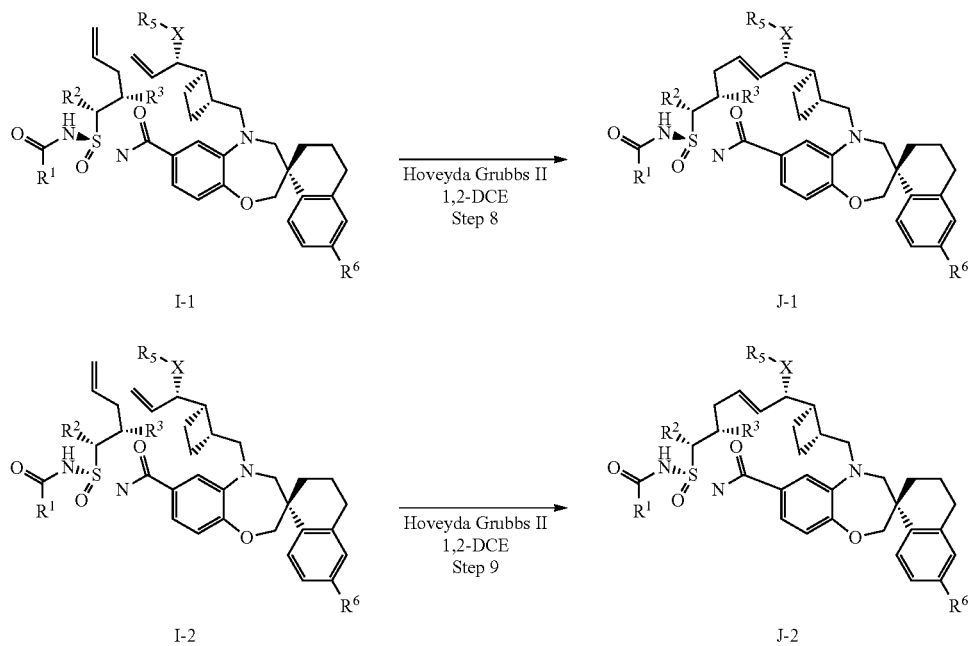

Intermediates A and E can be prepared using procedures described in International Publication No. WO 2016/033486.

Step 1

Intermediate B can be prepared by treating a solution of A in an appropriate solvent, for example THF, with an appropriate base such as sodium hydride, and then treating with an appropriate alkylating agent such as iodomethane.

Step 2

Intermediate C can be prepared by treating a solution of B in an appropriate solvent, for example DMF, with an appropriate base such as sodium hydride, and then treating the mixture with an appropriate alkylating agent such as iodomethane.

Step 3

Intermediate D can be prepared by treating Intermediate C with an appropriate base, such as aqueous NaOH, KOH or LiOH, in appropriate solvent, for example MeOH, EtOH or THF, at elevated temperature, preferably 60° C. overnight. After cooling the mixture, acidifying with an appropriate acidic agent such as HCl, concentrating, and filtering, the resulting solid carboxylic acid is dissolved in an appropriate solvent, such as $CH_2Cl_2$ or 1,2-dichloroethane. An appropriate acid chloride forming agent, for example thionyl chloride or oxalyl chloride, can be added to provide Intermediate D, which can be used immediately in the next step.

Step 4

Intermediate F can be prepared by dissolving Intermediate E in an appropriate solvent such as THF, DMF or $CH_2Cl_2$, treating with an appropriate organic base, such as trimethylamine, diisopropylethylamine or imidazole, and an appropriate silylating agent, such as TBDMSCl or TBDMSOTf, at appropriate temperature, preferably at 0° C.

Step 5

Intermediate G can be prepared by suspending $Ph_3PCl_2$ in an appropriate solvent, such as $CH_2Cl_2$ or 1,2-dichloroethane, under a $N_2$ atmosphere, adding an appropriate organic base, such as trimethylamine or diisopropylethylamine, and then adding a solution of Intermediate F in an appropriate solvent such as $CH_2Cl_2$ or 1,2-dichloroethane followed by bubbling ammonia gas.

Step 6

Intermediate H can be prepared by dissolving Intermediate D in an appropriate polar solvent, such as acetonitrile, and adding pyridazine, followed by Intermediate G in an appropriate polar solvent such as acetonitrile.

Step 7

Intermediates 1-1 and 1-2 can be prepared by adding triethylamine and acid chloride under ice-bath cooling to a solution of Intermediate H in an appropriate solvent such as CH₂Cl₂ or 1,2-dichloroethane. The two stereoisomers can be separated during purification.

Steps 8 and 9

J-1 and J-2 can be prepared by stirring the Intermediate 1-1 or 1-2, respectively, with Hoveyda Grubbs $2^{nd}$ generation catalyst in an appropriate solvent such as CH₂Cl₂ or 1,2-dichloroethane at elevated temperature, preferably 60° C. After concentration, the residue can be purified by prep-HPLC or by silica gel column chromatography.

Scheme 2: Preparation of Optically Pure Compounds of Formula (I)

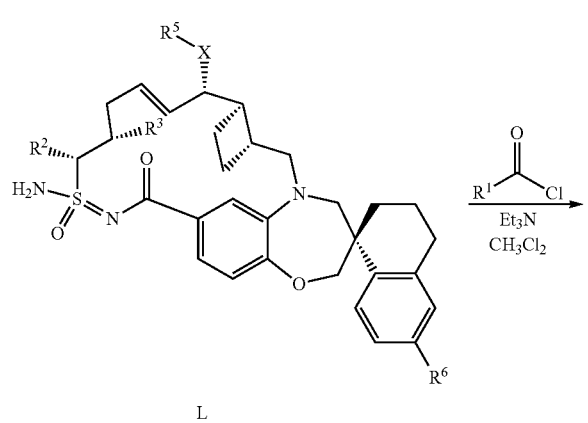

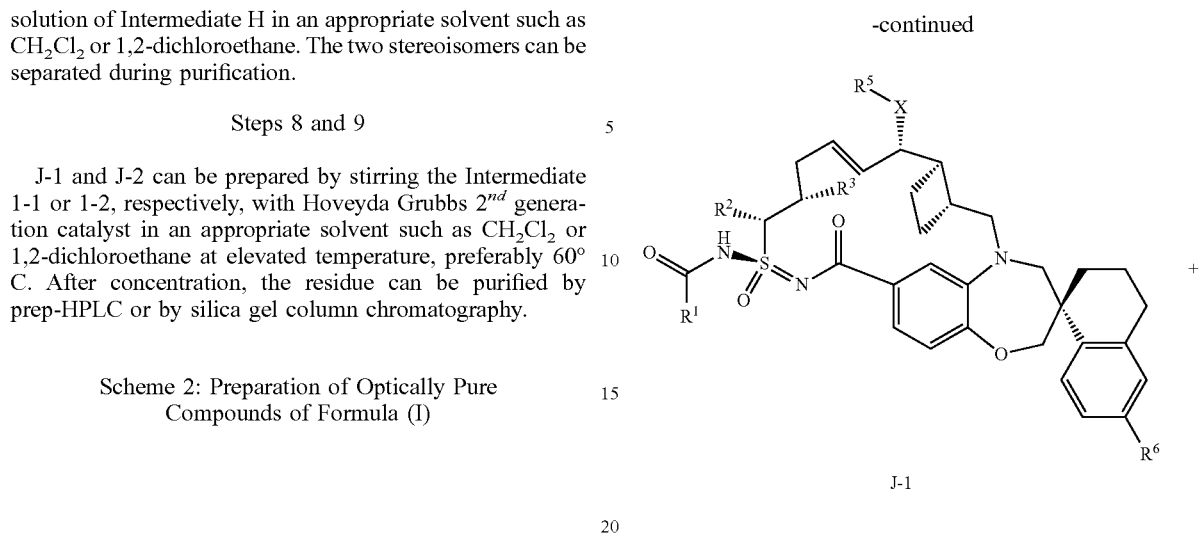

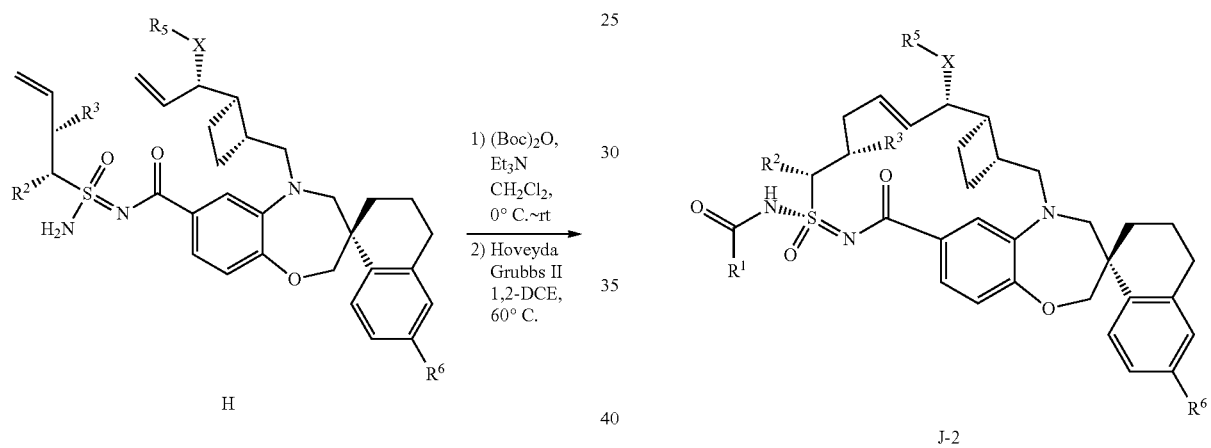

J-1 and J-2 can also be prepared from H as shown in Scheme 2. A solution of Intermediate H in an appropriate solvent, such as CH₂Cl₂ or 1,2-dichloroethane, can be treated with di-tert-butyl dicarbonate under ice bath cooling in the presence of appropriate base such as DIPEA or TEA, and stirring at rt overnight. After concentration and purification by silica gel chromatography, the mixture of Boc protected diastereomers can be treated with Hoveyda Grubbs $2^{nd}$ generation catalyst in an appropriate solvent, such as CH₂Cl₂ or 1,2-dichloroethane, at elevated temperature, preferably at 60° C. After concentration, the mixture of diastereomers L can be acylated with an appropriate acylating agent, such acid chloride and an organic base, or carboxylic acid with EDCI and an organic base.

Scheme 3: Preparation of Optically Pure Compounds of Formula (I)

J-1 and J-2 can also be separated by either silica gel column chromatography or by chiral HPLC after acylation of Intermediate H and macrocyclization of Intermediate I with Hoveyda Grubbs $2^{nd}$ generation catalyst.

Scheme 3
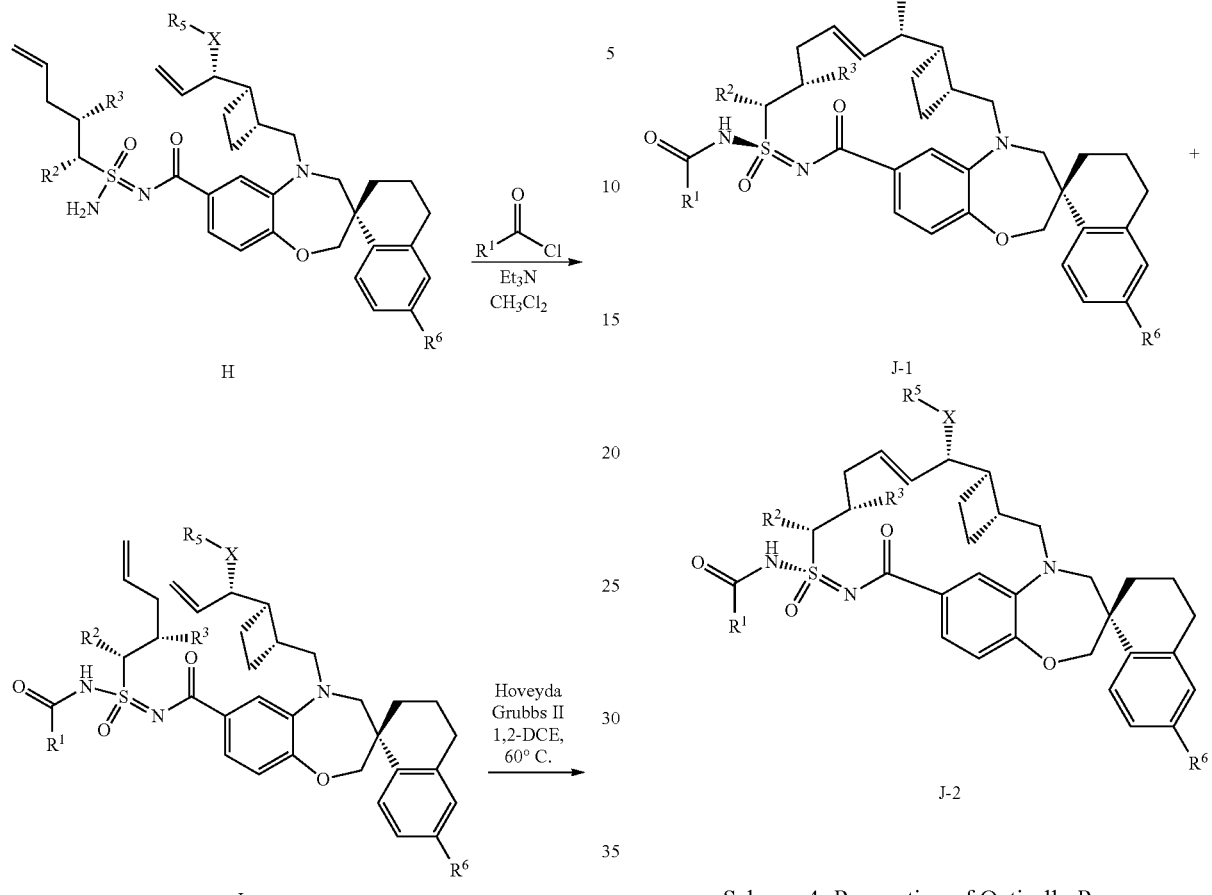
Scheme 4: Preparation of Optically Pure Compounds of Formula (I)
Scheme 4
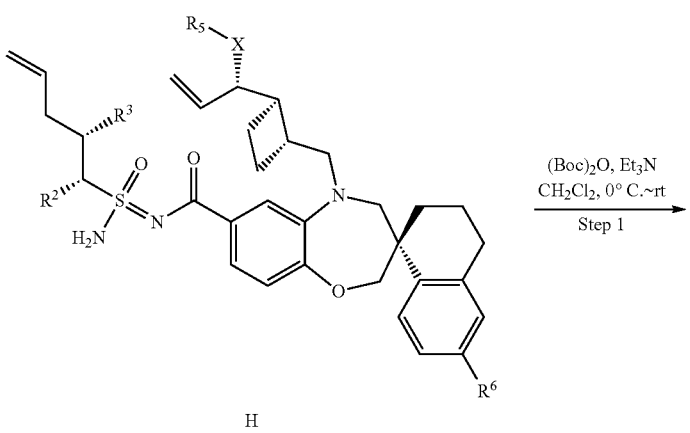

-continued

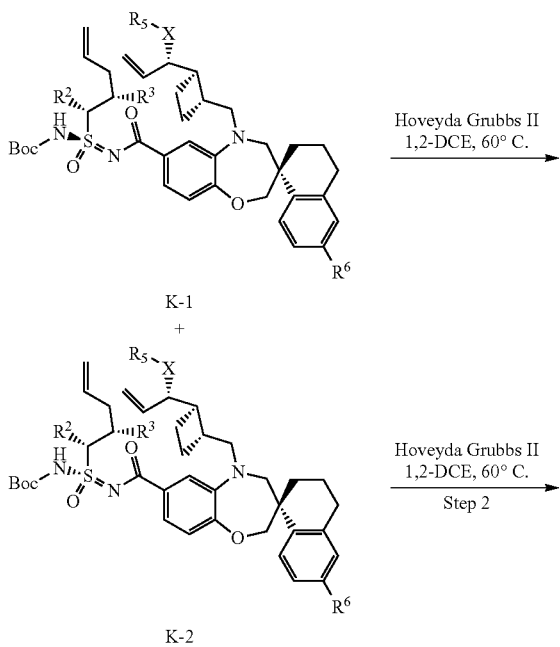

K-1

+

K-2

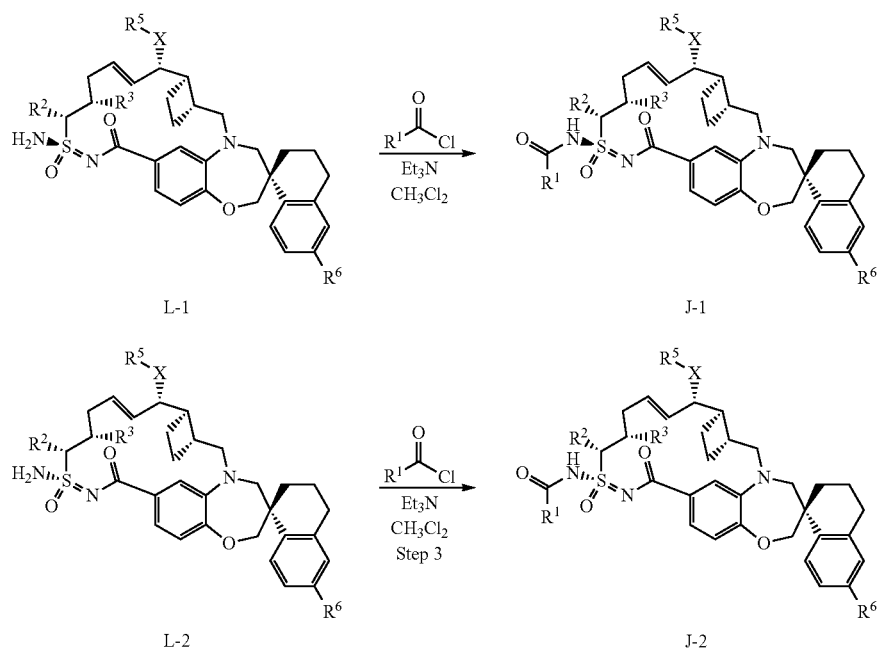

L-1 → J-1

L-2 → J-2

Step 1

Intermediates K-1 and K-2 can be prepared by adding triethylamine and di-tert-butyl dicarbonate to a solution of Intermediate H in an appropriate solvent, such as $CH_2Cl_2$ or 1,2-dichloroethane, under ice bath cooling, and stirring the mixture at rt overnight. After concentrating the reaction mixture, the residue can be purified by prep-HPLC or silica gel column chromatography to separate the diastereomers.

Steps 2 and 3

J-1 and J-2 can be prepared by stirring Intermediate K-1 or K-2 and Hoveyda Grubbs $2^{nd}$ generation catalyst in an appropriate solvent, such as $CH_2Cl_2$ or 1,2-dichloroethane, at elevated temperature, preferably at 60° C. After concentrating the reaction mixture and purifying the residue by prep-HPLC, an appropriate acylating agent, such acid chloride and an organic base, or carboxylic acid with EDCI and an organic base, are added to acylate Intermediate L-1 or L-2, which can be purified by prep-HPLC or by silica gel column chromatography to afford J-1 or J-2.

Scheme 5: Preparation of Optically Pure Compounds of Formula (I)

Intermediates L-1 and L-2 can be separated by either silica gel column chromatography or by chiral HPLC after Boc protection and macrocyclization with Hoveyda Grubbs $2^{nd}$ generation catalyst, and then acylated to provide J-1 and J-2 respectively.

Scheme 5

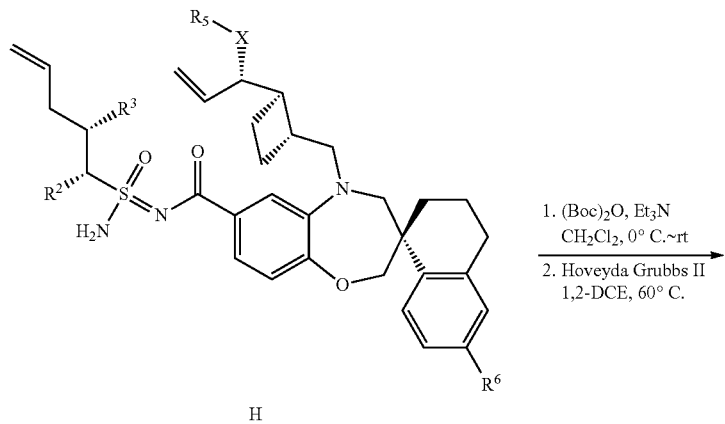

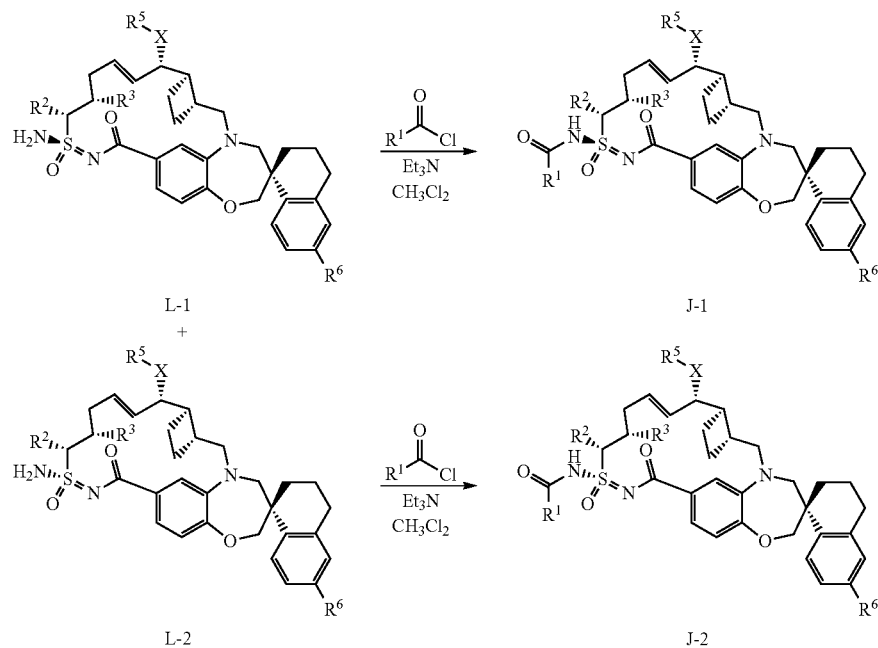

Scheme 6: Preparation of Optically Pure Compounds of Formula (I)

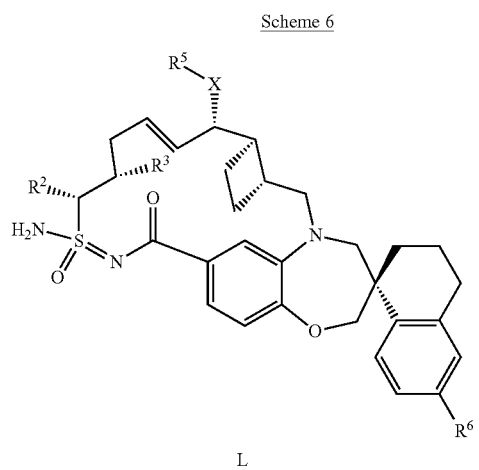

L

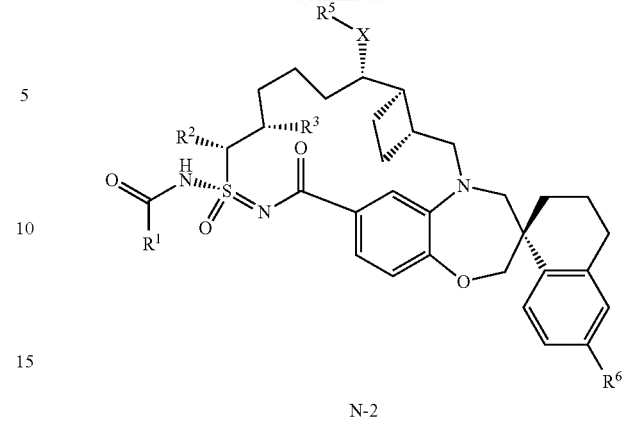

N-2

N-1 and N-2 can be prepared from L as shown in Scheme 6, separated by either silica gel column chromatography or by chiral HPLC after acylation followed by macrocyclization with Hoveyda Grubbs $2^{nd}$ generation catalyst.

Schemes 7 and 8: Preparation of Compounds of Formula (I) Wherein —C(O)R$^1$ is —C(O)NHR$^8$

Scheme 7

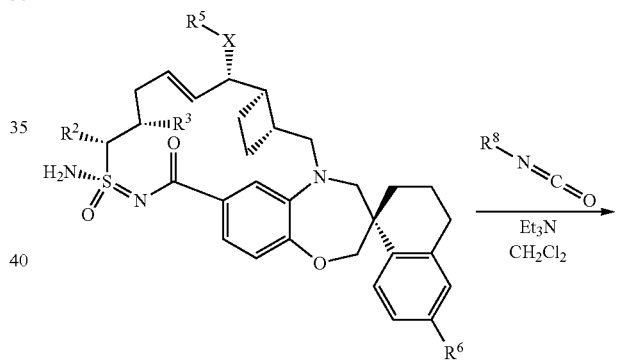

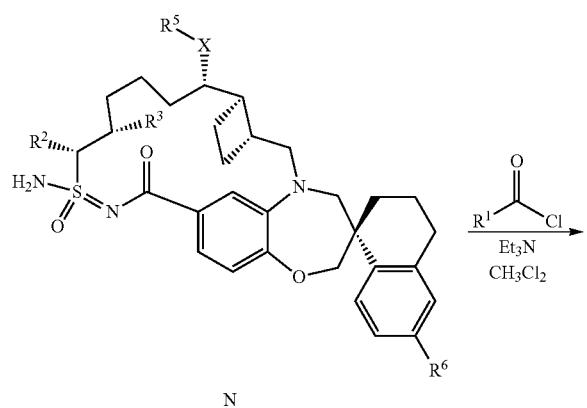

N

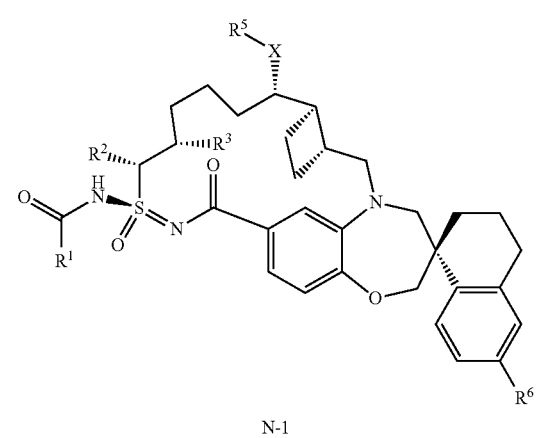

N-1

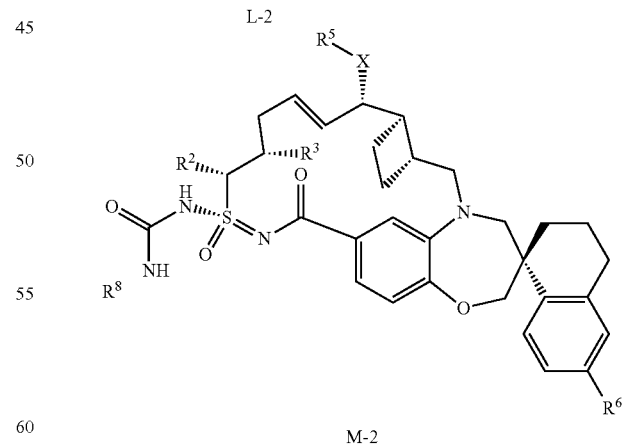

M-2

M-2 can be prepared from L-2 by adding triethylamine and substituted isocyanate in an appropriate solvent such as CH$_2$Cl$_2$ or 1,2-dichloroethane under ice-bath cooling.

Alternatively, the two stereoisomers M-1 and M-2 can be separated by either silica gel column chromatography or by chiral HPLC after treating L-2 with substituted isocyanate in an appropriate solvent such as $CH_2Cl_2$ or 1,2-dichloroethane in the presence of appropriate base such as triethylamine.

Scheme 9: Preparation of Compounds of Formula (I) Wherein —C(O)R$^1$ is —C(O)NR$^8$R$^9$

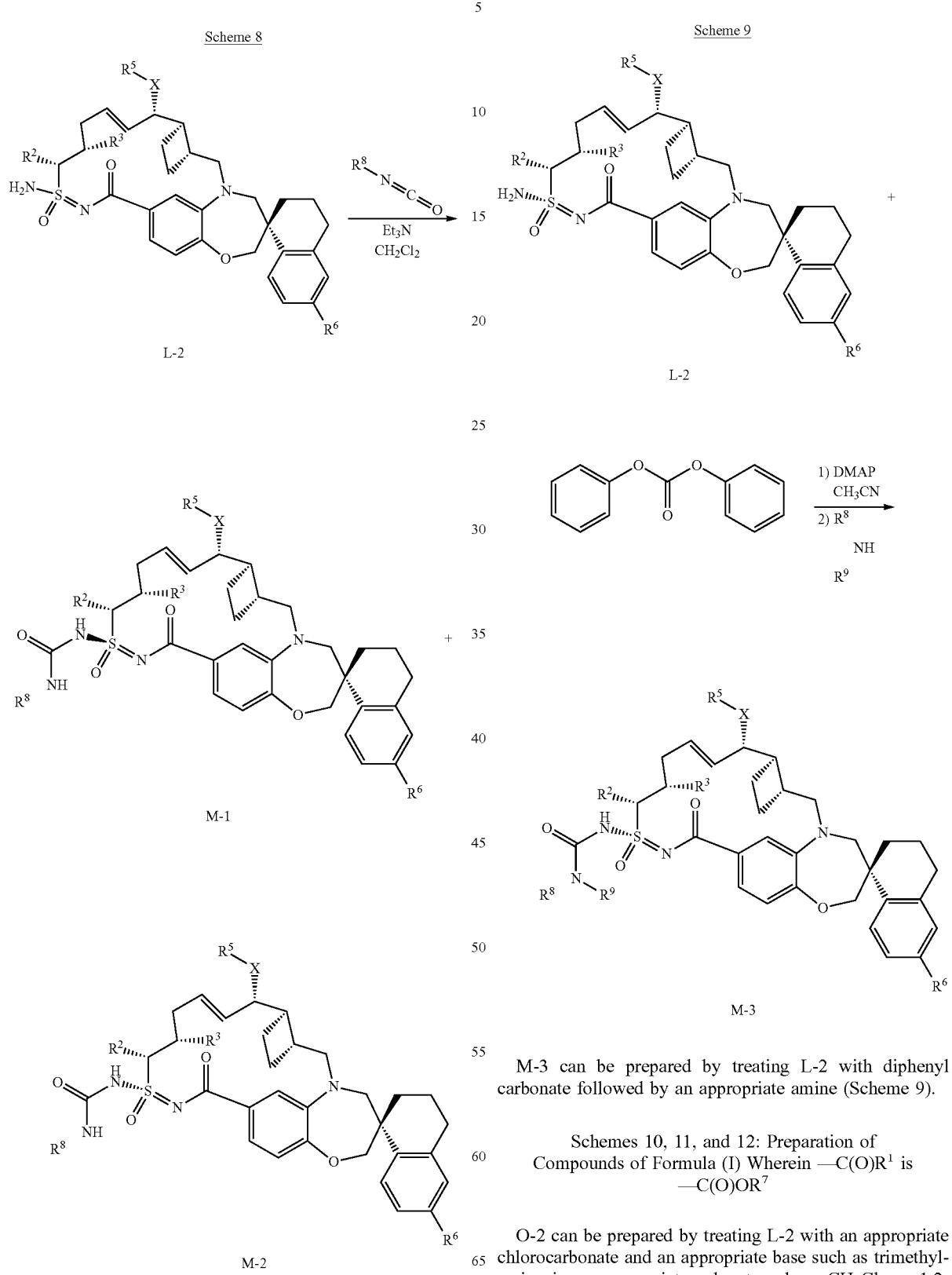

M-3 can be prepared by treating L-2 with diphenyl carbonate followed by an appropriate amine (Scheme 9).

Schemes 10, 11, and 12: Preparation of Compounds of Formula (I) Wherein —C(O)R$^1$ is —C(O)OR$^7$ O-2 can be prepared by treating L-2 with an appropriate chlorocarbonate and an appropriate base such as trimethylamine in an appropriate solvent such as $CH_2Cl_2$ or 1,2-dichloroethane.

Scheme 10

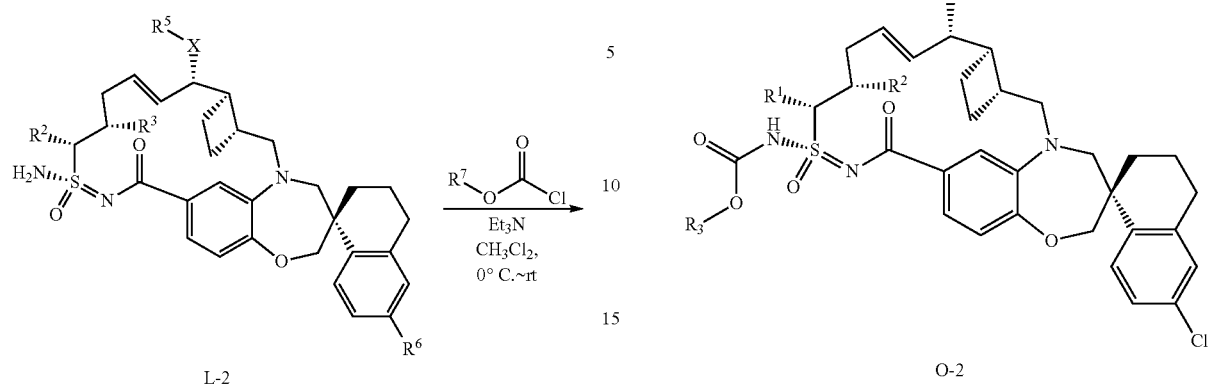

Alternatively, O-2 can be prepared by treating L-2 with diphenyl carbonate followed by an appropriate alcohol.

Alternatively, two stereoisomers can be separated by either silica gel column chromatography or by chiral HPLC after treating diastereomeric mixture L with diphenyl carbonate followed by an appropriate alcohol as the nucleophile or with substituted chloroformate, under ice-bath cooling to afford O-2 (Scheme 12).

Scheme 12

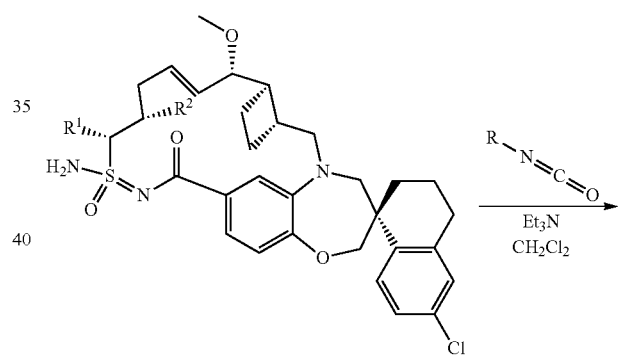

Scheme 11

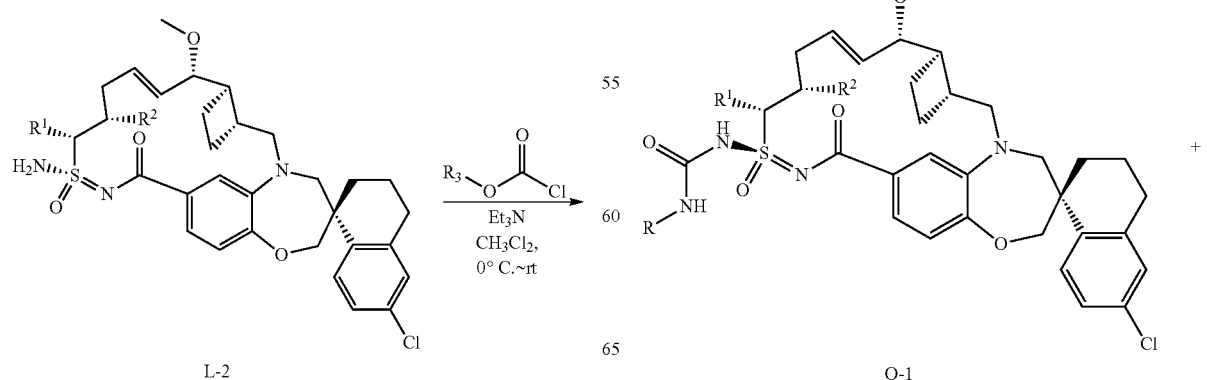

-continued

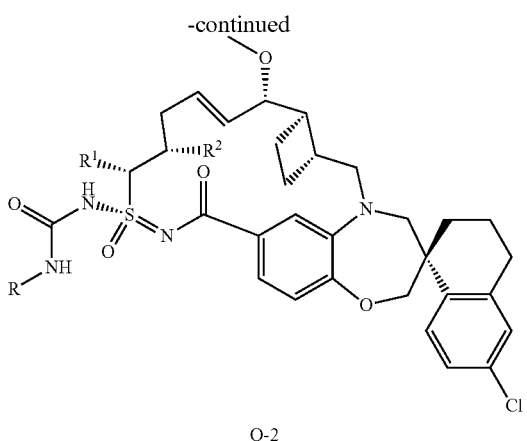

O-2

EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Example 1

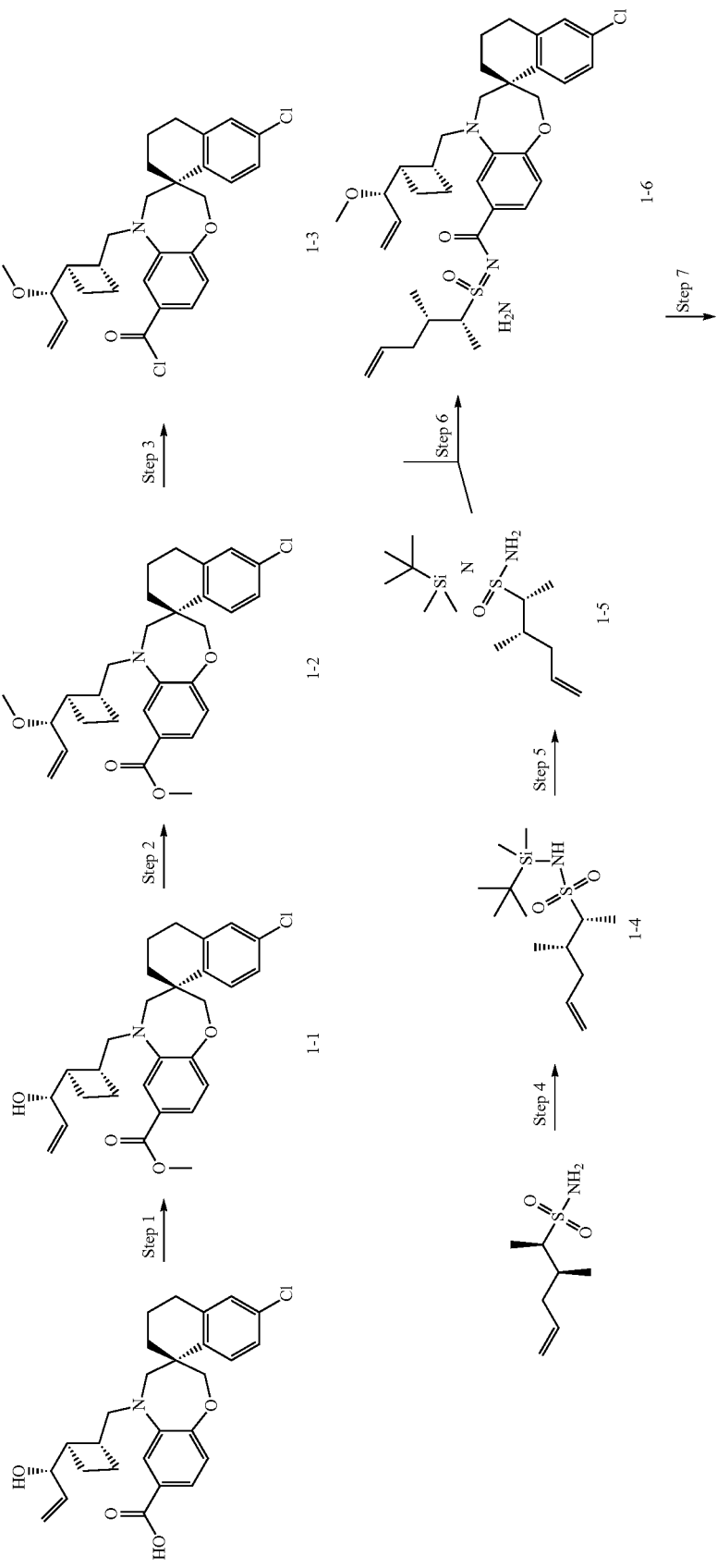

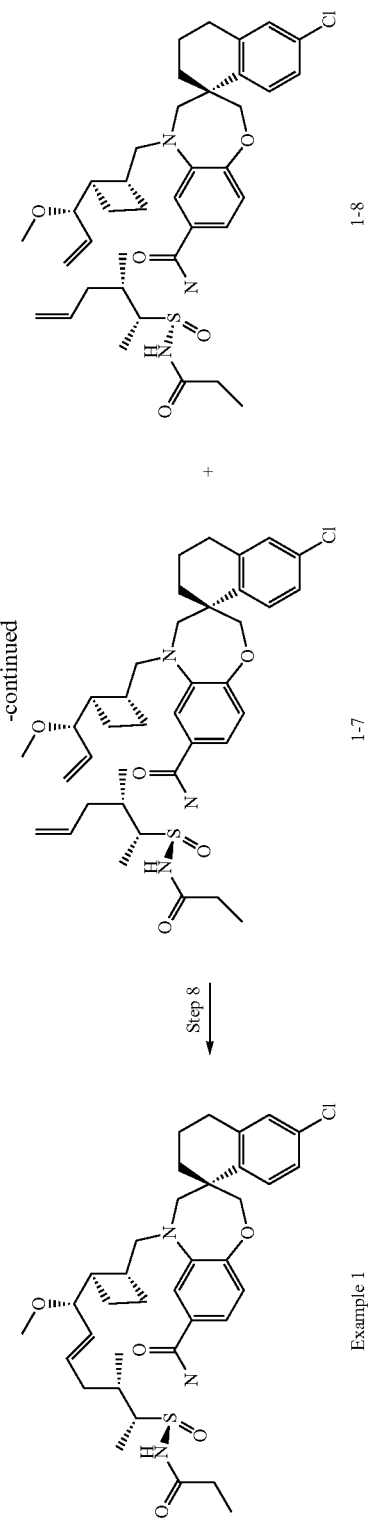

Step 1: Preparation of methyl (S)-6'-chloro-5-(((1R, 2R)-2-((S)-1-hydroxyallyl)cyclobutyl)methyl)-3',4, 4',5-tetrahydro-2H,2'H-spiro[benzo[b][1,4] oxazepine-3,1'-naphthalene]-7-carboxylate (1-1)

To a stirred solution of (S)-6'-chloro-5-(((1R,2R)-2-((S)-1-hydroxyallyl)cyclobutyl)methyl)-3',4,4',5-tetrahydro-2H, 2'H-spiro[benzo[b][1,4]oxazepine-3,1'-naphthalene]-7-carboxylic acid (prepared according to procedure described in International Patent Application No. WO 2016/033486) (1.02 g, 2.18 mmol) in THF (10 mL) was added sodium hydride (60% in mineral oil, 183.1 mg, 4.57 mmol) in an ice bath, followed by iodomethane (618.7 mg, 4.359 mmol). The resulting mixture was stirred at rt for 5 h. The reaction mixture was then poured into ice cold $H_2O$ and extracted with $CH_2Cl_2$. The organic layer was concentrated and purified by silica gel column (EtOAc/Hexanes=2/3) to afford methyl (S)-6'-chloro-5-(((1R,2R)-2-((S)-1-hydroxyallyl)cyclobutyl)methyl)-3',4,4',5-tetrahydro-2H,2'H-spiro[benzo [b][1,4]oxazepine-3,1'-naphthalene]-7-carboxylate. LCMS-ESI+: (m/z): [M+H]+ calcd for $C_{28}H_{32}ClNO_4$: 482.0; found: 482.2.

Step 2: Preparation of methyl (S)-6'-chloro-5-(((1R, 2R)-2-((S)-1-methoxyallyl)cyclobutyl)methyl)-3',4, 4',5-tetrahydro-2H,2'H-spiro[benzo[b][1,4] oxazepine-3,1'-naphthalene]-7-carboxylate (1-2)

To a stirred solution of methyl (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (707.0 mg, 1.4 mmol) in DMF (8 mL) was added sodium hydride (60% in mineral oil, 88.0 mg, 2.2 mmol) in an ice bath, followed by iodomethane (312.3 mg, 2.2 mmol). The resulting mixture was stirred at rt overnight. The reaction mixture was then poured into ice cold $H_2O$ and extracted with $CH_2Cl_2$. The organic layer was concentrated and purified by silica gel column (EtOAc/Hexanes=1/4) to afford methyl (S)-6'-chloro-5-(((1R,2R)-2-((S)-1-methoxyallyl)cyclobutyl)methyl)-3',4,4',5-tetrahydro-2H,2'H-spiro [benzo[b] [1,4]oxazepine-3,1'-naphthalene]-7-carboxylate. LCMS-ESI+: (m/z): [M+H]+ calcd for $C_{29}H_{34}ClNO_4$: 496.0; found: 496.2.

Step 3: Preparation of (S)-6'-chloro-5-(((1R,2R)-2-((S)-1-methoxyallyl) cyclobutyl)methyl)-3',4,4',5-tetrahydro-2H,2'H-spiro[benzo[b][1,4]oxazepine-3, 1'-naphthalene]-7-carbonyl chloride (1-3)

Methyl (S)-6'-chloro-5-(((1R,2R)-2-((S)-1-methoxyallyl) cyclobutyl)methyl)-3',4,4',5-tetrahydro-2H,2'H-spiro[benzo [b][1,4] oxazepine-3,1'-naphthalene]-7-carboxylate (659.0 mg, 1.33 mmol) was stirred in 2N aq NaOH (3 mL) and MeOH (8 mL) at 60° C. overnight. After cooling, the mixture was acidified with HCl and concentrated. The resulting solid was treated with $CH_2Cl_2$ and filtered. The filtrate was concentrated, and 174.5 mg (0.36 mmol) was dissolved in $CH_2Cl_2$ (6 mL). Thionyl chloride (1.5 mL) was added to the solution in an ice bath. The resulting mixture was stirred at rt for 2 h and concentrated. Crude (S)-6'-chloro-5-(((1R,2R)-2-((S)-1-methoxyallyl)cyclobutyl) methyl)-3',4,4',5-tetrahydro-2H,2'H-spiro[benzo[b][1,4] oxazepine-3,1'-naphthalene]-7-carbonyl chloride was used directly in the next step.

Step 4: Preparation of (2R,3S)—N-(tert-butyldimethylsilyl)-3-methylhex-5-ene-2-sulfonamide (1-4)

To a stirred solution of (2R,3S)-3-methylhex-5-ene-2-sulfonamide (2.00 g, 11.28 mmol) in THF (16 mL) was added triethylamine (3.15 mL, 22.57 mmol) in an ice bath, followed by TBDMSCl (2.13 g, 14.10 mmol) in THF (8 mL) slowly. The resulting mixture was stirred at rt for 2 days. The precipitate was filtered and washed with ether. The filtrate was concentrated and purified by silica gel column (EtOAc/Hexanes=1/4) to afford (2R,3S)—N-(tert-butyldimethylsilyl)-3-methylhex-5-ene-2-sulfonamide. $^1$H NMR (400 MHz, Chloroform-d) δ 5.76-5.67 (m, 1H), 5.08-5.02 (m, 2H), 3.95 (s, 1H), 3.95-2.97 (m, 1H), 2.44-2.41 (m, 1H), 2.14-2.08 (m, 1H), 2.02-1.96 (m, 1H), 1.27 (d, J=8.0 Hz, 3H), 1.02 (d, J=8.0 Hz, 3H), 0.94 (m, 9H), 0.27-0.26 (m, 6H).

Step 5: Preparation of (2R,3S)—N'-(tert-butyldimethylsilyl)-3-methylhex-5-ene-2-sulfonimidamide (1-5)

To a stirred suspension of $Ph_3PCh$ (754.33 mg, 2.264 mmol) in $CH_2Cl_2$ (4.0 mL) under a $N_2$ atmosphere, was added trimethylamine (0.43 mL, 3.087 mmol). The mixture was stirred for 10 min at rt, then cooled to 0° C., and a solution of (2R,3S)—N-(tert-butyldimethylsilyl)-3-methylhex-5-ene-2-sulfonamide (600.00 mg, 2.058 mmol) in $CH_2Cl_2$ (4 mL) was added. The reaction mixture was stirred for 1 h at 0° C. Ammonia gas was bubbled in the reaction mixture. The reaction vessel was sealed, stirred at 0° C. for 2 h. The resulting precipitate was filtered and washed with $CH_2Cl_2$. The filtrate was concentrated and purified by silica gel column (EtOAc/Hexanes=1/4) to afford (2R,3S)—N'-(tert-butyldimethylsilyl)-3-methylhex-5-ene-2-sulfonimidamide (1-5). $^1$H NMR (400 MHz, Chloroform-d) δ 5.80-5.69 (m, 1H), 5.08-5.02 (m, 2H), 4.17 (w, 2H), 3.06-2.98 (m, 1H), 2.54-2.46 (m, 1H), 2.11-1.95 (m, 2H), 1.29-1.26 (m, 3H), 1.01-0.98 (m, 3H), 0.92-0.88 (m, 9H), 0.13-0.11 (m, 6H).

Step 6: Preparation of (3S)—N-(amino((2R,3S)-3-methylhex-5-en-2-yl)(oxo)-16-sulfanylidene)-6'-chloro-5-(((1R,2R)-2-((S)-1-methoxyallyl) cyclobutyl) methyl)-3',4,4',5-tetrahydro-2H,2'H-spiro[benzo[b][1,4]oxazepine-3,1'-naphthalene]-7-carboxamide (1-6)

To a stirred solution of (S)-6'-chloro-5-(((1R,2R)-2-((S)-1-methoxyallyl)cyclobutyl)methyl)-3',4,4',5-tetrahydro-2H, 2'H-spiro[benzo[b][1,4] oxazepine-3,1'-naphthalene]-7-carbonyl chloride (181.00 mg, 0.362 mmol) in acetonitrile (2.0 mL) was added pyridazine (0.03 mL, 0.362 mmol)) in 2 mL of acetonitrile, followed by (2R,3S)—N'-(tert-butyldimethylsilyl)-3-methylhex-5-ene-2-sulfonimidamide (126.00 mg, 0.434 mmol) in acetonitrile solution (2.0 mL). The resulting mixture was stirred at rt for 3 h. After concentration the residue was purified by silica gel column (EtOAc/Hexanes=2/3) to afford (3S)—N-(amino((2R,3S)-3-methylhex-5-en-2-yl)(oxo)-16-sulfanylidene)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carboxamide. $^1$H NMR (400 MHz, Chloroform-d) δ 7.70 (d, J=11.6 Hz, 1H), 7.62-7.58 (m, 2H), 7.15 (d, J=8.8 Hz, 1H), 7.10-7.07 (m, 1H), 6.95 (d, J=8.4 Hz, 1H), 5.80-5.49 (m, 2H), 5.18-5.02 (m, 4H), 4.15 (dd, J=12.0, 5.2 Hz, 1H), 4.05 (dd, J=12.0, 4.4 Hz, 1H), 3.71-3.61 (m, 2H), 3.49-3.28 (m, 3H), 3.25-3.24 (m, 3H), 2.81-2.45 (m, 5H), 2.15-1.52 (m, 10H), 1.40 (dd, J=12.8, 6.8 Hz, 3H), 1.09 (dd, J=28.4, 6.8 Hz, 3H). LCMS-ESI+: (m/z): [M+H]+ calcd for $C_{35}H_{46}ClN_3O_4S$: 640.3; found: 640.3.

Step 7: Preparation of 1-7 and 1-8

To a stirred solution of (3S)—N-(amino((2R,3S)-3-methylhex-5-en-2-yl)(oxo)-16-sulfanylidene)-6'-chloro-5-(((1R,2R)-2-((S)-1-methoxyallyl)cyclobutyl)methyl)-3',4,4',5-tetrahydro-2H,2'H-spiro[benzo[b][1,4] oxazepine-3,1'-naphthalene]-7-carboxamide (30.00 mg, 0.047 mmol) in $CH_2Cl_2$ (4.0 mL) was added triethylamine (0.01 mL, 0.07 mmol) in an ice bath, followed by propionyl chloride (5.20 mg, 0.056 mmol). The resulting mixture was stirred at rt for 2 h. After concentration, the residue was purified by preparative HPLC (Phenomenex Luna 5 μm C18 (2), 150×21.2 mm, 50% to 90-95% acetonitrile/water with 0.1% trifluoroacetic acid, 15 mL/min, used throughout this experimental section unless otherwise mentioned) to afford the 1-7 (more polar fraction) and 1-8 (less polar fraction). LCMS-ESI+: (m/z): [M+H]+ calcd for $C_{38}H_{50}ClN_3O_5S$: 696.3; found: 696.3.

Step 8: Preparation of Example 1

The single diastereomer 1-7 from step 7 (11.0 mg, 0.016 mmol) and Hoveyda Grubbs generation 2 catalyst (2.0 mg, 0.003 mmol) were stirred in 1,2-dichloroethane (6.0 mL) at 60° C. for 4 h. After concentration, the residue was purified by preparative HPLC to afford Example 1. $^1$H NMR (400 MHz, Chloroform-d) δ 7.72 (d, J=8.4 Hz, 1H), 7.36 (dd, J=8.2, 1.8 Hz, 1H), 7.19-7.16 (m, 2H), 7.08 (d, J=2.4 Hz, 1H), 6.88 (d, J=8.0 Hz, 1H), 5.86-5.80 (m, 1H), 5.69 (dd, J=15.8, 7.4 Hz, 1H), 4.30-4.26 (m, 1H), 4.05 (dd, J=22.8, 12.0 Hz, 2H), 3.80-3.72 (m, 3H), 3.37 (d, J=14.4 Hz, 1H), 3.27 (s, 3H), 3.06 (dd, J=14.8, 10.8 Hz, 1H), 2.85-2.75 (m, 3H), 2.58-1.68 (m, 14H), 1.42 (d, J=6.8 Hz, 3H), 1.15 (t, J=7.6 Hz, 3H), 1.11 (d, J=6.8 Hz, 3H). LCMS-ESI+: (m/z): [M+H]+ calcd for $C_{36}H_{46}ClN_3O_5S$: 668.3; found: 668.3.

Example 2

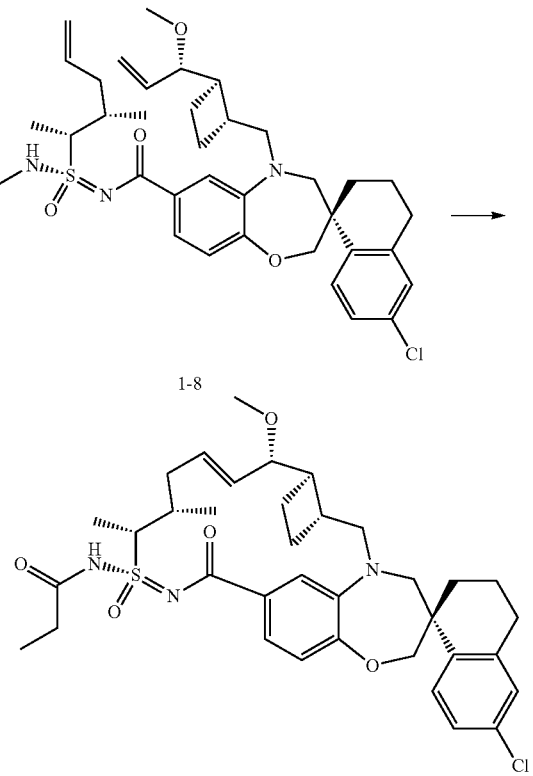

1-8

Example 2

Example 2 was synthesized in the same manner as Example 1 (Step 8) using diastereomer 1-8 instead of 1-7. $^1$H NMR (400 MHz, Chloroform-d) δ 7.70 (d, J=8.8 Hz, 1H), 7.18 (dd, J=8.4, 2.4 Hz, 1H), 7.13 (d, J=8.4 Hz, 1H), 7.08 (d, J=2.4 Hz, 1H), 7.02 (s, 1H), 6.94 (d, J=8.0 Hz, 1H), 5.99-5.92 (m, 1H), 5.50 (dd, J=15.2, 8.8 Hz, 1H), 4.47 (w, 1H), 4.13-4.04 (m, 2H), 3.82 (d, J=15.2 Hz, 1H), 3.71-3.65 (m, 2H), 3.31-3.24 (m, 1H), 3.22 (s, 3H), 2.99 (dd, J=15.2, 10.0 Hz, 1H), 2.80-2.70 (m, 3H), 2.49-1.64 (m, 13H), 1.54 (d, J=6.8 Hz, 3H), 1.42-1.36 (m, 1H), 1.17 (t, J=7.6 Hz, 3H), 1.02 (d, J=6.4 Hz, 3H). LCMS-ESI+ (m/z): [M+H]+ calcd for $C_{36}H_{46}ClN_3O_5S$: 668.3; found: 668.3.

Examples 3 and 4

Example 3

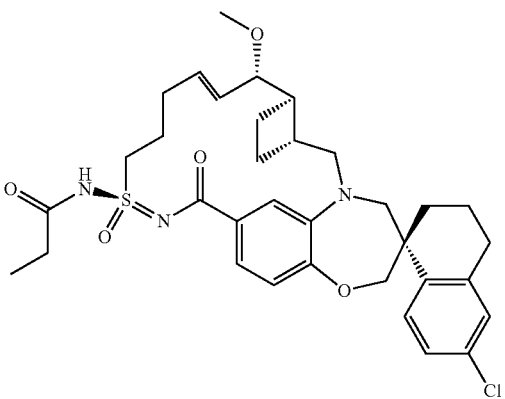

Example 4

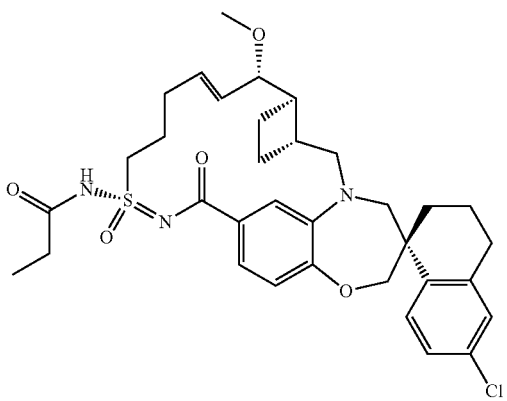

Step 1: Preparation of N'-(tert-butyldimethylsilyl) pent-4-ene-1-sulfonimidamide N'-(tert-butyldimethylsilyl)pent-4-ene-1-sulfonimidamide was prepared in the same manner as Example 1 (step 4 and step 5) using pent-4-ene-1-sulfonamide instead of (2R,3S)-3-methylhex-5-ene-2-sulfonamide). ¹H NMR (400 MHz, Chloroform-d) δ 5.78 (ddt, J=17.0, 10.2, 6.8 Hz, 1H), 5.09-5.01 (m, 2H), 3.13-3.05 (m, 2H), 2.22-2.16 (m, 2H), 1.98-1.90 (m, 2H), 0.90 (s, 9H), 0.12 (s, 3H), 0.11 (s, 3H).

Step 2: Preparation of (3S)—N-(amino(oxo)(pent-4-en-1-yl)-16-sulfanylidene)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carboxamide N'-(tert-butyldimethylsilyl)pent-4-ene-1-sulfonimidamide was treated with (S)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carbonyl chloride in the presence of pyridazine in similar manner as in Example 1 (step 6) to give the title compound.

Step 3: Preparation of (S)-6'-chloro-5-(((1R,2R)-2-((S)-1-methoxyallyl) cyclobutyl)methyl)-N—((R)-oxo(pent-4-en-1-yl)(propionamido)-16-sulfanylidene)-3',4,4',5-tetrahydro-2H,2'H-spiro[benzo[b][1,4]oxazepine-3,1'-naphthalene]-7-carboxamide To a stirred solution of (3S)—N-(amino(oxo)(pent-4-en-1-yl)-16-sulfanylidene)-6'-chloro-5-(((1R,2R)-2-((S)-1-methoxyallyl)cyclobutyl)methyl)-3',4,4',5-tetrahydro-2H, 2'H-spiro[benzo[b][1,4]oxazepine-3,1'-naphthalene]-7-carboxamide (66 mg, 0.11 mmol) in CH₂Cl₂ (5.0 mL) was added triethyl amine (0.02 mL, 0.162 mmol) in an ice bath, followed by propionyl chloride (11.97 mg, 0.129 mmol). The resulting mixture was stirred at rt for 2 h. After concentration, the residue was purified by preparative HPLC to afford (S)-6'-chloro-5-(((1R,2R)-2-((S)-1-methoxyallyl) cyclobutyl) methyl)-N—((R)-oxo(pent-4-en-1-yl)(propionamido)-16-sulfanylidene)-3',4,4',5-tetrahydro-2H,2'H-spiro[benzo[b][1,4]oxazepine-3,1'-naphthalene]-7-carboxamide.

Step 4: Preparation of Example 3 and Example 4

(S)-6'-chloro-5-(((1R,2R)-2-((S)-1-methoxyallyl)cyclobutyl)methyl)-N—((R)-oxo(pent-4-en-1-yl)(propionamido)-16-sulfanylidene)-3',4,4',5-tetrahydro-2H,2'H-spiro [benzo[b][1,4] oxazepine-3,1'-naphthalene]-7-carboxamide (55.0 mg, 0.082 mmol) and Hoveyda Grubbs generation 2 catalyst (5.14 mg, 0.008 mmol) were stirred in 1,2-dichloroethane (16.0 mL) at 60° C. for 4 h. After concentration, the residue was purified by preparative HPLC to afford Example 3 (more polar fraction) (LCMS-ESI+ (m/z): [M+H]+ calcd for C₃₄H₄₂ClN₃O₅S: 640.2; found: 640.2) and Example 4 (less polar fraction) (¹H NMR (400 MHz, Chloroform-d) δ 7.68 (d, J=9.2 Hz, 1H), 7.37-7.35 (m, 1H), 7.23 (s, 1H), 7.08-7.06 (m, 2H), 6.92 (d, J=8.4 Hz, 1H), 5.86-5.82 (m, 1H), 5.74-5.70 (m, 1H), 4.06 (d, J=12.0 Hz, 1H), 3.99-3.95 (m, 2H), 3.81-3.71 (m, 4H), 3.59-3.57 (m, 1H), 3.34 (d, J=14.8 Hz, 1H), 3.29 (s, 3H), 3.04-2.98 (m, 1H), 2.78-2.73 (m, 4H), 2.50 (q, J=7.4 Hz, 2H), 2.38-1.66 (m, 10H), 1.39-1.34 (m, 1H), 1.22 (t, J=7.4 Hz, 3H). LCMS-ESI+ (m/z): [M+H]+ calcd for C₃₄H₄₂ClN₃O₅S: 640.2; found: 640.2).

Examples 5 and 6

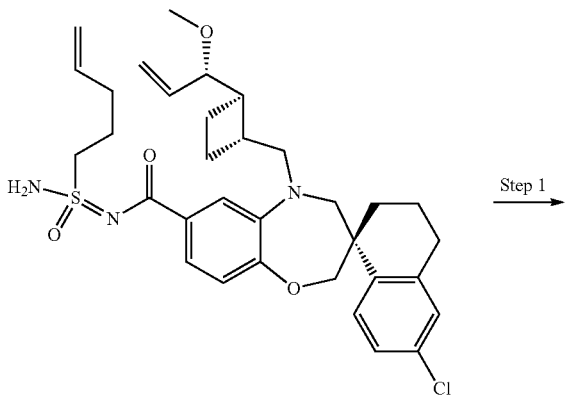

Step 1

-continued

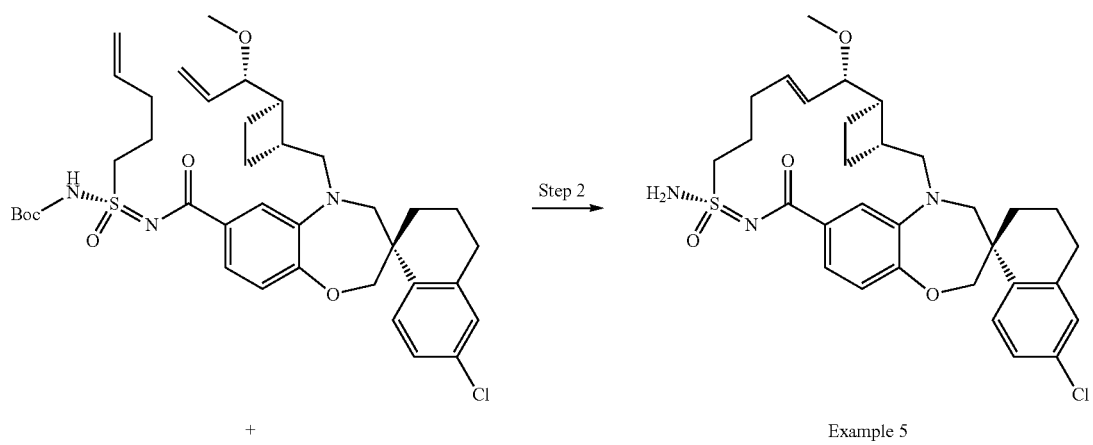

Example 5

+

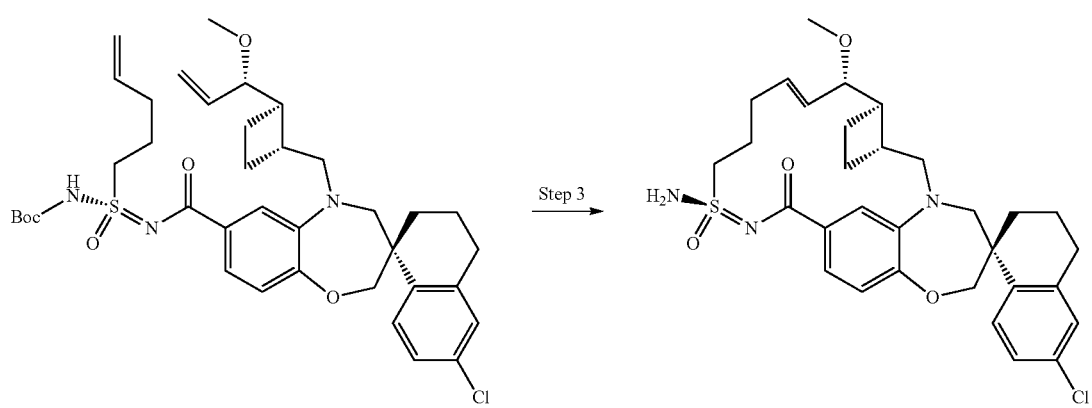

Example 6

Method 1

Step 1: Preparation of tert-butyl ((R)—N—((S)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carbonyl)pent-4-en-1-ylsulfonimidoyl)carbamate and tert-butyl (N—((S)-6'-chloro-5-(((1R,2R)-2-((S)-1-methoxyallyl)cyclobutyl) methyl)-3',4,4',5-tetrahydro-2H,2'H-spiro[benzo[b][1,4]oxazepine-3,1'-naphthalene]-7-carbonyl)pent-4-en-1-ylsulfonimidoyl)carbamate To a stirred solution of (3S)—N-(amino(oxo)(pent-4-en-1-yl)-16-sulfanylidene)-6'-chloro-5-(((1R,2R)-2-((S)-1-methoxyallyl)cyclobutyl)methyl)-3',4,4',5-tetrahydro-2H, 2'H-spiro[benzo[b][1,4] oxazepine-3,1'-naphthalene]-7-carboxamide (Example 3/4 step 2, 32.00 mg, 0.052 mmol) in CH$_2$Cl$_2$ (5.0 mL) was added triethylamine (0.02 mL, 0.105 mmol) in an ice bath, followed by di-tert-butyl dicarbonate (17.11 mg, 0.078 mmol). The resulting mixture was stirred at rt overnight. After concentration, the residue was purified by preparative HPLC to afford tert-butyl ((R)—N—((S)-6'-chloro-5-(((1R,2R)-2-((S)-1-methoxyallyl)cyclobutyl)methyl)-3',4,4',5-tetrahydro-2H,2'H-spiro[benzo[b][1,4] oxazepine-3,1'-naphthalene]-7-carbonyl)pent-4-en-1-ylsulfonimidoyl)carbamate from more polar fraction, and tert-butyl (N—((S)-6'-chloro-5-(((1R,2R)-2-((S)-1-methoxyallyl) cyclobutyl)methyl)-3',4,4',5-tetrahydro-2H, 2'H-spiro[benzo[b][1,4]oxazepine-3,1'-naphthalene]-7-carbonyl)pent-4-en-1-ylsulfonimidoyl)carbamate from less polar fraction.

Step 2: Preparation of Example 5 tert-butyl (N—((S)-6'-chloro-5-(((1R,2R)-2-((S)-1-methoxyallyl)cyclobutyl)methyl)-3',4,4',5-tetrahydro-2H, 2'H-spiro[benzo[b] [1,4]oxazepine-3,1'-naphthalene]-7-carbonyl)pent-4-en-1-ylsulfonimidoyl)carbamate (14 mg, 0.02 mmol) and Hoveyda Grubbs generation 2 catalyst (1.25 mg, 0.002 mmol) were stirred in 1,2-dichloroethane (6.0 mL) at 60° C. for 4 h. After concentration, the residue was purified by preparative HPLC to afford Example 5. LCMS-ESI+ (m/z): [M+H]+ calcd for C$_{31}$H$_{38}$ClN$_3$O$_4$S: 584.2; found: 584.2.

Step 3: Preparation of Example 6

Example 6 was synthesized in the same manner as Example 5 using tert-butyl ((R)—N—((S)-6'-chloro-5-(((1R,2R)-2-((S)-1-methoxyallyl)cyclobutyl)methyl)-3',4, 4',5-tetrahydro-2H,2'H-spiro[benzo[b][1,4] oxazepine-3,1'-naphthalene]-7-carbonyl)pent-4-en-1-ylsulfonimidoyl) carbamate. LCMS-ESI+ (m/z): [M+H]+ calcd for C$_{31}$H$_{38}$ClN$_3$O$_4$S: 584.2; found: 584.2.

Method 2

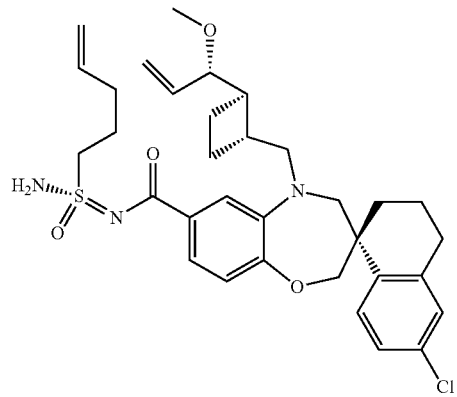

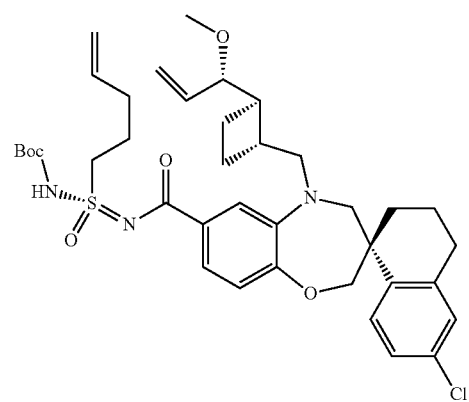

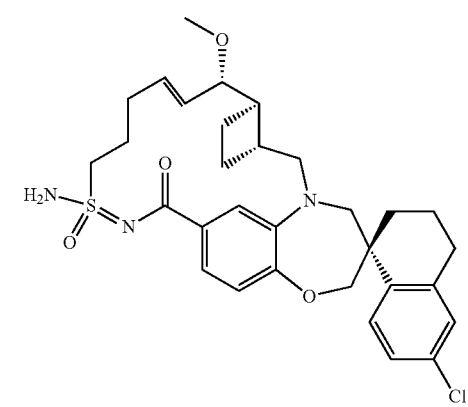

I

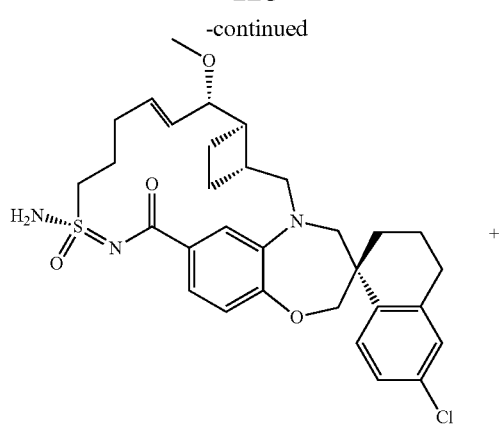

Example 5

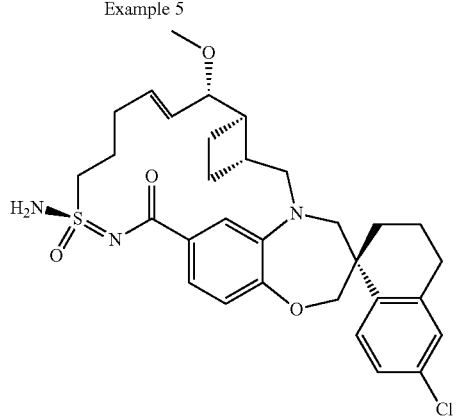

Example 6

Step 1: Preparation of tert-butyl ((R)—N—((S)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carbonyl)pent-4-en-1-ylsulfonimidoyl)carbamate To a stirred solution of (3S)—N-(amino(oxo)(pent-4-en-1-yl)-16-sulfanylidene)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carboxamide (140.00 mg, 0.229 mmol) in $CH_2Cl_2$ (5.0 mL) was added triethylamine (0.06 mL, 0.458 mmol) in an ice bath, followed by di-tert-butyl dicarbonate (74.97 mg, 0.343 mmol). The resulting mixture was stirred at rt overnight. After concentration, the residue was purified by prep-HPLC to afford tert-butyl ((R)—N—((S)-6'-chloro-5-(((1R,2R)-2-((S)-1-methoxyallyl) cyclobutyl)methyl)-3',4,4',5-tetrahydro-2H,2'H-spiro[benzo[b] [1,4]oxazepine-3,1'-naphthalene]-7-carbonyl)pent-4-en-1-ylsulfonimidoyl)carbamate as a mixture of diastereomers.

Step 2 and Step 3

The Boc protected mixture of diastereomers from Method 2 Step 1 (112.0 mg, 0.157 mmol) and Hoveyda Grubbs generation 2 catalyst (9.83 mg, 0.016 mmol) were stirred in 1,2-dichloroethane (6.0 mL) at 60° C. for 4 h. After concentration, the residue was purified by preparative HPLC to afford intermediate 5-1 as a mixture of diastereomers, which were purified by silica gel column chromatography (EtOAc/

Hexanes=3/2) to give Example 5 (less polar fraction) and Example 6 (more polar fraction).
Step 1: Preparation of (S)-4-nitrophenyl (1-phenyl-ethyl) carbonate (5-3-1)
The mixture of (1S)-1-(4-phenylphenyl)ethanol (8.7 g, 71.2 mmol) was dissolved in MeTHF (90 mL) and cooled to
Method 3
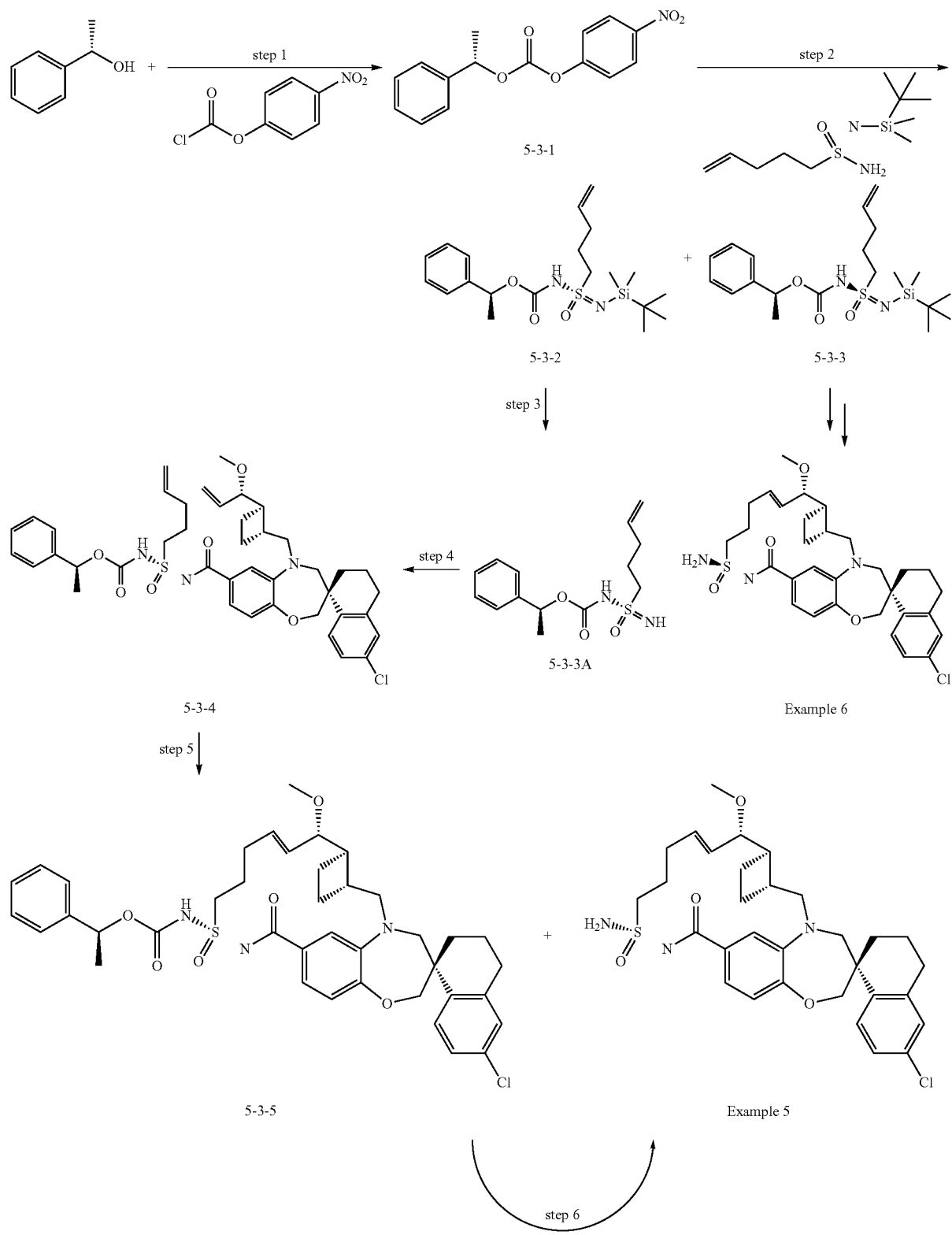

0° C. To this cold stirred solution was added pyridine (7.1 mL). A solution of 4-nitro-phenyl-chloroformate (14.4 g, 71.2 mmol) in MeTHF (60.0 mL) was then added dropwise via dropping funnel. After addition, the resulting mixture was removed from the cooling bath and stirred at ambient for 2 hrs. TLC showed (1S)-1-(4-phenylphenyl)ethanol has been consumed but 4-nitro-phenyl-chloroformate still remained. Additional (1S)-1-(4-phenylphenyl)ethanol (2.6 g, 21.3 mmol) and pyridine (1.0 mL) were added and stirring continued for overnight. The reaction was then washed with 1N HCl (2×), brine (2×), dried over sodium sulfate, filtered and concentrated. The residue was then dissolved in DCM and mixed with silica gel, concentrated to dryness, divided into two runs, purified by normal phase chromatography (silica gel, 0-20% EtOAc/Hexanes). Desired fractions were combined and concentrated to give 5-3-1. 1H NMR (400 MHz, Chloroform-d) δ 8.34-8.16 (m, 2H), 7.48-7.31 (m, 7H), 5.84 (q, J=6.6 Hz, 1H), 1.70 (d, J=6.6 Hz, 3H).

Step 2

A solution of N'-(tert-butyldimethylsilyl)pent-4-ene-1-sulfonimidamide (2.0 g, 7.18 mmol) in THF (100 mL) was cooled to −50° C. 1.6 M n-BuLi in hexanes (9.65 mL, 15.4 mmol) was added dropwise to this cold solution. The newly formed mixture was stirred at −50° C. for 20 min before a solution of (4-nitrophenyl) [(1S)-1-phenylethyl] carbonate in THF (60 mL) was added dropwise slowly. The resulting mixture was stirred at −50° C. for 15 min and then switched to ice-water bath and stirred at 0° C. for 3 hrs. The reaction was quenched with ice and extracted with EtOAc (1×). The organic layer was washed with 1N NaOH (3×), brine (1×), dried over sodium sulfate, filtered, concentrated, and purified by normal phase chromatography (silica gel, 0-20% EtOAc/Hexanes). The purification was repeated and the desired fractions were combined and concentrated to give a mixture of diastereomers (5-3-2) and (5-3-3). The mixture of diastereomers was subsequently separated into single diastereomers by chiral SFC. The first eluted peak was assigned the chirality as depicted in (5-3-2); the second eluted peak was assigned the chirality as depicted in (5-3-3). 1H NMR (400 MHz, Chloroform-d) for the mixture of diastereomers: δ 7.41-7.29 (m, 5H), 5.84-5.59 (m, 2H), 5.08-4.93 (m, 2H), 3.37-3.16 (m, 2H), 2.19-2.07 (m, 2H), 1.83 (h, J=7.3, 6.7 Hz, 2H), 1.57 (dq, J=6.6, 1.8 Hz, 3H), 0.91-0.85 (m, 9H), 0.18 (two sets of s, 3H), 0.12 (two sets of s, 3H). 1H NMR (400 MHz, Chloroform-d) for (5-3-2): δ 7.39-7.30 (m, 5H), 5.86-5.58 (m, 2H), 5.07-4.93 (m, 2H), 3.28 (tq, J=13.9, 7.9, 7.1 Hz, 2H), 2.13 (p, J=7.7, 7.2 Hz, 2H), 1.85 (p, J=7.2 Hz, 2H), 1.57 (dd, J=6.6, 2.2 Hz, 3H), 0.93-0.91 (m, 9H), 0.19 (two sets of s, 6H).

Step 3

The solution of intermediate (5-3-2) (858 mg, 2.1 mmol) in THF (24 mL) was treated with 1.0 M tetrabutylammonium fluoride in THF (6.3 mL, 6.3 mmol) at rt for 60 min. The reaction was then concentrated and purified by normal phase chromatography (silica gel, 0-80% EtOAc/Hexanes) to give 5-3-3A. 1H NMR (400 MHz, Chloroform-d) δ 7.45-7.31 (m, 4H), 5.83-5.59 (m, 2H), 5.12-4.96 (m, 2H), 3.35-3.21 (m, 2H), 2.28-2.11 (m, 2H), 2.01-1.87 (m, 2H), 1.59 (d, J=6.7 Hz, 3H).

Step 4

To the mixture of (3S)-6'-chloro-5-[[(1R,2R)-2-[(1S)-1-methoxyallyl]cyclobutyl]methyl]spiro[2,4-dihydro-1,5-benzoxazepine-3,1'-tetralin]-7-carbonyl chloride (215 mg, 0.45 mmol) in DCM (20 mL) at 0° C. was added 1-(3-dimethylaminopropyl)-3-ethylcarbodiimide (152 mg, 0.98 mmol) followed by 4-(dimethylamino)pyridine (120 mg, 0.98 mmol). After stirred for 5 min, a solution of intermediate (5-3-3A) (159 mg, 0.54 mmol) in DCM (3 mL) was added and the resulting mixture was removed from the cooling bath and stirred at rt overnight. The reaction was further diluted with DCM (30 mL) and washed with 1N HCl (15 mL), saturated sodium bicarbonate (15 mL) and brine (15 mL), dried over sodium sulfate, filtered, concentrated and purified by normal phase chromatography (silica gel column, 0-80% EtOAc/Hexanes) to give intermediate 5-3-4. LCMS-ESI+ (m/z): [M+H]+ calcd: 761.0, found: 759.9. 1H NMR (400 MHz, Chloroform-d) δ 7.67 (d, J=8.5 Hz, 1H), 7.50 (s, 1H), 7.39-7.28 (m, 6H), 7.16 (dd, J=8.5, 2.3 Hz, 1H), 7.08 (d, J=2.3 Hz, 1H), 6.91 (d, J=8.2 Hz, 1H), 5.86 (p, J=6.3 Hz, 1H), 5.77-5.48 (m, 2H), 5.21-5.08 (m, 2H), 5.08-4.96 (m, 2H), 4.14-4.04 (m, 2H), 3.81-3.71 (m, 2H), 3.70-3.48 (m, 3H), 3.39-3.13 (m, 5H), 2.84-2.69 (m, 2H), 2.52 (dd, J=10.7, 7.4 Hz, 1H), 2.16 (dt, J=13.3, 7.6 Hz, 3H), 2.01-1.74 (m, 7H), 1.70-1.39 (m, 7H).

Step 5

The solution intermediate 5-3-4 in DCE (10 mL) was sparged with nitrogen for 5 min before Hoveyda-Grubbs 2$^{nd}$ generation catalyst (7 mg, 0.011 mmol) was added. The newly formed mixture was degassed for another 2 minutes and then it was capped and heated at 60° C. for 16 hrs. The reaction was then cooled to rt, concentrated, purified by normal phase chromatography (silica gel, 0-5% DCM/MeOH (with 2.0 N NH$_3$)) to give Example 5 (first eluted peak: LCMS-ESI+ (m/z): [M+H]+ calcd: 584.2; found: 583.4); and the carbamate protected macrocycle intermediate 5-3-5 (second eluted peak: LCMS-ESI+ (m/z): [M+H]+ calcd: 732.3; found: 730.8).

Step 6

Intermediate 5-3-5 (15.8 mg, 0.022 mmol) was dissolved in DCM (1.0 mL) at 0° C. TFA (1.0 mL) was added to this cold solution. The resulting mixture was stirred at 0° C. for 2 min and then rt for 1 hr. The reaction was cooled back to 0° C. and basified with 1N NaOH to pH~8. The mixture was extracted with DCM (2×). Combined organic layers was washed with brine (1×), dried over sodium sulfate, filtered, concentrated and purified by Combiflash (silica gel, 0-100% EtOAc/Hexanes) to give Example 5. LCMS-ESI+ (m/z): [M+H]+ calcd: 584.2; found: 583.3. 1H NMR (400 MHz, Chloroform-d) for (8): δ 7.73 (d, J=8.6 Hz, 1H), 7.44-7.39 (m, 1H), 7.33 (d, J=1.8 Hz, 1H), 7.16 (dd, J=8.5, 2.3 Hz, 1H), 7.06 (d, J=2.3 Hz, 1H), 6.90 (d, J=8.2 Hz, 1H), 6.04-5.93 (m, 1H), 5.73-5.61 (m, 1H), 4.12-3.94 (m, 2H), 3.88-3.68 (m, 2H), 3.62-3.51 (m, 2H), 3.40-3.17 (m, 6H), 3.00 (dd, J=15.0, 11.0 Hz, 1H), 2.82-2.63 (m, 4H), 2.47-2.20 (m, 4H), 1.99-1.59 (m, 6H), 1.37 (t, J=13.1 Hz, 1H).

Example 6 was synthesized in the same manner as Example 5 (Method 3-Step 3-6) using intermediate 5-3-3 instead of intermediate 5-3-2.

Examples 7 and 8

Example 7

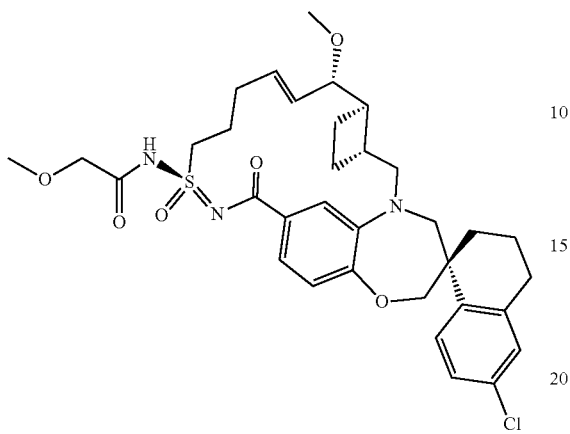

Example 8

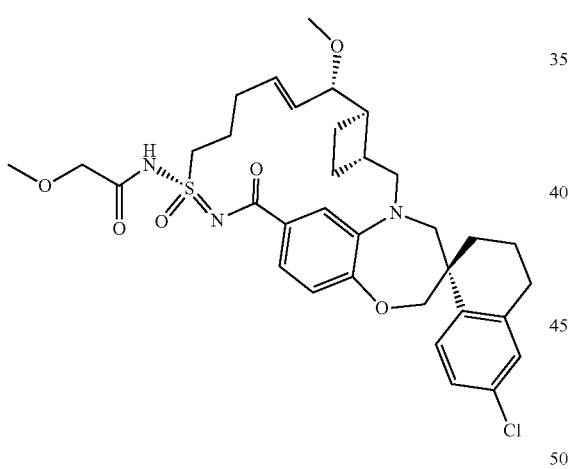

Example 7 and Example 8 were prepared in similar manner to Example 3 and Example 4 using 2-methoxyacetyl chloride instead of propionyl chloride.

Example 7

LCMS-ESI+ (m/z): [M+H]+ calcd for $C_{34}H_{42}ClN_3O_6S$: 656.2; found: 656.2.

Example 8

LCMS-ESI+ (m/z): [M+H]+ calcd for $C_{34}H_{42}ClN_3O_6S$: 656.2; found: 656.2.

Example 9 and 10

Example 9

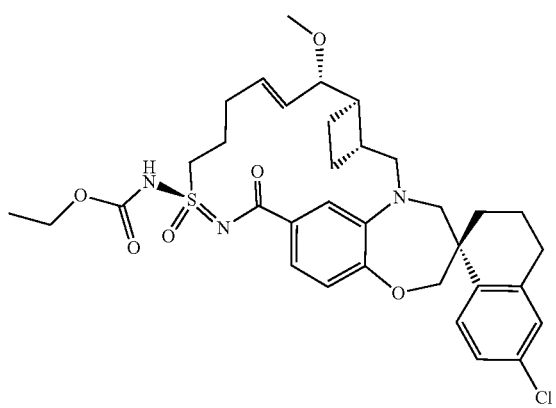

Example 10

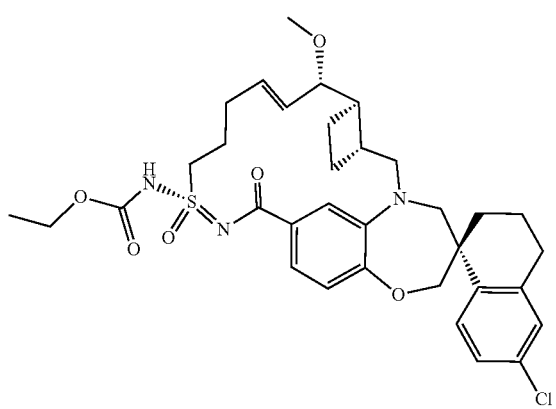

Preparation of Example 9 and Example 10

To a stirred solution of intermediate 5-1 (Example 5/6 Method 2, 10.40 mg, 0.018 mmol) in $CH_2Cl_2$ (5.0 mL) was added triethylamine (0.004 mL, 0.027 mmol) in an ice bath, followed by ethyl chloroformate (2.32 mg, 0.021 mmol). The resulting mixture was stirred at rt for 2 h. After concentration, the residue was purified by preparative HPLC to afford Example 9 (more polar fraction) (LCMS-ESI+ (m/z): [M+H]+ calcd for $C_{34}H_{42}ClN_3O_6S$: 656.2; found: 656.2) and Example 10 (less polar fraction).

Examples 11 and 12

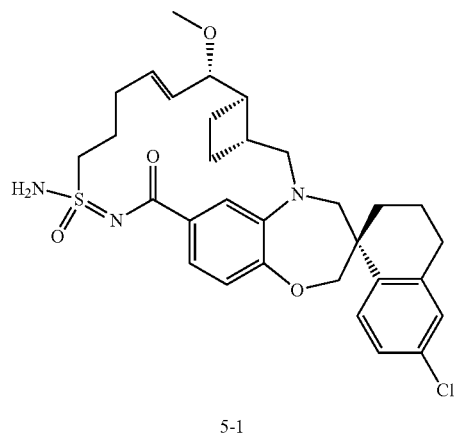

5-1

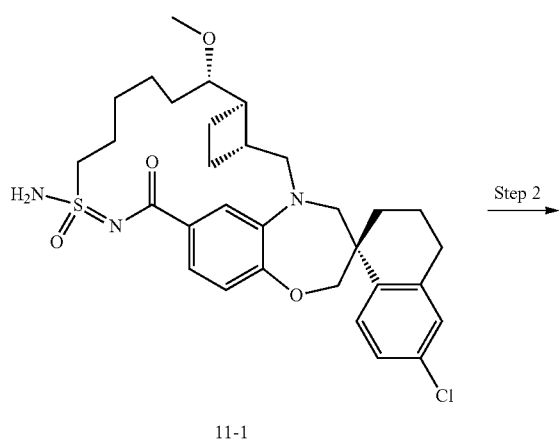

11-1

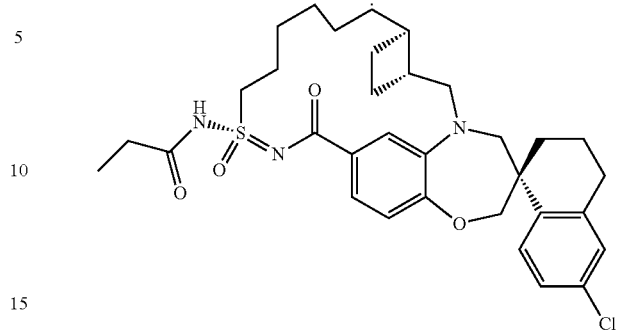

Example 12

Step 1: Preparation of Intermediate 11-1

To a stirred solution of intermediate 5-1 (Example 5/6 Method 2, 17.90 mg, 0.031 mmol) in EtOAc (5 mL) was added Platinum (IV) oxide (3.48 mg, 0.015 mmol). The resulting mixture was stirred at rt under $H_2$ for 0.5 h. Filtered the reaction mixture through Celite, and washed with EtOAc. The filtrate was concentrated. Crude product (18.0 mg) was used directly for next step.

Step 2: Preparation of Example 11 and Example 12

To a stirred solution of intermediate 11-1 (18.0 mg, 0.031 mmol) in $CH_2Cl_2$ (4.0 mL) was added triethylamine (0.006 mL, 0.046 mmol) in an ice bath, followed by propionyl chloride (3.41 mg, 0.037 mmol). The resulting mixture was stirred at rt for 2 h. After concentration, the residue was purified by preparative HPLC to afford Example 11 (more polar fraction) (LCMS-ESI+ (m/z): [M+H]+ calcd for $C_{34}H_{44}ClN_3O_5S$: 642.3; found: 642.2) and Example 12 (less polar fraction) (LCMS-ESI+ (m/z): [M+H]+ calcd for $C_{34}H_{44}ClN_3O_5S$: 642.3; found: 642.3).

Examples 13 and 14

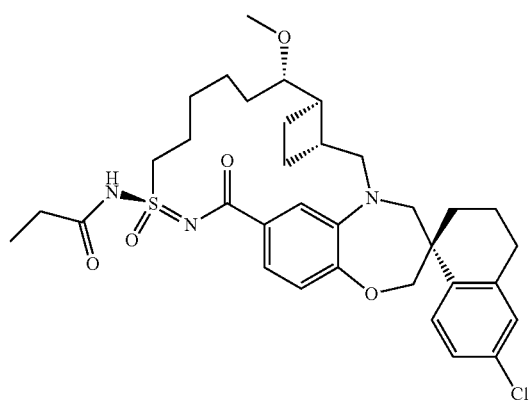

Example 11

+

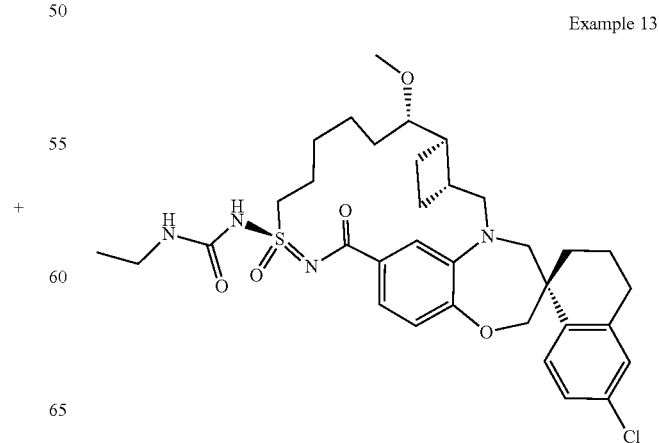

Example 13

Example 14

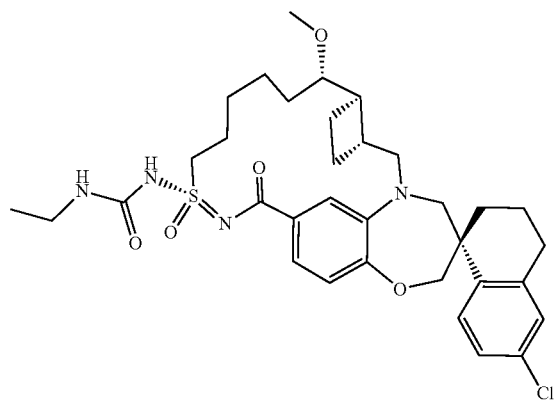

Examples 16 and 17

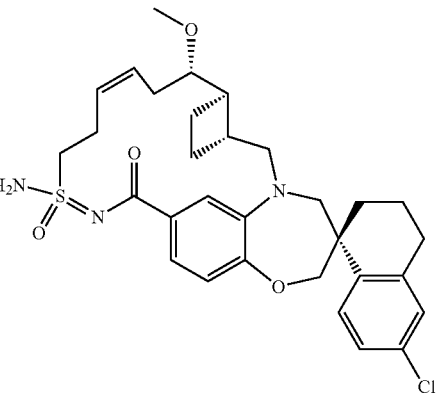

5-1

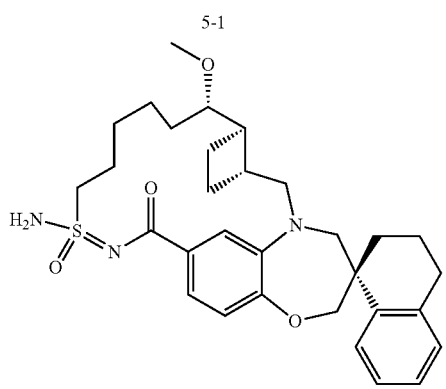

16-1

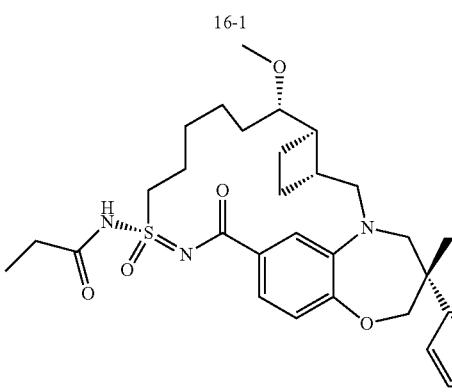

Example 16

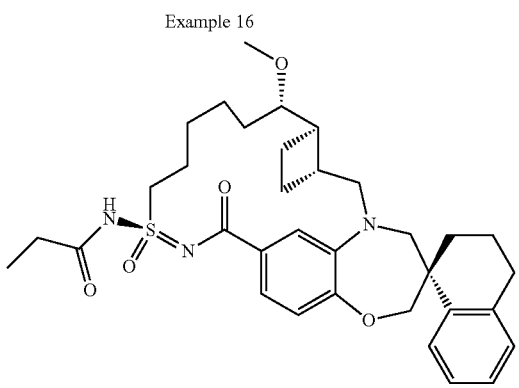

Example 17

Preparation of Example 13 and Example 14

To a stirred solution of intermediate 5-1 (Example 5 and 6 Method 2, 10.9 mg, 0.019 mmol) in CH$_2$Cl$_2$ (4.0 mL) was added triethyl amine (0.004 mL, 0.028 mmol) in an ice bath, followed by ethyl isocyanate (1.59 mg, 0.022 mmol). The resulting mixture was stirred at rt for 2 h. After concentration, the residue was purified by preparative HPLC followed by prep-TLC (5% MeOH/CH$_2$Cl$_2$) to afford Example 13 (more polar fraction) (LCMS-ESI+ (m/z): [M+H]+ calcd for C$_{34}$H$_{43}$ClN$_4$O$_5$S: 655.3; found: 655.2), and Example 14 (less polar fraction) ($^1$H NMR (400 MHz, chloroform-d) δ 7.71 (w, 1H), 7.31 (w, 1H), 7.16 (w, 2H), 7.02 (w, 1H), 6.78 (w, 1H), 5.76 (w, 2H), 4.02-3.94 (m, 2H), 3.72-2.65 (m, 11H), 2.34-0.84 (m, 17H). LCMS-ESI+ (m/z): [M+H]+ calcd for C$_{34}$H$_{43}$ClN$_4$O$_5$S: 655.3; found: 655.2.

Example 15

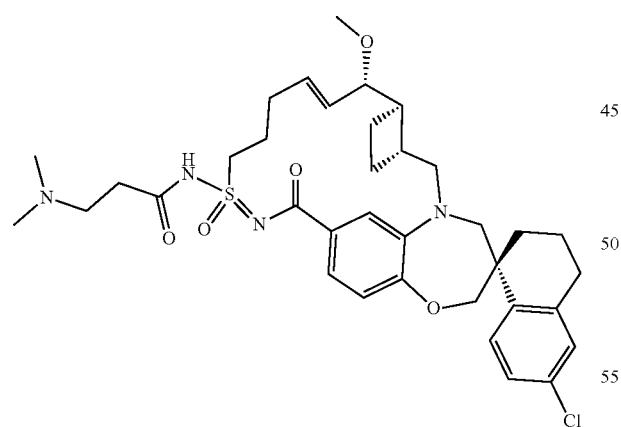

To a stirred solution of 3-(dimethylamino)propionic acid hydrochloride (3.94 mg, 0.026 mmol) in CH$_2$Cl$_2$ (3 mL) was added Et$_3$N (0.01 mL, 0.068 mmol), EDCI (5.32 mg, 0.034 mmol), and DMAP (4.18 mg, 0.034 mmol), followed by intermediate 5-1 (Example 5/6 Method 2, 10.00 mg, 0.017 mmol). The resulting mixture was stirred at rt for 3 h and concentrated. The residue was purified by preparative HPLC to afford Example 15. LCMS-ESI+ (m/z): [M+H]+ calcd for C$_{36}$H$_{47}$ClN$_4$O$_5$S: 683.3; found: 683.3.

Step 1: Preparation of Intermediate 16-1

To a stirred solution of intermediate 5-1 (Example 5/6 Method 2, 20.00 mg, 0.034 mmol) in MeOH (5 mL) was added Pd/C (10% weight, 0.36 mg, 0.03 mmol). The resulting mixture was stirred at rt under $H_2$ for 1.5 h. Filtered the reaction mixture through celite, and washed with MeOH. The filtrate was concentrated. Crude product was used directly for next step.

Step 2: Preparation of Example 16 and Example 17

Crude intermediate 16-1 from step 1 was then coupled with propionyl chloride and purified in similar manner to Example 11 and Example 12 to give Example 16 (less polar fraction) (LCMS-ESI+ (m/z): [M+H]+ calcd for $C_{34}H_{45}N_3O_5S$: 607.8; found: 608.3) and Example 17 (more polar fraction) (LCMS-ESI+ (m/z): [M+H]+ calcd for $C_{34}H_{45}N_3O_5S$: 607.8; found: 608.4.

Example 18

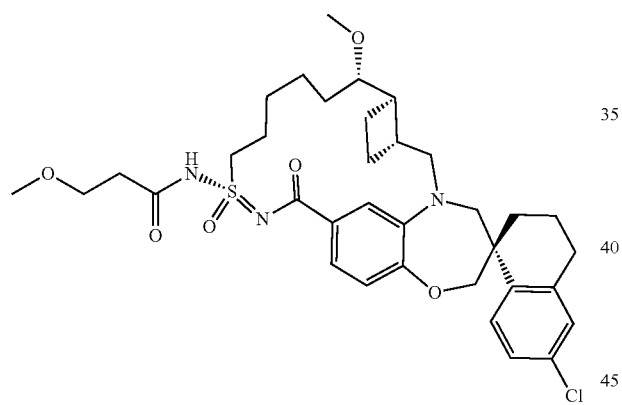

Example 18

To a stirred solution of 3-methoxypropionic acid (2.3 mg, 0.022 mmol) in $CH_2Cl_2$ (2 mL) was added EDCI (4.52 mg, 0.029 mmol), and DMAP (3.56 mg, 0.029 mmol), followed by Example 5 (8.50 mg, 0.015 mmol). The resulting mixture was stirred at rt for 3 h and concentrated. The residue was purified by preparative HPLC to afford Example 18. $^1$H NMR (400 MHz, Chloroform-d) δ 7.73 (d, J=8.8 Hz, 1H), 7.41 (dd, J=8.4, 2.0 Hz, 1H), 7.29-7.28 (m, 1H), 7.13 (dd, J=8.4, 2.4 Hz, 1H), 7.09 (d, J=2.4 Hz, 1H), 6.94 (d, J=8.4 Hz, 1H), 5.88 (dt, J=15.8, 5.0 Hz, 1H), 5.75 (dd, J=15.8, 7.8 Hz, 1H), 4.05 (dd, J=32.4, 12.0 Hz, 2H), 3.95-3.73 (m, 6H), 3.60 (dd, J=8.0, 3.2 Hz, 1H), 3.46 (s, 3H), 3.37 (d, J=14.4 Hz, 1H), 3.32 (s, 3H), 3.04 (dd, J=15.0, 11.0 Hz, 1H), 2.80-2.71 (m, 5H), 2.43-2.28 (m, 4H), 2.11-1.69 (m, 8H), 1.42-1.36 (m, 1H). LCMS-ESI+ (m/z): [M+H]+ calcd for $C_{35}H_{44}ClN_3O_6S$: 670.3; found: 670.4.

Example 19

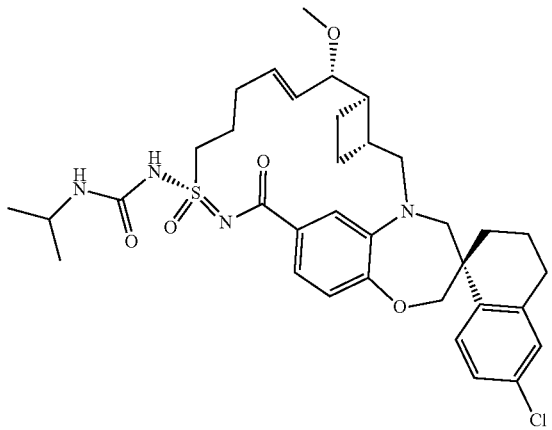 [SMILES: CO[C@H]1/C=C/CCC[S@@](=O)(NC(=O)NC(C)C)=NC(=O)c2ccc3c(c2)N(C[C@@H]2CC[C@H]21)C[C@@]1(CCCc2cc(Cl)ccc21)CO3]

To a stirred solution of Example 5 (8.5 mg, 0.015 mmol) in $CH_2Cl_2$ (2.0 mL) was added triethylamine (0.003 mL, 0.022 mmol) in an ice bath, followed by isopropyl isocyanate (1.86 mg, 0.022 mmol). The resulting mixture was stirred at rt for 2 h. After concentration, the residue was purified by preparative HPLC followed by prep-TLC (5% MeOH/$CH_2Cl_2$) to afford Example 19. LCMS-ESI+ (m/z): [M+H]+ calcd for $C_{35}H_{45}ClN_4O_5S$: 669.3; found: 691.3.

Example 20

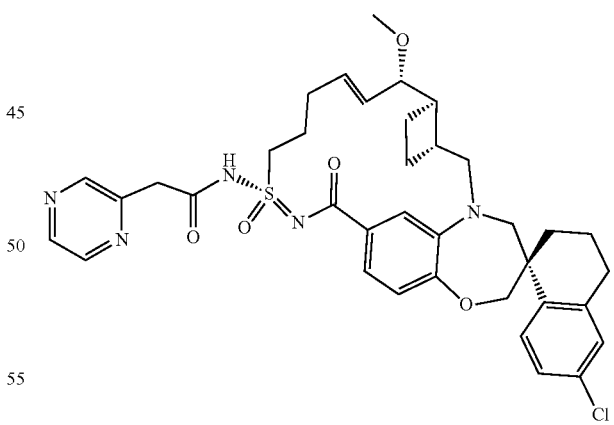

Example 20 was synthesized in the same manner as Example 18 using 2-(pyrazin-2-yl)acetic acid instead of 3-methoxypropionic acid. LCMS-ESI+ (m/z): [M+H]+ calcd for $C_{37}H_{42}ClN_5O_5S$: 704.3; found: 704.4.

Example 21

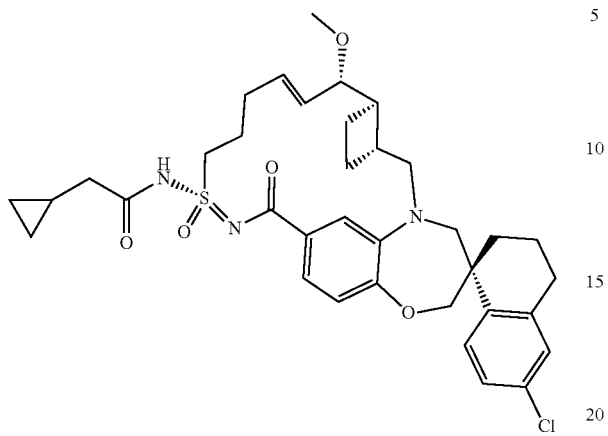

To a stirred solution of Example 5 (10.0 mg, 0.017 mmol) in CH$_2$Cl$_2$ (2.0 mL) was added triethylamine (0.004 mL, 0.026 mmol) in an ice bath, followed by cyclopropylacetyl chloride (3.04 mg, 0.026 mmol). The resulting mixture was stirred at rt for 2 h. After concentration, the residue was purified by preparative HPLC to afford Example 21. LCMS-ESI+ (m/z): [M+H]+ calcd for C$_{36}$H$_{44}$ClN$_3$O$_5$S: 666.3; found: 666.3.

Example 22

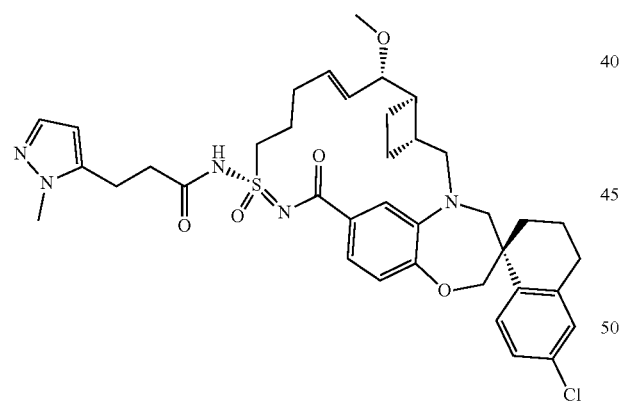

Example 22 was synthesized in the same manner as Example 18 using 3-(1-methyl-1H-pyrazol-5-yl)propanoic acid instead of 3-methoxypropionic acid. $^1$H NMR (400 MHz, Chloroform-d) δ 7.64 (d, J=2.0 Hz, 1H), 7.47 (d, J=8.8 Hz, 1H), 7.29-7.27 (m, 1H), 7.04 (d, J=2.0 Hz, 2H), 6.99 (d, J=8.0 Hz, 1H), 6.64-6.61 (m, 1H), 6.33 (d, J=2.4 Hz, 1H), 5.82 (d, J=4.8 Hz, 2H), 3.99-3.94 (m, 6H), 3.70-3.56 (m, 4H), 3.45-3.28 (m, 4H), 3.11-2.98 (m, 4H), 2.87-2.72 (m, 4H), 2.58-1.75 (m, 12H), 1.32-1.26 (m, 1H). LCMS-ESI+ (m/z): [M+H]+ calcd for C$_{38}$H$_{46}$ClN$_5$O$_5$S: 720.3; found: 720.4.

Example 23

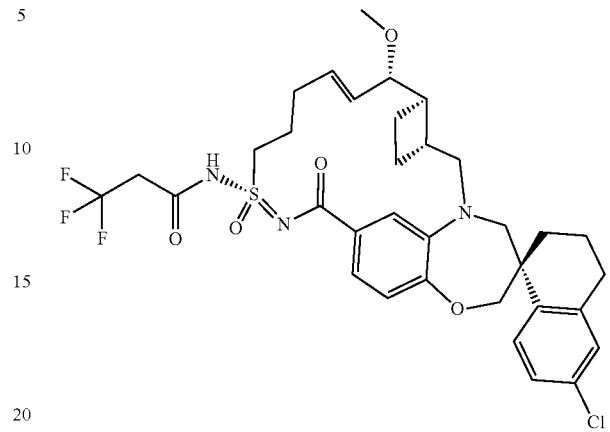

Example 23 was synthesized in the same manner as Example 21 using 3,3,3-trifluoropropionyl chloride instead of cyclopropylacetyl chloride. LCMS-ESI+ (m/z): [M+H]+ calcd for C$_{34}$H$_{39}$ClF$_3$N$_3$O$_5$S: 694.2; found: 694.4.

Example 24

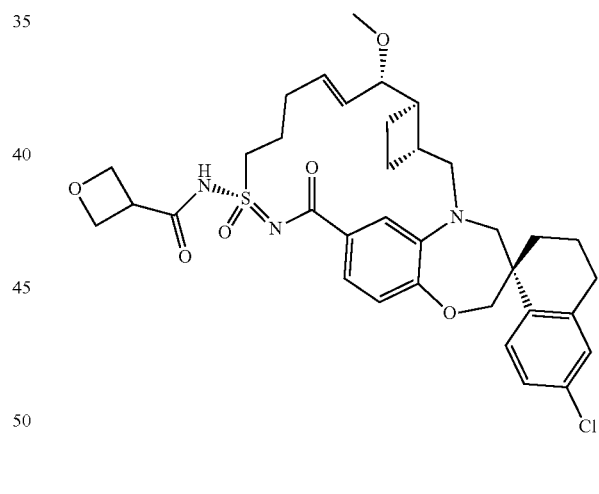

Example 24 was synthesized in the same manner as Example 18 using oxetane-3-carboxylic acid instead of 3-methoxypropionic acid. $^1$H NMR (400 MHz, Methanol-d4) δ 7.75 (d, J=8.4 Hz, 1H), 7.23 (dd, J=8.0, 2.0 Hz, 1H), 7.17-7.14 (m, 2H), 7.07 (d, J=2.4 Hz, 1H), 6.79 (d, J=8.0 Hz, 1H), 6.06 (dt, J=15.4, 6.2 Hz, 1H), 5.60 (dd, J=15.6, 8.8 Hz, 1H), 4.90-4.76 (m, 4H), 4.17-3.93 (m, 4H), 3.91-3.79 (m, 3H), 3.72-3.47 (m, 5H), 3.24 (s, 3H), 3.02 (dd, J=15.0, 10.6 Hz, 1H), 2.83-2.69 (m, 2H), 2.65-1.37 (m, 11H). LCMS-ESI+ (m/z): [M+H]+ calcd for C$_{35}$H$_{42}$ClN$_3$O$_6$S: 668.3; found: 668.6.

Example 25

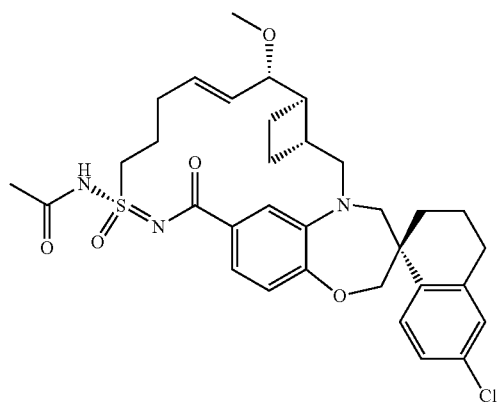 [SMILES: CO[C@H]1/C=C/CCC[S@@](=O)(NC(C)=O)=NC(=O)c2ccc3c(c2)N(C[C@@H]2CC[C@H]21)C[C@@]1(CCCc2cc(Cl)ccc21)CO3]

Example 25 was synthesized in the same manner Example 21 using acetyl chloride instead of cyclopropylacetyl chloride. LCMS-ESI+ (m/z): [M+H]+ calcd for $C_{33}H_{40}ClN_3O_5S$: 626.2; found: 626.4.

Example 26

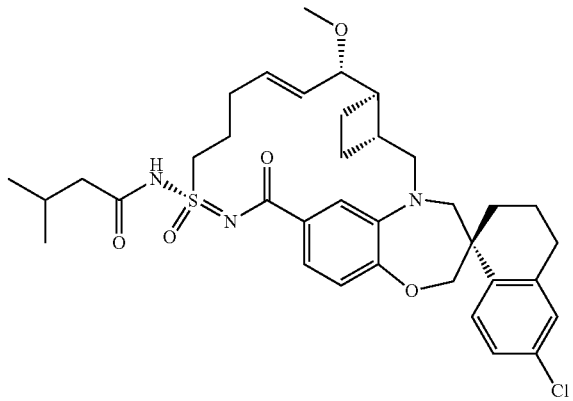 [SMILES: CO[C@H]1/C=C/CCC[S@@](=O)(NC(=O)CC(C)C)=NC(=O)c2ccc3c(c2)N(C[C@@H]2CC[C@H]21)C[C@@]1(CCCc2cc(Cl)ccc21)CO3]

Example 26 was synthesized in the same manner as Example 21 using isovaleryl chloride instead of cyclopropylacetyl chloride. LCMS-ESI+ (m/z): [M+H]+ calcd for $C_{36}H_{46}ClN_3O_5S$: 668.3; found: 668.4.

Example 27

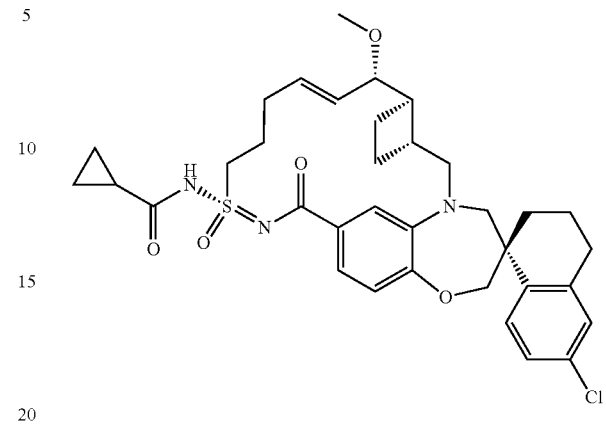

Example 27 was synthesized in the same manner as Example 21 using cyclopropylacetyl chloride instead of cyclopropylacetyl chloride. LCMS-ESI+ (m/z): [M+H]+ calcd for $C_{35}H_{42}ClN_3O_5S$: 652.3; found: 652.4.

Example 28

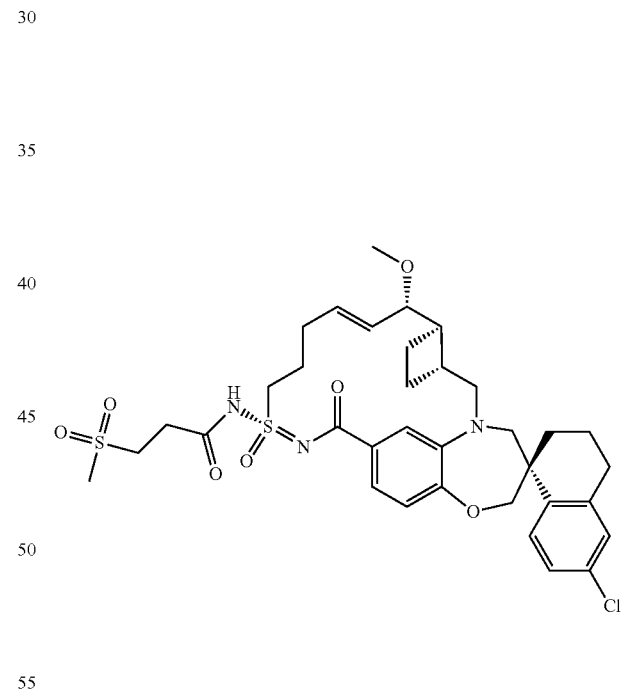

Example 28 was synthesized in the same manner as Example 18 using 3-(methylsulfonyl)propanoic acid instead of 3-methoxypropionic acid. LCMS-ESI+ (m/z): [M+H]+ calcd for $C_{35}H_{44}ClN_3O_7S_2$: 718.3; found: 718.3.

Example 29

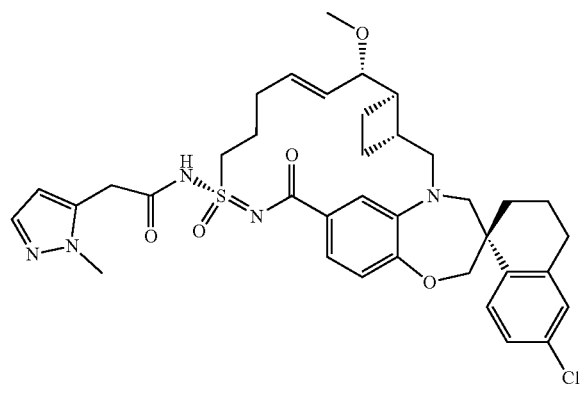 [SMILES: CO[C@H]1/C=C/CCC[S@@](=O)(NC(=O)Cc2ccnn2C)=NC(=O)c2ccc3c(c2)N(C[C@@H]2CC[C@H]21)C[C@@]1(CCCc2cc(Cl)ccc21)CO3]

Example 29 was synthesized in the same manner as Example 18 using 2-(1-methyl-1H-pyrazol-5-yl)acetic acid instead of 3-methoxypropionic acid. LCMS-ESI+ (m/z): [M+H]+ calcd for $C_{37}H_{44}ClN_5O_5S$: 706.3; found: 706.4.

Example 30

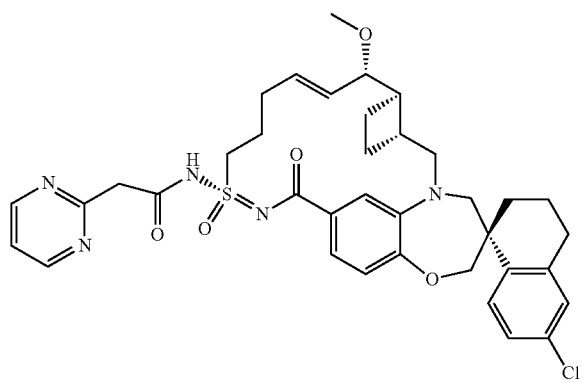 [SMILES: CO[C@H]1/C=C/CCC[S@@](=O)(NC(=O)Cc2ncccn2)=NC(=O)c2ccc3c(c2)N(C[C@@H]2CC[C@H]21)C[C@@]1(CCCc2cc(Cl)ccc21)CO3]

Example 30 was synthesized in the same manner as Example 18 using 2-(pyrimidin-2-yl)acetic acid instead of 3-methoxypropionic acid. LCMS-ESI+ (m/z): [M+H]+ calcd for $C_{37}H_{42}ClN_5O_5S$: 704.3; found: 704.3.

Example 31

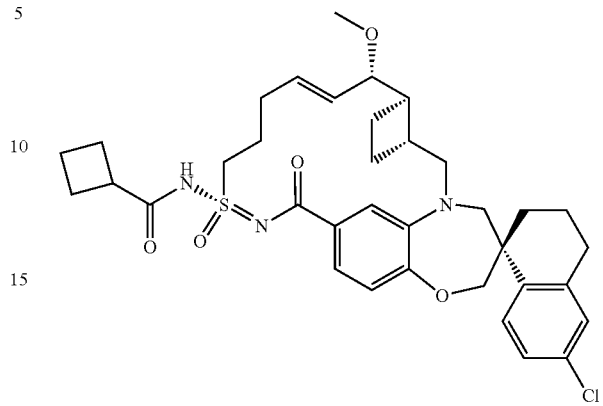

Example 31 was synthesized in the same manner as Example 21 using cyclobutanecarboxylic acid chloride instead of cyclopropylacetyl chloride. $^1$H NMR (400 MHz, Methanol-d4) δ 7.78 (d, J=8.4 Hz, 1H), 7.26 (d, J=8.4 Hz, 1H), 7.18 (d, J=8.4 Hz, 1H), 7.12 (d, J=8.4 Hz, 1H), 6.82 (d, J=8.4 Hz, 1H), 6.10 (dt, J=15.6, 6.4 Hz, 1H), 5.60 (dd, J=15.6, 8.8 Hz, 1H), 4.25-4.13 (m, 1H), 4.03 (dd, J=21.6, 12.0 Hz, 3H), 3.94-3.85 (m, 2H), 3.74-3.66 (m, 2H), 3.35-3.30 (m, 2H), 3.27 (s, 3H), 3.22 0 3.14 (m, 1H), 3.04 (dd, J=15.2, 10.4 Hz, 1H), 2.86-2.72 (m, 2H), 2.39-1.72 (m, 17H), 1.46-1.40 (m, 1H). LCMS-ESI+ (m/z): [M+H]+ calcd for $C_{36}H_{44}ClN_3O_5S$: 666.3; found: 666.4.

Example 32


Example 32 was synthesized in the same manner as Example 19 using 1-isocyanato-1-(trifluoromethyl)cyclopropane instead of isopropyl isocyanate. $^1$H NMR (400 MHz, Methanol-d4) δ 7.75 (d, J=8.4 Hz, 1H), 7.21 (d, J=8.4 Hz, 1H), 7.15 (dd, J=8.8, 2.4 Hz, 1H), 7.12 (s, 1H), 7.07 (d, J=2.4 Hz, 1H), 6.78 (d, J=8.4 Hz, 1H), 6.08-6.02 (m, 1H), 5.62-5.56 (m, 1H), 3.99 (dd, J=21.8, 12.2 Hz, 3H), 3.83-3.76 (m, 2H), 3.67-3.64 (m, 3H), 3.34-3.30 (m, 2H), 3.24 (s, 3H), 3.07-3.00 (m, 1H), 2.83-2.69 (m, 2H), 2.53-1.68 (m, 11H), 1.44-1.37 (m, 1H), 1.22-1.04 (m, 4H). LCMS-ESI+ (m/z): [M+H]+ calcd for $C_{36}H_{42}ClF_3N_4O_5S$: 735.3; found: 735.3.

Example 33

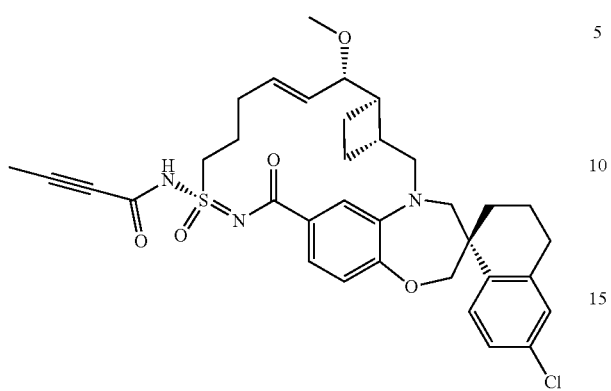

Example 33 was synthesized in the same manner as Example 18 using 2-butynoic acid instead of 3-methoxypropionic acid. LCMS-ESI+ (m/z): [M+H]+ calcd for $C_{35}H_{40}ClN_3O_5S$: 650.2; found: 650.3.

Example 34

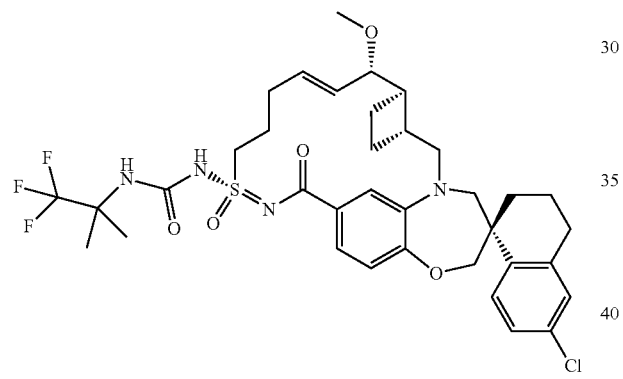

Example 34 was synthesized in the same manner as Example 19 using 1,1,1-trifluoro-2-isocyanato-2-methylpropane instead of isopropyl isocyanate. LCMS-ESI+ (m/z): [M+H]+ calcd for $C_{36}H_{44}ClF_3N_4O_5S$: 737.3; found: 737.3.

Example 35

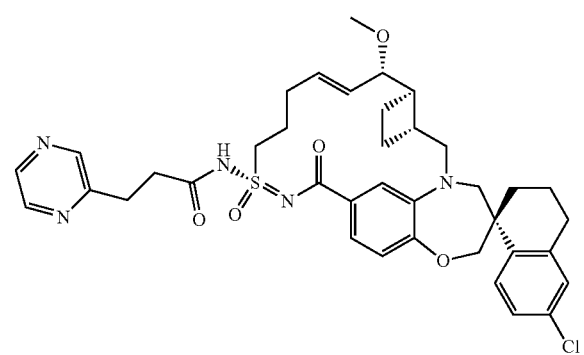 [SMILES: CO[C@H]1/C=C/CCC[S@@](=O)(NC(=O)CCc2cnccn2)=NC(=O)c2ccc3c(c2)N(C[C@@H]2CC[C@H]21)C[C@@]1(CCCc2cc(Cl)ccc21)CO3]

Example 35 was synthesized in the same manner as Example 18 using 3-(pyrazin-2-yl)propanoic acid instead of 3-methoxypropionic acid. ¹H NMR (400 MHz, Methanol-d4) δ 8.58 (s, 1H), 8.53 (s, 1H), 8.43 (d, J=2.8 Hz, 1H), 7.78 (d, J=8.4 Hz, 1H), 7.42-7.35 (m, 2H), 7.24-7.18 (m, 1H), 7.12 (s, 1H), 6.91 (d, J=8.4 Hz, 1H), 5.92-5.80 (m, 2H), 4.11-3.94 (m, 3H), 3.83-3.68 (m, 3H), 3.60-3.41 (m, 3H), 3.27 (s, 3H), 3.21-3.10 (m, 3H), 2.94 (t, J=7.0 Hz, 2H), 2.85-2.78 (m, 4H), 2.48-1.80 (m, 10H), 1.45 (t, J=12.8 Hz, 1H). LCMS-ESI+(m/z): [M+H]+ calcd for $C_{38}H_{44}ClN_5O_5S$: 718.3; found: 718.3.

Example 36

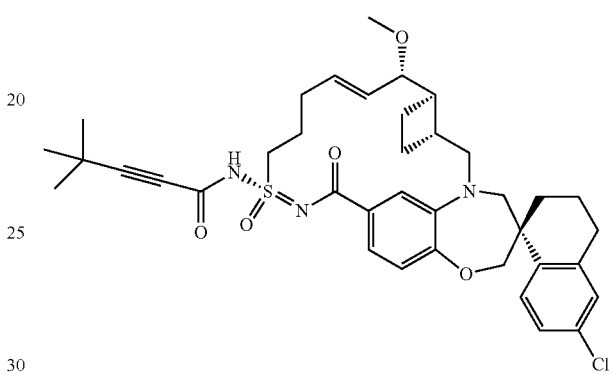

Example 36 was synthesized in the same manner as Example 18 using 4,4-dimethylpent-2-ynoic acid instead of 3-methoxypropionic acid. LCMS-ESI+ (m/z): [M+H]+ calcd for $C_{38}H_{46}ClN_3O_5S$: 692.3; found: 692.3.

Example 37

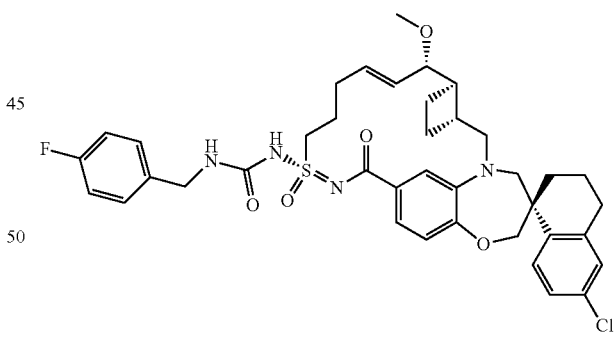

Example 37 was synthesized in the same manner as Example 19 using 4-fluorobenzyl isocyanate instead of isopropyl isocyanate. ¹H NMR (400 MHz, Methanol-d4) δ 7.76 (d, J=8.8 Hz, 1H), 7.36-7.27 (m, 4H), 7.17 (d, J=8.4 Hz, 1H), 7.12 (d, J=2.4 Hz, 1H), 7.04 (t, J=8.6 Hz, 2H), 6.90 (d, J=8.0 Hz, 1H), 5.99-5.93 (m, 1H), 5.77-5.71 (m, 1H), 4.36 (s, 2H), 4.05 (dd, J=26.4, 12.0 Hz, 2H), 3.92 (w, 2H), 3.83 (d, J=15.2 Hz, 1H), 3.72 (d, J=14.0 Hz, 1H), 3.63 (d, J=8.8 Hz, 1H), 3.51-3.38 (m, 3H), 3.30 (s, 3H), 3.15-3.08 (m, 1H), 2.85-2.77 (m, 3H), 2.66-1.79 (m, 10H), 1.44 (t, J=12.8 Hz, 1H). LCMS-ESI+ (m/z): [M+H]+ calcd for $C_{39}H_{44}ClFN_4O_5S$: 735.3; found: 735.3.

Example 38

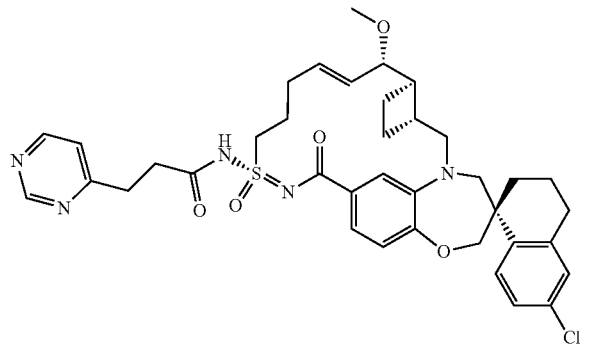 [SMILES: CO[C@H]1/C=C/CCC[S@@](=O)(NC(=O)CCc2ccncn2)=NC(=O)c2ccc3c(c2)N(C[C@@H]2CC[C@H]21)C[C@@]1(CCCc2cc(Cl)ccc21)CO3]

Example 38 was synthesized in the same manner as Example 18 using 3-pyrimidin-4-yl-propanoic acid instead of 3-methoxypropionic acid. $^1$H NMR (400 MHz, Methanol-d4) δ 9.04 (s, 1H), 8.62 (d, J=5.2 Hz, 1H), 7.78 (d, J=8.4 Hz, 1H), 7.47 (d, J=5.2 Hz, 1H), 7.42 (s, 1H), 7.36 (d, J=8.4 Hz, 1H), 7.19 (dd, J=9.0, 2.2 Hz, 1H), 7.12 (d, J=2.4 Hz, 1H), 6.91 (d, J=8.4 Hz, 1H), 5.92-5.80 (m, 2H), 4.11-3.94 (m, 3H), 3.81 (d, J=14.8 Hz, 1H), 3.75 (d, J=14.4 Hz, 1H), 3.62-3.42 (m, 5H), 3.27 (s, 3H), 3.19-3.10 (m, 3H), 2.94 (t, J=7.0 Hz, 2H), 2.85-2.77 (m, 3H), 2.54-1.78 (m, 10H), 1.45 (t, J=12.4 Hz, 1H). LCMS-ESI+ (m/z): [M+H]+ calcd for $C_{38}H_{44}ClN_5O_5S$: 718.3; found: 718.3.

Example 39

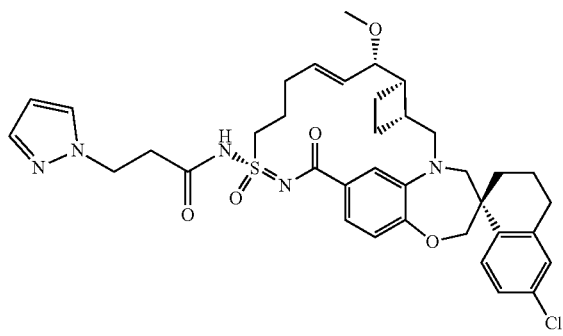 [SMILES: CO[C@H]1/C=C/CCC[S@@](=O)(NC(=O)CCn2cccn2)=NC(=O)c2ccc3c(c2)N(C[C@@H]2CC[C@H]21)C[C@@]1(CCCc2cc(Cl)ccc21)CO3]

Example 39 was synthesized in the same manner as Example 18 using 3-pyrazol-1-yl-propionic acid instead of 3-methoxypropionic acid. $^1$H NMR (400 MHz, Methanol-d4) δ 7.77 (d, J=8.4 Hz, 1H), 7.65 (d, J=2.4 Hz, 1H), 7.49 (d, J=1.6 Hz, 1H), 7.40 (d, J=2.0 Hz, 1H), 7.34 (dd, J=8.2, 1.8 Hz, 1H), 7.19 (d, J=8.0 Hz, 1H), 7.12 (d, J=2.4 Hz, 1H), 6.90 (d, J=8.4 Hz, 1H), 6.26-6.25 (m, 1H), 5.94-5.79 (m, 2H), 4.49 (t, J=6.6 Hz, 2H), 4.05 (dd, J=33.4, 12.2 Hz, 2H), 3.96-3.91 (m, 1H), 3.81 (d, J=15.2 Hz, 1H), 3.75 (d, J=14.4 Hz, 1H), 3.68-3.55 (m, 3H), 3.51-3.41 (m, 2H), 3.31 (s, 3H), 3.16-3.10 (m, 1H), 2.96 (t, J=6.6 Hz, 2H), 2.85-2.77 (m, 3H), 2.46-1.79 (m, 10H), 1.45 (t, J=12.6 Hz, 1H). LCMS-ESI+ (m/z): [M+H]+ calcd for $C_{37}H_{44}ClN_5O_5S$: 706.3; found: 706.3.

Example 40

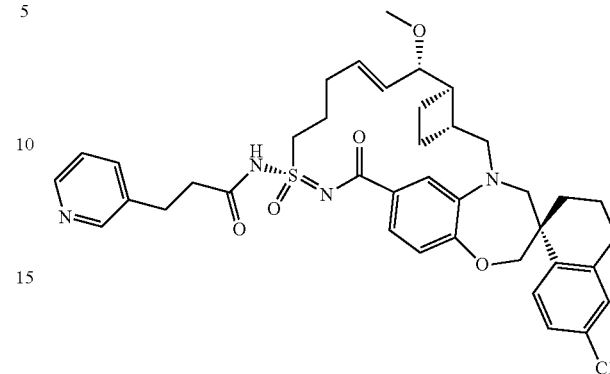

Example 40 was synthesized in the same manner as Example 18 using 3-pyridinepropionic acid instead of 3-methoxypropionic acid. $^1$H NMR (400 MHz, Methanol-D4) δ 8.78 (s, 1H), 8.65 (d, J=5.6 Hz, 1H), 8.50 (d, J=8.4 Hz, 1H), 7.90 (dd, J=8.0, 6.0 Hz, 1H), 7.77 (d, J=8.4 Hz, 1H), 7.40 (d, J=2.0 Hz, 1H), 7.29 (d, J=8.0 Hz, 1H), 7.18 (dd, J=8.6, 2.2 Hz, 1H), 7.12 (d, J=2.4 Hz, 1H), 6.92 (d, J=8.4 Hz, 1H), 5.92-5.81 (m, 2H), 4.11-3.95 (m, 4H), 3.81-3.73 (m, 2H), 3.56-3.43 (m, 4H), 3.32 (s, 3H), 3.25-3.11 (m, 3H), 2.90 (t, J=6.8 Hz, 2H), 2.85-2.78 (m, 2H), 2.26-1.80 (m, 11H), 1.44 (t, J=12.8 Hz, 1H). LCMS-ESI+(m/z): [M+H]+ calcd for $C_{39}H_{45}ClN_4O_5S$: 717.3; found: 717.4.

Example 41

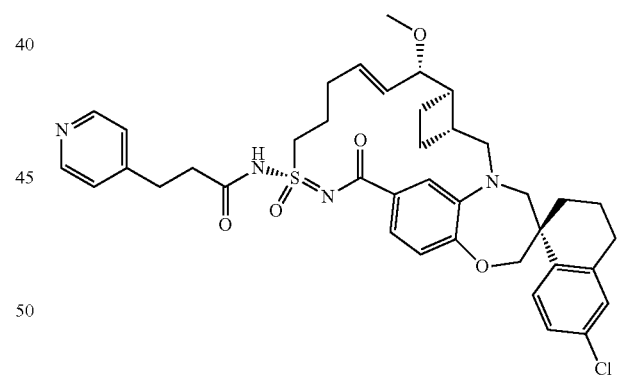

Example 41 was synthesized in the same manner as Example 18 using 3-(pyridin-4-yl)propanoic acid instead of 3-methoxypropionic acid. $^1$H NMR (400 MHz, Methanol-d4) δ 8.64 (d, J=6.0 Hz, 2H), 7.93 (d, J=5.6 Hz, 2H), 7.76 (d, J=8.4 Hz, 1H), 7.40 (d, J=2.0 Hz, 1H), 7.31 (dd, J=8.2, 1.8 Hz, 1H), 7.17 (dd, J=8.4, 2.4 Hz, 1H), 7.12 (d, J=2.4 Hz, 1H), 6.92 (d, J=8.0 Hz, 1H), 5.92-5.81 (m, 2H), 4.11-3.97 (m, 3H), 3.81-3.73 (m, 2H), 3.55-3.43 (m, 3H), 3.32 (s, 3H), 3.31-3.20 (m, 3H), 3.17-3.11 (m, 1H), 2.94 (t, J=7.0 Hz, 2H), 2.87-2.77 (m, 3H), 2.54-1.80 (m, 10H), 1.47-1.41 (m, 1H). LCMS-ESI+ (m/z): [M+H]+ calcd for $C_{39}H_{45}ClN_4O_5S$: 717.3; found: 717.3.

Example 42

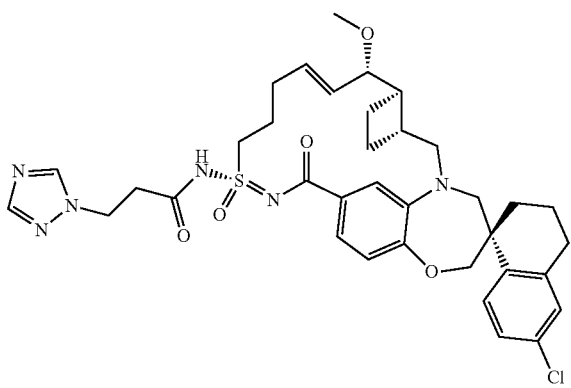 [SMILES: CO[C@H]1/C=C/CCC[S@@](=O)(NC(=O)CCn2cncn2)=NC(=O)c2ccc3c(c2)N(C[C@@H]2CC[C@H]21)C[C@@]1(CCCc2cc(Cl)ccc21)CO3]

Example 42 was synthesized in the same manner as Example 18 using 3-(1H-1,2,4-triazol-1-yl)propanoic acid instead of 3-methoxypropionic acid. LCMS-ESI+ (m/z): [M+H]+ calcd for $C_{36}H_{43}ClN_6O_5S$: 707.3; found: 707.3.

Example 43

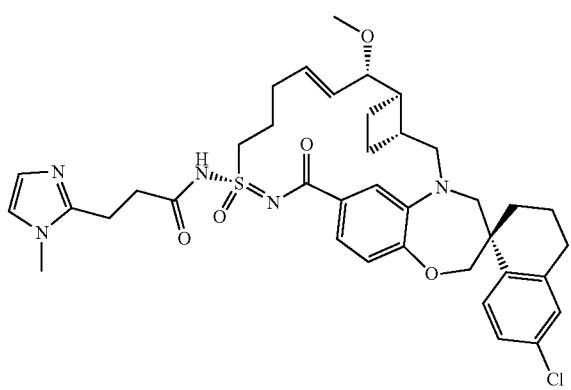 [SMILES: CO[C@H]1/C=C/CCC[S@@](=O)(NC(=O)CCc2nccn2C)=NC(=O)c2ccc3c(c2)N(C[C@@H]2CC[C@H]21)C[C@@]1(CCCc2cc(Cl)ccc21)CO3]

Example 43 was synthesized in the same manner as Example 18 using 3-(1-methyl-1H-imidazol-2-yl)propanoic acid instead of 3-methoxypropionic acid. LCMS-ESI+ (m/z): [M+H]+ calcd for $C_{38}H_{46}ClN_5O_5S$: 720.3; found: 721.3.

Example 44

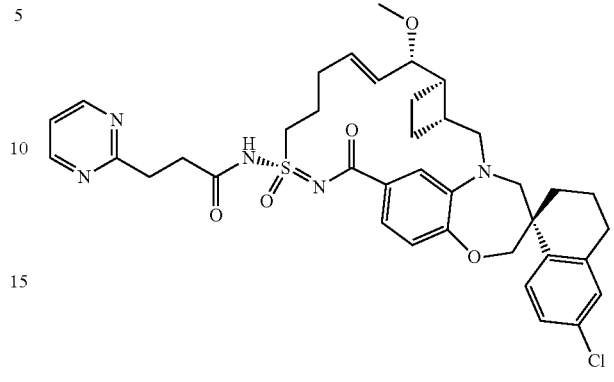

Example 44 was synthesized in the same manner as Example 18 using 3-(pyrimidin-2-yl)propanoic acid instead of 3-methoxypropionic acid. $^1$H NMR (400 MHz, Methanol-d4) δ 8.73 (d, J=4.8 Hz, 2H), 7.76 (d, J=8.8 Hz, 1H), 7.40 (d, J=2.0 Hz, 1H), 7.38-7.34 (m, 2H), 7.17 (dd, J=8.8, 2.4 Hz, 1H), 7.11 (d, J=2.0 Hz, 1H), 6.91 (d, J=8.4 Hz, 1H), 5.93-5.79 (m, 2H), 4.10-3.93 (m, 3H), 3.80 (d, J=15.2 Hz, 1H), 3.74 (d, J=14.4 Hz, 1H), 3.67-3.59 (m, 1H), 3.55 (dd, J=8.2, 3.0 Hz, 1H), 3.43 (d, J=14.4 Hz, 1H), 3.35-3.30 (m, 4H), 3.25 (s, 3H), 3.16-3.09 (m, 1H), 3.00 (t, J=6.8 Hz, 2H), 2.86-2.73 (m, 3H), 2.52-1.78 (m, 10H), 1.47-1.41 (m, 1H). LCMS-ESI+ (m/z): [M+H]+ calcd for $C_{38}H_{44}ClN_5O_5S$: 718.3; found: 719.4.

Example 45

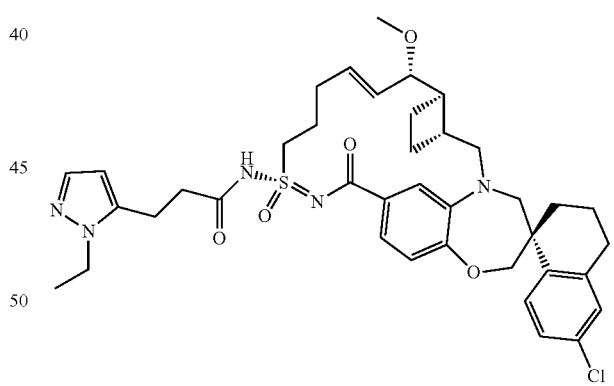

Example 45 was synthesized in the same manner as Example 18 using 3-(1-ethyl-1H-pyrazol-5-yl)propanoic acid instead of 3-methoxypropionic acid. $^1$H NMR (400 MHz, Methanol-d4) δ 7.77 (d, J=8.4 Hz, 1H), 7.42-7.35 (m, 3H), 7.17 (d, J=8.4 Hz, 1H), 7.12 (s, 1H), 6.91 (d, J=8.4 Hz, 1H), 6.14 (s, 1H), 5.93-5.81 (m, 2H), 4.17 (q, J=7.2 Hz, 2H), 4.11-3.94 (m, 3H), 3.81 (d, J=14.8 Hz, 1H), 3.74 (d, J=14.8 Hz, 1H), 3.63-3.50 (m, 2H), 3.44 (d, J=14.4 Hz, 1H), 3.34-3.31 (m, 2H), 3.31 (s, 3H), 3.17-3.10 (m, 1H), 3.02-3.00 (m, 2H), 2.87-2.79 (m, 5H), 2.55-1.79 (m, 10H), 1.48-1.35 (m, 4H). LCMS-ESI+ (m/z): [M+H]+ calcd for $C_{39}H_{48}ClN_5O_5S$: 734.4; found: 734.4.

Example 46

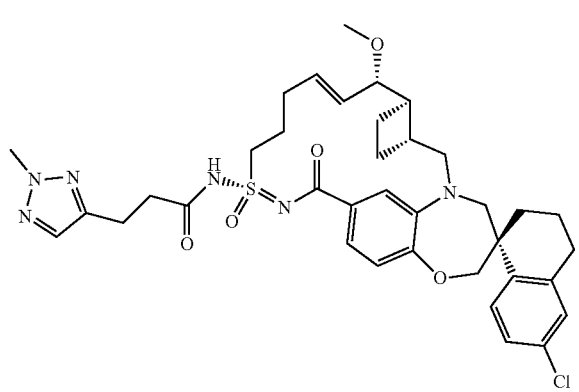 [SMILES: CO[C@H]1/C=C/CCC[S@@](=O)(NC(=O)CCc2cnn(C)n2)=NC(=O)c2ccc3c(c2)N(C[C@@H]2CC[C@H]21)C[C@@]1(CCCc2cc(Cl)ccc21)CO3]

Example 46 was synthesized in the same manner as Example 18 using 3-(2-methyl-2H-1,2,3-triazol-4-yl)propanoic acid instead of 3-methoxypropionic acid. $^1$H NMR (400 MHz, Methanol-d4) δ 7.77 (d, J=8.4 Hz, 1H), 7.47 (s, 1H), 7.40 (s, 1H), 7.35 (d, J=8.4 Hz, 1H), 7.19 (d, J=8.4 Hz, 1H), 7.12 (s, 1H), 6.90 (d, J=8.0 Hz, 1H), 5.96-5.90 (m, 1H), 5.82 (dd, J=16.2, 8.6 Hz, 1H), 4.10-3.94 (m, 6H), 3.82 (d, J=15.2 Hz, 1H), 3.74 (d, J=14.4 Hz, 1H), 3.68-3.50 (m, 2H), 3.42 (d, J=14.4 Hz, 1H), 3.34-3.32 (m, 2H), 3.31 (s, 3H), 3.16-3.09 (m, 1H), 3.01 (t, J=7.2 Hz, 2H), 2.85-2.75 (m, 5H), 2.50-1.78 (m, 10H), 1.48-1.42 (m, 1H). LCMS-ESI+ (m/z): [M+H]+ calcd for $C_{37}H_{45}ClN_6O_5S$: 721.3; found: 721.3.

Example 47

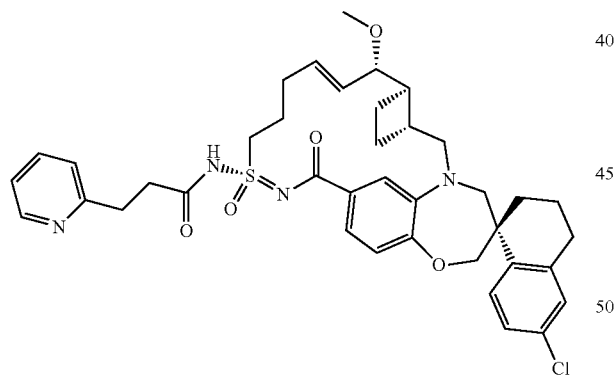

Example 47 was synthesized in the same manner as Example 18 using 2-pyridinpropanoic acid instead of 3-methoxypropionic acid. $^1$H NMR (400 MHz, Methanol-d4) δ 8.60 (d, J=5.6 Hz, 1H), 8.26 (t, J=7.8 Hz, 1H), 7.82 (d, J=8.0 Hz, 1H), 7.78 (d, J=8.4 Hz, 1H), 7.69 (t, J=6.6 Hz, 1H), 7.40 (s, 1H), 7.31 (dd, J=8.2, 1.8 Hz, 1H), 7.19 (d, J=8.8 Hz, 1H), 7.12 (s, 1H), 6.91 (d, J=8.0 Hz, 1H), 5.92-5.79 (m, 2H), 4.12-3.92 (m, 3H), 3.82-3.74 (m, 2H), 3.57-3.51 (m, 2H), 3.44 (d, J=14.8 Hz, 1H), 3.29 (s, 3H), 3.33-3.24 (m, 4H), 3.17-3.11 (m, 1H), 2.96 (t, J=6.8 Hz, 2H), 2.92-2.78 (m, 3H), 2.49-1.81 (m, 10H), 1.48-1.41 (m, 1H). LCMS-ESI+ (m/z): [M+H]+ calcd for $C_{39}H_{45}ClN_4O_5S$: 717.3; found: 717.5.

Example 48

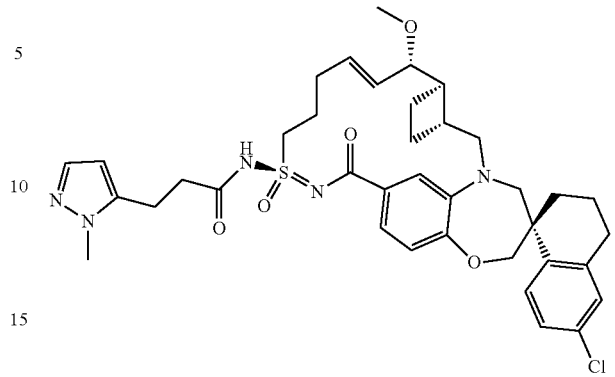

Example 48 was synthesized in a same manner as Example 18 using 3-(1-methyl-1H-pyrazol-5-yl)propanoic acid and Example 6 instead of 3-methoxypropionic acid and Example 5. LCMS-ESI+ (m/z): [M+H]+ calcd for $C_{38}H_{46}ClN_5O_5S$: 720.3; found: 720.0.

Example 49

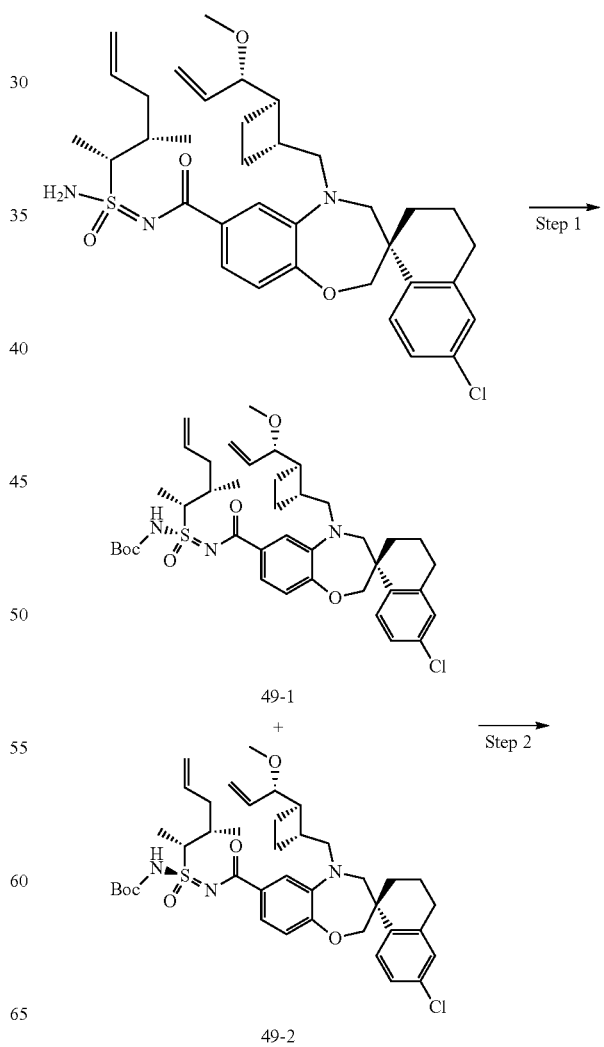

-continued

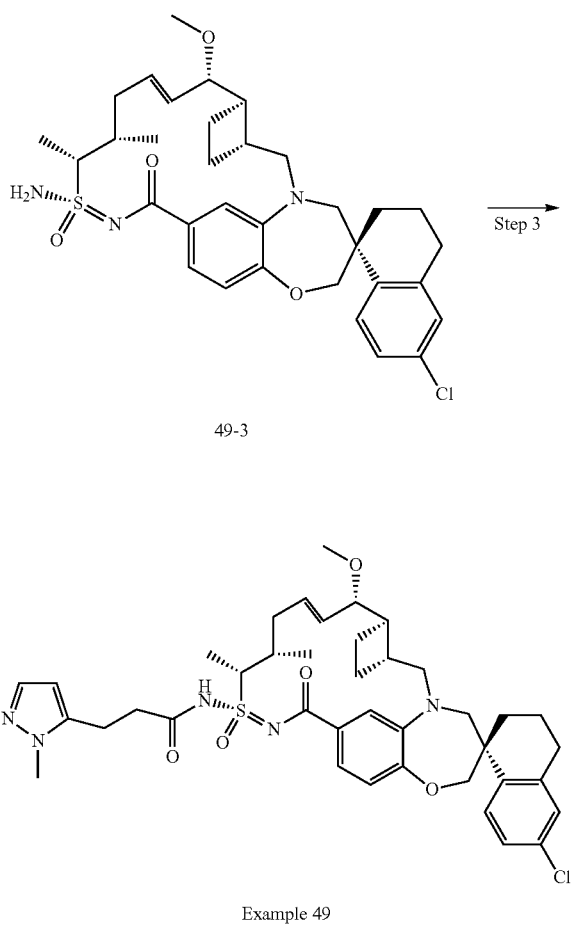

49-3

Example 49

Step 1

To a stirred solution of (3S)—N-(amino((2R,3S)-3-methylhex-5-en-2-yl)(oxo)-16-sulfanylidene)-6'-chloro-5-(((1R,2R)-2-((S)-1-methoxyallyl) cyclobutyl) methyl)-3',4,4',5-tetrahydro-2H,2'H-spiro[benzo[b][1,4]oxazepine-3,1'-naphthalene]-7-carboxamide 1-6 (309.00 mg, 0.483 mmol) in CH$_2$Cl$_2$ (15.0 mL) was added triethylamine (0.14 mL, 0.965 mmol) in an ice bath, followed by DMAP (23.58 mg, 0.193 mmol) and di-tert-butyl dicarbonate (157.99 mg, 0.724 mmol). The resulting mixture was stirred at rt overnight. After concentration, the mixtures of diastereomers were separated by preparative HPLC to afford 49-1 (less polar fraction) and 49-2 (more polar fraction).

Step 2

Intermediate 49-3 was synthesized from Intermediate 49-1 using a similar procedure shown in Example 5, Method 1 step 2.

Step 3

Example 49 was synthesized in the same manner as Example 18 using 3-(1-methyl-1H-pyrazol-5-yl)propanoic acid and intermediate 49-3. $^1$H NMR (400 MHz, Methanol-d4) δ 7.75 (d, J=8.8 Hz, 1H), 7.38 (s, 1H), 7.19 (d, J=8.4 Hz, 2H), 7.13 (d, J=2.0 Hz, 1H), 7.05 (s, 1H), 6.93 (d, J=8.4 Hz, 1H), 6.15 (s, 1H), 6.00-5.93 (m, 1H), 5.60 (dd, J=15.4, 9.0 Hz, 1H), 4.32-4.28 (m, 1H), 4.09 (s, 2H), 3.85-3.81 (m, 4H), 3.75-3.67 (m, 3H), 3.51-3.79 (m, 1H), 3.25 (s, 3H), 3.16-3.09 (m, 1H), 3.01 (t, J=12 Hz, 2H), 2.85-2.79 (m, 5H), 2.48-1.77 (m, 10H), 1.51-1.44 (m, 4H), 1.06 (d, J=5.6 Hz, 3H). LCMS-ESI+ (m/z): [M+H]+ calcd for C$_{40}$H$_{50}$ClN$_5$O$_5$S: 748.4; found: 748.0.

Example 50

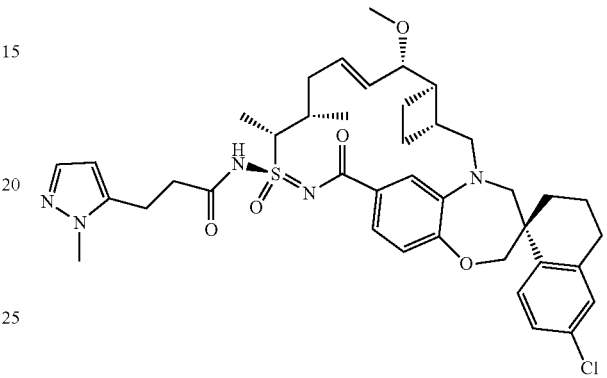

Example 50 was synthesized with the procedure described in Example 49 (step 2 and Step 3) using intermediate 49-2 instead of intermediate 49-1. LCMS-ESI+ (m/z): [M+H]+ calcd for C$_{40}$H$_{50}$ClN$_5$O$_5$S: 748.4; found: 748.0.

Example 51

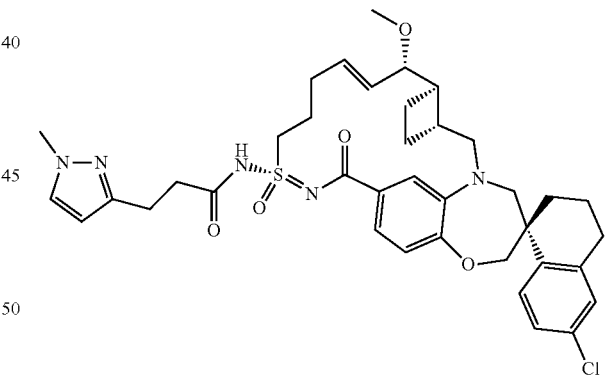

Example 51 was synthesized in the same manner as Example 18 using 3-(1-methyl-1H-pyrazol-3-yl)propanoic acid instead of 3-methoxypropionic acid. $^1$H NMR (400 MHz, Methanol-d4) δ 7.77 (d, J=8.4 Hz, 1H), 7.44 (d, J=8.4 Hz, 2H), 7.36 (d, J=8.0 Hz, 1H), 7.19 (d, J=8.4 Hz, 1H), 7.12 (s, 1H), 6.90 (d, J=8.4 Hz, 1H), 6.12 (d, J=2.4 Hz, 1H), 5.94-5.81 (m, 2H), 4.11-3.94 (m, 3H), 3.83-3.80 (m, 4H), 3.75 (d, J=14.4 Hz, 1H), 3.68-3.47 (m, 2H), 3.43 (d, J=14.8 Hz, 1H), 3.34-3.31 (m, 5H), 3.16-3.10 (m, 1H), 2.94 (t, J=7.8 Hz, 2H), 2.85-2.78 (m, 3H), 2.74 (t, J=7.6 Hz, 2H), 2.53-1.78 (m, 10H), 1.45 (t, J=12.6 Hz, 1H). LCMS-ESI+ (m/z): [M+H]+ calcd for C$_{38}$H$_{46}$ClN$_5$O$_5$S: 720.3; found: 720.0.

Example 52

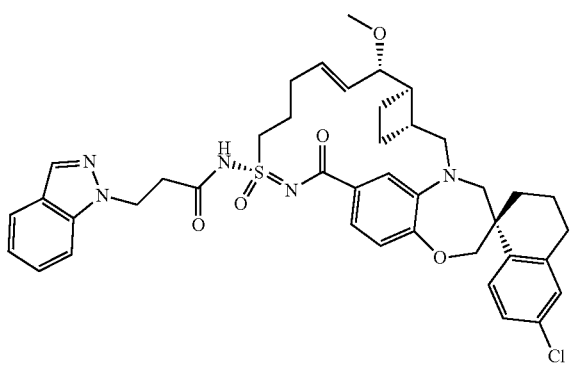 [SMILES: CO[C@H]1/C=C/CCC[S@@](=O)(NC(=O)CCn2ncc3ccccc32)=NC(=O)c2ccc3c(c2)N(C[C@@H]2CC[C@H]21)C[C@@]1(CCCc2cc(Cl)ccc21)CO3]

Example 52 was synthesized in the same manner as Example 18 using 3-indazol-1-yl-propanoic acid instead of 3-methoxypropionic acid. LCMS-ESI+ (m/z): [M+H]+ calcd for $C_{41}H_{46}ClN_5O_5S$: 756.4; found: 756.2.

Example 53

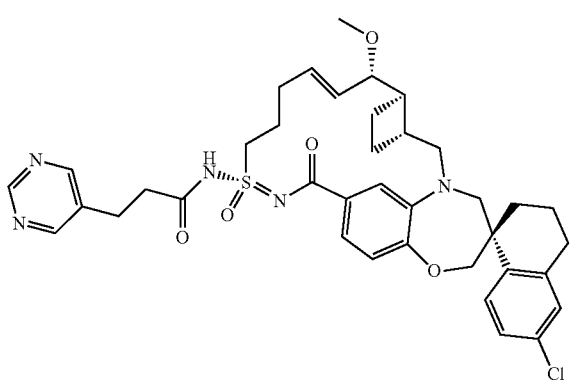 [SMILES: CO[C@H]1/C=C/CCC[S@@](=O)(NC(=O)CCc2cncnc2)=NC(=O)c2ccc3c(c2)N(C[C@@H]2CC[C@H]21)C[C@@]1(CCCc2cc(Cl)ccc21)CO3]

Example 53 was synthesized in the same manner as Example 18 using 3-(pyrimidin-5-yl)propanoic acid instead of 3-methoxypropionic acid. $^1$H NMR (400 MHz, Methanol-d4) δ 9.00 (s, 1H), 8.74 (s, 2H), 7.77 (d, J=8.4 Hz, 1H), 7.41 (s, 1H), 7.34 (dd, J=8.0, 1.6 Hz, 1H), 7.17 (d, J=8.4 Hz, 1H), 7.11 (s, 1H), 6.90 (d, J=8.4 Hz, 1H), 5.92-5.81 (m, 2H), 4.11-3.91 (m, 3H), 3.82-3.68 (m, 2H), 3.60-3.50 (m, 2H), 3.43 (d, J=14.4 Hz, 1H), 3.35-3.33 (m, 5H), 3.16-3.10 (m, 1H), 3.02 (t, J=7.3 Hz, 2H), 2.87-2.78 (m, 4H), 2.55-1.78 (m, 10H), 1.44 (t, J=12.8 Hz, 1H). LCMS-ESI+ (m/z): [M+H]+ calcd for $C_{38}H_{44}ClN_5O_5S$: 718.3; found: 718.1.

Example 54

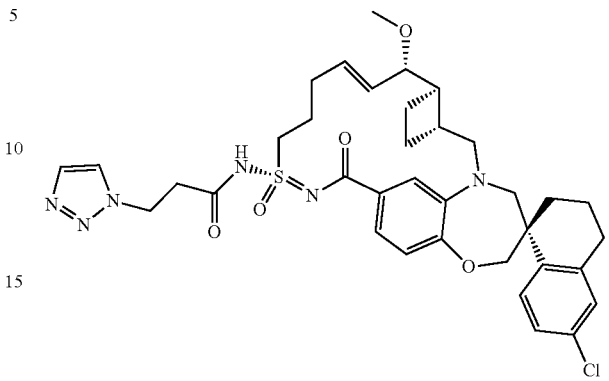

Example 54 was synthesized in the same manner as Example 18 using sodium 3-(1H-1,2,3-triazol-1-yl)propanoic acid instead of 3-methoxypropionic acid. LCMS-ESI+ (m/z): [M+H]+ calcd for $C_{36}H_{43}ClN_6O_5S$: 707.3; found: 707.1.

Example 55

Example 55 was synthesized in the same manner as Example 18 using 3-(4-chloro-1H-pyrazol-1-yl)propanoic acid instead of 3-methoxypropionic acid. $^1$H NMR (400 MHz, Methanol-d4) δ 7.77 (d, J=8.8 Hz, 1H), 7.73 (s, 1H), 7.44 (s, 1H), 7.41 (s, 1H), 7.35 (d, J=8.4 Hz, 1H), 7.19 (d, J=8.4 Hz, 1H), 7.12 (d, J=2.4 Hz, 1H), 6.90 (d, J=8.4 Hz, 1H), 5.94-5.79 (m, 2H), 4.44 (t, J=6.2 Hz, 2H), 4.05 (dd, J=33.8, 12.2 Hz, 2H), 3.97-3.89 (m, 1H), 3.81 (d, J=14.8 Hz, 1H), 3.75 (d, J=14.4 Hz, 1H), 3.64-3.50 (m, 2H), 3.43 (d, J=14.4 Hz, 1H), 3.34-3.31 (m, 5H), 3.16-3.10 (m, 1H), 2.96 (t, J=6.4 Hz, 2H), 2.85-2.77 (m, 3H), 2.53-1.79 (m, 10H), 1.45 (t, J=12.6 Hz, 1H). LCMS-ESI+ (m/z): [M+H]+ calcd for $C_{37}H_{43}Cl_2N_5O_5S$: 740.7; found: 740.0.

Example 56

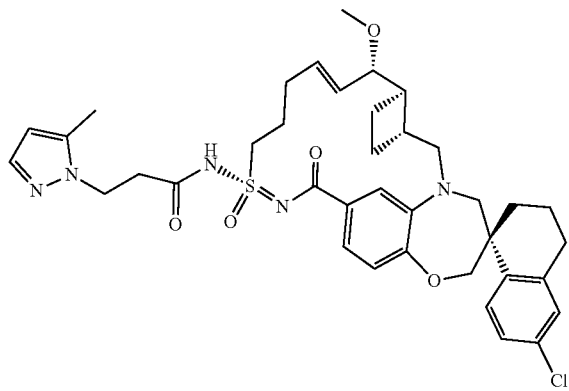 [SMILES: CO[C@H]1/C=C/CCC[S@@](=O)(NC(=O)CCn2nccc2C)=NC(=O)c2ccc3c(c2)N(C[C@@H]2CC[C@H]21)C[C@@]1(CCCc2cc(Cl)ccc21)CO3]

Example 56 was synthesized in the same manner as Example 18 using 3-(5-methyl-1H-pyrazol-1-yl)propanoic acid. LCMS-ESI+ (m/z): [M+H]+ calcd for $C_{38}H_{46}ClN_5O_5S$: 720.3; found: 720.1.

Example 57

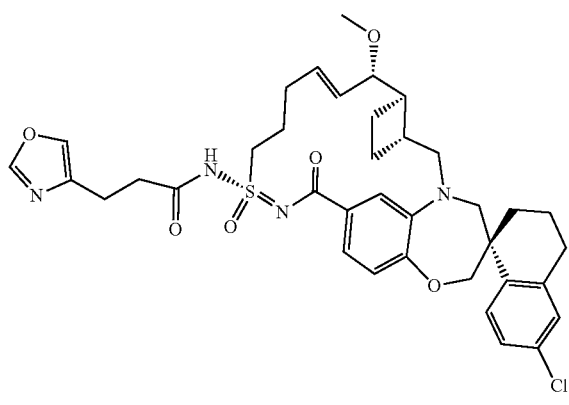 [SMILES: CO[C@H]1/C=C/CCC[S@@](=O)(NC(=O)CCc2cocn2)=NC(=O)c2ccc3c(c2)N(C[C@@H]2CC[C@H]21)C[C@@]1(CCCc2cc(Cl)ccc21)CO3]

Example 57 was synthesized in the same manner as Example 18 using 3-isoxazol-4-yl-propanoic acid instead of 3-methoxypropionic acid. $^1$H NMR (400 MHz, Methanol-d4) δ 8.51 (s, 1H), 8.35 (s, 1H), 7.77 (d, J=8.8 Hz, 1H), 7.42 (s, 1H), 7.36 (d, J=8.0 Hz, 1H), 7.17 (d, J=8.4 Hz, 1H), 7.12 (s, 1H), 6.91 (d, J=8.4 Hz, 1H), 5.93-5.81 (m, 2H), 4.11-3.92 (m, 3H), 3.81 (d, J=15.2 Hz, 1H), 3.75 (d, J=14.4 Hz, 1H), 3.64-3.49 (m, 2H), 3.44 (d, J=14.4 Hz, 1H), 3.36-3.31 (m, 7H), 3.17-3.10 (m, 1H), 2.87-2.77 (m, 3H), 2.70 (t, J=7.2 Hz, 2H), 2.55-1.79 (m, 10H), 1.45 (t, J=12.6 Hz, 1H). LCMS-ESI+ (m/z): [M+H]+ calcd for $C_{37}H_{43}ClN_4O_6S$: 707.3; found: 707.1.

Example 58

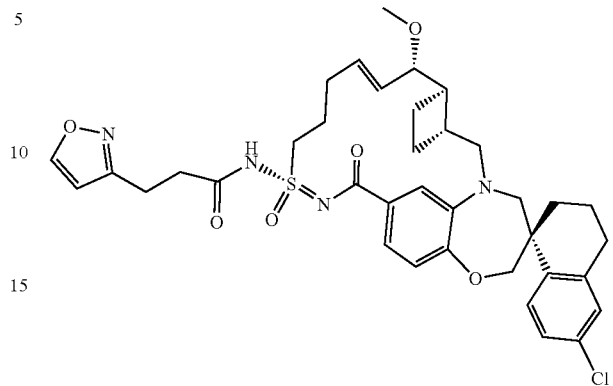

Example 58 was synthesized in the same manner as Example 18 using 3-(1,2-oxazol-3-yl)propanoic acid instead of 3-methoxypropionic acid. $^1$H NMR (400 MHz, Methanol-74) δ 8.54 (d, J=1.6 Hz, 1H), 7.77 (d, J=8.8 Hz, 1H), 7.40 (s, 1H), 7.35 (d, J=8.4 Hz, 1H), 7.18 (d, J=8.4 Hz, 1H), 7.12 (d, J=2.4 Hz, 1H), 6.90 (d, J=8.4 Hz, 1H), 6.43 (d, J=1.6 Hz, 1H), 5.95-5.89 (m, 1H), 5.82 (dd, J=16.0, 8.4 Hz, 1H), 4.11-3.92 (m, 3H), 3.82 (d, J=15.2 Hz, 1H), 3.74 (d, J=14.4 Hz, 1H), 3.68-3.47 (m, 2H), 3.42 (d, J=14.4 Hz, 1H), 3.35-3.32 (m, 2H), 3.31 (s, 3H), 3.16-3.04 (m, 3H), 2.85-2.72 (m, 5H), 2.51-1.78 (m, 10H), 1.45 (t, J=12.6 Hz, 1H). LCMS-ESI+ (m/z): [M+H]+ calcd for $C_{37}H_{43}ClN_4O_6S$: 707.3; found: 707.0.

Example 59

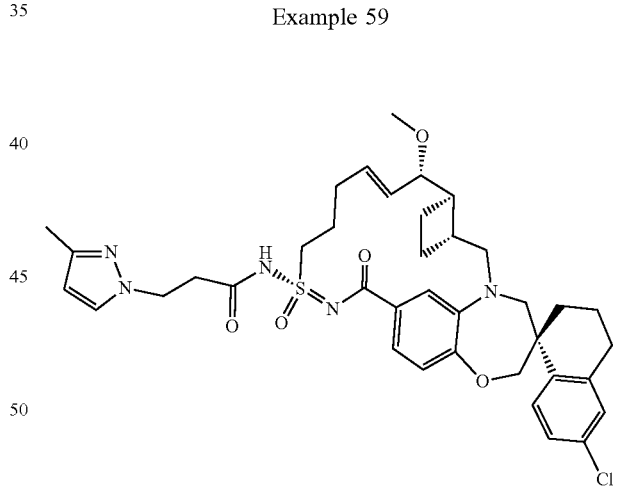

Example 59 was synthesized in the same manner as Example 18 using 3-(3-methyl-1H-pyrazol-1-yl)propanoic acid instead of 3-m ethoxy propionic acid. H NMR (400 MHz, Methanol-d4) δ 7.78 (d, J=8.8 Hz, 1H), 7.51 (d, J=2.4 Hz, 1H), 7.41 (s, 1H), 7.34 (dd, J=8.2, 1.8 Hz, 1H), 7.19 (d, J=8.4 Hz, 1H), 7.12 (s, 1H), 6.90 (d, J=8.4 Hz, 1H), 6.02 (d, J=2.4 Hz, 1H), 5.95-5.80 (m, 2H), 4.39 (t, J=6.6 Hz, 2H), 4.06 (dd, J=34.2, 12.2 Hz, 2H), 3.98-3.91 (m, 1H), 3.81 (d, J=15.2 Hz, 1H), 3.75 (d, J=14.4 Hz, 1H), 3.68-3.47 (m, 2H), 3.43 (d, J=14.4 Hz, 1H), 3.35-3.31 (m, 5H), 3.16-3.10 (m, 1H), 2.93 (t, J=6.4 Hz, 2H), 2.85-2.75 (m, 3H), 2.53-1.79 (m, 13H), 1.45 (t, J=12.6 Hz, 1H). LCMS-ESI+ (m/z): [M+H]+ calcd for $C_{38}H_{46}ClN_5O_5S$: 720.3; found: 720.1.

161
Example 60

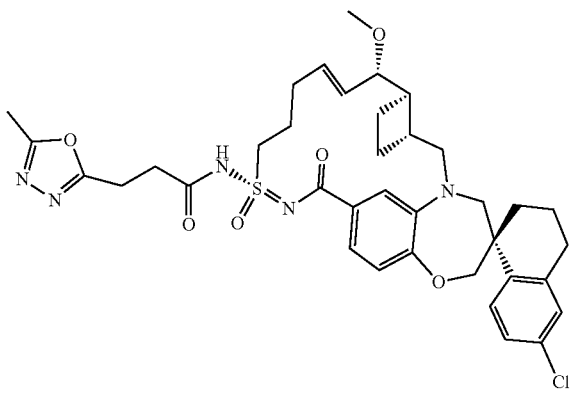 [SMILES: CO[C@H]1/C=C/CCC[S@@](=O)(NC(=O)CCc2nnc(C)o2)=NC(=O)c2ccc3c(c2)N(C[C@@H]2CC[C@H]21)C[C@@]1(CCCc2cc(Cl)ccc21)CO3]

Example 60 was synthesized in the same manner as Example 18 using lithium 3-(5-methyl-1,3,4-oxadiazol-2-yl)propanoate instead of 3-methoxypropionic acid. LCMS-ESI+ (m/z): [M+H]+ calcd for $C_{37}H_{44}ClN_5O_6S$: 722.3; found: 722.1.

Example 61

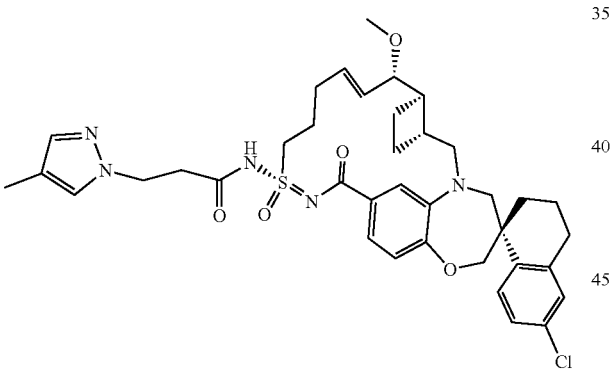

Example 61 was synthesized in the same manner as Example 18 using 3-(4-methyl-1H-pyrazol-1-yl)propanoic acid instead of 3-methoxypropionic acid. $^1$H NMR (400 MHz, Methanol-d4) δ 7.77 (d, J=8.4 Hz, 1H), 7.41 (s, 2H), 7.34 (d, J=8.0 Hz, 1H), 7.28 (s, 1H), 7.19 (d, J=8.4 Hz, 1H), 7.12 (s, 1H), 6.90 (d, J=8.4 Hz, 1H), 5.93-5.80 (m, 2H), 4.40 (td, J=6.4, 2.4 Hz, 2H), 3.81 (dd, J=34.0, 12.4 Hz, 2H), 3.97-3.90 (m, 1H), 3.81 (d, J=14.8 Hz, 1H), 3.75 (d, J=14.4 Hz, 1H), 3.63-3.47 (m, 2H), 3.43 (d, J=14.8 Hz, 1H), 3.35-3.33 (m, 5H), 3.17-3.10 (m, 1H), 2.92 (t, J=6.6 Hz, 2H), 2.85-2.75 (m, 3H), 2.52-1.78 (m, 13H), 1.45 (t, J=12.8 Hz, 1H). LCMS-ESI+ (m/z): [M+H]+ calcd for $C_{38}H_{46}ClN_5O_5S$: 720.3; found: 720.1.

162
Examples 62 and 63

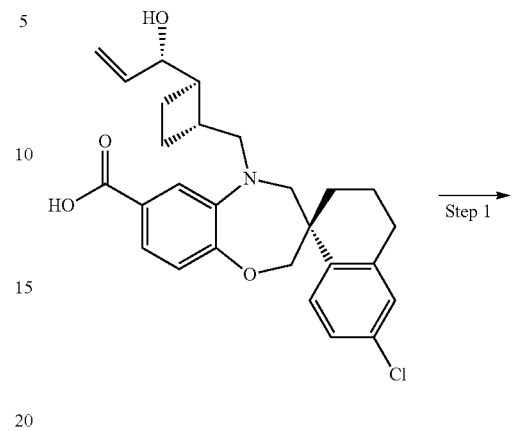

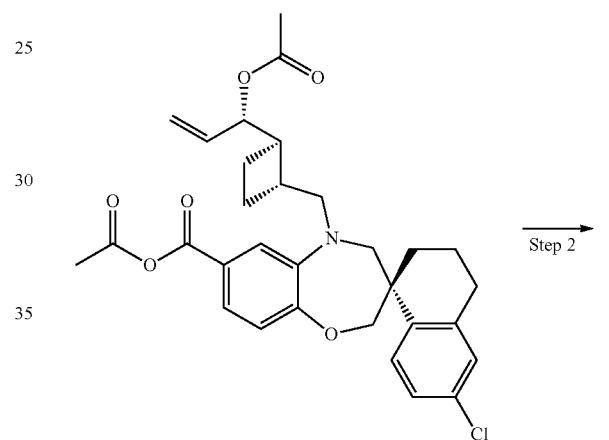

62-1

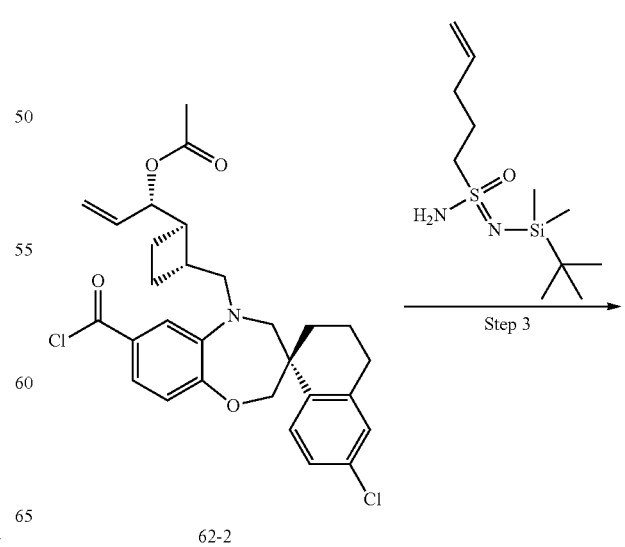

62-2

-continued

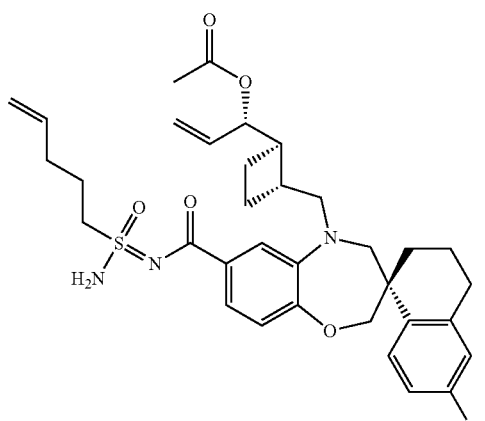

IV

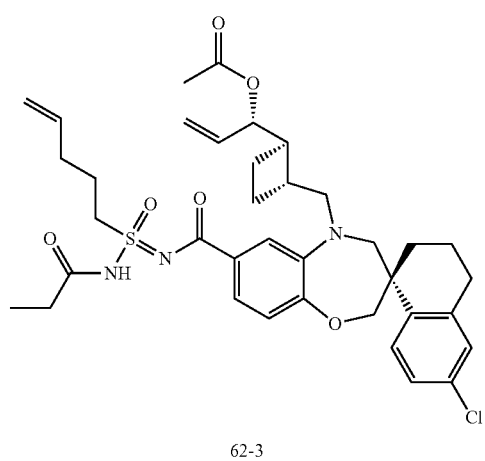

62-3

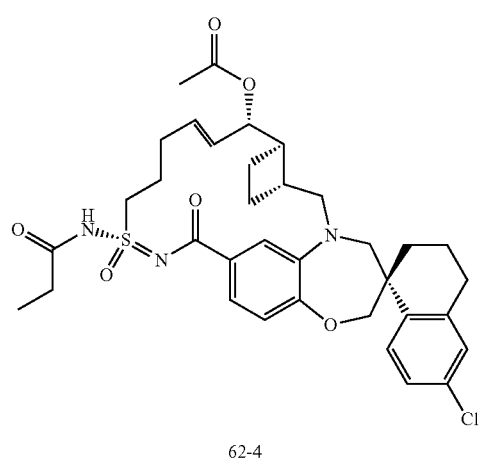

62-4

-continued

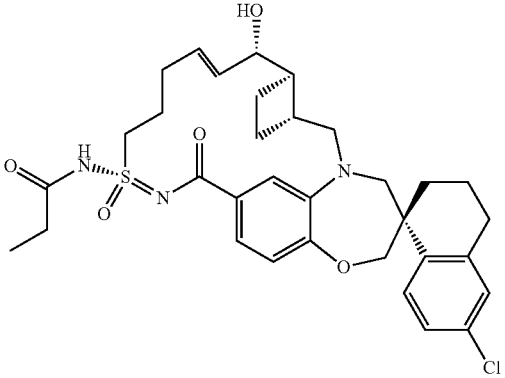

Example 62

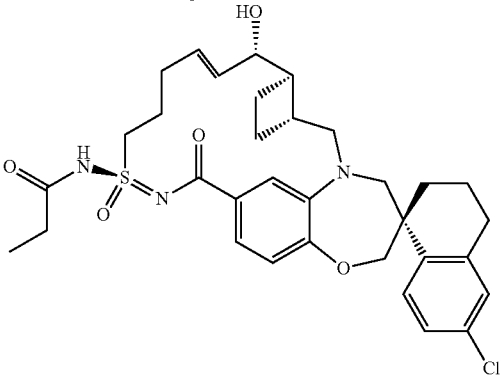

Example 63

Step 1

To a stirred solution of (S)-6'-chloro-5-(((1R,2R)-2-((S)-1-hydroxyallyl)cyclobutyl)methyl)-3',4,4',5-tetrahydro-2H,2'H-spiro[benzo[b] [1,4]oxazepine-3,1'-naphthalene]-7-carboxylic acid (2.0 g, 4.27 mmol) in tetrahydrofuran was added pyridine (1.0 g, 8.5 mmol) and acetic anhydride (1.3 g, 8.5 mmol). Mixture was stirred at room temperature for 48 hours followed by evaporation of the solvents. The residue was dissolved in ethyl acetate and washed with water. The organic layer was concentrated to give the crude anhydride 62-1.

Step 2

A stirred solution of anhydride 62-1 (2.0 gr, 3.6 mmol) in $CH_2Cl_2$ was cooled down to 0° C. To this mixture $SOCl_2$ (2 mL) was added dropwise under vigorous stirring. The mixture was stirred at 0° C. and let it warm slowly to room temperature. After reaction was completed it was evaporated to remove excess $SOCl_2$ to give acid chloride intermediate 62-2 that was used on next step immediately.

Step 3

To a solution of 62-2 (200 mg, 0.38 mmol) and pyridazine (30 mg, 0.38 mmol) in acetonitrile stirred for 5 min at room temperature was added the racemic mixture of (S)—N'-(tert-butyldimethylsilyl)pent-4-ene-1-sulfonimidamide and (R)—N'-(tert-butyldimethylsilyl)pent-4-ene-1-sulfonimidamide (99 mg, 0.38 mmol). After completion of the reaction, the residue was dissolved in ethyl acetate and washed with water. The organic layer was concentrated and purified by reversed phase chromatography Acetonitrile-water 50%-90% for 30 min to give diastereomeric mixture of Intermediate IV.

Step 4

A mixture of sulfonimidamide intermediate IV (150 mg, 0.23 mmol), propionyl chloride (26 mg, 0.29 mmol), and triethylamine (0.29 mmol) was stirred at room temperature in $CH_2Cl_2$ for one hour. The reaction mixture was evaporated under reduced pressure, dissolved in DMF and purified by reversed phase chromatography, acetonitrile-water 50-90% for 30 min to yield 62-3.

Step 5

Ester intermediate 62-3 (25 mg, 0.036 mmol) and Hoveyda-Grubbs $2^{nd}$ generation catalyst (2.2 mg, 0.004 mmol) was sealed in a microwave vial and purged with argon and then 1,2-DCE was added. The microwave vial was heated to 60° C. for 1 hour. After completion of the reaction, the reaction mixture was evaporated under reduced pressure, dissolved in DMF and purified by reversed phase chromatography acetonitrile-water 50%-90% for 30 min to yield the macrocycle intermediate 62-4 as mixture of diastereomers.

Step 6

Intermediate (62-4) were dissolved in methanol (3 mL) and water (0.3 mL). To this solution $K_2CO_3$ (10.8 mg, 0.08 mmol) was added and stirred at room temperature for 7 hr. The mixture was dissolved in ethyl acetate and washed with water. The organic layer was concentrated and purified by reversed phase chromatography Acetonitrile-water 50%-90% for 30 min to give Example 62 (less polar fraction) and Example 63 (more polar fraction).

Example 62

$^1$H NMR (400 MHz, Chloroform-d) δ 7.72 (d, J=8.5 Hz, 1H), 7.38 (d, J=8.9 Hz, 2H), 7.17 (dd, J=8.5, 2.3 Hz, 1H), 7.07 (d, J=2.3 Hz, 1H), 6.92 (d, J=8.0 Hz, 1H), 6.00 (dd, J=15.8, 7.6 Hz, 1H), 5.80 (dt, J=15.8, 5.2 Hz, 1H), 4.20-3.95 (m, 4H), 3.78 (t, J=14.7 Hz, 3H), 3.53-3.40 (m, 3H), 3.34 (d, J=14.4 Hz, 2H), 3.15-3.00 (m, 2H), 2.88-2.67 (m, 3H), 2.45 (q, J=7.5 Hz, 3H), 2.24 (dt, J=12.7, 6.3 Hz, 2H), 2.12-1.63 (m, 4H), 1.40 (d, J=13.3 Hz, 1H), 1.26 (t, J=7.1 Hz, 1H), 1.17 (t, J=7.4 Hz, 2H). LCMS-ESI+ (m/z): [M+H]+ calcd for $C_{33}H_{40}ClN_3O_5S$: 626.2; found: 626.2.

Example 63

$^1$H NMR (400 MHz, Chloroform-d) δ 8.05 (s, 1H), 7.72 (d, J=8.5 Hz, 1H), 7.44-7.33 (m, 2H), 7.18 (d, J=8.2 Hz, 1H), 7.08 (s, 1H), 6.91 (t, J=8.1 Hz, 1H), 5.91-5.71 (m, 2H), 4.15-4.00 (m, 3H), 3.99-3.85 (m, 1H), 3.71 (d, J=14.7 Hz, 2H), 3.58 (d, J=14.9 Hz, 1H), 3.43 (d, J=14.7 Hz, 1H), 3.27 (s, 2H), 3.00 (s, 2H), 2.95-2.87 (m, 2H), 2.80 (d, J=19.0 Hz, 3H), 2.46 (tt, J=7.4, 3.4 Hz, 3H), 2H), 1.90-1.60 (m, 6H), 1.23 (dt, J=18.1, 7.3 Hz, 4H). LCMS-ESI+ (m/z): [M+H]+ calcd for $C_{33}H_{40}ClN_3O_5S$: 626.2; found: 626.2.

Examples 64 and 65

Example 64

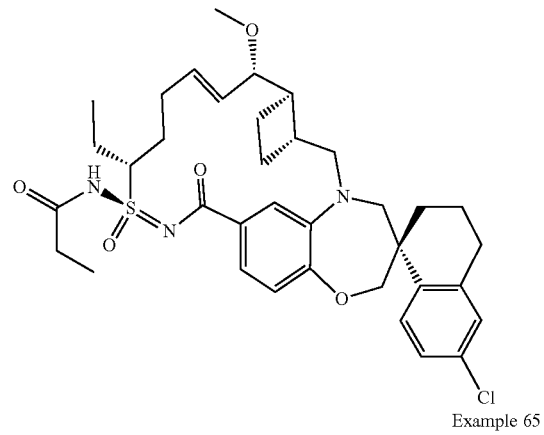

Example 65

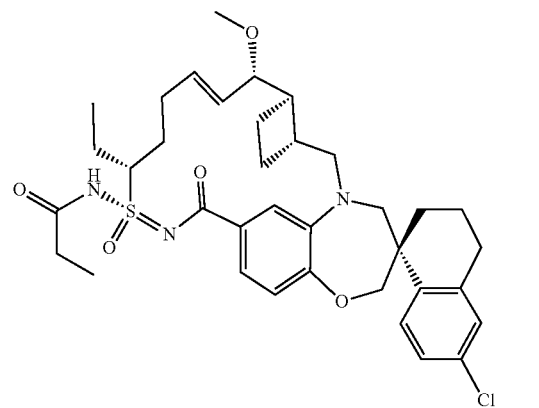

Step 1: Preparation of (R)—N-(tert-butyldimethylsilyl)hept-6-ene-3-sulfonamide

To a stirred solution of (R)-hept-6-ene-3-sulfonamide (prepared according to the procedure in International Publication No. WO17/147410, 1.5 g, 9.2 mmol) in THF was added $Et_3N$ (1.8 g, 18.3 mmol) in an ice bath, followed by tert-butylchloro dimethylsilane (1.7 g, 11.5 mmol) in THF. The resulting mixture was stirred at room temperature for 24 hrs. The precipitate was filtered off and washed with ether. The filtrate was concentrated and purified on normal phase chromatography Hexanes/EtOAc=3:1 to yield (R)—N-(tert-butyldimethylsilyl)hept-6-ene-3-sulfonamide.

Step 2: Preparation of (3R)—N'-(tert-butyldimethylsilyl)hept-6-ene-3-sulfonimidamide To a stirred suspension of $Ph_3PCl_2$ (4.2 g, 12.6 mmol) in $CH_2Cl_2$ under a nitrogen atmosphere, was added triethylamine (1.2 g, 12.6 mmol). The mixture was stirred for 10 min at room temperature, then cooled to 0° C. and a solution of (R)—N-(tert-butyldimethylsilyl)hept-6-ene-3-sulfonamide (2.2 g, 7.9 mmol) in $CH_2Cl_2$ was added. The reaction mixture was stirred for 1 hour at 0° C. To the reaction mixture was bubbled in ammonia gas. The mixture was stirred at 0° C. for 2 hours and then to room temperature for 24 hours. The precipitate was filtered off, and washed with CH$_2$Cl$_2$. The filtrate was concentrated and purified on normal phase chromatography (Hexanes:EtOAc=7:3) to yield (3R)—N'-(tert-butyldimethylsilyl)hept-6-ene-3-sulfonimidamide. $^1$H NMR (400 MHz, Chloroform-d) δ 5.78 (ddt, J=16.9, 10.5, 6.6 Hz, 1H), 5.13-4.85 (m, 2H), 4.38 (s, 2H), 2.75 (tt, J=7.0, 4.8 Hz, 1H), 2.32-2.10 (m, 2H), 2.06-1.86 (m, 2H), 1.79-1.54 (m, 2H), 1.03 (td, J=7.5, 1.7 Hz, 3H), 0.87 (s, 9H), 0.09 (d, J=1.1 Hz, 6H).

Step 3

Example 64 and Example 65 were prepared in the same manner as Example 3 and Example 4 using (3R)—N'-(tert-butyldimethylsilyl)hept-6-ene-3-sulfonimidamide instead of N'-(tert-butyldimethylsilyl)pent-4-ene-1-sulfonimidamide.

Example 64 (More Polar Fraction)

$^1$H NMR (400 MHz, Chloroform-d) δ 7.70 (t, J=8.2 Hz, 1H), 7.35 (d, J=8.5 Hz, 1H), 7.16 (t, J=4.2 Hz, 2H), 7.07 (s, 1H), 6.87 (d, J=8.0 Hz, 1H), 5.86 (s, 1H), 5.59 (dd, J=15.8, 7.8 Hz, 1H), 4.18-3.95 (m, 3H), 3.85-3.63 (m, 3H), 3.35-3.21 (m, 4H), 3.07-2.92 (m, 1H), 2.77 (s, 2H), 2.44 (t, J=7.9 Hz, 7H), 2.18-1.57 (m, 10H), 1.25 (s, 1H), 1.13 (dt, J=28.4, 7.2 Hz, 6H). LCMS-ESI+ (m/z): [M+H]+ calcd for C$_{36}$H$_{46}$ClN$_3$O$_5$S: 668.2; found: 668.3.

Example 65 (Less Polar Fraction)

$^1$H NMR (400 MHz, Chloroform-d) δ 7.70 (d, J=8.5 Hz, 1H), 7.17 (d, J=10.5 Hz, 2H), 7.08 (s, 2H), 6.92 (d, J=8.2 Hz, 1H), 6.10-6.00 (m, 1H), 5.50 (dd, J=15.4, 8.5 Hz, 1H), 4.29-3.99 (m, 3H), 3.87-3.59 (m, 3H), 3.25 (s, 4H), 3.00 (s, 1H), 2.76 (d, J=13.4 Hz, 2H), 2.43 (dd, J=19.8, 12.5 Hz, 6H), 2.24-1.54 (m, 11H), 1.41 (s, 1H), 1.28-1.05 (m, 6H). LCMS-ESI+ (m/z): [M+H]+ calcd for C$_{36}$H$_{46}$ClN$_3$O$_5$S: 668.2; found: 668.3.

Example 66

Step 1: Preparation of 66-1

A mixture of intermediate IV (900 mg, 1.4 mmol), di-tert-butyl dicarbonate (429 mg, 1.9 mmol), DMAP (17 mg, 0.14 mmol) and triethylamine (0.2 mL) was stirred at room temperature in CH$_2$Cl$_2$ for one hour. After completion of the reaction, the reaction mixture was evaporated under reduced pressure and purified by silica gel chromatography (Hex: EtOAc 1:1) to give intermediate 66-1.

Step 2

In a round bottle flask was added 66-1 (880 mg, 1.26 mmol) and Hoveyda-Grubbs 2$^{nd}$ generation catalyst (78 mg, 0.13 mmol). Flask was sealed and purged with argon and then 1,2-DCE was added. The flask was heated to 60° C. for 1 hour. After completion of the reaction, the reaction mixture was evaporated under reduced pressure to yield intermediate 66-2.

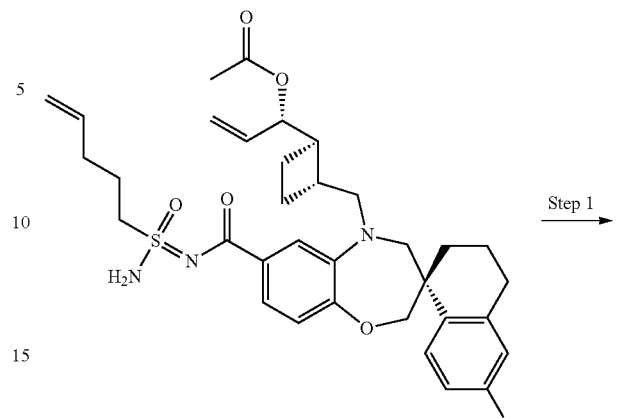

IV

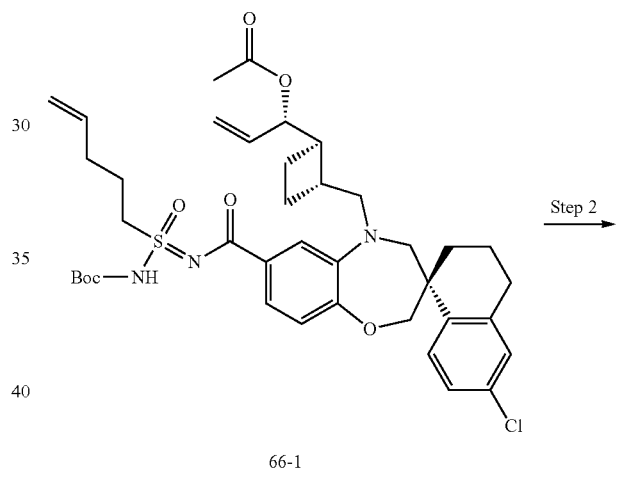

66-1

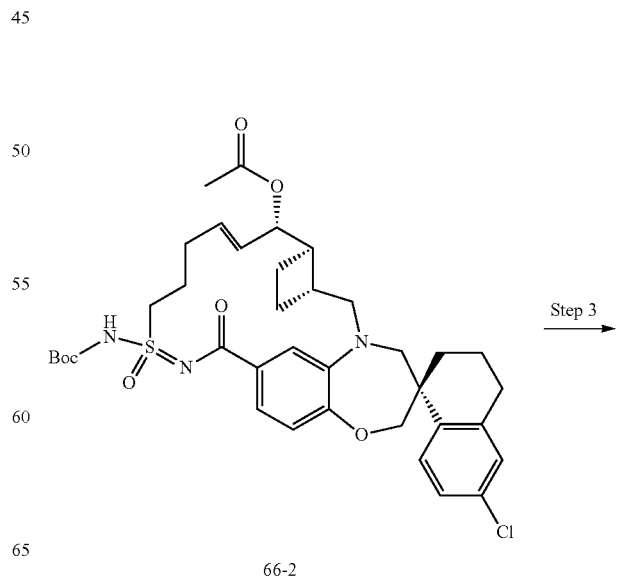

66-2

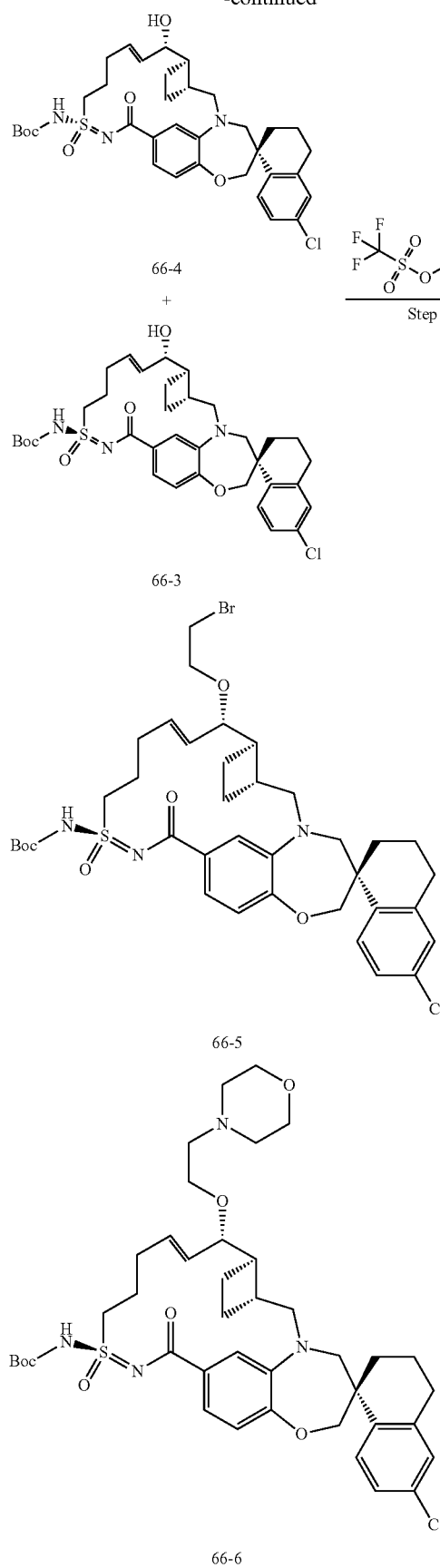

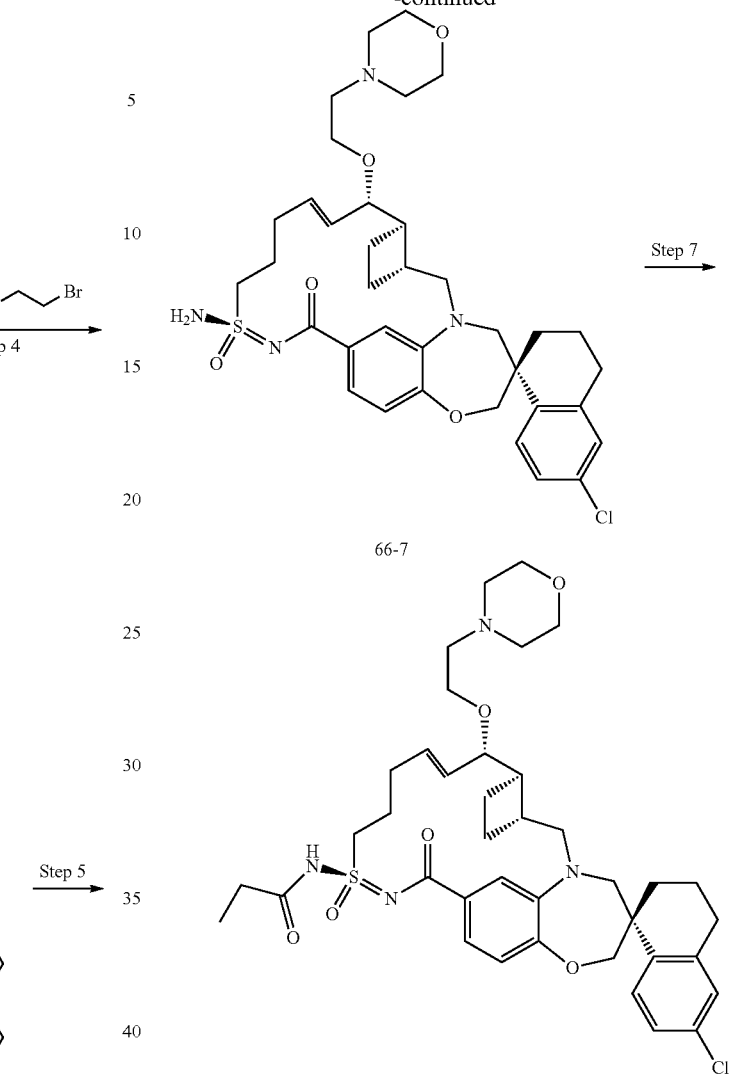

Example 66

Step 3

Intermediate 66-2 (600 mg, 0.84 mmol) were dissolved in methanol (6 mL) and water (0.6 mL). To this solution $K_2CO_3$ (406 mg, 2.94 mmol) was added and stirred at room temperature for 7 hours. The mixture was dissolved in ethyl acetate and washed with water. The organic layer was concentrated and purified by reversed phase chromatography (Acetonitrile-water 50%-90% for 30 min) to give diastereomers 66-3 (more polar fraction) and 66-4 (less polar fraction).

Step 4

Intermediate 66-3 (15 mg, 0.024 mmol) was dissolved in DMF and NaH (4 mg, 0.072 mmol) was added at room temperature, stirred for 10 min and then 2-bromoethyl trifluoromethanesulfonate (12 mg, 0.048 mmol) was added. The reaction mixture was stirred at room temperature for 5 hours and dissolved in ethyl acetate and washed with water. The organic layer was concentrated to give Bromo intermediate 66-5 which was used further without purification.

Step 5

Bromo intermediate 66-5 (15 mg, 0.02 mmol) was dissolved in morpholine and stirred at 50° C. for 1 hour. This mixture was evaporated under reduced pressure to give 66-6 which was used further without purification.

Step 6

Morpholine intermediate 66-6 (9 mg, 0.011 mmol) was treated with a mixture of $CH_2Cl_2$ (2 mL) and TFA (1 mL) and stirred at room temperature for 1 h. Mixture was dissolved in ethyl acetate and washed with a saturated aqueous solution of sodium bicarbonate. The organic layer was concentrated and purified by reversed phase chromatography acetonitrile-water 50%-90% for 30 min to intermediate 66-7.

Step 7

Intermediate 66-7 (5 mg, 0.007 mmol), propionyl chloride (1 mg, 0.007 mmol), and triethylamine (0.021 mmol) was stirred at room temperature in $CH_2Cl_2$ for one hour. After completion of reaction it was evaporated under reduced pressure, dissolved in DMF and purified by reversed phase chromatography, acetonitrile-water 50-90% for 30 min to give Example 66. 1H NMR (400 MHz, Chloroform-d) δ 7.72 (d, J=8.5 Hz, 1H), 7.46-7.39 (m, 1H), 7.31 (s, 1H), 7.22-7.15 (m, 1H), 7.07 (d, J=2.3 Hz, 1H), 6.92 (d, J=8.3 Hz, 1H), 5.94 (d, J=15.8 Hz, 1H), 5.73 (dd, J=15.9, 7.8 Hz, 1H), 4.10 (d, J=12.0 Hz, 1H), 4.03-3.75 (m, 7H), 3.66 (t, J=13.1 Hz, 5H), 3.51 (d, J=12.0 Hz, 1H), 3.36 (d, J=14.4 Hz, 2H), 3.27 (s, 2H), 3.14-2.92 (m, 3H), 2.76 (d, J=14.8 Hz, 3H), 2.53-2.39 (m, 3H), 2.32-1.64 (m, 10H), 1.41 (d, J=12.5 Hz, 2H), 1.22 (t, J=7.5 Hz, 3H). LCMS-ESI+ (m/z): [M+H]+ calcd for $C_{39}H_{51}ClN_4O_6S$: 739.3; found: 739.5.

Example 67

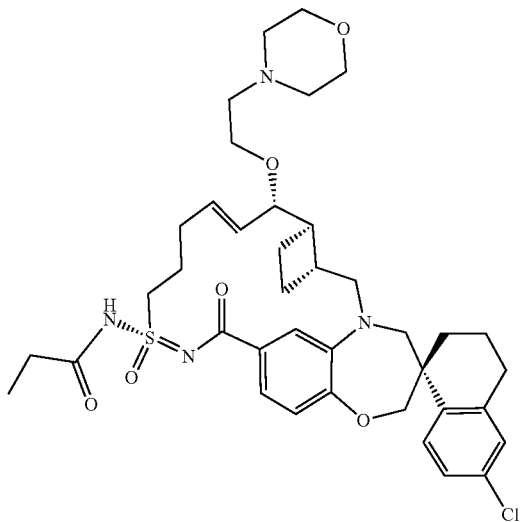 [SMILES: CCC(=O)N[S@@]1(=O)=NC(=O)c2ccc3c(c2)N(C[C@@H]2CC[C@H]2[C@@H](OCCN2CCOCC2)/C=C/CCC1)C[C@@]1(CCCc2cc(Cl)ccc21)CO3]

Example 67 was synthesized in the same manner as Example 66 using intermediate 66-4 (less polar fraction). 1H NMR (400 MHz, Chloroform-d) δ 7.74 (d, J=8.5 Hz, 1H), 7.43 (d, J=8.6 Hz, 1H), 7.32 (s, 1H), 7.18 (dd, J=8.6, 2.3 Hz, 1H), 7.08 (s, 1H), 6.93 (d, J=8.3 Hz, 1H), 5.83 (s, 2H), 4.11 (d, J=12.1 Hz, 1H), 3.99-3.75 (m, 6H), 3.61 (dd, J=37.3, 15.1 Hz, 6H), 3.49 (s, 1H), 3.40 (s, 1H), 3.32-3.18 (m, 2H), 3.06-2.97 (m, 1H), 2.90 (s, 2H), 2.82-2.66 (m, 3H), 2.49 (s, 4H), 2.28-1.62 (m, 9H), 1.37 (s, 2H), 1.27-1.11 (m, 4H). LCMS-ESI+ (m/z): [M+H]+ calcd for $C_{39}H_{51}ClN_4O_6S$: 739.3; found: 739.5.

Example 68

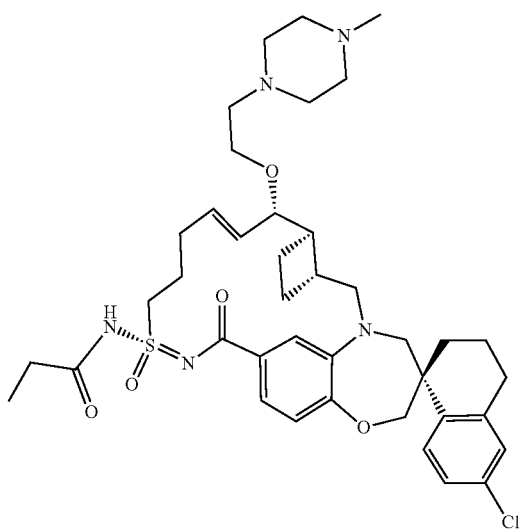 [SMILES: CCC(=O)N[S@@]1(=O)=NC(=O)c2ccc3c(c2)N(C[C@@H]2CC[C@H]2[C@@H](OCCN2CCN(C)CC2)/C=C/CCC1)C[C@@]1(CCCc2cc(Cl)ccc21)CO3]

Example 68 was synthesized in the same manner as Example 67 using intermediate 67-4 (less polar fraction) and 1-methylpiperazine instead of morpholine. $^1$H NMR (400 MHz, Chloroform-d) δ 7.74 (d, J=8.5 Hz, 1H), 7.47-7.30 (m, 2H), 7.21-7.13 (m, 1H), 7.07 (d, J=2.3 Hz, 1H), 6.92 (d, J=8.3 Hz, 1H), 6.11 (dd, J=15.9, 9.0 Hz, 1H), 5.75 (d, J=15.9 Hz, 1H), 4.12-3.93 (m, 4H), 3.85-3.49 (m, 8H), 3.36 (t, J=14.1 Hz, 4H), 3.16-3.00 (m, 3H), 2.87 (d, J=10.7 Hz, 4H), 2.82-2.60 (m, 4H), 2.09 (td, J=15.4, 14.9, 8.0 Hz, 6H), 1.98-1.59 (m, 6H), 1.46 (d, J=3.0 Hz, 1H), 1.42-1.20 (m, 2H), 1.12 (t, J=7.1 Hz, 2H). LCMS-ESI+ (m/z): [M+H]+ calcd for $C_{40}H_{54}ClN_5O_5S$: 752.3; found: 752.4.

Example 69

Step 1

N'-(tert-butyldimethylsilyl)hex-5-ene-1-sulfonimidamide was prepared in the same manner as Example 1 (step 4 and step 5) using hex-5-ene-1-sulfonamide instead of (2R,3S)-3-methylhex-5-ene-2-sulfonamide. $^1$H NMR (400 MHz, Chloroform-d) δ 5.87-5.63 (m, 1H), 5.07-4.84 (m, 2H), 4.71-4.01 (m, 2H), 3.04 (dddd, J=13.4, 10.0, 8.5, 5.0 Hz, 2H), 2.13-2.01 (m, 2H), 1.92-1.71 (m, 2H), 1.57-1.45 (m, 2H), 0.88 (d, J=5.9 Hz, 9H), 0.11-0.2 (m, 6H).

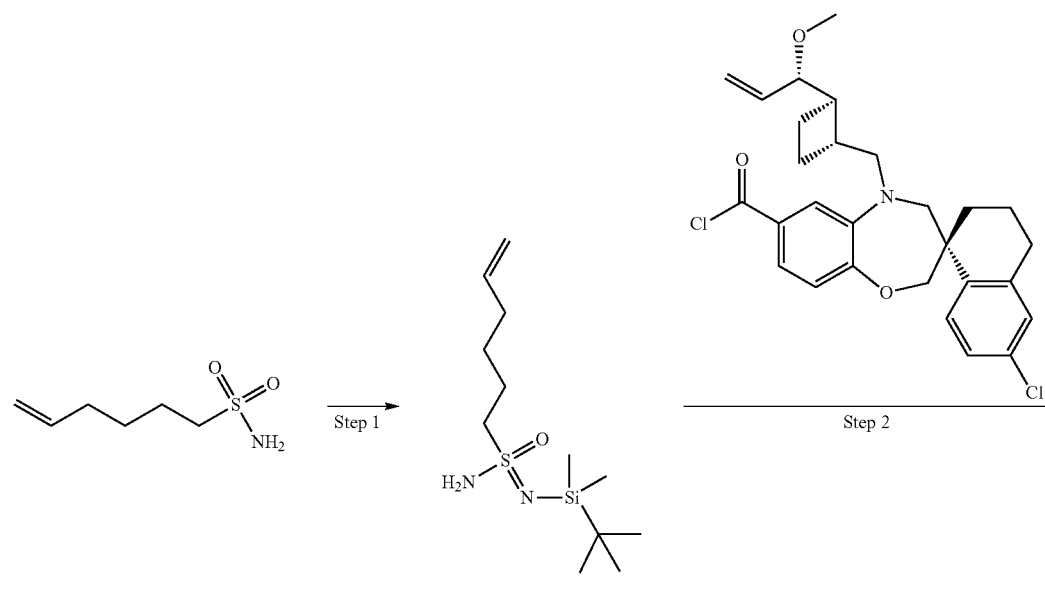
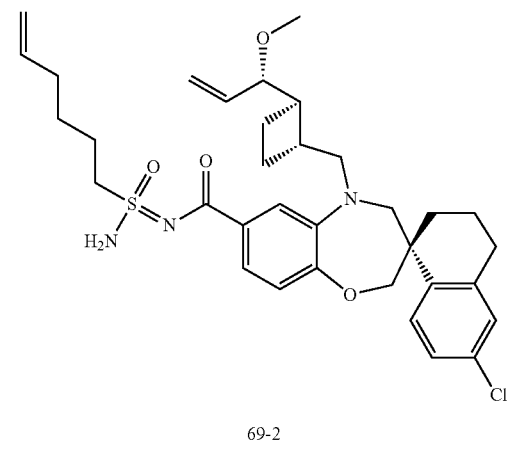
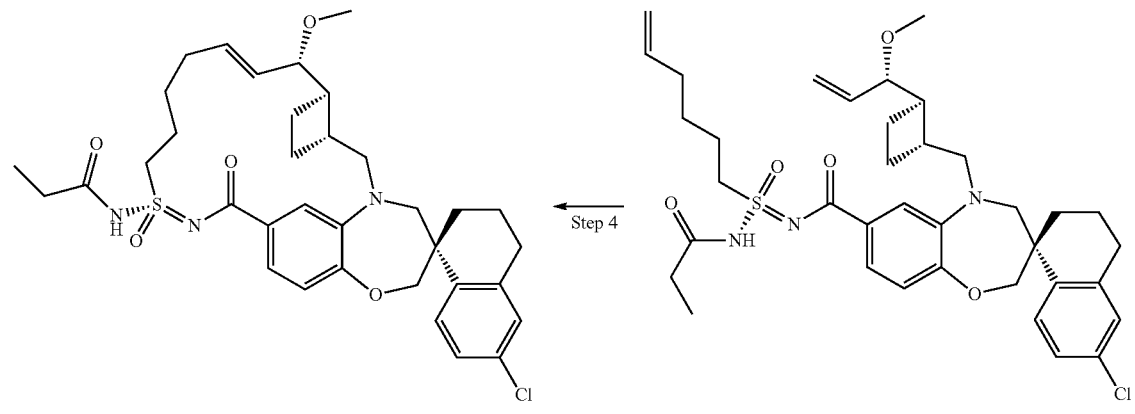

Step 2: Preparation of Intermediate 69-2

To a mixture of (S)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carbonyl chloride (from Example 1 step 3, 200 mg, 0.40 mmol) and pyridazine (32 mg, 0.40 mmol) in acetonitrile stirred for 5 min at room temperature was added N'-(tert-butyldimethylsilyl)hex-5-ene-1-sulfonimidamide 70-1, (121 mg, 0.44 mmol). After completion of the reaction the residue was dissolved in ethyl acetate and washed with water. The organic layer was concentrated and purified by normal phase chromatography Hex:AtOAc 1:1 to yield 69-2 as mixture of diastereomers.

Step 3: Preparation of Intermediate 69-3

Diastereomeric mixture 69-2 (160 mg, 0.25 mmol), propionyl chloride (28 mg, 0.30 mmol), and triethylamine (0.56 mmol) was stirred at room temperature in $CH_2Cl_2$ for one hour. After completion of the reaction, the reaction mixture was evaporated under reduced pressure, dissolved in DMF and purified by reversed phase chromatography, acetonitrile-water 50-90% for 30 min to yield 69-3 as mixture of the diastereoisomers.

Step 4: Preparation of Example 69

In a microwave vial was added the intermediate 69-3 (25 mg, 0.037 mmol) and Hoveyda-Grubbs II (2.2 mg, 0.004 mmol). Vial was sealed and purged with argon and then 1,2-DCE was added. The microwave vial was heated to 60° C. for one hour. After completion of the reaction, the reaction mixture was evaporated under reduced pressure, dissolved in DMF and purified by reversed phase chromatography acetonitrile-water 50-90% for 30 min to yield Example 69 (less polar fraction). $^1$H NMR (400 MHz, Chloroform-d) δ 7.67 (dd, J=8.6, 4.6 Hz, 1H), 7.46 (d, J=8.1 Hz, 1H), 7.32-7.05 (m, 3H), 6.96 (dd, J=18.1, 8.1 Hz, 1H), 5.63-5.30 (m, 2H), 4.25-4.01 (m, 2H), 3.86-3.56 (m, 4H), 3.49-3.27 (m, 5H), 3.22 (d, J=10.0 Hz, 2H), 2.76 (d, J=10.8 Hz, 2H), 2.58-2.37 (m, 4H), 2.15-1.74 (m, 10H), 1.63 (dt, J=18.7, 9.4 Hz, 6H), 1.23 (t, J=7.5 Hz, 2H). LCMS-ESI+ (m/z): [M+H]+ calcd for $C_{35}H_{44}ClN_3O_5S$: 654.4; found: 654.2.

Examples 70 and 71

Example 70

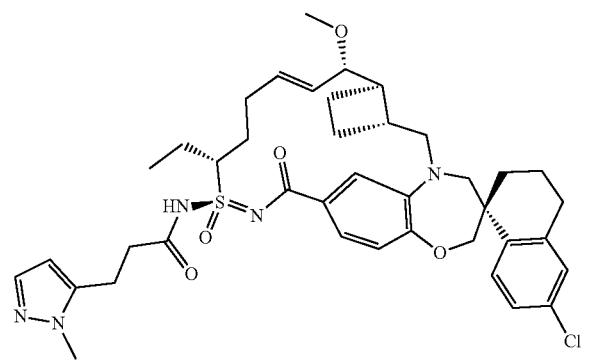

Example 71

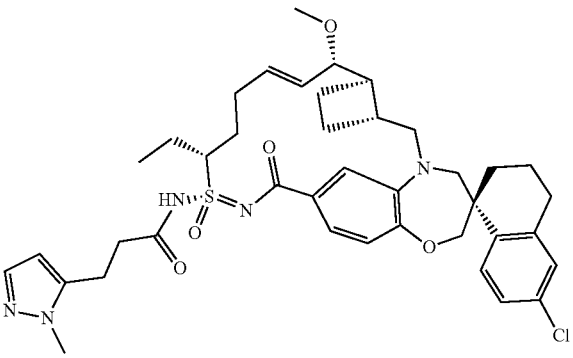

Examples 71 and 72 were synthesized in the same manner as Example 3 and 4 using (3R)—N'-(tert-butyldimethylsilyl)hept-6-ene-3-sulfonimidamide (Example 64 and 65 step 1) and 3-(1-methyl-1H-pyrazol-5-yl)propanoic acid.

Example 70

$^1$H NMR (400 MHz, Chloroform-d) δ 7.69 (d, J=8.5 Hz, 1H), 7.55 (d, J=2.2 Hz, 1H), 7.16 (td, J=8.5, 2.3 Hz, 1H), 7.09-7.01 (m, 2H), 7.00-6.87 (m, 2H), 6.16 (d, J=2.1 Hz, 1H), 5.94-5.80 (m, 1H), 5.51 (dd, J=15.3, 8.7 Hz, 1H), 4.31 (s, 1H), 4.12-4.02 (m, 2H), 3.93 (s, 2H), 3.78 (t, J=13.6 Hz, 1H), 3.71-3.59 (m, 4H), 3.25 (d, J=15.2 Hz, 3H), 3.05-2.89 (m, 6H), 2.87-2.72 (m, 4H), 2.48-2.19 (m, 4H), 2.16-1.57 (m, 11H), 1.49-1.30 (m, 1H), 1.16 (t, J=7.5 Hz, 2H). LCMS-ESI+ (m/z): [M+H]+ calcd for $C_{40}H_{50}ClN_5O_5S$: 748.2; found: 748.3.

Example 71

$^1$H NMR (400 MHz, Chloroform-d) δ 7.70 (d, J=8.5 Hz, 1H), 7.52 (d, J=2.1 Hz, 1H), 7.49-7.31 (m, 2H), 7.16 (dd, J=8.5, 2.4 Hz, 1H), 7.07 (d, J=2.3 Hz, 1H), 6.91 (dd, J=11.6, 8.3 Hz, 2H), 6.15 (d, J=2.1 Hz, 1H), 5.72 (td, J=10.8, 5.0 Hz, 1H), 5.37 (t, J=10.3 Hz, 1H), 4.10 (q, J=9.0, 8.0 Hz, 3H), 3.98-3.55 (m, 5H), 3.48-3.35 (m, 1H), 3.35-3.14 (m, 4H), 3.11-2.63 (m, 9H), 2.46-2.14 (m, 5H), 2.12-1.52 (m, 10H), 1.45-1.34 (m, 1H), 1.14 (q, J=5.1, 2.9 Hz, 1H), 1.03-0.82 (m, 2H). LCMS-ESI+ (m/z): [M+H]+ calcd for $C_{40}H_{50}ClN_5O_5S$: 748.2; found: 748.3.

Example 72

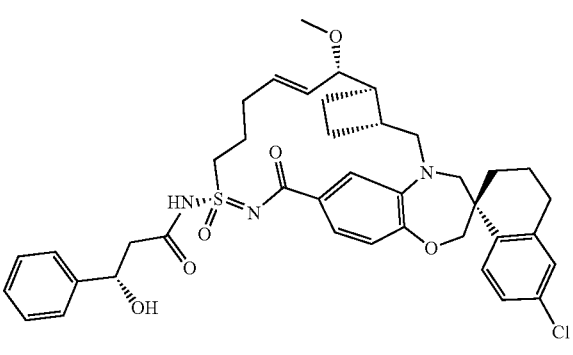 [SMILES: CO[C@H]1/C=C/CCC[S@@](=O)(NC(=O)C[C@H](O)c2ccccc2)=NC(=O)c2ccc3c(c2)N(C[C@@H]2CC[C@H]21)C[C@@]1(CCCc2cc(Cl)ccc21)CO3]

Example 72 was synthesized in the same manner as Example 18 using (S)-3-hydroxy-3-phenylpropanoic acid instead of 3-methoxypropionic acid. $^1$H NMR (400 MHz, Chloroform-d) δ 7.61 (d, J=8.5 Hz, 1H), 7.44-7.27 (m, 6H), 7.16 (d, J=1.7 Hz, 1H), 7.04 (d, J=2.3 Hz, 1H), 6.92 (d, J=8.3 Hz, 2H), 5.88-5.66 (m, 2H), 5.25 (dd, J=9.9, 2.7 Hz, 1H), 3.99 (q, J=12.0 Hz, 3H), 3.71 (dd, J=27.2, 14.6 Hz, 3H), 3.56 (dd, J=7.5, 3.2 Hz, 1H), 3.32 (s, 4H), 3.03 (dd, J=15.6, 10.2 Hz, 2H), 2.87-2.64 (m, 4H), 2.47-2.06 (m, 5H), 2.06-1.66 (m, 5H), 1.29 (d, J=30.9 Hz, 4H). LCMS-ESI+ (m/z): [M+H]+ calcd for $C_{40}H_{46}ClN_3O_6S$: 732.2; found: 732.0.

Example 73

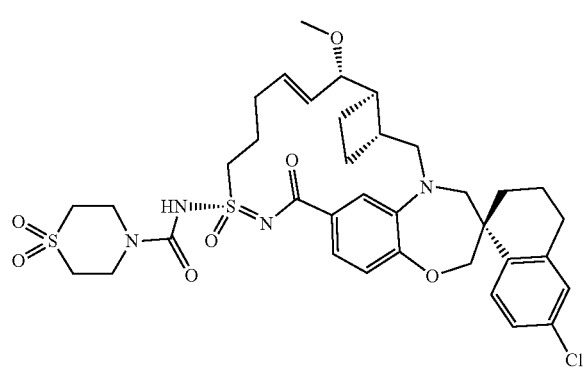 [SMILES: CO[C@H]1/C=C/CCC[S@@](=O)(NC(=O)N2CCS(=O)(=O)CC2)=NC(=O)c2ccc3c(c2)N(C[C@@H]2CC[C@H]21)C[C@@]1(CCCc2cc(Cl)ccc21)CO3]

To a solution of Example 5 (12 mg, 0.021 mmol) and diisopropylethylamine (0.041 mmol) in 3 mL dichloromethane was added dropwise a solution of thiomorpholine-4-carbonyl chloride 1,1-dioxide (8 mg, 0.041 mmol) in 1 mL dichloromethane and the mixture was allowed to stir at reflux for 16 hrs. LC/MS showed completion of the reaction. The solvent was evaporated under reduced pressure and the residue was dissolved in 3 mL methanol and purified using HPLC to afford Example 73. $^1$H NMR (400 MHz, Chloroform-d) δ 7.77-7.62 (m, 1H), 7.23-7.11 (m, 2H), 7.08 (d, J=2.3 Hz, 1H), 7.04-6.81 (m, 2H), 5.93-5.74 (m, 1H), 5.53 (dd, J=15.5, 8.4 Hz, 1H), 4.28-3.85 (m, 7H), 3.79-3.49 (m, 4H), 3.40-3.20 (m, 4H), 2.99 (d, J=34.6 Hz, 4H), 2.85-2.61 (m, 2H), 2.55-2.20 (m, 4H), 2.20-1.58 (m, 9H), 1.42 (t, J=12.8 Hz, 2H). LCMS-ESI+ (m/z): [M+H]+ calcd for $C_{36}H_{45}ClN_4O_7S_2$: 745.25; found:745.96.

Example 74

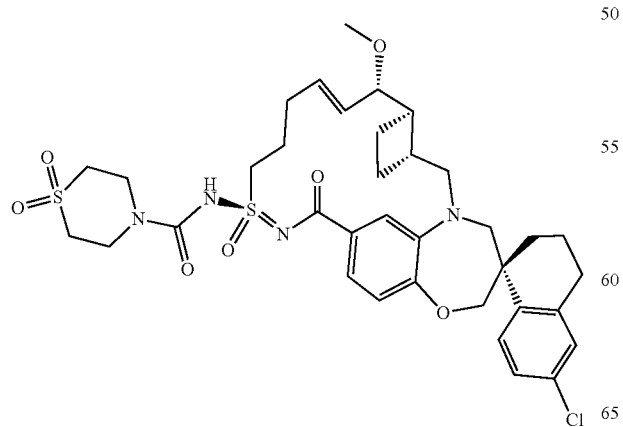

Example 74 was synthesized in the same manner as Example 73 using Example 6. LCMS-ESI+ (m/z): [M+H]+ calcd for $C_{36}H_{45}ClN_4O_7S_2$: 745.25; found: 745.96.

Example 75

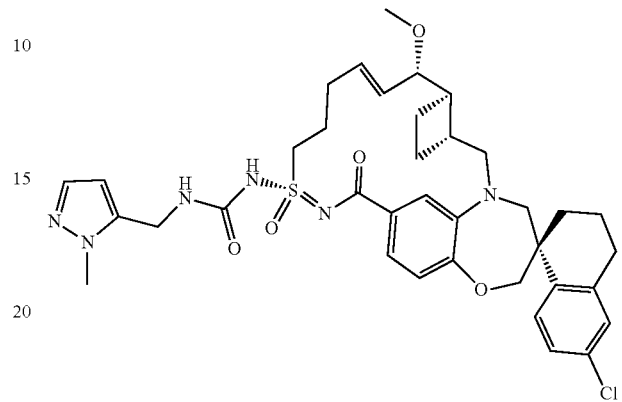

A solution of the Example 5 (12 mg, 0.021 mmol), diphenylcarbonate (5 mg, 0.023 mmol)) and DMAP (15 mg, 0.123 mmol) in 3 mL acetonitrile was allowed to stir at rt for 16 hrs. (1-Methyl-1H-pyrazol-5-yl)methanamine (6.8 mg, 0.062 mmol) was added and the mixture was further stirred at rt for 1 hr. LC/MS showed completion of the reaction. The solvent was evaporated under reduced pressure and the residue was dissolved in 3 mL methanol and purified using HPLC to afford Example 75. $^1$H NMR (400 MHz, Methanol-d4) δ 7.74 (d, J=8.5 Hz, 1H), 7.49-7.20 (m, 3H), 7.20-7.03 (m, 2H), 6.87 (d, J=8.2 Hz, 1H), 6.37 (d, J=1.9 Hz, 1H), 6.00-5.68 (m, 2H), 5.38-5.16 (m, 2H), 4.21-3.90 (m, 2H), 3.82-3.47 (m, 3H), 3.46-3.18 (m, 11H), 3.10 (dd, J=15.0, 10.7 Hz, 1H), 2.93-2.60 (m, 3H), 2.58-2.15 (m, 3H), 2.15-1.64 (m, 6H), 1.52-1.17 (m, 2H). LCMS-ESI+ (m/z): [M+H]+ calcd for $C_{37}H_{45}ClN_6O_5S$: 721.29; found:721.91.

Example 76

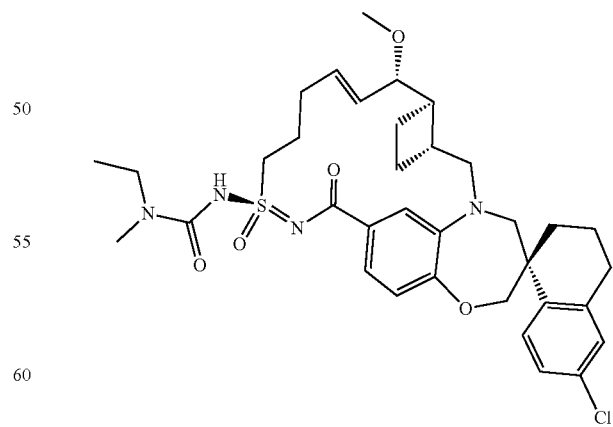

Example 76 was synthesized in the same manner as Example 75 using Example 6 and N-methylethanamine. LCMS-ESI+ (m/z): [M+H]+ calcd for $C_{35}H_{45}ClN_4O_5S$: 669.28; found: 669.88.

Example 77

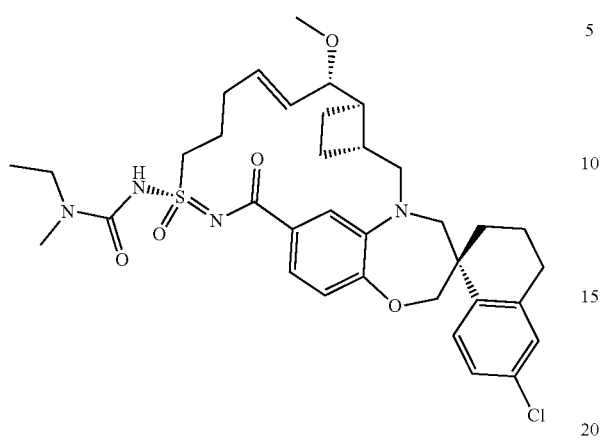

Example 77 was synthesized in the same manner as Example 77 using N-methylethanamine. LCMS-ESI+ (m/z): [M+H]+ calcd for $C_{35}H_{45}ClN_4O_5S$: 669.28; found: 669.88.

Example 78

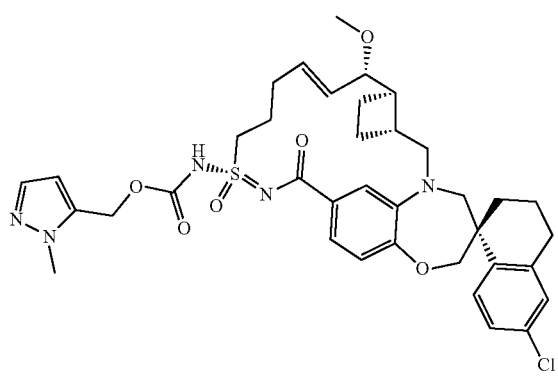 [SMILES: CO[C@H]1/C=C/CCC[S@@](=O)(NC(=O)OCc2ccnn2C)=NC(=O)c2ccc3c(c2)N(C[C@@H]2CC[C@H]21)C[C@@]1(CCCc2cc(Cl)ccc21)CO3]

Example 78 was synthesized in the same manner as Example 76 using (1-methyl-1H-pyrazol-5-yl)methanol. LCMS-ESI+ (m/z): [M+H]+ calcd for $C_{37}H_{44}ClN_5O_6S$: 722.27; found: 723.24.

Example 79

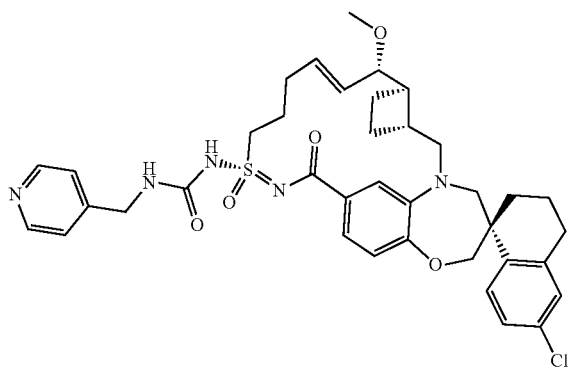 [SMILES: CO[C@H]1/C=C/CCC[S@@](=O)(NC(=O)NCc2ccncc2)=NC(=O)c2ccc3c(c2)N(C[C@@H]2CC[C@H]21)C[C@@]1(CCCc2cc(Cl)ccc21)CO3]

Example 79 was synthesized in the same manner as Example 76 using pyridin-4-ylmethanamine. 1H NMR (400 MHz, Methanol-d4) δ 8.70 (d, J=6.0 Hz, 2H), 7.96 (d, J=6.0 Hz, 2H), 7.68 (dd, J=8.9, 6.4 Hz, 1H), 7.41-7.16 (m, 2H), 7.18-6.98 (m, 2H), 6.91 (d, J=8.2 Hz, 1H), 5.89 (dt, J=15.8, 5.3 Hz, 1H), 5.76 (t, J=12.0 Hz, 1H), 4.64 (s, 2H), 4.21-3.46 (m, 6H), 3.39 (d, J=14.5 Hz, 1H), 3.34 (s, 6H), 3.10 (dd, J=15.1, 10.8 Hz, 1H), 2.97-2.58 (m, 3H), 2.35 (d, J=58.3 Hz, 3H), 2.19-1.68 (m, 6H), 1.54-1.17 (m, 2H). LCMS-ESI+ (m/z): [M+H]+ calcd for $C_{38}H_{44}ClN_5O_5S$: 718.28; found: 719.76.

Example 80

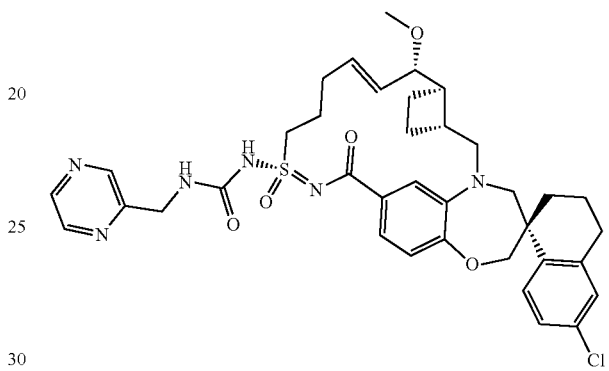

Example 80 was synthesized in the same manner as Example 76 using pyrazin-2-ylmethanamine. $^1$H NMR (400 MHz, Methanol-d4) δ 8.64 (s, 1H), 8.60-8.41 (m, 2H), 7.74 (dd, J=8.5, 5.2 Hz, 1H), 7.29 (dd, J=12.5, 8.1 Hz, 2H), 7.23-7.00 (m, 2H), 6.86 (dd, J=16.3, 8.1 Hz, 1H), 5.89 (dt, J=15.8, 5.3 Hz, 1H), 5.76 (t, J=12.0 Hz, 1H), 4.64 (s, 2H), 4.21-3.46 (m, 6H), 3.39 (d, J=14.5 Hz, 1H), 3.34 (s, 6H), 3.10 (dd, J=15.1, 10.8 Hz, 1H), 2.97-2.58 (m, 3H), 2.35 (d, J=58.3 Hz, 3H), 2.19-1.68 (m, 6H), 1.54-1.17 (m, 2H). LCMS-ESI+ (m/z): [M+H]+ calcd for $C_{37}H_{43}ClN_6O_5S$: 719.27; found: 719.71.

Example 81

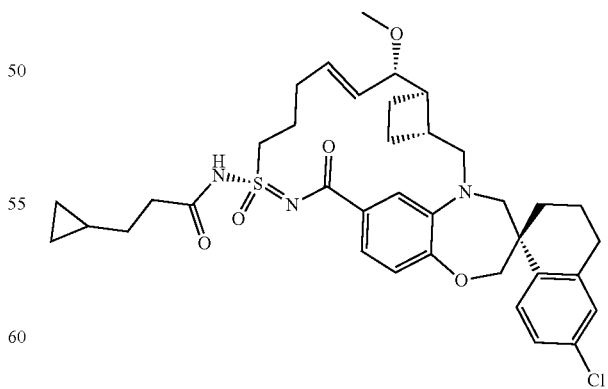

Example 81 was synthesized in the same manner as Example 18 using 3-cyclopropylpropanoic acid instead of 3-methoxypropionic acid. 1H NMR (400 MHz, Methanol-d4) δ 7.74 (d, J=8.5 Hz, 1H), 7.40 (d, J=1.9 Hz, 1H), 7.33

(dd, J=8.3, 1.9 Hz, 1H), 7.18-7.05 (m, 2H), 6.87 (d, J=8.2 Hz, 1H), 5.93-5.76 (m, 2H), 4.06 (d, J=12.1 Hz, 1H), 4.02-3.89 (m, 2H), 3.78 (d, J=14.9 Hz, 1H), 3.71 (d, J=14.3 Hz, 1H), 3.67-3.46 (m, 2H), 3.40 (d, J=14.4 Hz, 1H), 3.34 (s, 1H), 3.25 (s, 3H), 3.11 (dd, J=15.3, 10.8 Hz, 1H), 2.82-2.72 (m, 2H), 2.47 (t, J=7.3 Hz, 3H), 2.26-2.17 (m, 1H), 2.13-1.98 (m, 3H), 1.93 (s, 1H), 1.77 (t, J=6.3 Hz, 2H), 1.53 (q, J=7.2 Hz, 2H), 1.41 (t, J=13.1 Hz, 2H), 1.28 (s, 2H), 0.89 (t, J=6.6 Hz, 1H), 0.80-0.68 (m, 1H), 0.48-0.39 (m, 2H), 0.08 (t, J=4.7 Hz, 2H). LCMS-ESI+ (m/z): [M+H]+ calcd for $C_{37}H_{46}ClN_3O_5S$: 680.29; found: 680.98.

Example 82

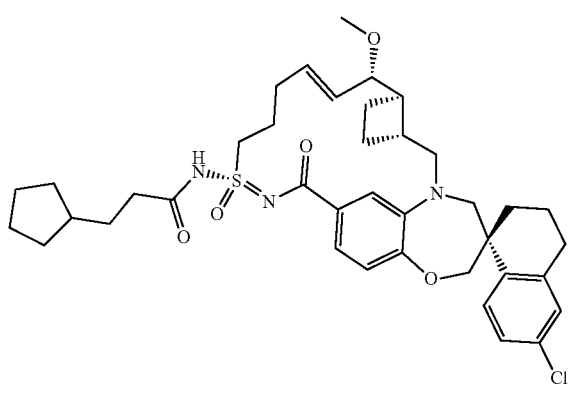 [SMILES: CO[C@H]1/C=C/CCC[S@@](=O)(NC(=O)CCC2CCCC2)=NC(=O)c2ccc3c(c2)N(C[C@@H]2CC[C@H]21)C[C@@]1(CCCc2cc(Cl)ccc21)CO3]

Example 82 was synthesized in the same manner as Example 18 using 3-cyclopentylpropanoic acid instead of 3-methoxypropionic acid. LCMS-ESI+ (m/z): [M+H]+ calcd for $C_{39}H_{50}ClN_3O_5S$: 709.32; found: 709.36.

Examples 83 and 84

Step 1: Preparation of trans-(±)-ethyl 2-(1-methyl-1H-pyrazol-5-yl)cyclopropane-1-carboxylate Sodium hydride (0.22 g, 9.1 mmol) and trimethyl sulfoxonium iodide (1.4 g, 18.1 mmol) were stirred for one hour in 7 mL DMSO at room temperature. Ethyl (E)-3-(1-methyl-1H-pyrazol-5-yl)acrylate (0.65 g, 3.6 mmol) was dissolved in 5 mL DMSO/THF (1:1) and added to the reaction mixture. After completion of the reaction (3 h, LC/MS) 1 N HCl is added and the reaction mixture extracted with diethyl ether. The combined organic layers are dried over MgSO4, the solvent was removed and the crude product was used without further purification.

Example 83

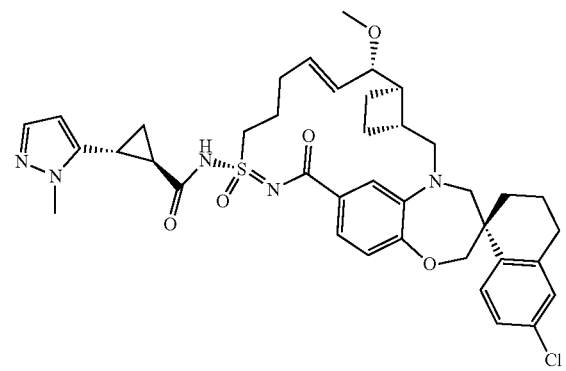

Example 84

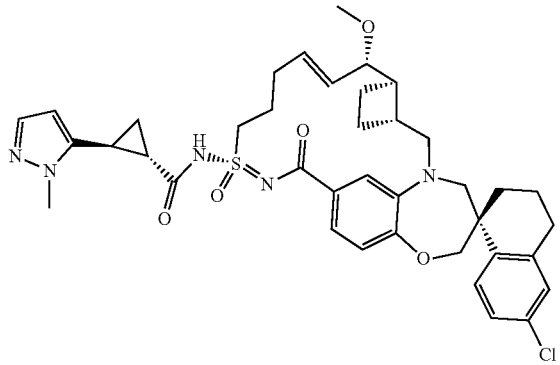

Step 2: Preparation of trans (±)-2-(1-methyl-1H-pyrazol-5-yl)cyclopropane-1-carboxylic Acid To a solution of trans-(±)-ethyl 2-(1-methyl-1H-pyrazol-5-yl)cyclopropane-1-carboxylate (0.4 g, 2.4 mmol) in 10 mL methanol was added 2 mL of 1 N NaOH and the reaction was stirred at rt for 3 hr. Methanol was removed under reduced pressure and aqueous solution was acidified to pH 4 using concentrated HCl. The precipitate formed was collected by filtration, washed with water and air-dried to give the acid which was used without further purification.

Step 3: Preparation of Example 83 and Example 84

The two diastereomers, Example 83 and Example 84 were synthesized in the same manner as Example 18 using trans (±)-2-(1-methyl-1H-pyrazol-5-yl)cyclopropane-1-carboxylic acid and Example 5. The two diastereomers were separated by a supercritical fluid chromatography (Chiralpak AD-H, 5 μM, 21×250 mm, 50% MeOH, flow 65 mL/min, 100 bar).

Example 83 (Less Polar Fraction)

$^1$H NMR (400 MHz, Methanol-d4) δ 7.74 (d, J=8.5 Hz, 1H), 7.55-7.24 (m, 3H), 7.24-7.02 (m, 2H), 6.88 (d, J=8.2 Hz, 1H), 6.01 (d, J=2.0 Hz, 1H), 5.85 (qd, J=15.8, 9.5 Hz, 2H), 4.19-3.82 (m, 5H), 3.84-3.36 (m, 6H), 3.34 (s, 3H), 3.21-3.00 (m, 2H), 2.93-2.67 (m, 3H), 2.46 (dt, J=10.6, 5.6 Hz, 3H), 2.24 (d, J=8.1 Hz, 2H), 2.15-1.94 (m, 4H), 1.85-1.54 (m, 3H), 1.50-1.14 (m, 4H). LCMS-ESI+ (m/z): [M+H]+ calcd for $C_{39}H_{46}ClN_5O_5S$: 732.29; found:732.00.

Example 84 (More Polar Fraction)

$^1$H NMR (400 MHz, Methanol-d4) δ 7.78 (d, J=8.8 Hz, 1H), 7.31 (d, J=2.0 Hz, 1H), 7.25 (dd, J=8.2, 1.8 Hz, 1H), 7.18 (dd, J=8.4, 2.4 Hz, 1H), 7.15 (d, J=2.0 Hz, 1H), 7.10 (d, J=2.4 Hz, 1H), 6.82 (d, J=8.0 Hz, 1H), 6.11 (dt, J=15.5, 6.4 Hz, 1H), 5.98 (d, J=2.0 Hz, 1H), 5.61 (dd, J=15.4, 9.0 Hz, 1H), 4.19-4.12 (m, 1H), 4.01 (dd, J=21.8, 11.8 Hz, 2H), 3.94-3.85 (m, 5H), 3.74-3.66 (m, 3H), 3.50 (p, J=1.6 Hz, 1H), 3.34-3.31 (m, 2H), 3.27 (s, 3H), 3.15 (p, J=1.6 Hz, 1H), 3.08-3.01 (m, 1H), 2.88-2.74 (m, 3H), 2.56-1.70 (m, 10H), 1.59-1.54 (m, 1H), 1.46-1.39 (m, 1H), 1.18-1.36 (m, 1H). LCMS-ESI+ (m/z): [M+H]+ calcd for $C_{39}H_{46}ClN_5O_5S$: 732.29; found: 732.06.

Example 85

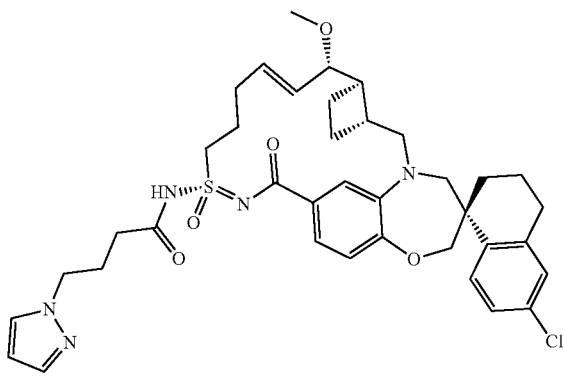 [SMILES: CO[C@H]1/C=C/CCC[S@@](=O)(NC(=O)CCCn2cccn2)=NC(=O)c2ccc3c(c2)N(C[C@@H]2CC[C@H]21)C[C@@]1(CCCc2cc(Cl)ccc21)CO3]

Example 85 was synthesized in the same manner as Example 18 using 4-(1H-pyrazol-1-yl)butanoic acid instead of 3-methoxypropionic acid. $^1$H NMR (400 MHz, Methanol-d4) δ 7.73 (d, J=8.5 Hz, 1H), 7.64 (d, J=2.3 Hz, 1H), 7.48 (dd, J=1.9, 0.7 Hz, 1H), 7.40 (d, J=1.9 Hz, 1H), 7.32 (dd, J=8.3, 1.9 Hz, 1H), 7.21-7.04 (m, 2H), 6.87 (d, J=8.2 Hz, 1H), 6.27 (t, J=2.1 Hz, 1H), 5.97-5.74 (m, 2H), 4.20 (t, J=6.8 Hz, 2H), 4.12-3.88 (m, 3H), 3.74 (dd, J=26.9, 14.7 Hz, 2H), 3.66-3.47 (m, 2H), 3.38 (d, J=32.3 Hz, 4H), 3.10 (dd, J=15.0, 10.9 Hz, 1H), 2.93-2.60 (m, 3H), 2.61-2.30 (m, 4H), 2.31-1.71 (m, 12H), 1.41 (t, J=13.2 Hz, 1H). LCMS-ESI+ (m/z): [M+H]+ calcd for $C_{38}H_{46}ClN_5O_5S$: 720.29; found: 720.97.

Example 86

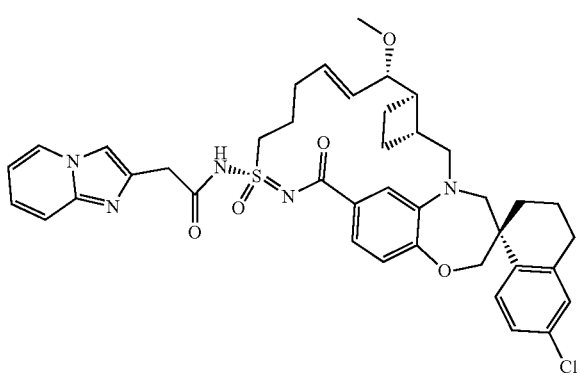 [SMILES: CO[C@H]1/C=C/CCC[S@@](=O)(NC(=O)Cc2cn3ccccc3n2)=NC(=O)c2ccc3c(c2)N(C[C@@H]2CC[C@H]21)C[C@@]1(CCCc2cc(Cl)ccc21)CO3]

Example 86 was synthesized in the same manner as Example 18 using 2-(imidazo[1,2-a]pyridin-2-yl)acetic acid instead of 3-methoxypropionic acid. LCMS-ESI+ (m/z): [M+H]+ calcd for $C_{40}H_{44}ClN_5O_5S$: 742.28; found: 742.10.

Example 87

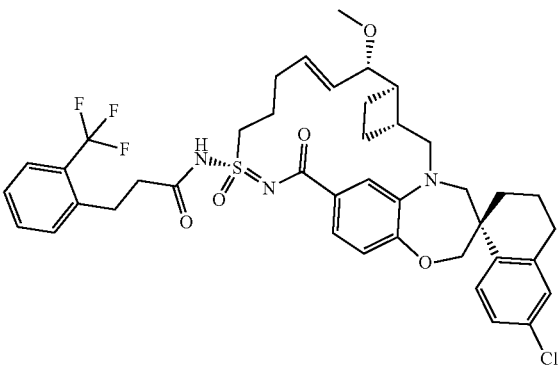 [SMILES: CO[C@H]1/C=C/CCC[S@@](=O)(NC(=O)CCc2ccccc2C(F)(F)F)=NC(=O)c2ccc3c(c2)N(C[C@@H]2CC[C@H]21)C[C@@]1(CCCc2cc(Cl)ccc21)CO3]

Example 87 was synthesized in the same manner as Example 18 using Example 5 and 3-(2-(trifluoromethyl)phenyl)propanoic acid instead of 3-methoxypropionic acid. LCMS-ESI+ (m/z): [M+H]+ calcd for $C_{41}H_{45}ClF_3N_3O_5S$: 784.2793; found: 784.392.

Example 88

Example 88 was synthesized in the same manner as Example 18 using 3-(furan-2-yl)propanoic acid instead of 3-methoxypropionic acid. $^1$H NMR (400 MHz, Chloroform-d) δ 7.70 (d, J=8.5 Hz, 1H), 7.34-7.29 (m, 2H), 7.22 (d, J=1.9 Hz, 1H), 7.12 (dd, J=8.2, 2.2 Hz, 1H), 7.07 (d, J=2.3 Hz, 2H), 6.92 (d, J=8.2 Hz, 2H), 5.85 (dt, J=15.5, 5.2 Hz, 1H), 5.69 (dd, J=15.8, 7.9 Hz, 1H), 4.12-3.95 (m, 2H), 3.60 (dd, J=7.8, 3.4 Hz, 1H), 3.30 (d, J=1.9 Hz, 3H), 3.08-2.94 (m, 4H), 2.82-2.64 (m, 6H), 2.30 (td, J=14.7, 13.8, 6.2 Hz, 4H), 2.06-1.64 (m, 12H). LCMS-ESI+ (m/z): calcd for $C_{38}H_{44}ClN_3O_6S$: 706.2712; found: 706.305.

Example 89

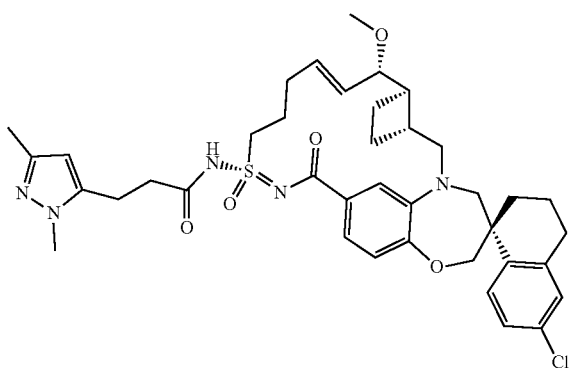 [SMILES: CO[C@H]1/C=C/CCC[S@@](=O)(NC(=O)CCc2cc(C)nn2C)=NC(=O)c2ccc3c(c2)N(C[C@@H]2CC[C@H]21)C[C@@]1(CCCc2cc(Cl)ccc21)CO3]

Preparation of
3-(1,3-dimethyl-1H-pyrazol-5-yl)propanoic Acid

Step 1

Sodium hydride (70 mg, 3 mmol) was dissolved in THF (6 mL) and then cooled to 0° C. then ethyl 2-(dimethoxyphosphoryl)acetate (650 mg, 3 mmol) was added to the mixture and stirred for 20 min. Then 1,3-dimethyl-1H-pyrazole-5-carbaldehyde (300 mg. 2.417 mmol) was added to the reaction and was warmed to room temperature for 30 min. After the reaction was complete by TLC the contents were diluted with ethyl acetate and aqueous ammonium chloride and then the organic layer was dried over MgSO$_4$, filtered and concentrated. Then the crude reaction mixture was purified on silica gel chromatography in a 2/1 hexane ethyl acetate to yield ethyl (E)-3-(1,3-dimethyl-1H-pyrazol-5-yl)acrylate (405 mg) LCMS-ESI+ (m/z): calcd for C$_{10}$H$_{14}$N$_2$O$_2$: 195.113; found: 195.132.

Step 2

Ethyl (E)-3-(1,3-dimethyl-1H-pyrazol-5-yl)acrylate (405 mg, 2 mmol) was charged to reaction flask in ethanol (7 mL). Then palladium on carbon was added and the reaction was stirred and the contents were purged and evacuated with nitrogen. Then hydrogen gas from a balloon was added and the reaction was stirred for 3 hours. LCMS indicated complete conversion to the hydrogenated product. Then the contents were filtered through a fritted funnel and diluted with ethyl acetate. The palladium frit was wetted with water. The contents were concentrated and the product was carried to the next step without further purification to yield ethyl 3-(1,3-dimethyl-1H-pyrazol-5-yl)propanoate. LCMS-ESI+ (m/z): [M+H] calcd for C$_{10}$H$_{17}$N$_2$O$_2$: 197.129; found: 197.090.

Step 3

Ethyl 3-(1,3-dimethyl-1H-pyrazol-5-yl)propanoate (404 mg, 2 mmol) was dissolved in THF (2 mL), ethanol (1 mL) and water (1 mL) then sodium hydroxide (412 mg, 10 mmol) was added. The reaction was then stirred for 1 hour. LCMS indicated complete conversion. The reaction was diluted with DCM and then acidified to pH 4 with 1N HCl. Then the organic layer was dried over MgSO$_4$ and concentrated to yield 3-(1,3-dimethyl-1H-pyrazol-5-yl)propanoic acid. LCMS-ESI+ (m/z): [M+H] calcd for C8H$_{13}$N$_2$O$_2$: 169.0972; found: 169.082.

Preparation of Example 89

Example 89 was synthesized in the same manner as Example 18 using 3-(1,3-dimethyl-1H-pyrazol-5-yl)propanoic acid instead of 3-methoxypropionic acid. $^1$H NMR (400 MHz, Chloroform-d) δ 7.55-7.46 (m, 2H), 7.23 (d, J=8.2 Hz, 1H), 7.02 (d, J=2.6 Hz, 2H), 6.94 (d, J=8.2 Hz, 1H), 6.69 (d, J=8.4 Hz, 1H), 5.77 (d, J=7.5 Hz, 2H), 3.99 (s, 3H), 3.89 (d, J=15.3 Hz, 1H), 3.65 (t, J=12.8 Hz, 2H), 3.56-3.50 (m, 1H), 3.39 (d, J=14.3 Hz, 1H), 3.35 (s, 3H), 3.11-2.98 (m, 2H), 2.96-2.84 (m, 2H), 2.84-2.60 (m, 4H), 2.51-2.35 (m, 2H), 2.31-2.22 (m, 2H), 2.11 (d, J=8.7 Hz, 2H), 2.08 (s, 3H), 1.99 (d, J=17.1 Hz, 4H), 1.89-1.73 (m, 3H), 1.36-1.20 (m, 3H). LCMS-ESI+ (m/z): [M+H] calcd for C$_{39}$H$_{48}$ClN$_5$O$_5$S: 734.3137; found: 734.400.

Example 90

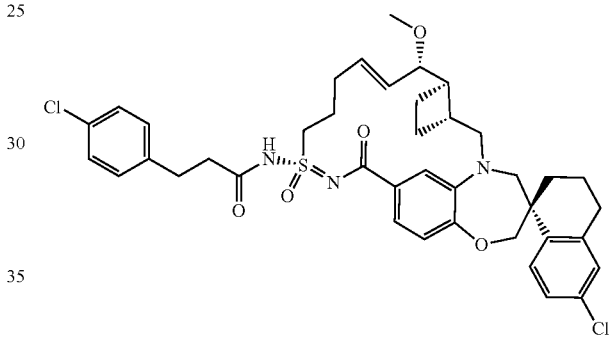

Example 90 was synthesized in the same manner as Example 18 using 3-(4-chlorophenyl)propanoic acid instead of 3-m ethoxy propionic acid. LCMS-ESI+ (m/z): [M+H] calcd for C$_{39}$H$_{45}$Cl$_2$N$_3$O$_5$S: 750.253; found: 750.976.

Example 91

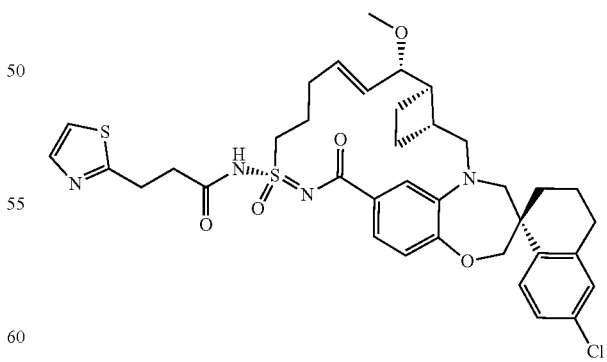

Example 91 was synthesized in the same manner as Example 18 using 3-(thiazol-2-yl)propanoic acid instead of 3-methoxypropionic acid. $^1$H NMR (400 MHz, Chloroform-d) δ 7.88 (d, J=3.6 Hz, 1H), 7.70-7.64 (m, 1H), 7.40 (d, J=3.5 Hz, 1H), 7.24 (d, J=1.9 Hz, 1H), 7.18-7.14 (m, 2H), 7.09-7.04 (m, 2H), 6.92 (d, J=8.2 Hz, 1H), 5.91-5.62 (m, 2H), 4.09-3.96 (m, 2H), 3.84-3.67 (m, 3H), 3.62-3.52 (m, 3H), 3.30 (s, 3H), 3.11-2.95 (m, 3H), 2.82-2.71 (m, 2H), 2.45-2.23 (m, 4H), 2.09-1.99 (m, 2H), 1.94 (q, J=9.6 Hz, 4H), 1.88-1.64 (m, 4H), 1.27 (d, J=9.8 Hz, 2H). LCMS-ESI+ (m/z): [M+H] calcd for $C_{37}H_{43}ClN_4O_5S_2$: 723.2436; found: 723.971.

Example 92

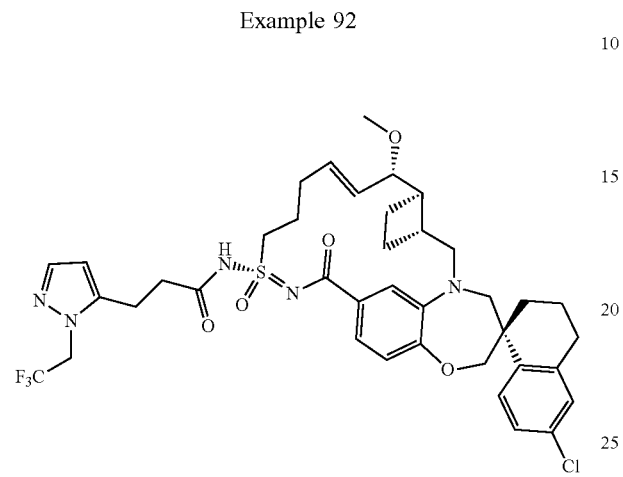

Preparation of 3-(1-(2,2,2-trifluoroethyl)-1H-pyrazol-5-yl)propanoic Acid

Step 1

(1-(2,2,2-trifluoroethyl)-1H-pyrazol-5-yl)methanol (750 mg, 4.16 mmol) was charged into a round bottom flask and then was dissolved in DCM (10 mL). Then Dess Martin Periodinane (2.2 g, 5 mmol) was added. The reaction was allowed to stir for 45 min. Then LCMS indicated completion of the reaction the contents were diluted with sodium bicarbonate aqueous solution and then the organic layer was dried over $MgSO_4$ and then filtered and concentrated. The crude material was purified by silica gel chromatography in 1/1 hexane ethyl acetate to yield 1-(2,2,2-trifluoroethyl)-1H-pyrazole-5-carbaldehyde. LCMS-ESI+ (m/z): [M+H] calcd for $C_6H_5F_3N_2O$: 179.043; found: 179.016.

Step 2-4

3-(1-(2,2,2-trifluoroethyl)-1H-pyrazol-5-yl)propanoic acid was synthesized in the same manner as 3-(1,3-dimethyl-1H-pyrazol-5-yl)propanoic acid in Example 90 (Step 1-3).

Preparation of Example 92

Example 92 was synthesized in the same manner as Example 18 using 3-(1-(2,2,2-trifluoroethyl)-1H-pyrazol-5-yl)propanoic acid instead of 3-methoxypropionic acid. ¹H NMR (400 MHz, Chloroform-d) δ 7.60 (d, J=2.1 Hz, 1H), 7.49 (d, J=8.6 Hz, 1H), 7.10-6.99 (m, 2H), 6.95 (d, J=8.4 Hz, 1H), 6.71 (d, J=8.3 Hz, 1H), 6.28 (d, J=2.1 Hz, 1H), 5.78 (d, J=7.3 Hz, 2H), 4.91 (q, J=8.3 Hz, 2H), 3.94 (s, 3H), 3.72-3.58 (m, 3H), 3.58-3.53 (m, 1H), 3.36 (s, 3H), 3.09-2.91 (m, 4H), 2.88-2.66 (m, 4H), 2.44 (s, 2H), 2.33-2.21 (m, 3H), 2.04-1.91 (m, 4H), 1.89-1.74 (m, 4H), 1.33-1.21 (m, 2H). LCMS-ESI+ (m/z): [M+H] calcd for $C_{39}H_{45}ClN_5O_5S_2$: 788 0.2855; found: 788.261.

Example 93

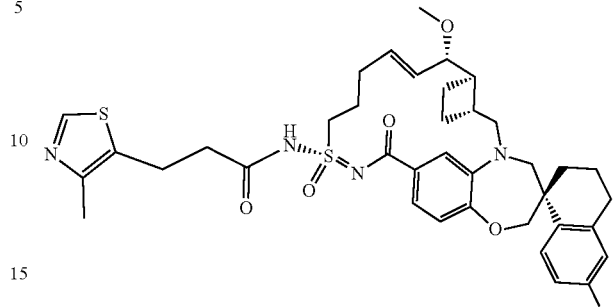

Example 93 was synthesized in the same manner as Example 18 using 3-(4-methylthiazol-5-yl)propanoic acid instead of 3-methoxypropionic acid. LCMS-ESI+ (m/z): [M+H] calcd for $C_{38}H_{45}ClN_4O_5S_2$: 737.2593; found: 737.220.

Example 94

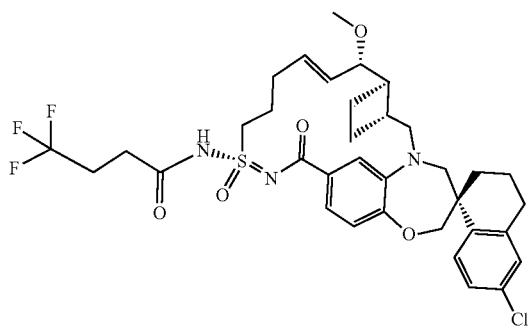

Example 94 was synthesized in the same manner as Example 18 using 4,4,4-trifluorobutanoic acid instead of 3-methoxypropionic acid. ¹H NMR (400 MHz, Chloroform-d) δ 7.64 (d, J=8.5 Hz, 1H), 7.20-7.04 (m, 3H), 7.03-6.97 (m, 1H), 6.94 (d, J=8.5 Hz, 1H), 5.91-5.64 (m, 2H), 4.01 (q, J=12.0 Hz, 3H), 3.73 (dd, J=31.3, 14.6 Hz, 3H), 3.59 (dd, J=8.1, 3.2 Hz, 1H), 3.31 (s, 3H), 3.18 (dt, J=12.1, 6.0 Hz, 1H), 3.02 (dd, J=15.2, 10.7 Hz, 1H), 2.80-2.63 (m, 4H), 2.59-2.46 (m, 2H), 2.39-2.27 (m, 3H), 2.08-1.90 (m, 5H), 1.88-1.78 (m, 2H), 1.76-1.65 (m, 2H), 0.98-0.77 (m, 2H). LCMS-ESI+ (m/z): [M+H] calcd for $C_{35}H_{41}ClF_3N_3O_5S$: 708.248; found: 708.865.

Example 95

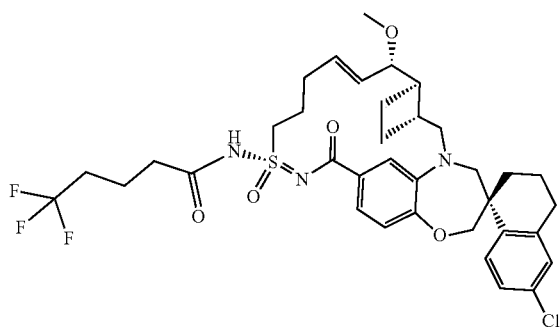

Example 95 was synthesized in the same manner as Example 18 using 5,5,5-trifluoropentanoic acid instead of 3-methoxypropionic acid. $^1$H NMR (400 MHz, Chloroform-d) δ 7.61 (d, J=8.5 Hz, 1H), 7.31 (d, J=8.3 Hz, 1H), 7.14 (s, 1H), 7.05 (d, J=2.3 Hz, 1H), 6.94 (dd, J=8.6, 4.0 Hz, 2H), 5.89-5.66 (m, 2H), 3.99 (q, J=11.8 Hz, 2H), 3.72 (dd, J=29.4, 14.8 Hz, 3H), 3.57 (dd, J=7.6, 3.1 Hz, 1H), 3.32 (s, 3H), 3.02 (dd, J=15.1, 10.9 Hz, 1H), 2.80-2.67 (m, 3H), 2.65-2.53 (m, 2H), 2.46-2.14 (m, 7H), 1.97 (dq, J=14.9, 7.4 Hz, 6H), 1.86-1.67 (m, 4H), 1.33 (t, J=12.9 Hz, 2H). LCMS-ESI+ (m/z): [M+H] calcd for $C_{36}H_{43}ClF_3N_3O_5S$: 722.264; found: 722.274.

Example 97

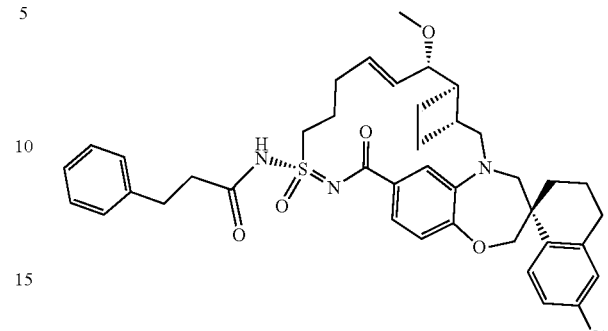

Example 97 was synthesized in the same manner as Example 18 using 3-phenylpropanoic acid instead of 3-methoxypropionic acid. $^1$H NMR (400 MHz, chloroform-d) δ 7.67 (dd, J=14.8, 8.6 Hz, 1H), 7.34-7.27 (m, 3H), 7.25-7.16 (m, 4H), 7.10-7.00 (m, 2H), 6.91 (d, J=8.3 Hz, 1H), 5.95-5.56 (m, 2H), 4.09-3.94 (m, 2H), 3.88 (q, J=14.4, 11.1 Hz, 1H), 3.74 (dd, J=25.2, 14.8 Hz, 3H), 3.59 (dd, J=7.9, 3.3 Hz, 1H), 3.33 (s, 3H), 3.08-2.91 (m, 3H), 2.86-2.51 (m, 5H), 2.48-2.23 (m, 2H), 2.24-2.14 (m, 1H), 2.04 (t, J=10.7 Hz, 2H), 1.98-1.63 (m, 6H), 1.41-1.23 (m, 2H), 0.86 (t, J=10.0 Hz, 1H). LCMS-ESI+ (m/z): [M+H] calcd for $C_{40}H_{46}ClN_3O_5S$: 716.292; found: 716.069.

Example 96

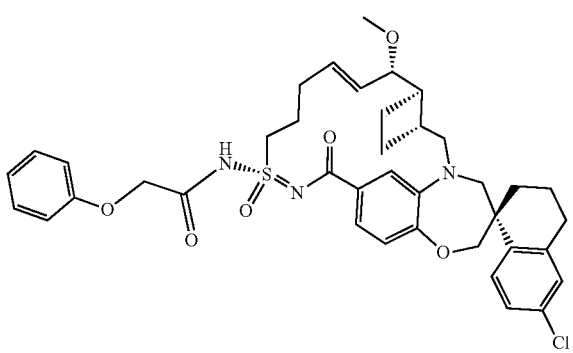

Example 96 was synthesized in the same manner as Example 18 using 2-phenoxyacetic acid instead of 3-methoxypropionic acid. $^1$H NMR (400 MHz, chloroform-d) δ 7.73 (d, J=8.3 Hz, 1H), 7.50-7.27 (m, 4H), 7.18 (dd, J=8.5, 2.2 Hz, 1H), 7.12-6.97 (m, 4H), 6.93 (dd, J=8.2, 2.8 Hz, 1H), 5.95-5.65 (m, 2H), 4.10 (d, J=12.0 Hz, 1H), 4.04-3.91 (m, 2H), 3.91-3.83 (m, 1H), 3.75 (q, J=14.1, 13.1 Hz, 2H), 3.61 (dd, J=7.7, 3.4 Hz, 1H), 3.28 (s, 3H), 3.24-3.16 (m, 1H), 3.07-2.94 (m, 1H), 2.84-2.61 (m, 3H), 2.46-2.23 (m, 3H), 2.08-1.56 (m, 8H), 1.44-1.29 (m, 3H), 0.88 (t, J=8.1 Hz, 1H). LCMS-ESI+ (m/z): [M+H] calcd for $C_{39}H_{44}ClN_3O_6S$: 718.271; found: 718.109.

Example 98

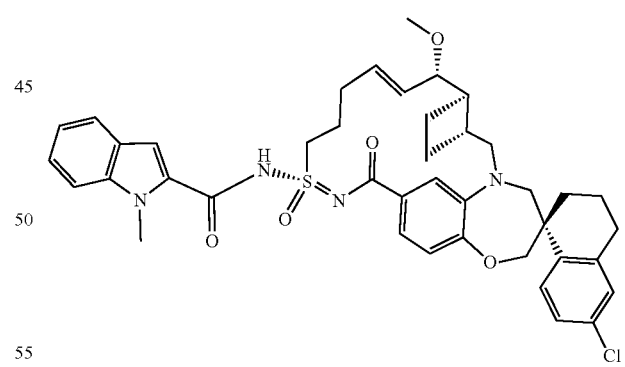

Example 98 was synthesized in the same manner as Example 18 using 1-methyl-1H-indole-2-carboxylic acid instead of 3-methoxypropionic acid. LCMS-ESI+ (m/z): [M+H] calcd for $C_{41}H_{45}ClN_4O_5S$: 741.287; found: 741.886.

Example 99

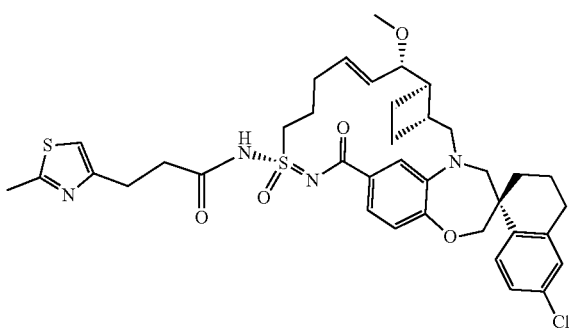

Example 99 was synthesized in the same manner as Example 18 using 3-(2-methylthiazol-4-yl)propanoic acid instead of 3-methoxypropionic acid. $^1$H NMR (400 MHz, Chloroform-d) δ 7.73 (d, J=8.2 Hz, 1H), 7.38 (dd, J=25.3, 8.7 Hz, 1H), 7.23 (s, 1H), 7.21-7.13 (m, 2H), 7.08 (s, 1H), 6.90 (d, J=8.2 Hz, 1H), 5.97-5.63 (m, 2H), 4.09 (d, J=12.1 Hz, 1H), 4.01 (t, J=10.3 Hz, 1H), 3.84 (t, J=14.5 Hz, 1H), 3.73 (s, 3H), 3.60 (d, J=7.4 Hz, 1H), 3.27 (d, J=3.9 Hz, 3H), 3.06-2.91 (m, 1H), 2.78 (s, 2H), 2.65 (s, 2H), 2.28 (d, J=31.5 Hz, 4H), 2.07-1.60 (m, 8H), 1.43-1.12 (m, 6H), 0.94-0.72 (m, 2H). LCMS-ESI+ (m/z): [M+H] calcd for $C_{38}H_{45}ClN_4O_5S_2$: 737.295; found: 737.040.

Example 100

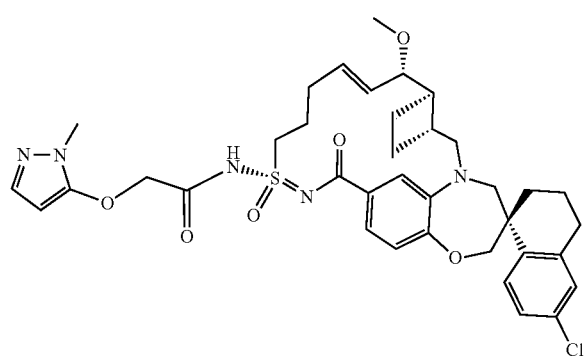

Preparation of 2-((1-methyl-1H-pyrazol-5-yl)oxy)acetic Acid

Step 1

1-Methyl-1H-pyrazol-5-ol (250 mg, 3 mmol) was charged into a round bottom flask and then potassium carbonate (387 mg, 3 mmol) was added. Then THF (5 mL) was added. Ethyl bromoacetate (547 mg, 3 mmol) was added then the reaction was stirred at 50° C. for 1 hour. TLC indicated consumption of 1-methyl-1H-pyrazol-5-ol. The contents were then diluted with ethyl acetate and water, and then the organic layer was dried over $MgSO_4$ filtered and concentrated to yield ethyl 2-((1-methyl-1H-pyrazol-5-yl)oxy)acetate.

Step 2

Ethyl 2-((1-methyl-1H-pyrazol-5-yl)oxy)acetate (0.265 mg, 1.44 mmol) was then diluted in THF (2 mL) water (1 mL) and ethanol (1 mL) then sodium hydroxide (115 mg, 2.88 mmol) was added. The reaction was stirred for 2 hours and then dilute with sec-butanol and 1N HCl to pH~4 and the organic layer was dried over $MgSO_4$ filtered and concentrated to yield 2-((1-methyl-1H-pyrazol-5-yl)oxy)acetic acid. LCMS-ESI+ (m/z): [M+H] calcd for $C_6H_8N_2O_3$: 157.061; found: 157.088.

Preparation of Example 100

Example 100 was synthesized in the same manner as Example 18 using 2-((1-methyl-1H-pyrazol-5-yl)oxy)acetic acid instead of 3-methoxypropionic acid. $^1$H NMR (400 MHz, acetone-d6) δ 7.77 (d, J=8.6 Hz, 1H), 7.43 (s, 1H), 7.32 (d, J=8.3 Hz, 1H), 7.22 (dd, J=8.5, 2.3 Hz, 1H), 7.11 (d, J=2.4 Hz, 2H), 7.04 (s, 1H), 6.88 (d, J=8.2 Hz, 1H), 5.96-5.78 (m, 2H), 4.13-3.92 (m, 4H), 3.79 (dd, J=23.4, 14.6 Hz, 2H), 3.63 (dd, J=13.4, 7.6 Hz, 1H), 3.53 (dd, J=7.7, 3.0 Hz, 1H), 3.45 (d, J=14.4 Hz, 1H), 3.26 (s, 3H), 3.04 (t, J=7.2 Hz, 2H), 2.90-2.80 (m, 2H), 2.62 (s, 3H), 2.46 (d, J=7.2 Hz, 2H), 2.34-2.18 (m, 2H), 2.01-1.91 (m, 5H), 1.84-1.70 (m, 3H), 1.57-1.39 (m, 2H). LCMS-ESI+ (m/z): [M+H] calcd for $C_{37}H_{44}ClN_5O_6S$: 722.277; found: 722.907.

Example 101

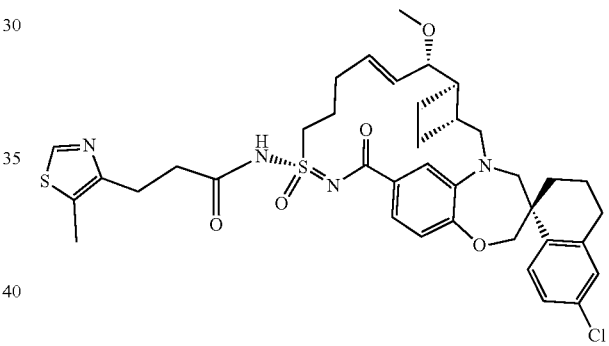

Example 101 was synthesized in the same manner as Example 18 using 3-(5-methylthiazol-4-yl)propanoic acid instead of 3-methoxypropionic acid. LCMS-ESI+ (m/z): [M+H] calcd for $C_{38}H_{45}ClN_4O_5S_2$: 737.2953; found: 737.894.

Example 102

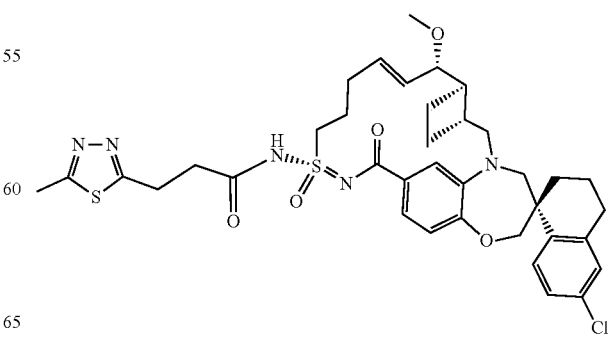

Example 102 was synthesized in the same manner as Example 18 using 3-(5-methyl-1,3,4-thiadiazol-2-yl)propanoic acid (prepared in the same manner as 3-(1,3-dimethyl-1H-pyrazol-5-yl)propanoic acid as Example 89 from 5-methyl-1,3,4-thiadiazole-2-carbaldehyde). $^1$H NMR (400 MHz, chloroform-d) δ 7.64 (d, J=8.5 Hz, 1H), 7.27 (d, J=2.7 Hz, 1H), 7.15 (s, 1H), 7.06 (d, J=2.3 Hz, 1H), 7.00 (d, J=8.5 Hz, 1H), 6.93 (d, J=8.3 Hz, 1H), 5.91-5.64 (m, 2H), 4.01 (q, J=12.1 Hz, 2H), 3.89 (s, 1H), 3.83-3.65 (m, 3H), 3.59 (dd, J=8.2, 3.1 Hz, 1H), 3.50-3.35 (m, 2H), 3.32 (s, 3H), 3.04 (dd, J=16.7, 9.6 Hz, 3H), 2.78 (s, 3H), 2.76-2.62 (m, 3H), 2.47-2.22 (m, 4H), 2.09-1.91 (m, 4H), 1.81 (p, J=9.9 Hz, 2H), 1.71 (t, J=9.3 Hz, 1H), 1.43-1.14 (m, 3H). LCMS-ESI+ (m/z): [M+H] calcd for $C_{37}H_{44}ClN_5O_5S_2$: 738.255; found: 738.054.

Example 103

Example 103 was synthesized in the same manner as Example 18 using 3-(1,4-Dimethyl-1H-pyrazol-5-yl)propanoic acid (prepared in the same manner as 3-(1,3-dimethyl-1H-pyrazol-5-yl)propanoic acid in Example 89 from 5-methyl-1,3,4-thiadiazole-2-carbaldehyde). NMR (400 MHz, chloroform-d) δ 7.54 (d, J=7.0 Hz, 2H), 7.22 (d, J=7.3 Hz, 1H), 7.14-6.99 (m, 2H), 6.94 (d, J=8.2 Hz, 1H), 6.80 (d, J=8.4 Hz, 1H), 5.90-5.66 (m, 2H), 4.06-3.94 (m, 4H), 3.85 (s, 1H), 3.66 (dd, J=22.7, 14.0 Hz, 2H), 3.58-3.50 (m, 1H), 3.37 (d, J=23.2 Hz, 3H), 3.04 (t, J=12.4 Hz, 2H), 2.99-2.65 (m, 5H), 2.40 (d, J=19.5 Hz, 2H), 2.24 (d, J=11.3 Hz, 2H), 2.11 (s, 2H), 2.09 (s, 3H), 1.99 (d, J=12.9 Hz, 4H), 1.90-1.65 (m, 3H), 1.37-1.20 (m, 3H), 0.80 (dd, J=55.2, 11.8 Hz, 1H). LCMS-ESI+ (m/z): [M+H] calcd for $C_{39}H_{48}ClN_5O_5S$: 734.314; found: 734.132.

Example 104 was synthesized in the same manner as Example 18 using 1-ethyl-1H-pyrazole-4-carboxylic acid instead of 3-methoxypropionic acid. $^1$H NMR (400 MHz, methanol-d4) δ 8.43 (s, 1H), 7.93 (s, 1H), 7.65 (d, J=8.5 Hz, 1H), 7.34 (d, J=8.2 Hz, 1H), 7.26 (s, 1H), 7.06 (s, 1H), 6.93 (dd, J=13.2, 8.6 Hz, 2H), 5.97-5.78 (m, 2H), 4.22 (q, J=7.3 Hz, 2H), 3.98 (d, J=15.3 Hz, 3H), 3.83-3.62 (m, 2H), 3.58 (dd, J=8.3, 2.9 Hz, 1H), 3.52-3.40 (m, 2H), 3.35 (s, 3H), 3.19-2.99 (m, 2H), 2.86-2.68 (m, 3H), 2.49 (s, 2H), 2.37-2.24 (m, 2H), 2.08 (d, J=12.7 Hz, 3H), 1.94 (s, 3H), 1.83 (t, J=6.7 Hz, 2H), 1.46 (t, J=7.3 Hz, 3H). LCMS-ESI+(m/z): calcd for H+$C_{37}H_{44}ClN_5O_5S$: 706.22824; found: 706.194.

Example 105

Example 105 was synthesized in the same manner as Example 18 using 2-((tetrahydro-2H-pyran-4-yl)oxy)acetic acid instead of 3-methoxypropionic acid. 1H NMR (400 MHz, chloroform-d) δ 7.73 (d, J=8.5 Hz, 1H), 7.41 (dd, J=8.3, 1.8 Hz, 1H), 7.30 (d, J=2.0 Hz, 1H), 7.16 (dd, J=8.5, 2.3 Hz, 1H), 7.07 (d, J=2.3 Hz, 1H), 6.91 (d, J=8.2 Hz, 1H), 5.86 (dt, J=15.8, 5.2 Hz, 1H), 5.73 (dd, J=15.9, 7.5 Hz, 1H), 4.15 (s, 2H), 4.12-3.92 (m, 4H), 3.92-3.63 (m, 4H), 3.55 (dddd, J=20.5, 11.9, 6.3, 3.2 Hz, 3H), 3.32-3.25 (m, 4H), 3.01 (dd, J=14.9, 11.0 Hz, 1H), 2.84-2.66 (m, 3H), 2.50-2.18 (m, 4H), 2.14-1.56 (m, 12H), 1.47-1.18 (m, 2H). LCMS-ESI+ (m/z): [M+H]+ calcd for $C_{38}H_{48}ClN_3O_7S$: 726.29; found: 726.22.

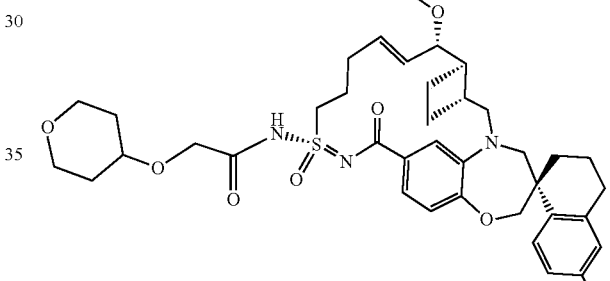

Example 106

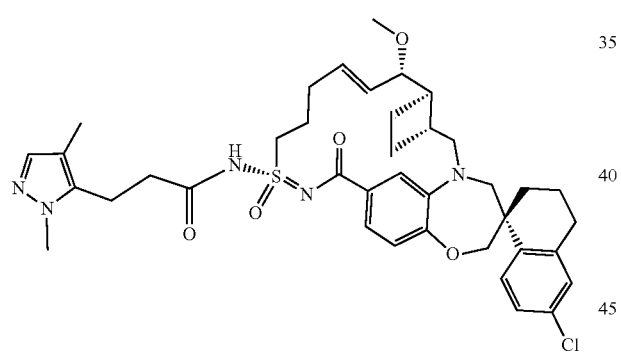

Example 104

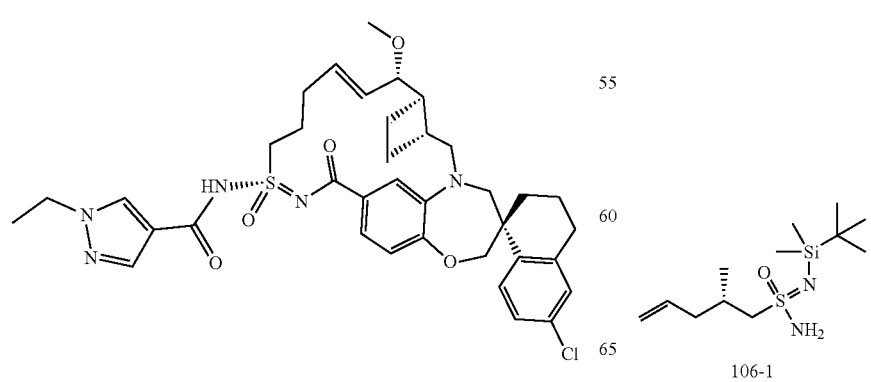

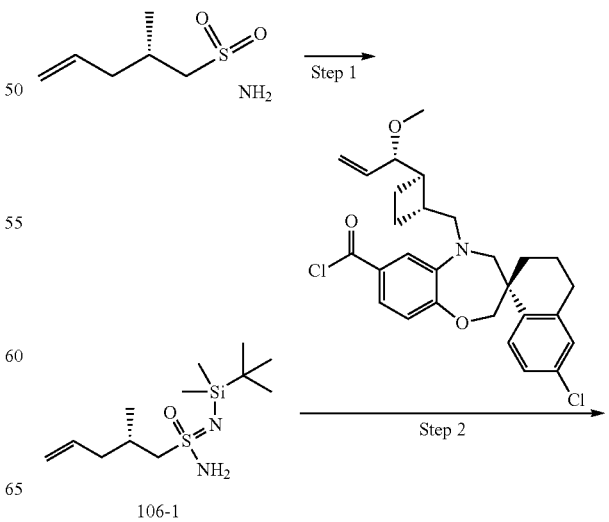

106-1

195

-continued

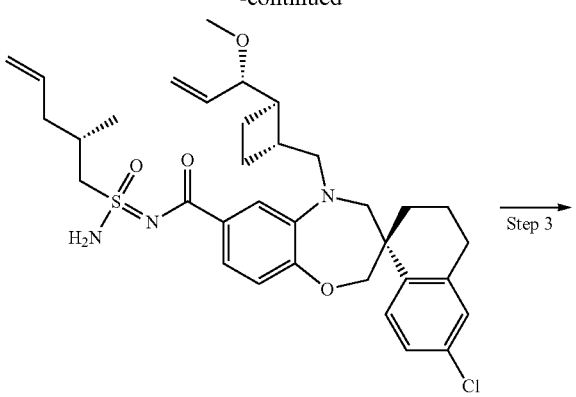

106-2

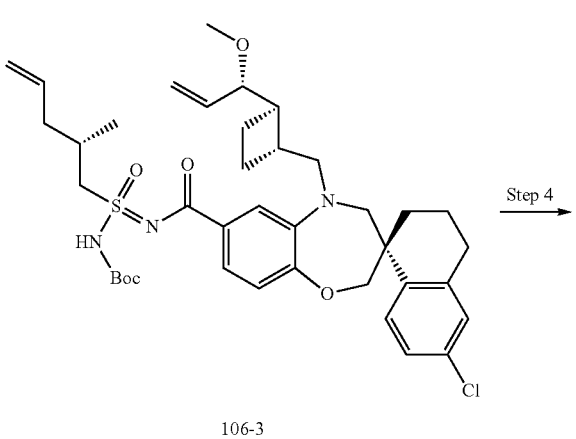

106-3

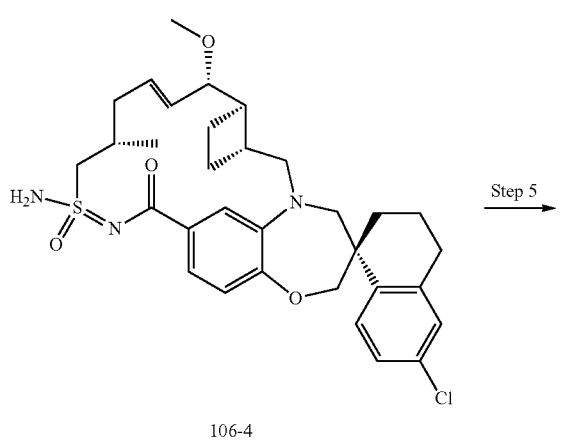

106-4

196

-continued

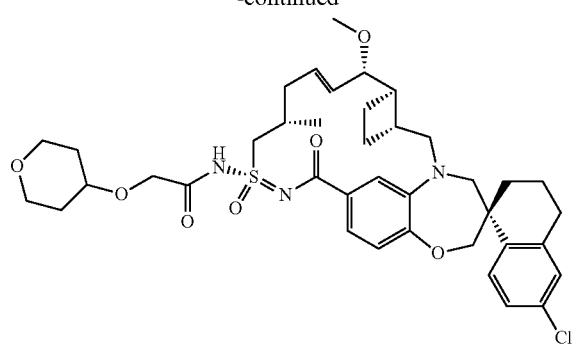

Example 106

Step 1

N'-(tert-butyldimethylsilyl)hex-5-ene-1-sulfonimidamide was prepared in the same manner as Example 1 (step 4 and step 5) using (S)-2-methylpent-4-ene-1-sulfonamide instead of (2R,3S)-3-methylhex-5-ene-2-sulfonamide. $^1$H NMR (400 MHz, Chloroform-d) δ 5.75 (ddt, J=19.5, 9.5, 7.0 Hz, 1H), 5.06 (d, J=1.4 Hz, 1H), 5.03 (dq, J=5.1, 1.7 Hz, 1H), 4.75 (d, J=7.7 Hz, 2H), 3.13 (ddd, J=18.6, 13.7, 4.6 Hz, 1H), 2.91 (ddd, J=22.5, 13.8, 7.1 Hz, 1H), 2.32-2.16 (m, 2H), 2.16-2.02 (m, 2H), 1.10 (dd, J=6.6, 4.2 Hz, 3H), 0.88 (s, 9H), 0.10 (d, J=3.0 Hz, 6H).

Step 2: Preparation of Intermediate 106-2

To a stirred solution of (S)-6'-chloro-5-(((1R,2R)-2-((S)-1-methoxyallyl)cyclobutyl)methyl)-3',4,4',5-tetrahydro-2H,2'H-spiro[benzo[b][1,4]oxazepine-3,1'-naphthalene]-7-carbonyl chloride (1.56 g, 3.11 mmol) in acetonitrile (30 mL) was added pyridazine (0.22 ml, 3.11 mmol) in acetonitrile (6 mL), followed by (2S)—N'-(tert-butyldimethylsilyl)-2-methylpent-4-ene-1-sulfonimidamide (0.9 g, 3.27 mmol) in acetonitrile (6 mL). The resulting mixture was stirred at rt overnight. The reaction mixture was concentrated and the residue was purified by silica gel column (0-50% EtOAc in hexanes).

Step 3: Preparation of Intermediate 106-3

To a stirred solution of intermediate 106-2 (1.54 g, 2.46 mmol) in CH$_2$Cl$_2$ (15 mL) was added triethylamine (0.69 mL, 4.92 mmol) in an ice bath, followed by di-tert-butyl dicarbonate (0.81 g, 3.69 mmol) and 4-(dimethylamino)-pyridine (120.17 mg, 0.98 mmol). The resulting mixture was stirred at rt for 3 h. The reaction mixture was concentrated and the residue was purified by silica gel column. The fraction was concentrated, dissolved in EtOAc and washed with 1% HCl solution, then washed with saturated aqueous NaHCO$_3$ solution. The organic phase was dried over MgSO$_4$, filtered, concentrated and the residue was purified again by silica gel column to give the desired product.

Step 4: Preparation of Intermediate 106-4

The reaction mixture intermediate 106-3 (330 mg, 0.45 mmol), Hoveyda-Grubbs 2$^{nd}$ generation catalyst (85.18 mg, 0.14 mmol) in 1,2-dichloroethane (150 mL) was degassed with argon. The reaction mixture was stirred at 60° C. overnight. The reaction mixture was concentrated and the residue was purified by silica gel column. Two diastereomers were isolated (the less polar product is 106-4).

Step 5: Preparation of Example 106

Example 106 was synthesized in the same manner as Example 18 using 2-((tetrahydro-2H-pyran-4-yl)oxy)acetic acid (3.61 mg, 0.023 mmol) instead of 3-methoxypropionic acid and the less polar diastereomer intermediate 106-4 (9 mg, 0.015 mmol). $^1$H NMR (400 MHz, Methanol-d4) δ 7.76 (d, J=8.5 Hz, 1H), 7.27 (d, J=8.5 Hz, 1H), 7.19 (dd, J=8.5, 2.4 Hz, 1H), 7.15-7.06 (m, 2H), 6.91 (d, J=8.2 Hz, 1H), 6.10 (dt, J=14.7, 7.0 Hz, 1H), 5.63 (dd, J=15.3, 8.4 Hz, 1H), 4.22 (s, 2H), 4.15 (dd, J=14.8, 6.9 Hz, 1H), 4.11-4.01 (m, 2H), 4.00-3.92 (m, 2H), 3.92-3.81 (m, 2H), 3.77 (d, J=8.0 Hz, 1H), 3.71 (td, J=10.0, 9.4, 4.9 Hz, 2H), 3.53-3.45 (m, 2H), 3.29 (s, 3H), 3.07 (dd, J=15.1, 9.7 Hz, 2H), 2.93-2.69 (m, 3H), 2.48 (d, J=21.0 Hz, 3H), 2.37-2.06 (m, 4H), 2.06-1.88 (m, 4H), 1.88-1.73 (m, 3H), 1.65 (dtt, J=13.4, 9.0, 4.3 Hz, 2H), 1.45 (t, J=12.1 Hz, 1H), 1.15 (d, J=6.8 Hz, 3H). LCMS-ESI+: calc'd for $C_{39}H_{50}ClN_3O_7S$: 740.3 (M+H); found: 740.0 (M+H).

Example 107

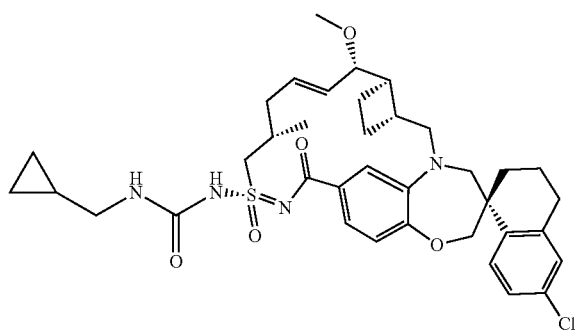 [SMILES: CO[C@H]1/C=C/C[C@H](C)C[S@@](=O)(NC(=O)NCC2CC2)=NC(=O)c2ccc3c(c2)N(C[C@@H]2CC[C@H]21)C[C@@]1(CCCc2cc(Cl)ccc21)CO3]

Example 107 was synthesized in the same manner as Example 75 using intermediate 106-4 from Example 106 and cyclopropylmethanamine. 1H NMR (400 MHz, methanol-d4) δ 7.73 (d, J=8.4 Hz, 1H), 7.24 (d, J=8.3 Hz, 1H), 7.12 (d, J=11.4 Hz, 2H), 7.02 (s, 1H), 6.89 (d, J=8.2 Hz, 1H), 6.06 (dd, J=14.6, 7.3 Hz, 1H), 5.60 (dd, J=15.3, 8.8 Hz, 1H), 4.25 (dd, J=14.9, 6.7 Hz, 1H), 4.11-3.99 (m, 2H), 3.84 (d, J=15.1 Hz, 2H), 3.78 (dd, J=8.9, 3.5 Hz, 1H), 3.67 (d, J=14.2 Hz, 1H), 3.28 (s, 3H), 3.13-3.01 (m, 3H), 2.88-2.69 (m, 2H), 2.46 (dt, J=23.9, 13.6 Hz, 3H), 2.18 (ddd, J=36.0, 20.5, 10.7 Hz, 3H), 1.99-1.89 (m, 3H), 1.79 (dt, J=17.4, 9.2 Hz, 3H), 1.43 (t, J=11.9 Hz, 1H), 1.31 (s, 1H), 1.14 (d, J=6.6 Hz, 3H), 1.08-0.97 (m, 1H), 0.57-0.47 (m, 2H), 0.25 (dt, J=5.9, 4.4 Hz, 2H). LCMS-ESI+: calc'd for $C_{37}H_{47}ClN_4O_5S$: 695.3 (M+H); found: 694.8 (M+H).

Example 108

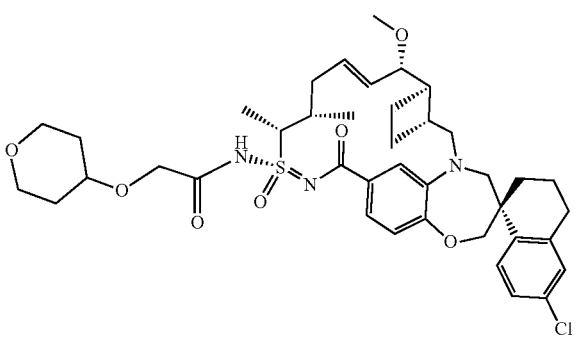

Example 108 was synthesized in the same manner as Example 18 using 2-((tetrahydro-2H-pyran-4-yl)oxy)acetic acid instead of 3-methoxypropionic acid and intermediate 49-3. $^1$H NMR (400 MHz, methanol-d4) δ 7.75 (d, J=8.4 Hz, 1H), 7.19 (dd, J=8.4, 2.4 Hz, 1H), 7.16-7.12 (m, 2H), 7.00 (s, 1H), 6.94 (d, J=8.0 Hz, 1H), 6.00-5.93 (m, 1H), 5.59 (dd, J=15.2, 9.2 Hz, 1H), 4.38-4.32 (m, 1H), 4.18 (s, 2H), 4.00-3.93 (m, 2H), 3.83 (d, J=14.8 Hz, 1H), 3.76-3.65 (m, 3H), 3.52-3.45 (m, 3H), 3.37-3.34 (m, 3H), 3.24 (s, 3H), 3.16-3.06 (m, 1H), 2.86-2.73 (m, 3H), 2.49-1.72 (m, 12H), 1.67-1.58 (m, 2H), 1.54 (d, J=6.8 Hz, 3H), 1.50-1.42 (m, 1H), 1.14 (d, J=6.8 Hz, 3H). LCMS-ESI+ (m/z): [M+H]+ calcd for $C_{40}H_{52}ClN_3O_7S$: 754.4; found: 754.2.

Example 109

Method 1

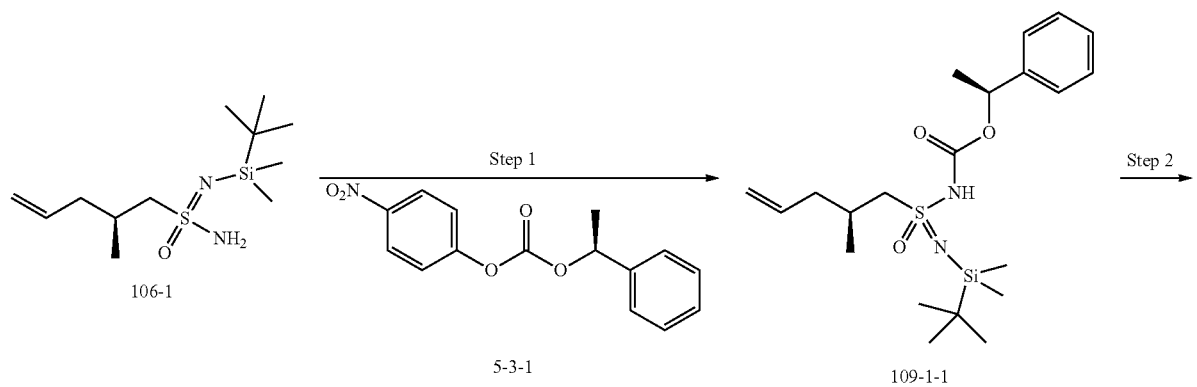

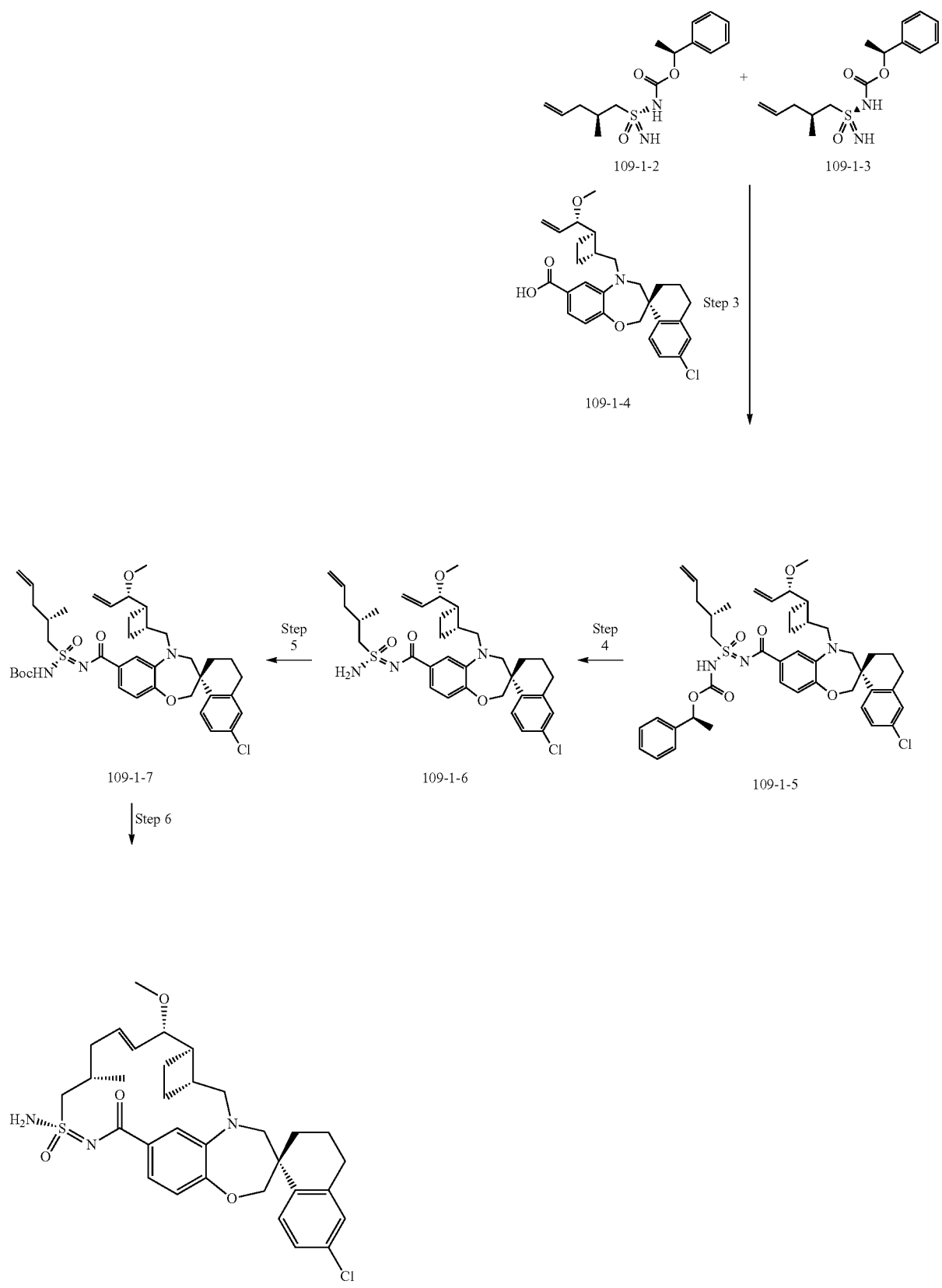

Step 1

(4S)-5-[S-amino-N-[tert-butyl(dimethyl)silyl]sulfonimidoyl]-4-methyl-pent-1-ene (106-1, 14.9 g, 53.9 mmol) was azeotroped with anhydrous toluene (3×50 mL) and dissolved in anhydrous tetrahydrofuran (250 mL) under an atmosphere of argon. The solution was cooled to −50° C. (internal temperature probe). A solution of 2.5 M n-BuLi in hexanes (46.3 mL, 116 mmol) was added dropwise over 5 min. This mixture was left to stir for 15 min. Concurrently (4-nitrophenyl) [(1S)-1-phenylethyl] carbonate (5-3-1, 20.1 g, 70.1 mmol) was azeotroped with toluene (3×50 mL). The material was taken up in anhydrous tetrahydrofuran (50 mL) under an atmosphere of argon. The solution was added to the reaction via cannula over 5 min. The reaction was initially yellow but turned very dark (green). After 15 min the reaction was warmed to 0° C. (ice bath). The reaction turned yellow while warming. After 1 h, TLC (20% ethyl acetate/hexanes visualized with KMnO$_4$ stain) showed the reaction was complete. The reaction was quenched with water (150 mL) at 0° C. Ethyl acetate (150 mL) was added. The phases were separated and the aqueous phase was extracted with ethyl acetate (2×75 mL). The combined organic phases were washed with sat NaHCO$_3$ (150 mL) and brine (150 mL). The organic phase was dried over sodium sulfate and the solvent was removed under reduced pressure, providing, crude [(1S)-1-phenylethyl] N—[N-[tert-butyl(dimethyl)silyl]-S-[(2S)-2-methylpent-4-enyl]sulfonimidoyl]carbamate (109-1-1).

Step 2

A solution of tetrabutylammonium fluoride in tetrahydrofuran (1.0 M, 63.6 mL, 63.6 mmol) was added to a solution of the 109-1-1 (22.5 g, 53.0 mmol) in anhydrous tetrahydrofuran at 0° C. After 90 min at 0° C., the reaction was complete. The solvent was removed under reduced pressure. The residue was diluted with water (150 mL) and ethyl acetate (150 mL). The phases were separated and the aqueous phase was extracted with ethyl acetate (3×100 mL). The combined organic phases were washed with brine and dried over sodium sulfate. The solvent was removed pressure and the residue was subjected to flash chromatography (0-65% ethyl acetate/hexanes 120 g gold Teledyne ISCO column with solid loading). An evaporative light scattering detector (ELSD) along with UV was used for peak detection. The fractions containing product were combined and the solvent was removed under reduced pressure to give ((2S)-2-methylpent-4-en-1-ylsulfonimidoyl)carbamate as a mixture of diastereomers at sulfur. The solids were subjected to chiral SFC separation, with ethanol as a co-solvent using a ChiralPak IC column. Alternatively, methanol was used as a co-solvent on a ChiralPak AD-H column. Fractions containing the same diastereomer were combined and the solvent was removed under reduced pressure, providing (S)-1-phenylethyl ((2S)-2-methylpent-4-en-1-ylsulfonimidoyl)carbamate as two diastereomers.

The first eluted diastereomer (109-1-2, Rt=3.05 min on ChiralPak IC with 15% ethanol co-solvent, absolute stereochemistry tentatively assigned as drawn): $^1$H NMR (400 MHz, chloroform-d) δ 7.43-7.33 (m, 4H), 7.33-7.29 (m, 1H), 5.74 (q, J=6.7 Hz, 1H), 5.62 (ddt, J=16.0, 11.0, 7.1 Hz, 1H), 5.05 (d, J=1.3 Hz, 1H), 5.04-4.99 (m, 1H), 3.43 (dd, J=14.4, 4.5 Hz, 1H), 3.06 (dd, J=14.4, 7.9 Hz, 1H), 2.30-2.20 (m, 1H), 2.20-2.04 (m, 2H), 1.59 (d, J=6.7 Hz, 3H), 1.14 (d, J=6.7 Hz, 3H).

The second eluted diastereomer (109-1-3, Rt=4.92 min on ChiralPak IC with 15% ethanol co-solvent, absolute stereochemistry tentatively assigned as drawn): $^1$H NMR (400 MHz, chloroform-d) δ 7.44-7.32 (m, 4H), 7.32-7.30 (m, 1H), 5.79-5.73 (m, 1H), 5.73-5.66 (m, 1H), 5.16-5.05 (m, 2H), 3.38 (dd, J=14.5, 4.4 Hz, 1H), 3.20 (dd, J=14.4, 7.7 Hz, 1H), 2.27 (dq, J=12.5, 6.8 Hz, 1H), 2.22-2.10 (m, 2H), 1.59 (d, J=6.7 Hz, 3H), 1.14 (d, J=6.7 Hz, 3H).

Step 3 i) Preparation of (S)-6'-chloro-5-(((1R,2R)-2-((S)-1-methoxyallyl) cyclobutyl) methyl)-3',4,4',5-tetrahydro-2H,2'H-spiro[benzo[b][1,4] oxazepine-3,1'-naphthalene]-7-carboxylic acid (109-1-4): Methyl (S)-6'-chloro-5-(((1R,2R)-2-((S)-1-methoxyallyl)cyclobutyl)methyl)-3',4,4',5-tetrahydro-2H,2'H-spiro[benzo[b][1,4] oxazepine-3,1'-naphthalene]-7-carboxylate, 1-3 (11.2 g, 22.5 mmol) was stirred in 2 N aq NaOH (10 mL) and a mixture of MeOH/THF (1/1) (200 mL) at 60° C. overnight. After cooling, the mixture was neutralized with HCl and concentrated. The resulting solid was suspended in water and then extracted with DCM. The organic phase was dried over anhydrous magnesium sulfate and the solvent removed under reduced pressure to give 109-1-4 which was further used without purification. LCMS-ESI+ (m/z): [M+H]+ calcd for $C_{28}H_{32}ClNO_4$: 482.20; found: 482.14.

ii) Preparation of intermediate 109-1-5: To a stirred solution of intermediate 109-1-4 (9.68 g, 20.1 mmol) in DCM (200 mL) was added intermediate 109-1-2 (first eluting diastereomer) (6.17 g, 19.9 mmol), 1-(3-dimethylaminopropyl)-3-ethylcarbodiimide HCl (7.62 g, 39.75 mmol) and 4-(dimethylamino)pyridine (4.21 g, 34.46 mmol). The reaction mixture was stirred at rt overnight. Then the reaction mixture was diluted with DCM, washed with 1 N HCl and brine. The organic phase was dried over MgSO$_4$, filtered, concentrated to give 109-1-5 which was further used without purification.

Step 4

To a solution of intermediate 109-1-5 (12.7 g, 16.4 mmol) in DCM (130 mL), was added TFA (25 mL). The reaction mixture was stirred at rt. After the reaction is finished, the solvent was removed under vacuum. The residue was dissolved in DCM, washed with saturated NaHCO$_3$ solution. The organic phase was separated, dried over MgSO$_4$, filtered, and concentrated to give 109-1-6 which was further used without purification.

Step 5

To a solution of intermediate 109-1-6 (10 g, 15.97 mmol) in DCM, was added triethylamine (4.45 mL, 31.94 mmol), 4-(dimethylamino)-pyridine (500 mg, 4.09 mmol) and di-tert-butyl dicarbonate (5.23 g, 23.95 mmol). The reaction mixture was stirred at rt overnight. The reaction mixture was washed with 1N HCl (aq) and brine. The organic phase was separated, dried over MgSO$_4$, filtered, concentrated down and purified silica gel column chromatography (0-100% EtOAc/hexanes) to give intermediate 109-1-7.

Step 6

Intermediate 109-1-7 (1 g, 1.38 mmol), Hoveyda-Grubbs II (258.13 mg, 0.41 mmol) in 1,2-dichloroethane (400 mL) was degassed with argon. The reaction mixture was stirred at 60° C. overnight. The reaction mixture was concentrated, and the residue was purified by column chromatography (SiO₂, 0-70% EtOAc/hexanes) to give Example 109. ¹H NMR (400 MHz, chloroform-d) δ 7.76 (d, J=8.5 Hz, 1H), 7.43 (dd, J=8.2, 1.9 Hz, 1H), 7.32 (d, J=2.0 Hz, 1H), 7.20 (dd, J=8.5, 2.3 Hz, 1H), 7.10 (d, J=2.3 Hz, 1H), 6.93 (d, J=8.2 Hz, 1H), 6.27 (ddd, J=15.1, 7.9, 5.2 Hz, 1H), 5.99 (s, 2H), 5.56 (dd, J=15.3, 8.2 Hz, 1H), 4.20 (s, 2H), 4.06 (t, J=11.4 Hz, 2H), 3.92-3.82 (m, 1H), 3.82-3.69 (m, 2H), 3.47 (d, J=5.6 Hz, 2H), 3.36 (d, J=14.6 Hz, 1H), 3.28 (s, 3H), 3.02 (dd, J=15.0, 11.0 Hz, 1H), 2.80 (dt, J=11.3, 5.1 Hz, 2H), 2.63-2.53 (m, 1H), 2.47-2.36 (m, 2H), 2.26 (dt, J=14.4, 7.3 Hz, 2H), 2.03-1.84 (m, 3H), 1.84-1.57 (m, 4H), 1.41 (t, J=13.4 Hz, 1H), 1.16 (d, J=6.1 Hz, 3H). LCMS-ESI+ (m/z): [M+H]+ calcd for $C_{32}H_{40}ClN_3O_4S$: 598.2; found: 598.1.

Method 2

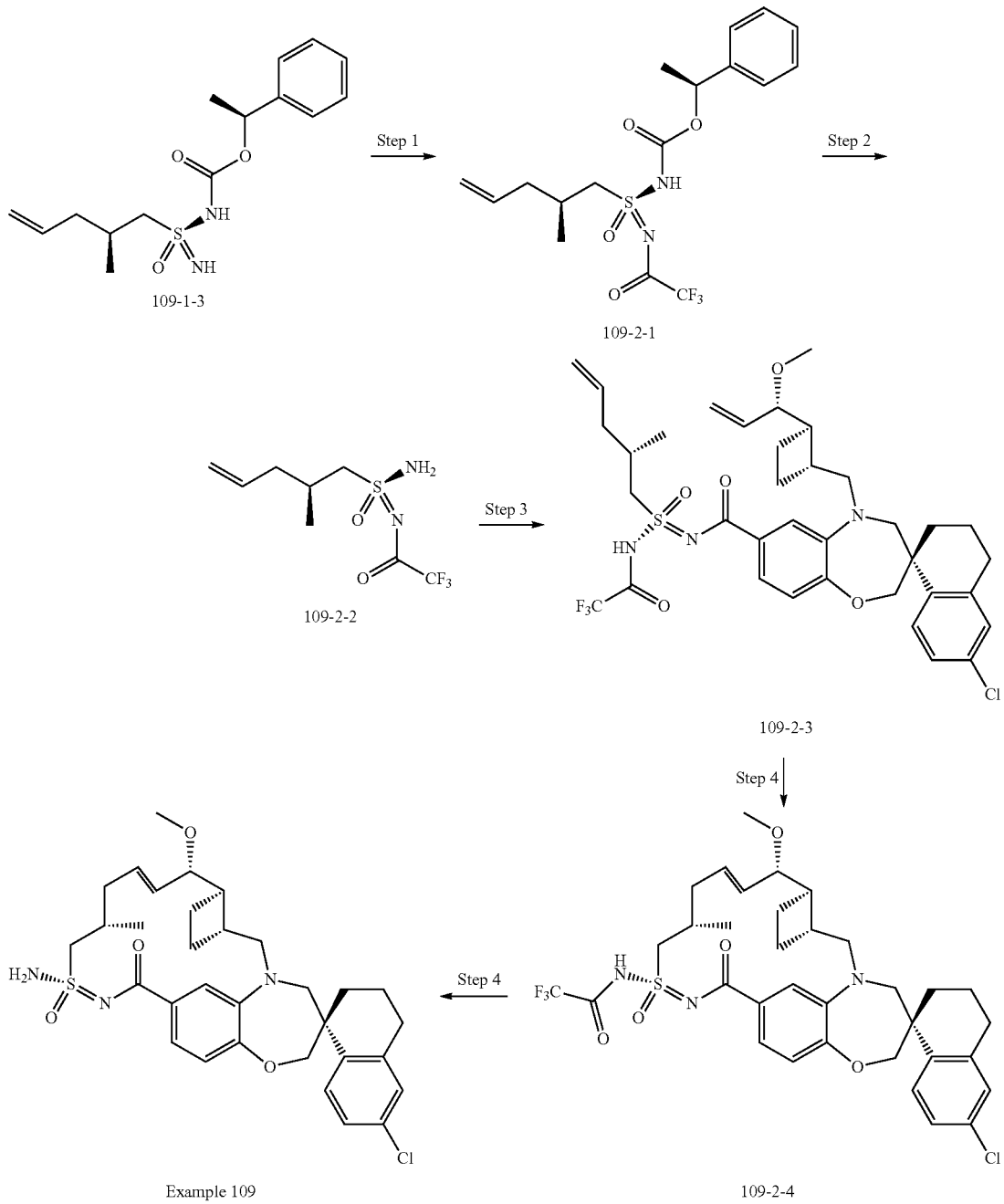

Step 1

To a solution of intermediate 109-1-3 (second eluting diasteromer from Example 109-method 1-step 2, 1.1 g, 3.54 mmol) in DCM (50 mL) at 0° C. was added triethylamine (1.48 mL, 10.63 mmol) and trifluoroacetic acid anhydride (1 mL, 7.08 mmol). The reaction mixture was stirred at 0° C. for 30 min. The reaction was quenched with brine. Then the reaction mixture was diluted with DCM, washed with saturated NaHCO$_3$ solution. The organic phase was separated, dried over MgSO$_4$, filtered, and concentrated to give intermediate 109-2-1 which was used further without purification.

Step 2

To a solution of intermediate 109-2-1 (1.4 g, 3.44 mmol) in DCM (30 mL) was added TFA (10 mL). The reaction mixture was stirred at rt. After completion, the reaction mixture was concentrated, and the residue was purified by silica gel column chromatography (0-50% EtOAc/hexanes) to give intermediate 109-2-2.

Step 3

To a stirred solution of intermediate 109-1-4 (1.5 g, 3.11 mmol) in DCM (200 mL) was added intermediate 109-2-2 (790 mg, 3.06 mmol), 1-(3-dimethylaminopropyl)-3-ethyl-carbodiimide HCl (1.5 g, 7.78 mmol) and 4-(dimethylamino)pyridine (760 mg, 6.22 mmol). The reaction mixture was stirred at rt overnight. Then the reaction mixture was diluted with DCM, washed with 1 N HCl and brine. The organic phase was dried over MgSO$_4$, filtered, concentrated, and the residue was purified by silica gel column chromatography (0-100% EtOAc/hexanes) to give intermediate 109-2-3.

Step 4

To a solution of intermediate 109-2-3 (72 mg, 0.1 mmol) in DCE (10 mL) was added TFA (0.02 mL, 0.2 mmol) and Hoveyda-grubbs 2$^{nd}$ generation catalyst (12.46 mg, 0.02 mmol). The reaction mixture was degassed with argon and then stirred at 60° C. overnight. The reaction mixture was concentrated, and the residue was purified by silica gel column chromatography (0-100% EtOAc/hexanes) to give intermediate 109-2-4.

Step 5

To a solution of intermediate 109-2-4 (130 mg, 0.19 mmol) in MeOH (10 mL) and H$_2$O (2 mL), was added potassium carbonate (129.4 mg, 0.94 mmol). The reaction mixture was stirred at 60° C. overnight. The reaction mixture was concentrated, dissolved in ethyl acetate, washed with water, back extracted with ethyl acetate. The organic phase was separated, dried over MgSO$_4$, filtered, concentrated, and purified by silica gel column chromatography (0-70% EtOAc/hexanes) to give Example 109.

Method 3

Step 1

To a solution of intermediate 106-1 (690 mg, 2.5 mmol) in THF (10 mL) at −40° C., was added n-butyl lithium (1.6 M in hexanes, 1.87 mL). The resulting mixture was stirred at −40° C. for 20 min. Then the solution of (4-nitrophenyl) [(1S)-1-phenylethyl] carbonate (5-3-1, 1.43 g, 4.99 mmol) in THF (6 mL) was added dropwise and the reaction mixture was allowed to warm up to rt and stirred for 3 h. The reaction was quenched with water and extracted with EtOAc. The organic layer was separated, dried over MgSO$_4$, filtered, and concentrated. The residue was purified by silica gel column (0-20% EtOAc/hexanes). The two diastereomers were separated.

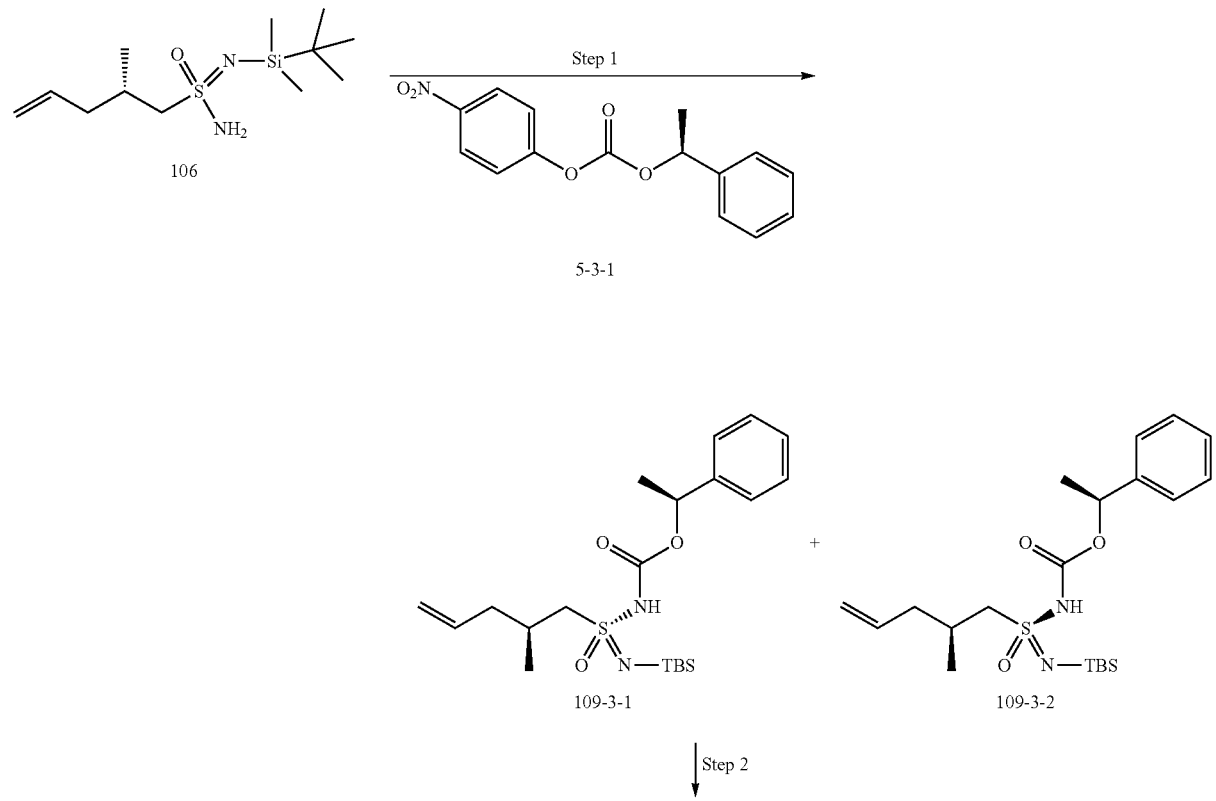

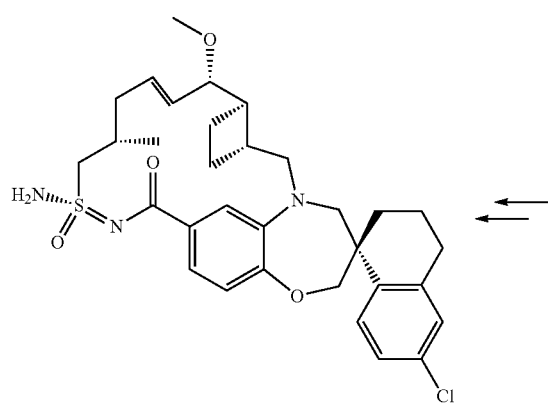

Example 109

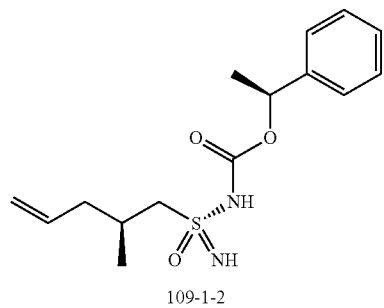

109-1-2

First eluted diasteromer (109-3-1, absolute stereochemistry tentatively assigned as drawn): ¹H NMR (400 MHz, chloroform-d) δ 7.49-7.29 (m, 5H), 5.84 (dq, J=23.2, 6.6 Hz, 1H), 5.74-5.47 (m, 1H), 5.08-4.93 (m, 2H), 3.32 (dd, J=14.1, 4.6 Hz, 1H), 3.18-2.95 (m, 1H), 2.29-2.10 (m, 2H), 2.03 (ddt, J=13.8, 6.9, 1.3 Hz, 1H), 1.59 (d, J=6.6 Hz, 3H), 1.09 (d, J=6.6 Hz, 3H), 0.93 (s, 9H), 0.21 (d, J=3.1 Hz, 6H).

Second eluted diasteromer (109-3-2, absolute stereochemistry tentatively assigned as drawn): ¹H NMR (400 MHz, chloroform-d) δ 7.45-7.25 (m, 5H), 5.81 (t, J=6.6 Hz, 1H), 5.78-5.63 (m, 1H), 5.11-4.95 (m, 2H), 3.40 (dd, J=13.9, 4.2 Hz, 1H), 3.07 (dd, J=14.0, 7.5 Hz, 1H), 2.27-2.13 (m, 2H), 2.13-2.07 (m, 1H), 1.59 (d, J=6.6 Hz, 3H), 1.09 (dd, J=6.7, 3.2 Hz, 3H), 0.88 (s, 9H), 0.17-0.09 (m, 6H).

Step 2

To a stirred solution of intermediate 109-3-1 (40 mg, 0.094 mmol) in THF (5 mL) in an ice-bath was added tetrabutylammonium fluoride (1.0 M THF, 0.14 ml) slowly. The reaction mixture was stirred at 0° C. for 20 min and then it was slowly warmed up to rt. The reaction mixture was stirred at rt for 2.5 h. The reaction mixture was concentrated, and the residue was purified by silica gel column (0-60% EtOAc/hexanes) to give intermediate 109-1-2. 1H NMR (400 MHz, chloroform-d) δ 7.42-7.37 (m, 2H), 7.37-7.24 (m, 3H), 5.72 (q, J=6.6 Hz, 1H), 5.62 (ddt, J=15.9, 11.1, 7.1 Hz, 1H), 5.51 (s, 2H), 5.07-4.97 (m, 2H), 3.42 (dd, J=14.4, 4.5 Hz, 1H), 3.06 (dd, J=14.4, 7.9 Hz, 1H), 2.33-2.01 (m, 3H), 1.57 (d, J=6.7 Hz, 3H), 1.12 (d, J=6.8 Hz, 3H).

Method 4

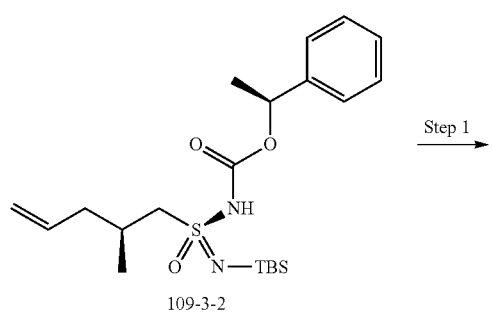

109-3-2

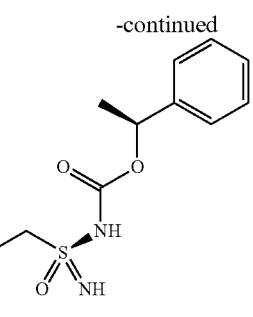

109-1-3

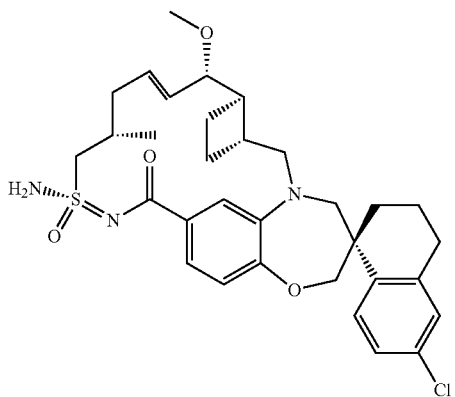

Example 109

Step 1

Intermediate 109-1-3 was also prepared in similar manner to method 3-step 2 (Example 109) using intermediate 109-3-2 instead of intermediate 109-3-1. Example 109 was synthesized in the same manner as Example 109 (Method 2) using intermediate 109-1-3.

Example 110

Method 1

Step 1

1-[S-amino-N-[tert-butyl(dimethyl)silyl]sulfonimidoyl] hexane (1-5, 5.9 g, 20.1 mmol) was azeotroped with anhydrous toluene (3×20 mL) and dissolved in anhydrous tetrahydrofuran (150 mL) under an atmosphere of argon. The solution was cooled to −50° C. (internal temperature probe). A solution of 2.5 M n-BuLi in hexanes (17.3 mL, 43.3 mmol) was added dropwise over 5 min. This mixture was left to stir for 15 min. Concurrently (4-nitrophenyl) [(1S)-1-phenylethyl] carbonate (5-3-1, 7.5 g, 26.2 mmol) was azeotroped with toluene (3×20 mL). The material was taken up in anhydrous tetrahydrofuran (60 mL) under an atmosphere of argon. The solution was added to the reaction via cannula over 5 min. The reaction was initially yellow but turned very dark (green). After 15 min, the reaction was warmed to 0° C. (ice bath). The reaction turned yellow while warming. After 1 h, TLC (20% EtOAc/hexanes visualized with KMnO₄ stain) showed the reaction was complete. The reaction was quenched with water (75 mL) at 0° C. EtOAc (50 mL) was added. The phases were separated and the aqueous phase was extracted with EtOAc (2×50 mL). The combined organic phases were washed with sat NaHCO₃ (75 mL) and brine (75 mL). The organic phase was dried over sodium sulfate and the solvent was removed under reduced pressure, providing crude [(1S)-1-phenylethyl] N—[N-[tert-butyl(dimethyl)silyl]-S-[(1R,2S)-1,2-dimethylpent-4-enyl]sulfonimidoyl]carbamate (110-1-1).

Step 2

A solution of TBAF (1.0 M, 19.7 mL, 19.7 mmol) was added to a solution of 110-1-1 (6.64 g, 15.1 mmol) in anhydrous THF at 0° C. After 1 h at 0° C., the reaction was complete. The THF was removed under reduced pressure. The residue was diluted with water (80 mL) and EtOAc (80 mL). The phases were separated, and the aqueous phase was extracted with EtOAc (3×50 mL). The combined organic phases were washed with brine and dried over sodium sulfate. The solvent was removed pressure and the residue was subjected to flash chromatography (0-65% EtOAc/hexanes 120 g gold isco column with solid loading). ELSD along with UV were used for peak detection. The fractions containing product were combined and the solvent was removed under reduced pressure, providing [(1S)-1-phenylethyl] N-[[(1R,2S)-1,2-dimethylpent-4-enyl]sulfonimidoyl]carbamate as a mixture of diastereomers at sulfur. The solid was subjected to chiral SFC separation, with methanol as a co-solvent using a ChiralPak IC column.

The first eluted diasteromer (110-1-2, RT=2.37 min on ChiralPak IC with 15% methanol co-solvent, absolute stereochemistry tentatively assigned as drawn). 1H NMR (400 MHz, chloroform-d) δ 7.45-7.33 (m, 4H), 7.33-7.30 (m, 1H), 5.73 (q, J=6.7 Hz, 1H), 5.48 (dddd, J=16.4, 10.1, 8.2, 6.0 Hz, 1H), 5.06-4.93 (m, 2H), 3.41 (qd, J=7.0, 2.2 Hz, 1H), 2.53-2.39 (m, 1H), 2.07 (dt, J=14.0, 6.2 Hz, 1H), 2.00-1.86 (m, 1H), 1.59 (d, J=6.7 Hz, 3H), 1.34 (d, J=7.0 Hz, 3H), 1.02 (d, J=6.8 Hz, 3H).

The second eluted diasteromer (110-1-3, Rt=3.92 min on ChiralPak IC with 15% methanol co-solvent, absolute stereochemistry tentatively assigned as drawn). 1H NMR (400 MHz, chloroform-d) δ 7.43-7.32 (m, 4H), 7.33-7.29 (m, 1H), 5.75 (q, J=6.6 Hz, 1H), 5.71-5.62 (m, 1H), 5.13-5.03 (m, 2H), 3.38 (qd, J=7.1, 2.3 Hz, 1H), 2.47 (dtd, J=8.9, 6.9, 2.2 Hz, 1H), 2.11 (dtt, J=13.1, 6.5, 1.4 Hz, 1H), 2.07-1.96 (m, 1H), 1.59 (d, J=6.7 Hz, 3H), 1.31 (d, J=7.0 Hz, 3H), 1.04 (d, J=6.9 Hz, 3H).

Example 110 was synthesized in the same manner as Example 109 (Method 1-Steps 3-6) using intermediate 110-1-2 instead of intermediate 109-1-2. 1H NMR (400 MHz, Chloroform-d) δ 7.778 (d, J=8.5 Hz, 1H), 7.45 (dd, J=8.3, 1.9 Hz, 1H), 7.30 (d, J=2.0 Hz, 1H), 7.20 (dd, J=8.5, 2.3 Hz, 1H), 7.10 (d, J=2.4 Hz, 1H), 6.93 (d, J=8.3 Hz, 1H), 5.91 (dt, J=15.8, 5.8 Hz, 1H), 5.69 (dd, J=15.8, 6.8 Hz, 1H), 4.18-3.95 (m, 2H), 3.87 (dd, J=14.9, 3.4 Hz, 1H), 3.73 (s, 5H), 3.41-3.23 (m, 4H), 3.01 (dd, J=15.0, 10.9 Hz, 1H), 2.89-2.72 (m, 2H), 2.62 (s, 2H), 2.46 (s, 1H), 2.31-2.01 (m, 3H), 1.99-1.64 (m, 6H), 1.46 (s, 3H), 1.11 (d, J=6.9 Hz, 3H). LCMS-ESI+ (m/z): calcd for H+C₃₃H₄₂ClN₃O₄S: 612.26; found: 612.06.

Method 2

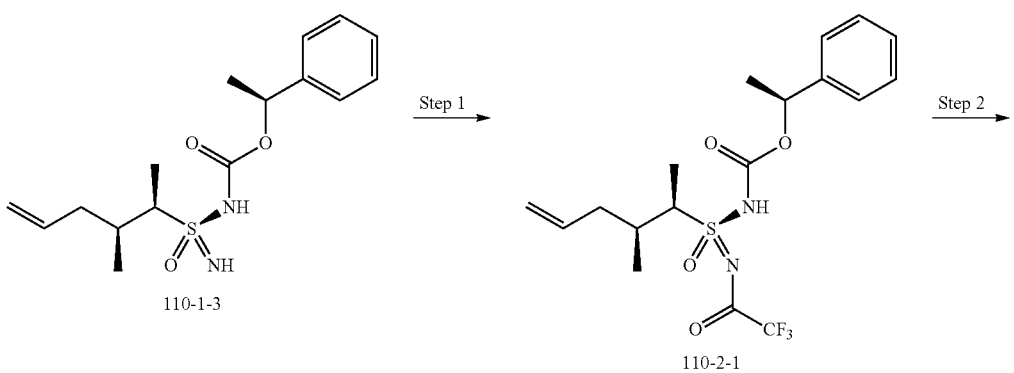

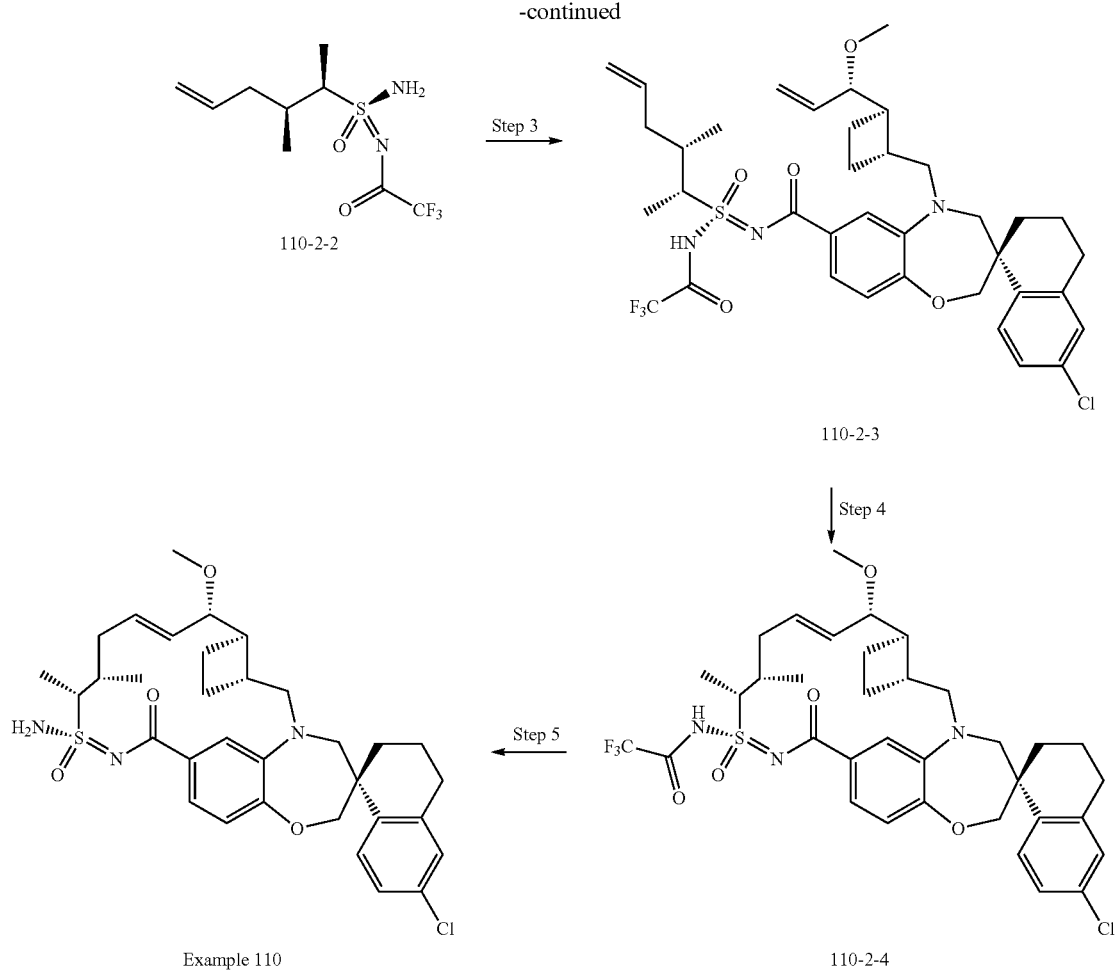

Example 110

110-2-4

Step 1

To an ice-cold solution of intermediate 110-1-3 (second eluting diasteromer from Example 110-method 1-step 2, 3.6 g, 11.10 mmol) and trifluoroacetic anhydride (3.5 g, 16.64 mmol) in anhydrous dichloromethane was added TEA (2.32 mL, 16.64 mmol) under argon, and then the solution was stirred for 30 min. The reaction mixture was concentrated to yield intermediate 110-2-1.

Step 2

To a stirred mixture of dichloromethane/trifluoroacetic acid (3/1) (200 mL) was added intermediate 110-2-1 (4.2 g, 9.98 mmol). The mixture was stirred at room temperature overnight. The solvent was removed under reduced pressure. Then water was added, and the mixture was extracted with dichloromethane. The organic phase was dried over anhydrous magnesium sulfate, and the solvent was removed under reduced pressure. The residue thus obtained was purified by normal phase chromatography (SiO$_2$, 1:2 Hex: EtOAc) to yield intermediate 110-2-2. 1H NMR (400 MHz, Chloroform-d) δ 5.70 (dddd, J=17.0, 10.2, 8.3, 5.8 Hz, 1H), 5.58 (s, 2H), 5.22-5.01 (m, 2H), 3.56 (qd, J=7.0, 2.2 Hz, 1H), 2.63-2.42 (m, 1H), 2.19 (dtt, J=15.1, 6.0, 1.6 Hz, 1H), 2.05-1.91 (m, 1H), 1.43 (d, J=7.0 Hz, 3H), 1.08 (d, J=6.8 Hz, 3H).

Step 3

To a stirred solution of intermediate 109-1-4 (4.0 g, 8.29 mmol) in DCM was added EDCI (2.5 g, 16.6 mmol) and DMAP (2.0 g, 16.6 mmol). The reaction mixture was stirred for 10 mins at room temperature. Intermediate 110-2-2 (2.4 g, 9.13 mmol) was added and the resulting suspension was stirred overnight at room temperature. The reaction mixture was quenched with water and washed with DCM, aqueous NaHCO$_3$, 1 N aqueous HCl, and brine. The organic layer was dried with Mg$_2$SO$_4$ and the solvent was removed under reduced pressure to afford the crude residue, which was subjected to column chromatography (SiO$_2$, 50-90% Hex/EtOAc) to give the desired intermediate 110-2-3.

Step 4

Intermediate 110-2-3 (1.2 g, 1.57 mmol), TFA (360 mg, 3.15 mmol) and Hoveyda Grubbs generation 2 catalyst (196 mg, 0.32 mmol) were stirred in 1,2-dichloroethane (150 mL) at 60° C. for 2 h. More catalyst was added (196 mg, 0.32 mmol) and the mixture stirred at 60° C. for 24 hr. After concentration, the residue was purified by silica gel column chromatography (5-95% Hex/EtOAc) to afford intermediate 110-2-4.

Step 5

To a stirred solution of intermediate 110-2-4 (200 mg, 0.28 mmol) in MeOH (10 ml) was added water (2 mL) and then K$_2$CO$_3$ (195 mg, 1.41 mmol). The reaction mixture was stirred at 60° C. for 24 hrs. Mixture was evaporated under reduced pressure and then dissolved in DCM. Water was added, and then the mixture was extracted with DCM. Combined organic layers was washed with brine, dried over Mg$_2$SO$_4$, filtered, concentrated, and purified by silica gel column chromatography (50-90% hexanes/EtOAc) to give Example 110.

Method 3

Step 1

To a solution of intermediate 1-5 (Example 1-step 5, 1 g, 3.44 mmol) in THF (50 mL) at −50° C., was added n-butyl The resulting crude product was redissolved in hexanes and purified by flash column chromatography (silica gel, 0 to 100% dichloromethane in hexanes, ELSD detector). ELSD-active fractions were assayed by silica gel TLC (3:1 hexanes:ethyl acetate, KMnO$_4$ stain); and the diastereomeric products were co-eluted at 70-100% dichloromethane. The crude product mixture was redissolved in hexanes and again purified by flash column chromatography (silica gel, 0 to 20% ethyl acetate in hexanes, ELSD detector). ELSD-active fractions were assayed by silica gel TLC (3:1 hexanes:ethyl acetate, KMnO$_4$ stain). The first-eluting peak eluted (110-3-1, absolute stereochemistry tentatively assigned as drawn) at 10% ethyl acetate, while the later eluting peak (110-3-2, absolute stereochemistry tentatively assigned as drawn) eluted at 15% ethyl acetate,

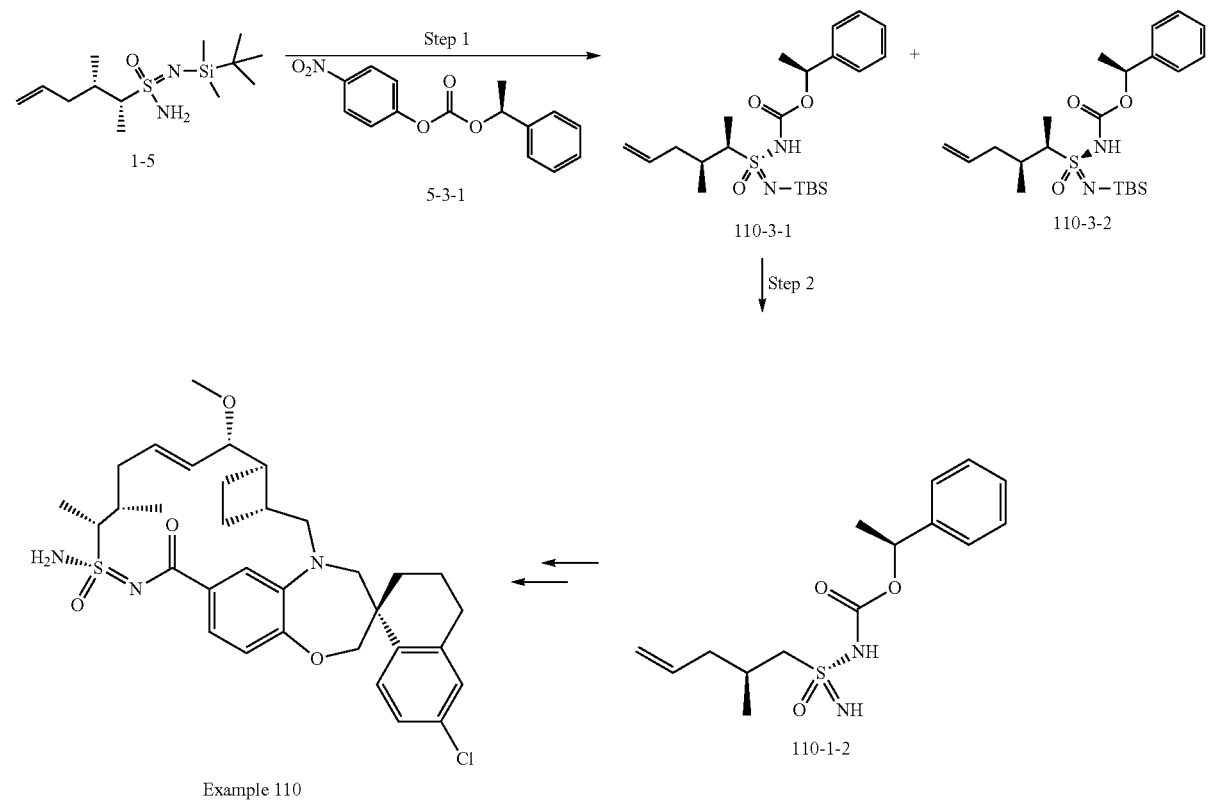

Example 110 lithium (1.6 M in hexanes, 4.6 mL, 7.40 mmol) was added dropwise over 5 min. The mixture was left to stir for 15 min. Concurrently (4-nitrophenyl) [(1S)-1-phenylethyl] carbonate (5-3-1, 1.3 g, 4.47 mmol) was azeotroped with toluene (3×20 mL). The material was taken up in anhydrous tetrahydrofuran (30 mL) under an atmosphere of argon. The solution was added to the reaction via cannula over 5 min. The reaction was initially yellow but turned very dark (green). After 15 min the reaction was warmed to 0° C. (ice bath). The reaction turned yellow while warming. After 3 h, TLC (20% EtOAc/hexanes visualized with KMnO$_4$ stain) showed the reaction was complete. The reaction was quenched with water (75 mL) at 0° C. EtOAc (50 mL) was added. The phases were separated, and the aqueous phase was extracted with EtOAc (2×50 mL). The combined organic phases were washed with sat NaHCO$_3$ (75 mL) and brine (75 mL). The organic phase was dried over sodium sulfate and the solvent was removed under reduced pressure.

Step 2

A solution of TBAF (1.0 M, 2.84 mL, 2.84 mmol) was added to a solution of the intermediate 110-3-1 (830 mg, 1.89 mmol) in anhydrous THF at 0° C. After 60 min at 0° C., the reaction was complete. The solvent was removed under reduced pressure. The residue was diluted with water (80 mL) and EtOAc (80 mL). The phases were separated, and the aqueous phase was extracted with EtOAc (3×50 mL). The combined organic phases were washed with brine, and dried over sodium sulfate. The solvent was removed pressure and the residue was subjected to flash chromatography (0-50% EtOAc/hexanes, 80 g silica gel). ELSD along with UV were used for peak detection. The fractions containing product were combined and the solvent was removed under reduced pressure, to give intermediate 110-1-2.

215

Preparation of Example 110

Example 110 was synthesized in the same manner as Example 110 (Method 1) using intermediate 110-1-2.

Method 4

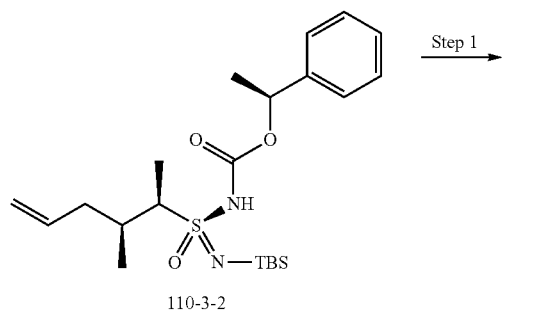

Step 1

Intermediate 110-1-3 was also prepared in similar manner to method 3-step 2 (Example 110) using intermediate 110-3-2 instead of intermediate 110-3-1.

Preparation of Example 110

Example 110 was synthesized in the same manner as Example 109 (Method 2) using intermediate 110-1-3.

216

Example 111

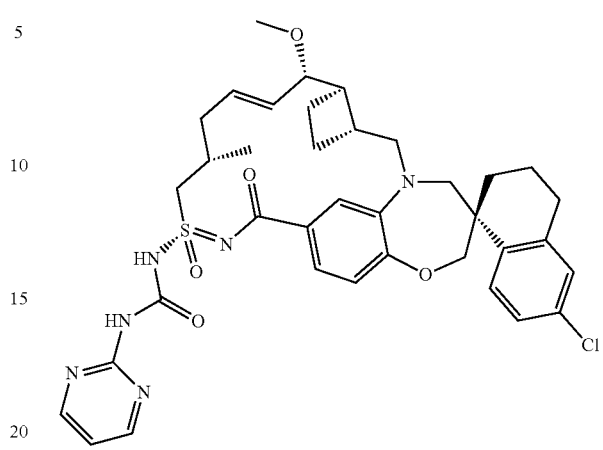

To the mixture of Example 109 (10 mg, 0.0167 mmol) in DCM (0.6 mL) was added ACN (1.7 mL) at rt. Then 4-dimethylaminopyridine (10.2 mg, 0.0836 mmol) and diphenyl carbonate (28.6 mg, 0.134 mmol) were added to the mixture and stirred at room temperature. After 5 hours, pyrimidin-2-amine (12.7 mg, 0.134 mmol) was added and the reaction was heated at 60° C. for 5 hours and then room temperature overnight. The reaction was concentrated, redissolved in DMF (1.2 mL), filtered, and purified by Gilson reverse phase prep HPLC, eluted with 60-100% ACN/H$_2$O with 0.1% TFA. $^1$H NMR (400 MHz, Methanol-d4) δ 8.73 (d, J=5.1 Hz, 2H), 7.76 (d, J=8.5 Hz, 1H), 7.38-6.82 (m, 7H), 6.14 (dq, J=14.4, 6.6 Hz, 1H), 5.62 (dd, J=15.4, 8.3 Hz, 1H), 4.21 (dd, J=14.8, 6.3 Hz, 1H), 4.12-4.01 (m, 3H), 3.91-3.64 (m, 3H), 3.29 (s, 3H), 3.08 (dd, J=15.2, 10.0 Hz, 1H), 2.89-2.71 (m, 2H), 2.60-2.37 (m, 3H), 2.32-2.06 (m, 3H), 2.02-1.67 (m, 7H), 1.45 (t, J=11.1 Hz, 1H), 1.15 (dd, J=8.4, 6.3 Hz, 3H). LCMS-ESI+ (m/z): [M+H]+ calcd for C$_{37}$H$_{43}$ClN$_6$O$_5$S: 719.2; found: 719.5.

Example 112

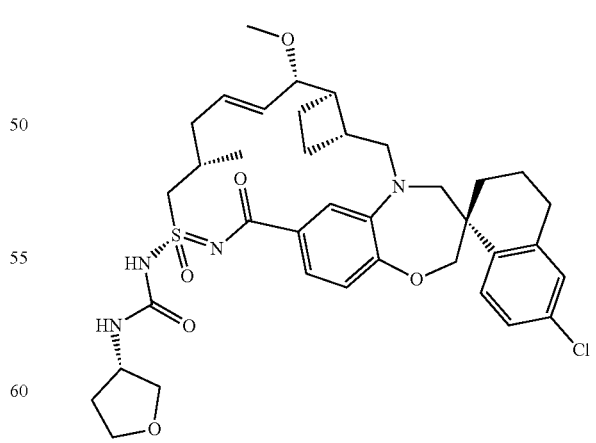

Example 112 was synthesized in the same manner as Example 111 using (3S)-tetrahydrofuran-3-amine hydrochloride instead of pyrimidin-2-amine, Hunig's base (8.64 mg, 0.0669 mmol) was also added to this reaction. 1H NMR (400 MHz, Methanol-d4) δ 7.74 (d, J=8.5 Hz, 1H), 7.24-7.10 (m, 3H), 7.03-6.88 (m, 2H), 6.23-5.97 (m, 1H), 5.64-5.50 (m, 1H), 4.37-4.21 (m, 2H), 4.11-4.01 (m, 2H), 3.98-3.75 (m, 6H), 3.72-3.48 (m, 3H), 3.28 (s, 3H), 3.08 (dd, J=15.3, 10.2 Hz, 1H), 2.89-2.71 (m, 2H), 2.57-2.33 (m, 3H), 2.31-2.09 (m, 3H), 1.98-1.73 (m, 8H), 1.44 (t, J=11.8 Hz, 1H), 1.14 (d, J=6.6 Hz, 3H). LCMS-ESI+ (m/z): [M+H]+ calcd for $C_{37}H_{47}ClN_4O_6S$: 711.3; found: 710.8.

Example 113

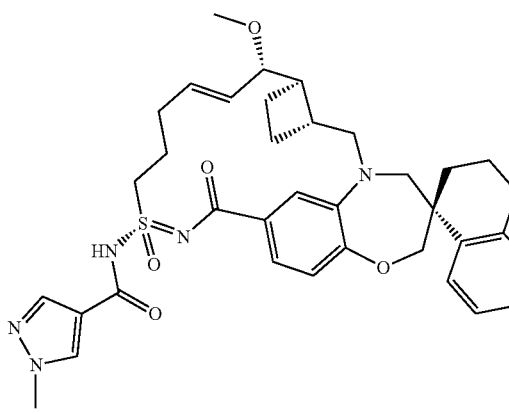

To the mixture of 1-methylpyrazole-4-carboxylic acid (3.76 mg, 0.0298 mmol) in DCM (1.0 mL) was added 1-(3-dimethylaminopropyl)-3-ethylcarbodiimide HCl (5.71 mg, 0.0298 mmol) and 4-dimethylaminopyridine (3.64 mg, 0.0298 mmol). The mixture was stirred at rt for 5 minutes, then Example 5 (8.7 mg, 0.0149 mmol) was added, and the reaction was stirred at room temperature overnight. The reaction mixture was then concentrated, redissolved in DMF (1.2 mL), filtered, and purified by Gilson reverse phase prep HPLC, eluted with 60-100% ACN/H2O with 0.1% TFA to give Example 113. $^1$H NMR (400 MHz, Methanol-d4) δ 8.42 (s, 1H), 7.91 (s, 1H), 7.65 (d, J=8.6 Hz, 1H), 7.36 (d, J=8.0 Hz, 1H), 7.26 (s, 1H), 7.07 (d, J=2.1 Hz, 1H), 6.99-6.83 (m, 2H), 5.98-5.90 (m, 1H), 5.86 (dd, J=16.0, 8.2 Hz, 1H), 3.97 (d, J=29.0 Hz, 6H), 3.77 (d, J=15.0 Hz, 1H), 3.71-3.65 (m, 2H), 3.62-3.55 (m, 2H), 3.47 (d, J=14.3 Hz, 1H), 3.37 (s, 3H), 3.16 (d, J=26.2 Hz, 1H), 2.88-2.74 (m, 3H), 2.50 (s, 2H), 2.30 (d, J=9.2 Hz, 2H), 2.10 (d, J=14.0 Hz, 3H), 2.00-1.84 (m, 4H), 1.41 (d, J=11.9 Hz, 1H). LCMS-ESI+ (m/z): [M+H]+ calcd for $C_{36}H_{42}ClN_5O_5S$: 692.2; found: 691.973.

Example 114

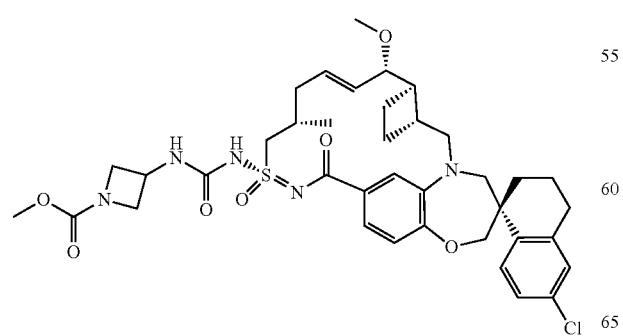

Example 114 was synthesized in the same manner as Example 75 using Example 109 and methyl 3-aminoazetidine-1-carboxylate. $^1$H NMR (400 MHz, methanol-d4) δ 7.72 (d, J=8.5 Hz, 1H), 7.17-7.12 (m, 2H), 7.09 (d, J=2.3 Hz, 1H), 6.94 (s, 1H), 6.90 (d, J=8.2 Hz, 1H), 6.07-5.89 (m, 1H), 5.57 (dd, J=15.3, 9.0 Hz, 1H), 4.60-4.41 (m, 1H), 4.25 (t, J=8.5 Hz, 3H), 4.13-3.98 (m, 2H), 3.96-3.79 (m, 3H), 3.75 (dd, J=9.0, 3.7 Hz, 1H), 3.69-3.62 (m, 1H), 3.66 (s, 3H), 3.29-3.23 (m, 1H), 3.25 (s, 3H), 3.06 (dd, J=15.3, 10.3 Hz, 1H), 2.88-2.66 (m, 2H), 2.53-2.28 (m, 3H), 2.24-2.05 (m, 3H), 2.00-1.65 (m, 7H), 1.42 (t, J=12.4 Hz, 1H), 1.12 (d, J=6.5 Hz, 3H). LCMS-ESI+: calc'd for $C_{38}H_{48}ClN_5O_7S$: 754.29 (M+H); found: 753.97 (M+H).

Example 115

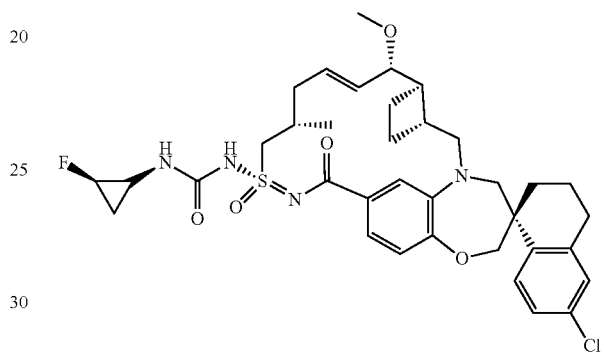

Example 115 was synthesized in the same manner as Example 75 using Example 109 and (1S,2R)-2-fluorocyclopropanamine. $^1$H NMR (400 MHz, Methanol-d4) δ 7.75 (d, J=8.5 Hz, 1H), 7.24-7.15 (m, 2H), 7.12 (d, J=2.3 Hz, 1H), 7.03-6.97 (m, 1H), 6.91 (d, J=8.2 Hz, 1H), 6.03 (dd, J=15.0, 7.6 Hz, 1H), 5.59 (dd, J=15.2, 8.9 Hz, 1H), 4.79-4.54 (m, 1H), 4.29 (dd, J=14.9, 6.4 Hz, 1H), 4.14-4.01 (m, 2H), 3.91-3.73 (m, 3H), 3.68 (d, J=14.5 Hz, 1H), 3.31-3.24 (m, 1H), 3.27 (s, 3H), 3.07 (dd, J=15.2, 10.3 Hz, 1H), 2.89-2.72 (m, 2H), 2.68 (dt, J=10.2, 5.5 Hz, 1H), 2.57-2.31 (m, 3H), 2.28-2.07 (m, 3H), 2.03-1.65 (m, 6H), 1.44 (t, J=12.5 Hz, 1H), 1.24-1.07 (m, 4H), 1.01-0.84 (m, 1H). LCMS-ESI+: calc'd for $C_{36}H_{44}ClFN_4O_5S$: 699.27 (M+H); found: 698.73 (M+H).

Example 116

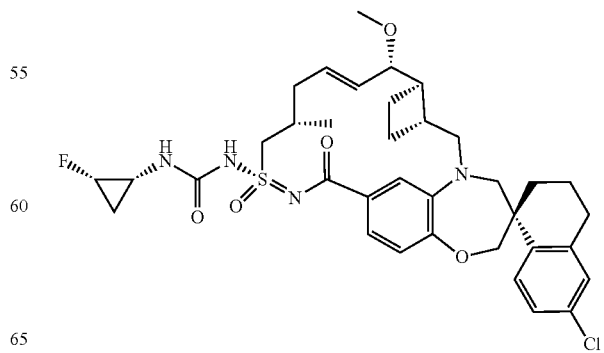

Example 116 was synthesized in the same manner as Example 75 using Example 109 and (1R,2S)-2-fluorocyclopropanamine. ¹H NMR (400 MHz, Methanol-d₄) δ 7.75 (d, J=8.5 Hz, 1H), 7.24-7.15 (m, 2H), 7.12 (d, J=2.3 Hz, 1H), 7.00 (s, 1H), 6.91 (d, J=8.2 Hz, 1H), 6.11-5.97 (m, 1H), 5.58 (dd, J=15.3, 8.9 Hz, 1H), 4.66 (dtd, J=64.4, 5.7, 3.2 Hz, 1H), 4.30 (dd, J=14.9, 6.3 Hz, 1H), 4.15-3.99 (m, 2H), 3.86 (d, J=14.8 Hz, 2H), 3.78 (dd, J=9.0, 3.7 Hz, 1H), 3.68 (d, J=14.6 Hz, 1H), 3.31-3.28 (m, 1H), 3.27 (s, 3H), 3.07 (dd, J=15.2, 10.3 Hz, 1H), 2.89-2.71 (m, 2H), 2.67 (dt, J=9.4, 5.3 Hz, 1H), 2.55-2.30 (m, 3H), 2.26-2.08 (m, 3H), 2.01-1.67 (m, 6H), 1.44 (t, J=12.2 Hz, 1H), 1.21-1.06 (m, 4H), 1.02-0.87 (m, 1H). LCMS-ESI+: calc'd for $C_{36}H_{44}ClFN_4O_5S$: 699.27 (M+H); found: 698.65 (M+H).

Example 117

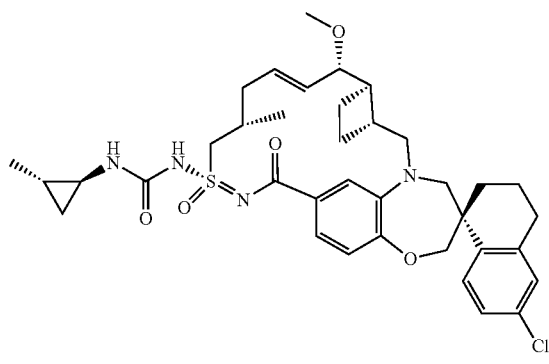 [SMILES: CO[C@H]1/C=C/C[C@H](C)C[S@@](=O)(NC(=O)N[C@H]2C[C@@H]2C)=NC(=O)c2ccc3c(c2)N(C[C@@H]2CC[C@H]21)C[C@@]1(CCCc2cc(Cl)ccc21)CO3]

Example 117 was prepared in a similar manner to Example 75 using (1S, 2R)-2-methylcyclopropan-1-amine hydrochloride, triethylamine and Example 109. 1H NMR (400 MHz, methanol-d4) δ 7.76 (d, J=8.5 Hz, 2H), 7.38 (s, 2H), 7.18 (d, J=9.3 Hz, 2H), 7.12 (s, 2H), 6.85 (s, 2H), 6.24 (s, 2H), 5.59 (s, 2H), 4.60 (s, 1H), 4.11-3.97 (m, 4H), 3.83-3.66 (m, 9H), 2.80 (d, J=19.4 Hz, 4H), 2.63 (s, 3H), 2.32 (s, 4H), 2.20-2.03 (m, 5H), 1.96 (s, 6H), 1.77 (s, 6H), 1.46 (s, 3H), 1.31 (s, 1H), 1.07 (d, J=6.1 Hz, 23H), 0.83 (ddt, J=12.2, 6.1, 3.0 Hz, 3H), 0.61 (ddd, J=9.0, 5.1, 3.6 Hz, 4H), 0.51-0.39 (m, 6H). LCMS-ESI+ (m/z): [M+H] Calculated for $C_{37}H_{47}ClN_4O_5S$: 695.32; found 694.99.

Example 118

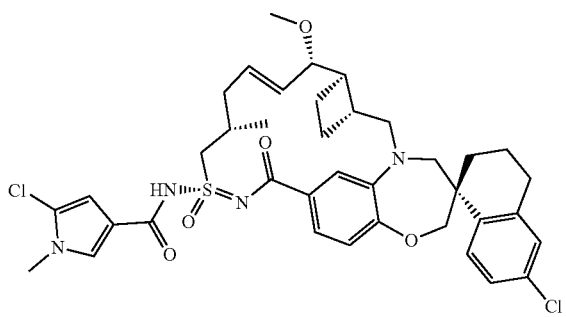 [SMILES: CO[C@H]1/C=C/C[C@H](C)C[S@@](=O)(NC(=O)c2cc(Cl)n(C)c2)=NC(=O)c2ccc3c(c2)N(C[C@@H]2CC[C@H]21)C[C@@]1(CCCc2cc(Cl)ccc21)CO3]

Synthesis of 5-chloro-1-methyl-1H-pyrrole-3-carboxylic acid: To a solution of 5-chloro-1H-pyrrole-3-carboxylic acid (0.075 g; 0.515 mmol) in 1.0 mL DMSO was added freshly ground potassium hydroxide (KOH (solid); 0.231 g; 4.12 mmol). The heterogeneous slurry was stirred for 50 minutes before addition of iodomethane (MeI; 0.048 mL; 0.109 g; 0.773 mmol). The mixture was allowed to stir at ambient temperature for 4 hours before diluting the reaction mixture with 10 mL of each CH₂Cl₂ and 1 N HCl (aq.) The biphasic mixture was stirred for at least ten minutes before layers were separated. The aqueous layer was back extracted with 10 mL of each isopropyl acetate and ethyl acetate. The combined organic phases were washed with 10 mL H₂O and dried over anhydrous Na₂SO₄. The organic phases were concentrated to dryness in vacuo and used directly in the next step (vida infra) (62 mg; 82.7% yield) (¹H NMR (400 MHz, DMSO-d₆) δ 11.98 (s, 1H), 7.47 (d, J=2.1 Hz, 1H), 6.39 (d, J=2.1 Hz, 1H), 3.60 (s, 3H), 2.55 (s, 1H). LCMS-ESI+ (m/z): [M+H] calculated for $C_6H_6ClNO_2$: 160.01; found 160.07.

Example 118 was prepared in a similar manner to Example 106 using 5-chloro-1-methyl-1H-pyrrole-3-carboxylic acid and Example 109. 1H NMR (400 MHz, methanol-d4) δ 7.74 (d, J=8.5 Hz, 1H), 7.38-7.27 (m, 2H), 7.15 (dd, J=8.5, 2.4 Hz, 1H), 7.11-7.01 (m, 2H), 6.81 (d, J=8.1 Hz, 1H), 6.48 (s, 1H), 6.17 (dd, J=14.8, 7.4 Hz, 1H), 5.51 (dd, J=15.4, 8.7 Hz, 1H), 4.15 (s, 1H), 4.10 (d, J=7.1 Hz, 0H), 4.09-3.95 (m, 2H), 3.86-3.70 (m, 2H), 3.60 (s, 4H), 3.25 (s, 4H), 3.03 (dd, J=15.0, 9.8 Hz, 1H), 2.86-2.67 (m, 2H), 2.59 (d, J=10.4 Hz, 1H), 2.41 (s, 3H), 2.22-2.05 (m, 4H), 1.99 (d, J=9.6 Hz, 2H), 1.91 (d, J=7.5 Hz, 2H), 1.79 (dd, J=19.5, 8.7 Hz, 1H), 1.73 (s, 2H), 1.69 (d, J=8.8 Hz, 0H), 1.41 (t, J=12.7 Hz, 1H), 1.33-1.19 (m, 2H), 1.06 (d, J=6.5 Hz, 3H), 0.89 (dd, J=7.3, 3.8 Hz, 1H). LCMS-ESI+ (m/z): [M+H] calculated for $C_{38}H_{44}Cl_2N_4O_5S$: 739.24; found: 739.75 (M+H).

Example 119

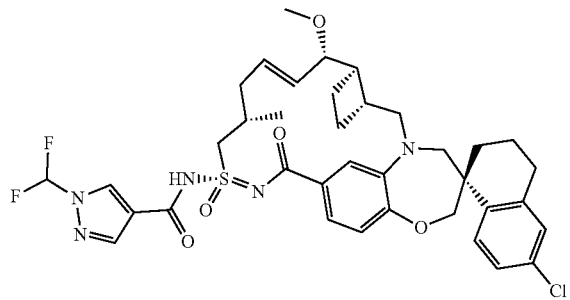 [SMILES: CO[C@H]1/C=C/C[C@H](C)C[S@@](=O)(NC(=O)c2cnn(C(F)F)c2)=NC(=O)c2ccc3c(c2)N(C[C@@H]2CC[C@H]21)C[C@@]1(CCCc2cc(Cl)ccc21)CO3]

Example 119 was prepared in a similar manner to Example 18 using 1-(difluoromethyl)-1H-pyrazole-4-carboxylic acid and Example 109. ¹H NMR (400 MHz, Methanol-d₄) δ 8.48 (s, 1H), 8.09 (s, 1H), 7.77 (d, J=8.5 Hz, 1H), 7.66 (s, 0H), 7.52 (s, 1H), 7.40-7.32 (m, 1H), 7.18 (dd, J=8.5, 2.4 Hz, 1H), 7.10 (dd, J=6.4, 2.1 Hz, 2H), 6.84 (d, J=8.2 Hz, 1H), 6.22 (dt, J=14.4, 6.9 Hz, 1H), 5.56 (dd, J=15.4, 8.6 Hz, 1H), 4.22-3.98 (m, 3H), 3.87-3.74 (m, 2H), 3.78-3.61 (m, 4H), 3.55 (dt, J=11.6, 2.8 Hz, 0H), 3.35 (s, 0H), 3.28 (s, 3H), 3.06 (dd, J=15.2, 10.2 Hz, 1H), 2.88-2.70 (m, 2H), 2.70-2.61 (m, 1H), 2.52-2.38 (m, 1H), 2.29 (s, 1H), 2.21 (dt, J=14.1, 7.0 Hz, 1H), 2.12 (d, J=13.7 Hz, 1H), 1.94 (d, J=7.0 Hz, 3H), 1.88-1.69 (m, 2H), 1.44 (t, J=11.9 Hz, 1H), 1.31 (s, 0H), 1.11 (d, J=6.8 Hz, 3H). ¹⁹F NMR (376 MHz, methanol-d₄) δ -97.35. LCMS-ESI+ (m/z): [M+H] calculated for $C_{37}H_{42}ClF_2N_5O_5S$: 742.26; found 742.13.

Example 120

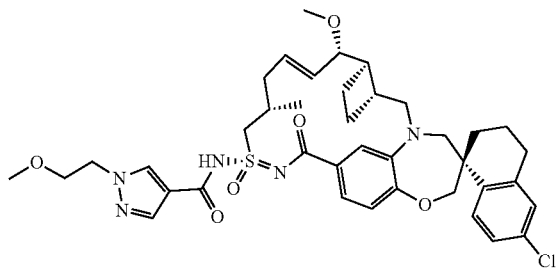 [SMILES: COCCn1cc(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)cn1]

Example 118 was prepared in a similar manner to Example 18, using 1-(2-methoxyethyl)-1H-pyrazole-4-carboxylic acid and Example 109. $^1$H NMR (400 MHz, methanol-d$_4$) δ 8.11 (s, 1H), 7.92 (s, 1H), 7.77 (d, J=8.6 Hz, 1H), 7.41-7.24 (m, 3H), 7.18 (dd, J=8.4, 2.3 Hz, 1H), 7.13-7.06 (m, 2H), 6.83 (d, J=8.2 Hz, 1H), 6.22 (dt, J=14.4, 6.8 Hz, 1H), 5.75-5.67 (m, 0H), 5.55 (dd, J=15.4, 8.7 Hz, 1H), 5.07 (s, 0H), 4.31 (t, J=5.1 Hz, 2H), 4.22-3.97 (m, 3H), 3.84 (d, J=14.8 Hz, 1H), 3.82-3.63 (m, 7H), 3.61-3.51 (m, 0H), 3.29 (d, J=12.4 Hz, 5H), 3.06 (dd, J=15.0, 10.0 Hz, 1H), 2.88-2.74 (m, 2H), 2.64 (d, J=13.8 Hz, 1H), 2.43 (s, 2H), 2.27 (s, 1H), 2.23-2.08 (m, 3H), 1.94 (d, J=6.3 Hz, 3H), 1.88-1.68 (m, 2H), 1.52 (d, J=6.6 Hz, 1H), 1.50-1.38 (m, 1H), 1.31 (s, 3H), 1.10 (dd, J=6.7, 3.6 Hz, 4H), 0.93 (d, J=5.7 Hz, 0H), 0.90 (s, 2H), 0.12 (s, 1H). LCMS-ESI+ (m/z): [M+H] calculated for C$_{39}$H$_{48}$ClN$_5$O$_6$S: 750.30; found 750.08.

Example 121

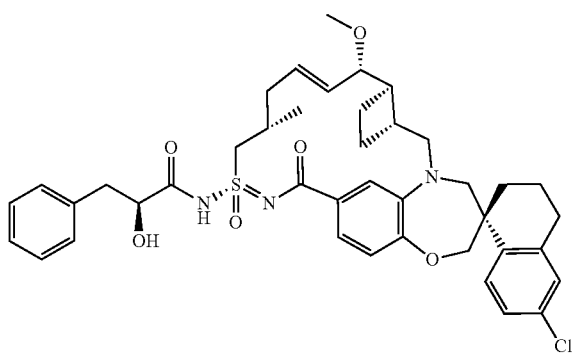 [SMILES: CO[C@H]1/C=C/C[C@H](C)C[S@@](=O)(NC(=O)[C@@H](O)Cc2ccccc2)=NC(=O)c2ccc3c(c2)N(C[C@@H]2CC[C@H]21)C[C@@]1(CCCc2cc(Cl)ccc21)CO3]

Example 121 was synthesized in the same manner as Example 18 using (S)-2-hydroxy-3-phenylpropionic acid and Example 109. 1H NMR (400 MHz, Acetonitrile-d3) δ 7.72 (d, J=8.5 Hz, 1H), 7.36-7.21 (m, 6H), 7.19 (dd, J=8.6, 2.4 Hz, 1H), 7.16-7.10 (m, 2H), 6.88 (d, J=8.2 Hz, 1H), 6.01 (dt, J=14.0, 6.5 Hz, 1H), 5.57 (dd, J=15.5, 7.9 Hz, 1H), 4.43 (dd, J=8.1, 4.2 Hz, 1H), 4.06 (d, J=12.1 Hz, 1H), 4.00 (d, J=12.1 Hz, 1H), 3.86 (s, 1H), 3.80 (d, J=15.3 Hz, 1H), 3.74-3.66 (m, 2H), 3.34 (d, J=14.3 Hz, 1H), 3.20 (s, 3H), 3.17 (dd, J=14.1, 4.2 Hz, 1H), 3.05 (dd, J=15.2, 10.1 Hz, 1H), 2.94 (dd, J=14.0, 8.2 Hz, 1H), 2.86-2.68 (m, 2H), 2.52-2.34 (m, 3H), 2.14 (t, J=8.5 Hz, 2H), 2.10-2.00 (m, 1H), 1.90-1.59 (m, 9H), 1.41 (dt, J=14.6, 7.8 Hz, 1H), 1.05 (d, J=6.3 Hz, 3H). $^{19}$F NMR (376 MHz, acetonitrile-d3) 5-77.38. LCMS-ESI+ (m/z): [M+H]+ calcd for C$_{41}$H$_{48}$ClN$_3$O$_6$S: 746.3; found: 746.0.

Example 122

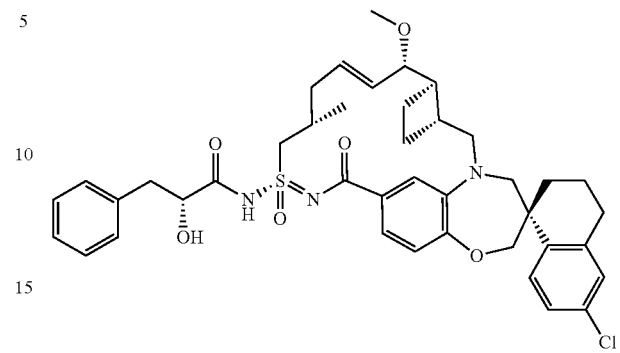

Example 122 was synthesized in the same manner as Example 18 using (R)-2-hydroxy-3-phenylpropionic acid and Example 109. 1H NMR (400 MHz, Acetonitrile-d3) δ 7.73 (d, J=8.5 Hz, 1H), 7.36-7.27 (m, 4H), 7.28-7.22 (m, 1H), 7.20 (dd, J=8.5, 2.4 Hz, 1H), 7.14 (dd, J=9.3, 2.2 Hz, 2H), 6.88 (d, J=8.3 Hz, 1H), 6.00 (dt, J=14.6, 6.9 Hz, 1H), 5.55 (dd, J=15.6, 7.9 Hz, 1H), 4.49 (dd, J=7.6, 4.1 Hz, 1H), 4.06 (d, J=12.1 Hz, 1H), 4.00 (d, J=12.1 Hz, 1H), 3.83-3.75 (m, 2H), 3.75-3.64 (m, 2H), 3.34 (d, J=14.3 Hz, 1H), 3.20 (s, 3H), 3.15 (dd, J=14.1, 4.1 Hz, 1H), 3.04 (dd, J=15.1, 10.3 Hz, 1H), 2.96 (dd, J=14.1, 7.6 Hz, 1H), 2.86-2.64 (m, 2H), 2.49-2.32 (m, 3H), 2.11-1.99 (m, 2H), 1.92-1.57 (m, 10H), 1.40 (dt, J=15.1, 8.0 Hz, 1H), 0.99 (d, J=6.9 Hz, 3H). 19F NMR (376 MHz, Acetonitrile-d3) 5-77.38. LCMS-ESI+ (m/z): [M+H]+ calcd for C$_{41}$H$_{48}$ClN$_3$O$_6$S: 746.3; found: 746.0.

Example 123

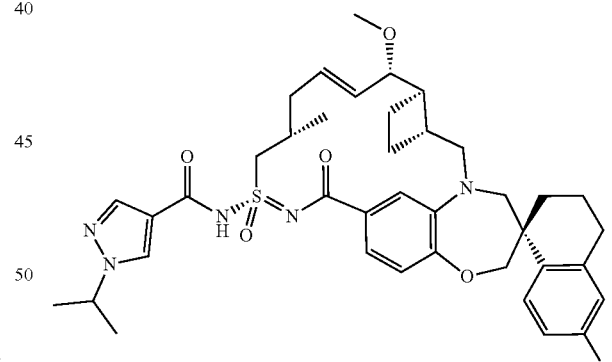

Example 123 was synthesized in the same manner as Example 18 using 1-cyclopropyl-1H-pyrazole-4-carboxylic acid and Example 109. $^1$H NMR (400 MHz, Acetonitrile-d3) δ 8.29 (s, 1H), 7.90 (d, J=0.6 Hz, 1H), 7.60 (d, J=8.5 Hz, 1H), 7.23 (dd, J=8.2, 1.9 Hz, 1H), 7.08 (d, J=2.3 Hz, 1H), 7.04-6.92 (m, 2H), 6.83 (d, J=8.2 Hz, 1H), 6.01 (dt, J=13.7, 6.6 Hz, 1H), 5.60 (dd, J=15.4, 8.4 Hz, 1H), 4.54 (hept, J=6.6 Hz, 1H), 4.12 (dd, J=14.8, 6.3 Hz, 1H), 3.97 (s, 2H), 3.86-3.67 (m, 3H), 3.63 (d, J=14.4 Hz, 1H), 3.35 (d, J=14.4 Hz, 1H), 3.21 (s, 3H), 3.06 (dd, J=15.2, 10.2 Hz, 1H), 2.86-2.65 (m, 2H), 2.59 (d, J=13.3 Hz, 1H), 2.47-2.32 (m, 2H), 2.19 (dq, J=14.5, 7.2 Hz, 2H), 2.08-1.97 (m, 2H), 1.90

(d, J=4.0 Hz, 2H), 1.83-1.63 (m, 3H), 1.46 (t, J=6.8 Hz, 6H), 1.34 (dt, J=13.3, 8.0 Hz, 1H), 1.08 (d, J=6.4 Hz, 3H). $^{19}$F NMR (376 MHz, Acetonitrile-d3) 5-77.37. LCMS-ESI+ (m/z): [M+H]+ calcd for $C_{39}H_{48}ClN_5O_5S$: 734.3; found: 733.8.

Example 124

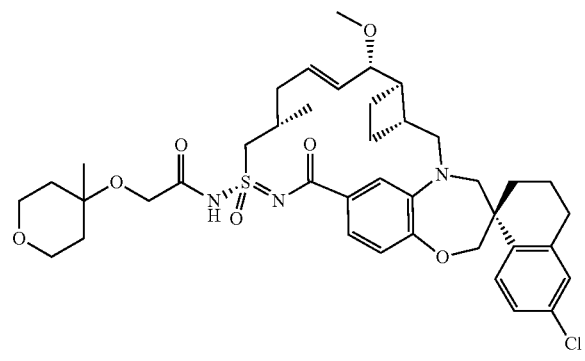 [SMILES: CO[C@H]1/C=C/C[C@H](C)C[S@@](=O)(NC(=O)COC2(C)CCOCC2)=NC(=O)c2ccc3c(c2)N(C[C@@H]2CC[C@H]21)C[C@@]1(CCCc2cc(Cl)ccc21)CO3]

Example 124 was synthesized in the same manner as Example 18 using 2-((4-methyltetrahydro-2H-pyran-4-yl)oxy)acetic acid and Example 109. $^1$H NMR (400 MHz, Acetonitrile-d3) δ 7.72 (d, J=8.5 Hz, 1H), 7.34 (dd, J=8.2, 1.9 Hz, 1H), 7.24 (d, J=2.0 Hz, 1H), 7.19 (dd, J=8.5, 2.4 Hz, 1H), 7.13 (d, J=2.3 Hz, 1H), 6.88 (d, J=8.3 Hz, 1H), 6.04 (dt, J=14.7, 6.7 Hz, 1H), 5.58 (ddd, J=15.5, 7.5, 1.4 Hz, 1H), 4.08 (d, J=1.0 Hz, 2H), 4.05 (d, J=12.1 Hz, 1H), 3.99 (d, J=12.1 Hz, 1H), 3.90 (dd, J=15.0, 5.3 Hz, 1H), 3.81 (d, J=7.1 Hz, 1H), 3.79-3.75 (m, 1H), 3.75-3.66 (m, 3H), 3.61 (dt, J=11.6, 4.2 Hz, 2H), 3.36 (d, J=14.5 Hz, 1H), 3.21 (s, 3H), 3.05 (dd, J=15.1, 10.8 Hz, 1H), 2.85-2.66 (m, 2H), 2.57-2.45 (m, 2H), 2.45-2.34 (m, 1H), 2.33-2.21 (m, 1H), 2.15 (dt, J=14.7, 7.4 Hz, 1H), 2.09-1.99 (m, 1H), 1.92-1.85 (m, 3H), 1.84-1.56 (m, 8H), 1.40 (dt, J=14.9, 7.6 Hz, 1H), 1.25 (s, 3H), 1.07 (d, J=6.9 Hz, 3H). $^{19}$F NMR (376 MHz, acetonitrile-d3) 5-77.38. LCMS-ESI+ (m/z): [M+H]+ calcd for $C_{40}H_{52}ClN_3O_7S$: 754.3; found: 753.9.

Example 125

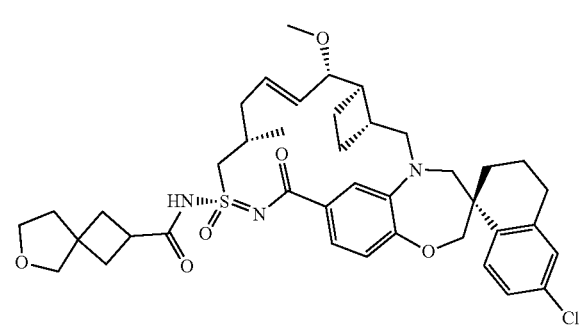 [SMILES: CO[C@H]1/C=C/C[C@H](C)C[S@@](=O)(NC(=O)C2CC3(CCOC3)C2)=NC(=O)c2ccc3c(c2)N(C[C@@H]2CC[C@H]21)C[C@@]1(CCCc2cc(Cl)ccc21)CO3]

Example 125 was synthesized in the same manner as Example 18 using 6-oxaspiro[3.4]octane-2-carboxylic acid and Example 109. $^1$H NMR (400 MHz, Acetonitrile-d$_3$) δ 7.59 (d, J=8.5 Hz, 1H), 7.28 (dd, J=8.2, 1.9 Hz, 1H), 7.09 (d, J=2.3 Hz, 1H), 7.04 (d, J=2.0 Hz, 1H), 6.94 (dd, J=8.6, 2.3 Hz, 1H), 6.80 (d, J=8.3 Hz, 1H), 6.15-5.99 (m, 1H), 5.64

(dd, J=15.5, 8.2 Hz, 1H), 4.01-3.90 (m, 3H), 3.85 (ddd, J=14.7, 4.9, 3.1 Hz, 1H), 3.79-3.64 (m, 6H), 3.61 (d, J=5.6 Hz, 2H), 3.45-3.29 (m, 2H), 3.26 (s, 4H), 3.07 (dd, J=15.2, 10.1 Hz, 1H), 2.75 (dtt, J=43.7, 17.9, 8.8 Hz, 4H), 2.51-2.13 (m, 7H), 2.10-1.99 (m, 3H), 1.95-1.89 (m, 2H), 1.88-1.63 (m, 2H), 1.43-1.23 (m, 2H), 1.10 (dd, J=6.8, 1.1 Hz, 3H). LCMS-ESI+(m/z): calcd for $H+C_{40}H_{50}ClN_3O_6S$: 736.3; found: 736.12.

Example 126

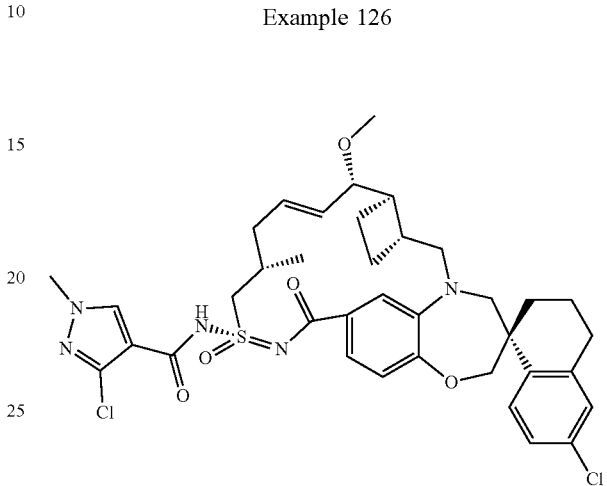

Example 126 was synthesized in the same manner as Example 18 using 3-chloro-1-methyl-1H-pyrazole-4-carboxylic acid and Example 109. $^1$H NMR (400 MHz, methanol-d$_4$) δ 8.23 (s, 1H), 7.72 (d, J=8.3 Hz, 1H), 7.18 (dd, J=8.1, 1.9 Hz, 1H), 7.13 (s, 1H), 7.11 (s, 2H), 7.00-6.87 (m, 2H), 6.04 (dd, J=15.0, 7.3 Hz, 1H), 5.62 (dd, J=15.2, 8.9 Hz, 1H), 4.37 (dd, J=14.8, 6.4 Hz, 1H), 4.07 (s, 2H), 3.89 (s, 3H), 3.88-3.75 (m, 3H), 3.67 (d, J=14.2 Hz, 1H), 3.28 (s, 3H), 3.19-3.00 (m, 1H), 2.91-2.70 (m, 2H), 2.62-2.45 (m, 1H), 2.44-2.07 (m, 4H), 2.05-1.73 (m, 3H), 1.44 (t, J=12.7 Hz, 1H), 1.31 (s, 1H), 1.17 (d, J=6.3 Hz, 3H). LCMS-ESI+ (m/z): calcd for $C_{37}H_{43}C_{12}N_5O_5S$: 739.24; found: 739.99.

Example 127

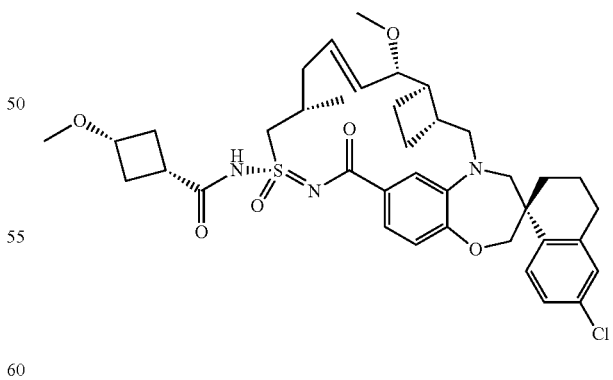

Example 127 was synthesized in the same manner as Example 18 using cis-3-methoxycyclobutanecarboxylic acid and Example 109. $^1$H NMR (400 MHz, methanol-d$_4$) δ 7.75 (d, J=8.5 Hz, 1H), 7.30 (dd, J=8.2, 1.9 Hz, 1H), 7.17 (dd, J=8.5, 2.4 Hz, 1H), 7.10 (dd, J=9.1, 2.1 Hz, 2H), 6.88 (d, J=8.2 Hz, 1H), 6.13 (dt, J=14.4, 6.9 Hz, 1H), 5.61 (dd, J=15.4, 8.5 Hz, 1H), 4.17 (dd, J=14.8, 6.7 Hz, 1H), 4.11-4.00

(m, 2H), 3.96 (dd, J=14.8, 5.3 Hz, 1H), 3.91-3.80 (m, 2H), 3.76 (d, J=8.6 Hz, 1H), 3.68 (d, J=14.2 Hz, 1H), 3.27 (d, J=13.7 Hz, 7H), 3.06 (dd, J=15.1, 9.8 Hz, 1H), 2.88-2.70 (m, 3H), 2.58-2.47 (m, 3H), 2.45 (s, 2H), 2.34-2.19 (m, 3H), 2.14 (dd, J=19.5, 10.9 Hz, 3H), 1.95 (s, 3H), 1.90-1.70 (m, 3H), 1.44 (t, J=12.4 Hz, 1H), 1.13 (d, J=6.8 Hz, 3H). LCMS-ESI+: calc'd for $C_{38}H_{48}ClN_3O_6S$: 710.3 (M+H); found: 710.1 (M+H).

Example 128

6.10-6.01 (m, 1H), 5.70-5.59 (m, 1H), 4.23 (dd, J=14.8, 6.8 Hz, 1H), 4.02 (s, 2H), 3.83 (s, 5H), 3.65 (d, J=14.2 Hz, 1H), 3.37 (s, 1H), 3.30 (s, 4H), 3.08 (dd, J=15.2, 9.9 Hz, 1H), 2.92-2.51 (m, 5H), 2.45 (s, 2H), 2.23 (s, 2H), 2.08 (t, J=11.5 Hz, 2H), 2.02-1.85 (m, 4H), 1.81 (d, J=7.5 Hz, 2H), 1.40 (t, J=12.9 Hz, 1H), 1.19-1.12 (m, 3H), 1.03 (q, J=6.3 Hz, 1H). LCMS-ESI+: calc'd for $C_{40}H_{49}ClN_6O_5S$: 761.3 (M+H); found: 760.8 (M+H).

Example 130

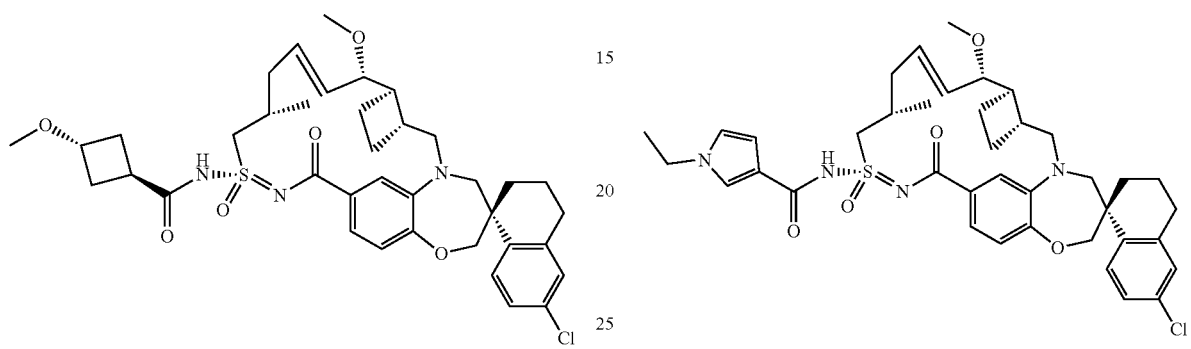

Example 128 was synthesized in the same manner as Example 18 using trans-3-methoxycyclobutanecarboxylic acid and Example 109. $^1$H NMR (400 MHz, methanol-d$_4$) δ 7.76 (d, J=8.5 Hz, 1H), 7.31 (dd, J=8.1, 1.9 Hz, 1H), 7.18 (dd, J=8.5, 2.4 Hz, 1H), 7.11 (dd, J=4.1, 2.2 Hz, 2H), 6.88 (d, J=8.2 Hz, 1H), 6.14 (dt, J=14.5, 6.9 Hz, 1H), 5.62 (dd, J=15.4, 8.4 Hz, 1H), 4.20-4.08 (m, 2H), 4.06 (dd, J=7.6, 3.7 Hz, 2H), 4.03-3.93 (m, 2H), 3.85 (d, J=15.0 Hz, 1H), 3.77 (dd, J=8.5, 2.8 Hz, 1H), 3.69 (d, J=14.2 Hz, 1H), 3.36 (s, 1H), 3.30 (s, 3H), 3.26 (s, 3H), 3.21-3.12 (m, 1H), 3.07 (dd, J=15.2, 9.8 Hz, 1H), 2.89-2.70 (m, 2H), 2.57 (qd, J=8.1, 4.1 Hz, 2H), 2.46 (s, 2H), 2.36-2.17 (m, 3H), 2.12 (d, J=13.9 Hz, 2H), 2.02-1.67 (m, 6H), 1.45 (t, J=12.5 Hz, 1H), 1.14 (d, J=6.9 Hz, 3H). LCMS-ESI+: calc'd for $C_{38}H_{48}ClN_3O_6S$: 710.3 (M+H); found: 710.1 (M+H).

Example 129

Example 130 was synthesized in the same manner as Example 18 using 1-ethylpyrrole-3-carboxylic acid and Example 109. 1H NMR (400 MHz, methanol-d4) δ 7.74 (d, J=8.4 Hz, 1H), 7.62 (t, J=1.9 Hz, 1H), 7.33 (d, J=8.5 Hz, 1H), 7.18-7.08 (m, 3H), 6.90 (d, J=8.2 Hz, 1H), 6.81 (dd, J=3.0, 2.1 Hz, 1H), 6.64 (dd, J=2.9, 1.8 Hz, 1H), 6.12 (dt, J=14.4, 6.6 Hz, 1H), 5.62 (dd, J=15.4, 8.5 Hz, 1H), 4.24 (dd, J=14.6, 6.3 Hz, 1H), 4.12-3.98 (m, 4H), 3.86 (d, J=15.0 Hz, 1H), 3.82-3.75 (m, 1H), 3.69 (d, J=14.3 Hz, 1H), 3.38 (s, 1H), 3.29 (s, 3H), 3.08 (dd, J=15.1, 10.0 Hz, 1H), 2.89-2.70 (m, 2H), 2.57 (dd, J=12.9, 6.5 Hz, 1H), 2.46 (s, 2H), 2.32-2.15 (m, 2H), 2.12 (d, J=13.7 Hz, 1H), 1.96 (d, J=6.2 Hz, 3H), 1.88-1.69 (m, 3H), 1.46 (t, J=7.3 Hz, 4H), 1.31 (s, 1H), 1.14 (d, J=6.5 Hz, 3H). LCMS-ESI+: calc'd for $C_{39}H_{47}ClN_4O_5S$: 719.3 (M+H); found: 718.8 (M+H).

Example 131

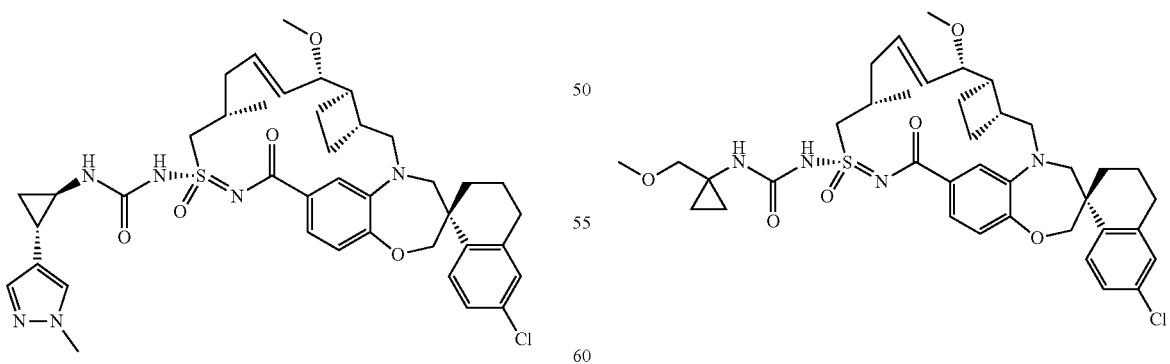

Example 129 was synthesized in the same manner as Example 75 using Example 109 and trans-rac-(1R,2S)-2-(1-methylpyrazol-4-yl)cyclopropanamine hydrogen chloride and triethylamine. $^1$H NMR (400 MHz, methanol-d$_4$) δ 7.67 (d, J=8.6 Hz, 1H), 7.42 (s, 1H), 7.34 (s, 1H), 7.22 (d, J=8.2 Hz, 1H), 7.09 (s, 1H), 6.98 (s, 2H), 6.88 (d, J=8.2 Hz, 1H), Example 131 was synthesized in the same manner as Example 75 using Example 109 and 1-(methoxymethyl) cyclopropanamine. 1H NMR (400 MHz, methanol-d4) δ 7.75 (d, J=8.5 Hz, 1H), 7.25-7.14 (m, 2H), 7.11 (d, J=2.3 Hz, 1H), 7.01 (s, 1H), 6.90 (d, J=8.2 Hz, 1H), 6.03 (dd, J=14.7, 7.4 Hz, 1H), 5.59 (dd, J=15.3, 8.9 Hz, 1H), 4.31-4.22 (m, 1H), 4.13-4.00 (m, 2H), 3.90-3.73 (m, 3H), 3.68 (d, J=14.2

Hz, 1H), 3.46 (d, J=8.2 Hz, 1H), 3.39 (s, 3H), 3.27 (s, 4H), 3.07 (dd, J=15.3, 10.2 Hz, 1H), 2.92-2.70 (m, 3H), 2.48 (d, J=7.6 Hz, 2H), 2.39 (d, J=9.2 Hz, 1H), 2.19 (dt, J=14.1, 7.0 Hz, 1H), 2.12 (d, J=13.1 Hz, 2H), 2.01-1.87 (m, 3H), 1.77 (tq, J=17.6, 9.3, 8.8 Hz, 3H), 1.44 (t, J=11.6 Hz, 1H), 1.14 (d, J=6.6 Hz, 3H), 0.83 (d, J=12.6 Hz, 3H). LCMS-ESI+: calc'd for $C_{38}H_{49}ClN_4O_6S$: 725.3 (M+H); found: 724.8 (M+H).

Example 132

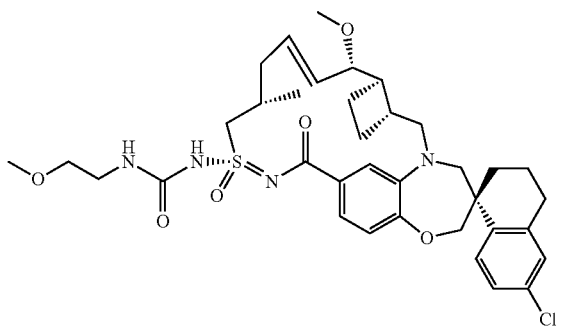 [SMILES: COCCNC(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Example 132 was synthesized in the same manner as Example 75 using Example 109 and 2-methoxyethan-1-amine. 1H NMR (400 MHz, methanol-d4) δ 7.75 (d, J=8.6 Hz, 1H), 7.23 (d, J=8.3 Hz, 1H), 7.18 (dd, J=8.5, 2.4 Hz, 1H), 7.11 (d, J=2.3 Hz, 1H), 7.02 (s, 1H), 6.90 (d, J=8.2 Hz, 1H), 6.06 (dd, J=15.0, 6.9 Hz, 1H), 5.58 (dd, J=15.3, 8.9 Hz, 1H), 4.27 (d, J=14.7, 6.5 Hz, 1H), 4.14-3.96 (m, 2H), 3.91-3.62 (m, 4H), 3.49 (d, J=5.3 Hz, 2H), 3.38 (s, 3H), 3.27 (s, 3H), 3.07 (dd, J=15.2, 10.2 Hz, 1H), 2.91-2.66 (m, 3H), 2.57-2.28 (m, 3H), 2.28-2.04 (m, 3H), 2.02-1.87 (m, 3H), 1.87-1.66 (m, 3H), 1.54-1.36 (m, 2H), 1.31 (s, 1H), 1.13 (d, J=6.6 Hz, 3H). LCMS-ESI+: calc'd for $C_{36}H_{47}ClN_4O_6S$: 699.3 (M+H); found: 698.6 (M+H).

Example 133

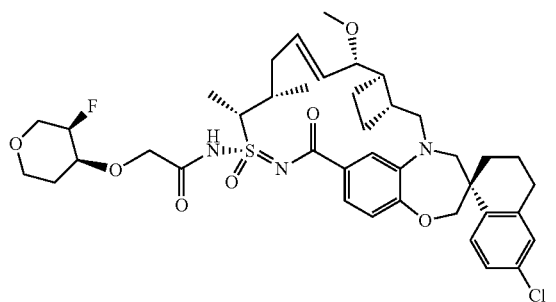 [SMILES: CO[C@H]1/C=C/C[C@H](C)[C@@H](C)[S@@](=O)(NC(=O)CO[C@H]2CCOC[C@H]2F)=NC(=O)c2ccc3c(c2)N(C[C@@H]2CC[C@H]21)C[C@@]1(CCCc2cc(Cl)ccc21)CO3]

Example 133 was synthesized in the same manner as Example 18 using 2-(((3R,4S)-3-fluorotetrahydro-2H-pyran-4-yl)oxy)acetic acid and Example 110. 1H NMR (400 MHz, methanol-d4) δ 7.73 (d, J=8.8 Hz, 1H), 7.37 (dd, J=8.2, 1.8 Hz, 1H), 7.17 (dd, J=8.4, 2.4 Hz, 1H), 7.11 (d, J=2.0 Hz, 1H), 7.08 (d, J=2.0 Hz, 1H), 6.80 (d, J=8.4 Hz, 1H), 5.56 (dd, J=15.2, 8.8 Hz, 1H), 6.12-6.05 (m, 1H), 4.18-4.11 (m, 2H), 4.08-3.83 (m, 4H), 3.81-3.72 (m, 2H), 3.68 (s, 2H), 3.61 (d, J=14.4 Hz, 1H), 3.55-3.40 (m, 3H), 3.37-3.31 (m, 2H), 3.26 (s, 3H), 3.16-3.08 (m, 1H), 2.88- 2.69 (m, 3H), 2.51-1.61 (m, 12H), 1.54-1.46 (m, 1H), 1.43 (d, J=6.8 Hz, 3H), 1.13 (d, J=6.8 Hz, 3H). LCMS-ESI+: calc'd for $C_{40}H_{51}ClFN_3O_7S$: 772.3 (M+H); found: 772.2 (M+H).

Example 134

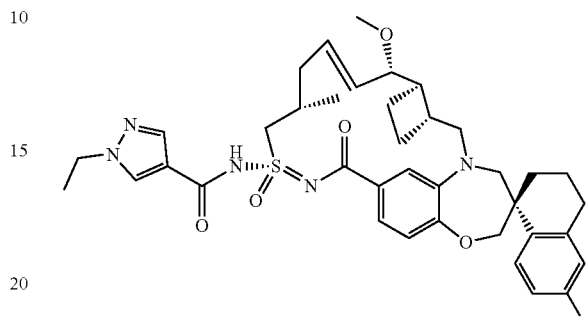

Example 134 was synthesized in the same manner as Example 18 using 1-ethyl-1H-pyrazole-4-carboxylic acid and Example 109. 1H NMR (400 MHz, methanol-d4) δ 8.29 (s, 1H), 7.96 (s, 1H), 7.71 (d, J=9.0 Hz, 1H), 7.23 (dd, J=8.2, 1.8 Hz, 1H), 7.14-7.07 (m, 2H), 6.99 (d, J=1.9 Hz, 1H), 6.91 (d, J=8.2 Hz, 1H), 6.07 (dt, J=14.3, 6.7 Hz, 1H), 5.62 (dd, J=15.3, 8.8 Hz, 1H), 4.34 (dd, J=14.8, 6.5 Hz, 1H), 4.24 (q, J=7.3 Hz, 2H), 4.06 (d, J=1.5 Hz, 2H), 3.92 (dd, J=14.7, 5.2 Hz, 1H), 3.84 (d, J=15.1 Hz, 1H), 3.78 (dd, J=8.8, 3.3 Hz, 1H), 3.67 (d, J=14.3 Hz, 1H), 3.36 (d, J=2.5 Hz, 1H), 3.29 (s, 3H), 3.09 (dd, J=15.2, 9.9 Hz, 1H), 2.93-2.65 (m, 3H), 2.56 (d, J=10.0 Hz, 1H), 2.43 (dd, J=17.5, 8.9 Hz, 2H), 2.25 (dt, J=26.4, 9.7 Hz, 2H), 2.11 (d, J=13.5 Hz, 1H), 1.98 (dd, J=16.3, 5.2 Hz, 2H), 1.82 (dt, J=23.0, 9.3 Hz, 4H), 1.50 (t, J=7.3 Hz, 3H), 1.16 (d, J=6.6 Hz, 3H). LCMS-ESI+: calc'd for $C_{38}H_{46}ClN_5O_5S$: 720.3 (M+H); found: 719.0 (M+H).

Example 135

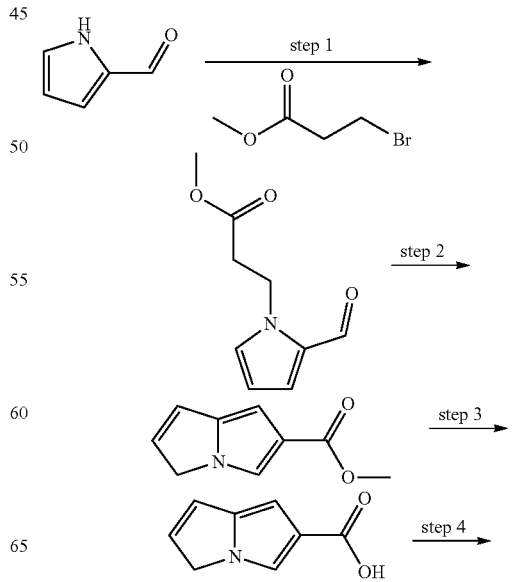

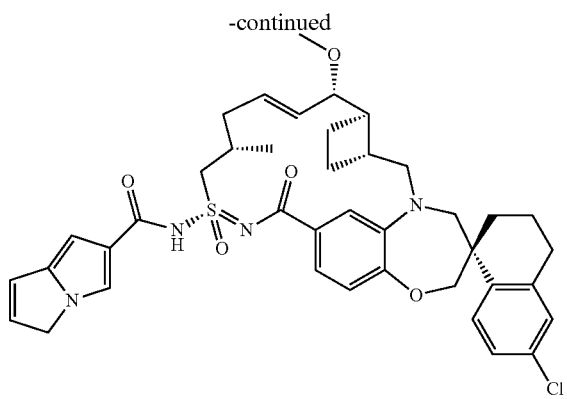

Step 1: Preparation of methyl 3-(2-formyl-1H-pyrrol-1-yl)propanoate

A solution of pyrrolcarboxaldehyde (5.0 g, 0.053 mol) in dry DMF (10 mL) was added dropwise, under nitrogen atmosphere, to a stirred suspension of 60% sodium hydride (oil dispersion) (2.56 g, 0.063 mol) in dry DMF (40 mL). The temperature of the mixture was maintained at 0° C. After addition was completed, stirring was continued at the same temperature for 30 min. Then a solution of methyl 3-bromopropanoate (13.17 g, 0.079 mol) was added dropwise and the temperature was allowed to rise to room temperature. The reaction mixture was stirred at this temperature for 48 h. Then water was added and the mixture was extracted with dichloromethane. The organic phase was dried over anhydrous magnesium sulfate and the solvent removed under reduced pressure and purified by normal phase chromatography (silica gel column, 0-80% EtOAc/Hexanes) to give methyl 3-(2-formyl-1H-pyrrol-1-yl)propanoate.

Step 2: Preparation of methyl 3H-pyrrolizine-6-carboxylate

A solution of methyl 3-(2-formyl-1H-pyrrol-1-yl)propanoate (2.0 g, 11.04 mmol) in MeOH (20 mL) was added NaOMe (2.62 g, 12.14 mmol). The reaction mixture was stirred at 45° C. for 48 h. Then water was added and the mixture was extracted with dichloromethane. The organic phase was dried over anhydrous magnesium sulfate and the solvent was removed under reduced pressure and purified by normal phase chromatography (silica gel column, 0-80% EtOAc/hexanes) to give intermediate methyl 3H-pyrrolizine-6-carboxylate. $^1$H NMR (400 MHz, chloroform-d) δ 7.58 (p, J=1.2 Hz, 1H), 6.60 (dtd, J=6.1, 2.2, 0.7 Hz, 1H), 6.36 (q, J=0.9 Hz, 1H), 6.31-6.21 (m, 1H), 4.50 (tt, J=2.2, 1.0 Hz, 2H), 3.83 (s, 3H).

Step 3: Preparation of 3H-pyrrolizine-6-carboxylic Acid

To a stirred solution of methyl 3H-pyrrolizine-6-carboxylate (0.3 g, 1.8 mmol) in methanol (6 mL) was added 2N of LiOH (1 mL), and the reaction mixture was stirred at rt for 3 h. To the reaction mixture was added 2N HCl (1 mL) and concentrated. Water was added and the mixture was extracted with dichloromethane. The organic phase was dried over anhydrous magnesium sulfate and the solvent was removed under reduced pressure to give 3H-pyrrolizine-6-carboxylic acid.

Step 4

Example 135 was synthesized in the same manner as Example 18 using 3H-pyrrolizine-6-carboxylic acid and Example 109. 1H NMR (400 MHz, chloroform-d) δ 7.86-7.61 (m, 2H), 7.40 (d, J=8.3 Hz, 1H), 7.20 (d, J=6.6 Hz, 2H), 7.10 (d, J=2.3 Hz, 1H), 6.96 (d, J=8.2 Hz, 1H), 6.63 (d, J=6.1 Hz, 1H), 6.44 (s, 1H), 6.34 (d, J=6.1 Hz, 1H), 6.04-5.86 (m, 1H), 5.62 (dd, J=15.7, 7.7 Hz, 1H), 4.56 (s, 2H), 4.20-3.94 (m, 3H), 3.82 (dd, J=42.9, 13.7 Hz, 3H), 3.58-3.39 (m, 1H), 3.29 (s, 3H), 3.11-2.88 (m, 2H), 2.88-2.69 (m, 2H), 2.46 (t, J=30.6 Hz, 4H), 2.16-1.66 (m, 7H), 1.28 (s, 2H), 1.13 (d, J=6.8 Hz, 3H). LCMS-ESI+ (m/z): [M+H]+ calcd for $C_{40}H_{45}ClN_4O_5S$: 729.26; found: 729.30.

Example 136

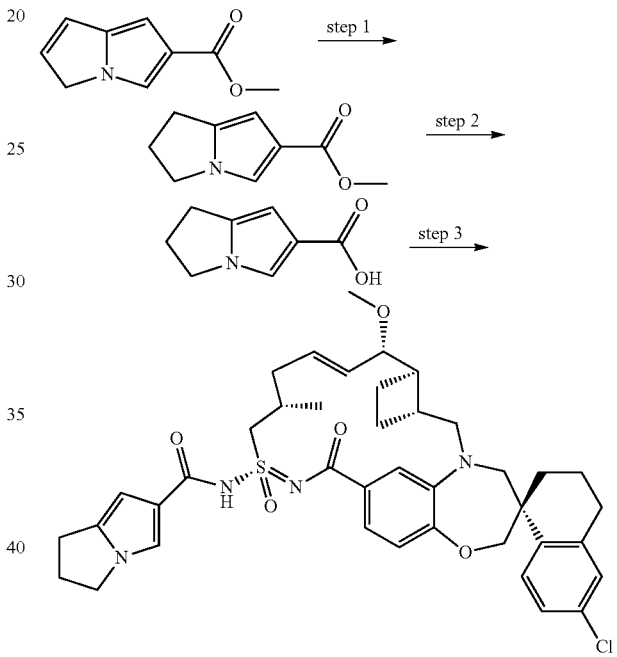

Step 1: Preparation of methyl 2,3-dihydro-1H-pyrrolizine-6-carboxylate methyl 3H-pyrrolizine-6-carboxylate (300 mg, 1.85 mmol) and rhodium (5% on alumina) were mixed in ethanol (10 mL). The mixture was degassed, hydrogen gas was injected, and then the mixture was stirred for 5 h. The mixture was filtered through silica and concentrated. Then water was added and the mixture was extracted with dichloromethane. The organic phase was dried over anhydrous magnesium sulfate and the solvent was removed under reduced pressure to yield methyl 2,3-dihydro-1H-pyrrolizine-6-carboxylate. $^1$H NMR (400 MHz, chloroform-d) δ 7.21 (d, J=1.4 Hz, 1H), 6.22 (q, J=1.2 Hz, 1H), 3.99-3.86 (m, 2H), 3.78 (s, 3H), 2.80 (ddd, J=7.7, 6.7, 1.2 Hz, 2H), 2.48 (tt, J=8.0, 6.8 Hz, 2H).

Step 2

2,3-dihydro-1H-pyrrolizine-6-carboxylic acid was synthesized in the same manner as Example 133 (step 3) using methyl 2,3-dihydro-1H-pyrrolizine-6-carboxylate instead of methyl 3H-pyrrolizine-6-carboxylate.

Step 3

Example 136 was synthesized in the same manner as Example 18 using 2,3-dihydro-1H-pyrrolizine-6-carboxylic acid and Example 109. 1H NMR (400 MHz, chloroform-d) δ 7.76 (d, J=8.5 Hz, 1H), 7.48-7.37 (m, 2H), 7.25-7.15 (m, 2H), 7.10 (d, J=2.3 Hz, 1H), 6.95 (d, J=8.3 Hz, 1H), 6.35 (d, J=1.4 Hz, 1H), 6.05-5.89 (m, 1H), 5.62 (dd, J=15.6, 7.5 Hz, 1H), 4.18-3.69 (m, 7H), 3.30 (s, 4H), 3.08-2.94 (m, 1H), 2.92-2.74 (m, 3H), 2.61-2.32 (m, 5H), 2.21-1.62 (m, 13H), 1.41 (t, J=12.9 Hz, 1H), 1.13 (d, J=6.8 Hz, 2H). LCMS-ESI+(m/z): [M+H]+ calcd for $C_{40}H_{47}ClN_4O_5S$: 731.30; found: 731.22.

Example 137

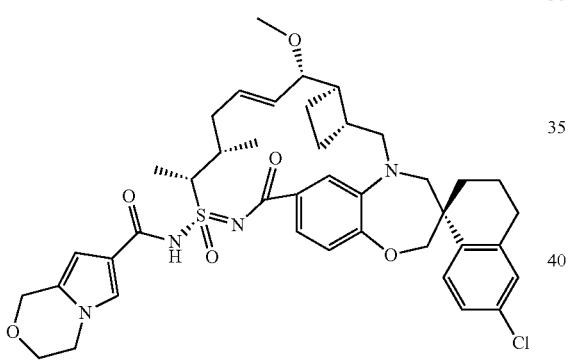

Example 137 was synthesized in the same manner as Example 18 using 3,4-dihydro-1H-pyrrolo[2,1-c][1,4]oxazine-7-carboxylic acid and Example 110. 1H NMR (400 MHz, chloroform-d) δ 7.74 (d, J=8.6 Hz, 1H), 7.33 (d, J=1.7 Hz, 1H), 7.21 (dd, J=8.4, 2.5 Hz, 2H), 7.11 (d, J=2.3 Hz, 1H), 7.04 (s, 1H), 6.98 (d, J=8.2 Hz, 1H), 6.35 (d, J=1.6 Hz, 1H), 5.99 (d, J=11.2 Hz, 1H), 5.52 (dd, J=15.2, 8.9 Hz, 1H), 4.81 (dd, J=3.3, 1.1 Hz, 2H), 4.57 (s, 1H), 4.18-3.96 (m, 3H), 3.92-3.79 (m, 2H), 3.76-3.65 (m, 2H), 3.26 (s, 3H), 3.02 (dd, J=15.2, 9.9 Hz, 1H), 2.87-2.70 (m, 3H), 2.42 (dt, J=25.8, 9.3 Hz, 3H), 2.29-1.93 (m, 5H), 1.82 (q, J=9.2 Hz, 3H), 1.72-1.55 (m, 4H), 1.41 (t, J=12.8 Hz, 1H), 1.28 (s, 2H), 1.01 (d, J=6.2 Hz, 3H). LCMS-ESI+ (m/z): [M+H]+ calcd for $C_{41}H_{49}ClN_4O_6S$: 761.29; found: 761.22.

Example 138

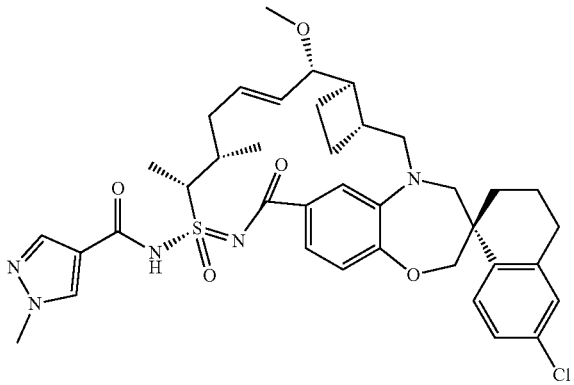 [SMILES: CO[C@H]1/C=C/C[C@H](C)[C@@H](C)[S@@](=O)(NC(=O)c2cnn(C)c2)=NC(=O)c2ccc3c(c2)N(C[C@@H]2CC[C@H]21)C[C@@]1(CCCc2cc(Cl)ccc21)CO3]

Example 138 was synthesized in the same manner as Example 18 using 1-methyl-1H-pyrazole-4-carboxylic acid and Example 110. 1H NMR (400 MHz, chloroform-d) δ 8.01 (d, J=0.7 Hz, 1H), 7.93 (s, 1H), 7.73 (d, J=8.5 Hz, 1H), 7.21 (dd, J=8.5, 2.3 Hz, 1H), 7.18-7.07 (m, 2H), 7.06-6.89 (m, 2H), 5.96 (dd, J=15.1, 8.6 Hz, 1H), 5.53 (dd, J=15.2, 9.0 Hz, 1H), 4.67 (d, J=7.3 Hz, 2H), 4.12 (s, 2H), 3.99 (s, 2H), 3.86 (d, J=15.0 Hz, 2H), 3.76-3.61 (m, 2H), 3.26 (s, 3H), 3.02 (dd, J=15.2, 10.2 Hz, 2H), 2.79 (d, J=15.3 Hz, 3H), 2.41 (dt, J=45.0, 9.2 Hz, 3H), 2.27-1.92 (m, 5H), 1.84 (t, J=8.9 Hz, 2H), 1.70-1.58 (m, 3H), 1.41 (t, J=12.4 Hz, 2H), 0.96 (d, J=6.2 Hz, 2H). LCMS-ESI+ (m/z): [M+H]+ calcd for $C_{38}H_{46}ClN_5O_5S$: 720.29; found: 720.23.

Example 139

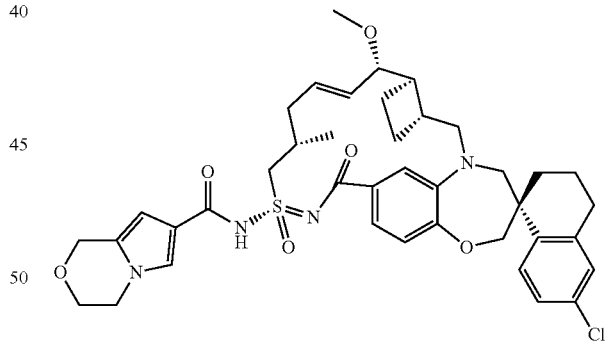

Example 139 was synthesized in the same manner as Example 18 using 3,4-dihydro-1H-pyrrolo[2,1-c][1,4]oxazine-7-carboxylic acid and Example 109. 1H NMR (400 MHz, chloroform-d) δ 7.74 (d, J=8.5 Hz, 1H), 7.39 (dd, J=15.0, 1.8 Hz, 2H), 7.18 (dd, J=8.4, 2.3 Hz, 2H), 7.10 (d, J=2.3 Hz, 1H), 6.95 (d, J=8.3 Hz, 1H), 6.37 (q, J=1.2 Hz, 1H), 5.99 (dt, J=13.7, 6.5 Hz, 1H), 5.62 (dd, J=15.6, 7.7 Hz, 1H), 4.84 (d, J=1.1 Hz, 2H), 4.18-3.95 (m, 6H), 3.94-3.69 (m, 4H), 3.31 (s, 4H), 3.09-2.95 (m, 2H), 2.90-2.68 (m, 2H), 2.59-2.25 (m, 4H), 2.21-2.03 (m, 2H), 2.02-1.82 (m, 3H), 1.81-1.60 (m, 3H), 1.41 (t, J=12.7 Hz, 2H), 1.13 (d, J=6.8 Hz, 3H). LCMS-ESI+ (m/z): [M+H]+ calcd for $C_{40}H_{47}ClN_4O_6S$: 747.29; found: 747.04.

Example 140

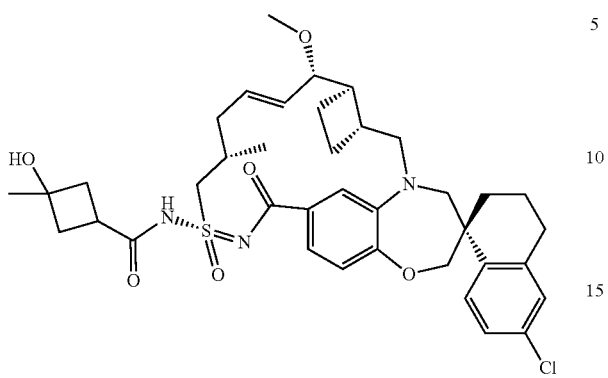

The mixture of 3-hydroxy-3-methyl-cyclobutanecarboxylic acid (2.61 mg, 0.02 mmol) and Example 109 (8.0 mg, 0.0134 mmol) in DCM (1.0 mL) was cooled to 0° C. 1-(3-dimethylaminopropyl)-3-ethylcarbodiimide HCl (5.11 mg, 0.0268 mmol) was added followed by DMAP (3.27 mg, 0.0267 mmol). The reaction was removed from the cooling bath and stirred at ambient for overnight. The reaction was then concentrated by removing DCM, diluted with DMF (1 mL), filtered, and purified by Gilson reverse phase prep HPLC (60-100% ACN/H$_2$O with 0.1% TFA) to give Example 140. 1H NMR (400 MHz, methanol-d4) δ 7.76-7.67 (m, 1H), 7.31 (dd, J=8.2, 1.9 Hz, 1H), 7.14-7.04 (m, 3H), 6.86 (d, J=8.2 Hz, 1H), 6.14 (dt, J=14.6, 7.0 Hz, 1H), 5.63 (dd, J=15.4, 8.4 Hz, 1H), 4.14 (dd, J=14.8, 6.9 Hz, 1H), 4.08-3.93 (m, 3H), 3.88-3.73 (m, 2H), 3.67 (d, J=14.3 Hz, 1H), 3.30 (s, 3H), 3.12-2.98 (m, 1H), 2.92-2.70 (m, 3H), 2.59-2.20 (m, 8H), 2.16-2.03 (m, 2H), 2.03-1.71 (m, 7H), 1.38 (s, 4H), 1.14 (d, J=6.9 Hz, 3H). LCMS-ESI+ (m/z): calcd [M+H]+ calcd for C$_{38}$H$_{48}$ClN$_3$O$_6$S: 710.3; found: 710.1.

Example 141

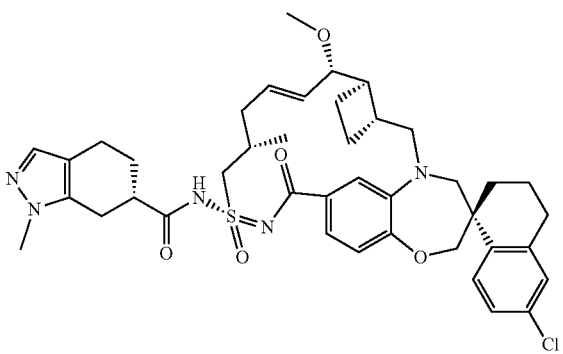 [SMILES: CO[C@H]1/C=C/C[C@H](C)C[S@@](=O)(NC(=O)[C@H]2CCc3cnn(C)c3C2)=NC(=O)c2ccc3c(c2)N(C[C@@H]2CC[C@H]21)C[C@@]1(CCCc2cc(Cl)ccc21)CO3]

Example 141 was synthesized in the same manner as Example 140 using racemic 1-methyl-4,5,6,7-tetrahydroindazole-6-carboxylic acid instead of 3-hydroxy-3-methyl-cyclobutanecarboxylic acid. The later eluted peak from reverse phase prep HPLC was arbitrarily assigned as "S", no actual stereochemistry was determined. 1H NMR (400 MHz, methanol-d4) δ 7.75 (d, J=8.5 Hz, 1H), 7.40 (s, 1H), 7.29 (dd, J=8.2, 1.8 Hz, 1H), 7.16 (dd, J=8.5, 2.4 Hz, 1H), 7.10 (dd, J=8.5, 2.1 Hz, 2H), 6.90 (d, J=8.2 Hz, 1H), 6.14 (dt, J=14.6, 7.0 Hz, 1H), 5.64 (dd, J=15.4, 8.3 Hz, 1H), 4.15 (dd, J=14.8, 7.0 Hz, 1H), 4.11-4.02 (m, 2H), 3.96 (dd, J=14.8, 4.9 Hz, 1H), 3.88-3.64 (m, 6H), 3.30 (s, 3H), 3.13-3.02 (m, 1H), 2.99-2.66 (m, 6H), 2.65-2.29 (m, 5H), 2.26-2.06 (m, 3H), 2.01-1.69 (m, 8H), 1.51-1.38 (m, 1H), 1.18 (d, J=6.9 Hz, 3H). LCMS-ESI+ (m/z): calcd [M+H] C$_{41}$H$_{50}$ClN$_5$O$_5$S: 760.3; found: 760.1.

Example 142

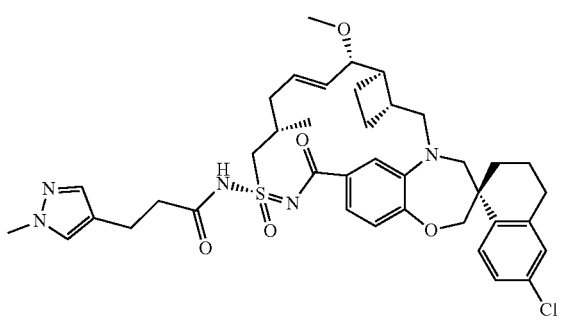 [SMILES: CO[C@H]1/C=C/C[C@H](C)C[S@@](=O)(NC(=O)CCc2cnn(C)c2)=NC(=O)c2ccc3c(c2)N(C[C@@H]2CC[C@H]21)C[C@@]1(CCCc2cc(Cl)ccc21)CO3]

Example 142 was synthesized in the same manner as Example 140 using 3-(1-methylpyrazol-4-yl)propanoic acid instead of 3-hydroxy-3-methyl-cyclobutanecarboxylic acid in DMF (1.0 mL) was also added as co-solvent for this reaction). 1H NMR (400 MHz, methanol-d4) δ 7.75-7.69 (m, 1H), 7.51 (s, 1H), 7.45-7.41 (m, 1H), 7.31 (dd, J=8.3, 1.9 Hz, 1H), 7.14-7.05 (m, 3H), 6.86 (d, J=8.2 Hz, 1H), 6.18-6.06 (m, 1H), 5.62 (dd, J=15.5, 8.4 Hz, 1H), 4.14-3.97 (m, 3H), 3.92 (dd, J=14.8, 4.8 Hz, 1H), 3.87-3.73 (m, 5H), 3.67 (d, J=14.2 Hz, 1H), 3.30 (s, 3H), 3.11-3.00 (m, 1H), 2.90-2.74 (m, 4H), 2.74-2.66 (m, 2H), 2.57-2.38 (m, 3H), 2.31-2.19 (m, 1H), 2.14-2.05 (m, 1H), 2.03-1.71 (m, 8H), 1.47-1.36 (m, 1H), 1.07 (d, J=6.9 Hz, 3H). LCMS-ESI+ (m/z): [M+H]+ calcd for C$_{39}$H$_{48}$ClN$_5$O$_5$S 734.35; found: 734.07.

Example 143

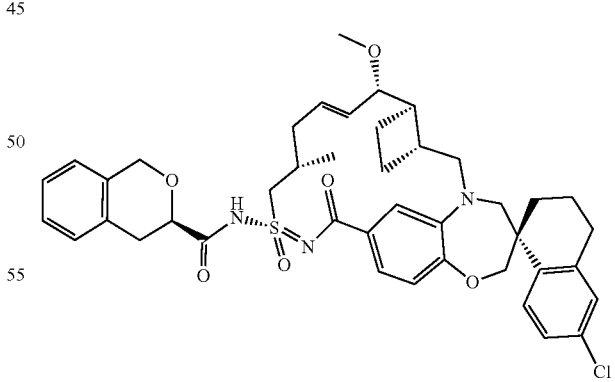

Example 143 was synthesized in the same manner as Example 140 using isochromane-3-carboxylic acid instead of 3-hydroxy-3-methyl-cyclobutanecarboxylic acid. The earlier eluted peak from reverse phase prep HPLC was arbitrarily assigned as "R", no actual stereochemistry was determined. 1H NMR (400 MHz, methanol-d4) δ 7.76 (d, J=8.5 Hz, 1H), 7.28 (dd, J=8.2, 1.9 Hz, 1H), 7.25-7.15 (m, 4H), 7.14-7.05 (m, 3H), 6.92 (d, J=8.2 Hz, 1H), 6.10 (dt, J=14.5, 6.9 Hz, 1H), 5.64 (dd, J=15.4, 8.3 Hz, 1H), 5.06-4.89 (m, 2H) 4.44 (dd, J=9.7, 4.7 Hz, 1H), 4.22-4.01 (m, 3H), 3.95 (dd, J=14.9, 5.0 Hz, 1H), 3.85 (d, J=14.9 Hz, 1H), 3.77 (dd, J=8.4, 3.0 Hz, 1H), 3.70 (d, J=14.3 Hz, 1H), 3.30 (s, 3H), 3.18-3.02 (m, 3H), 2.90-2.75 (m, 2H), 2.56-2.40 (m, 3H), 2.34-2.22 (m, 1H), 2.22-2.07 (m, 2H), 2.00-1.71 (m, 7H), 1.51-1.39 (m, 1H), 1.15 (d, J=6.8 Hz, 3H). LCMS-ESI+ (m/z): [M+H]+ calcd for $C_{42}H_{48}ClN_3O_6S$: 758.37; found: 758.07.

Example 144

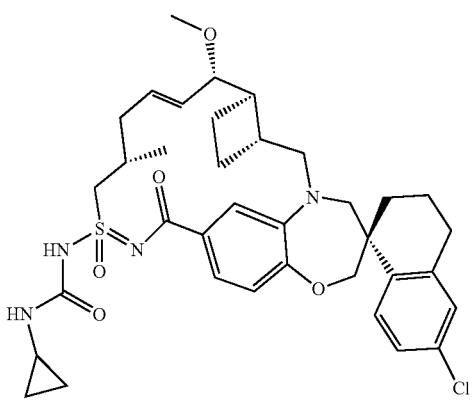 [SMILES: CO[C@H]1/C=C/C[C@H](C)CS(=O)(NC(=O)NC2CC2)=NC(=O)c2ccc3c(c2)N(C[C@@H]2CC[C@H]21)C[C@@]1(CCCc2cc(Cl)ccc21)CO3]

Example 109 (350 mg, 0.59 mmol) was dissolved in DCM (5.9 mL) at rt, triethylamine (0.24 g, 2.34 mmol) was added followed by isocyanatocyclopropane (107 mg, 1.3 mmol) in DCM (1 mL). The resulting mixture was stirred at rt for 2 hrs before the reaction was concentrated by removing DCM, the resulting residue was redissolved in EtOAc (30 mL), and washed with 1N HCl (15 mL). The aqueous layer was extracted with EtOAc (2×10 mL). The combined organic layer was washed with saturated $NaHCO_3$ (15 mL), brine (15 mL), dried over sodium sulfate, filtered, concentrated, redissolved in DCM, mixed with silica gel, concentrated to dryness, and purified by combiflash twice (12 g silica gel, 0-10% DCM/2.0 N $NH_3$ in MeOH, dry loading). Desired fractions were combined and concentrated to give Example 144. $^1$H NMR (400 MHz, acetone-$d_6$) δ 7.75 (d, J=8.5 Hz, 1H), 7.32-7.05 (m, 4H), 6.84 (d, J=8.2 Hz, 1H), 6.14 (dt, J=14.2, 6.6 Hz, 1H), 5.56 (dd, J=15.4, 8.4 Hz, 1H), 4.04 (q, J=11.9 Hz, 3H), 3.85 (d, J=15.1 Hz, 1H), 3.71 (d, J=14.8 Hz, 2H), 3.39 (d, J=14.2 Hz, 1H), 3.23 (s, 3H), 3.12 (dd, J=15.0, 9.8 Hz, 1H), 2.89-2.71 (m, 3H), 2.69-2.60 (m, 1H), 2.58-2.40 (m, 3H), 2.20-2.10 (m, 3H), 2.00-1.89 (m, 3H), 1.83-1.69 (m, 3H), 1.51-1.34 (m, 1H), 1.08 (d, J=6.3 Hz, 3H), 0.66 (d, J=6.9 Hz, 2H), 0.56-0.48 (m, 2H). LCMS-ESI+ (m/z): [M+H]+ calcd for $C_{36}H_{45}ClN_4O_5S$: 681.28; found: 680.81.

Example 145

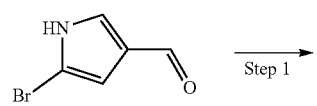

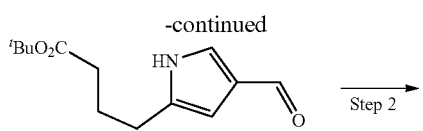

145-1

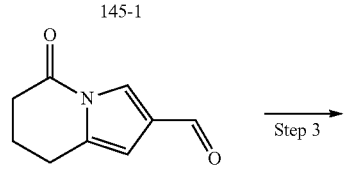

145-2

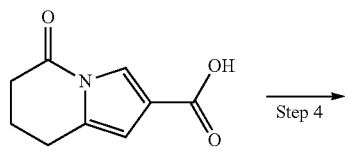

145-3

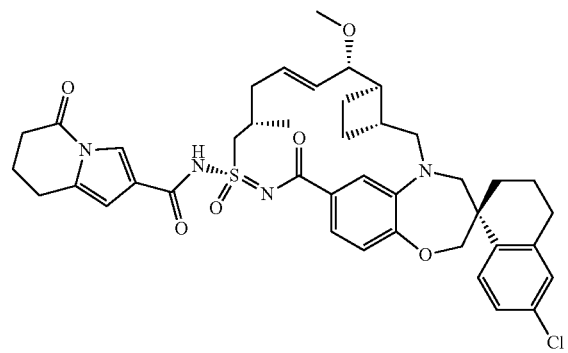

Example 145

Step 1 tert-Butyl but-3-enoate (1.40 mL, 5.75 mmol) was added over 2 min via syringe to a stirred 9-borabicyclo[3.3.1]nonane solution (0.5 M in tetrahydrofuran, 17.2 mL, 9 mmol) at 0° C., and the resulting mixture was warmed to room temperature. After 4.5 h, 5-bromo-1H-pyrrole-3-carbaldehyde (1.00 g, 5.75 mmol), [1,1′-bis(diphenylphosphino)ferrocene]dichloropalladium(II) (210 mg, 0.287 mmol), potassium carbonate (1.59 g, 11.5 mmol), and N,N-dimethylformamide (30 mL) were added sequentially, and the resulting mixture was heated to 75° C. After 50 min, the reaction mixture was heated to 100° C. After 23 h, the resulting mixture was cooled to room temperature, and diethyl ether (400 mL) and saturated aqueous ammonium chloride solution (50 mL) were added sequentially. The organic layer was washed with water (2×350 mL), dried over anhydrous magnesium sulfate, filtered, and concentrated under reduced pressure. The residue was purified by flash column chromatography on silica gel (0 to 80% ethyl acetate in hexanes) to give 145-1.

Step 2

Aqueous lithium hydroxide solution (2.0 M, 11.0 mL, 22 mmol) was added via syringe to a vigorously stirred solution of 145-1 (517 mg, 2.18 mmol) in tetrahydrofuran (17 mL), water (5.0 mL), and methanol (5.0 mL) at room temperature. After 1 h, the resulting mixture was heated to 70° C. After 3.5 h, the resulting mixture was cooled to room temperature, and aqueous hydrogen chloride solution (2.0 M, 20 mL) and ethyl acetate (100 mL) were added sequentially. The organic layer was washed with a mixture of water and brine (1:1 v:v, 2×80 mL), dried over anhydrous magnesium sulfate, filtered, and concentrated under reduced pressure. The residue was dissolved in dichloromethane (24 mL) and N,N-dimethylformamide (4.0 mL), 4-dimethylaminopyridine (400 mg, 3.27 mmol) was added, and the resulting mixture was stirred at room temperature. After 2 min, N-(3-dimethylaminopropyl)-N'-ethylcarbodiimide hydrochloride (774 mg, 4.36 mmol) was added. After 14 h, diethyl ether (120 mL) was added. The organic layer was washed sequentially with aqueous hydrogen chloride solution (0.05 M, 100 mL) and water (100 mL), dried over anhydrous magnesium sulfate, filtered, and concentrated under reduced pressure. The residue was purified by flash column chromatography on silica gel (0 to 80% ethyl acetate in hexanes) to give 145-2.

Step 3

A mixture of aqueous sodium chlorite solution (2.0 M, 469 mL, 0.94 mmol) and sodium dihydrogen phosphate monohydrate (120 mg, 0.868 mmol) was added via syringe to a vigorously stirred mixture of 145-2 (22 mg, 0.14 mmol) and 2-methyl-2-butene (143 mL, 1.35 mmol) in tert-butanol (0.4 mL) at room temperature. After 16.5 h, aqueous hydrogen chloride solution (2.0 M, 20 mL) and ethyl acetate (100 mL) were added sequentially. The organic layer was washed with a mixture of water and brine (1:1 v:v, 2/80 mL), dried over anhydrous magnesium sulfate, filtered, and concentrated under reduced pressure to give 145-3.

Step 4: Preparation of Example 145

Example 145 was synthesized in the same manner as Example 18 using 145-3 and Example 109. $^1$H NMR (400 MHz, acetone-$d_6$) δ 7.88 (s, 1H), 7.78 (d, J=8.5 Hz, 1H), 7.32-7.21 (m, 2H), 7.19-7.12 (m, 2H), 6.91 (d, J=8.2 Hz, 1H), 6.39 (d, J=1.7 Hz, 1H), 6.20-6.06 (m, 1H), 5.60 (dd, J=15.4, 8.4 Hz, 1H), 4.11 (d, J=12.1 Hz, 1H), 4.05 (d, J=12.1 Hz, 1H), 3.93-3.65 (m, 3H), 3.40 (d, J=14.2 Hz, 1H), 3.24 (s, 3H), 3.24-3.08 (m, 1H), 2.96-1.22 (m, 23H), 1.13 (d, J=6.2 Hz, 3H). LCMS-ESI+: calc'd for $C_{41}H_{48}ClN_4O_6S$: 759.3 (M+H); found: 759.0 (M+H).

Example 146

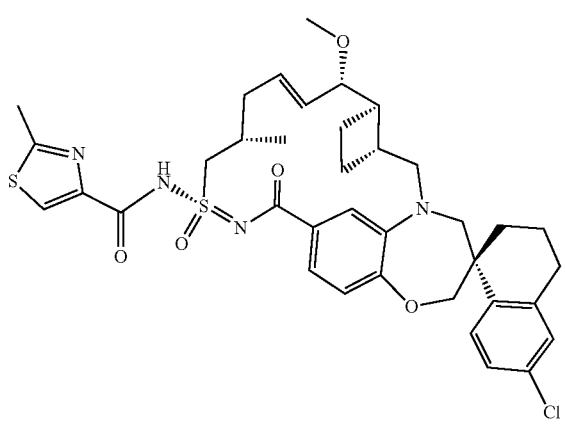 [SMILES: CO[C@H]1/C=C/C[C@H](C)C[S@@](=O)(NC(=O)c2csc(C)n2)=NC(=O)c2ccc3c(c2)N(C[C@@H]2CC[C@H]21)C[C@@]1(CCCc2cc(Cl)ccc21)CO3]

Example 146 was synthesized in the same manner as Example 18 using 2-methylthiazole-4-carboxylic acid and Example 109. $^1$H NMR (400 MHz, methanol-$d_4$) δ 8.28 (s, 1H), 7.74 (d, J=8.5 Hz, 1H), 7.22 (dd, J=8.2, 1.9 Hz, 1H), 7.17 (dd, J=8.5, 2.3 Hz, 1H), 7.10 (d, J=2.3 Hz, 1H), 7.03 (d, J=2.0 Hz, 1H), 6.94 (d, J=8.2 Hz, 1H), 6.04 (dt, J=14.4, 6.8 Hz, 1H), 5.60 (dd, J=15.4, 8.7 Hz, 1H), 4.34 (dd, J=15.0, 6.4 Hz, 1H), 4.13-4.03 (m, 2H), 3.98 (dd, J=15.0, 5.7 Hz, 1H), 3.85 (d, J=15.0 Hz, 1H), 3.76 (dd, J=8.8, 3.5 Hz, 1H), 3.69 (d, J=14.3 Hz, 1H), 3.33 (s, 1H), 3.26 (s, 3H), 3.07 (dd, J=15.3, 10.0 Hz, 1H), 2.77 (s, 3H), 2.53-2.35 (m, 3H), 2.24 (tt, J=14.3, 7.2 Hz, 1H), 2.11 (d, J=13.9 Hz, 2H), 1.97-1.88 (m, 1H), 1.79 (dt, J=20.3, 8.5 Hz, 2H), 1.49-1.38 (m, 1H), 1.29 (s, 1H), 1.11 (d, J=6.7 Hz, 3H). LCMS-ESI+ (m/z): calcd for $H+C_{37}H_{43}ClN_4O_5S_2$: 723.248; found: 723.221.

Example 147

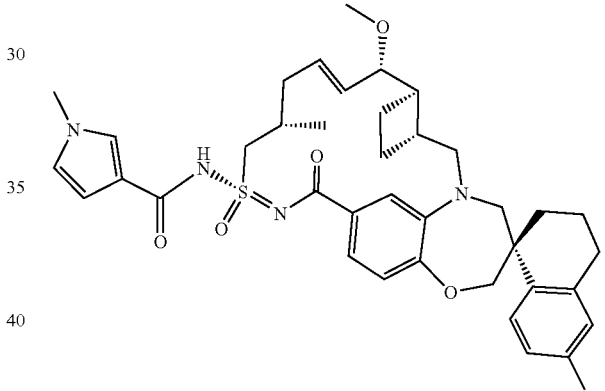

Example 147 was synthesized in the same manner as Example 18 using 1-methyl-1H-pyrrole-3-carboxylic acid and Example 109. $^1$H NMR (400 MHz, methanol-$d_4$) δ 7.74 (d, J=8.5 Hz, 1H), 7.49 (s, 1H), 7.30 (d, J=8.3 Hz, 1H), 7.15 (d, J=8.4 Hz, 1H), 7.09 (s, 2H), 6.89 (d, J=8.2 Hz, 1H), 6.72 (d, J=2.7 Hz, 1H), 6.66-6.53 (m, 1H), 6.16-6.00 (m, 1H), 5.59 (dd, J=15.3, 8.5 Hz, 1H), 4.23 (dd, J=16.1, 5.8 Hz, 1H), 4.10-3.98 (m, 2H), 3.85 (d, J=14.9 Hz, 1H), 3.77 (d, J=8.5 Hz, 1H), 3.72 (s, 3H), 3.68 (d, J=14.3 Hz, 1H), 3.27 (s, 3H), 3.10-3.00 (m, 1H), 2.80 (s, 2H), 2.44 (s, 2H), 2.28-2.15 (m, 1H), 2.10 (d, J=15.0 Hz, 1H), 1.76 (s, 2H), 1.49-1.38 (m, 1H), 1.29 (s, 2H), 1.12 (d, J=6.5 Hz, 3H). LCMS-ESI+ (m/z): calcd for $H+C_{38}H_{45}ClN_4O_5S$: 705.288; found: 705.295.

Example 148

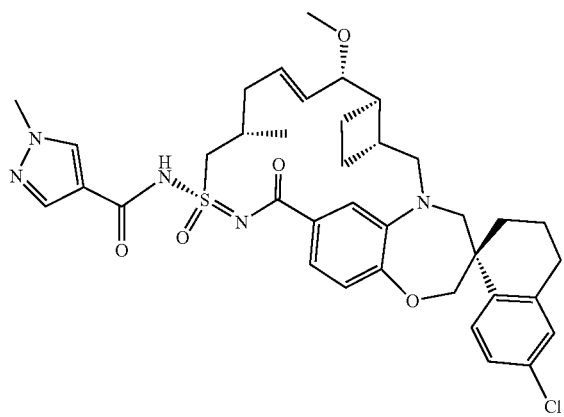 [SMILES: CO[C@H]1/C=C/C[C@H](C)C[S@@](=O)(NC(=O)c2cnn(C)c2)=NC(=O)c2ccc3c(c2)N(C[C@@H]2CC[C@H]21)C[C@@]1(CCCc2cc(Cl)ccc21)CO3]

Example 148 was synthesized in the same manner as Example 18 using 1-methyl-1H-pyrazole-4-carboxylic acid and Example 109. $^1$H NMR (400 MHz, methanol-$d_4$) δ 7.74 (d, J=8.5 Hz, 1H), 7.17 (t, J=9.6 Hz, 2H), 7.09 (d, J=6.8 Hz, 2H), 6.85 (d, J=7.6 Hz, 1H), 6.35-6.01 (m, 1H), 5.55 (dd, J=15.2, 8.6 Hz, 1H), 4.03 (q, J=12.1 Hz, 2H), 3.84 (d, J=14.9 Hz, 1H), 3.78 (d, J=8.6 Hz, 1H), 3.67 (d, J=14.3 Hz, 1H), 3.42 (s, 2H), 3.27 (d, J=1.4 Hz, 3H), 3.11-2.99 (m, 1H), 2.89 (s, 6H), 2.80 (s, 1H), 2.60 (s, 0H), 2.43 (s, 2H), 2.23-2.08 (m, 1H), 2.06-1.97 (m, 1H), 1.92 (d, J=10.7 Hz, 2H), 1.76 (d, J=6.9 Hz, 3H), 1.42 (t, J=13.0 Hz, 1H), 1.23 (d, J=7.5 Hz, 3H), 1.09 (d, J=6.5 Hz, 3H). LCMS-ESI+ (m/z): calcd for H+$C_{37}H_{44}ClN_5O_5S$: 706.28; found: 706.27.

Example 149

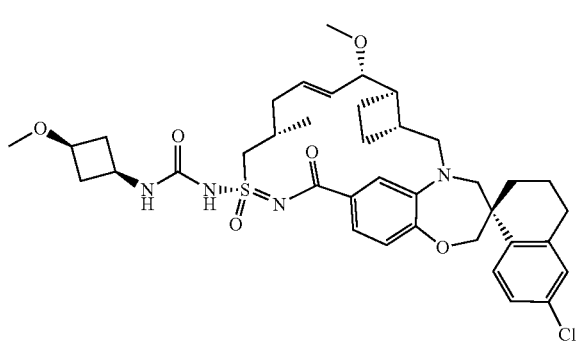 [SMILES: CO[C@H]1/C=C/C[C@H](C)C[S@@](=O)(NC(=O)N[C@H]2C[C@@H](OC)C2)=NC(=O)c2ccc3c(c2)N(C[C@@H]2CC[C@H]21)C[C@@]1(CCCc2cc(Cl)ccc21)CO3]

Example 149 was synthesized in the same manner as Example 75 using Example 109 and cis-3-methoxycyclobutan-1-amine hydrochloride. 1H NMR (400 MHz, Acetone-d6) δ 7.75 (d, J=8.5 Hz, 1H), 7.39 (br s, 1H), 7.31-7.15 (m, 2H), 7.10 (s, 1H), 6.81 (d, J=8.0 Hz, 1H), 6.23 (br s, 1H), 5.57 (br s, 1H), 4.05 (q, J=10.0 Hz, 2H), 4.00 (m, 2H) 3.88-3.61 (m, 4H), 3.44 (d, J=14.4 Hz, 1H), 3.26 (s, 3H), 3.19 (s, 3H), 3.13 (dd, J=15.2, 10.3 Hz, 1H), 2.89-2.68 (m, 2H), 2.67-2.37 (m, 2H), 2.37-2.16 (m, 7H), 2.16-2.07 (m, 3H), 1.95 (m, 2H), 1.88 (m, 2H), 1.74 (m, 1H), 1.48-1.33 (m, 1H), 1.29 (s, 1H), 1.14 (d, J=6.4 Hz, 3H). LCMS-ESI+: calc'd for $C_{38}H_{50}ClN_4O_6S$: 725.3 (M+H); found: 724.8 (M+H).

Example 150

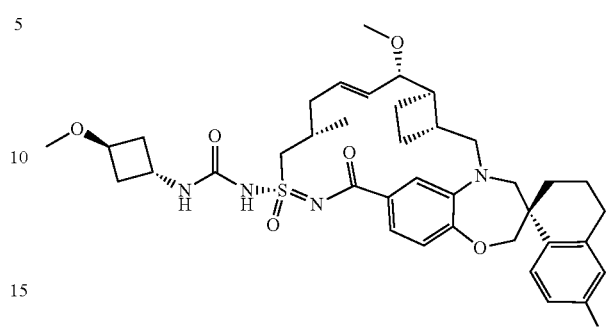

Example 150 was synthesized in the same manner as Example 75 using Example 109 and trans-3-methoxycyclobutan-1-amine hydrochloride. 1H NMR (400 MHz, Acetone-d6) δ 7.64 (d, J=8.4 Hz, 1H), 7.25 (d, J=8.3 Hz, 1H), 7.07 (m, 2H), 6.97 (d, J=8.2 Hz, 1H), 6.85 (d, J=8.2 Hz, 1H), 6.16-6.02 (m, 1H), 5.67 (dd, J=15.5, 8.3 Hz, 1H), 4.31 (q, J=7.1 Hz, 1H), 4.00 (m, 2H) 3.88-3.61 (m, 4H), 3.44 (d, J=14.4 Hz, 1H), 3.26 (s, 3H), 3.19 (s, 3H), 3.13 (dd, J=15.2, 10.3 Hz, 1H), 2.89-2.68 (m, 2H), 2.67-2.37 (m, 2H), 2.37-2.16 (m, 7H), 2.16-2.07 (m, 3H), 1.95 (m, 2H), 1.88 (m, 2H), 1.74 (m, 1H), 1.48-1.33 (m, 1H), 1.29 (s, 1H), 1.14 (d, J=6.4 Hz, 3H). LCMS-ESI+: calc'd for $C_{38}H_{50}ClN_4O_6S$: 725.3 (M+H); found: 724.5 (M+H).

Example 151

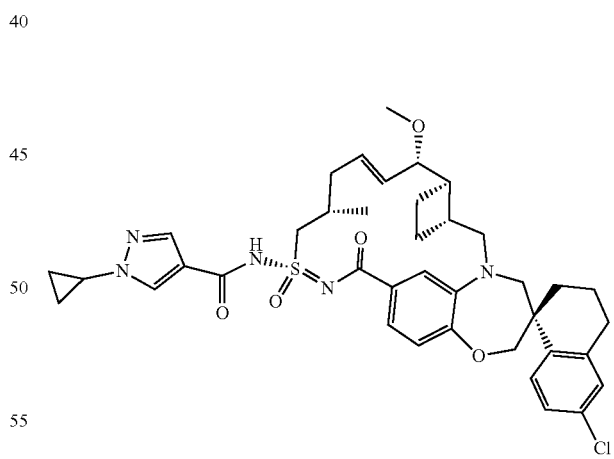

Example 151 was synthesized in the same manner as Example 18 using 1-cyclopropyl-1H-pyrazole-4-carboxylic acid and Example 109. LCMS-ESI+ (m/z): [M+H]+ calcd for $C_{39}H_{46}ClN_5O_5S$: 732.3; found: 732.3.

241
Example 152

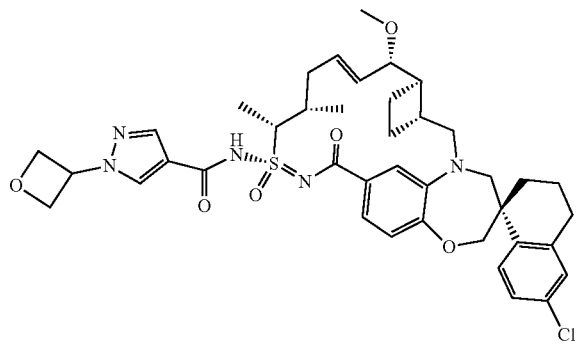 [SMILES: CO[C@H]1/C=C/C[C@H](C)[C@@H](C)[S@@](=O)(NC(=O)c2cnn(C3COC3)c2)=NC(=O)c2ccc3c(c2)N(C[C@@H]2CC[C@H]21)C[C@@]1(CCCc2cc(Cl)ccc21)CO3]

Example 152 was synthesized in the same manner as Example 18 using 1-(oxetan-3-yl)-1H-pyrazole-4-carboxylic acid and Example 110. $^1$H NMR (400 MHz, methanol-d4) δ 8.11 (s, 1H), 7.96 (s, 1H), 7.76 (d, J=8.4 Hz, 1H), 7.32 (dd, J=8.0, 2.0 Hz, 1H), 7.17 (dd, J=8.4, 2.4 Hz, 1H), 7.10 (d, J=2.4 Hz, 1H), 7.03 (d, J=2.0 Hz, 1H), 6.79 (d, J=8.0 Hz, 1H), 6.16-6.09 (m, 1H), 5.59-5.50 (m, 2H), 5.05 (d, J=6.8 Hz, 4H), 4.31-4.25 (m, 1H), 4.15-4.00 (m, 3H), 3.84 (d, J=14.8 Hz, 1H), 3.78 (d, J=8.4 Hz, 1H), 3.62 (d, J=14.4 Hz, 1H), 3.37-3.30 (m, 2H), 3.24 (s, 3H), 3.10-3.04 (m, 1H), 2.85-2.72 (m, 2H), 2.47-1.68 (m, 10H), 1.51 (d, J=6.8 Hz, 3H), 1.48-1.41 (m, 1H), 1.18 (d, J=6.8 Hz, 3H). LCMS-ESI+ (m/z): [M+H]+ calcd for $C_{40}H_{48}ClN_5O_6S$: 762.3; found: 762.1.

Example 153

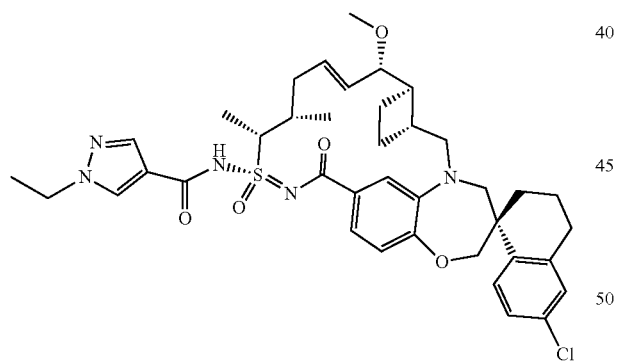

Example 153 was synthesized in the same manner as Example 18 using 1-ethyl-1H-pyrazole-4-carboxylic acid instead of 3-methoxypropionic acid and Example 110. $^1$H NMR (400 MHz, methanol-d4) δ 8.00 (s, 1H), 7.84 (s, 1H), 7.72 (d, J=8.4 Hz, 1H), 7.38 (dd, J=8.0, 1.6 Hz, 1H), 7.16 (dd, J=8.6, 2.2 Hz, 1H), 7.11 (d, J=2.0 Hz, 2H), 6.77 (d, J=8.0 Hz, 1H), 6.15-6.08 (m, 1H), 5.57 (dd, J=15.6, 8.8 Hz, 1H), 4.18 (q, J=7.2 Hz, 2H), 4.12 (q, J=7.0 Hz, 2H), 4.07-4.00 (m, 2H), 3.78-3.75 (m, 2H), 3.60 (d, J=14.4 Hz, 1H), 3.39-3.33 (m, 2H), 3.25 (s, 3H), 3.16-3.09 (m, 1H), 2.86-2.73 (m, 2H), 2.50-1.71 (m, 10H), 1.52-1.44 (m, 7H), 1.21 (d, J=6.8 Hz, 3H). LCMS-ESI+ (m/z): [M+H]+ calcd for H+$C_{39}H_{48}ClN_5O_5S$: 734.4; found: 734.2.

242
Example 154

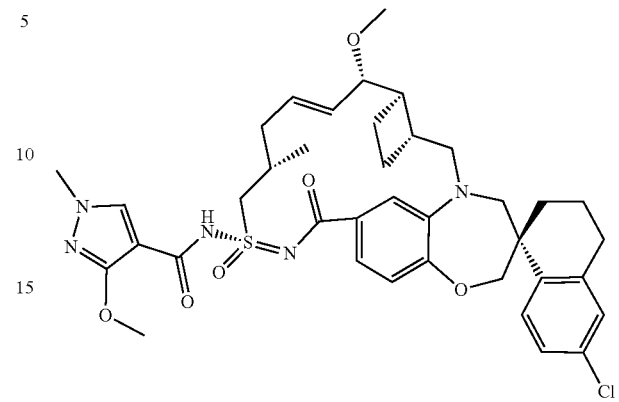

Example 154 was synthesized in the same manner as Example 18 using 3-methoxy-1-methyl-1H-pyrazole-4-carboxylic acid and Example 109. Example 109 (620 mg, 1.04 mmol) was dissolved in dichloromethane (12 mL). 3-Methoxy-1-methyl-1H-pyrazole-4-carboxylic acid (324 mg, 2.08 mmol, 2 equiv.) and N-(3-dimethylaminopropyl)-N'-ethylcarbodiimide hydrochloride (400 mg, 2.08 mmol, 2 equiv.) were added. The reaction mixture was stirred for 5 minutes at room temperature before DMAP (253 mg, 2.08 mmol, 2 equiv.) was added in a single portion. The reaction mixture was stirred overnight at room temperature and the progress of the reaction was monitored by LCMS. Upon completion, the reaction mixture was concentrated under reduced pressure, and the residue was purified by Gilson reverse phase prep HPLC (60-100% ACN/H$_2$O with 0.1% TFA) to give Example 154. $^1$H NMR (400 MHz, methanol-d$_4$) δ 8.07 (s, 1H), 7.76 (d, J=8.6 Hz, 1H), 7.34 (d, J=8.2 Hz, 1H), 7.22-7.10 (m, 3H), 6.92 (d, J=8.2 Hz, 1H), 6.20-6.05 (m, 1H), 5.63 (dd, J=15.5, 8.0 Hz, 1H), 4.10 (d, J=12.0 Hz, 1H), 4.06 (s, 4H), 3.91-3.83 (m, 1H), 3.82 (s, 3H), 3.79 (s, 1H), 3.72 (d, J=14.4 Hz, 1H), 3.38 (d, J=14.5 Hz, 1H), 3.30 (s, 3H), 3.09 (dd, J=15.1, 10.0 Hz, 1H), 2.89-2.72 (m, 2H), 2.51 (d, J=26.7 Hz, 2H), 2.24 (dd, J=10.9, 6.0 Hz, 2H), 2.12 (d, J=13.7 Hz, 1H), 2.02-1.70 (m, 4H), 1.54-1.40 (m, 1H), 1.14 (d, J=6.1 Hz, 3H). LCMS-ESI+ (m/z): calcd for $C_{38}H_{46}ClN_5O_6S$: 735.28; found: 735.94.

Example 155

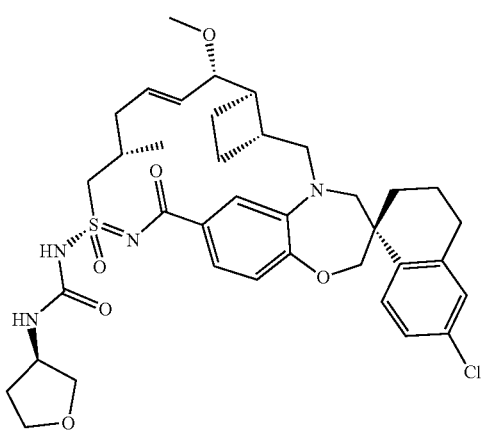 [SMILES: CO[C@H]1/C=C/C[C@H](C)C[S@@](=O)(NC(=O)N[C@@H]2CCOC2)=NC(=O)c2ccc3c(c2)N(C[C@@H]2CC[C@H]21)C[C@@]1(CCCc2cc(Cl)ccc21)CO3]

Example 155 was synthesized in the same manner as Example 75 using Example 109 and (3R)-tetrahydrofuran-3-amine. 1H NMR (400 MHz, Methanol-d4) δ 7.73 (d, J=8.4 Hz, 1H), 7.20 (d, J=6.9 Hz, 1H), 7.17-7.09 (m, 2H), 6.99 (s, 1H), 6.90 (d, J=8.2 Hz, 1H), 6.10-5.98 (m, 1H), 5.60 (dd, J=15.4, 8.8 Hz, 1H), 4.35-4.23 (m, 2H), 4.10-4.01 (m, 2H), 3.96-3.75 (m, 6H), 3.72-3.62 (m, 3H), 3.28 (s, 3H), 3.08 (dd, J=15.1, 10.2 Hz, 1H), 2.84-2.72 (m, 2H), 2.55-2.37 (m, 3H), 2.32-2.07 (m, 3H), 1.97-1.76 (m, 8H), 1.43 (t, J=12.6 Hz, 1H), 1.14 (d, J=6.6 Hz, 3H). LCMS-ESI+ (m/z): calcd H+ for $C_{37}H_{47}ClN_4O_6S$, Calc'd: 711.29; found: 710.79.

ylic acid and Example 109. $^1$H NMR (400 MHz, Acetonitrile-d$_3$) δ 7.87 (d, J=8.0 Hz, 1H), 7.74 (s, 1H), 7.71 (d, J=8.5 Hz, 1H), 7.26 (d, J=8.0 Hz, 1H), 7.19 (dd, J=8.5, 2.4 Hz, 1H), 7.16-7.07 (m, 2H), 6.96 (s, 1H), 6.93 (d, J=8.1 Hz, 1H), 5.92 (dt, J=14.2, 6.5 Hz, 1H), 5.55 (dd, J=15.3, 8.9 Hz, 1H), 4.77 (s, 2H), 4.33 (dd, J=15.3, 5.6 Hz, 1H), 4.05 (d, J=2.2 Hz, 2H), 3.94 (t, J=5.7 Hz, 2H), 3.84-3.64 (m, 3H), 3.26 (d, J=14.3 Hz, 1H), 3.18 (s, 3H), 3.05 (dd, J=15.3, 10.4 Hz, 1H), 2.89 (t, J=5.7 Hz, 2H), 2.84-2.65 (m, 3H), 2.50-2.21 (m, 3H), 2.19-2.00 (m, 3H), 1.91-1.81 (m, 3H), 1.79-1.63 (m, 3H), 1.47-1.35 (m, 1H), 1.05 (d, J=6.3 Hz, 3H). LCMS-ESI+ (m/z): [M+H]$^+$ calculated for $C_{42}H_{48}ClN_3O_6S$: 758.33; found: 758.0.

Example 158

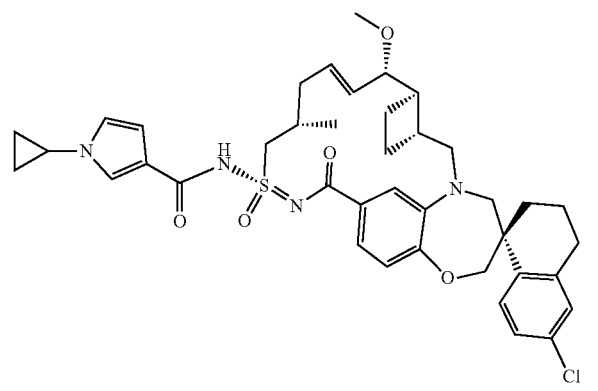 [SMILES: CO[C@H]1/C=C/C[C@H](C)C[S@@](=O)(NC(=O)c2ccn(C3CC3)c2)=NC(=O)c2ccc3c(c2)N(C[C@@H]2CC[C@H]21)C[C@@]1(CCCc2cc(Cl)ccc21)CO3]

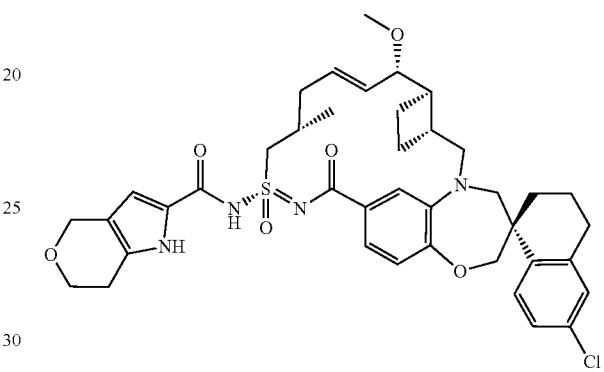

Example 156 was synthesized in the same manner as Example 18, using Example 109 instead of Example 5, and 1-cyclopropyl-1H-pyrrole-3-carboxylic acid was used instead of 3-methoxypropionic acid. 1H NMR (400 MHz, Methanol-d4) δ 7.76 (d, J=8.5 Hz, 1H), 7.62 (t, J=2.0 Hz, 1H), 7.32 (d, J=8.0 Hz, 1H), 7.18 (dd, J=8.5, 2.3 Hz, 1H), 7.15-7.05 (m, 2H), 6.95-6.84 (m, 2H), 6.61 (dd, J=3.0, 1.8 Hz, 1H), 6.11 (dt, J=14.5, 6.8 Hz, 1H), 5.61 (dd, J=15.4, 8.6 Hz, 1H), 4.27 (dd, J=14.8, 6.4 Hz, 1H), 4.14-3.94 (m, 3H), 3.87 (d, J=15.1 Hz, 1H), 3.79 (d, J=7.5 Hz, 1H), 3.70 (d, J=14.2 Hz, 1H), 3.56-3.46 (m, 1H), 3.36 (s, 1H), 3.29 (s, 3H), 3.08 (dd, J=15.0, 9.4 Hz, 2H), 2.89-2.71 (m, 2H), 2.60-2.35 (m, 3H), 2.32-2.06 (m, 3H), 1.94 (d, J=11.6 Hz, 3H), 1.88-1.66 (m, 3H), 1.45 (t, J=12.1 Hz, 1H), 1.13 (d, J=6.7 Hz, 3H), 1.08-0.93 (m, 4H). LCMS-ESI+ (m/z): [M+H]+ calcd for $C_{40}H_{47}ClN_4O_5S$: 731.35; found: 729.83.

Example 158 was prepared in a similar manner to Example 18 using 1,4,6,7-tetrahydropyrano[4,3-b]pyrrole-2-carboxylic acid and Example 109. $^1$H NMR (400 MHz, Acetonitrile-d$_3$) δ 9.87 (s, 1H), 7.64 (d, J=8.5 Hz, 1H), 7.20 (d, J=8.2 Hz, 1H), 7.09 (s, 1H), 7.06 (d, J=8.7 Hz, 1H), 7.01 (s, 1H), 6.85 (d, J=8.2 Hz, 1H), 6.78 (s, 1H), 5.98 (dt, J=13.9, 6.5 Hz, 1H), 5.58 (dd, J=15.4, 8.4 Hz, 1H), 4.56 (d, J=2.7 Hz, 2H), 4.13 (dd, J=15.0, 5.9 Hz, 1H), 4.00 (s, 2H), 3.87 (t, J=5.6 Hz, 2H), 3.82-3.70 (m, 3H), 3.66 (d, J=15.1 Hz, 1H), 3.32 (d, J=14.6 Hz, 1H), 3.20 (s, 3H), 3.05 (dd, J=15.3, 10.1 Hz, 1H), 2.84-2.65 (m, 3H), 2.52 (dd, J=11.6, 5.3 Hz, 1H), 2.40 (dt, J=16.5, 6.2 Hz, 2H), 2.27-2.08 (m, 3H), 2.07-1.98 (m, 1H), 1.91-1.81 (m, 3H), 1.81-1.62 (m, 3H), 1.37 (dt, J=15.1, 7.8 Hz, 1H), 1.06 (d, J=6.3 Hz, 3H). LCMS-ESI+ (m/z): [M+H]$^+$ calculated for $C_{40}H_{47}ClN_4O_6S$: 747.30; found: 747.0.

Example 157

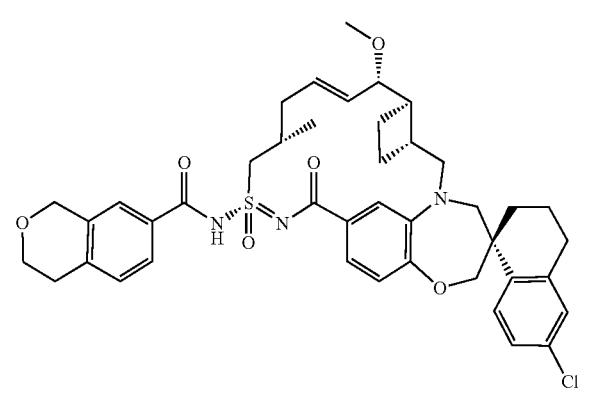 [SMILES: CO[C@H]1/C=C/C[C@H](C)C[S@@](=O)(NC(=O)c2ccc3c(c2)COCC3)=NC(=O)c2ccc3c(c2)N(C[C@@H]2CC[C@H]21)C[C@@]1(CCCc2cc(Cl)ccc21)CO3]

Example 157 was prepared in a similar manner to Example 18 using 3,4-dihydro-1H-2-benzopyran-7-carbox- Example 159

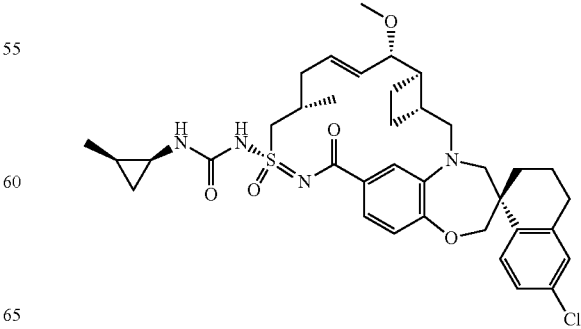

Example 109 (11 mg, 0.018 mmol), (1S,2R)-2-methylcyclopropane-1-carboxylic acid (0.014 mL, 0.147 mmol), diphenyl phosphoryl azide (0.032 mL, 0.147 mmol) and trimethylamine (0.028 mL, 0.202 mmol) were suspended in MeCN (2 mL). The reaction mixture was heated to 50° C. overnight, then cooled to RT. i-PrOAc (10 mL) and saturated NH$_4$Cl (8 mL) were added, and the mixture was stirred for 10 min. The layers were separated, and the aqueous phase was extracted with i-PrOAc. The organic phases were combined and washed twice with water, then dried over MgSO$_4$, filtered, and concentrated under reduced pressure. The crude residue was purified by silica column chromatography (50% EtOAc/Hex to 40% MeOH/EtOAc) to afford Example 159 (6 mg). 1H NMR (400 MHz, Methanol-d4) δ 7.73 (d, J=8.5 Hz, 2H), 7.41 (s, 1H), 7.29 (s, 1H), 7.19-7.06 (m, 4H), 6.82 (d, J=8.1 Hz, 2H), 6.17 (s, 2H), 5.56 (s, 2H), 4.08-3.95 (m, 3H), 3.86-3.77 (m, 4H), 3.69 (d, J=32.3 Hz, 4H), 3.27 (s, 3H), 3.08 (d, J=12.6 Hz, 1H), 2.77 (d, J=21.0 Hz, 3H), 2.62 (s, 3H), 2.50 (td, J=7.3, 4.1 Hz, 1H), 2.38 (s, 2H), 2.26 (s, 1H), 2.19 (s, 1H), 2.09 (d, J=13.6 Hz, 2H), 1.93 (s, 5H), 1.78-1.70 (m, 2H), 1.41 (d, J=13.7 Hz, 1H), 1.29 (s, 1H), 1.06 (dd, J=18.0, 10.9 Hz, 14H), 0.89 (ddd, J=15.2, 8.9, 4.2 Hz, 6H), 0.15-0.06 (m, 4H). LCMS-ESI+: calculated for C$_{37}$H$_{47}$ClN$_4$O$_5$S: 695.3 (M+H); found: 695.2 (M+H).

Example 160

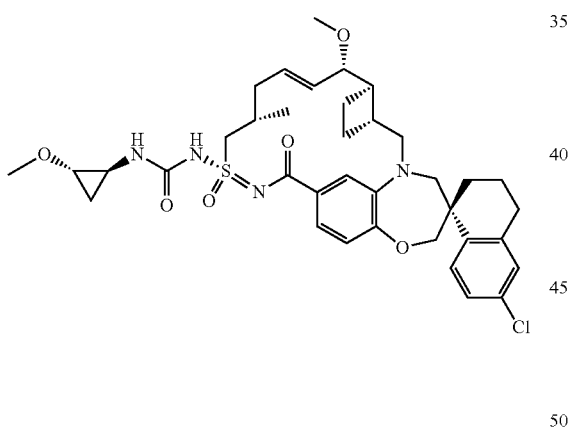

Example 160 was synthesized as a mixture of diastereomers in the same manner as Example 364, using Example 109 and rac-(1S*,2S*)-2-methoxy cyclopropane-1-carboxylic acid. LCMS-ESI+ (m/z): [M+H]$^+$ calc'd for C$_{37}$H$_{47}$ClN$_4$O$_6$S: 711.2978; found: 710.68. $^1$H NMR (400 MHz, Methanol-d$_4$) δ 7.72 (dd, J=8.4, 2.3 Hz, 1H), 7.22-7.04 (m, 3H), 7.00-6.84 (m, 2H), 6.10-5.92 (m, 1H), 5.58 (dd, J=15.2, 8.9 Hz, 1H), 4.25 (d, J=15.3 Hz, 1H), 4.12-3.96 (m, 2H), 3.90-3.71 (m, 3H), 3.66 (d, J=14.3 Hz, 1H), 3.43 (d, J=1.8 Hz, 3H), 3.29-3.24 (m, 1H), 3.26 (s, 3H), 3.06 (dd, J=15.2, 10.2 Hz, 1H), 2.88-2.69 (m, 2H), 2.62 (s, 1H), 2.55-2.28 (m, 3H), 2.26-2.04 (m, 3H), 2.01-1.67 (m, 7H), 1.41 (t, J=12.8 Hz, 1H), 1.12 (d, J=6.5 Hz, 3H), 1.06-0.97 (m, 1H), 0.86-0.76 (m, 1H).

Example 161

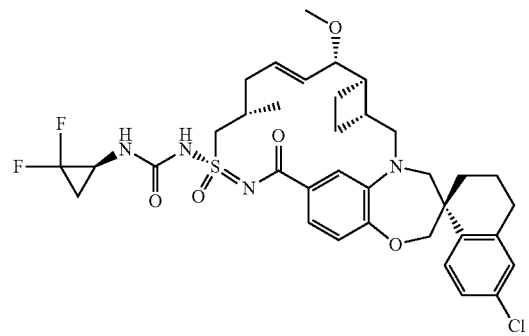 [SMILES: CO[C@H]1/C=C/C[C@H](C)C[S@@](=O)(NC(=O)N[C@H]2CC2(F)F)=NC(=O)c2ccc3c(c2)N(C[C@@H]2CC[C@H]21)C[C@@]1(CCCc2cc(Cl)ccc21)CO3]

Example 161 was synthesized in the same manner as Example 364, using Example 109 and (1R)-2,2-difluorocyclopropanecarboxylic acid. LCMS-ESI+ (m/z): [M+H]$^+$ calc'd for C$_{36}$H$_{43}$ClF$_2$N$_4$O$_5$S: 717.2684; found: 716.58. $^1$H NMR (400 MHz, Methanol-d4) δ 7.73 (d, J=8.5 Hz, 1H), 7.20-7.07 (m, 3H), 7.00-6.86 (m, 2H), 5.98 (dd, J=14.7, 7.7 Hz, 1H), 5.58 (dd, J=15.2, 9.0 Hz, 1H), 4.30 (dd, J=15.1, 6.2 Hz, 1H), 4.16-3.98 (m, 2H), 3.92-3.59 (m, 4H), 3.29-3.24 (m, 1H), 3.25 (s, 3H), 3.06 (dd, J=15.3, 10.3 Hz, 1H), 2.89-2.64 (m, 2H), 2.56-2.25 (m, 3H), 2.26-2.05 (m, 3H), 2.00-1.66 (m, 6H), 1.52-1.34 (m, 2H), 1.12 (d, J=6.4 Hz, 3H).

Example 162

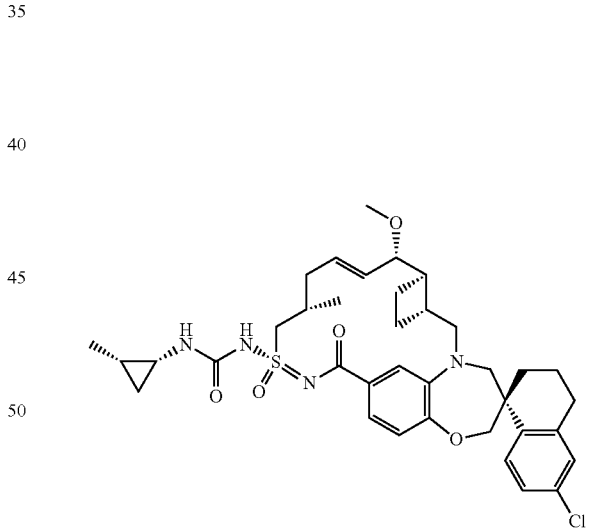

Example 162 was prepared in a similar manner to Example 159 using (1R,2S)-2-methylcyclopropane-1-carboxylic acid (0.014 mL, 0.147 mmol), diphenyl phosphoryl azide, triethylamine and Example 109. LCMS-ESI+: calculated for C$_{37}$H$_{47}$ClN$_4$O$_5$S: 695.3 (M+H); found: 695.2 (M+H).

Example 163

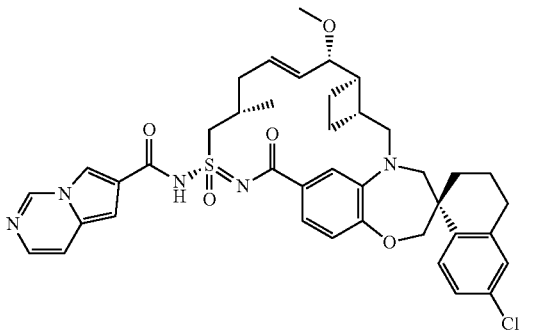 [SMILES: CO[C@H]1/C=C/C[C@H](C)C[S@@](=O)(NC(=O)c2cc3ccncn3c2)=NC(=O)c2ccc3c(c2)N(C[C@@H]2CC[C@H]21)C[C@@]1(CCCc2cc(Cl)ccc21)CO3]

Example 163 was prepared in a similar manner to Example 18 using pyrrolo[1,2-c]pyrimidine-6-carboxylic acid and Example 109. $^1$H NMR (400 MHz, Acetonitrile-$d_3$) δ 8.97 (s, 1H), 8.12 (s, 1H), 7.68 (d, J=8.4 Hz, 1H), 7.42 (d, J=6.6 Hz, 1H), 7.36 (d, J=6.5 Hz, 1H), 7.18 (d, J=8.1 Hz, 1H), 7.13 (d, J=8.6 Hz, 1H), 7.12 (s, 1H), 7.00 (d, J=1.8 Hz, 1H), 6.91 (d, J=8.2 Hz, 1H), 6.85 (s, 1H), 6.03-5.90 (m, 1H), 5.57 (dd, J=15.3, 8.6 Hz, 1H), 4.26 (d, J=15.1 Hz, 1H), 4.04 (s, 2H), 3.79 (d, J=15.2 Hz, 2H), 3.74-3.64 (m, 2H), 3.30 (d, J=14.3 Hz, 1H), 3.19 (s, 3H), 3.06 (dd, J=15.3, 10.4 Hz, 2H), 2.85-2.66 (m, 3H), 2.52-2.27 (m, 4H), 2.22-2.13 (m, 2H), 2.05 (d, J=13.9 Hz, 1H), 1.83-1.64 (m, 3H), 1.39 (dt, J=14.5, 7.4 Hz, 1H), 1.09 (d, J=6.1 Hz, 2H). LCMS-ESI+ (m/z): [M+H]$^+$ calculated for $C_{40}H_{44}ClN_5O_5S$: 742.28; found: 742.0.

Example 164

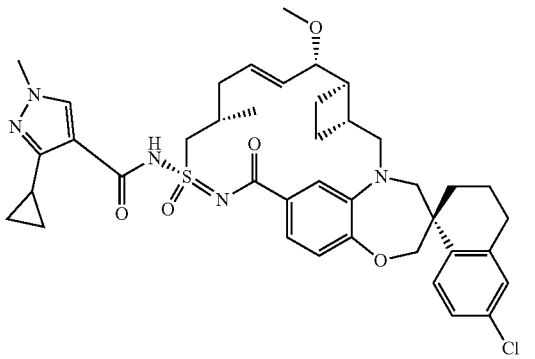 [SMILES: CO[C@H]1/C=C/C[C@H](C)C[S@@](=O)(NC(=O)c2cn(C)nc2C2CC2)=NC(=O)c2ccc3c(c2)N(C[C@@H]2CC[C@H]21)C[C@@]1(CCCc2cc(Cl)ccc21)CO3]

Example 164 was synthesized in the same manner as Example 18 using 3-cyclopropyl-1-methyl-1H-pyrazole-4-carboxylic acid and Example 109. $^1$H NMR (400 MHz, Methanol-$d_4$) δ 8.28 (s, 1H), 7.65 (d, J=8.5 Hz, 1H), 7.28 (d, J=8.1 Hz, 1H), 7.07 (d, J=2.2 Hz, 1H), 6.99 (d, J=1.9 Hz, 1H), 6.86 (d, J=8.3 Hz, 1H), 6.19-6.05 (m, 1H), 5.66 (dd, J=15.3, 8.7 Hz, 1H), 4.25 (s, 1H), 4.02 (s, 2H), 3.82 (s, 5H), 3.65 (d, J=14.3 Hz, 1H), 3.39 (d, J=14.5 Hz, 1H), 3.31 (s, 3H), 3.18-3.03 (m, 1H), 2.90-2.62 (m, 3H), 2.52 (d, J=39.0 Hz, 3H), 2.28 (d, J=10.7 Hz, 2H), 2.16-2.04 (m, 2H), 1.96 (m, 4H), 1.83 (s, 3H), 1.40 (t, J=12.5 Hz, 1H), 1.18 (d, J=6.2 Hz, 3H), 1.01-0.79 (m, 5H). LCMS-ESI+ (m/z): [M+H]+ calcd for $C_{40}H_{48}ClN_5O_5S$: 746.3; found: 746.0.

Example 165

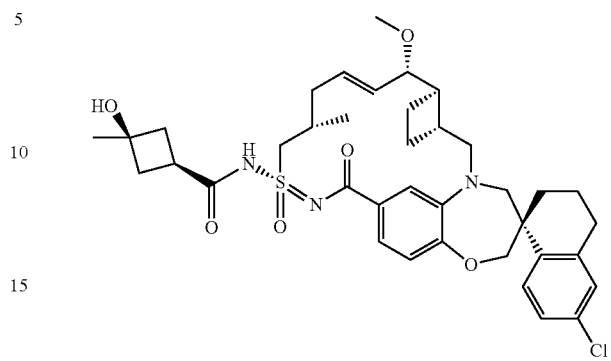

Example 165 was synthesized in the same manner as Example 18 using Example 109 and cis-3-hydroxy-3-methyl-cyclobutanecarboxylic acid. 1H NMR (400 MHz, Methanol-d4) δ 7.72 (d, J=9.1 Hz, 1H), 7.31 (dd, J=8.2, 1.8 Hz, 1H), 7.09 (dt, J=7.5, 2.0 Hz, 3H), 6.86 (d, J=8.3 Hz, 1H), 6.14 (dt, J=14.6, 7.0 Hz, 1H), 5.63 (dd, J=15.4, 8.4 Hz, 1H), 4.14 (dd, J=14.8, 7.0 Hz, 1H), 4.08-3.93 (m, 3H), 3.87-3.74 (m, 2H), 3.67 (d, J=14.3 Hz, 1H), 3.30 (s, 3H), 3.11-3.02 (m, 1H), 2.92-2.70 (m, 3H), 2.58-2.23 (m, 8H), 2.15-2.05 (m, 2H), 2.04-1.72 (m, 7H), 1.38 (s, 4H), 1.14 (d, J=6.9 Hz, 3H). LCMS-ESI+ (m/z): calcd H+ for $C_{38}H_{48}ClN_3O_6S$: 710.30; found: 710.05.

Example 166

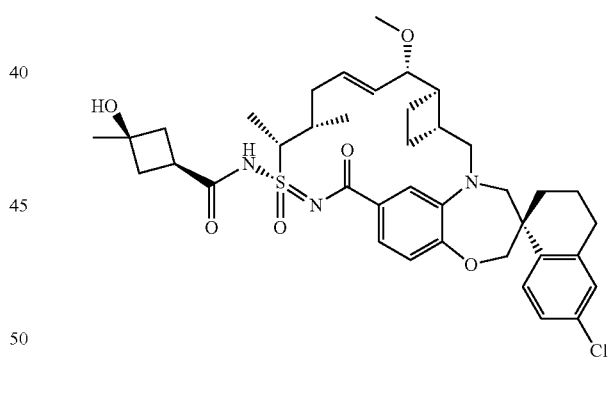

Example 166 was synthesized in the same manner as Example 18 using Example 110 and cis-3-hydroxy-3-methyl-cyclobutanecarboxylic acid. 1H NMR (400 MHz, Methanol-d4) δ 7.75 (d, J=8.5 Hz, 1H), 7.25-7.15 (m, 2H), 7.12 (d, J=2.3 Hz, 1H), 7.10-7.02 (m, 1H), 6.92 (d, J=8.2 Hz, 1H), 6.03-5.92 (m, 1H), 5.61 (dd, J=15.3, 8.7 Hz, 1H), 4.38-4.27 (m, 1H), 4.13-4.03 (m, 2H), 3.83 (d, J=15.1 Hz, 1H), 3.77-3.71 (m, 1H), 3.68 (d, J=14.3 Hz, 1H), 3.25 (s, 3H), 3.18-3.08 (m, 1H), 2.90-2.71 (m, 3H), 2.50-2.20 (m, 9H), 2.16-2.07 (m, 1H), 2.01-1.72 (m, 7H), 1.55 (d, J=7.1 Hz, 3H), 1.52-1.41 (m, 1H), 1.38 (s, 3H), 1.14-1.05 (m, 3H). LCMS-ESI+ (m/z): calcd H+ for $C_{39}H_{50}ClN_3O_6S$: 724.31; found: 723.99.

Example 167

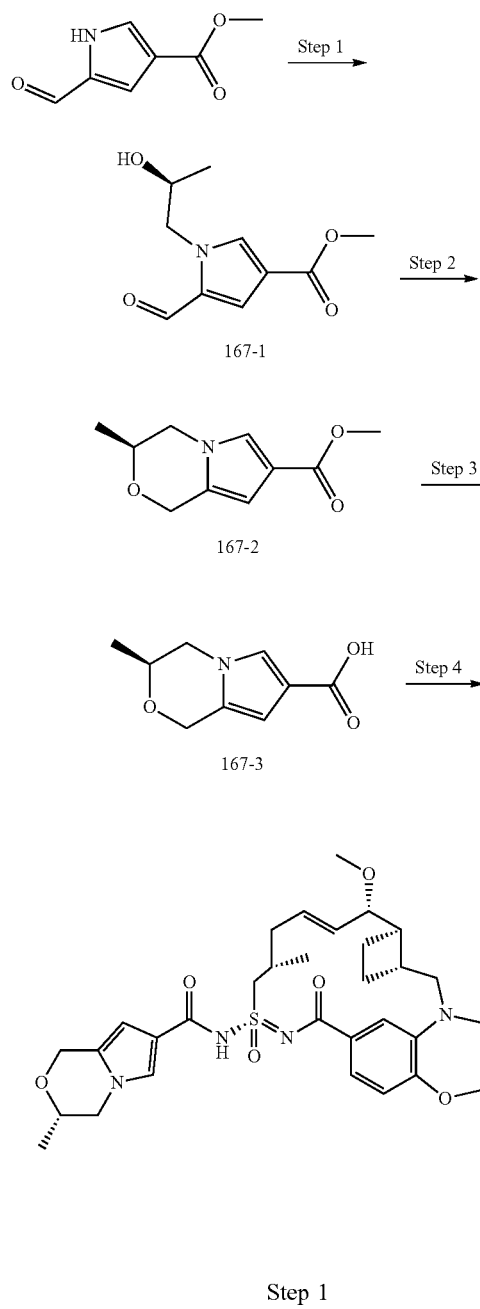

Step 1

A vigorously stirred mixture of methyl 5-formyl-1H-pyrrole-3-carboxylate (500 mg, 3.27 mmol), (S)-2-methyloxirane (458 µL, 6.53 mmol), and cesium carbonate (2.13 g, 6.53 mmol) in acetonitrile (6.0 mL) and methanol (2.0 mL) was heated to 60° C. After 45 min, the reaction mixture was allowed to cool to room temperature, and ethyl acetate (60 mL) was added. The organic layer was washed with a mixture of water and brine (1:1 v:v, 40 mL), dried over anhydrous sodium sulfate, filtered, and concentrated under reduced pressure. The residue was purified by flash column chromatography on silica gel (0 to 70% ethyl acetate in hexanes) to give 167-1.

Step 2

Trifluoroacetic acid (163 µL, 2.13 mmol) was added via syringe to a stirred solution of 167-1 (150 mg, 0.710 mmol) in dichloromethane (40 mL) at room 0° C. After 2 min, triethylsilane (343 µL, 2.15 mmol) was added via syringe, and the resulting mixture was warmed to room temperature. After 45 min, triethylamine (1.0 mL) was added via syringe, and the resulting mixture was concentrated under reduced pressure. The residue was purified by flash column chromatography on silica gel (0 to 40% ethyl acetate in hexanes) to give 167-2.

Step 3

Aqueous sodium hydroxide solution (2.0 M, 800 µL, 1.6 mmol) was added via syringe to a stirred solution of 167-2 (53.6 mg, 0.275 mmol) in tetrahydrofuran (1.0 mL) and methanol (3.0 mL) at room temperature, and the resulting mixture was heated to 60° C. After 3 h, the resulting mixture was allowed to cool to room temperature, and aqueous hydrogen chloride solution (2.0 M, 1.0 mL) and ethyl acetate (30 mL) were added sequentially. The organic layer was washed with brine, dried over anhydrous sodium sulfate, filtered, and concentrated under reduced pressure to give 167-3.

Step 4: Preparation of Example 167

Example 167 was synthesized in a manner similar to Example 109 using 167-3 instead of 2-((tetrahydro-2H-pyran-4-yl)oxy)acetic acid. 1H NMR (400 MHz, Acetone-d6) δ 7.78 (d, J=8.4 Hz, 1H), 7.45-7.21 (m, 4H), 7.13 (d, J=2.3 Hz, 1H), 6.88 (d, J=8.2 Hz, 1H), 6.32-5.99 (m, 2H), 5.70-5.58 (m, 1H), 4.89 (d, J=14.4 Hz, 1H), 4.71 (d, J=14.3 Hz, 1H), 4.23-3.59 (m, 9H), 3.43 (d, J=14.3 Hz, 1H), 3.24 (s, 3H), 3.21-3.10 (m, 1H), 2.85-1.17 (m, 19H), 1.12 (d, J=6.8 Hz, 3H). LCMS: 761.0.

Example 168

Example 168 was synthesized in a manner similar to Example 167 using (R)-2-methyloxirane in step 1 instead of (S)-2-methyloxirane. 1H NMR (400 MHz, Acetone-d6) δ 7.79 (d, J=8.5 Hz, 1H), 7.33 (d, J=7.3 Hz, 2H), 7.24 (d, J=7.4 Hz, 2H), 7.14 (s, 1H), 6.89 (d, J=8.2 Hz, 1H), 6.27 (s, 1H), 6.24-6.11 (m, 1H), 5.59 (dd, J=15.4, 7.9 Hz, 1H), 4.89 (d, J=14.4 Hz, 1H), 4.71 (d, J=14.4 Hz, 1H), 4.17-3.59 (m, 9H), 3.42 (d, J=14.4 Hz, 1H), 3.24 (s, 3H), 3.13 (dd, J=15.2, 10.4 Hz, 1H), 2.84-1.15 (m, 19H), 1.12 (d, J=6.8 Hz, 3H). LCMS: 761.0.

Example 169

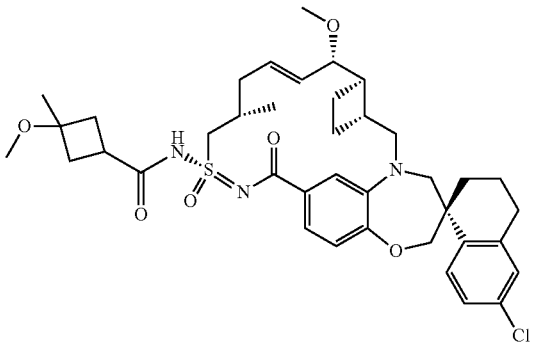 [SMILES: CO[C@H]1/C=C/C[C@H](C)C[S@@](=O)(NC(=O)C2CC(C)(OC)C2)=NC(=O)c2ccc3c(c2)N(C[C@@H]2CC[C@H]21)C[C@@]1(CCCc2cc(Cl)ccc21)CO3]

Preparation of 3-methoxy-3-methyl-cyclobutanecarboxylic acid: 3-hydroxy-3-methyl-cyclobutanecarboxylic acid (116 mg, 0.891 mmol) was dissolved in DMF (2.0 mL), the resulting solution was cooled to 0° C. To this stirred mixture was added 55% sodium hydride dispersion in mineral oil (61.4 mg, 1.47 mmol). The newly formed mixture was stirred at 0° C. for 30 min before MeI (758 mg, 5.37 mmol) was added. The reaction was then removed from cooling bath and stirred at room temperature for overnight. The reaction was quenched with ice, partitioned between EtOAc (15.0 mL) and water (5.0 mL). The organic layer was washed with brine (5.0 mL), dried over sodium sulfate, filtered, and concentrated to crude product. The crude product was then dissolved in a mixture of MeOH (2.0 mL) and THF (2.0 mL), and treated with 1 N NaOH (4.45 mL, 4.45 mmol). The resulting mixture was heated at 50° C. for 1 hr. The reaction was concentrated. The resulting residue was diluted with EtOAc (20.0 mL), acidified with 1N HCl (5.0 mL) and the organic layer was washed with brine (2×5.0 mL), dried over sodium sulfate, filtered, and concentrated to provide the title compound. 1H NMR (400 MHz, Chloroform-d) δ 3.21 (s, 3H), 2.83-2.69 (m, 1H), 2.49-2.41 (m, 2H), 2.23-2.14 (m, 2H), 1.37 (s, 3H).

Example 169 was synthesized in a manner similar to Example 18 using Example 109 and 3-methoxy-3-methyl-cyclobutanecarboxylic acid. 1H NMR (400 MHz, Methanol-d4) δ 7.75 (d, J=8.5 Hz, 1H), 7.31 (dd, J=8.3, 1.8 Hz, 1H), 7.18-7.13 (m, 1H), 7.10 (dd, J=9.2, 2.1 Hz, 2H), 6.88 (d, J=8.2 Hz, 1H), 6.14 (dt, J=14.4, 7.0 Hz, 1H), 5.62 (dd, J=15.4, 8.5 Hz, 1H), 4.16 (dd, J=14.8, 6.8 Hz, 1H), 4.10-3.92 (m, 3H), 3.84 (d, J=15.0 Hz, 1H), 3.77 (d, J=8.0 Hz, 1H), 3.68 (d, J=14.2 Hz, 1H), 3.30 (s, 3H), 3.21 (s, 3H), 3.12-3.01 (m, 1H), 2.96-2.70 (m, 3H), 2.54-2.24 (m, 6H), 2.22-2.05 (m, 4H), 2.00-1.72 (m, 7H), 1.39 (s, 4H), 1.14 (d, J=6.9 Hz, 3H). [M+H]+ calcd for $C_{39}H_{50}ClN_3O_6S$: 724.35; found: 724.09.

Example 170

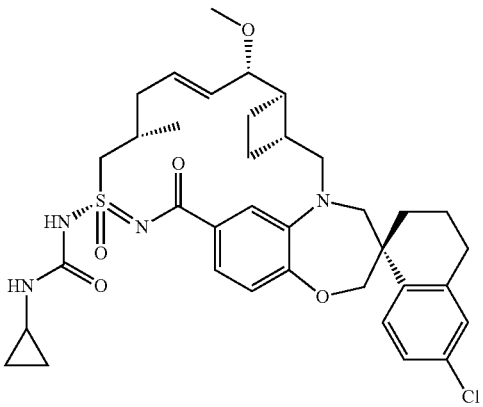 [SMILES: CO[C@H]1/C=C/C[C@H](C)C[S@@](=O)(NC(=O)NC2CC2)=NC(=O)c2ccc3c(c2)N(C[C@@H]2CC[C@H]21)C[C@@]1(CCCc2cc(Cl)ccc21)CO3]

PtO$_2$ (1.33 mg) was suspended in a solution of Example 144 (20 mg) in EtOH (5.0 mL), one drop of TFA from the tip of the glass pipette was added. The atmosphere was exchanged with hydrogen (balloon). The mixture was stirred for 3 hours. The reaction was degassed and flushed with nitrogen, filtered through Nalgene PTFE filter disc, and concentrated. The resulting residue was then dissolved in DMF (1.2 mL), filtered and purified by Gilson reverse phase prep HPLC. Desired fractions were combined and concentrated, retreated with a mixture of ACN/H$_2$O, and frozen dried to give Example 170 (6.30 mg). 1H NMR (400 MHz, Methanol-d4) δ 7.77 (d, J=8.5 Hz, 1H), 7.28 (d, J=8.1 Hz, 1H), 7.21-7.09 (m, 3H), 6.92 (d, J=8.2 Hz, 1H), 4.15-4.02 (m, 3H), 3.88-3.80 (m, 1H), 3.68 (d, J=14.2 Hz, 1H), 3.40-3.34 (m, 5H), 3.16-3.07 (m, 1H), 2.88-2.72 (m, 2H), 2.68-2.57 (m, 2H), 2.46-2.34 (m, 1H), 2.15-1.86 (m, 5H), 1.81-1.61 (m, 4H), 1.60-1.29 (m, 7H), 1.12 (d, J=6.7 Hz, 3H), 0.75 (d, J=7.1 Hz, 2H), 0.60-0.49 (m, 2H). [M+H]+ calcd for $C_{36}H_{47}ClN_4O_5S$: 683.30; found: 682.85.

Example 171

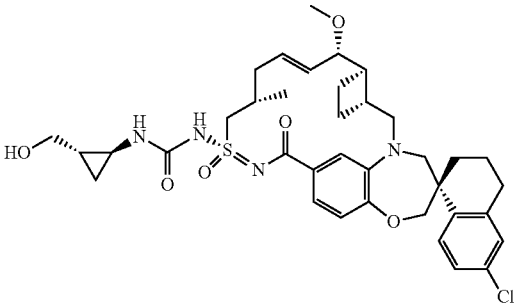 [SMILES: CO[C@H]1/C=C/C[C@H](C)C[S@@](=O)(NC(=O)N[C@H]2C[C@@H]2CO)=NC(=O)c2ccc3c(c2)N(C[C@@H]2CC[C@H]21)C[C@@]1(CCCc2cc(Cl)ccc21)CO3]

Example 171 was synthesized as a mixture of diastereomers in the same manner as Example 75, using Example 109 and [rac-(1R*,2R*)-2-aminocyclopropyl]methanol. LCMS-ESI+ (m/z): [M+H]$^+$ calc'd for $C_{37}H_{47}ClN_4O_6S$: 711.2978; found: 710.93. 1H NMR (400 MHz, Methanol-d4) δ 7.72 (d, J=8.5 Hz, 1H), 7.24-7.04 (m, 3H), 6.97 (s, 1H), 6.88 (d, J=8.2 Hz, 1H), 6.01 (dd, J=14.9, 7.5 Hz, 1H), 5.58 (dd, J=15.3, 8.9 Hz, 1H), 4.24 (dd, J=14.9, 6.5 Hz, 1H), 4.12-3.97 (m, 2H), 3.89-3.71 (m, 3H), 3.71-3.60 (m, 1H), 3.51-

3.40 (m, 2H), 3.29-3.24 (m, 1H), 3.26 (s, 3H), 3.05 (dd, J=15.2, 10.2 Hz, 1H), 2.88-2.67 (m, 2H), 2.56-2.30 (m, 4H), 2.26-2.05 (m, 3H), 2.00-1.67 (m, 6H), 1.42 (t, J=12.3 Hz, 1H), 1.24-1.16 (m, 1H), 1.12 (d, J=6.5 Hz, 3H), 0.83-0.65 (m, 2H).

Example 172

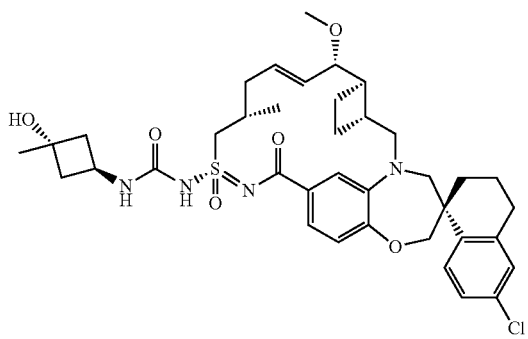 [SMILES: CO[C@H]1/C=C/C[C@H](C)C[S@@](=O)(NC(=O)N[C@H]2C[C@](C)(O)C2)=NC(=O)c2ccc3c(c2)N(C[C@@H]2CC[C@H]21)C[C@@]1(CCCc2cc(Cl)ccc21)CO3]

Example 172 was synthesized in the same manner as Example 75 using Example 109 and trans-3-amino-1-methylcyclobutan-1-ol HCl salt and DIEA. 1H NMR (400 MHz, Methanol-d4) δ 7.67 (d, J=8.5 Hz, 1H), 7.23 (d, J=8.1 Hz, 1H), 7.08 (s, 1H), 7.04-6.95 (m, 2H), 6.87 (d, J=8.1 Hz, 1H), 6.12-6.01 (m, 1H), 5.71-5.58 (m, 1H), 4.40-4.28 (m, 1H), 4.27-4.15 (m, 1H), 4.05-3.99 (m, 2H), 3.85-3.76 (m, 3H), 3.65 (d, J=14.3 Hz, 1H), 3.30 (s, 3H), 3.13-3.03 (m, 1H), 2.89-2.70 (m, 2H), 2.63-2.36 (m, 5H), 2.33-1.74 (m, 13H), 1.45-1.35 (m, 4H), 1.15 (d, J=6.6 Hz, 3H). LCMS-ESI+ (m/z): calcd H+ for $C_{38}H_{49}ClN_4O_6S$: 725.31; found: 724.80.

Example 173

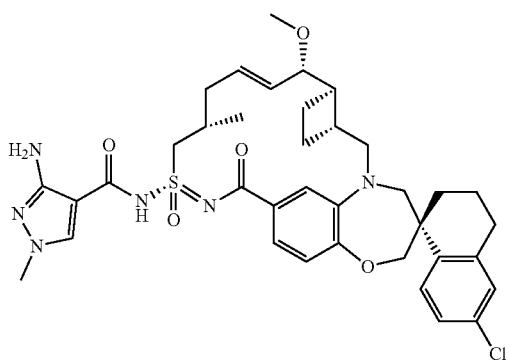 [SMILES: CO[C@H]1/C=C/C[C@H](C)C[S@@](=O)(NC(=O)c2cn(C)nc2N)=NC(=O)c2ccc3c(c2)N(C[C@@H]2CC[C@H]21)C[C@@]1(CCCc2cc(Cl)ccc21)CO3]

Example 173 was prepared in a similar manner to Example 18 using 3-amino-1-methyl-1H-pyrazole-4-carboxylic acid and Example 109. $^1$H NMR (400 MHz, Acetonitrile-d$_3$) δ 8.01 (s, 1H), 7.62 (d, J=8.5 Hz, 1H), 7.15 (d, J=8.5 Hz, 1H), 7.10 (d, J=2.3 Hz, 1H), 7.03 (s, 1H), 6.93 (d, J=2.0 Hz, 1H), 6.86 (d, J=8.3 Hz, 1H), 6.04-5.88 (m, 1H), 5.59 (dd, J=15.3, 8.8 Hz, 1H), 4.23 (dd, J=19.5, 8.9 Hz, 1H), 4.00 (s, 2H), 3.80-3.71 (m, 2H), 3.70 (s, 3H), 3.63 (s, 2H), 3.32 (d, J=14.2 Hz, 1H), 3.20 (s, 3H), 3.06 (dd, J=15.3, 10.5 Hz, 1H), 2.88-2.64 (m, 3H), 2.59-2.33 (m, 3H), 2.18 (d, J=10.6 Hz, 2H), 2.03 (d, J=13.9 Hz, 2H), 1.91 (d, J=4.1 Hz, 1H), 1.84-1.65 (m, 3H), 1.38 (t, J=7.3 Hz, 1H), 1.08 (d, J=6.1 Hz, 3H). LCMS-ESI (m/z): [M+H]+ calculated for $C_{37}H_{45}ClN_6O_5S$: 721.29; found: 721.0.

Example 174

Step 1: Preparation of 174-1

A solution of 3,4-dihydro-1H-pyrrolo[2,1-c][1,4]oxazine-7-carboxylic acid (1.1 g, 6.9 mmol) in DCM (12 mL) was added dropwise oxalyl chloride (1.3 g, 10.41 mmol) and then DMF (0.5 mL). The temperature of the mixture was maintained at 0° C. After addition was completed, stirring was continued at the same temperature for 60 min. Then the solvent was evaporated under reduced pressure. The resulting residue was dissolved in a solution of 2-methylpropan-2-ol (1.5 g, 20.8 mmol) in DCM (5 mL) and then stirred at room temperature for 30 min. After reaction was completed, the solvent was removed under reduced pressure and purified by normal phase chromatography (silica gel column, 0-100% EtOAc/Hexanes) to give 174-1.

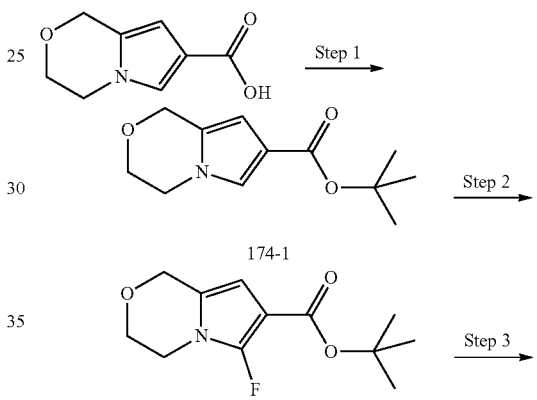

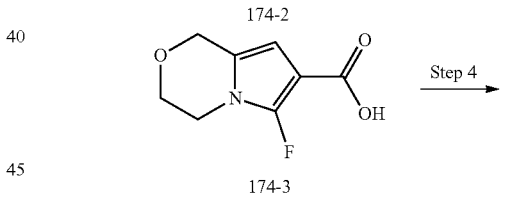

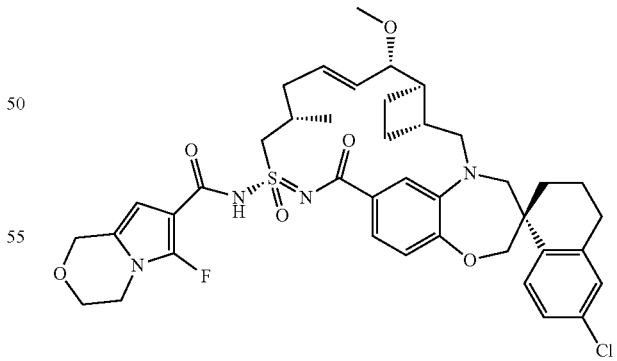

Example 174

Step 2: Preparation of 174-2

174-1 (0.4 g, 1.79 mmol) in ACN (10 mL) at 0° C. was added Selectfluor (0.63 g, 1.79 mmol). The reaction mixture was stirred at 0° C. for 2 h. A saturated aqueous solution of NaHCO₃ was added and the mixture was extracted with dichloromethane. The organic phase was dried over anhydrous magnesium sulfate, the solvent was removed under reduced pressure, and the residue was purified by normal phase chromatography (silica gel column, 0-100% EtOAc/hexanes) to give 174-2.

Step 3: Preparation of 174-3

174-2 (40 mg, 0.16 mmol) in DMC (4 mL) was added TFA (2 mL) and stirred at rt for 1 h. The reaction mixture was evaporated and used as crude for next step.

Step 4: Synthesis of Example 174

To a stirred solution of 174-3 (4.6 mg, 0.025 mmol) in DCM (5 mL), 1-(3-dimethylaminopropyl)-3-ethylcarbodiimide HCl (5.1 mg, 0.033 mmol) and 4-(dimethylamino)pyridine (4 mg, 0.033 mmol) were added. The reaction mixture was stirred for 10 minutes at room temperature and then Example 109 (10 mg, 0.017 mmol) was added. The reaction mixture was stirred at room temperature for 4 hr. Then the reaction mixture was diluted with DCM, washed with 1 N HCl and brine. The organic phase was dried over MgSO₄, filtered, and concentrated to yield Example 174. 1H NMR (400 MHz, Chloroform-d) δ 7.76 (d, J=8.5 Hz, 1H), 7.39 (d, J=8.5 Hz, 2H), 7.24-7.14 (m, 2H), 7.08 (s, 1H), 6.95 (d, J=8.3 Hz, 1H), 6.19 (d, 3.9 Hz, 1H), 6.06-5.89 (m, 1H), 5.61 (dd, J=15.5, 7.6 Hz, 1H), 4.74 (s, 1H), 4.17-3.99 (m, 3H), 3.98-3.68 (m, 5H), 3.29 (s, 1H), 3.01 (dd, J=15.1, 10.2 Hz, 2H), 2.79 (d, J=15.2 Hz, 2H), 2.59-2.25 (m, 3H), 2.19-1.59 (m, 9H), 1.41 (t, J=12.5 Hz, 1H), 1.28 (s, 1H), 1.13 (d, J=6.8 Hz, 3H). LCMS-ESI+ (m/z): [M+H]+ calcd for C₄₀H₄₆ClFN₄O₆S: 765.27; found: 765.25.

Example 175

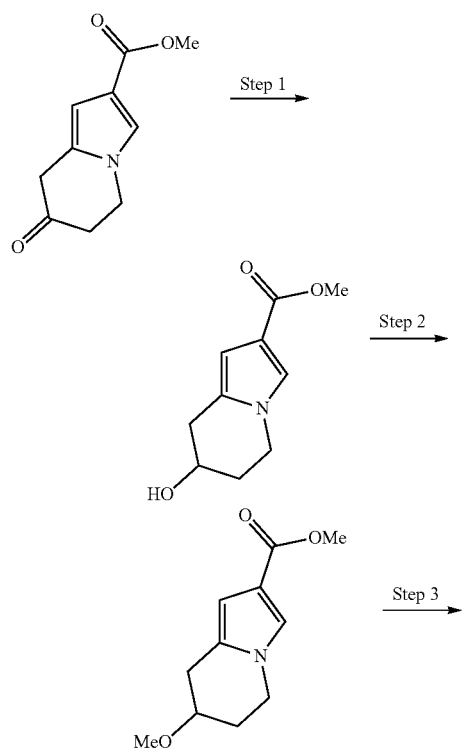

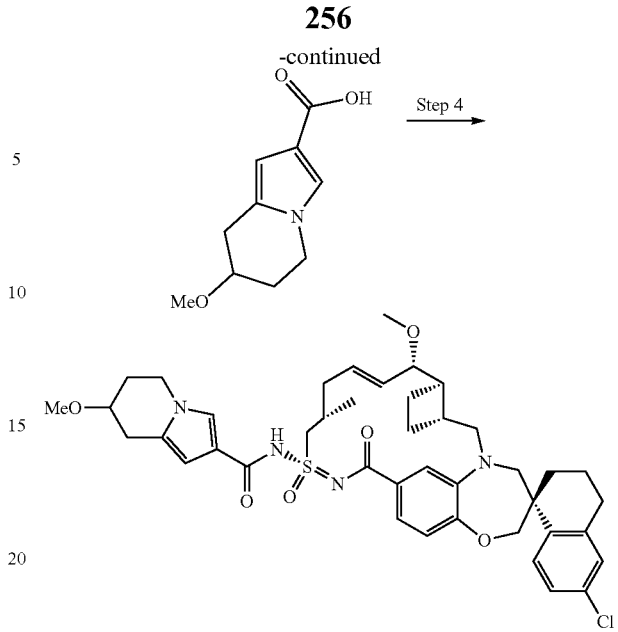

Step 1

Methyl 7-oxo-5,6,7,8-tetrahydroindolizine-2-carboxylate (50 mg, 0.26 mmol) was dissolved in MeOH (2.6 mL) and the reaction mixture was cooled to 0° C. Sodium borohydride (excess) was added in one portion as a solid. The reaction was monitored by TLC. Upon completion, the reaction mixture was concentrated under reduced pressure and the residue was purified via silica gel chromatography to afford methyl 7-hydroxy-5,6,7,8-tetrahydroindolizine-2-carboxylate.

Step 2

Methyl 7-hydroxy-5,6,7,8-tetrahydroindolizine-2-carboxylate (20 mg, 0.1 mmol) was dissolved in DMF and sodium hydride (60% oil dispersion, 10 mg) was added in one portion. The reaction mixture was stirred for 5 min before iodomethane (excess) was added via pipette. The progress of the reaction was monitored by TLC. Upon completion, the reaction mixture was diluted with EtOAc. The organic layer was washed with saturated NH₄Cl (1×) followed by brine (2×). The organic layer was dried over sodium sulfate, filtered, and concentrated under reduced pressure. The crude residue was used in the next step without further purification.

Step 3

Methyl 7-methoxy-5,6,7,8-tetrahydroindolizine-2-carboxylate was dissolved in 1:1 mixture of dioxane/1 N NaOH. The reaction mixture was heated to 80° C. for 1 hour before it was cooled to room temperature. The reaction mixture was washed with 1 N HCl and diluted with EtOAc. The organic layer was separated, dried over sodium sulfate, filtered, and concentrated under reduced pressure. The residue was used in the next step without further purification.

Step 4

Example 175 was synthesized in the same manner as Example 18 using 7-methoxy-5,6,7,8-tetrahydroindolizine- 2-carboxylic acid and Example 109. ¹H NMR (400 MHz, Chloroform-d) δ 7.73 (d, J=8.5 Hz, 1H), 7.37 (d, J=8.6 Hz, 1H), 7.31 (t, J=1.8 Hz, 1H), 7.17 (d, J=10.9 Hz, 2H), 7.08 (d, J=2.3 Hz, 1H), 6.93 (d, J=8.2 Hz, 1H), 6.36 (s, 1H), 5.98 (dt, J=14.1, 6.4 Hz, 1H), 5.59 (dd, J=15.5, 7.6 Hz, 1H), 4.21-3.91 (m, 6H), 3.92-3.71 (m, 4H), 3.41 (s, 3H), 3.29 (m, 4H), 3.05-2.68 (m, 5H), 2.56-2.26 (m, 5H), 2.13 (m, 4H), 2.01-1.79 (m, 3H), 1.80-1.61 (m, 3H), 1.39 (t, J=12.8 Hz, 1H), 1.09 (d, J=6.8 Hz, 3H). LCMS-ESI+(m/z): [M+H]+ calcd for $C_{42}H_{51}ClN_4O_6S$: 775; found: 774.9.

Example 176

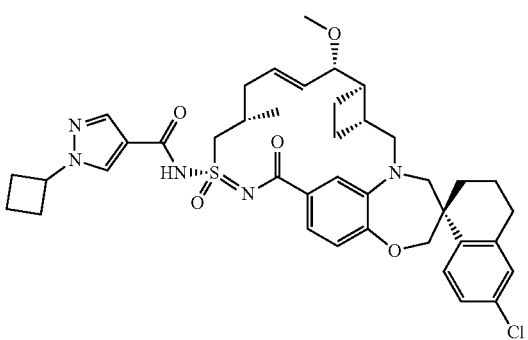 [SMILES: CO[C@H]1/C=C/C[C@H](C)C[S@@](=O)(NC(=O)c2cnn(C3CCC3)c2)=NC(=O)c2ccc3c(c2)N(C[C@@H]2CC[C@H]21)C[C@@]1(CCCc2cc(Cl)ccc21)CO3]

Example 176 was synthesized in the same manner as Example 18 using Example 109 and 1-cyclobutyl-1H-pyrazole-4-carboxylic acid. ¹H NMR (400 MHz, Methanol-d4) δ 8.21 (s, 1H), 7.97 (s, 1H), 7.79 (d, J=8.5 Hz, 1H), 7.28 (dd, J=8.1, 1.7 Hz, 1H), 7.19 (dd, J=8.5, 2.4 Hz, 1H), 7.11 (d, J=2.3 Hz, 1H), 6.97 (d, J=1.8 Hz, 1H), 6.84 (d, J=8.1 Hz, 1H), 6.18 (dt, J=13.9, 6.4 Hz, 1H), 5.49 (dd, J=15.2, 9.3 Hz, 1H), 4.84 (J=8.3 Hz, 1H), 4.48 (dd, J=14.0, 6.5 Hz, 1H), 4.09-3.99 (m, 2H), 3.99-3.87 (m, 2H), 3.82 (dd, J=9.4, 3.5 Hz, 1H), 3.66 (d, J=14.1 Hz, 1H), 3.29-3.22 (m, 4H), 3.02 (dd, J=15.1, 10.0 Hz, 1H), 2.88-2.69 (m, 2H), 2.67-2.45 (m, 5H), 2.39 (m, 1H), 2.13 (d, J=13.8 Hz, 1H), 2.09-2.00 (m, 2H), 2.00-1.85 (m, 5H), 1.85-1.64 (m, 3H), 1.43 (t, J=12.4 Hz, 1H), 1.04 (d, J=6.0 Hz, 3H). LCMS-ESI+: calc'd for $C_{40}H_{49}ClN_5O_5S$: 746.31 (M+H); found: 746.17 (M+H).

Example 177

Step 1

A vigorously stirred mixture of methyl 5-formyl-1H-pyrrole-3-carboxylate (1.50 g, 9.80 mmol), ethylene bromide (10.0 mL, 188 mmol), and potassium carbonate (1.62 g, 11.8 mmol) in acetonitrile (20.0 mL) was heated to 80° C. After 60 min, the reaction mixture was allowed to cool to room temperature and ethyl acetate (60 mL) was added. The organic layer was washed with a mixture of water and brine (1:1 v:v, 40 mL), dried over anhydrous sodium sulfate, filtered, and concentrated under reduced pressure. The residue was purified by flash column chromatography on silica gel (0 to 35% ethyl acetate in hexanes) to give 177-1.

Step 2

A vigorously stirred mixture of 177-1 (600 mg, 2.31 mmol) and sodium azide (240 mg, 3.69 mmol) in dimethyl sulfoxide (3.0 mL) was heated to 85° C. After 45 min, the resulting mixture was cooled to room temperature, and diethyl ether (120 mL) was added. The organic layer was washed with water (3×100 mL), dried over anhydrous magnesium sulfate, filtered, and concentrated under reduced pressure. The residue was dissolved in tetrahydrofuran (20 mL) and stirred at room temperature. Trimethylphosphine solution (1.0 M in tetrahydrofuran, 3.46 mL, 3.5 mmol) was added via syringe. After 39 min, the resulting mixture was cooled to 0° C. Sodium borohydride (349 mg, 9.23 mmol) and ethanol (20 mL) were added sequentially, and the resulting mixture was allowed to warm to room temperature. After 20 min, diethyl ether (100 mL) was added. The organic layer was extracted with a mixture of water and brine (1:1 v:v, 2×100 mL). Tetrahydrofuran (80 mL) and di-tert-butyl dicarbonate (1.51 g, 6.92 mmol) were added sequentially to the vigorously stirred combined aqueous layers at room temperature. After 60 min, the aqueous layer was extracted with dichloromethane (4×150 mL). The combined organic layers were dried over anhydrous magnesium sulfate, filtered, and concentrated under reduced pressure. The residue was purified by flash column chromatography on silica gel (0 to 50% ethyl acetate in hexanes) to give 177-2.

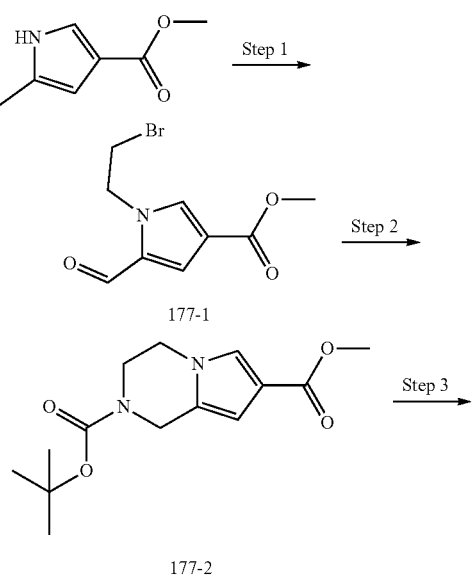

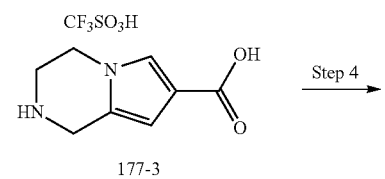

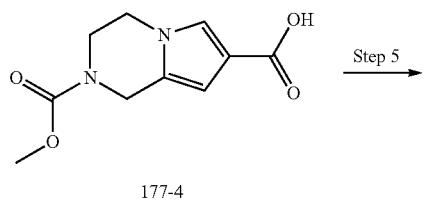

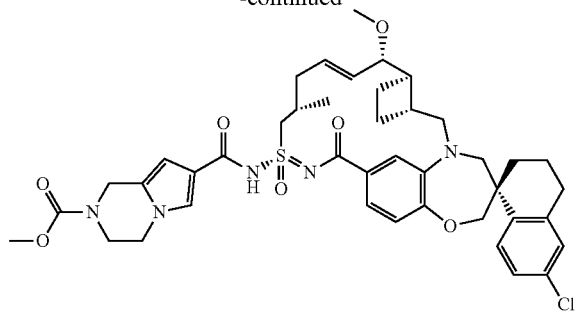

Example 177

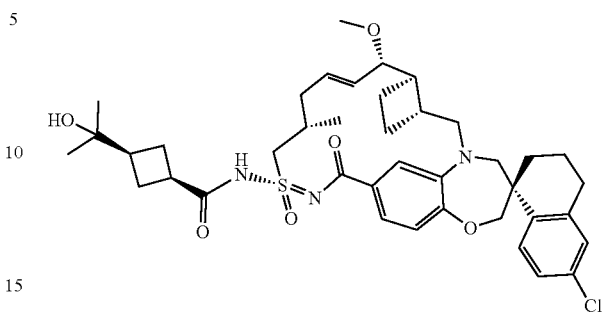

Example 178

Step 3

Aqueous sodium hydroxide solution (2.0 M, 1.47 mL, 2.9 mmol) was added via syringe to a stirred solution of 177-2 (514 mg, 1.83 mmol) in methanol (2.5 mL) and tetrahydrofuran (3.0 mL) at room temperature, and the resulting mixture was heated to 70° C. After 2 h, the resulting mixture was cooled to room temperature, and aqueous hydrogen chloride solution (2.0 M, 5 mL), brine (30 mL), and water (10 mL) were added sequentially. The aqueous layer was extracted with dichloromethane (2×60 mL). The combined organic layers were dried over anhydrous magnesium sulfate, filtered, and concentrated under reduced pressure. The residue was dissolved in benzene (30 mL), and the resulting mixture was concentrated under reduced pressure. The residue was dissolved in dichloromethane (6 mL) at room temperature, 2,6-lutidine (854 μL, 7.33 mmol) was added via syringe, and the resulting mixture was stirred. Trimethylsilyl trifluoromethanesulfonate (995 μL, 5.50 mmol) was added via syringe. After 10 min, methanol (10.0 mL) was added via syringe. After 10 min, the resulting mixture was concentrated under reduced pressure, and the residue was dissolved in benzene (10 mL). The resulting mixture was concentrated under reduced pressure to give 177-3.

Step 4

Methyl chloroformate (50.5 μL, 791 μmol) was added via syringe to a stirred mixture of 177-3 (50.0 mg, 158 μmol) and triethylamine (353 μL, 2.53 mmol) in dichloromethane at room temperature. After 10 min, trifluoroacetic acid (0.2 mL) was added, and the resulting mixture was purified by flash column chromatography on silica gel (0 to 8% methanol in dichloromethane) to give 177-4.

Step 5: Preparation of Example 177

Example 177 was synthesized in a manner similar to Example 109 using 177-4 instead of 2-((tetrahydro-2H-pyran-4-yl)oxy)acetic acid. 1H NMR (400 MHz, Acetone-d6) δ 7.77 (d, J=8.5 Hz, 1H), 7.51 (s, 1H), 7.34 (d, J=8.2 Hz, 1H), 7.29-7.19 (m, 2H), 7.14 (d, J=2.3 Hz, 1H), 6.92 (d, J=8.2 Hz, 1H), 6.43 (s, 1H), 6.21-6.07 (m, 1H), 5.64 (dd, J=15.5, 7.9 Hz, 1H), 4.66 (s, 2H), 4.17 (s, 2H), 4.11 (d, J=12.0 Hz, 1H), 4.04 (d, J=12.1 Hz, 1H), 4.01-3.65 (m, 6H), 3.72 (s, 3H), 3.44 (d, J=14.4 Hz, 1H), 3.25 (s, 3H), 3.15 (dd, J=15.2, 10.2 Hz, 1H), 2.89-1.21 (m, 16H), 1.14 (d, J=6.4 Hz, 3H). LCMS: 804.0.

Example 178 was synthesized in the same manner as Example 18 using Example 109 and 3-(1-hydroxy-1-methyl-ethyl)cyclobutanecarboxylic acid. 1H NMR (400 MHz, Methanol-d4) δ 7.76 (d, J=8.5 Hz, 1H), 7.32 (dd, J=8.2, 1.8 Hz, 1H), 7.22-7.15 (m, 1H), 7.14-7.07 (m, 2H), 6.88 (d, J=8.2 Hz, 1H), 6.14 (dt, J=14.5, 6.9 Hz, 1H), 5.61 (dd, J=15.3, 8.5 Hz, 1H), 4.17 (dd, J=14.7, 6.7 Hz, 1H), 4.11-4.01 (m, 2H), 3.98 (dd, J=14.9, 5.2 Hz, 1H), 3.85 (d, J=15.0 Hz, 1H), 3.77 (d, J=8.9 Hz, 1H), 3.69 (d, J=14.3 Hz, 1H), 3.29 (s, 3H), 3.11-3.00 (m, 2H), 2.89-2.75 (m, 2H), 2.51-2.40 (m, 3H), 2.36-2.23 (m, 4H), 2.18-2.06 (m, 4H), 2.01-1.72 (m, 7H), 1.49-1.40 (m, 1H), 1.14-1.09 (m, 9H). LCMS-ESI+ (m/z): calcd H+ for $C_{40}H_{52}ClN_3O_6S$: 738.33; found: 738.03.

Example 179

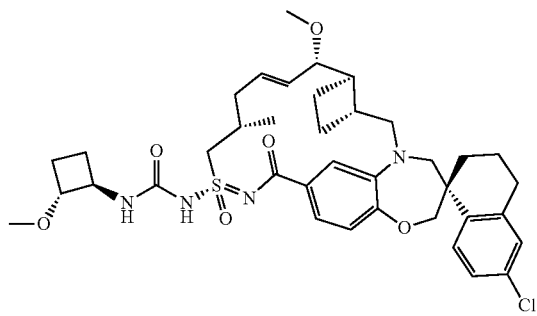 [SMILES: CO[C@H]1/C=C/C[C@H](C)C[S@@](=O)(NC(=O)N[C@@H]2CC[C@H]2OC)=NC(=O)c2ccc3c(c2)N(C[C@@H]2CC[C@H]21)C[C@@]1(CCCc2cc(Cl)ccc21)CO3]

Example 179 was synthesized in the same manner as Example 75 using Example 109 and trans-2-methoxycyclobutanamine HCl salt and DIEA. 1H NMR (400 MHz, methanol-d4) δ 7.77-7.67 (m, 1H), 7.21 (d, J=8.4 Hz, 1H), 7.17-7.07 (m, 2H), 6.99 (s, 1H), 6.90 (dd, J=8.1, 3.6 Hz, 1H), 6.11-5.99 (m, 1H), 5.60 (t, J=12.5 Hz, 1H), 4.31-4.21 (m, 1H), 4.09-4.01 (m, 3H), 3.88-3.64 (m, 6H), 3.28 (s, 3H), 3.08 (dd, J=15.2, 10.1 Hz, 1H), 2.89-2.71 (m, 2H), 2.56-2.33 (m, 3H), 2.25-2.02 (m, 6H), 2.02-1.71 (m, 7H), 1.59-1.36 (m, 4H), 1.13 (d, J=6.5 Hz, 3H). LCMS-ESI+ (m/z): calcd H+ for $C_{38}H_{49}ClN_4O_6S$: 725.31; found: 724.85.

Example 180

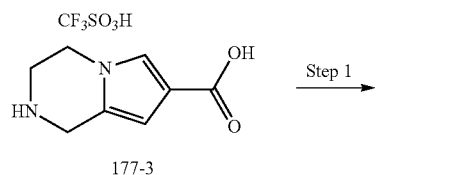

177-3

Step 1 →

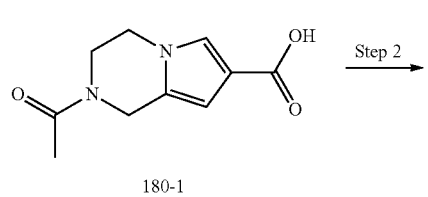

180-1

Step 2 →

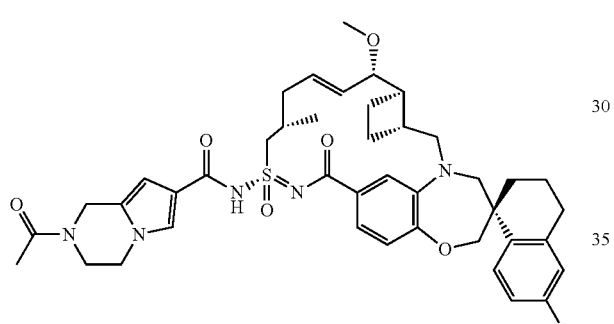

Example 180

Step 1

Acetic anhydride (74.7 μL, 791 μmol) was added via syringe to a stirred mixture of 177-3 (50.0 mg, 158 μmol) and triethylamine (353 μL, 2.53 mmol) in dichloromethane at room temperature. After 10 min, the resulting mixture was concentrated under reduced pressure. The residue was purified by reverse phase preparative hplc (0.1% trifluoroacetic acid in acetonitrile/water) to give 180-1.

Step 2

Example 180 was synthesized in a manner similar to Example 109 using 180-1 instead of 2-((tetrahydro-2H-pyran-4-yl)oxy)acetic acid. 1H NMR (400 MHz, Acetone-d6) δ 7.78 (d, J=8.5 Hz, 1H), 7.52 (s, 1H), 7.34 (d, J=8.3 Hz, 1H), 7.28-7.18 (m, 2H), 7.14 (d, J=2.3 Hz, 1H), 6.93 (d, J=8.2 Hz, 1H), 6.43 (d, J=1.8 Hz, 1H), 6.19-6.06 (m, 1H), 5.64 (dd, J=15.4, 7.9 Hz, 1H), 4.80 (s, 0.92H), 4.69 (s, 1.08H), 4.34-3.60 (m, 10H), 3.44 (d, J=14.5 Hz, 1H), 3.25 (s, 3H), 3.15 (dd, J=15.1, 10.2 Hz, 1H), 2.90-1.23 (m, 19H), 1.18-1.09 (m, 3H). LCMS: 788.0.

Example 181

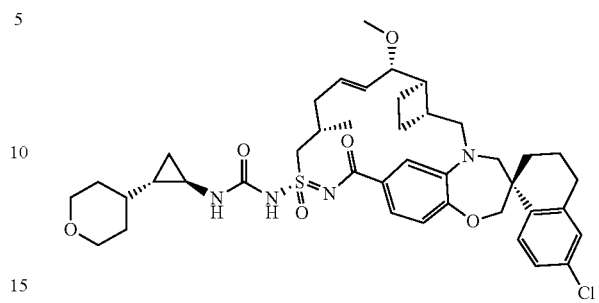

Example 181 was synthesized in the same manner as Example 75 using Example 109 and (1R,2S)-2-tetrahydro-pyran-4-ylcyclopropanamine HCl salt and DIEA. 1H NMR (400 MHz, Methanol-d4) δ 7.75-7.67 (m, 1H), 7.26-7.16 (m, 1H), 7.13-7.05 (m, 2H), 6.99 (s, 1H), 6.89 (d, J=8.2 Hz, 1H), 6.12-6.00 (m, 1H), 5.62 (dd, J=15.3, 8.9 Hz, 1H), 4.30-4.19 (m, 1H), 4.10-4.00 (m, 2H), 4.00-3.91 (m, 2H), 3.83 (d, J=14.8 Hz, 1H), 3.78 (dd, J=8.9, 3.4 Hz, 1H), 3.67 (d, J=14.2 Hz, 1H), 3.44-3.37 (m, 1H), 3.29 (s, 3H), 3.12-3.03 (m, 1H), 2.88-2.73 (m, 2H), 2.57-2.37 (m, 4H), 2.28-2.07 (m, 3H), 2.01-1.72 (m, 8H), 1.71-1.62 (m, 1H), 1.57-1.36 (m, 4H), 1.14 (d, J=6.6 Hz, 3H), 1.03-0.90 (m, 2H), 0.86-0.75 (m, 1H), 0.75-0.62 (m, 2H). LCMS-ESI+ (m/z): calcd H+ for $C_{41}H_{53}ClN_4O_6S$: 765.34; found: 764.86.

Example 182

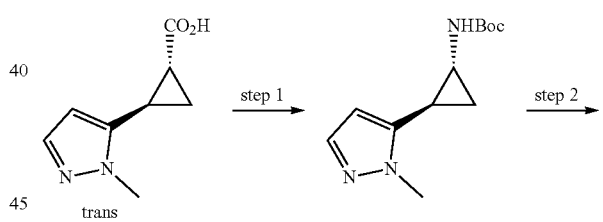

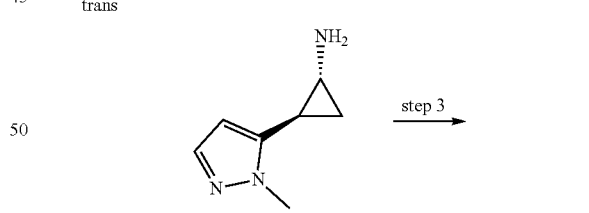

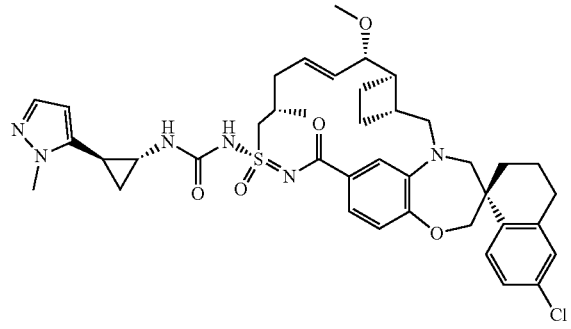

Step 1: Preparation of rac-tert-butyl ((1R,2R)-2-(1-methyl-1H-pyrazol-5-yl)cyclopropyl)carbamate The reaction mixture of trans-rac-(1R,2R)-2-(1-methyl-1H-pyrazol-5-yl)cyclopropane-1-carboxylic (70 mg, 0.42 mmol), diphenyl phosphoryl azide (0.095 mL, 0.44 mmol) and triethylamine (0.065 mL, 0.46 mmol) in toluene (1.0 mL) was heated at 100° C. for 2 h. Then the reaction mixture was cooled to rt and to the mixture was added t-butanol (0.2 mL, 2 mmol). The mixture was stirred at rt overnight. The reaction mixture was concentrated, and the residue was purified by silica gel column chromatography (0-100% EtOAc/hexane) to give the product (25 mg).

Step 2: Preparation of rac-(1R,2R)-2-(1-methyl-1H-pyrazol-5-yl)cyclopropane-1-amine The reaction mixture of rac-tert-butyl ((1R,2R)-2-(1-methyl-1H-pyrazol-5-yl)cyclopropyl)carbamate (85 mg, 0.36 mmol) in DCM (2.0 mL) and TFA (0.5 mL) was stirred at rt. After the reaction was finished, the reaction mixture was concentrated, and the residue was used in the next step without purification.

Step 3: Preparation of Example 182

The reaction mixture of Example 109 (16 mg, 0.027 mmol), diphenyl carbonate (36 mg, 0.168 mmol) and 4-dimethylaminopyridine (13.07 mg, 0.107 mol) in ACN (1.5 mL) was stirred at rt for 7 h. To the mixture was added triethylamine (0.19 mL, 1.34 mmol) and rac-(1R,2R)-2-(1-methyl-1H-pyrazol-5-yl)cyclopropan-1-amine (36.7 mg, 0.27 mmol). The reaction mixture was stirred at 45° C. overnight. The reaction mixture was concentrated, the residue was purified by reverse phase HPLC (60-100% CAN/H2O, with 0.1% TFA) to give the product (10 mg). 1H NMR (400 MHz, Methanol-d4) δ 7.69 (t, J=8.8 Hz, 1H), 7.37 (d, J=1.9 Hz, 1H), 7.20 (d, J=8.2 Hz, 1H), 7.10 (s, 2H), 6.97 (s, 1H), 6.94-6.76 (m, 1H), 6.19-5.94 (m, 2H), 5.62 (d, J=13.6 Hz, 1H), 4.38-4.18 (m, 1H), 4.13-3.92 (m, 4H), 3.80 (dd, J=22.8, 12.1 Hz, 3H), 3.66 (d, J=14.3 Hz, 1H), 3.29 (d, J=3.7 Hz, 3H), 3.08 (dd, J=15.3, 9.9 Hz, 1H), 2.81 (q, J=14.8, 11.3 Hz, 3H), 2.50 (d, J=35.6 Hz, 3H), 2.34-2.14 (m, 2H), 2.14-1.87 (m, 5H), 1.80 (d, J=8.1 Hz, 3H), 1.56-1.18 (m, 5H), 1.23-1.03 (m, 3H). LCMS-ESI+ (m/z): [M+H]+ calcd for $C_{40}H_{49}ClN_6O_5S$: 761.32; found: 760.53.

Example 183 and Example 184

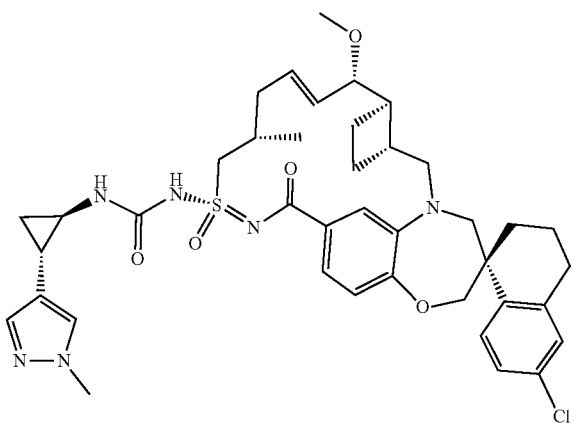

Example 183

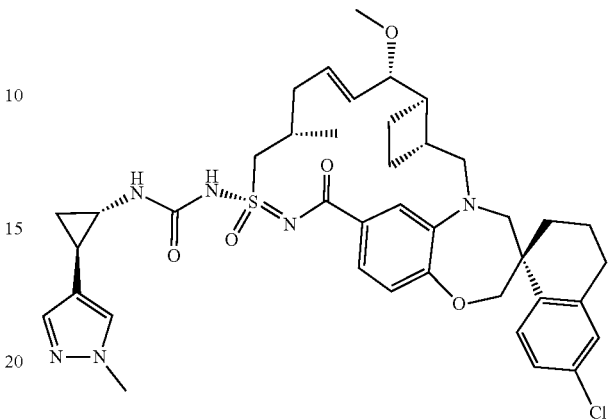

Example 184

Example 183 and example 184 were synthesized in the same manner as Example 182, using rac-(1R,2S)-2-(1-methylpyrazol-4-yl)cyclopropanamine instead of rac-(1R,2R)-2-(1-methyl-1H-pyrazol-5-yl)cyclopropan-1-amine. The mixture of HPLC purified product was separated by chiral SFC separation to give example 183 and example 184. The structure for each compound was arbitrary assigned.

Example 183

1H NMR (400 MHz, Methanol-d4) δ 7.74 (d, J=8.6 Hz, 1H), 7.45 (s, 1H), 7.36 (s, 1H), 7.24-7.09 (m, 3H), 6.99 (s, 1H), 6.91 (d, J=8.2 Hz, 1H), 6.02 (s, 1H), 5.59 (dd, J=15.2, 8.9 Hz, 1H), 4.27 (dd, J=15.0, 6.4 Hz, 1H), 4.17-4.01 (m, 2H), 3.85 (s, 3H), 3.77 (dd, J=8.9, 3.6 Hz, 2H), 3.68 (d, J=14.1 Hz, 1H), 3.27 (s, 3H), 3.08 (dd, J=15.2, 10.2 Hz, 1H), 2.89-2.70 (m, 3H), 2.65 (s, 1H), 2.48 (d, J=7.8 Hz, 2H), 2.39 (d, J=9.2 Hz, 1H), 2.28-2.08 (m, 3H), 2.08-1.99 (m, 1H), 1.96 (s, 2H), 1.80 (ddd, J=29.3, 20.8, 9.4 Hz, 4H), 1.44 (t, J=12.3 Hz, 1H), 1.34-1.22 (m, 1H), 1.14 (s, 3H), 1.04 (q, J=6.3 Hz, 2H). LCMS-ESI+ (m/z): [M+H]+ calcd for $C_{40}H_{49}ClN_6O_5S$: 761.32; found: 760.96.

Example 184

1H NMR (400 MHz, Methanol-d4) δ 7.71 (d, J=8.3 Hz, 1H), 7.42 (s, 1H), 7.34 (s, 1H), 7.21 (d, J=8.3 Hz, 1H), 7.10 (s, 2H), 6.98 (s, 1H), 6.89 (d, J=8.2 Hz, 1H), 6.05 (d, J=15.1 Hz, 1H), 5.62 (dd, J=14.8, 8.6 Hz, 1H), 4.25 (dd, J=14.5, 6.5 Hz, 1H), 4.18-3.96 (m, 2H), 3.90-3.72 (m, 4H), 3.67 (d, J=14.2 Hz, 1H), 3.29 (s, 3H), 3.08 (dd, J=15.1, 10.0 Hz, 1H), 2.92-2.70 (m, 2H), 2.66 (dt, J=7.5, 3.9 Hz, 1H), 2.46 (dd, J=30.1, 19.3 Hz, 3H), 2.32-2.14 (m, 2H), 2.14-1.93 (m, 4H), 1.93-1.66 (m, 4H), 1.50-1.23 (m, 4H), 1.23-1.09 (m, 3H), 1.04 (q, J=6.3 Hz, 2H). LCMS-ESI+ (m/z): [M+H]+ calcd for $C_{40}H_{49}ClN_6O_5S$: 761.32; found: 761.90.

Example 185

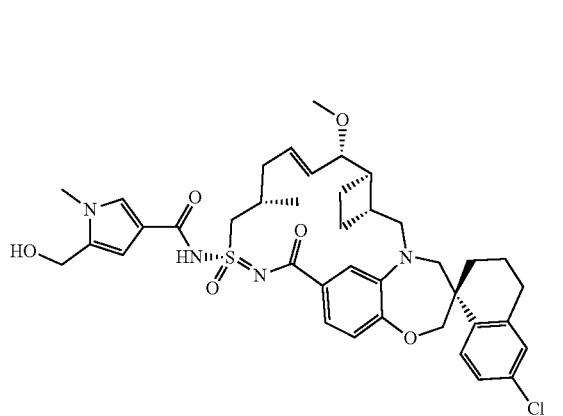 [SMILES: CO[C@H]1/C=C/C[C@H](C)C[S@@](=O)(NC(=O)c2cc(CO)n(C)c2)=NC(=O)c2ccc3c(c2)N(C[C@@H]2CC[C@H]21)C[C@@]1(CCCc2cc(Cl)ccc21)CO3]

3-(Ethyliminomethyleneamino)-N,N-dimethyl-propan-1-amine hydrochloride (9.6 mg, 0.050 mmol), and 4-(dimethylamino)pyridine (6.1 mg, 0.050 mmol) were added to a solution of 5-formyl-1-methyl-pyrrole-3-carboxylic acid (5.1 mg, 0.033 mmol) in dichloromethane (1 mL). After 5 minutes, Example 109 (10 mg, 0.016 mmol) was added. After 17 h the reaction was diluted with ethyl acetate (8 mL) and washed with water (5 mL) and saturated ammonium chloride (5 mL). The organic phase was dried over sodium sulfate and the solvent was removed under reduced pressure. The residue was taken up in methanol (2 mL), and sodium borohydride (1.0 mg, 0.024 mmol) was added. After 3 h the reaction was diluted with ethyl acetate (8 mL) and washed with saturated sodium bicarbonate (5 mL) and saturated ammonium chloride (5 mL). The organic phase was dried over sodium sulfate. The solvent was removed under reduced pressure. The residue was subjected to flash chromatography (0-100% ethyl acetate/hexanes followed by 20% methanol/ethyl acetate flush). The clean fractions containing product were combined and the solvent was removed under reduced pressure. The residue was co-evaporated with acetonitrile. The residue was taken up in acetonitrile (2 mL) and water (2 mL). The solution was subjected to lyophilization, providing Example 185. $^1$H NMR (400 MHz, Methanol-d4) δ 7.78 (d, J=8.5 Hz, 1H), 7.44 (d, J=1.9 Hz, 1H), 7.30 (dd, J=8.1, 1.8 Hz, 1H), 7.18 (dd, J=8.5, 2.4 Hz, 1H), 7.11 (d, J=2.3 Hz, 1H), 7.07-6.98 (m, 1H), 6.86 (d, J=8.1 Hz, 1H), 6.58 (t, J=1.7 Hz, 1H), 6.16 (dt, J=13.9, 6.5 Hz, 1H), 5.53 (dd, J=15.3, 9.0 Hz, 1H), 4.56 (d, J=10.2 Hz, 2H), 4.48-4.30 (m, 1H), 4.12-3.99 (m, 2H), 3.96 (d, J=13.5 Hz, 1H), 3.88 (d, J=14.9 Hz, 1H), 3.81 (dd, J=9.0, 3.1 Hz, 1H), 3.72 (d, J=2.1 Hz, 3H), 3.67 (d, J=14.2 Hz, 1H), 3.27 (s, 4H), 3.04 (dd, J=15.1, 9.5 Hz, 1H), 2.89-2.69 (m, 2H), 2.57 (m, 1H), 2.51-2.35 (m, 2H), 2.12 (d, J=12.1 Hz, 3H), 2.04-1.86 (m, 2H), 1.77 (ddt, J=24.2, 17.1, 9.1 Hz, 3H), 1.51-1.35 (m, 1H), 1.07 (d, J=5.9 Hz, 3H), 0.91 (d, J=6.3 Hz, 1H). LCMS-ESI+: calc'd for $C_{39}H_{48}ClN_4O_6S$: 735.29 (M+H); found: 735.07 (M+H).

Example 186

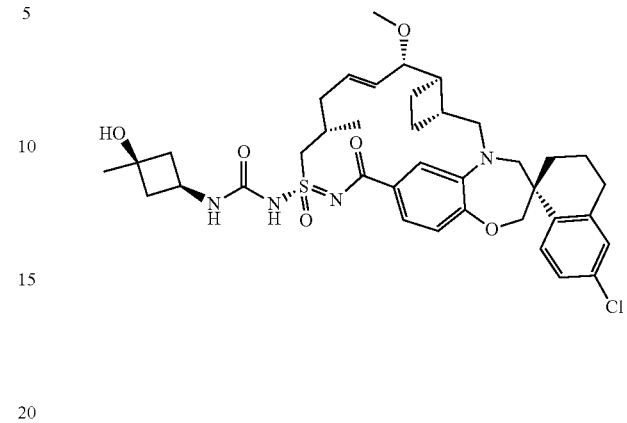

Example 186 was synthesized in the same manner as Example 75 using Example 109 and cis-3-amino-1-methyl-cyclobutan-1-ol and DIEA. 1H NMR (400 MHz, Methanol-d4) δ 7.69 (d, J=9.0 Hz, 1H), 7.19 (d, J=8.2 Hz, 1H), 7.10-7.02 (m, 2H), 6.98 (s, 1H), 6.86 (d, J=8.2 Hz, 1H), 6.08-5.97 (m, 1H), 5.58 (dd, J=15.4, 8.7 Hz, 1H), 4.26-4.16 (m, 1H), 4.06-3.97 (m, 2H), 3.85-3.71 (m, 4H), 3.64 (d, J=14.1 Hz, 1H), 3.26 (s, 3H), 3.09-3.01 (m, 1H), 2.86-2.71 (m, 2H), 2.52-2.36 (m, 5H), 2.23-1.90 (m, 9H), 1.81-1.70 (m, 3H), 1.45-1.37 (m, 1H), 1.33 (s, 3H), 1.11 (d, J=6.6 Hz, 3H). LCMS-ESI+ (m/z): calcd H+ for $C_{38}H_{49}ClN_4O_6S$: 725.31, Found: 724.78.

Example 187

Example 187 was synthesized in the same manner as Example 18 using 3-ethyl-1-methyl-1H-pyrazole-4-carboxylic acid and Example 109. $^1$H NMR (400 MHz, Methanol-d$_4$) δ 8.39 (s, 1H), 7.62 (d, J=8.4 Hz, 1H), 7.29 (d, J=8.3 Hz, 1H), 7.06 (s, 1H), 6.98 (d, J=1.9 Hz, 1H), 6.91 (s, 1H), 6.84 (d, J=8.2 Hz, 1H), 6.12 (d, J=15.4 Hz, 1H), 5.67 (dd, J=15.4, 8.5 Hz, 1H), 4.22 (s, 1H), 4.00 (s, 2H), 3.87 (s, 3H), 3.80 (d, J=10.8 Hz, 2H), 3.64 (d, J=14.4 Hz, 1H), 3.41 (d, J=14.5 Hz, 1H), 3.35 (m, 2H), 3.32 (s, 3H), 3.11 (dt, J=15.0, 8.3 Hz, 1H), 2.80 (tdd, J=22.6, 15.1, 8.6 Hz, 5H), 2.47 (s, 2H), 2.29 (s, 2H), 2.25-2.05 (m, 2H), 1.90 (d, J=47.6 Hz, 4H), 1.38 (t, J=12.9 Hz, 1H), 1.26-1.10 (m, 6H). LCMS-ESI+ (m/z): [M+H]+ calcd for $C_{39}H_{48}ClN_5O_5S$: 734.3; found: 734.0.

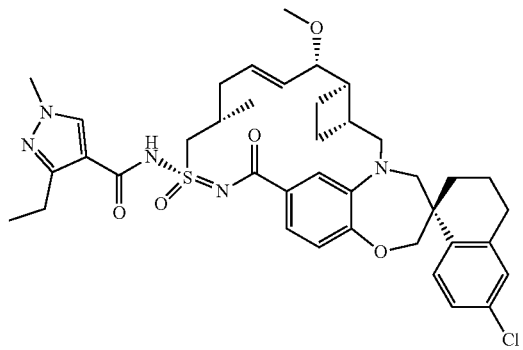 [SMILES: CCc1nn(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Example 188

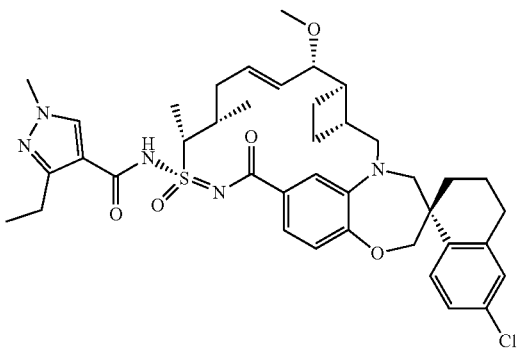 [SMILES: CCc1nn(C)cc1C(=O)N[S@@]1(=O)=NC(=O)c2ccc3c(c2)N(C[C@@H]2CC[C@H]2[C@@H](OC)/C=C/C[C@H](C)[C@H]1C)C[C@@]1(CCCc2cc(Cl)ccc21)CO3]

Example 188 was synthesized in the same manner as Example 18 using 3-methoxy-1-methyl-1H-pyrazole-4-carboxylic acid and Example 110. $^1$H NMR (400 MHz, Methanol-$d_4$) δ 7.93 (s, 1H), 7.75 (d, J=8.5 Hz, 1H), 7.18 (dd, J=8.5, 2.5 Hz, 1H), 7.12 (d, J=2.3 Hz, 1H), 6.99 (d, J=16.9 Hz, 1H), 6.93 (d, J=8.2 Hz, 1H), 6.00 (m, 1H), 5.58 (dd, J=15.3, 8.9 Hz, 1H), 4.38 (d, J=7.5 Hz, 1H), 4.09 (s, 2H), 3.96 (s, 3H), 3.84 (d, J=15.0 Hz, 1H), 3.78 (s, 3H), 3.72 (dd, J=8.9, 3.1 Hz, 1H), 3.66 (d, J=14.3 Hz, 1H), 3.35 (m, 2H), 3.24 (s, 3H), 3.17-3.05 (m, 1H), 2.89-2.72 (m, 2H), 2.52-2.06 (m, 6H), 2.05-1.70 (m, 6H), 1.60 (d, J=7.0 Hz, 3H), 1.52-1.41 (m, 1H), 1.19 (d, J=6.8 Hz, 3H). LCMS-ESI+ (m/z): [M+H]+ calcd for $C_{39}H_{48}ClN_5O_6S$: 750.3; found: 749.9.

Example 189

Example 189 was synthesized in the same manner as Example 75 using trans-(3-aminocyclobutyl)methanol and Example 109. $^1$H NMR (400 MHz, Acetone-$d_6$) δ 7.69 (d, J=8.2 Hz, 1H), 7.24 (d, J=8.4 Hz, 1H), 7.08 (d, J=10.1 Hz, 4H), 6.87 (d, J=8.2 Hz, 1H), 6.08 (d, J=14.8 Hz, 1H), 5.72-5.54 (m, 1H), 4.32 (q, J=7.8 Hz, 1H), 4.18-3.95 (m, 3H), 3.90-3.65 (m, 4H), 3.60 (d, J=6.7 Hz, 2H), 3.41 (d, J=14.5 Hz, 1H), 3.24 (s, 3H), 3.13 (dd, J=15.2, 10.0 Hz, 1H), 2.78 (dt, J=25.3, 16.7 Hz, 2H), 2.51 (d, J=33.4 Hz, 3H), 2.40-1.65 (m, 9H), 1.45-1.35 (m, 1H), 1.13 (d, J=6.2 Hz, 3H). LCMS-ESI+ (m/z): [M+H]+ calcd for $C_{38}H_{50}ClN_4O_6S$: 725.31; found: 724.79.

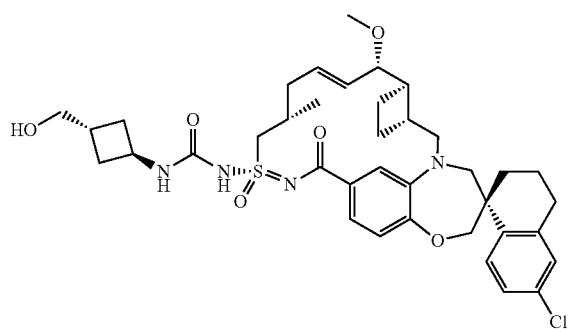 [SMILES: CO[C@H]1/C=C/C[C@H](C)C[S@@](=O)(NC(=O)N[C@H]2C[C@H](CO)C2)=NC(=O)c2ccc3c(c2)N(C[C@@H]2CC[C@H]21)C[C@@]1(CCCc2cc(Cl)ccc21)CO3]

Example 190

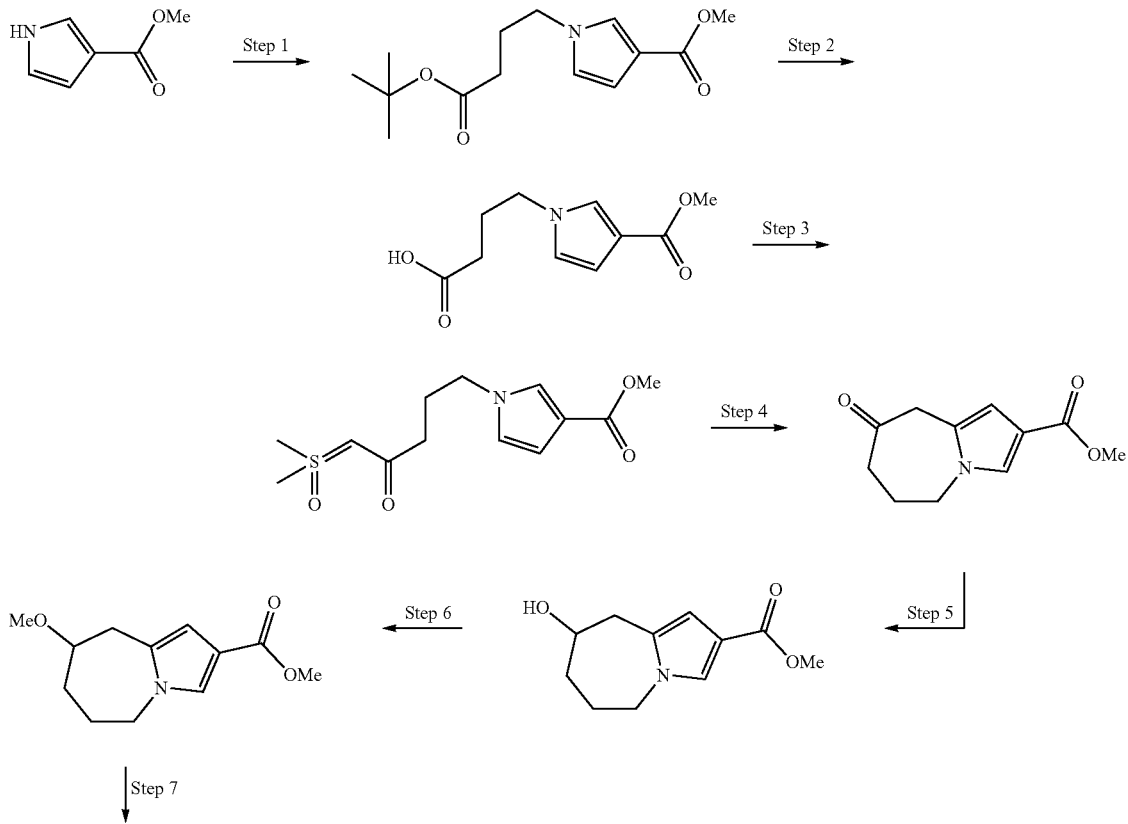

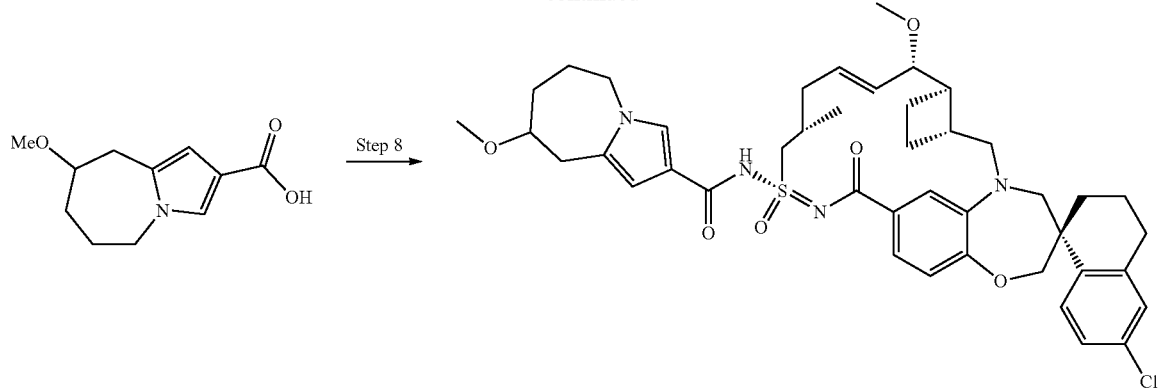

Step 1

Methyl 1H-pyrrole-3-carboxylate (1.0 g, 7.99 mmol) was dissolved in DMF (15 mL), and the reaction mixture was cooled to 0° C. via an ice bath. Sodium hydride (480 mg, 60% oil dispersion, 12 mmol, 1.5 equiv.) was added portionwise. The reaction mixture was stirred at that temperature for 15 min and then heated to 55° C. for an hour. Tert-butyl 4-bromobutanoate (2.23 g, 10 mmol, 1.25 equiv.) was added via syringe. The reaction mixture was heated to 60° C. and progress of the reaction was monitored by TLC (1:2 EtOAc: Hexanes). Upon completion, the reaction was cooled to room temperature. The reaction mixture was diluted with EtOAc (100 mL) and washed with water (40 mL) then brine (40 mL). The organic layer was dried over sodium sulfate, filtered and concentrated under reduced pressure. The residue was purified via column chromatography (100% hexanes→1:1 EtOAc:Hexanes) to afford methyl 1-(4-(tert-butoxy)-4-oxobutyl)-1H-pyrrole-3-carboxylate.

Step 2

Methyl 1-(4-(tert-butoxy)-4-oxobutyl)-1H-pyrrole-3-carboxylate (1 g, 3.7 mmol) was dissolved in a 1:3 solution of trifluoroacetic acid (5 mL) and dichloromethane (15 mL) at room temperature. The reaction mixture was stirred at room temperature for 24 hours then concentrated under reduced pressure. The residue was azeotroped with toluene (40 mL) to afford 4-(3-(methoxycarbonyl)-1H-pyrrol-1-yl)butanoic acid (785 mg, 99%).

Step 3

To a suspension of 4-(3-(m ethoxy carbonyl)-1H-pyrrol-1-yl)butanoic acid (900 mg, 4.26 mmol) and HATU (1620 mg, 4.26 mmol, 1 equiv.) in THF (12 mL) was added trimethylamine (1293 mg, 12.78 mmol, 3 equiv.). The reaction mixture was stirred for 24 hours at room temperature. In a separate vessel, a suspension of trimethylsulfoxonium chloride (1.64 g, 12.78 mmol, 3 equiv.) and potassium tert-butoxide (1.43 g, 12.78 mmol, 3 equiv.) were heated to 60° C. via a metal block for 1.5 h. The heating block was then removed and the reaction mixture was cooled to 0° C. for 15 min via an ice bath. The HATU adduct was then added dropwise via syringe over 10 min, during which the reaction mixture turned dark red. The reaction mixture was stirred for an additional 1 h at 0° C. before it was concentrated under reduced pressure. The crude material was purified via silica gel chromatography (5% MeOH/DCM) to afford methyl 1-(5-(dimethyl(oxo)-$\lambda^6$-sulfanylidene)-4-oxopentyl)-1H-pyrrole-3-carboxylate.

Step 4

Methyl 1-(5-(dimethyl(oxo)-$\lambda^6$-sulfanylidene)-4-oxopentyl)-1H-pyrrole-3-carboxylate (315 mg, 1.104 mmol) and Chloro(1,5-cyclooctadiene) Iridium (I) dimer (74 mg, 0.11 mmol, 0.1 equiv.) were dissolved in 1,2-dichloroethane (25 mL). The reaction mixture was sparged with an atmospheric stream of argon for 10 min before it was heated to 80° C. for about 10 min, during which the reaction mixture turned green. The reaction mixture was concentrated under reduced pressure and the crude residue was purified via silica gel chromatography for afford methyl 8-oxo-6,7,8,9-tetrahydro-5H-pyrrolo[1,2-a]azepine-2-carboxylate.

Step 5

Methyl 8-oxo-6,7,8,9-tetrahydro-5H-pyrrolo[1,2-a]azepine-2-carboxylate (50 mg, 0.24 mmol) was dissolved in MeOH (2.4 mL) and the reaction mixture was cooled to 0° C. Sodium borohydride (excess) was added in one portion as a solid. The reaction was monitored by TLC. Upon completion, the reaction mixture was concentrated under reduced pressure and the residue was purified via silica gel chromatography afford methyl 8-hydroxy-6,7,8,9-tetrahydro-5H-pyrrolo[1,2-a]azepine-2-carboxylate.

Step 6

8-Hydroxy-6,7,8,9-tetrahydro-5H-pyrrolo[1,2-a]azepine-2-carboxylate (23 mg, 0.11 mmol) was dissolved in DMF and sodium hydride (60% oil dispersion, 10 mg) was added in one portion. The reaction mixture was stirred for 5 min before iodomethane (excess) was added via pipette. The progress of the reaction was monitored by TLC. Upon completion, the reaction mixture was diluted with EtOAc. The organic layer was washed with saturated NH$_4$Cl (1×) followed by brine (2×). The organic layer was dried over sodium sulfate, filtered, and concentrated under reduced pressure. The crude residue was used in the next step without further purification.

Step 7

Methyl 8-methoxy-6,7,8,9-tetrahydro-5H-pyrrolo[1,2-a]azepine-2-carboxylate was dissolved in 1:1 mixture of dioxane/1 N NaOH. The reaction mixture was heated to 80° C. for 1 hour before it was cooled to room temperature. The reaction mixture was washed with 1 N HCl and diluted with EtOAc. The organic layer was separated, dried over sodium sulfate, filtered, and concentrated under reduced pressure. The residue was used in the next step without further purification.

Step 8

Example 190 was synthesized in the same manner as Example 18 using 8-methoxy-6,7,8,9-tetrahydro-5H-pyrrolo[1,2-a]azepine-2-carboxylic acid and Example 109. LCMS-ESI+ (m/z): [M+H]+ calcd for $C_{43}H_{53}ClN_4O_6S$: 789.3, found: 789.2.

Example 191

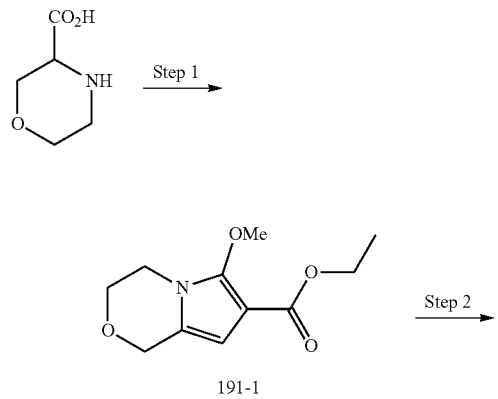

Step 1

Ethyl propiolate (421 µL, 4.16 mmol) was added over 2 min via syringe to a stirred mixture of morpholine-3-carboxylic acid (545 mg, 4.16 mmol) and N,N-diisopropylethylamine (2.17 mL, 12.5 mmol) in tetrahydrofuran (24 mL) and ethanol (16 mL) at room temperature. After 2 h, the resulting mixture was concentrated under reduced pressure. The residue was dried azeotropically by concentration under reduced pressure from toluene (2×20 mL). The residue was dissolved in dichloromethane (77 mL). 4-(Dimethylamino) pyridine (254 mg, 2.08 mmol), N,N-diisopropylethylamine (1.59 mL, 9.14 mmol), and triphenylphosphine (1.28 g, 4.86 mmol) were added sequentially, and the resulting mixture was stirred and cooled to 0° C. Iodine (1.21 g, 4.78 mmol) was added. After 5 min, the resulting mixture was warmed to room temperature. After 33 min, the resulting mixture was heated to 50° C. After 1 h, the resulting mixture was cooled to room temperature, and ethyl acetate (250 mL) was added. The organic layer was washed sequentially with aqueous hydrogen chloride solution (200 mL) and brine (150 mL), dried over anhydrous magnesium sulfate, filtered, and concentrated under reduced pressure. The residue was dissolved in acetone (30 mL), cesium carbonate (5.42 g, 16.6 mmol) was added, and the resulting mixture was stirred at room temperature. Methyl sulfate (1.97 mL, 20.8 mmol) was added via syringe. After 1 h, the resulting mixture was filtered, and the filter cake was extracted with dichloromethane (75 mL). Silica gel (12 g) was added to the combined filtrates, and the resulting slurry was concentrated under reduced pressure. The residue was purified by flash column chromatography on silica gel (0 to 35% ethyl acetate in hexanes) to give 191-1.

Step 2

Aqueous sodium hydroxide solution (2.0 M, 5.22 mL, 10 mmol) was added via syringe to a stirred solution of 191-1 (338.3 mg, 1.50 mmol) in methanol (1.5 mL) and tetrahydrofuran (1.5 mL) at room temperature, and the resulting mixture was heated to 70° C. After 1 h, the resulting mixture was cooled to room temperature, and aqueous hydrogen chloride solution (2.0 M, 6 mL) and brine (20 mL) were added sequentially. The aqueous layer was extracted sequentially with dichloromethane (2×30 mL) and ethyl acetate (30 mL). The combined organic layers were dried over anhydrous magnesium sulfate, were filtered, and were concentrated under reduced pressure. The residue was purified by reverse phase preparative HPLC (0.1% trifluoroacetic acid in acetonitrile/water) to give 191-2.

Step 3

Example 191 was synthesized in a manner similar to Example 109 using 191-2 instead of 2-((tetrahydro-2H-pyran-4-yl)oxy)acetic acid. 1H NMR (400 MHz, Acetone-d6) δ 7.79 (d, J=8.5 Hz, 1H), 7.45 (dd, J=8.2, 1.9 Hz, 1H), 7.36-7.29 (m, 2H), 7.25 (dd, J=8.5, 2.4 Hz, 1H), 7.14 (d, J=2.3 Hz, 1H), 6.92 (d, J=8.2 Hz, 1H), 6.19 (dt, J=14.4, 6.8 Hz, 1H), 5.66 (dd, J=15.6, 7.6 Hz, 1H), 4.97 (d, J=14.1 Hz, 1H), 4.92 (d, J=14.1 Hz, 1H), 4.21-3.57 (m, 10H), 3.97 (s, 3H), 3.47 (d, J=14.4 Hz, 1H), 3.26 (s, 3H), 3.15 (dd, J=15.1, 11.0 Hz, 1H), 3.02-1.39 (m, 16H), 1.13 (d, J=6.8 Hz, 3H). LCMS: 777.0.

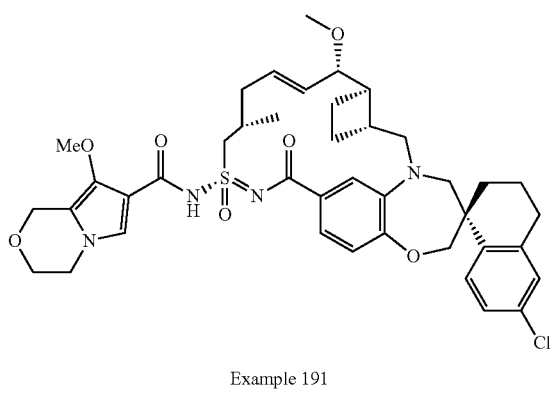

Example 191

273
Example 192

274
Example 193

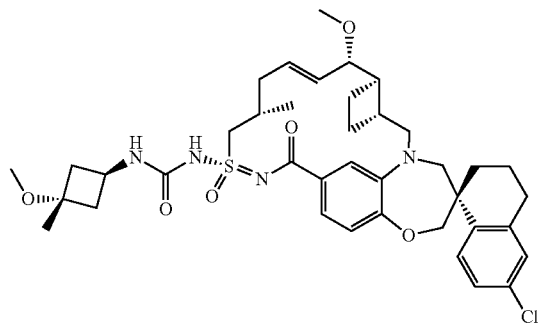 [SMILES: CO[C@H]1/C=C/C[C@H](C)C[S@@](=O)(NC(=O)N[C@H]2C[C@](C)(OC)C2)=NC(=O)c2ccc3c(c2)N(C[C@@H]2CC[C@H]21)C[C@@]1(CCCc2cc(Cl)ccc21)CO3]

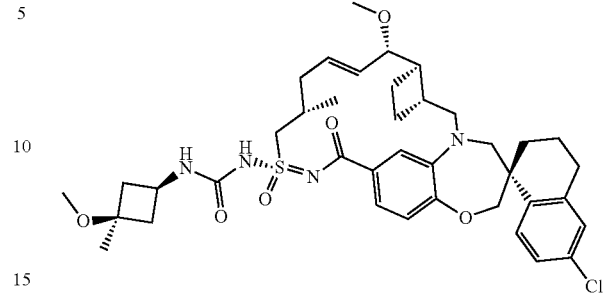

Example 192 was made in the same sequence as Example 225 except at step 1 trans-3-amino-1-methyl-cyclobutanol HCl salt was used. 1H NMR (400 MHz, Methanol-d4) δ 7.66 (d, J=8.5 Hz, 1H), 7.23 (d, J=8.1 Hz, 1H), 7.08 (s, 1H), 7.03-6.95 (m, 2H), 6.87 (d, J=8.2 Hz, 1H), 6.12-6.01 (m, 1H), 5.70-5.59 (m, 1H), 4.27-4.14 (m, 2H), 4.05-3.99 (m, 2H), 3.84-3.75 (m, 3H), 3.66 (d, J=14.3 Hz, 1H), 3.30 (s, 3H), 3.22 (s, 3H), 3.13-3.03 (m, 1H), 2.87-2.75 (m, 2H), 2.57-2.43 (m, 5H), 2.26-1.77 (m, 12H), 1.44-1.38 (m, 1H), 1.35 (s, 3H), 1.15 (d, J=6.6 Hz, 3H). [M+H]+ calcd for $C_{39}H_{51}ClN_4O_6S$: 739.36; found: 738.74.

Example 193 was made in the same sequence as Example 225 except in step 2 iodomethane was used in place of iodoethane. 1H NMR (400 MHz, Methanol-d4) δ 7.72 (d, J=8.5 Hz, 1H), 7.21 (d, J=8.3 Hz, 1H), 7.12 (d, J=7.6 Hz, 2H), 6.99 (s, 1H), 6.90 (d, J=8.1 Hz, 1H), 6.04 (dd, J=15.2, 7.5 Hz, 1H), 5.61 (dd, J=15.3, 8.9 Hz, 1H), 4.25 (dd, J=15.0, 6.5 Hz, 1H), 4.05 (d, J=2.4 Hz, 2H), 3.96-3.73 (m, 4H), 3.67 (d, J=14.3 Hz, 1H), 3.28 (s, 3H), 3.20 (s, 3H), 3.08 (dd, J=15.2, 10.1 Hz, 1H), 2.89-2.71 (m, 2H), 2.55-2.32 (m, 5H), 2.26-1.91 (m, 9H), 1.80 (dt, J=17.1, 9.2 Hz, 3H), 1.43 (t, J=12.0 Hz, 1H), 1.35 (s, 3H), 1.13 (d, J=6.5 Hz, 3H). [M+H]+ calcd for $C_{39}H_{51}ClN_4O_6S$: 739.36; found: 738.79.

Example 194

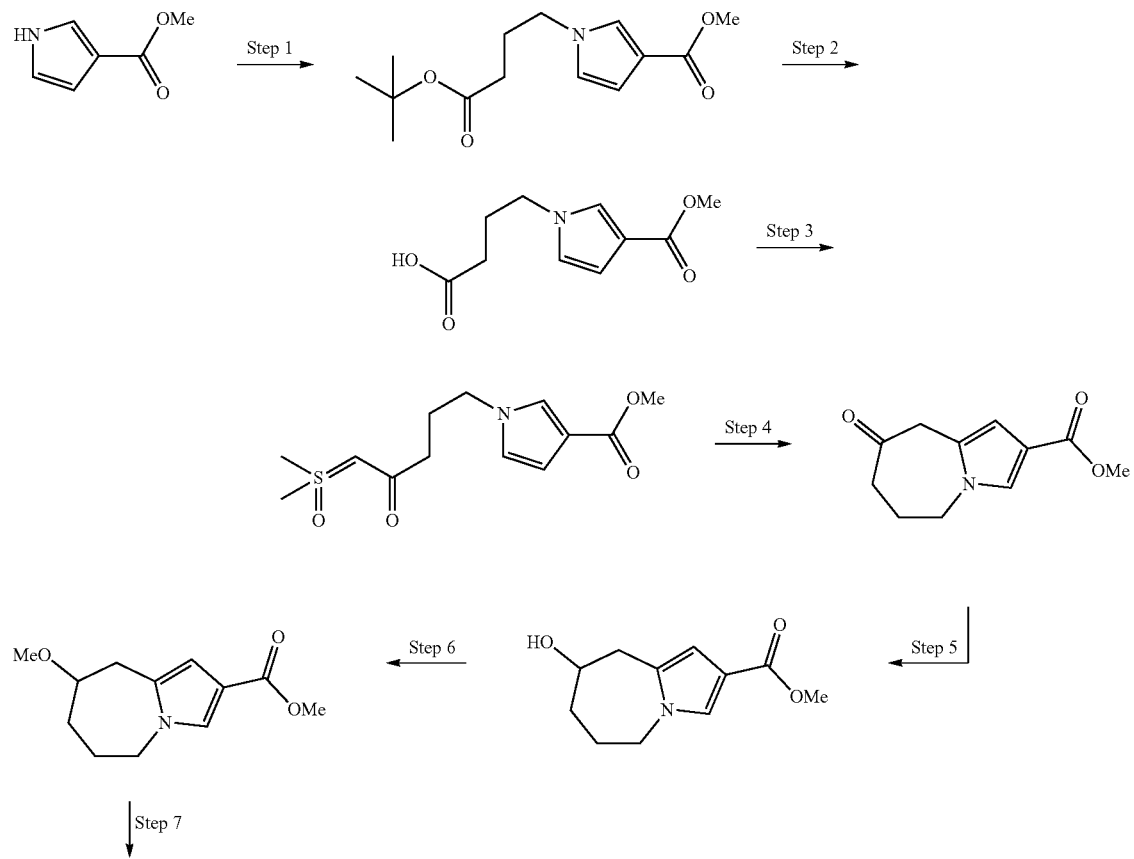

-continued

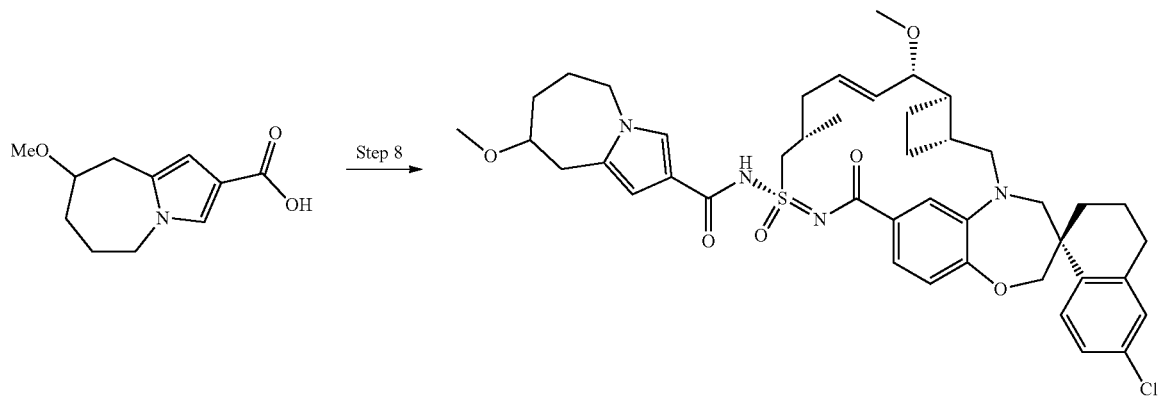

Step 1

3-hydroxy-1-methyl-1H-pyrazole-4-carboxylic acid (100 mg, 0.704 mmol) was dissolved in DMF (3 mL) and sodium hydride (60% dispersion, 84 mg, 2.1 mmol, 3 equiv.) was added in one portion. Iodoethane (2.1 mmol, 328 mg, 3 equiv.) was added via pipette. The reaction mixture was heated to 80° C. until TLC indicated the complete consumption of starting material. The reaction mixture was quenched with saturated NH$_4$Cl (3 mL) then diluted with EtOAc (10 mL). The organic layer was washed with saturated NaHCO$_3$ (10 mL) and brine (10 mL). The organic layer was dried over Na$_2$SO$_4$, filtered, and concentrated under reduced pressure. The residue was purified via column chromatography to afford ethyl 3-ethoxy-1-methy 1-1H-pyrazole-4-carboxylate.

Step 2 ethyl 3-ethoxy-1-methyl-1H-pyrazole-4-carboxylate (20 mg, 0.1 mmol) was dissolved in a 1:1 mixture of 1,2-dioxane (1 mL) and 1 N NaOH solution (1 mL). The reaction mixture was heated to 80° C. for 4 hours (reaction monitored by TLC and LCMS). The reaction mixture was then cooled to room temperature and quenched with 1 M HCl (1.5 mL) then diluted with EtOAc (5 mL). The organic layer was washed with saturated NaHCO$_3$ (5 mL) and brine (5 mL). The organic layer was dried over Na$_2$SO$_4$, filtered, and concentrated under reduced pressure to afford 3-ethoxy-1-methyl-1H-pyrazole-4-carboxylic acid which was used without further purification.

Step 3

Example 194 was synthesized in the same manner as Example 18 using 3-ethoxy-1-methyl-1H-pyrazole-4-carboxylic acid and Example 109. LCMS-ESI+ (m/z): [M+H]+ calcd for C$_{39}$H$_{48}$ClN$_5$O$_6$S: 750.3; found: 750.1.

Example 195 and Example 196

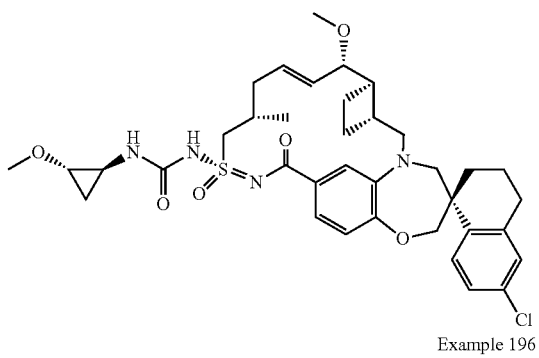

Example 195

Example 196

Example 195 and Example 196 were purified from Example 160 by chiral SFC separation and stereochemistry is assigned tentatively.

Example 195

1H NMR (400 MHz, Methanol-d4) δ 7.73 (d, J=8.4 Hz, 1H), 7.19 (d, J=7.7 Hz, 1H), 7.12 (d, J=9.0 Hz, 2H), 7.02-6.95 (m, 1H), 6.88 (d, J=8.1 Hz, 1H), 6.10-6.01 (m, 1H), 5.59 (dd, J=15.2, 8.8 Hz, 1H), 4.26 (s, 1H), 4.04 (d, J=4.7 Hz, 2H), 3.89-3.74 (m, 3H), 3.67 (d, J=14.3 Hz, 1H), 3.45 (s, 3H), 3.37 (s, 2H), 3.27 (d, J=4.3 Hz, 3H), 3.07 (dd, J=15.2, 10.2 Hz, 1H), 2.87-2.72 (m, 2H), 2.64 (s, 1H), 2.48 (ddd, J=34.7, 22.9, 8.1 Hz, 3H), 2.17 (ddd, J=33.0, 21.9, 10.5 Hz, 3H), 1.97 (d, J=14.6 Hz, 3H), 1.85-1.72 (m, 3H), 1.43 (t, J=12.3 Hz, 1H), 1.13 (d, J=6.4 Hz, 3H), 1.02 (ddd, J=8.9, 6.8, 3.8 Hz, 1H), 0.87-0.79 (m, 1H). LCMS-ESI+ (m/z): [M+H]+ calcd for $C_{37}H_{47}ClN_4O_6S$: 711.29; found: 710.76.

Example 196

1H NMR (400 MHz, Methanol-d4) δ 7.76 (d, J=8.5 Hz, 1H), 7.23-7.07 (m, 3H), 6.97 (s, 1H), 6.89 (d, J=8.1 Hz, 1H), 6.11-6.02 (m, 1H), 5.56 (dd, J=15.2, 9.0 Hz, 1H), 4.31 (dd, J=14.6, 6.4 Hz, 1H), 4.14-4.00 (m, 2H), 3.91-3.74 (m, 3H), 3.67 (d, J=14.1 Hz, 1H), 3.44 (s, 3H), 3.27 (s, 3H), 3.21 (s, 1H), 3.06 (dd, J=15.3, 10.3 Hz, 1H), 2.91-2.69 (m, 3H), 2.63 (s, 1H), 2.51 (d, J=20.7 Hz, 2H), 2.37 (t, J=8.9 Hz, 1H), 2.14 (t, J=15.4 Hz, 3H), 2.02-1.87 (m, 3H), 1.78 (tt, J=16.9, 9.3 Hz, 3H), 1.43 (t, J=12.5 Hz, 1H), 1.12 (d, J=6.3 Hz, 3H), 1.02 (ddd, J=8.8, 6.7, 3.8 Hz, 1H), 0.85-0.78 (m, 1H). LCMS-ESI+ (m/z): [M+H]+ calcd for $C_{37}H_{47}ClN_4O_6S$: 711.29; found: 710.92.

Example 197

Example 197 was synthesized in the same manner as Example 18, using Example 109 instead of Example 5 and 6,7-dihydro-5H-pyrazolo[5,1-b][1,3]oxazine-2-carboxylic acid was used instead of 3-methoxypropionic acid. 1H NMR (400 MHz, Methanol-d4) δ 7.77 (d, J=8.5 Hz, 1H), 7.26 (dd, J=8.2, 1.9 Hz, 1H), 7.19 (dd, J=8.5, 2.3 Hz, 1H), 7.12 (d, J=2.3 Hz, 1H), 7.08 (d, J=1.9 Hz, 1H), 6.95 (d, J=8.2 Hz, 1H), 6.09 (t, J=7.3 Hz, 1H), 6.04 (s, 1H), 5.62 (dd, J=15.3, 8.6 Hz, 1H), 4.40-4.36 (m, 1H), 4.29 (dt, J=13.4, 6.6 Hz, 2H), 4.15-3.95 (m, 3H), 3.90-3.69 (m, 3H), 3.37 (s, 3H), 3.28 (s, 2H), 3.09 (dd, J=15.2, 9.7 Hz, 2H), 2.90-2.71 (m, 3H), 2.47 (s, 3H), 2.33 (p, J=5.9 Hz, 2H), 2.28-2.08 (m, 3H), 1.95 (d, J=3.7 Hz, 3H), 1.79 (q, J=11.1, 9.0 Hz, 3H), 1.46 (t, J=13.1 Hz, 1H), 1.12 (d, J=6.7 Hz, 3H). LCMS-ESI+ (m/z): [M+H]+ calcd for $C_{39}H_{46}ClN_5O_6S$: 748.29; found: 746.89.

Example 198

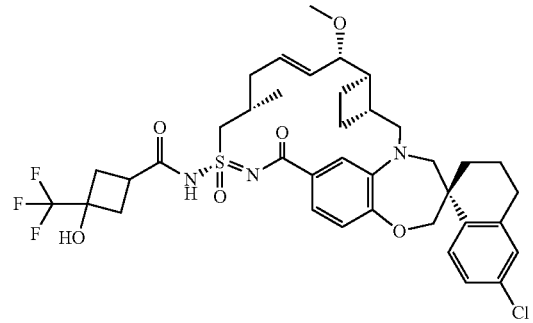 [SMILES: CO[C@H]1/C=C/C[C@H](C)C[S@@](=O)(NC(=O)C2CC(O)(C(F)(F)F)C2)=NC(=O)c2ccc3c(c2)N(C[C@@H]2CC[C@H]21)C[C@@]1(CCCc2cc(Cl)ccc21)CO3]

Example 198 was synthesized in the same manner as Example 18 using 3-hydroxy-3-(trifluoromethyl)cyclobutane-1-carboxylic acid and Example 109. 1H NMR (400 MHz, Acetonitrile-d3) δ 7.73 (d, J=8.5 Hz, 1H), 7.25 (dd, J=8.2, 1.9 Hz, 1H), 7.19 (dd, J=8.4, 2.3 Hz, 1H), 7.15 (d, J=2.3 Hz, 1H), 7.09 (d, J=1.9 Hz, 1H), 6.89 (d, J=8.2 Hz, 1H), 6.04 (dt, J=14.5, 6.9 Hz, 1H), 5.60 (dd, J=15.4, 8.3 Hz, 1H), 4.14-3.96 (m, 3H), 3.88-3.64 (m, 4H), 3.33 (d, J=14.3 Hz, 1H), 3.23 (s, 3H), 3.04 (dq, J=17.7, 9.3, 8.7 Hz, 2H), 2.87-2.66 (m, 4H), 2.46 (dq, J=24.9, 8.8, 7.2 Hz, 4H), 2.06 (s, 4H), 1.91 (t, J=4.9 Hz, 3H), 1.84-1.63 (m, 4H), 1.42 (dt, J=14.9, 7.7 Hz, 1H), 1.09 (d, J=6.8 Hz, 3H). LCMS-ESI+ (m/z): [M+H]+ calcd for $C_{38}H_{45}ClF_3N_3O_6S$: 764.26; found: 764.09.

Example 199

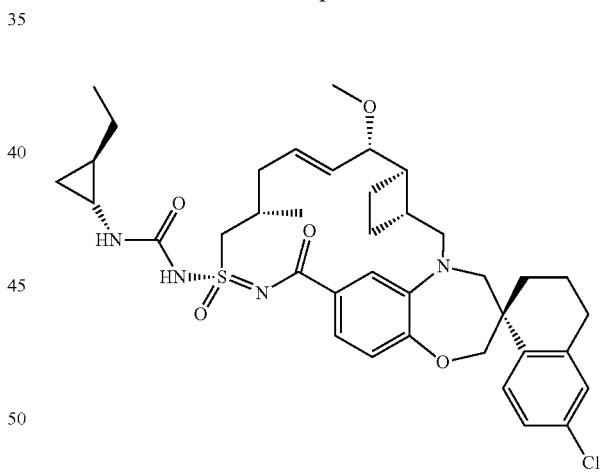

Example 199 was synthesized in the same manner as Example 75 using Example 109 and trans-ethylcyclopropan-1-amine hydrochloride. $^1$H NMR (400 MHz, Methanol-d4) δ 7.77 (d, J=8.5 Hz, 1H), 7.18 (dd, J=8.4, 2.5 Hz, 2H), 7.11 (d, J=2.3 Hz, 1H), 6.97 (s, 1H), 6.84 (d, J=8.1 Hz, 1H), 6.20-6.04 (m, 1H), 5.52 (dd, J=15.2, 9.1 Hz, 1H), 4.30 (d, J=14.3 Hz, 1H), 4.12-3.98 (m, 2H), 3.87 (d, J=15.0 Hz, 1H), 3.80 (dd, J=9.1, 3.4 Hz, 1H), 3.66 (d, J=14.1 Hz, 1H), 3.27 (s, 4H), 3.03 (dd, J=15.2, 9.9 Hz, 1H), 2.88-2.70 (m, 2H), 2.55 (m, 1H), 2.42 (m, 1H), 2.32 (s, 1H), 2.22 (dt, J=7.0, 3.4 Hz, 1H), 2.12 (d, J=12.4 Hz, 3H), 2.03-1.85 (m, 2H), 1.77 (ddt, J=25.7, 17.3, 9.2 Hz, 3H), 1.40 (dd, J=14.0, 70 Hz, 2H), 1.23 (dt, J=14.5, 7.2 Hz, 1H), 1.12-1.06 (m, 3H), 1.04 (d, J=2.7 Hz, 1H), 1.02 (d, J=2.7 Hz, 2H), 1.00 (d, J=2.8 Hz, 1H), 0.89-0.77 (m, 1H), 0.69-0.55 (m, 2H), 0.50 (m, 2H). LCMS-ESI+: calc'd for $C_{38}H_{50}ClN_4O_5S$: 709.31 (M+H); found: 709.38 (M+H).

Example 200

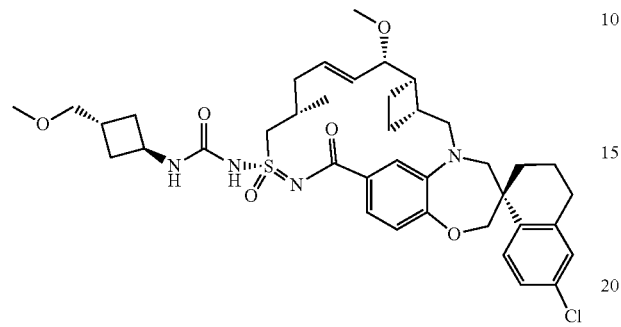

Example 189 (6.0 mg) was treated with sodium hydride (75.0 mg, 60% dispersion in mineral oil) and iodomethane (12 mg, 0.008 mmol, 10 equiv.) in THF at rt. The reaction mixture was quenched with water (30 mL) and the whole was extracted with EtOAc (30 mL). Obtained organic layer was washed with brine (30 mL) and dried over $Na_2SO_4$. The solvent was removed under a reduced pressure. Obtained crude mixture was purified by a silica-gel preparative TLC (5% MeOH/DCM, developed twice) to give Example 200. 1H NMR (400 MHz, Acetone-$d_6$) δ 7.74 (d, J=8.5 Hz, 1H), 7.39-7.08 (m, 4H), 6.92-6.84 (m, 1H), 6.13-6.03 (m, 1H), 5.55-5.64 (m, 1H), 4.36-4.24 (m, 1H), 4.12-4.00 (m, 2H), 3.88-3.77 (m, 1H), 3.71 (d, J=14.6 Hz, 2H), 3.40 (d, J=7.0 Hz, 2H), 3.31 (s, 3H), 3.23 (s, 3H), 3.00-2.10 (m, 19H), 2.00-1.64 (m, 4H), 1.50-1.40 (m, 1H), 1.11 (d, J=6.3 Hz, 3H). LCMS-ESI+ (m/z): [M+H]+ calcd for $C_{39}H_{52}ClN_4O_6S$: 739.32; found: 738.65.

Example 201

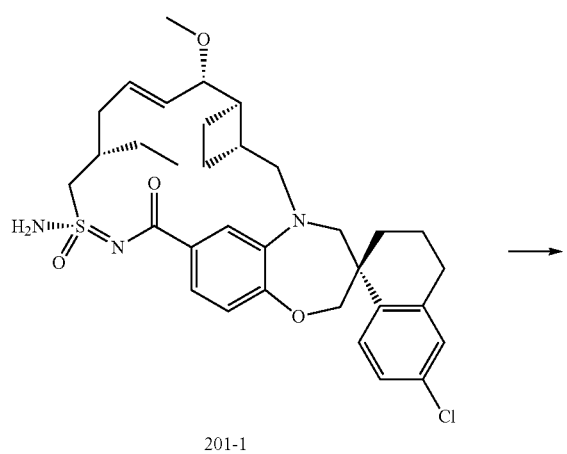

201-1

→

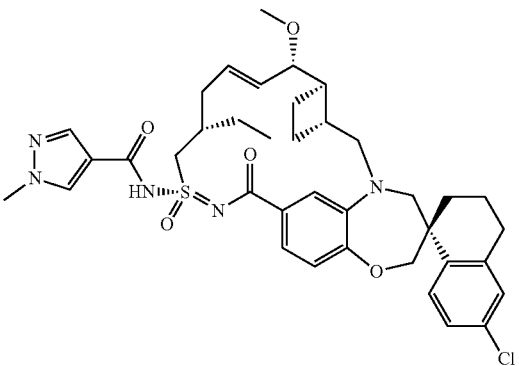

Example 201

Intermediate 201-1 was prepared in similar manner to Example 109-Method 1 using (2S)—N'-(tert-butyldimethylsilyl)-2-ethylpent-4-ene-1-sulfonimidamide (prepared from (S)-2-ethylpent-4-ene-1-sulfonamide) instead of (4S)-5-[S-amino-N-[tert-butyl(dimethyl)silyl]sulfonimidoyl]-4-methyl-pent-1-ene. $^1$H NMR (400 MHz, Chloroform-d) δ 7.76 (d, J=8.5 Hz, 1H), 7.43 (dd, J=8.2, 1.9 Hz, 1H), 7.32 (d, J=2.0 Hz, 1H), 7.20 (dd, J=8.5, 2.4 Hz, 1H), 7.10 (d, J=2.3 Hz, 1H), 6.93 (d, J=8.2 Hz, 1H), 6.33 (dt, J=14.8, 7.1 Hz, 1H), 5.89 (s, 2H), 5.53 (dd, J=15.3, 8.4 Hz, 1H), 4.11-4.01 (m, 2H), 3.87 (d, J=14.7 Hz, 1H), 3.84-3.75 (m, 1H), 3.71 (dd, J=8.5, 3.9 Hz, 1H), 3.61 (dd, J=14.5, 3.6 Hz, 1H), 3.42 (d, J=9.5 Hz, 1H), 3.39 (d, J=9.5 Hz, 1H), 3.27 (s, 3H), 3.01 (dd, J=15.0, 11.1 Hz, 1H), 2.88-2.71 (m, 2H), 2.58 (d, J=9.6 Hz, 1H), 2.46 (dq, J=20.6, 10.6, 9.1 Hz, 1H), 2.32 (dt, J=14.3, 6.9 Hz, 1H), 2.07 (s, 2H), 1.99-1.85 (m, 1H), 1.74 (dq, J=33.7, 9.2, 8.8 Hz, 2H), 1.50 (t, J=7.2 Hz, 2H), 1.42 (q, J=13.3, 12.9 Hz, 1H), 0.96 (t, J=7.4 Hz, 3H). LCMS-ESI+ (m/z): [M+H]+ calcd for $C_{33}H_{42}ClN_3O_4S$: 612.3; found: 612.5.

Example 201 was synthesized in the same manner as Example 18 using intermediate 201-1 and 1-methyl-1H-pyrazole-4-carboxylic acid. $^1$H NMR (400 MHz, Methanol-d4) δ 8.07 (s, 1H), 7.94 (d, J=0.6 Hz, 1H), 7.79 (d, J=8.5 Hz, 1H), 7.24 (dd, J=8.0, 1.7 Hz, 1H), 7.19 (dd, J=8.5, 2.4 Hz, 1H), 7.11 (d, J=2.3 Hz, 1H), 6.93 (d, J=1.9 Hz, 1H), 6.83 (d, J=8.1 Hz, 1H), 6.17 (ddd, J=14.6, 9.0, 5.1 Hz, 1H), 5.48 (dd, J=15.3, 9.3 Hz, 1H), 4.50 (dd, J=14.1, 9.3 Hz, 1H), 4.11-3.96 (m, 3H), 3.95-3.86 (m, 4H), 3.82 (dd, J=9.4, 3.8 Hz, 1H), 3.67 (d, J=14.1 Hz, 1H), 3.25 (m, 4H), 3.00 (dd, J=15.2, 10.1 Hz, 1H), 2.90-2.75 (m, 2H), 2.71 (d, J=15.0 Hz, 1H), 2.53-2.41 (m, 1H), 2.37 (m, 1H), 2.19-2.05 (m, 2H), 2.05-1.82 (m, 4H), 1.82-1.64 (m, 2H), 1.49-1.27 (m, 4H), 0.90 (t, J=7.4 Hz, 3H). LCMS-ESI+: calc'd for $C_{38}H_{47}ClN_5O_5S$: 720.19 (M+H); found: 720.31 (M+H).

Example 202

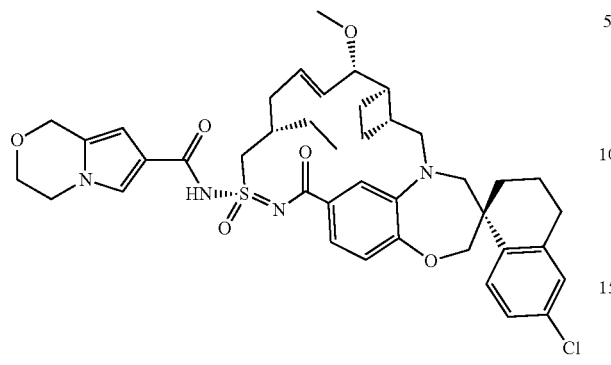

Example 202 was synthesized in the same manner as Example 18 using intermediate 201-1 and 3,4-dihydro-1H-pyrrolo[2,1-c][1,4]oxazine-7-carboxylic acid. $^1$H 1H NMR (400 MHz, Methanol-d4) δ 7.77 (d, J=8.5 Hz, 1H), 7.43 (s, 1H), 7.28 (d, J=8.2 Hz, 1H), 7.16 (d, J=8.9 Hz, 1H), 7.11 (d, J=2.3 Hz, 1H), 7.01 (s, 1H), 6.87 (d, J=8.1 Hz, 1H), 6.34 (s, 1H), 6.15 (d, J=7.8 Hz, 1H), 5.61-5.49 (m, 1H), 4.78 (s, 2H), 4.34 (s, 1H), 4.04 (m, 6H), 3.87 (d, J=15.0 Hz, 1H), 3.83-3.75 (m, 1H), 3.68 (d, J=14.2 Hz, 1H), 3.27 (s, 3H), 3.04 (dd, J=15.1, 9.4 Hz, 1H), 2.79 (m, 2H), 2.68 (m, 1H), 2.41 (m, 2H), 2.24 (m, 1H), 2.12 (m, 1H), 1.98 (m, 3H), 1.86-1.64 (m, 3H), 1.57-1.38 (m, 2H), 0.33 (m, 4H), 0.94 (t, J=7.3 Hz, 3H). LCMS-ESI+: calc'd for $C_{41}H_{50}ClN_4O_6S$: 761.31 (M+H); found: 761.34 (M+H).

Example 203

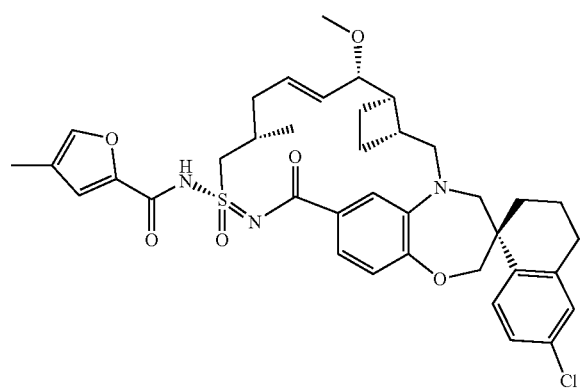 [SMILES: CO[C@H]1/C=C/C[C@H](C)C[S@@](=O)(NC(=O)c2cc(C)co2)=NC(=O)c2ccc3c(c2)N(C[C@@H]2CC[C@H]21)C[C@@]1(CCCc2cc(Cl)ccc21)CO3]

Example 203 was prepared in a similar manner to Example 18 using 4-methylfuran-2-carboxylic acid and Example 109. $^1$H NMR (400 MHz, Acetone-d$_6$) δ 7.75 (d, J=8.5 Hz, 1H), 7.60 (s, 1H), 7.31-7.15 (m, 3H), 7.12 (d, J=2.5 Hz, 2H), 6.93 (d, J=8.2 Hz, 1H), 6.04 (dd, J=14.7, 7.3 Hz, 1H), 5.61 (dd, J=14.8, 8.8 Hz, 1H), 4.17-3.99 (m, 2H), 3.88 (d, J=15.0 Hz, 2H), 3.80-3.68 (m, 2H), 3.38 (d, J=14.3 Hz, 1H), 3.22 (s, 3H), 3.14 (dd, J=15.1, 9.9 Hz, 1H), 2.93-2.67 (m, 2H), 2.61-2.36 (m, 3H), 2.33-2.18 (m, 2H), 2.16-2.07 (m, 3H), 2.08 (s, 3H) 2.00-1.85 (m, 2H), 1.84-1.65 (m, 3H), 1.46 (dt, J=15.2, 7.5 Hz, 1H), 1.14 (d, J=6.2 Hz, 3H). LCMS-ESI+ (m/z): [M+H]+ calcd for $C_{38}H_{45}ClN_3O_6S$: 706.26; found: 705.95.

Example 204

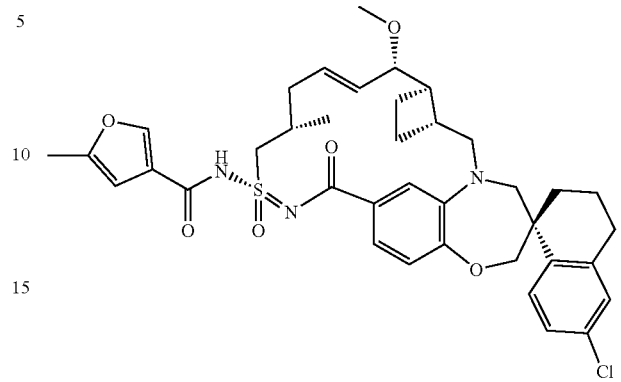

Example 204 was prepared in a similar manner to Example 18 using 5-methylfuran-3-carboxylic acid and Example 109. $^1$H NMR (400 MHz, Acetone-d$_6$) δ 8.09 (s, 1H), 7.74 (d, J=8.5 Hz, 1H), 7.20 (dt, J=8.4, 3.2 Hz, 2H), 7.15-7.05 (m, 2H), 6.92 (d, J=8.2 Hz, 1H), 6.43 (s, 1H), 6.06 (dt, J=14.3, 6.6 Hz, 1H), 5.61 (dd, J=15.5, 8.5 Hz, 1H), 4.27 (d, J=15.9 Hz, 1H), 4.15-4.00 (m, 2H), 3.85 (t, J=15.3 Hz, 2H), 3.77-3.67 (m, 2H), 3.38 (d, J=14.3 Hz, 1H), 3.22 (s, 3H), 3.13 (dd, J=15.3, 9.9 Hz, 1H), 2.91-2.68 (m, 2H), 2.49 (d, J=20.3 Hz, 4H), 2.31 (d, J=1.1 Hz, 3H), 2.29-2.07 (m, 3H), 2.09 (s, 4H), 2.02-1.89 (m, 3H), 1.77 (ddt, J=25.6, 15.2, 7.9 Hz, 3H), 1.45 (dt, J=15.0, 7.6 Hz, 1H), 1.14 (d, J=6.5 Hz, 3H). LCMS-ESI+(m/z): [M+H]+ calcd for $C_{38}H_{45}ClN_3O_6S$: 706.26; found: 706.06.

Example 205

Step 1

A solution of methyl 1H-pyrrole-3-carboxylate (4.3 g, 0.034 mol) in dry DMF (10 mL) was added dropwise, under nitrogen atmosphere, to a stirred suspension of NaH 60% (oil dispersion) (1.6 g, 0.041 mol) in dry DMF (40 mL). The temperature of the mixture was maintained at 0° C. After addition was completed, stirring was continued at the same temperature for 30 min. Then a solution of tert-butyl 2-bromoacetate (10.1 g, 0.052 mol) was added dropwise and the temperature was allowed to rise to room temperature. The reaction mixture was stirred at this temperature for 48 h. Then water was added and the mixture extracted with dichloromethane. The organic phase was dried over anhydrous magnesium sulfate and the solvent was removed under reduced pressure, then the residue was purified by normal phase chromatography (silica gel column, 0-100% EtOAc/Hexanes) to give 205-1.

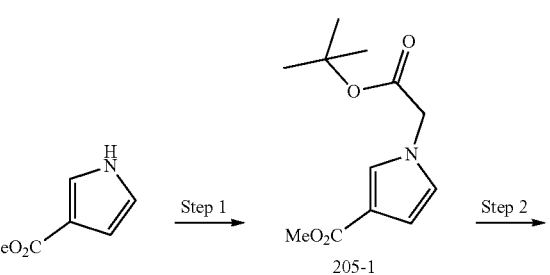

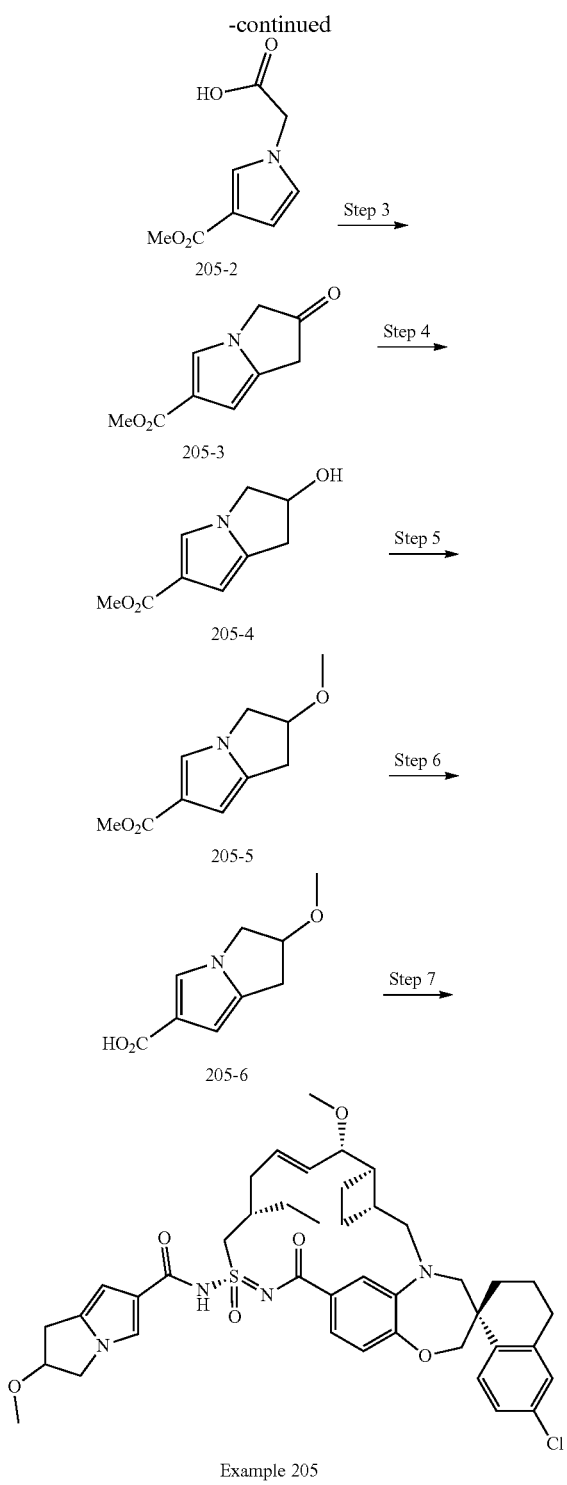

Example 205

Step 2

A solution of 205-1 (7.2 g, 0.30 mol) in DCM (45 mL) was added TFA (15 mL) and stirred at room temperature overnight. Then water was added and layers were separated. The organic phase was dried over anhydrous magnesium sulfate and the solvent was removed under reduced pressure to give 205-2.

Step 3

A suspension of 205-2 (4.3 g, 0.023 mol) and HATU (8.9 g, 0.023 mol) in THF (60 mL) was treated with TEA (7.2 mL, 0.070 mol) and the resulting solution was stirred at rt for about 16 h. Separately, a suspension of potassium tert-butoxide (7.4 g, 0.066 mol) and trimethylsulfoxonium chloride (8.4 g, 0.066 mol) in THF (70 mL) was heated at about 60° C. for about 2 h, and then cooled in an ice-water bath for about 15 min. The solution of activated ester was then added drop-wise at about 0° C. over a period of about 45 min. The reaction mixture was further stirred for about 1 h, after which the reaction was concentrated under reduced pressure. The residue was partitioned between DCM and water. After separating the layers, the organic phase was washed with saturated aqueous NaCl, dried over Mg$_2$SO$_4$, filtered, and concentrated under reduced pressure. The crude material was purified on silica gel (80 g) using a gradient of 0-100% EtOAc in hexanes. A solution of activated acid and chloro (1,5-cyclooctadiene)iridium(I) dimer (60 mg) in DCE (80 mL) was degassed. The mixture was heated in uw at about 80° C. for about 10 min, and then cooled to rt. The reaction mixture was concentrated under reduced pressure. The residue was purified on silica gel 5-80% EtOAc in hexanes to give 205-3.

Step 4

To a stirred solution of 205-3 (50 mg, 0.27 mmol) in methanol (5 mL) at 0° C. was added in small portions NaBH$_4$ (11 mg, 0.27 mmol) and stirred at 0° C. for 1 h and diluted with a 10% aqueous ammonium chloride solution. The organic solvent was removed using an evaporator. The remaining aqueous solution was subjected to two extractions with ethyl acetate. The organic layer was washed with saturated brine, then dried over sodium sulfate and then concentrated. The residue was purified by reverse phase chromatography ACN/Water 15-90% for 15 min with 0.1% TFA to give 205-4.

Step 5: Preparation of 205-5

To a stirred solution of 205-4 (32 mg, 0.17 mmol) in DMF (3 mL) was added NaH 60% (7 mg, 0.17 mmol) and stirred at room temperature for 1 h. The reaction mixture was subjected to two extractions with DCM. The organic layer was washed with saturated brine, then dried over sodium sulfate and then concentrated. The residue was used on next step.

Step 6

To a stirred solution of 205-5 (30 mg, 0.15 mmol) in methanol (3 mL) was added 1N of NaOH (1 mL) and stirred at rt for 1 h. To the reaction mixture was added 1N HCl (1 mL) and the reaction mixture was concentrated. Water was added and the mixture was extracted with dichloromethane. The organic phase was dried over anhydrous magnesium sulfate and the solvent was removed under reduced pressure to give 205-6.

Step 7

Example 205 was synthesized in the same manner as Example 174 using intermediate 205-6 and Example 109. $^1$H NMR (400 MHz, Chloroform-d) δ 7.75 (dd, J=8.5, 1.7 Hz, 1H), 7.46-7.35 (m, 2H), 7.19 (d, J=9.2 Hz, 2H), 7.10 (d, J=2.2 Hz, 1H), 6.95 (dt, J=8.2, 1.5 Hz, 1H), 6.38 (s, 1H), 6.00 (dt, J=13.6, 6.4 Hz, 1H), 5.62 (dd, J=15.6, 7.6 Hz, 1H), 4.57 (dt, J=6.1, 3.0 Hz, 1H), 4.21 (ddd, J=11.9, 5.9, 2.5 Hz, 1H), 4.14-3.95 (m, 3H), 3.93-3.65 (m, 3H), 3.43 (s, 3H), 3.31 (s, 3H), 3.20-2.66 (m, 5H), 2.58-2.26 (m, 3H), 2.19-1.61 (m, 6H), 1.28 (m, 5H), 1.12 (d, J=6.8 Hz, 3H), 0.95-0.63 (m, 2H). LCMS-ESI+ (m/z): [M+H]+ calcd for $C_{41}H_{49}ClN_4O_6S$: 761.31; found: 761.59.

Example 206

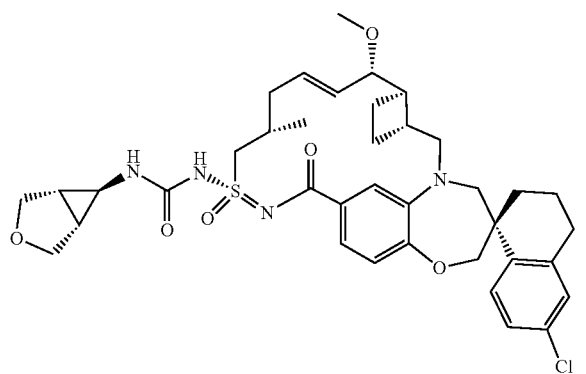 [SMILES: CO[C@H]1/C=C/C[C@H](C)C[S@@](=O)(NC(=O)N[C@H]2[C@@H]3COC[C@@H]32)=NC(=O)c2ccc3c(c2)N(C[C@@H]2CC[C@H]21)C[C@@]1(CCCc2cc(Cl)ccc21)CO3]

Example 206 was synthesized in the same manner as Example 75 using (1R,5S,6R)-3-oxabicyclo[3.1.0]hexan-6-amine and Example 109. $^1$H NMR (400 MHz, Methanol-d$_4$) δ 7.73 (d, J=8.5 Hz, 1H), 7.18 (d, J=8.3 Hz, 1H), 7.13 (d, J=14.6 Hz, 2H), 6.97 (s, 1H), 6.91 (d, J=8.2 Hz, 1H), 6.03 (d, J=14.8 Hz, 1H), 5.60 (dd, J=15.2, 8.9 Hz, 1H), 4.26 (br, 1H), 4.06 (m, 2H), 3.98 (d, J=8.5 Hz, 2H), 3.84 (d, J=15.0 Hz, 1H), 3.81-3.71 (m, 3H), 3.67 (d, J=14.2 Hz, 1H), 3.35-3.32 (m, 4H), 3.27 (s, 3H), 3.07 (dd, J=15.2, 10.3 Hz, 1H), 2.89-2.71 (m, 2H), 2.45 (d, J=28.6 Hz, 4H), 2.29-2.06 (m, 3H), 2.03-1.69 (m, 5H), 1.43 (t, J=12.8 Hz, 1H), 1.14 (d, J=6.5 Hz, 3H). LCMS-ESI+ (m/z): [M+H]+ calcd for $C_{38}H_{47}ClN_4O_6S$: 723.3; found: 722.9.

Example 207

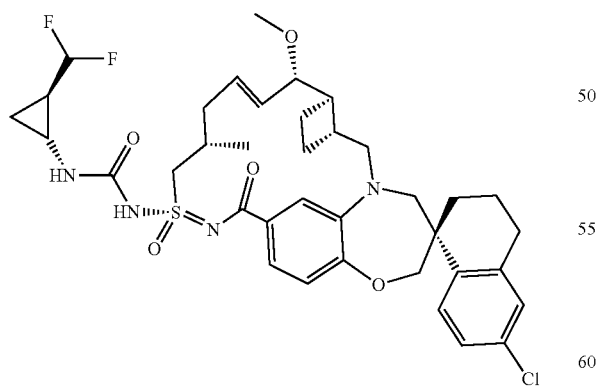

Example 207 was synthesized in the same manner as Example 75 using Example 109 and trans-2-(difluoromethyl)cyclopropan-1-amine hydrochloride. $^1$H NMR (400 MHz, Methanol-d4) δ 7.74 (d, J=8.5 Hz, 1H), 7.16 (d, J=8.1 Hz, 2H), 7.11 (d, J=2.3 Hz, 1H), 6.97 (s, 1H), 6.92 (d, J=8.2 Hz, 1H), 6.08-5.99 (m, 1H), 5.99-5.67 (m, 1H), 5.59 (dd, J=15.3, 8.9 Hz, 1H), 4.33-4.22 (m, 1H), 4.11-4.01 (m, 2H), 3.85 (d, J=15.1 Hz, 1H), 3.77 (dd, J=9.0, 3.7 Hz, 1H), 3.68 (d, J=14.3 Hz, 1H), 3.27 (s, 4H), 3.08 (dd, J=15.3, 10.3 Hz, 1H), 2.79 (ddd, J=22.7, 17.7, 9.6 Hz, 3H), 2.48 (d, J=8.1 Hz, 2H), 2.37 (t, J=8.3 Hz, 1H), 2.28-2.04 (m, 3H), 2.04-1.88 (m, 2H), 1.79 (m, 2H), 1.69-1.49 (m, 1H), 1.44 (t, J=12.9 Hz, 1H), 1.33 (d, J=17.3 Hz, 2H), 1.14 (d, J=6.4 Hz, 3H), 1.09 (q, J=6.4 Hz, 1H), 0.95 (m, 2H). LCMS-ESI+: calc'd for $C_{37}H_{46}ClF_2N_4O_5S$: 731.28 (M+H); found: 731.05 (M+H).

Example 208 and Example 209

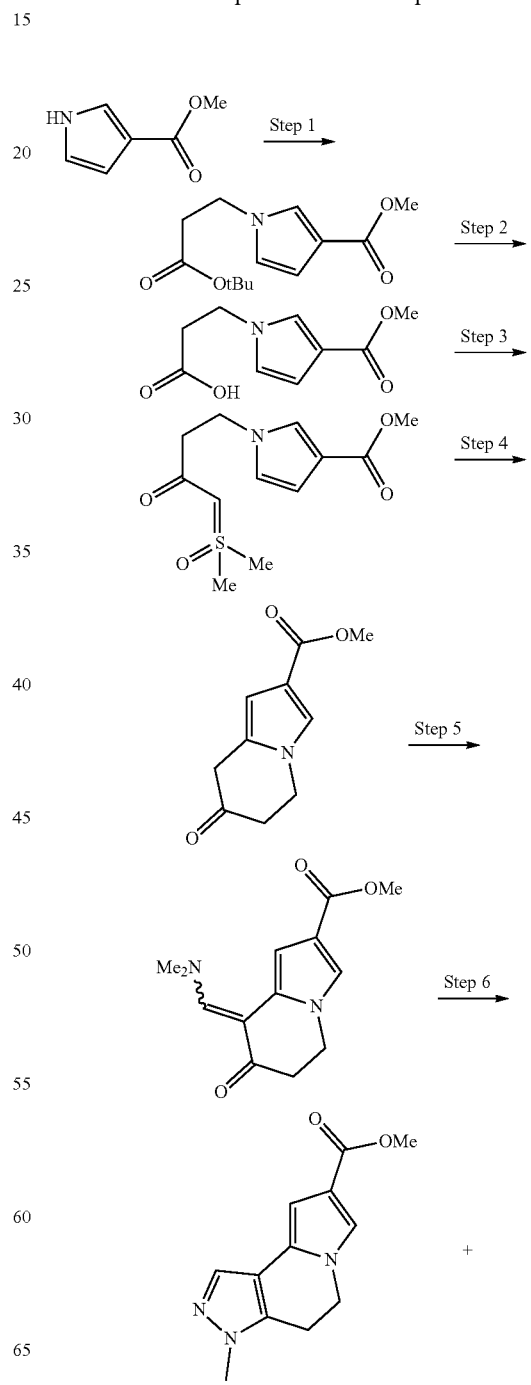

-continued

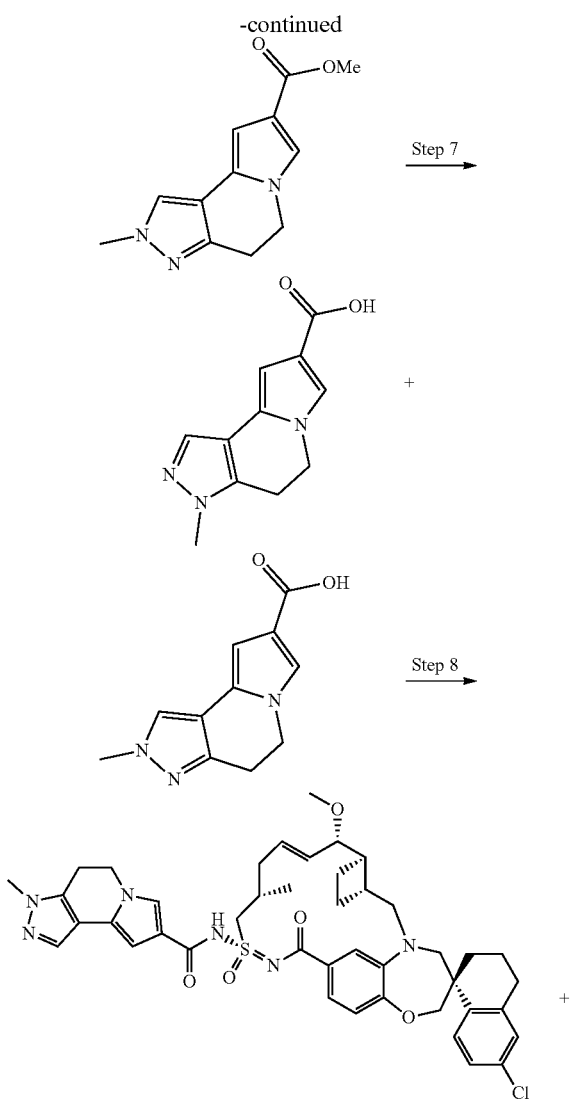

Example 208

Example 209

Step 1 methyl 1H-pyrrole-3-carboxylate (2.0 g, 15.98 mmol) was dissolved in acetonitrile (30 mL), and tert-butyl acrylate (2.46 g, 19.18 mmol, 1.2 equiv.) was added via syringe. 1,8-diazabicyclo[5.4.0]undec-7-ene (2.43 g, 15.98 mmol, 1 equiv.) was added dropwise at room temperature over 2 min. The reaction mixture was heated to 80° C. and progress of the reaction was monitored by TLC (1:2 EtOAc:Hexanes).

Upon completion, the reaction was cooled to room temperature and concentrated under reduced pressure. The residue was diluted with EtOAc (40 mL) and washed with saturated ammonium chloride (40 mL) then brine (40 mL). The organic layer was dried over sodium sulfate, filtered, and concentrated under reduced pressure. The residue was purified via column chromatography (100% hexanes→1:1 EtOAc:Hexanes) to afford methyl 1-(3-(tert-butoxy)-3-oxopropyl)-1H-pyrrole-3-carboxylate (4.05 g, 94%).

Step 2 methyl 1-(3-(tert-butoxy)-3-oxopropyl)-1H-pyrrole-3-carboxylate (3.8 g, 15 mmol) was dissolved in a 1:3 solution of trifluoroacetic acid (10 mL) and dichloromethane (30 mL) at room temperature. The reaction mixture was stirred at room temperature for 24 hours then concentrated under reduced pressure. The residue was azeotroped with toluene (40 mL) to afford 3-(3-(methoxycarbonyl)-1H-pyrrol-1-yl)propanoic acid (2.95 g, 99%).

Step 3

To a suspension of 3-(3-(methoxycarbonyl)-1H-pyrrol-1-yl)propanoic acid (2.00 g, 10.14 mmol) and HATU (3.86 g, 10.14 mmol, 1 equiv.) in THF (30 mL) was added trimethylamine (3.91 g, 30.43 mmol, 3 equiv.). The reaction mixture was stirred for 24 hours at room temperature. In a separate vessel, a suspension of trimethyl sulfoxonium chloride (3.91 g, 30.43 mmol, 3 equiv.) and potassium tert-butoxide (3.41 g, 30.43 mmol, 3 equiv.) were heated to 60° C. via a metal block for 1.5 h. The heating block was then removed, and the reaction mixture was cooled to 0° C. for 15 min via an ice bath. The HATU adduct was then added dropwise via syringe over 10 min, during which the reaction mixture turned dark red. The reaction mixture was stirred for an additional 1 h at 0° C. before it was concentrated under reduced pressure. The crude material was purified via silica gel chromatography (5% MeOH/DCM) to afford methyl 1-(4-(dimethyl(oxo)-$\lambda^6$-sulfanylidene)-3-oxobutyl)-1H-pyrrole-3-carboxylate.

Step 4

Methyl 1-(4-(dimethyl(oxo)-$\lambda^6$-sulfanylidene)-3-oxobutyl)-1H-pyrrole-3-carboxylate (150 mg, 0.553 mmol) and chloro(1,5-cyclooctadiene) Iridium (I) dimer (37 mg, 0.00553 mmol, 0.1 equiv.) were dissolved in 1,2-dichloroethane (15 mL). The reaction mixture was sparged with an atmospheric stream of argon for 10 min before it was heated to 80° C. for about 10 min, during which the reaction mixture turned green. The reaction mixture was concentrated under reduced pressure and the crude residue was purified via silica gel chromatography for afford methyl 7-oxo-5,6,7,8-tetrahydroindolizine-2-carboxylate.

Step 5

Methyl 7-oxo-5,6,7,8-tetrahydroindolizine-2-carboxylate (40 mg, 0.207 mmol) was dissolved in DMF-DMA/EtOH (0.5 mL/0.5 mL) and the reaction mixture was heated to about 80° C. for 16 hours before it was cooled to room temperature, and then concentrated under reduced pressure. The residue was used in the next step without further purification.

Step 6

Methyl 8-((dimethylamino)methylene)-7-oxo-5,6,7,8-tetrahydroindolizine-2-carboxylate (15 mg) was dissolved in EtOH (0.5 mL) and methylhydrazine (0.1 mL) was added. The reaction mixture was refluxed for 2 hours before it was cooled to room temperature and concentrated under reduced pressure. The residue was purified with silica gel chromatography to afford methyl 2-methyl-4,5-dihydro-2H-pyrazolo[3,4-g]indolizine-8-carboxylate and methyl 3-methyl-4,5-dihydro-3H-pyrazolo[3,4-g]indolizine-8-carboxylate.

Step 7

Methyl 2-methyl-4,5-dihydro-2H-pyrazolo[3,4-g]indolizine-8-carboxylate and methyl 3-methyl-4,5-dihydro-3H-pyrazolo[3,4-g]indolizine-8-carboxylate (10 mg) were dissolved in 1:1 mixture of dioxane/1 N NaOH. The reaction mixture was heated to 80° C. for 1 hour before it was cooled to room temperature. The reaction mixture was washed with 1 N HCl and diluted with EtOAc. The organic layer was separated, dried over sodium sulfate, filtered and concentrated under reduced pressure. The residue was used in the next step without further purification.

Step 8

The mixture of regio-isomers, methyl 2-methyl-4,5-dihydro-2H-pyrazolo[3,4-g]indolizine-8-carboxylate and methyl 3-methyl-4,5-dihydro-3H-pyrazolo[3,4-g]indolizine-8-carboxylate were coupled to Example 109 in the same manner as Example 18 and separated by reverse phase chromatography to give Example 208 and Example 209 respectively. The regio-chemistry is tentatively assigned. LCMS-ESI+ (m/z): [M+H]+ calcd for $C_{43}H_{49}ClN_6O_5S$: 797.3; found: 797.0.

Example 210

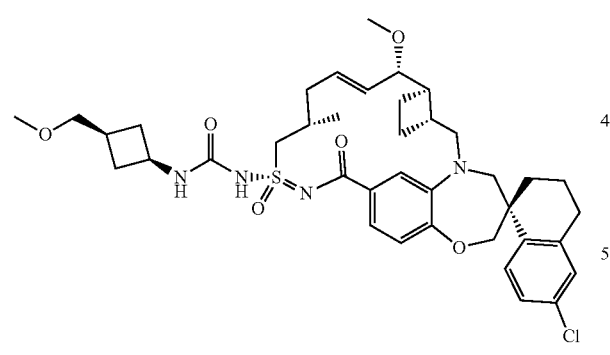

Example 210 was synthesized in the same manner as Example 75 using cis-3-(methoxymethyl)cyclobutan-1-amine hydrochloric acid and Example 109. $^1$H NMR (400 MHz, Acetone-$d_6$) δ 7.69 (d, J=8.6 Hz, 1H), 7.23 (br, 1H), 7.09 (br, 3H), 6.87 (d, J=8.0 Hz, 1H), 6.07 (m, 1H), 5.63 (dd, J=15.4, 8.4 Hz, 1H), 4.23-3.96 (m, 4H), 3.88-3.79 (m, 2H), 3.71 (t, J=11.3 Hz, 2H), 3.41 (d, J=13.0 Hz, 1H), 3.31 (d, J=6.0 Hz, 2H), 3.26 (s, 3H), 3.24 (s, 3H), 3.13 (dd, J=15.2, 10.1 Hz, 1H), 2.90-2.67 (m, 3H), 2.61-2.07 (m, 9H), 2.01-1.66 (m, 6H), 1.42 (s, 1H), 1.13 (d, J=6.4 Hz, 3H). LCMS-ESI+ (m/z): [M+H]+ calcd for $C_{39}H_{52}ClN_4O_6S$: 739.32; found: 738.87.

Example 211

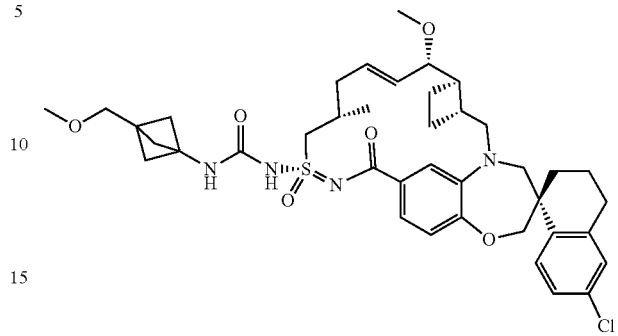

Example 211 was synthesized in the same manner as Example 75 using 3-(methoxymethyl)bicyclo[1.1.1]pentan-1-amine hydrochloric acid and Example 109. $^1$H NMR (400 MHz, Acetone-$d_6$) δ 7.66 (d, J=8.5 Hz, 1H), 7.33-7.17 (m, 2H), 7.05 (d, J=22.1 Hz, 2H), 6.87 (d, J=8.2 Hz, 1H), 6.06 (s, 1H), 5.66 (dd, J=15.5, 8.5 Hz, 1H), 4.18-3.92 (m, 3H), 3.89-3.62 (m, 3H), 3.44 (s, 2H), 3.42 (d, J=10.2 Hz, 1H), 3.29 (s, 3H), 3.25 (s, 3H), 3.13 (dd, J=15.2, 10.2 Hz, 1H), 2.79-2.06 (m, 11H), 1.99 (s, 6H), 1.97-1.67 (m, 3H), 1.48-1.33 (m, 1H), 1.14 (d, J=6.5 Hz, 3H). LCMS-ESI+ (m/z): [M+H]+ calcd for $C_{40}H_{52}ClN_4O_6S$: 751.32; found: 750.72.

Example 212

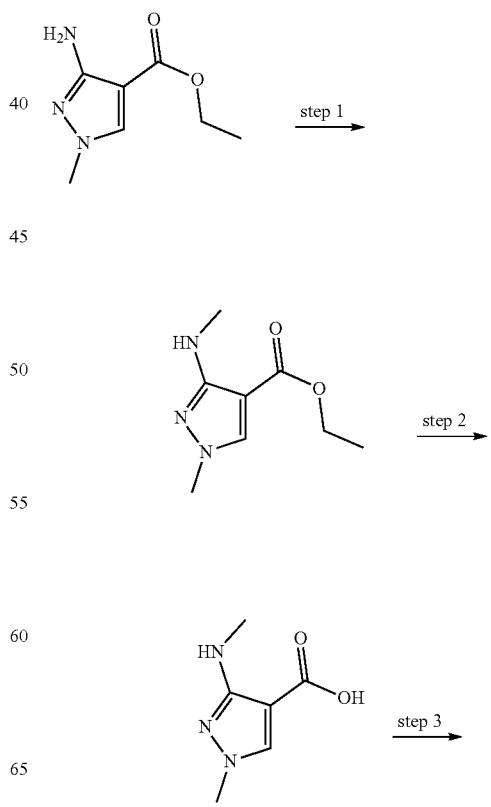

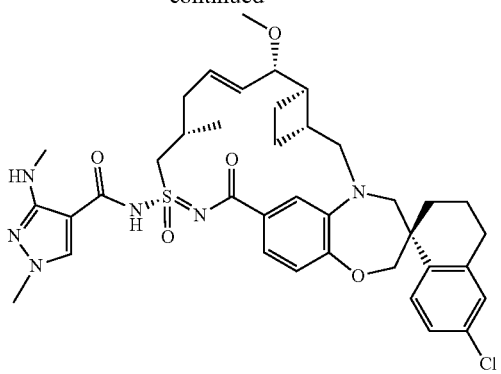

Step 1: Preparation of Ethyl 1-methyl-3-(methylamino)-1H-pyrazole-4-carboxylate A roundbottom flask was charged with ethyl 3-amino-1-methyl-pyrazole-4-carboxylate (267 mg, 1.58 mmol). The flask was placed under high vacuum for 5 min then back-filled with nitrogen atmosphere. THF (8 mL, 0.2 M limiting reagent) was added, followed by sodium hydride (60% dispersion in mineral oil, 73 mg, 1.89 mmol) at 20° C. The reaction mixture was stirred at 20° C. for 45 min, and then iodomethane (0.20 mL, 3.1 mmol) was added. The reaction was stirred at 20° C. for 19 hr. More iodomethane (0.10 mL, 1.6 mmol) was added. A reflux condenser was installed under nitrogen atmosphere and the reaction was warmed to 70° C. in a metal heating block for 2 hr. The reaction was monitored by LCMS until formation of both ethyl 1-methyl-3-(methylamino)-1H-pyrazole-4-carboxylate and ethyl 3-(dimethylamino)-1-methyl-1H-pyrazole-4-carboxylate were observed. The reaction was removed from the heating block and allowed to cool to 20° C. The reaction was quenched with water and extracted into ethyl acetate. The combined organic phases were washed with brine, dried over magnesium sulfate, filtered, and concentrated in vacuo. The resulting residue was dissolved in dichloromethane and purified by flash column chromatography (silica gel, 24 g, 0 to 100% ethyl acetate in hexanes). The first UV-active product was eluted at 40% ethyl acetate, the second UV-active product was eluted at 50% ethyl acetate, and the third UV-active product was eluted at 70% ethyl acetate. Fractions containing the second UV-active product were collected and concentrated in vacuo to obtain ethyl 1-methyl-3-(methylamino)-1H-pyrazole-4-carboxylate (135 mg). 1H NMR (400 MHz, Chloroform-d) δ 7.53 (s, 1H), 4.22 (q, J=7.1 Hz, 2H), 3.72 (s, 3H), 2.93 (s, 3H), 1.29 (t, J=7.1 Hz, 3H).

Step 2: Preparation of 1-methyl-3-(methylamino)-1H-pyrazole-4-carboxylic Acid To a glass screwtop vial charged with ethyl 1-methyl-3-(methylamino)-1H-pyrazole-4-carboxylate (135 mg, 0.74 mmol) was added THF (7 mL), then methanol (3.5 mL), then sodium hydroxide (2 M in water, 1.8 mL, 3.6 mmol). The resulting mixture was stirred vigorously at 20° C. for 16 hr. The reaction was diluted with ethyl acetate, and washed with water, then brine. The organic phase was dried over magnesium sulfate, filtered, and concentrated in vacuo. The resulting crude product was dissolved in THF (3.8 mL), then sodium hydroxide (2 M in water, 0.96 mL, 1.92 mmol) was added. The resulting mixture was stirred vigorously at 20° C. for 21 hr. More sodium hydroxide (2 M in water, 0.96 mL, 1.92 mmol) was added, followed by methanol (0.1 mL). The reaction was warmed to 60° C. in a metal heating block for 4 hr. The reaction was monitored by silica gel TLC (1:1 hexanes:ethyl acetate) until complete consumption of starting ester was observed. The vial was removed from the heating block and allowed to cool to 20° C. The reaction was quenched with 2 N HCl, which was added dropwise until pH<3 by pH paper. The resulting mixture was extracted three times with ethyl acetate. The combined organic phases were dried over magnesium sulfate, filtered, and concentrated in vacuo. NMR was consistent with 1-methyl-3-(methylamino)-1H-pyrazole-4-carboxylic acid, in at least 95% purity (50 mg). 1H NMR (400 MHz, Methanol-d4) δ 7.76 (s, 1H), 3.71 (s, 3H), 2.87 (s, 3H).

Step 3

Example 212 was synthesized in the same manner as Example 18 using 1-methyl-3-(methylamino)-1H-pyrazole-4-carboxylic acid and Example 109. 1H NMR (400 MHz, Acetonitrile-d3) δ 8.18 (s, 1H), 7.54 (d, J=8.6 Hz, 1H), 7.18 (d, J=8.2 Hz, 1H), 7.06 (d, J=2.3 Hz, 1H), 6.97-6.84 (m, 2H), 6.80 (d, J=8.2 Hz, 1H), 6.04-5.93 (m, 1H), 5.61 (dd, J=15.3, 8.6 Hz, 1H), 4.24-4.08 (m, 1H), 3.95 (d, J=3.0 Hz, 2H), 3.81-3.65 (m, 2H), 3.74 (s, 3H), 3.59 (d, J=14.4 Hz, 1H), 3.36 (d, J=14.4 Hz, 1H), 3.21 (s, 3H), 3.07 (dd, J=15.4, 10.4 Hz, 1H), 2.89 (s, 3H), 2.83-2.57 (m, 3H), 2.48-2.33 (m, 2H), 2.29-2.05 (m, 3H), 2.05-1.97 (m, 1H), 1.92-1.66 (m, 7H), 1.33 (dd, J=14.6, 8.2 Hz, 1H), 1.08 (d, J=6.3 Hz, 3H). LCMS-ESI+ (m/z): [M+H]+ calculated for $C_{38}H_{47}ClN_6O_5S$: 735.31; found: 735.05.

Example 213

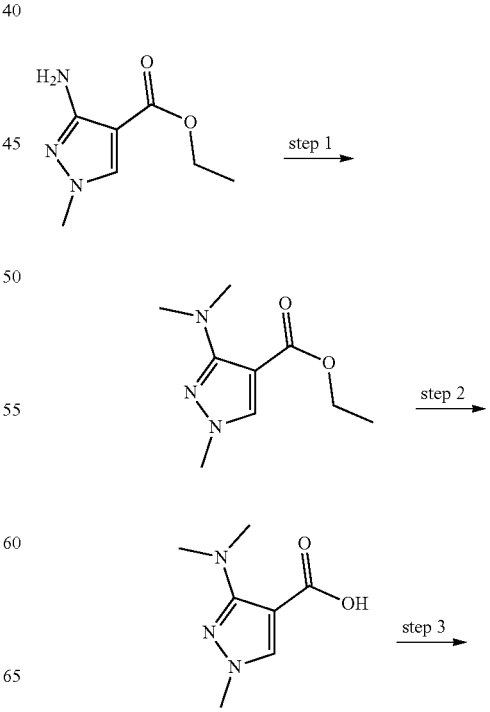

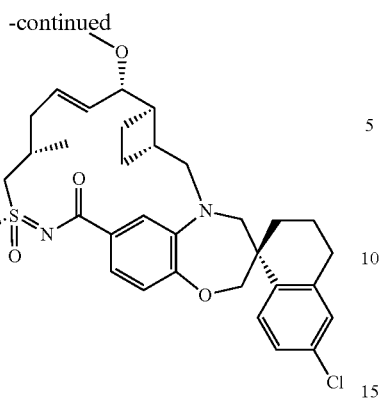

Step 1: Preparation of Ethyl 3-(dimethylamino)-1-methyl-1H-pyrazole-4-carboxylate A roundbottom flask was charged with ethyl 3-amino-1-methyl-pyrazole-4-carboxylate (267 mg, 1.58 mmol). The flask was placed under high vacuum for 5 min, then backfilled with nitrogen atmosphere. THF (8 mL, 0.2 M limiting reagent) was added, followed by sodium hydride (60% dispersion in mineral oil, 73 mg, 1.89 mmol) at 20° C. The flask was stirred at 20° C. for 45 min, then iodomethane (0.20 mL, 3.1 mmol) was added. The reaction was stirred at 20° C. for 19 hr. More iodomethane (0.10 mL, 1.6 mmol) was added. A reflux condenser was installed under nitrogen atmosphere and the reaction was warmed to 70° C. in a metal heating block for 2 hr. The reaction was monitored by LCMS until formation of both ethyl 1-methyl-3-(methylamino)-1H-pyrazole-4-carboxylate and ethyl 3-(dimethylamino)-1-methyl-1H-pyrazole-4-carboxylate were observed. The reaction was removed from the heating block and allowed to cool to 20° C. The reaction was quenched with water and extracted into ethyl acetate. The combined organic phases were washed with brine, dried over magnesium sulfate, filtered, and concentrated in vacuo. The resulting residue was dissolved in dichloromethane and purified by flash column chromatography (silica gel, 24 g, 0 to 100% ethyl acetate in hexanes). The first UV-active product was eluted at 40% ethyl acetate, the second UV-active product was eluted at 50% ethyl acetate, and the third UV-active product was eluted at 70% ethyl acetate. Fractions containing primarily the first UV-active product were collected and concentrated in vacuo to obtain ethyl 3-(dimethylamino)-1-methyl-1H-pyrazole-4-carboxylate (35 mg). 1H NMR (400 MHz, Chloroform-d) δ 7.69 (s, 1H), 4.22 (q, J=7.1 Hz, 2H), 3.72 (s, 3H), 2.89 (s, 6H), 1.29 (t, J=7.1 Hz, 3H).

Step 2: Preparation of 3-(dimethylamino)-1-methyl-1H-pyrazole-4-carboxylic Acid To a glass screwtop vial charged with starting material was added THF, then methanol, then sodium hydroxide (2 M in water). The resulting mixture was stirred vigorously at 20° C. for 16 hr. The reaction was quenched by careful addition of 2 N aqueous HCl until pH<3 by pH paper. The mixture was extracted with ethyl acetate, and washed with water, then brine. The organic phase was dried over magnesium sulfate, filtered, and concentrated in vacuo. The resulting residue was re-dissolved in THF (1.4 mL), then sodium hydroxide (2 M in water, 0.34 mL) was added. The resulting mixture was stirred vigorously at 20° C. for 18 hr. Then more sodium hydroxide (2 M in water, 0.34 mL) was added, followed by methanol (100 µL). The reaction was warmed to 60° C. in a metal heating block for 12 hr. The reaction was monitored by silica gel TLC (1:1 hexanes:ethyl acetate) until all starting material was consumed. The reaction was quenched with 2 N HCl, which was added dropwise until pH<3 by pH paper. The resulting mixture was extracted three times with ethyl acetate. The combined organic phases were dried over magnesium sulfate, filtered, and concentrated in vacuo to give 3-(dimethylamino)-1-methyl-1H-pyrazole-4-carboxylic acid (20 mg), which was used in the next step without any further purification. 1H NMR (400 MHz, Methanol-d4) δ 7.93 (s, 1H), 3.74 (s, 3H), 2.86 (s, 6H).

Step 3

Example 213 was synthesized in the same manner as Example 18 using 3-(dimethylamino)-1-methyl-1H-pyrazole-4-carboxylic acid and Example 109. 1H NMR (400 MHz, Acetonitrile-d3) δ 8.04 (s, 1H), 7.70 (d, J=8.5 Hz, 1H), 7.19 (dd, J=8.5, 2.4 Hz, 1H), 7.13 (d, J=2.3 Hz, 1H), 7.08 (dd, J=8.2, 1.9 Hz, 1H), 6.92 (d, J=8.1 Hz, 1H), 6.89 (d, J=2.0 Hz, 1H), 5.90 (dt, J=14.2, 6.7 Hz, 1H), 5.56 (dd, J=15.2, 9.1 Hz, 1H), 4.41 (dd, J=15.0, 6.3 Hz, 1H), 4.05 (s, 2H), 3.88 (s, 3H), 3.79 (dd, J=15.0, 4.0 Hz, 2H), 3.72-3.59 (m, 2H), 3.24 (s, 6H), 3.17 (s, 3H), 3.06 (dd, J=15.3, 10.5 Hz, 1H), 2.84-2.65 (m, 2H), 2.51-2.31 (m, 2H), 2.25 (t, J=8.6 Hz, 1H), 2.19-2.10 (m, 1H), 2.05 (d, J=13.8 Hz, 2H), 1.89 (d, J=7.1 Hz, 4H), 1.81-1.61 (m, 4H), 1.46-1.35 (m, 1H), 1.07 (d, J=6.7 Hz, 3H). LCMS-ESI+ (m/z): [M+H]+ calculated for $C_{39}H_{49}ClN_6O_5S$: 749.32; found: 749.18.

Example 214

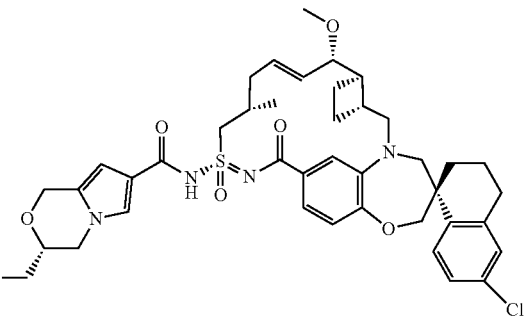

Example 214 was synthesized in a manner similar to Example 167 using (R)-2-(methoxymethyl)oxirane instead of (S)-2-methyloxirane and Example 109. 1H NMR (400 MHz, Acetone-d6) δ 7.78 (d, J=8.5 Hz, 1H), 7.48 (s, 1H), 7.34 (d, J=8.2 Hz, 1H), 7.29-7.20 (m, 2H), 7.14 (d, J=2.3 Hz, 1H), 6.92 (d, J=8.2 Hz, 1H), 6.33 (s, 1H), 6.26-6.00 (m, 1H), 5.70-5.56 (m, 1H), 4.95 (d, J=14.4 Hz, 1H), 4.74 (d, J=14.4 Hz, 1H), 4.26-3.68 (m, 9H), 3.64 (dd, J=10.4, 5.4 Hz, 1H), 3.55 (dd, J=10.4, 4.8 Hz, 1H), 3.44 (d, J=14.3 Hz, 1H), 3.39 (s, 3H), 3.25 (s, 3H), 3.15 (dd, J=15.2, 10.3 Hz, 1H), 2.90-1.40 (m, 16H), 1.14 (d, J=6.4 Hz, 3H). LCMS: 813.2 (M+Na)+.

Example 215

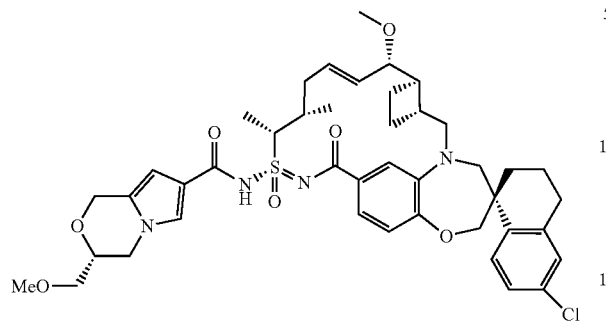

Example 215 was synthesized in a manner similar to Example 214 using Example 110 instead of 109. 1H NMR (400 MHz, Acetone-d6) δ 7.78 (d, J=8.5 Hz, 1H), 7.51-7.19 (m, 4H), 7.14 (s, 1H), 7.05-6.92 (m, 1H), 6.34-6.21 (m, 1H), 6.09-5.95 (m, 1H), 5.63-5.53 (m, 1H), 4.91 (d, J=14.3 Hz, 1H), 4.72 (d, J=14.4 Hz, 1H), 4.64-3.60 (m, 10H), 3.54 (dd, J=10.5, 4.9 Hz, 1H), 3.46-3.11 (m, 2H), 3.39 (s, 3H), 3.19 (s, 3H), 2.93-0.81 (m, 21H). LCMS: 827.1 (M+Na)+.

Example 216

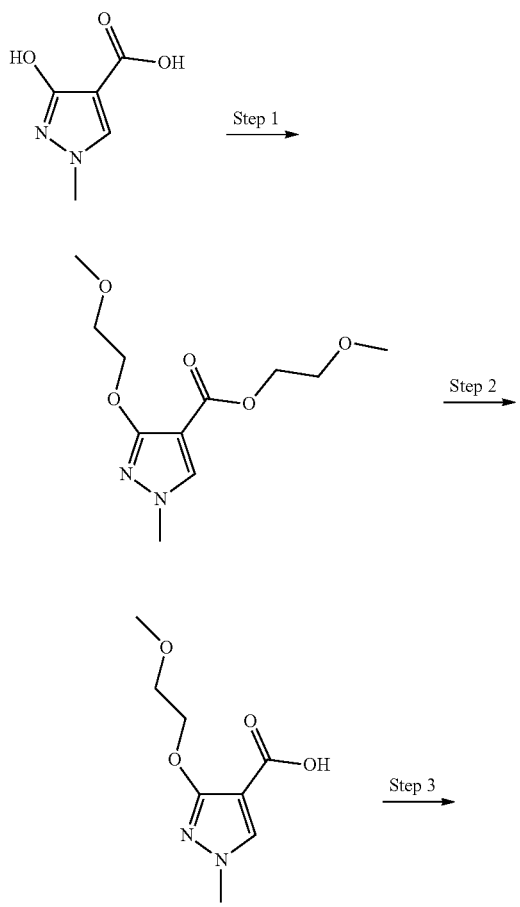

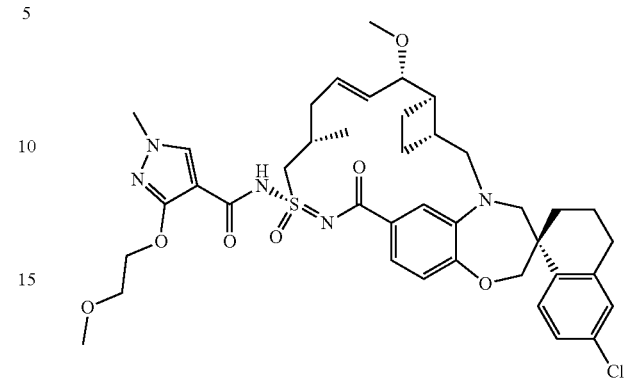

Step 1

3-hydroxy-1-methyl-1H-pyrazole-4-carboxylic acid (100 mg, 0.704 mmol) was dissolved in DMF (3 mL) and sodium hydride (60% dispersion, 84 mg, 2.1 mmol, 3 equiv.) was added in one portion. 1-Iodo-2-m ethoxy ethane (2.1 mmol, 391 mg, 3 equiv.) was added via pipette. The reaction mixture was heated to 80° C. until TLC indicated the complete consumption of starting material. The reaction mixture was quenched with saturated $NH_4Cl$ (3 mL), then diluted with EtOAc (10 mL). The organic layer was washed with saturated $NaHCO_3$ (10 mL) and brine (10 mL). The organic layer was dried over $Na_2SO_4$, filtered, and concentrated under reduced pressure. The residue was purified via column chromatography to afford 2-methoxy ethyl 3-(2-m ethoxy ethoxy)-1-methyl-1H-pyrazole-4-carboxylate.

Step 2

2-methoxyethyl 3-(2-methoxyethoxy)-1-methyl-1H-pyrazole-4-carboxylate (20 mg, 0.08 mmol) was dissolved in a 1:1 mixture of 1,2-dioxane (1 mL) and 1 N NaOH solution (1 mL). The reaction mixture was heated to 80° C. for 4 hours (reaction monitored by TLC and LCMS). The reaction mixture was then cooled to room temperature and quenched with 1 M HCl (1.5 mL) then diluted with EtOAc (5 mL). The organic layer was washed with saturated $NaHCO_3$ (5 mL) and brine (5 mL). The organic layer was dried over $Na_2SO_4$, filtered, and concentrated under reduced pressure to afford 3-(2-methoxyethoxy)-1-methyl-1H-pyrazole-4-carboxylic acid which was used without further purification.

Step 3

Example 216 was synthesized in the same manner as Example 18 using 3-(2-methoxyethoxy)-1-methyl-1H-pyrazole-4-carboxylic acid and Example 109. LCMS-ESI+(m/z): [M+H]+ calcd for $C_{40}H_{49}ClN_5O_7S$: 780.3; found: 780.0.

Example 217

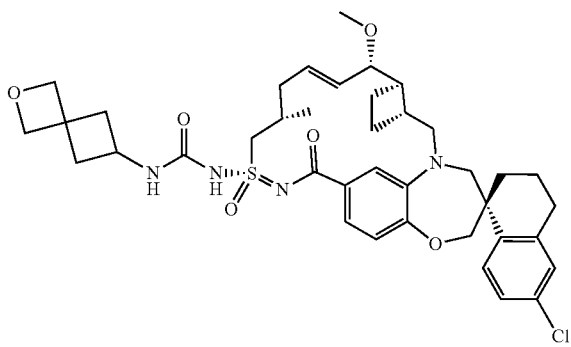 [SMILES: CO[C@H]1/C=C/C[C@H](C)C[S@@](=O)(NC(=O)NC2CC3(COC3)C2)=NC(=O)c2ccc3c(c2)N(C[C@@H]2CC[C@H]21)C[C@@]1(CCCc2cc(Cl)ccc21)CO3]

Example 217 was synthesized in the same manner as Example 75 using 2-oxaspiro[3.3]heptan-6-amine hydrochloride acid and Example 109. $^1$H NMR (400 MHz, Acetone-d$_6$) δ 7.59 (d, J=8.5 Hz, 1H), 7.24 (d, J=8.3 Hz, 1H), 7.05 (d, J=3.8 Hz, 2H), 6.84 (d, J=8.6 Hz, 2H), 6.08 (d, J=13.1 Hz, 1H), 5.73 (d, J=12.7 Hz, 1H), 4.65 (s, 2H), 4.55-4.47 (AB q, 2H), 4.17-4.01 (m, 2H), 3.86-3.70 (m, 2H), 3.66 (d, J=14.3 Hz, 1H), 3.46 (d, J=14.4 Hz, 1H), 3.27 (s, 3H), 3.20-3.07 (m, 1H), 3.03-2.08 (m, 12H), 2.02-1.67 (m, 3H), 1.15 (d, J=6.6 Hz, 3H). LCMS-ESI+ (m/z): [M+H]+ calcd for $C_{39}H_{50}ClN_4O_6S$: 737.31; found: 737.05.

Example 218

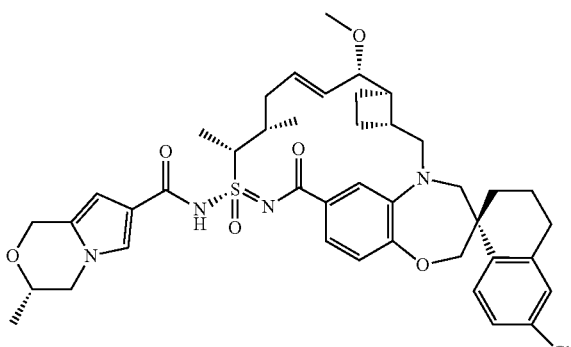

Example 218 was synthesized in a manner similar to Example 167 using Example 110 instead of Example 109. 1H NMR (400 MHz, Acetone-d6) δ 7.78 (d, J=8.5 Hz, 1H), 7.39 (d, J=1.7 Hz, 1H), 7.28-7.24 (m, 1H), 7.24-7.20 (m, 1H), 7.17-7.07 (m, 2H), 7.01 (d, J=8.1 Hz, 1H), 6.29 (d, J=1.5 Hz, 1H), 6.04-5.95 (m, 1H), 5.57 (dd, J=15.3, 8.7 Hz, 1H), 4.89 (dd, J=14.3, 0.9 Hz, 1H), 4.71 (d, J=14.4, 1.3 Hz, 1H), 4.54-4.38 (m, 1H), 4.19-4.06 (m, 3H), 4.04-3.92 (m, 1H), 3.92-3.81 (m, 1H), 3.79-3.60 (m, 3H), 3.39 (d, J=14.2 Hz, 1H), 3.26-3.11 (m, 1H), 3.17 (s, 3H), 2.91-1.67 (m, 15H), 1.58 (d, J=7.1 Hz, 3H), 1.54-1.41 (m, 1H), 1.32 (d, J=6.1 Hz, 3H), 1.05 (d, J=6.8 Hz, 3H). LCMS: 775.0.

Example 219

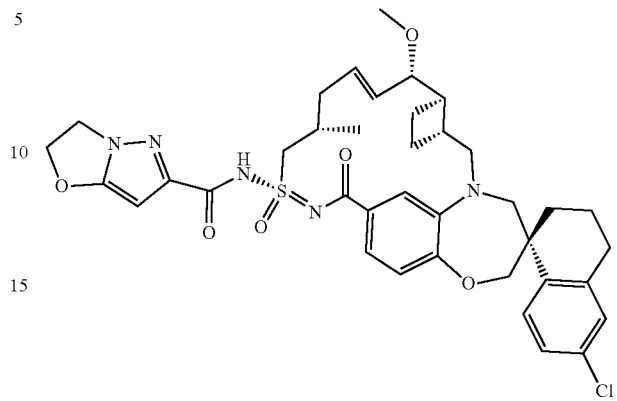

Example 219 was synthesized in the same manner as Example 18, using Example 109 instead of Example 5 and 2,3-dihydropyrazolo[5,1-b]oxazole-6-carboxylic acid was used instead of 3-methoxypropionic acid. 1H NMR (400 MHz, Methanol-d4) δ 7.77 (d, J=8.5 Hz, 1H), 7.26 (dd, J=8.3, 1.8 Hz, 1H), 7.19 (dd, J=8.5, 2.3 Hz, 1H), 7.12 (d, J=2.3 Hz, 1H), 7.08 (s, 1H), 6.95 (d, J=8.2 Hz, 1H), 6.07 (dt, J=14.2, 6.8 Hz, 1H), 5.96 (s, 1H), 5.62 (dd, J=15.3, 8.7 Hz, 1H), 5.16 (t, J=8.1 Hz, 2H), 4.49-4.37 (m, 2H), 4.29 (dd, J=15.0, 6.3 Hz, 2H), 4.15-3.94 (m, 3H), 3.87 (d, J=15.0 Hz, 1H), 3.83-3.75 (m, 1H), 3.71 (d, J=14.3 Hz, 1H), 3.29 (s, 3H), 3.09 (dd, J=15.3, 9.6 Hz, 2H), 2.90-2.71 (m, 3H), 2.47 (s, 3H), 2.33-2.07 (m, 3H), 2.05-1.88 (m, 3H), 1.81 (dd, J=21.4, 8.9 Hz, 3H), 1.46 (t, J=11.8 Hz, 1H), 1.13 (d, J=6.6 Hz, 3H). LCMS-ESI+ (m/z): [M+H]+ calcd for $C_{38}H_{44}ClN_5O_6S$: 734.27; found: 733.75.

Example 220

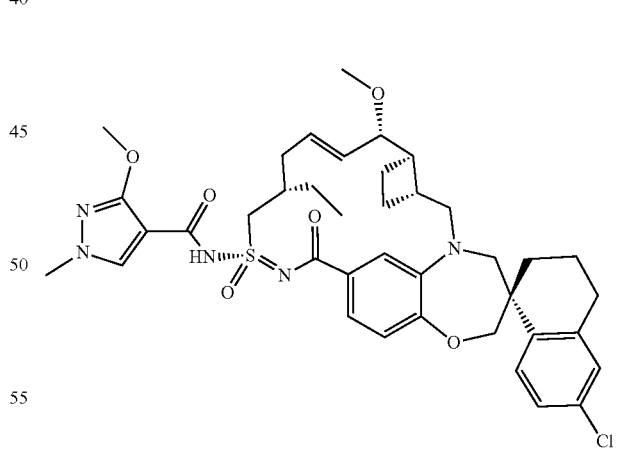

Example 220 was synthesized in the same manner as Example 18 using intermediate 201-1 and 3-methoxy-1-methyl-1H-pyrazole-4-carboxylic acid. $^1$H NMR (400 MHz, Methanol-d4) δ 7.98 (s, 1H), 7.79 (d, J=8.6 Hz, 1H), 7.25 (s, 1H), 7.19 (d, J=9.1 Hz, 1H), 7.11 (d, J=2.3 Hz, 1H), 6.99 (s, 1H), 6.85 (d, J=8.3 Hz, 1H), 6.17 (s, 1H), 5.52 (s, 1H), 4.10-3.99 (m, 2H), 3.95 (d, J=3.3 Hz, 2H), 3.89 (d, J=15.1 Hz, 1H), 3.84-3.79 (m, 1), 3.77 (s, 3H), 3.68 (d, J=14.2 Hz, 1H), 3.26 (s, 4H), 3.07-2.89 (m, 1H), 2.89-2.73 (m, 2H), 2.69 (d, J=17.0 Hz, 1H), 2.43 (s, 2H), 2.13 (m, 3H), 1.97 (m, 3H), 1.76 (d, J=9.2 Hz, 3H), 1.53-1.32 (m, 4), 0.93 (t, J=7.3 Hz, 3H). LCMS-ESI+: calc'd for $C_{39}H_{49}ClN_5O_6S$: 750.30 (M+H); found: 750.80 (M+H).

Example 221

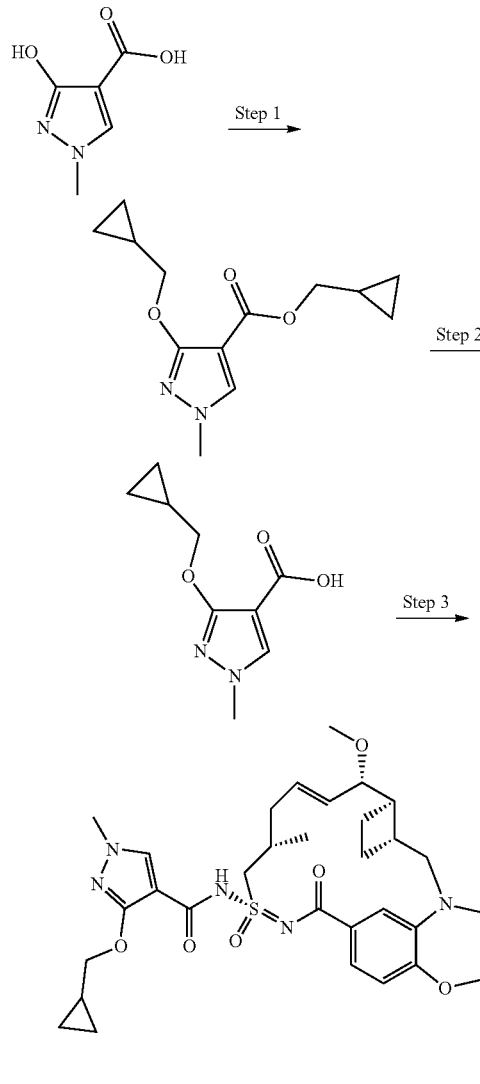

Step 1

3-Hydroxy-1-methyl-1H-pyrazole-4-carboxylic acid (100 mg, 0.704 mmol) was dissolved in DMF (3 mL) and sodium hydride (60% dispersion, 84 mg, 2.1 mmol, 3 equiv.) was added in one portion. (Iodomethyl)cyclopropane (2.1 mmol, 382 mg, 3 equiv.) was added via pipette. The reaction mixture was heated to 80° C. until TLC indicated the complete consumption of starting material. The reaction mixture was quenched with saturated NH₄Cl (3 mL), then diluted with EtOAc (10 mL). The organic layer was washed with saturated NaHCO₃ (10 mL) and brine (10 mL). The organic layer was dried over Na₂SO₄, filtered, and concentrated under reduced pressure. The residue was purified via column chromatography to afford cyclopropylmethyl 3-(cyclopropylmethoxy)-1-methyl-1H-pyrazole-4-carboxylate.

Step 2

Cyclopropylmethyl 3-(cyclopropylmethoxy)-1-methyl-1H-pyrazole-4-carboxylate (20 mg, 0.08 mmol) was dissolved in a 1:1 mixture of 1,2-dioxane (1 mL) and 1 N NaOH solution (1 mL). The reaction mixture was heated to 80° C. for 4 hours (reaction was monitored by TLC and LCMS). The reaction mixture was then cooled to room temperature, quenched with 1 M HCl (1.5 mL), then diluted with EtOAc (5 mL). The organic layer was washed with saturated NaHCO₃ (5 mL) and brine (5 mL). The organic layer was dried over Na₂SO₄, filtered, and concentrated under reduced pressure to afford 3-(cyclopropylmethoxy)-1-methyl-1H-pyrazole-4-carboxylic acid that was used without further purification.

Step 3

Example 221 was synthesized in the same manner as Example 18 using 3-(cyclopropylmethoxy)-1-methyl-1H-pyrazole-4-carboxylic acid and Example 109. LCMS-ESI+ (m/z) [M+H]+: calcd for $C_{41}H_{50}ClN_5O_6S$: 776.3, found: 776.0.

Example 222

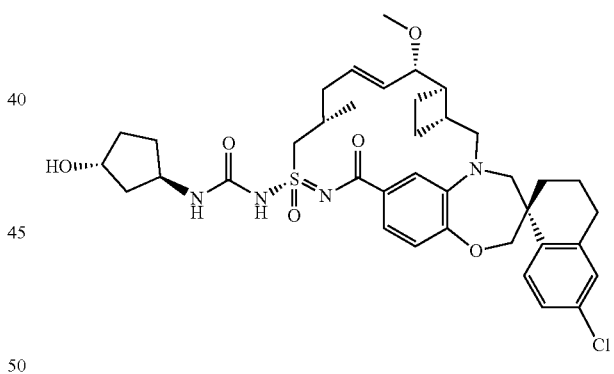

Example 222 was prepared in a similar manner to Example 75 using (1R,3R)-3-aminocyclopentan-1-ol, triethylamine and Example 109. 1H NMR (400 MHz, DMSO-d6) δ 7.63 (d, J=8.5 Hz, 1H), 7.24 (dd, J=8.5, 2.3 Hz, 1H), 7.18-7.08 (m, 2H), 6.96 (s, 1H), 6.86 (d, J=8.0 Hz, 2H), 6.06-5.86 (m, 1H), 5.47 (dd, J=15.3, 8.7 Hz, 1H), 4.20-3.97 (m, 4H), 3.92 (d, J=12.2 Hz, 1H), 3.84 (d, J=13.7 Hz, 1H), 3.73 (d, J=14.8 Hz, 1H), 3.66-3.48 (m, 2H), 3.31 (s, 6H), 3.20 (d, J=14.2 Hz, 1H), 3.12 (s, 3H), 3.05-2.92 (m, 1H), 2.86-2.58 (m, 3H), 2.43-2.17 (m, 2H), 2.15-1.55 (m, 8H), 1.55-1.24 (m, 2H), 0.98 (d, J=6.8 Hz, 3H). LCMS-ESI+ (m/z): [M+H]+ calcd for $C_{38}H_{49}ClN_4O_6S$: 725.31; found: 724.82.

Example 223

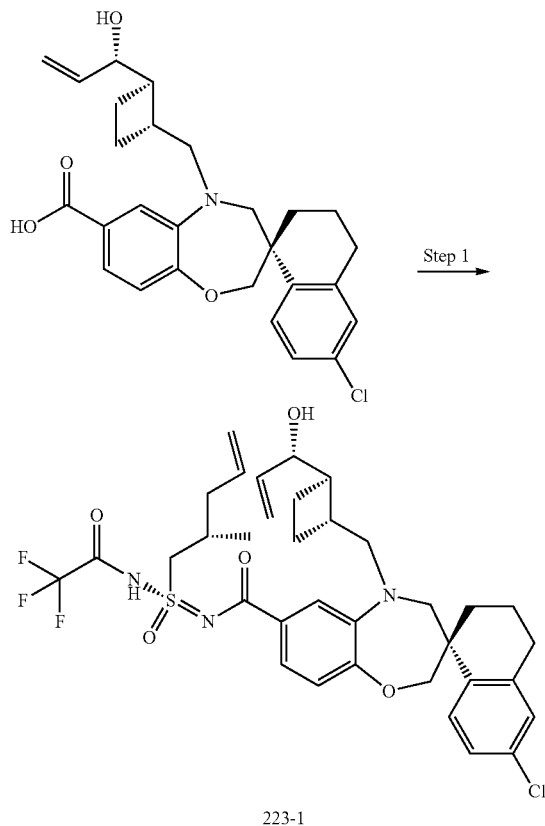

223-1

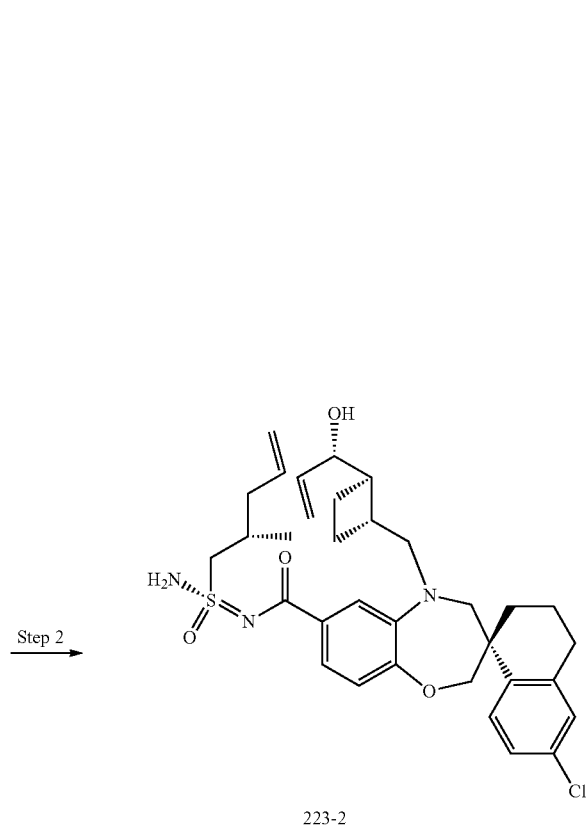

223-2

Example 223

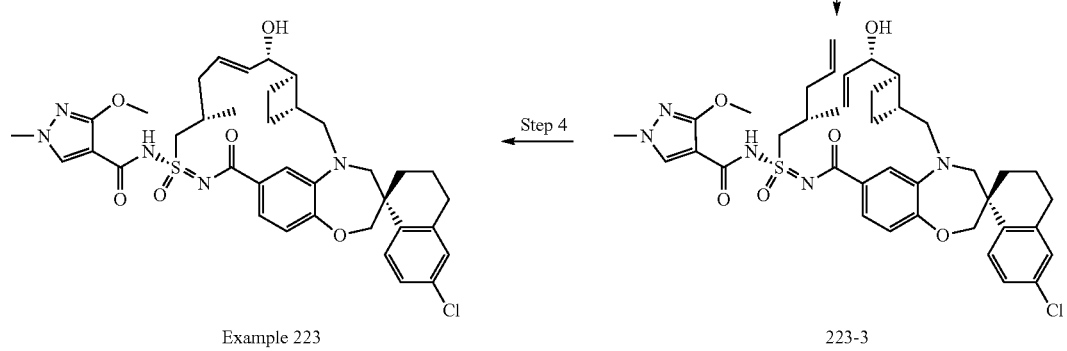

223-3

Step 1

To a stirred solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4] oxazepine-3,1'-naphthalene]-7-carboxylic acid (1140 mg, 2.4 mmol) in DCM (100 mL) was added 109-2-2 (703 mg, 2.55 mmol), 1-(3-dimethylaminopropyl)-3-ethylcarbodiimide HCl (756 mg, 4.87 mmol) and 4-(dimethylamino)pyridine (595 mg, 4.87 mmol). The reaction mixture was stirred at room temperature for 4 hr. Then the reaction mixture was diluted with DCM, washed with 1 N HCl and brine. The organic phase was dried over MgSO$_4$, filtered, and concentrated to give intermediate 223-1.

Step 2

To a stirred solution of 223-1 (1300 mg, 1.83 mmol) in methanol (50 mL) was added water (5 mL), K$_2$CO$_3$ (899 mg, 9.17 mmol), and the reaction mixture was stirred at 60° C. for 24 hrs. More water was added and the mixture was extracted with dichloromethane. The organic phase was dried over anhydrous magnesium sulfate and the solvent was removed under reduced pressure down to yield 223-2.

Step 3

To a stirred solution of 223-2 (1000 mg, 1.63 mmol) in DCM (25 mL) was added 3-methoxy-1-methyl-1H-pyrazole-4-carboxylic acid (280 mg, 1.79 mmol), 1-(3-dimethylaminopropyl)-3-ethylcarbodiimide HCl (507 mg, 3.26 mmol) and 4-(dimethylamino)pyridine (399 mg, 3.26 mmol). The reaction mixture was stirred at room temperature for 24 h. Then the reaction mixture was diluted with DCM, and washed with 1 N HCl and brine. The organic phase was dried over MgSO₄, filtered, concentrated, and purified on normal phase chromatography 0-10% DCM/MeOH to yield 223-3.

Step 4

To a stirred solution of 223-3 (1000 mg, 1.33 mmol), Hoveyda-Grubbs II (339 mg, 0.40 mmol) and TFA (455 mg, 3.99 mmol) in 1,2-dichloroethane (370 mL) was degassed with argon. The reaction mixture was stirred at 80° C. for 1 hr. The reaction mixture was concentrated and purified on reversed phase chromatography 0.1% TFA 70-95% acetonitrile to give Example 223. 1H NMR (400 MHz, Chloroform-d) δ 7.83 (s, 1H), 7.77 (d, J=8.5 Hz, 1H), 7.50 (dd, J=8.2, 1.9 Hz, 1H), 7.40 (d, J=2.0 Hz, 1H), 7.20 (dd, J=8.5, 2.4 Hz, 1H), 7.11 (d, J=2.3 Hz, 1H), 6.96 (d, J=8.2 Hz, 1H), 5.64 (t, J=7.3 Hz, 2H), 4.74-4.64 (m, 1H), 4.21-4.01 (m, 4H), 3.96 (d, J=15.1 Hz, 1H), 3.86-3.63 (m, 4H), 3.35 (d, J=14.4 Hz, 1H), 3.16 (dd, J=15.3, 9.1 Hz, 1H), 2.79 (dd, J=10.0, 5.3 Hz, 2H), 2.67-2.48 (m, 2H), 2.45-2.21 (m, 5H), 1.46 (td, J=14.8, 6.9 Hz, 2H), 1.28 (s, 4H), 1.13 (d, J=7.1 Hz, 4H), 0.96-0.77 (m, 3H). LCMS-ESI+ (m/z): [M+H]+ calcd for $C_{37}H_{44}ClN_5O_6S$: 722.27; found: 722.33.

Example 224

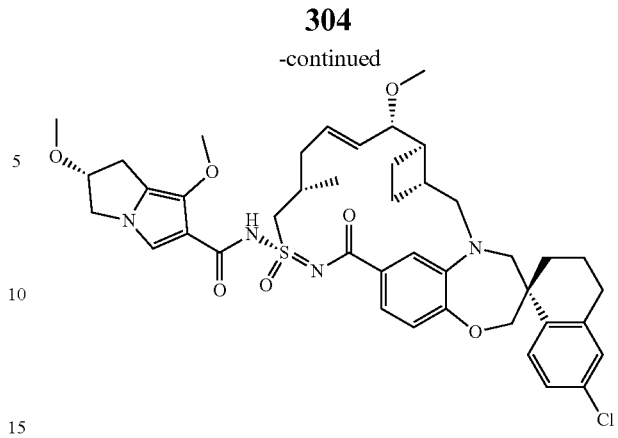

Example 224

Step 1

To a stirred solution of (2S,4R)-4-methoxypyrrolidine-2-carboxylic acid (1.5 g, 10.33 mmol), DIPEA (5.4 mL, 31.0 mmol) in THF (48 mL) and EtOH (32 mL) was added ethyl propiolate (1.0 g, 10.33 mmol) over 2 min at room temperature. The reaction was stirred at room temperature for 2 hours, and then concentrated under reduced pressure. Solids were dissolved with 150 mL of DCM and then DMAP (0.63 g, 5.2 mmol), DIPEA (3.9 mL, 22.7 mmol) and triphenyl phosphine (3.1 g, 12.0 mmol) were added. The mixture was cooled down to 0° C. and iodine (3.0 g, 11.9 mmol) was added. The mixture was stirred vigorously over 40 min to reach room temperature and then heated at 50° C. for 1 hr. DCM, 0.2M HCl, and brine were added, organic phase was extracted, dried over Mg₂SO₄, and concentrated under reduced pressure. The resulting residue was dissolved in acetone (60 mL) and combined with Cs₂CO₃ (13.5 g, 41.3 mmol) and methyl sulfate (6.5 g, 51.7 mmol), stirred at room temperature for 60 min. Solids were filtered out and organic layers were purified on normal phase chromatography (0 to 35% EtOAc/hexanes) to yield 224-1.

Step 2

To a stirred solution of 224-1 (120 mg, 0.53 mmol) in methanol (3 mL) was added THF (3 mL) and 2 N of NaOH (1 mL) and stirred at room temperature for 48 h. To the reaction mixture was added 2 N HCl (1 mL) and the reaction mixture was concentrated. Water was added and the mixture was extracted with dichloromethane. The organic phase was dried over anhydrous magnesium sulfate and the solvent was removed under reduced pressure to give 224-2.

Step 3

Example 224 was synthesized in the same manner as Example 174 (step 3) using (R)-2,7-dimethoxy-2,3-dihydro-1H-pyrrolizine-6-carboxylic acid and Example 109. 1H NMR (400 MHz, Chloroform-d) δ 7.76 (d, J=8.5 Hz, 1H), 7.48 (dd, J=8.2, 1.8 Hz, 1H), 7.24-7.15 (m, 3H), 7.10 (d, J=2.3 Hz, 1H), 6.93 (d, J=8.3 Hz, 1H), 6.11 (dt, J=14.0, 6.6 Hz, 1H), 5.60 (dd, J=15.6, 7.8 Hz, 1H), 4.53 (tt, J=6.2, 3.5 Hz, 1H), 4.22-3.92 (m, 6H), 3.91-3.68 (m, 3H), 3.43 (m, 3H), 3.37-3.22 (m, 6H), 3.18-2.92 (m, 3H), 2.90-2.70 (m, 2H), 2.66-2.27 (m, 4H), 2.23-1.61 (m, 6H), 1.28 (m, 4H), 1.11 (d, J=6.8 Hz, 3H), 0.96-0.72 (m, 1H). LCMS-ESI+ (m/z): [M+H]+ calcd for $C_{42}H_{51}ClN_4O_7S$: 791.32; found: 791.35.

Example 225

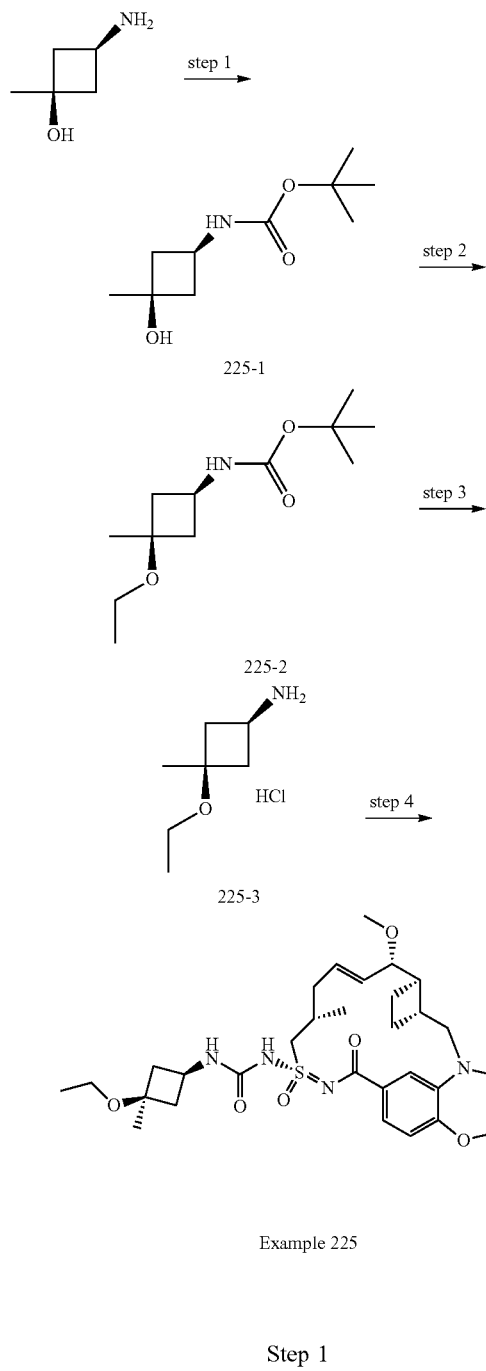

Example 225

Step 1

Synthesis of 225-1: cis-3-Amino-1-methyl-cyclobutanol HCl salt (340 mg, 3.36 mmol) was treated with DCM (3.0 mL) and DMF (1.5 mL) at room temperature. DIEA (1.303 g, 10.1 mmol) was added followed by di-tert-butyl dicarbonate (880 mg, 4.03 mmol). The resulting mixture was stirred at rt for 4 hrs. The reaction was then diluted with EtOAc (15.0 mL), washed with 1 N HCl (3.0 mL), sat. NaHCO$_3$ (3.0 mL), brine (3.0 mL), dried over sodium sulfate, filtered, and concentrated to give crude 225-1 for using directly.

Step 2

Synthesis of 225-2: 225-1 (147 mg, 0.73 mmol) in a mixture of THF (1.5 mL) and DMF (1.5 mL) was cooled to 0° C., NaH (60 wt % dispersion in mineral oil, 42 mg, 1.10 mmol) was added. After stirred for 20 min, EtI (137 mg, 0.876 mmol) was added. The reaction was slowly warmed up to rt and stirred at room temperature for 3 hrs. The reaction was then partitioned between EtOAc (15.0 mL) and water (3.0 mL). The organic layer was washed with brine (3.0 mL), dried over sodium sulfate, filtered, and concentrated to give crude product, which was purified by combiflash (4 g silica gel, 0-43% EtOAc/Hexanes). The 2nd eluted peak was the desired product. 1H NMR (400 MHz, Chloroform-d) δ 4.71-4.61 (m, 1H), 3.90-3.80 (m, 1H), 3.35 (q, J=7.0 Hz, 2H), 2.44-2.35 (m, 2H), 1.97-1.88 (m, 2H), 1.45 (s, 9H), 1.32 (d, J=0.9 Hz, 3H), 1.19 (t, J=7.0 Hz, 3H).

Step 3: Preparation of 225-3

225-2 from previous step was dissolved in DCM (2.4 mL) at room temperature, 4 N HCl in 1,4-dioxane (0.8 mL) was added dropwise. The reaction was stirred at rt for 1 hr. The reaction was concentrated, and co-evaporated with EtOAc (3×) to give 225-3.

Step 4

Example 225 was synthesized in the same manner as Example 75 with Example 109 and 225-3 and DIEA. 1H NMR (400 MHz, Methanol-d4) δ 7.69 (d, J=8.5 Hz, 1H), 7.24-7.17 (m, 1H), 7.11-7.05 (m, 2H), 6.99 (s, 1H), 6.88 (d, J=8.1 Hz, 1H), 6.10-5.99 (m, 1H), 5.62 (dd, J=15.4, 8.9 Hz, 1H), 4.23 (dd, J=14.8, 7.0 Hz, 1H), 4.07-4.00 (m, 2H), 3.96-3.86 (m, 1H), 3.86-3.74 (m, 3H), 3.66 (d, J=14.3 Hz, 1H), 3.42 (q, J=7.0 Hz, 2H), 3.29 (s, 3H), 3.12-3.02 (m, 1H), 2.89-2.73 (m, 2H), 2.57-2.31 (m, 6H), 2.28-2.02 (m, 7H), 1.86-1.73 (m, 4H), 1.41 (t, J=11.0 Hz, 1H), 1.31 (s, 3H), 1.19 (t, J=7.0 Hz, 3H), 1.14 (d, J=6.7 Hz, 3H). [M+H]+ calcd for C$_{40}$H$_{53}$ClN$_4$O$_6$S: 753.39; found: 752.79.

Example 226

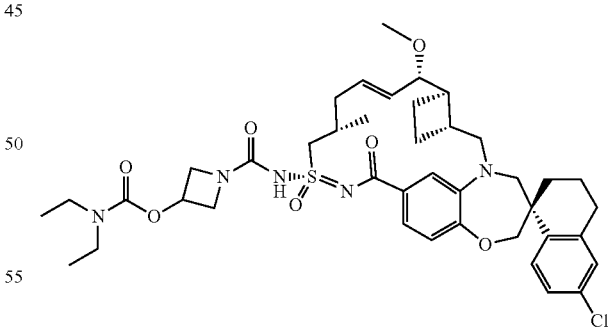

Example 226 was synthesized in the same manner as Example 75 using trans-3-aminocyclobutyl diethylcarbamate tetrakis-trifluoroacetic acid and Example 109. 1H NMR (400 MHz, Methanol-d4) δ 7.72 (d, J=8.5 Hz, 1H), 7.16 (d, J=8.8 Hz, 1H), 7.09 (d, J=5.7 Hz, 2H), 6.95-6.86 (m, 2H), 5.95 (dt, J=14.3, 6.9 Hz, 1H), 5.56 (dd, J=15.2, 9.1 Hz, 1H), 5.15-5.05 (m, 1H), 4.45-4.22 (m, 3H), 4.15-3.89 (m, 4H), 3.83 (d, J=15.1 Hz, 1H), 3.74 (dd, J=9.2, 3.6 Hz, 1H), 3.70-3.54 (m, 2H), 3.35 (m, 4H), 3.27 (d, J=14.8 Hz, 1H), 3.24 (s, 3H), 3.06 (dd, J=15.3, 10.3 Hz, 1H), 2.89-2.66 (m, 2H), 2.54-2.39 (m, 2H), 2.33 (q, J=9.1 Hz, 1H), 2.24-2.03 (m, 3H), 2.01-1.65 (m, 6H), 1.43 (t, J=13.4 Hz, 1H), 1.13 (d, J=6.6).

Example 227

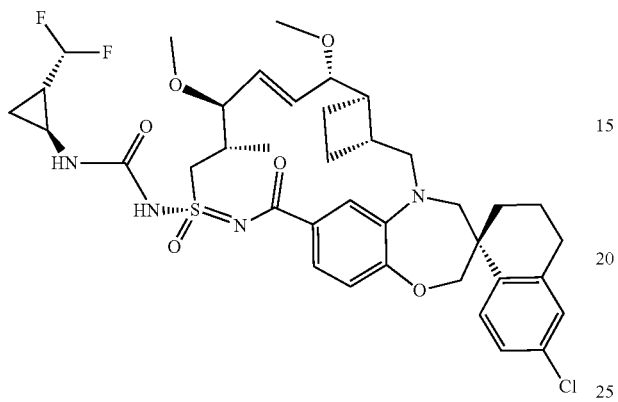

Example 227 was synthesized in the same manner as Example 237 using intermediate 375-2 and (1S,2R)-2-(difluoromethyl)cyclopropan-1-amine hydrochloride. $^1$H NMR (400 MHz, Methanol-d4) δ 7.74 (d, J=8.5 Hz, 1H), 7.24-7.14 (m, 2H), 7.12 (d, J=2.3 Hz, 1H), 7.00 (s, 1H), 6.91 (d, J=8.2 Hz, 1H), 6.02-5.91 (m, 1H), 5.86-5.66 (m, 2H), 4.23 (dd, J=15.1, 3.3 Hz, 1H), 4.08 (s, 2H), 3.95-3.76 (m, 2H), 3.72 (d, J=8.1 Hz, 1H), 3.67 (d, J=14.3 Hz, 1H), 3.31 (d, J=1.2 Hz, 7H), 3.15-3.05 (m, 1H), 2.92-2.69 (m, 3H), 2.54 (d, J=9.7 Hz, 1H), 2.46-2.29 (m, 1H), 2.17-2.00 (m, 2H), 2.00-1.91 (m, 2H), 1.91-1.68 (m, 2H), 1.54 (m, 1H), 1.45 (t, J=13.2 Hz, 1H), 1.31 (s, 1H), 1.25 (d, J=6.8 Hz, 3H), 1.10 (q, J=6.6 Hz, 1H), 0.93 (m, 2H). LCMS-ESI+: calc'd for $C_{38}H_{48}ClF_2N_4O_6S$: 761.29 (M+H); found: 761.26 (M+H).

Example 228

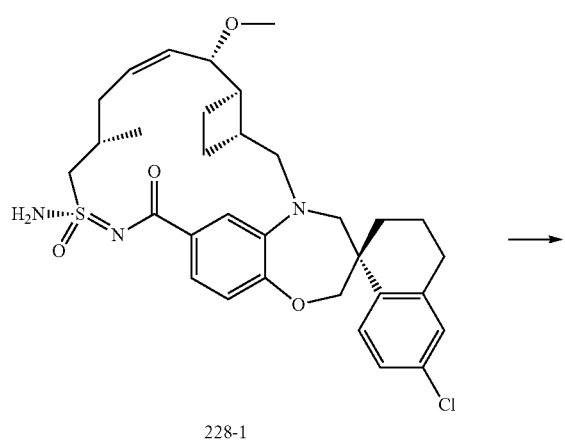

228-1

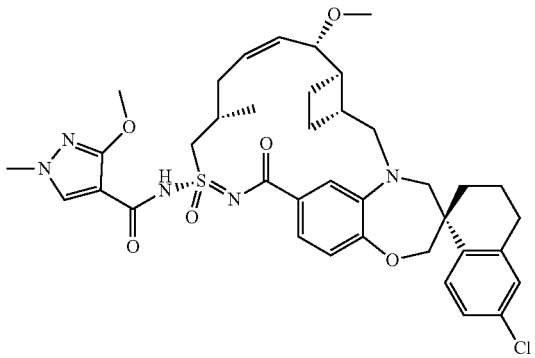

Example 228

Preparation of Intermediate 228-1: A stirred mixture of 106-2 (2.14 g, 3.42 mmol), magnesium oxide (413 mg, 10.3 mmol), and (1,3-bis-(2,4,6-trimethylphenyl)-2-imidazolidinylidene)dichloro(o-isopropoxyphenylmethylene)ruthenium (449 mg, 717 μmol) in 1,2-dichloroethane (485 mL) was heated 80° C. After 18.5 h, the resulting mixture was cooled to room temperature, filtered through celite, and concentrated under reduced pressure. The residue was dissolved in a mixture of ethyl acetate (50 mL) and toluene (100 mL). Silica gel (40 g) was added, and the resulting slurry was concentrated under reduced pressure. The residue was purified by flash column chromatography on silica gel (0 to 65% ethyl acetate in hexanes) to give a mixture of intermediate 106-4 and Intermediate 228-1. The mixture was purified by reverse phase preparative hplc (0.1% trifluoroacetic acid in acetonitrile/water) to give Intermediate 228-1. 1H NMR (400 MHz, Acetone-d6) δ 7.79 (d, J=8.5 Hz, 1H), 7.39 (d, J=1.9 Hz, 1H), 7.31 (dd, J=8.2, 1.9 Hz, 1H), 7.24 (dd, J=8.5, 2.4 Hz, 1H), 7.14 (d, J=2.3 Hz, 1H), 7.07 (s, 1H), 6.89 (d, J=8.2 Hz, 1H), 5.82 (td, J=9.8, 6.1 Hz, 1H), 5.54-5.43 (m, 1H), 4.28-4.17 (m, 1H), 4.11 (d, J=12.1 Hz, 1H), 4.01 (d, J=12.1 Hz, 1H), 3.94 (d, J=15.1 Hz, 1H), 3.78 (d, J=14.3 Hz, 1H), 3.64 (dd, J=14.3, 3.4 Hz, 1H), 3.49 (d, J=14.3 Hz, 1H), 3.40 (dd, J=14.3, 8.1 Hz, 1H), 3.28 (dd, J=15.2, 10.7 Hz, 1H), 3.23 (s, 3H), 2.88-1.27 (m, 15H), 1.17 (d, J=6.9 Hz, 3H). LCMS: 598.2.

Example 228 was synthesized in the same manner as Example 18 using Intermediate 228-1and 3-methoxy-1-methyl-pyrazole-4-carboxylic acid. 1H NMR (400 MHz, Methanol-d4) δ 8.14 (s, 1H), 7.78-7.68 (m, 1H), 7.37 (dd, J=8.2, 1.9 Hz, 1H), 7.32 (d, J=2.0 Hz, 1H), 7.16-7.09 (m, 2H), 6.91 (d, J=8.2 Hz, 1H), 5.88-5.76 (m, 1H), 5.55-5.45 (m, 1H), 4.31-4.24 (m, 1H), 4.14-3.98 (m, 6H), 3.95-3.88 (m, 1H), 3.82 (s, 3H), 3.79-3.66 (m, 2H), 3.48 (d, J=14.3 Hz, 1H), 3.30 (s, 3H), 3.27-3.19 (m, 1H), 2.97-2.72 (m, 3H), 2.57-2.35 (m, 3H), 2.34-2.23 (m, 1H), 2.17-2.08 (m, 1H), 2.02-1.90 (m, 3H), 1.89-1.79 (m, 3H), 1.53-1.42 (m, 1H), 1.14 (d, J=7.0 Hz, 3H). LCMS-ESI+ (m/z): calcd H+ for $C_{38}H_{46}ClN_5O_6S$: 736.29; found: 736.08.

Example 229

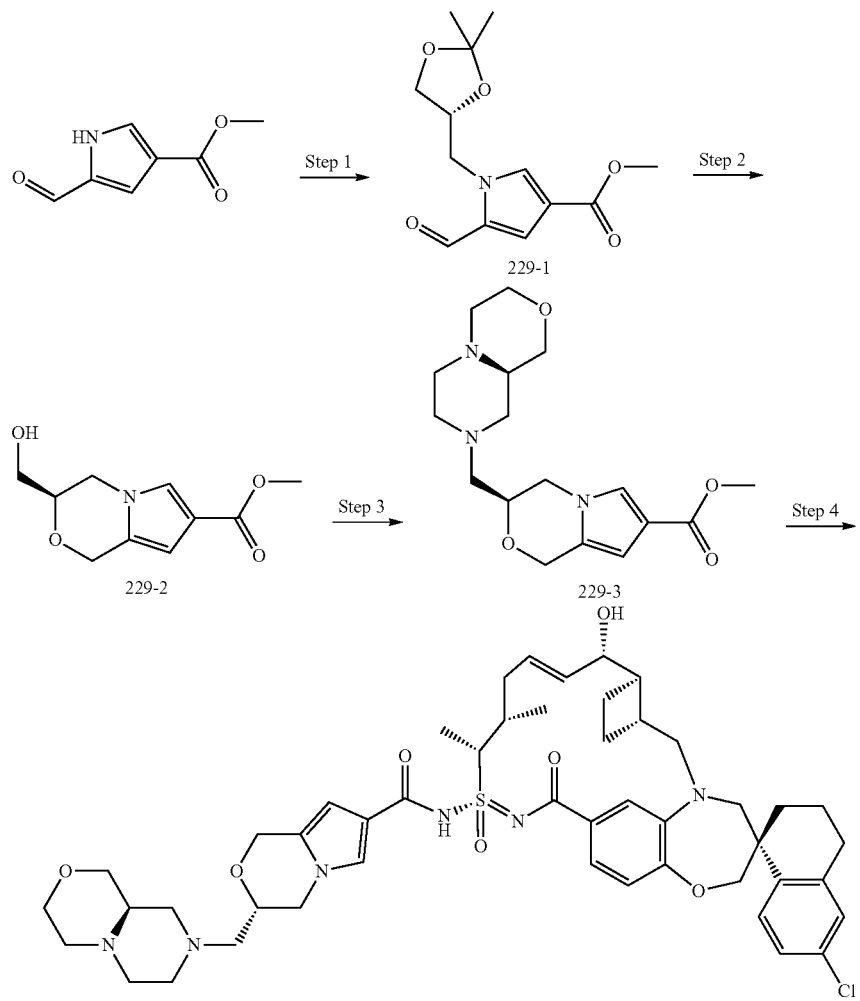

Step 1

A stirred mixture of methyl 5-formyl-1H-pyrrole-3-carboxylate (700 mg, 4.57 mmol), (S)-4-(iodomethyl)-2,2-dimethyl-1,3-dioxolane (2.12 g, 8.76 mmol), and potassium carbonate (1.58 g, 11.4 mmol) in N,N-dimethylformamide (18 mL) was heated to 85° C. After 16 h, the resulting mixture was cooled to room temperature, and diethyl ether (250 mL), ethyl acetate (150 mL), and saturated aqueous ammonium chloride solution (20 mL) were added sequentially. The organic layer was washed with water (2×400 mL), dried over anhydrous magnesium sulfate, filtered, and concentrated under reduced pressure. The residue was purified by flash column chromatography on silica gel (0 to 45% ethyl acetate in hexanes) to give 229-1.

Step 2

Aqueous hydrogen chloride solution (6.0 M, 2.87 mL, 17 mmol) was added via syringe to a stirred solution of 229-1 (766 mg, 2.87 mmol) in methanol (11.5 mL) at room temperature. After 30 min, saturated aqueous sodium carbonate solution (9 mL), brine (30 mL), and water (20 mL) were added sequentially. The aqueous layer was extracted with dichloromethane (4×60 mL). The combined organic layers were dried over anhydrous magnesium sulfate, filtered, and concentrated under reduced pressure. The residue was dissolved in dichloromethane (200 mL) and methanol (1.16 mL), and the mixture was stirred at room temperature. Trifluoroacetic acid (2.19 mL, 28.7 mmol) was added via syringe. After 1 min, triethylsilane (4.81 mL, 30.1 mmol) was added via syringe. After 40 min, trifluoroacetic acid (4.38 mL, 57.4 mmol) and triethylsilane (9.6 mL, 60.2 mmol) were added sequentially via syringe. After 30 min, saturated aqueous sodium carbonate solution (43 mL) and brine (100 mL) were added sequentially. The organic layer was separated, and the aqueous layer was extracted with dichloromethane (100 mL). The combined organic layers were dried over anhydrous magnesium sulfate, filtered, and concentrated under reduced pressure. The residue was purified by flash column chromatography on silica gel (0 to 75% ethyl acetate in hexanes) to give 229-2.

Step 3

Iodine (37.7 mg, 148 µmol) was added to a stirred mixture of 229-2 (15 mg, 71 µmol), triphenylphosphine (38.9 mg, 148 µmol), and imidazole (14.5 mg, 213 µmol) in tetrahydrofuran (1.0 mL) at room temperature. After 50 min, (R)-octahydropyrazino[2,1-c][1,4]oxazine dihydrochloride (153 mg, 710 µmol), potassium carbonate (294 mg, 2.13 mmol), and acetonitrile (1.0 mL) were added sequentially, and the resulting mixture was heated to 60° C. After 135 min, the resulting mixture was cooled to room temperature, and water (15 mL) and brine (15 mL) were added sequentially. The aqueous layer was extracted sequentially with dichloromethane (30 mL) and ethyl acetate (30 mL). The combined organic layers were dried over anhydrous magnesium sulfate, filtered, and concentrated under reduced pressure. The residue was purified by flash column chromatography on silica gel (0 to 9% methanol in dichloromethane) to give 229-3.

Step 4: Preparation of Example 229

Aqueous sodium hydroxide solution (2.0 M, 54 µL, 108 µmol) was added via syringe to a stirred mixture of 229-3 (3.0 mg, 14 µmol) in tetrahydrofuran (0.7 mL) and methanol (0.2 mL) at room temperature. The resulting mixture was heated to 80° C. After 17.5 h, the resulting mixture was cooled to room temperature and was concentrated under reduced pressure. The residue was dried azeotropically by concentration under reduced pressure from toluene (2 mL). Tetrahydrofuran (2 mL) and hydrogen chloride solution (2.0 M in 1,4-dioxane, 27.2 µL) were added sequentially, and the resulting mixture was concentrated under reduced pressure. The residue was dried azeotropically by concentration under reduced pressure from toluene (2 mL). Intermediate 359-4 (6.5 mg, 11 µmol), 4-dimethylaminopyridine (4.0 mg, 33 µmol), trimethylamine (6.1 µL, 43 µmol) and dichloromethane (1.0 mL) were added sequentially, and the resulting mixture was stirred at room temperature. 3-(((Ethylimino)methylene)amino)-N,N-dimethylpropan-1-amine hydrochloride (2.7 mg, 14 µmol) was added, and the resulting mixture was heated to 45° C. After 60 min, the resulting mixture was cooled to room temperature and was concentrated under reduced pressure. The residue was purified by reverse phase preparative HPLC (0.1% trifluoroacetic acid in acetonitrile/water) to give Example 229. 1H NMR (400 MHz, Acetone-d6) δ 7.78 (d, J=8.3 Hz, 1H), 7.42 (s, 1H), 7.31-7.17 (m, 3H), 7.15 (d, J=2.6 Hz, 1H), 7.00 (d, J=8.0 Hz, 1H), 6.31 (s, 1H), 5.93-5.79 (m, 1H), 5.74 (dd, J=15.3, 7.3 Hz, 1H), 4.93 (d, J=14.6 Hz, 1H), 4.79 (d, J=14.5 Hz, 1H), 4.54-1.66 (m, 40H), 1.56 (d, J=7.1 Hz, 3H), 1.54-1.43 (m, 1H), 1.10-0.98 (m, 3H). LCMS: 901.3.

Example 230

Example 230 was prepared in a similar manner to Example 75 using 1-oxa-6-azaspiro[3.3]heptane, triethylamine and Example 109. $^1$H NMR (400 MHz, DMSO-d$_6$) δ 7.65 (d, J=8.5 Hz, 1H), 7.28 (dd, J=8.5, 2.4 Hz, 1H), 7.18 (d, J=2.4 Hz, 1H), 7.05 (dd, J=8.2, 1.8 Hz, 1H), 6.92 (d, J=8.1 Hz, 1H), 6.85 (d, J=1.9 Hz, 1H), 5.88 (dt, J=14.3, 6.8 Hz, 1H), 5.49 (dd, J=15.2, 8.8 Hz, 1H), 4.40 (t, J=7.4 Hz, 2H), 4.27-3.91 (m, 5H), 3.86-3.53 (m, 4H), 3.19 (dd, J=13.7, 10.6 Hz, 1H), 3.13 (s, 3H), 3.01 (dd, J=15.2, 10.4 Hz, 1H), 2.89-2.58 (m, 4H), 2.41-2.29 (m, 3H), 2.29-2.04 (m, 2H), 2.02-1.59 (m, 7H), 1.36 (d, J=9.7 Hz, 1H), 1.24 (s, 1H), 1.01 (d, J=6.8 Hz, 3H). LCMS-ESI+ (m/z): [M+H] Calculated for C$_{38}$H$_{47}$ClN$_4$O$_6$S: 723.21; found 722.71.

Example 231

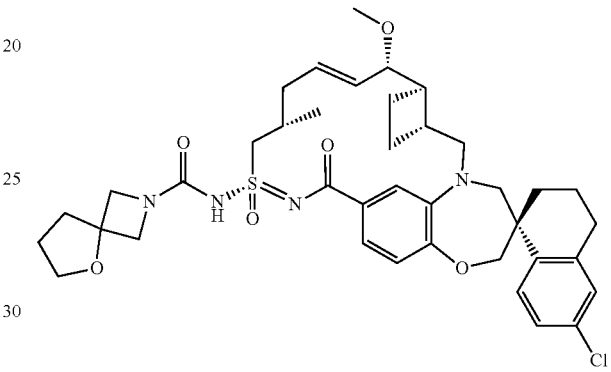

Example 231 was prepared in a similar manner to Example 75 using 5-oxa-2-azaspiro[3.4]octane, triethylamine and Example 109. $^1$H NMR (400 MHz, DMSO-d$_6$) δ 7.65 (d, J=8.5 Hz, 1H), 7.28 (dd, J=8.5, 2.4 Hz, 1H), 7.18 (d, J=2.4 Hz, 1H), 7.06 (dd, J=8.2, 1.8 Hz, 1H), 6.92 (d, J=8.1 Hz, 1H), 6.86 (d, J=1.9 Hz, 1H), 5.89 (dt, J=14.3, 6.8 Hz, 1H), 5.49 (dd, J=15.2, 8.8 Hz, 1H), 4.14-3.84 (m, 5H), 3.75 (t, J=6.7 Hz, 3H), 3.66-3.54 (m, 2H), 3.20 (d, J=14.2 Hz, 1H), 3.13 (s, 3H), 3.01 (dd, J=15.3, 10.4 Hz, 1H), 2.86-2.60 (m, 3H), 2.43-2.28 (m, 2H), 2.29-2.08 (m, 2H), 2.07-1.91 (m, 4H), 1.84 (dq, J=11.3, 5.4, 4.1 Hz, 4H), 1.70 (ddt, J=23.7, 15.0, 7.1 Hz, 3H), 1.48-1.17 (m, 2H), 1.02 (d, J=6.8 Hz, 3H). LCMS-ESI+ (m/z): [M+H] Calculated for C$_{39}$H$_{49}$ClN$_4$O$_6$S: 737.31; found 736.84.

Example 232

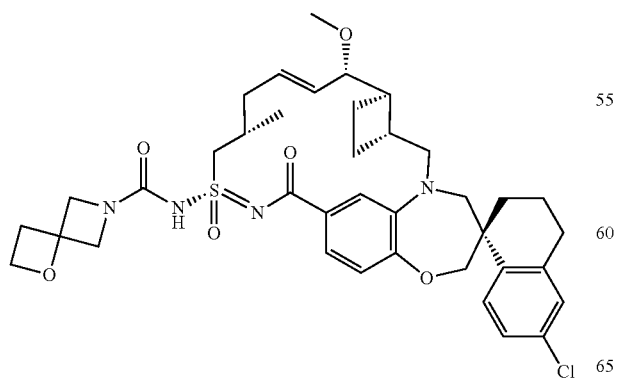

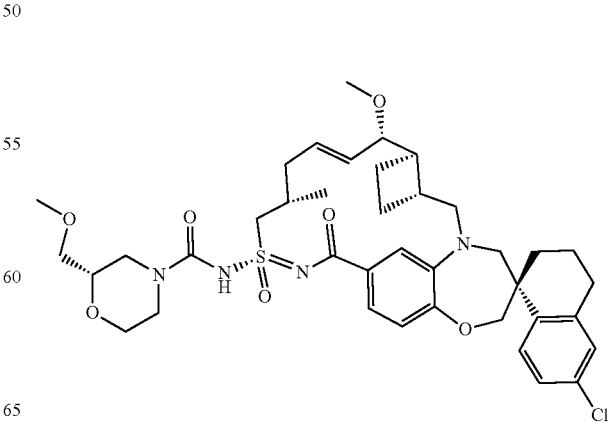

Example 232 was synthesized in the same manner as Example 75 with Example 109 and (2S)-2-(methoxymethyl)morpholine; hydrochloride and DIEA. 1H NMR (400 MHz, Methanol-d4) δ 7.75 (d, J=8.5 Hz, 1H), 7.19 (dd, J=8.5, 2.4 Hz, 1H), 7.15-7.05 (m, 2H), 6.94 (d, J=8.1 Hz, 1H), 6.87 (d, J=2.0 Hz, 1H), 6.00-5.90 (m, 1H), 5.58 (dd, J=15.2, 9.3 Hz, 1H), 4.39 (dd, J=14.9, 6.4 Hz, 1H), 4.27-4.02 (m, 4H), 3.89 (dd, J=28.9, 13.1 Hz, 2H), 3.76 (dd, J=9.3, 3.7 Hz, 1H), 3.67 (d, J=14.6 Hz, 1H), 3.63-3.41 (m, 4H), 3.39 (s, 3H), 3.28-3.23 (m, 4H), 3.12-3.02 (m, 1H), 2.88-2.70 (m, 3H), 2.55-2.41 (m, 2H), 2.38-2.26 (m, 1H), 2.23-2.07 (m, 3H), 2.00-1.69 (m, 7H), 1.50-1.36 (m, 2H), 1.14 (d, J=6.4 Hz, 3H). LCMS-ESI+ (m/z): calcd H+ for $C_{39}H_{51}ClN_4O_7S$: 755.32; found: 754.99.

Example 233

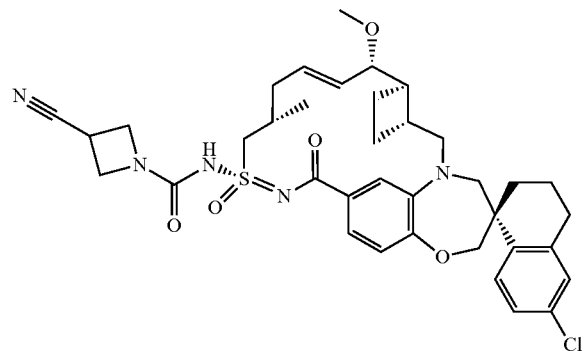

Example 233 was synthesized in the same manner as Example 75 using Example 109 and 3-cyanoazetidine hydrogen chloride and triethylamine. $^1$H NMR (400 MHz, Acetonitrile-d$_3$) δ 7.71 (d, J=8.5 Hz, 1H), 7.20 (dd, J=8.5, 2.4 Hz, 1H), 7.13 (d, J=2.4 Hz, 1H), 7.00 (dd, J=8.2, 1.9 Hz, 1H), 6.91 (d, J=8.1 Hz, 1H), 6.88 (d, J=1.9 Hz, 1H), 5.84 (dt, J=14.1, 6.7 Hz, 1H), 5.53 (dd, J=15.2, 9.2 Hz, 1H), 4.32 (dd, J=15.1, 6.4 Hz, 1H), 4.24 (s, 2H), 4.14 (s, 2H), 4.05 (d, J=1.9 Hz, 2H), 3.79 (d, J=15.5 Hz, 1H), 3.70 (d, J=14.1 Hz, 1H), 3.67-3.61 (m, 1H), 3.55 (tt, J=9.1, 6.0 Hz, 1H), 3.39 (dd, J=15.0, 4.9 Hz, 1H), 3.22 (d, J=14.2 Hz, 1H), 3.16 (s, 3H), 3.03 (dd, J=15.4, 10.3 Hz, 1H), 2.85-2.66 (m, 2H), 2.42 (dd, J=9.4, 5.6 Hz, 1H), 2.33 (dd, J=14.3, 5.9 Hz, 1H), 2.22 (p, J=9.4 Hz, 1H), 2.14-1.97 (m, 3H), 1.90-1.61 (m, 6H), 1.45-1.33 (m, 1H), 1.05 (d, J=6.6 Hz, 3H). LCMS-ESI+ (m/z): [M+H]$^+$ calculated for $C_{37}H_{44}ClN_5O_5S$: 706.28; found: 705.8.

Example 234

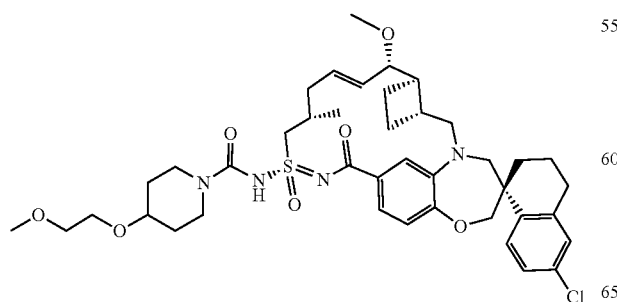

Example 234 was synthesized in the same manner as Example 75 with Example 109 and 4-(2-methoxyethoxy)piperidine. 1H NMR (400 MHz, Methanol-d4) δ 7.75 (d, J=8.6 Hz, 1H), 7.19 (dd, J=8.5, 2.4 Hz, 1H), 7.14-7.06 (m, 2H), 6.94 (d, J=8.1 Hz, 1H), 6.88 (d, J=2.0 Hz, 1H), 6.02-5.89 (m, 1H), 5.63-5.52 (m, 1H), 4.37 (dd, J=14.9, 6.3 Hz, 1H), 4.13-4.04 (m, 2H), 4.04-3.80 (m, 3H), 3.76 (dd, J=9.3, 3.7 Hz, 1H), 3.71-3.51 (m, 7H), 3.39 (s, 3H), 3.30 (s, 1H), 3.28-3.23 (m, 4H), 3.08 (dd, J=15.3, 10.3 Hz, 1H), 2.89-2.69 (m, 2H), 2.55-2.40 (m, 2H), 2.38-2.26 (m, 1H), 2.23-2.03 (m, 3H), 2.01-1.68 (m, 8H), 1.61-1.29 (m, 4H), 1.14 (d, J=6.6 Hz, 3H). LCMS-ESI+ (m/z): calcd H+ for $C_{41}H_{55}ClN_4O_7S$: 783.35; found: 783.61.

Example 235

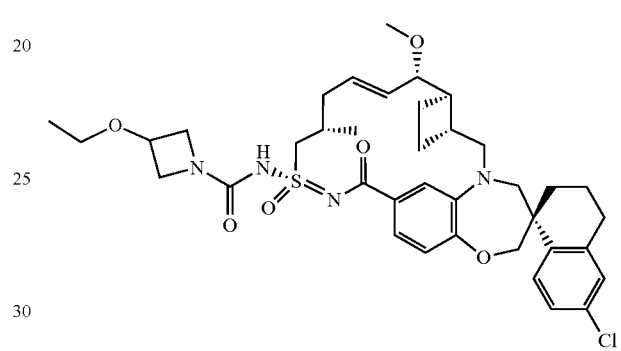

Example 235 was synthesized in the same manner as Example 182, using 3-ethoxyazetidine instead of rac-(1R, 2R)-2-(1-methyl-1H-pyrazol-5-yl)cyclopropan-1-amine. 1H NMR (400 MHz, Methanol-d4) δ 7.76 (d, J=8.6 Hz, 1H), 7.28-7.04 (m, 3H), 7.01-6.77 (m, 2H), 6.03 (s, 1H), 5.54 (dd, J=15.1, 9.4 Hz, 1H), 4.46-4.10 (m, 4H), 4.06 (d, J=2.2 Hz, 2H), 3.86 (d, J=14.6 Hz, 2H), 3.78 (dd, J=9.1, 3.5 Hz, 1H), 3.66 (d, J=13.9 Hz, 2H), 3.57-3.41 (m, 2H), 3.26 (s, 3H), 3.05 (dd, J=15.1, 10.3 Hz, 2H), 2.79 (d, J=18.0 Hz, 2H), 2.48 (s, 2H), 2.36 (d, J=9.8 Hz, 2H), 2.12 (d, J=13.4 Hz, 2H), 1.94 (d, J=12.1 Hz, 2H), 1.77 (tt, J=17.9, 9.5 Hz, 2H), 1.43 (t, J=13.0 Hz, 1H), 1.31 (s, 3H), 1.22 (t, J=7.0 Hz, 2H), 1.12 (d, J=6.2 Hz, 2H), 0.95-0.88 (m, 1H). LCMS-ESI+ (m/z): [M+H]+ calcd for $C_{38}H_{44}ClN_5O_6S$: 725.31; found: 724.71.

Example 236

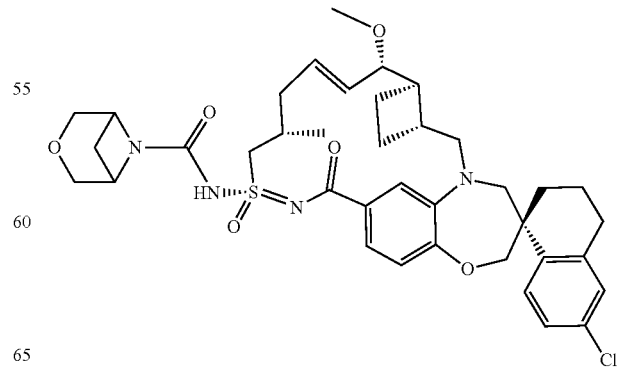

Example 236 was synthesized in the same manner as Example 75 using Example 109 and 3-oxa-6-azabicyclo[3.1.1]heptane tosylate. $^1$H NMR (400 MHz, Methanol-d4) δ 7.75 (d, J=8.6 Hz, 1H), 7.21-7.17 (m, 1H), 7.12 (d, J=2.3 Hz, 2H), 6.93 (d, J=8.2 Hz, 2H), 5.98 (dd, J=14.8, 7.4 Hz, 1H), 5.59 (dd, J=15.2, 8.9 Hz, 1H), 4.33 (m, 2H), 4.27 (m, 3H), 4.13-4.01 (m, 2H), 3.89-3.80 (m, 3H), 3.77 (dd, J=9.2, 3.7 Hz, 1H), 3.67 (d, J=14.1 Hz, 2H), 3.27 (d, J=5.6 Hz, 4H), 3.08 (dd, J=15.4, 10.3 Hz, 1H), 2.88-2.74 (m, 2H), 2.66 (q, J=6.9 Hz, 1H), 2.56-2.43 (m, 3H), 2.35 (t, J=9.1 Hz, 1H), 2.25-2.07 (m, 4H), 2.04-1.87 (m, 2H), 1.87-1.70 (m, 3H), 1.45 (t, J=12.6 Hz, 1H), 1.14 (d, J=6.5 Hz, 3H). LCMS-ESI+: calc'd for $C_{38}H_{48}ClN_4O_6S$: 723.29 (M+H); found: 722.97 (M+H).

Example 237

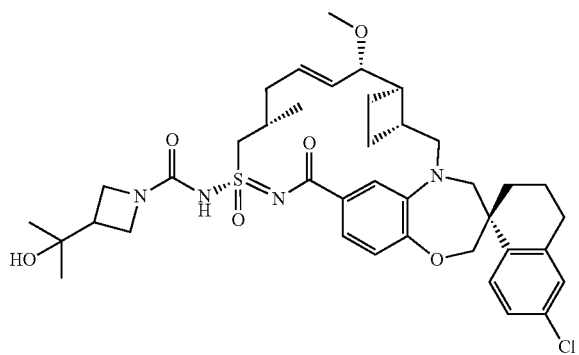

To the mixture of Example 109 (10 mg, 0.017 mmol) in dichloromethane (2 mL) was added 4-nitrophenyl chloroformate (6.7 mg, 0.033 mmol), DMAP (8 mg, 0.067 mmol), and triethylamine. The reaction mixture was stirred at room temperature. After 4 hours, 2-(azetidin-3-yl)propan-2-ol (6.7 mg, 0.059 mmol) was added and the mixture was continuously stirred for 30 minutes. The reaction was concentrated, dissolved in MeOH (2 mL), filtered, and purified by reverse phase preparative HPLC, eluted with 60-100% ACN/H2O with 0.1% TFA to afford Example 237. $^1$H NMR (400 MHz, Methanol-d$_4$) δ 7.72 (d, J=8.5 Hz, 1H), 7.25-7.02 (m, 3H), 6.90 (d, J=8.3 Hz, 2H), 5.95 (dd, J=14.9, 7.6 Hz, 1H), 5.56 (dd, J=15.2, 9.0 Hz, 1H), 4.27 (dd, J=14.9, 6.3 Hz, 1H), 4.11-3.87 (m, 7H), 3.85-3.69 (m, 2H), 3.63 (t, J=15.5 Hz, 2H), 3.24 (s, 3H), 3.14-2.98 (m, 1H), 2.88-2.54 (m, 3H), 2.54-2.23 (m, 3H), 2.23-2.00 (m, 3H), 2.00-1.62 (m, 7H), 1.42 (t, J=12.8 Hz, 1H), 1.20-1.06 (m, 9H). LCMS-ESI+ (m/z): [M+H] Calculated for $C_{39}H_{51}ClN_4O_6S$: 739.33; found 738.98.

Example 238

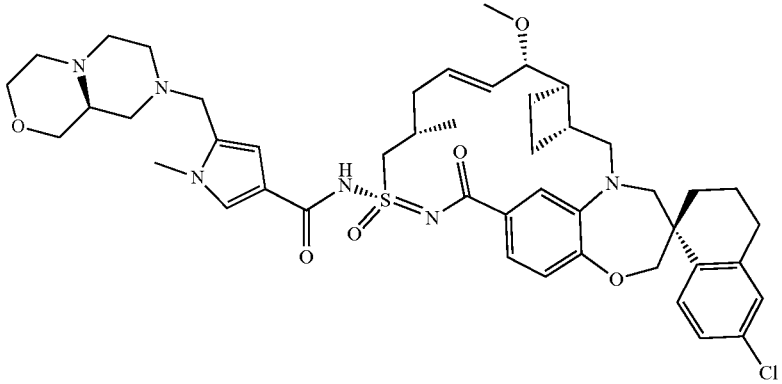

Example 238 was synthesized in the same sequence as Example 284 except in Step 1 (9aS)-1,3,4,6,7,8,9,9a-octahydropyrazino[2,1-c][1,4]oxazine; dihydrochloride was used and triethyl amine (2 eq) was also added to the reaction mixture prior to the addition of STAB. $^1$H NMR (400 MHz, Methanol-d4) δ 7.71 (d, J=1.9 Hz, 1H), 7.58 (d, J=8.5 Hz, 1H), 7.35 (dd, J=8.3, 1.8 Hz, 1H), 7.03 (dd, J=10.5, 2.2 Hz, 2H), 6.86-6.75 (m, 3H), 6.22-6.11 (m, 1H), 5.69 (dd, J=15.4, 8.2 Hz, 1H), 4.17-4.08 (m, 1H), 4.05-3.90 (m, 7H), 3.84-3.73 (m, 7H), 3.63 (d, J=14.7 Hz, 1H), 3.46 (d, J=14.0 Hz, 1H), 3.24-3.07 (m, 5H), 3.05-2.68 (m, 8H), 2.59-2.38 (m, 4H), 2.34-2.21 (m, 3H), 2.07 (d, J=13.7 Hz, 1H), 2.01-1.92 (m, 3H), 1.90-1.81 (m, 3H), 1.40-1.30 (m, 1H), 1.16 (d, J=6.2 Hz, 3H). LCMS-ESI+ (m/z): calcd H+ for $C_{46}H_{59}ClN_6O_6S$: 859.39; found: 859.15.

Example 239

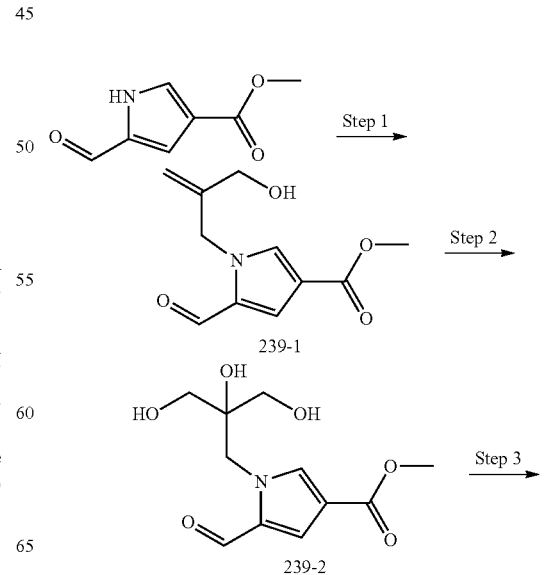

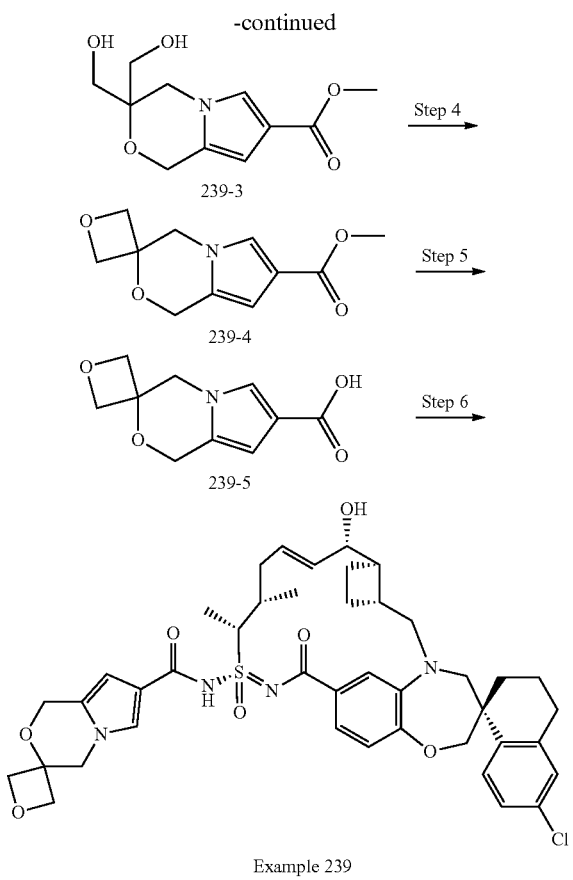

Example 239

Step 1

Di-tert-butyl-diazene-1,2-dicarboxylate (4.51 g, 19.6 mmol) was added in three equal portions over 5 min to a stirred mixture of methyl 5-formyl-1H-pyrrole-3-carboxylate (2.00 g, 13.1 mmol), 2-methylenepropane-1,3-diol (5.32 mL, 65.3 mmol), and triphenylphosphine (6.17 g, 23.5 mmol) in tetrahydrofuran (120 mL) at 0° C., and the reaction mixture was allowed to slowly warm to room temperature. After 42 h, the resulting mixture was concentrated under reduced pressure. The residue was purified by flash column chromatography on silica gel (0 to 43% ethyl acetate in hexanes) to give 239-1.

Step 2

AD-mix-β (14.9 g) was added to a vigorously stirred solution of 239-1 (2.06 g, 9.24 mmol) in tert-butyl alcohol (55 mL) and water (55 mL) at room temperature. After 21 h, saturated aqueous sodium bisulfite solution (34 mL) was added. After 30 min, brine (50 mL) and water (20 mL) were added sequentially. The aqueous layer was extracted sequentially with ethyl acetate (2×200 mL) and dichloromethane (200 mL). The combined organic layers were dried over anhydrous magnesium sulfate, filtered, and concentrated under reduced pressure. Methanol (300 mL) was added to the aqueous layer, and the resulting inhomogeneous mixture was filtered and concentrated under reduced pressure. The filtrate was combined with the residue from concentration of the combined organic layers, and the resulting mixture was concentrated under reduced pressure. Methanol (300 mL) and tetrahydrofuran (200 mL) were added sequentially, and the resulting inhomogeneous layer was triturated vigorously and then stirred vigorously. After 15 min, the resulting mixture was filtered and was concentrated under reduced pressure. Methanol (100 mL) and tetrahydrofuran (200 mL) were added sequentially. Silica gel (24 g) was added, and the resulting slurry was concentrated under reduced pressure. The residue was purified by flash column chromatography on silica gel (0 to 20% methanol in dichloromethane) to give 239-2.

Step 3

Trifluoracetic acid (3.65 mL, 47.7 mmol) was added via syringe to a stirred solution of 239-2 (1.23 g, 4.77 mmol) in dichloromethane (300 mL) and methanol (3.87 mL) at room temperature. After 1 min, triethylsilane (8.00 mL, 50.1 mmol) was added via syringe. After 7 min, trifluoroacetic acid (9.13 mL, 119 mmol) and triethylsilane (19.0 mL, 119 mmol) were added sequentially via syringe. After 7 h, basic alumina (35 g) was added, and the resulting slurry was concentrated under reduced pressure. The residue was purified by flash column chromatography on silica gel (0 to 9% methanol in dichloromethane) to give 239-3.

Step 4

Di-iso-propy 1-diazene-1,2-dicarboxylate (147 µL, 746 µmol) was added via syringe to a stirred mixture of 239-3 (60.0 mg, 249 µmol) and triphenylphosphine (209 mg, 796 µmol) in toluene (3.0 mL) at room temperature, and the resulting mixture was heated to 140° C. in a microwave reactor. After 30 min, the resulting mixture was cooled to room temperature and purified by flash column chromatography on silica gel (0 to 48% ethyl acetate in hexanes) to give 239-4.

Step 5

Aqueous sodium hydroxide solution (2.0 M, 400 µL, 800 µmol) was added via syringe to a stirred solution of 239-4 (16 mg, 69 µmol) in tetrahydrofuran (0.6 mL) and methanol (0.4 mL) at room temperature, and the resulting mixture was heated to 75° C. After 110 min, the resulting mixture was cooled to room temperature, and aqueous hydrogen chloride solution (2.0 M, 0.7 mL) and brine (5 mL) were added sequentially. The aqueous layer was extracted sequentially with dichloromethane (2×15 mL) and ethyl acetate (15 mL). The combined organic layers were dried over anhydrous magnesium sulfate, filtered, and concentrated under reduced pressure to give 239-5.

Step 6

Example 239 was synthesized in a manner similar to Example 106 using Intermediate 359-4 instead of Example 109 and using 239-5 instead of 2-((tetrahydro-2H-pyran-4-yl)oxy)acetic acid. 1H NMR (400 MHz, Acetone-d6) δ 7.78 (d, J=8.5 Hz, 1H), 7.48 (s, 1H), 7.29-7.13 (m, 4H), 7.00 (d, J=8.0 Hz, 1H), 6.31 (s, 1H), 5.93-5.80 (m, 1H), 5.74 (dd, J=15.3, 7.4 Hz, 1H), 4.90 (s, 2H), 4.71 (d, J=7.0 Hz, 2H), 4.51 (dd, J=7.1, 2.8 Hz, 2H), 4.47-4.04 (m, 5H), 3.88 (d, J=15.2 Hz, 1H), 3.74 (d, J=14.3 Hz, 1H), 3.40 (d, J=14.3 Hz, 1H), 3.19 (dd, J=15.3, 8.9 Hz, 1H), 2.97-1.63 (m, 15H), 1.56 (d, J=7.1 Hz, 3H), 1.54-1.45 (m, 1H), 1.12-0.99 (m, 3H). LCMS: 789.0.

Example 240

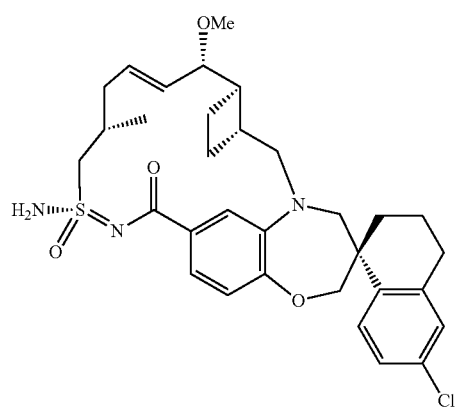

106-4

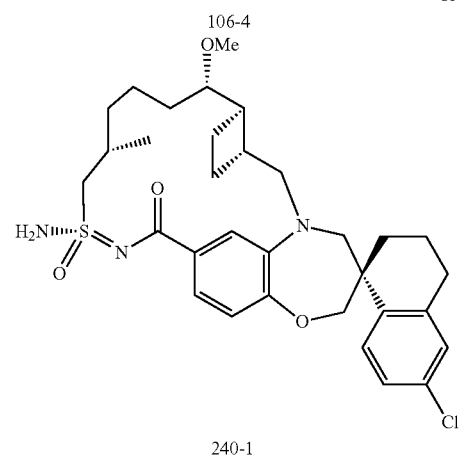

240-1

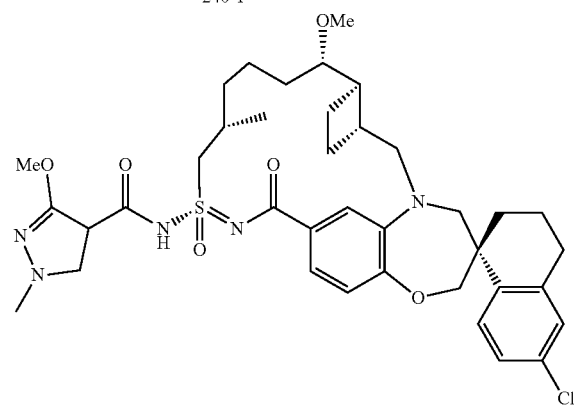

Example 240

Step 1

A vigorously stirred mixture of 106-4 (30.0 mg, 50.2 µmol) and platinum (IV) oxide (5.7 mg, 25.1 µmol) in ethanol (1.5 mL) was placed under an atmosphere of hydrogen gas (1 atm) at room temperature. After 220 min, the resulting mixture was filtered through celite and was concentrated under reduced pressure to give 240-1.

Step 2

Example 240 was synthesized in a manner similar to Example 106 using 240-1 instead of 106-4. 1H NMR (400 MHz, Acetone-d6) δ 8.13 (s, 1H), 7.80 (d, J=8.5 Hz, 1H), 7.46 (dd, J=8.2, 1.9 Hz, 1H), 7.41 (d, J=1.9 Hz, 1H), 7.26 (dd, J=8.5, 2.4 Hz, 1H), 7.15 (d, J=2.3 Hz, 1H), 6.94 (d, J=8.2 Hz, 1H), 4.13 (d, J=12.1 Hz, 1H), 4.08 (s, 3H), 4.05 (d, J=12.1 Hz, 1H), 3.91 (d, J=14.6 Hz, 1H), 3.86 (s, 3H), 3.74 (t, J=16.3 Hz, 2H), 3.46 (d, J=14.4 Hz, 1H), 3.40-3.30 (m, 1H), 3.32 (s, 3H), 3.19 (dd, J=15.1, 9.7 Hz, 1H), 3.07-1.33 (m, 20H), 1.07 (d, J=6.6 Hz, 3H). LCMS: 738.1.

Example 241

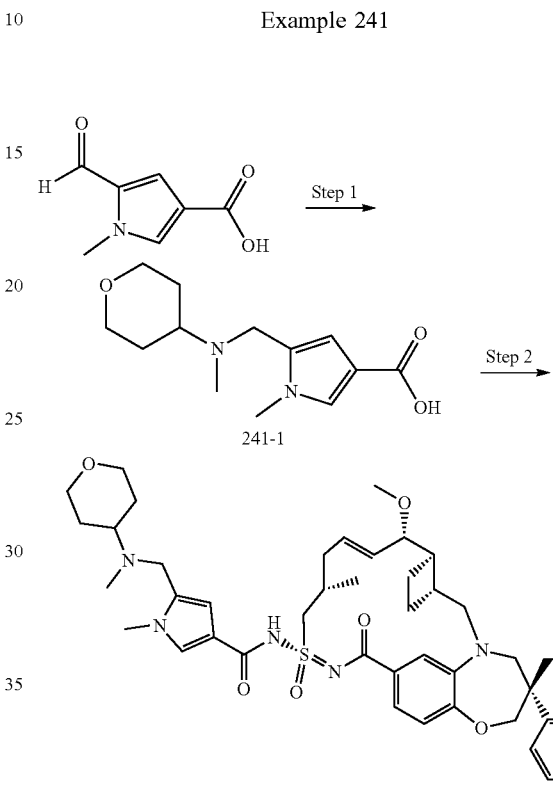

Step 1

A mixture of 5-formyl-1-methyl-1H-pyrrole-3-carboxylic acid (150 mg, 0.98 mmol), N-methyltetrahydro-2H-pyran-4-amine (118 mg, 1.03 mmol) and acetic acid (0.11 mL, 1.96 mmol) in DCE (10 mL) was stirred at room temperature over two days. Sodium borohydride (74 mg, 1.96 mmol) was added and the reaction mixture was stirred at room temperature for another 16 h. 5 mL of water was added to quench the reaction. It was then concentrated to dryness. The crude residue was loaded onto silica gel and purified by column chromatography using 10-50% MeOH in DCM to afford intermediate 241-1. LCMS-ESI+: [M+H]+ calc'd for $C_{13}H_{20}N_2O_3$: 253.16; found: 252.82.

Step 2

Example 241 was synthesized in the same manner as Example 18 using intermediate 241-1 and Example 109. 1H NMR (400 MHz, Methanol-d4) δ 8.12 (d, J=7.6 Hz, 1H), 7.66 (s, 2H), 7.29 (d, J=8.2 Hz, 1H), 7.09 (s, 1H), 7.01 (d, J=8.3 Hz, 2H), 6.86 (d, J=8.2 Hz, 1H), 6.14 (d, J=14.7 Hz, 1H), 5.65 (t, J=12.0 Hz, 1H), 4.63 (s, 2H), 4.27 (s, 2H), 4.14 (d, J=11.5 Hz, 2H), 4.03 (s, 1H), 3.97-3.90 (m, 1H), 3.79 (s, 3H), 3.66 (d, J=14.2 Hz, 2H), 3.53 (d, J=12.7 Hz, 2H), 3.31

(s, 3H), 3.27 (s, 2H), 3.19 (s, 2H), 2.83 (s, 4H), 2.66 (s, 1H), 2.47 (s, 2H), 2.23 (d, J=7.8 Hz, 2H), 2.11 (d, J=11.6 Hz, 2H), 2.00-1.89 (m, 3H), 1.82 (s, 2H), 1.41 (s, 2H), 1.31 (s, 3H), 1.15 (d, J=6.3 Hz, 2H), 0.98-0.85 (m, 2H). LCMS-ESI+[M+H]$^+$ calc'd for $C_{45}H_{58}ClN_5O_6S$: 832.39; found: 832.40.

Example 242

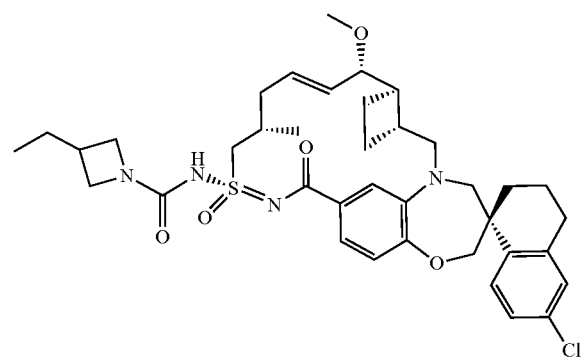

Example 242 was synthesized in the same manner as Example 75 using Example 109 and 3-ethylazetidine. 1H NMR (400 MHz, Chloroform-d) δ 7.70 (d, J=8.5 Hz, 1H), 7.18 (dd, J=8.5, 2.4 Hz, 1H), 7.12-7.06 (m, 2H), 6.94-6.89 (m, 2H), 5.92 (dt, J=13.6, 6.4 Hz, 1H), 5.53 (dd, J=15.2, 8.9 Hz, 1H), 4.40 (d, J=14.8 Hz, 1H), 4.18-4.01 (m, 4H), 3.82 (d, J=15.3 Hz, 1H), 3.77-3.61 (m, 4H), 3.25 (s, 4H), 2.96 (dd, J=15.2, 10.3 Hz, 1H), 2.76 (dd, J=11.6, 4.4 Hz, 2H), 2.63-2.21 (m, 2H), 2.18-1.89 (m, 5H), 1.78 (dq, J=17.1, 9.6 Hz, 2H), 1.69-1.57 (m, 3H), 1.38 (q, J=12.9, 11.5 Hz, 1H), 1.25 (s, 1H), 1.09 (d, J=6.4 Hz, 3H), 0.89 (t, J=7.3 Hz, 3H). LCMS-ESI+ (m/z): [M+H]$^+$ calculated for $C_{38}H_{49}ClN_4O_5S$: 709.31; found: 708.95.

Example 243

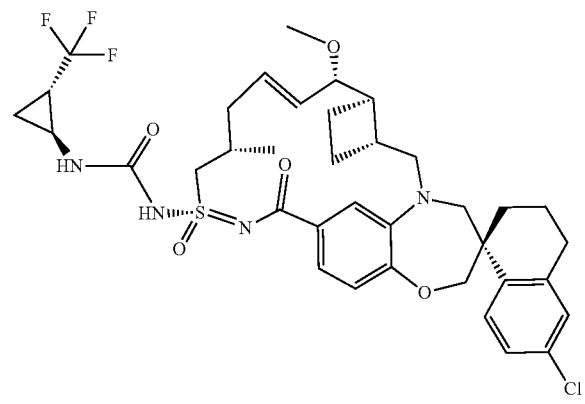

Example 243 was synthesized in the same manner as Example 75 using Example 109 and (1S,2S)-2-(trifluoromethyl)cyclopropan-1-amine hydrochloride. $^1$H NMR (400 MHz, Methanol-d4) δ 7.77-7.67 (m, 1H), 7.17 (d, J=8.0 Hz, 1H), 7.10 (s, 2H), 6.96-6.87 (m, 2H), 6.02 (t, J=7.9 Hz, 1H), 5.61 (dd, J=15.1, 8.9 Hz, 1H), 4.26 (d, J=13.3 Hz, 1H), 4.05 (s, 2H), 3.87-3.68 (m, 2H), 3.66 (d, J=14.2 Hz, 1H), 3.28 (m, 4H), 3.12-3.06 (m, 1H), 3.03 (dd, J=7.9, 4.6 Hz, 1H), 2.84 (d, J=16.2 Hz, 1H), 2.79-2.69 (m, 1H), 2.48 (d, J=15.1 Hz, 2H), 2.38 (s, 1H), 2.32-2.15 (m, 1H), 2.10 (d, J=13.6 Hz, 1H), 2.06-1.92 (m, 2H), 1.87 (d, J=10.6 Hz, 1H), 1.80 (q, J=6.8, 5.7 Hz, 1H), 1.62 (m, 1H), 1.40 (dd, J=25.6, 13.0 Hz, 2H), 1.31 (d, J=3.7 Hz, 2H), 1.20 (dt, J=7.6, 6.1 Hz, 1H), 1.15 (m, 4H). LCMS-ESI+: calc'd for $C_{37}H_{45}ClF_3N_4O_5S$: 749.27 (M+H); found: 749.40 (M+H).

Example 244

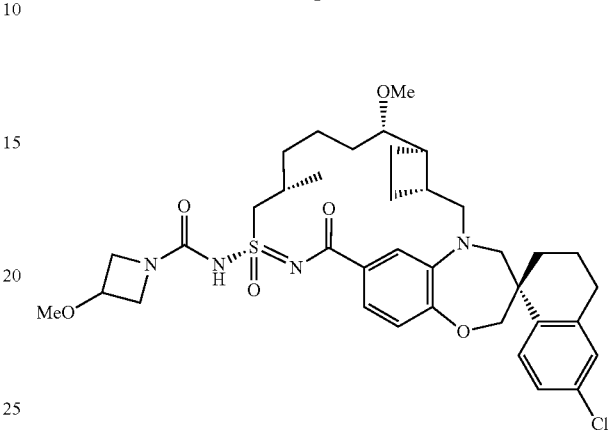

Diphenyl carbonate (29.4 mg, 137 μmol) was added to a stirred mixture of 240-1 (9.5 mg, 16 μmol) and 4-(dimethylamino)pyridine (9.7 mg, 79 μmol) in acetonitrile (0.6 mL) at room temperature. After 21 h, 4-methoxyazetidine hydrochloride (48.9 mg, 396 μmol) and N,N-diisopropylethylamine (152 μL, 871 μmol) were added sequentially, and the resulting mixture was heated to 55° C. After 150 min, the resulting mixture was cooled to room temperature and was purified by reverse phase preparative HPLC (0.1% trifluoroacetic acid in acetonitrile/water) to give Example 244. 1H NMR (400 MHz, Acetone-d6) δ 7.79 (d, J=8.6 Hz, 1H), 7.31-7.21 (m, 2H), 7.17-7.11 (m, 2H), 6.98 (d, J=8.1 Hz, 1H), 4.35-3.78 (m, 7H), 3.73 (d, J=14.3 Hz, 1H), 3.49-3.22 (m, 4H), 3.30 (s, 3H), 3.24 (s, 3H), 3.16 (dd, J=15.4, 8.6 Hz, 1H), 2.92-1.25 (m, 16H), 1.12 (d, J=6.7 Hz, 3H). LCMS: 713.1.

Example 245

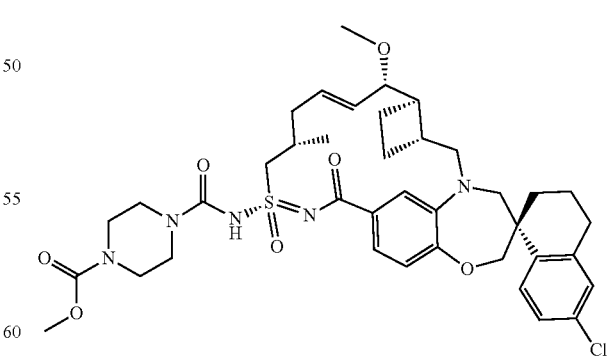

Example 245 was synthesized in the same manner as Example 75 using Example 109 and methyl piperazine-1-carboxylate. 1H NMR (400 MHz, Methanol-d4) δ 7.74 (d, J=8.6 Hz, 1H), 7.19 (dd, J=8.5, 2.4 Hz, 1H), 7.14-7.06 (m, 2H), 6.94 (d, J=8.1 Hz, 1H), 6.87 (d, J=2.0 Hz, 1H), 6.00-5.89 (m, 1H), 5.58 (dd, J=15.2, 9.3 Hz, 1H), 4.39 (dd, J=14.9, 6.4 Hz, 1H), 4.12-4.02 (m, 2H), 3.85 (d, J=15.1 Hz, 1H), 3.79-3.71 (m, 4H), 3.70-3.56 (m, 5H), 3.53-3.43 (m, 4H), 3.27-3.24 (m, 4H), 3.08 (dd, J=15.3, 10.3 Hz, 1H), 2.87-2.71 (m, 2H), 2.54-2.41 (m, 2H), 2.37-2.26 (m, 1H), 2.23-2.07 (m, 3H), 2.00-1.86 (m, 3H), 1.86-1.68 (m, 4H), 1.50-1.37 (m, 1H), 1.14 (d, J=6.6 Hz, 3H). LCMS-ESI+ (m/z): calcd H+ for $C_{39}H_{50}ClN_5O_7S$:768.31; found: 767.73.

Example 246

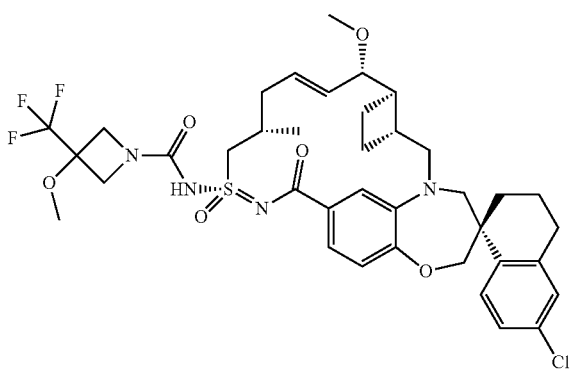 [SMILES: CO[C@H]1/C=C/C[C@H](C)C[S@@](=O)(NC(=O)N2CC(OC)(C(F)(F)F)C2)=NC(=O)c2ccc3c(c2)N(C[C@@H]2CC[C@H]21)C[C@@]1(CCCc2cc(Cl)ccc21)CO3]

Example 246 was synthesized in the same manner as Example 237 using Example 109 and 3-methoxy-3-(trifluoromethyl)azetidine hydrochloride. $^1$H NMR (400 MHz, Methanol-d4) δ 7.75 (d, J=8.5 Hz, 1H), 7.19 (dd, J=8.4, 2.4 Hz, 1H), 7.12 (d, J=2.3 Hz, 1H), 7.09 (dd, J=8.1, 1.9 Hz, 1H), 6.94 (d, J=8.1 Hz, 1H), 6.89 (d, J=2.0 Hz, 1H), 5.96 (dt, J=14.3, 6.8 Hz, 1H), 5.59 (dd, J=15.2, 9.2 Hz, 1H), 4.35 (dd, J=14.9, 6.4 Hz, 1H), 4.15 (d, J=24.8 Hz, 5H), 4.09 (d, J=1.2 Hz, 2H), 3.85 (d, J=15.1 Hz, 1H), 3.76 (dd, J=9.2, 3.7 Hz, 1H), 3.64 (dd, J=23.7, 14.6 Hz, 2H), 3.53 (d, J=1.1 Hz, 3H), 3.26 (m, 4H), 3.08 (dd, J=15.3, 10.3 Hz, 1H), 2.90-2.65 (m, 2H), 2.46 (dd, J=14.8, 5.5 Hz, 2H), 2.33 (p, J=9.1 Hz, 1H), 2.19 (dt, J=14.6, 7.2 Hz, 1H), 2.12 (d, J=12.9 Hz, 2H), 2.03-1.86 (m, 1H), 1.79 (tt, J=17.7, 9.6 Hz, 3H), 1.45 (t, J=12.5 Hz, 1H), 1.33 (d, J=16.3 Hz, 1H), 1.15 (d, J=6.7 Hz, 3H). LCMS-ESI+: calc'd for $C_{38}H_{47}ClF_3N_4O_6S$: 779.28 (M+H); found: 779.62 (M+H).

Example 247

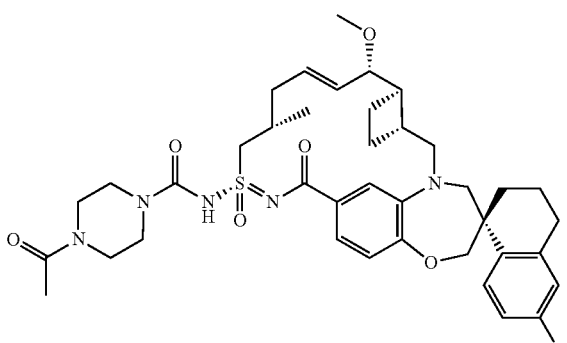

Example 247 was prepared in a similar manner to Example 237 using 1-(piperazin-1-yl)ethan-1-one, triethylamine and Example 109. LCMS-ESI+ (m/z): [M+H] Calculated for $C_{39}H_{50}ClN_5O_6S$: 752.32; found 751.80.

Example 248

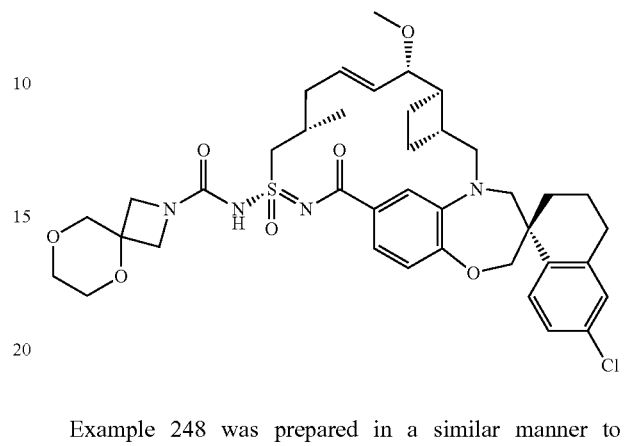

Example 248 was prepared in a similar manner to Example 237 using 5,8-dioxa-2-azaspiro[3.5]nonane, triethylamine and Example 109. LCMS-ESI+ (m/z): [M+H] Calculated for $C_{39}H_{49}ClN_4O_7S$: 753.30; found 752.88.

Example 249

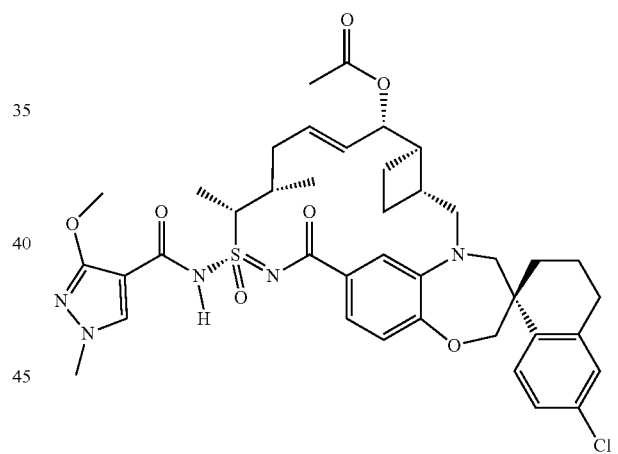

To a stirred solution of Example 359 (60 mg, 0.081 mmol) in acetic anhydride (10 mL) was heated at 60° C. for 4 hours. Water was added and the mixture was extracted with dichloromethane. The organic phase was dried over anhydrous magnesium sulfate and the solvent was removed under reduced pressure, and purified on reversed phase chromatography 0.1% TFA 70-95% acetonitrile to yield Example 249. 1H NMR (400 MHz, Chloroform-d) δ 7.86-7.61 (m, 3H), 7.35-7.15 (m, 3H), 7.10 (d, J=2.3 Hz, 1H), 6.93 (d, J=8.3 Hz, 1H), 5.83 (s, 1H), 5.60 (dd, J=15.4, 6.7 Hz, 1H), 5.37-5.17 (m, 1H), 4.21-3.96 (m, 5H), 3.92 (d, J=15.2 Hz, 1H), 3.82 (d, J=12.5 Hz, 3H), 3.75-3.63 (m, 2H), 3.26 (d, J=14.7 Hz, 1H), 3.01 (dd, J=15.6, 7.5 Hz, 1H), 2.78 (dd, J=10.7, 5.1 Hz, 2H), 2.63-2.46 (m, 2H), 2.16 (d, J=16.3 Hz, 3H), 2.01-1.82 (m, 4H), 1.82-1.63 (m, 3H), 1.57 (d, J=7.2 Hz, 3H), 1.42 (d, J=9.3 Hz, 2H), 1.26 (d, J=13.1 Hz, 4H). LCMS-ESI+ (m/z): [M+H]+ calcd for $C_{40}H_{48}ClN_5O_7S$: 778.30; found: 778.35.

Example 250

Step 1

To a solution of tert-butyl (2R,3S)-3-hydroxy-2-methylazetidine-1-carboxylate (50 mg, 0.267 mmol) in dry THF (1.3 mL), was added 60% sodium hydride (oil dispersion) (15 mg, 0.401 mmol). The temperature of the mixture was maintained at 0° C. After addition was completed, stirring was continued at the same temperature for 10 min. Then iodomethane (0.02 mL, 0.321 mmol) was added dropwise and the temperature was allowed to rise to rt. The reaction mixture was stirred at this temperature for 1 h. Solvent was removed under reduced pressure to give tert-butyl (2R,3S)-3-methoxy-2-methylazetidine-1-carboxylate.

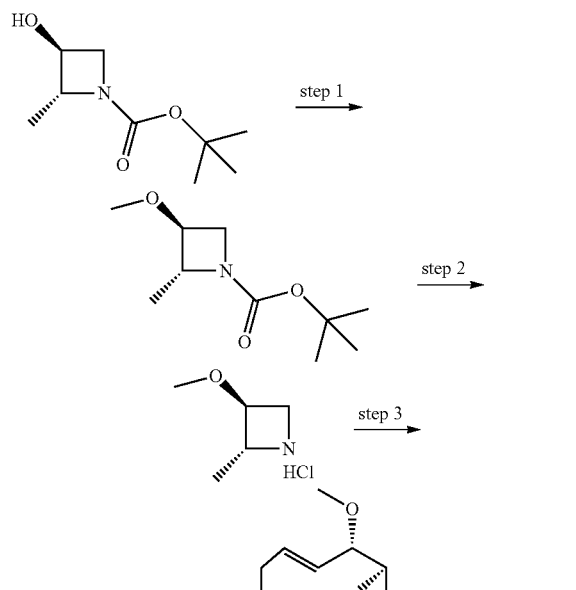

Step 2

To a solution of tert-butyl (2R,3 S)-3-m ethoxy-2-methylazetidine-1-carboxylate (53.7 mg, 0.267 mmol) in isopropyl alcohol (1.65 mL), was added a solution of hydrogen chloride in dioxane (4 M, 0.2 mL, 0.8 mmol). The reaction mixture was stirred at 50° C. for 25 h. Solvent was removed under reduced pressure to give (2R,3S)-3-methoxy-2-methylazetidine hydrochloride.

Step 3

To a solution of Example 109 (10 mg, 0.0167 mmol), nitrophenyl chloroformate (4.04 mg, 0.0201 mmol), and DMAP (4.08 mg, 0.0334 mmol) in DCM (0.4 mL), was added triethylamine (0.04 mL, 0.29 mmol) and stirred at rt for 4 h. A solution of (2R,3S)-3-methoxy-2-methylazetidine hydrochloride (11.5 mg, 0.0836 mmol) and triethylamine (0.05 mL, 0.359 mmol) in DCM (0.4 mL) was added, and stirred for 1 h. Solvent was removed under reduced pressure, residue was redissolved in DMSO (2 mL) and purified by Gilson reverse phase prep HPLC, and eluted with 50-100% ACN/H$_2$O with 0.1% TFA to afford Example 250. 1H NMR (400 MHz, Methanol-d4) δ 7.73 (d, J=8.5 Hz, 1H), 7.17 (dd, J=8.5, 2.4 Hz, 1H), 7.12-7.07 (m, 2H), 6.91 (d, J=8.1 Hz, 1H), 6.89 (d, J=2.0 Hz, 1H), 5.95 (dt, J=14.4, 6.6 Hz, 1H), 5.56 (dd, J=15.2, 9.1 Hz, 1H), 4.31 (dd, J=14.8, 6.2 Hz, 1H), 4.23-4.11 (m, 2H), 4.06 (d, J=1.8 Hz, 2H), 3.83 (d, J=15.1 Hz, 1H), 3.77-3.71 (m, 3H), 3.65 (d, J=14.2 Hz, 1H), 3.61-3.52 (m, 1H), 3.24 (s, 3H), 3.06 (dd, J=15.3, 10.3 Hz, 1H), 2.90-2.62 (m, 2H), 2.54-2.39 (m, 2H), 2.39-2.22 (m, 1H), 2.22-2.02 (m, 3H), 1.97-1.63 (m, 6H), 1.50-1.38 (m, 4H), 1.13 (d, J=6.4 Hz, 3H). LCMS-ESI+ (m/z): [M+H]$^+$ calculated for C$_{38}$H$_{49}$ClN$_4$O$_6$S: 725.31; found: 724.92.

Example 251

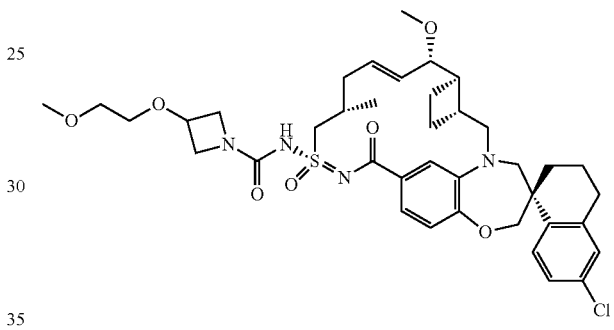

Example 251 was prepared in the same manner as Example 362 with Example 109 and 3-(2-methoxyethoxy)azetidine hydrochloride. LCMS-ESI+ (m/z): [M+H]$^+$ calc'd for C$_{39}$H$_{51}$ClN$_4$O$_7$S: 755.3240; found: 754.79. $^1$H NMR (400 MHz, Methanol-d4) δ 7.73 (d, J=8.5 Hz, 1H), 7.17 (dd, J=8.6, 2.4 Hz, 1H), 7.13-7.06 (m, 2H), 6.95-6.85 (m, 2H), 5.96 (dt, J=14.1, 6.7 Hz, 1H), 5.56 (dd, J=15.2, 9.1 Hz, 1H), 4.40-4.13 (m, 4H), 4.12-4.00 (m, 2H), 3.98-3.80 (m, 3H), 3.74 (dd, J=9.2, 3.7 Hz, 1H), 3.65 (d, J=14.2 Hz, 1H), 3.62-3.52 (m, 5H), 3.37 (s, 3H), 3.29-3.25 (m, 1H), 3.24 (s, 3H), 3.06 (dd, J=15.3, 10.3 Hz, 1H), 2.87-2.69 (m, 2H), 2.52-2.41 (m, 2H), 2.32 (p, J=8.6, 7.9 Hz, 1H), 2.24-2.04 (m, 3H), 2.00-1.66 (m, 6H), 1.42 (t, J=12.7 Hz, 1H), 1.13 (d, J=6.6 Hz, 3H).

Example 252

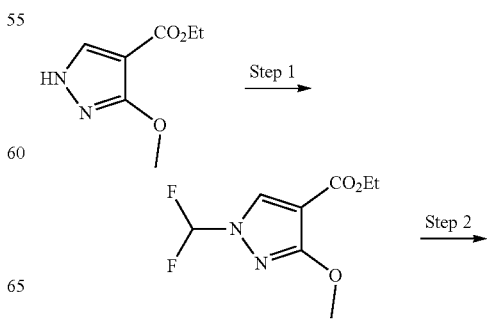

327

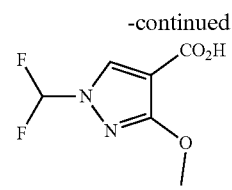

Step 3 →

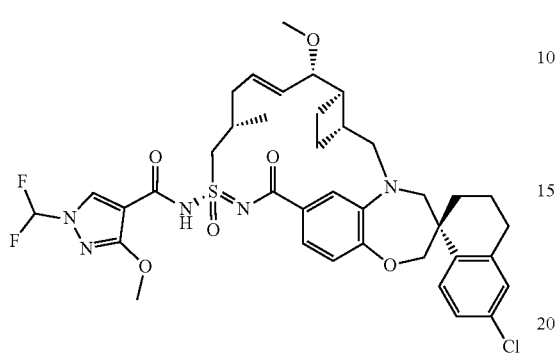

Step 1

To a suspension of ethyl 3-methoxy-1H-pyrazole-4-carboxylate (350 mg, 2.05 mmol) in dioxane (1 mL) and water (0.7 mL), was added KOH (346 mg, 6.17 mmol). To stirred mixture was bubbled $CHIF_2$ gas over 30 min. Two Regioisomer products were formed with same Mass at 221 (RT=0.39 and 0.49). The reaction mixture was diluted with ether (50 mL), washed with water followed by brine solution. The organic extract was dried over sodium sulfate to give crude product which was carried onto the next step without purification. LCMS-ESI+ (m/z): [M+H] Calculated for $C_8H_{11}F_2N_3O_2$: 220.08; found 220.90.

Step 2

To a suspension of ethyl 1-(difluoromethyl)-3-methoxy-1H-pyrazole-4-carboxylate (300 mg, 1.36 mmol) in MeOH (3 mL), THF (10 mL) was added 2 N NaOH solution (3 mL). The reaction mixture was stirred at 50° C. for 90 min. Solvent was concentrated, and the crude residue was dissolved in water (30 mL). This solution was acidified with 1.5 N HCl by drop wise addition to maintain pH 2-3 and stirred for 5 min. The product was filtered, washed with water, and dried. The crude product 1-(difluoromethyl)-3-methoxy-1H-pyrazole-4-carboxylic acid was used for next step. LCMS-ESI+ (m/z): [M+H] Calculated for $C_6H_6F_2N_2O_3$: 193.03; found 193.02.

Step-3

Example 252 synthesized in the same manner as Example 18 using 1-(difluoromethyl)-3-methoxy-1H-pyrazole-4-carboxylic acid and Example 109. $^1$H NMR (400 MHz, Methanol-d$_4$) δ 8.50 (s, 1H), 7.75 (d, J=8.5 Hz, 1H), 7.57-7.23 (m, 1H), 7.23-7.20 (m, 1H), 7.17 (dd, J=8.5, 2.4 Hz, 1H), 7.11 (d, J=2.3 Hz, 1H), 7.04 (d, J=2.0 Hz, 1H), 6.94 (d, J=8.2 Hz, 1H), 6.05 (dt, J=14.2, 6.5 Hz, 1H), 5.61 (dd, J=15.3, 8.6 Hz, 1H), 4.29 (dd, J=14.9, 6.0 Hz, 1H), 4.07 (d, J=2.4 Hz, 5H), 3.99-3.62 (m, 5H), 3.36 (s, 1H), 3.28 (s, 3H), 3.16-3.00 (m, 1H), 2.79 (dddd, J=22.7, 16.7, 11.7, 5.2 Hz, 2H), 2.60-2.33 (m, 2H), 2.32-2.04 (m, 3H), 2.03-1.86 (m, 3H), 1.78 (qd, J=9.4, 8.5, 5.3 Hz, 3H), 1.44 (ddd, J=14.2, 11.7, 3.1 Hz, 1H),

328

1.15 (d, J=6.2 Hz, 3H). LCMS-ESI+ (m/z): [M+H]+ calcd for $C_{38}H_{44}ClF_2N_5O_6S$: 772.27; found: 772.04.

Example 253

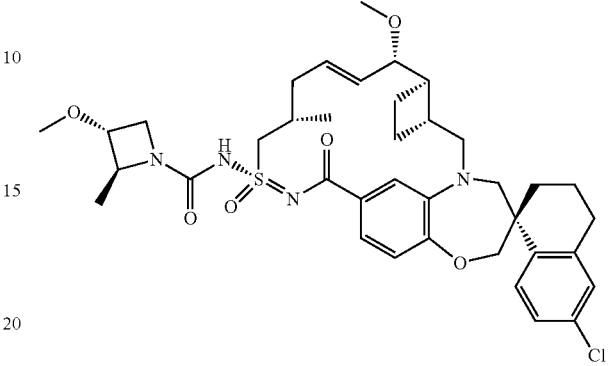

Example 253 was synthesized in the same manner as Example 250 using tert-butyl (2S,3R)-3-hydroxy-2-methyl-azetidine-1-carboxylate and Example 109. 1H NMR (400 MHz, Methanol-d4) δ 7.73 (d, J=8.5 Hz, 1H), 7.17 (dd, J=8.5, 2.3 Hz, 1H), 7.09 (dd, J=7.8, 2.0 Hz, 2H), 6.92 (d, J=8.1 Hz, 1H), 6.88 (s, 1H), 5.94 (dt, J=14.2, 6.7 Hz, 1H), 5.56 (dd, J=15.2, 9.2 Hz, 1H), 4.30 (dd, J=14.9, 6.2 Hz, 1H), 4.19-4.13 (m, 1H), 4.06 (d, J=1.2 Hz, 2H), 3.83 (d, J=15.2 Hz, 1H), 3.77-3.69 (m, 3H), 3.65 (d, J=14.1 Hz, 1H), 3.24 (s, 3H), 3.16-2.99 (m, 1H), 2.88-2.69 (m, 2H), 2.66 (s, 0H), 2.52-2.37 (m, 1H), 2.33 (q, J=9.0 Hz, 1H), 2.23-2.02 (m, 3H), 2.00-1.64 (m, 4H), 1.47 (d, J=6.5 Hz, 3H), 1.44-1.24 (m, 2H), 1.14 (d, J=6.6 Hz, 3H). LCMS-ESI+ (m/z): [M+H]$^+$ calculated for $C_{38}H_{49}ClN_4O_6S$: 725.31; found: 724.93.

Example 254

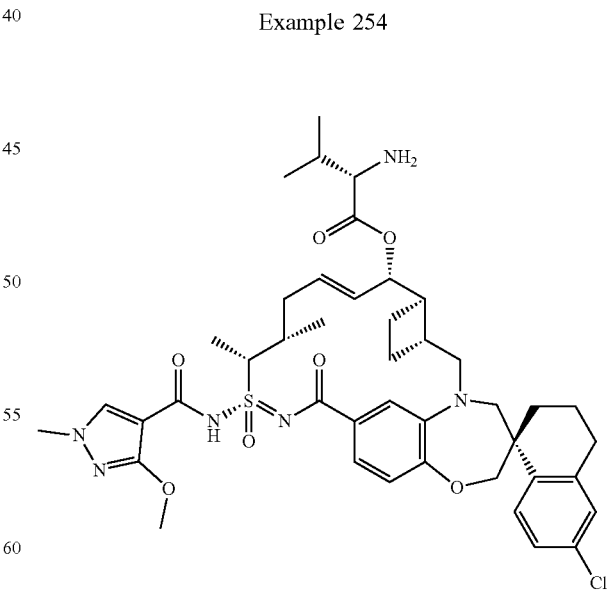

Example 359 (10 mg, 0.14 mmol), (((9H-fluoren-9-yl) methoxy)carbonyl)-L-valine (9.21 mg, 0.02 mmol), EDCI.HCl (6.5 mg, 0.034 mmol), and DMAP (3.3 mg, 0.027 mmol) were combined in a 8 mL vial, and DCM (3 mL) was added. This mixture was sonicated for 3 min for complete dissolution and stirred at 0° C. for 2 h. The solvent was concentrated, and to the crud product was added 20% piperidine in DMF (2 mL). This solution was stirred at RT for 20 min. The reaction mixture was filtered and purified by reverse phase preparative HPLC, eluted with 60-100% ACN/H$_2$O with 0.1% TFA to afford Example 254. $^1$H NMR (400 MHz, DMSO-d$_6$) δ 8.26 (s, 3H), 7.98 (s, 1H), 7.63 (d, water (30 mL), brine (20 mL), and saturated aqueous ammonium chloride solution (10 mL) were added sequentially. The aqueous layer was extracted with dichloromethane (2×60 mL). The combined organic layers were dried over anhydrous magnesium sulfate, filtered, and concentrated under reduced pressure. The residue was purified by flash column chromatography on silica gel (0 to 25% ethyl acetate in hexanes) to give 255-1.

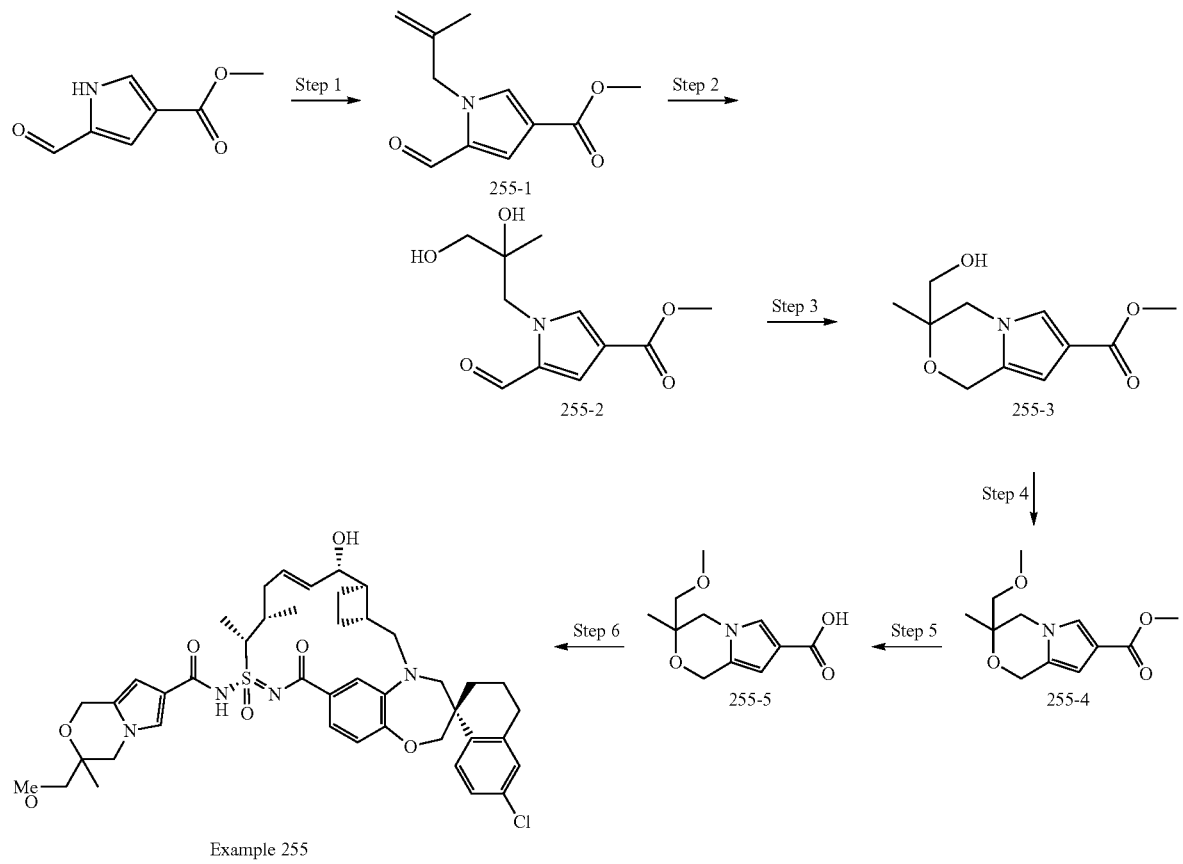

Example 255

J=8.5 Hz, 1H), 7.26 (dd, J=8.4, 2.3 Hz, 1H), 7.16 (d, J=2.3 Hz, 1H), 7.05 (d, J=8.2 Hz, 1H), 6.95 (d, J=8.1 Hz, 1H), 6.89 (s, 1H), 6.51 (s, 2H), 5.98 (t, J=12.5 Hz, 1H), 5.79 (dd, J=15.1, 8.7 Hz, 1H), 5.42 (dd, J=8.7, 3.3 Hz, 1H), 4.15-3.94 (m, 3H), 3.95-3.85 (m, 2H), 3.81 (s, 4H), 3.70 (s, 3H), 3.58 (d, J=14.0 Hz, 1H), 3.25-2.94 (m, 2H), 2.85-2.59 (m, 2H), 2.35 (d, J=35.9 Hz, 1H), 2.21-1.60 (m, 10H), 1.42 (d, J=7.0 Hz, 4H), 1.03 (d, J=5.9 Hz, 3H), 0.96 (dd, J=12.0, 6.9 Hz, 6H). LCMS-ESI+ (m/z): [M+H]+ calcd for C$_{43}$H$_{55}$ClN$_6$O$_7$S: 835.35; found: 834.95.

Example 255

Step 1

A stirred mixture of 5-formyl-1H-pyrrole-3-carboxylate (500 mg, 3.27 mmol), 1-chloro-2-methyl-2-propene (639 μL, 6.53 mmol), and cesium carbonate (2.03 g, 6.24 mmol) in acetonitrile (6 mL) was heated to 65° C. After 150 min, the resulting mixture was cooled to room temperature, and Step 2

Osmium tetroxide solution (2.5% wt. in tert-butyl alcohol, 234 μL, 19 μmol) was added over 1 min via syringe to a stirred mixture of 255-1 (387 mg, 1.87 mmol), 4-(dimethylamino)pyridine (6.9 mg, 56 μmol), and 4-methylmorpholine-A-oxide (328 mg, 2.80 mmol) in tert-butyl alcohol (3.0 mL), water (1.0 mL), and tetrahydrofuran (1.0 mL) at room temperature. After 74 min, the resulting mixture was heated to 90° C. After 76 min, the resulting mixture was cooled to room temperature, and sodium sulfite (471 mg) and water (1.0 mL) were added sequentially. After 20 min, the resulting mixture was filtered through celite, and the filter cake was extracted with ethyl acetate (100 mL). The combined filtrates were dried over magnesium sulfate, filtered, and concentrated under reduced pressure. The residue was purified by flash column chromatography on silica gel (0 to 100% ethyl acetate in dichloromethane) to give 255-2.

Step 3

Trifluoroacetic acid (1.43 mL, 18.7 mmol) was added via syringe to a stirred solution of 255-2 (451 mg, 1.87 mmol)

in dichloromethane (117 mL) and methanol (1.52 mL) at room temperature. After 1 min, triethylsilane (3.14 mL, 19.6 mmol) was added via syringe. After 19 min, trifluoroacetic acid (3.58 mL, 46.8 mmol) and triethylsilane (7.48 mL, 46.7 mmol) were added sequentially via syringe. After 55 min, saturated aqueous sodium carbonate solution (55 mL) was added, and the resulting biphasic mixture was stirred vigorously. After 15 min, brine (30 mL) was added, and the layers were separated. The aqueous layer was extracted with dichloromethane (60 mL). The combined organic layers were dried over anhydrous magnesium sulfate, filtered, and concentrated under reduced pressure. The residue was purified by flash column chromatography on silica gel (0 to 70% ethyl acetate in hexanes) to give 255-3.

Step 4

Potassium bis(trimethylsilyl)amide solution (1.0 M in tetrahydrofuran, 466 µL, 466 µmol) was added via syringe to a stirred solution of 255-3 (35.0 mg, 155 µmol) in tetrahydrofuran at 0° C. After 6 min, iodomethane (48.5 µL, 777 µmol) was added via syringe, and the resulting mixture was warmed to room temperature. After 25 min, saturated aqueous ammonium chloride solution (5 mL) and ethyl acetate (30 mL) were added sequentially. The organic layer was washed with water (20 mL), was dried over anhydrous magnesium sulfate, was filtered, and was concentrated under reduced pressure. The residue was purified by flash column chromatography on silica gel (0 to 40% ethyl acetate in hexanes) to give 255-4.

Step 5

Aqueous sodium hydroxide solution (2.0 M, 900 µL, 1.80 mmol) was added via syringe to a stirred solution of 255-4 (37.0 mg, 155 µmol) in tetrahydrofuran (0.65 mL) and methanol (1.5 mL) at room temperature, and the resulting mixture was heated to 70° C. After 16 h, the resulting mixture was cooled to room temperature, and aqueous hydrogen chloride solution (2.0 M, 1.0 mL) and brine (10 mL) were added sequentially. The aqueous layer was extracted sequentially with dichloromethane (2×15 mL) and ethyl acetate (15 mL). The combined organic layers were dried over anhydrous magnesium sulfate, were filtered, and were concentrated under reduced pressure to give 255-5.

Step 6: Preparation of Example 255

Example 255 was synthesized in a manner similar to Example 106 using Intermediate 359-4 instead of 106-4 and using 255-5 instead of 2-((tetrahydro-2H-pyran-4-yl)oxy) acetic acid. 1H NMR (400 MHz, Acetone-d6) δ 7.78 (d, J=8.6 Hz, 1H), 7.45-7.12 (m, 5H), 6.97 (s, 1H), 6.30 (s, 1H), 5.99-5.83 (m, 1H), 5.83-5.69 (m, 1H), 4.80 (s, 2H), 4.24-3.38 (m, 11H), 3.36 (s, 3H), 3.19 (dd, J=15.4, 9.0 Hz, 1H), 2.98-1.14 (m, 21H), 1.14-1.04 (m, 3H). LCMS: 805.1.

Example 256

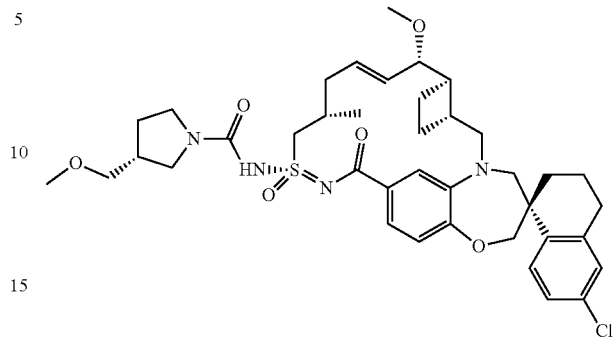

Example 256 was synthesized in the same manner as Example 237 using Example 109 and (R)-3-(methoxymethyl)pyrrolidine. $^1$H NMR (400 MHz, Methanol-d4) δ 7.75 (d, J=8.5 Hz, 1H), 7.19 (dd, J=8.5, 2.4 Hz, 1H), 7.12 (td, J=3.8, 1.8 Hz, 2H), 6.94 (d, J=8.1 Hz, 1H), 6.91 (d, J=2.0 Hz, 1H), 5.97 (dt, J=14.1, 6.5 Hz, 1H), 5.58 (dd, J=15.2, 9.1 Hz, 1H), 4.33 (dd, J=14.8, 5.9 Hz, 1H), 4.08 (d, J=1.8 Hz, 2H), 3.90-3.81 (m, 1H), 3.76 (dd, J=9.2, 3.7 Hz, 1H), 3.67 (m, 2H), 3.63-3.52 (m, 2H), 3.42 (d, J=8.1 Hz, 1H), 3.37 (m, 4H), 3.26 (s, 4H), 3.22-3.14 (m, 1H), 3.08 (dd, J=15.2, 10.3 Hz, 1H), 2.90-2.70 (m, 2H), 2.59-2.40 (m, 4H), 2.35 (q, J=9.0 Hz, 1H), 2.17 (m, 3H), 2.07 (m, 1H), 2.01-1.86 (m, 4H), 1.77 (m, 4H), 1.44 (t, J=12.5 Hz, 1H), 1.15 (d, J=6.3 Hz, 3H). LCMS-ESI+: calc'd for $C_{39}H_{52}ClN_4O_6S$: 739.32 (M+H); found: 739.80 (M+H).

Example 257

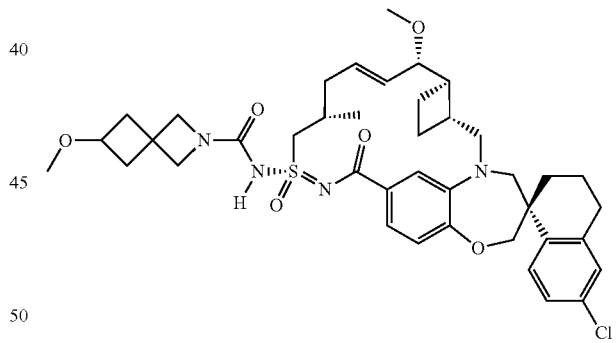

Example 257 was synthesized in the same manner as Example 237 using Example 109 and 6-methoxy-2-azaspiro [3.3]heptane hydrochloride. $^1$H NMR (400 MHz, Methanol-d4) δ 7.75 (d, J=8.5 Hz, 1H), 7.19 (dd, J=8.5, 2.4 Hz, 1H), 7.13 (dd, J=6.4, 2.1 Hz, 2H), 6.96-6.87 (m, 2H), 5.98 (dt, J=14.3, 6.8 Hz, 1H), 5.58 (dd, J=15.2, 9.1 Hz, 1H), 4.29 (dd, J=14.9, 6.4 Hz, 1H), 4.15-4.04 (m, 2H), 4.00 (m, 4H), 3.90-3.79 (m, 2H), 3.76 (dd, J=9.1, 3.7 Hz, 1H), 3.67 (d, J=14.2 Hz, 1H), 3.65-3.57 (m, 1H), 3.26 (m, 4H), 3.24 (s, 3H), 3.08 (dd, J=15.2, 10.3 Hz, 1H), 2.89-2.70 (m, 2H), 2.57-2.42 (m, 4H), 2.35 (q, J=9.0 Hz, 1H), 2.24-2.15 (m, 1H), 2.15-2.06 (m, 3H), 1.93 (m, 3H), 1.77 (m, 4H), 1.44 (t, J=12.5 Hz, 1H), 1.33 (d, J=16.3 Hz, 1H), 1.14 (d, J=6.6 Hz, 3H). LCMS-ESI+: calc'd for $C_{40}H_{52}ClN_4O_6S$: 752.32 (M+H); found: 751.53 (M+H).

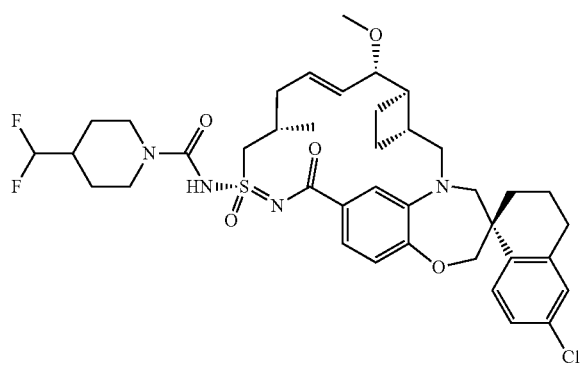 [SMILES: CO[C@H]1/C=C/C[C@H](C)C[S@@](=O)(NC(=O)N2CCC(C(F)F)CC2)=NC(=O)c2ccc3c(c2)N(C[C@@H]2CC[C@H]21)C[C@@]1(CCCc2cc(Cl)ccc21)CO3]

Example 258 was synthesized in the same manner as Example 237 using Example 109 and 4-(difluoromethyl) piperidine hydrochloride. $^1$H NMR (400 MHz, Methanol-d4) δ 7.75 (d, J=8.5 Hz, 1H), 7.19 (dd, J=8.5, 2.4 Hz, 1H), 7.12 (d, J=2.3 Hz, 1H), 7.09 (dd, J=8.1, 1.9 Hz, 1H), 6.94 (d, J=8.1 Hz, 1H), 6.88 (d, J=2.0 Hz, 1H), 5.95 (dt, J=14.2, 6.7 Hz, 1H), 5.89-5.61 (m, 1H), 5.61-5.53 (m, 1H), 4.45 (s, 2H), 4.38 (dd, J=14.9, 6.3 Hz, 1H), 4.09 (s, 2H), 3.85 (d, J=15.2 Hz, 1H), 3.76 (dd, J=9.3, 3.7 Hz, 1H), 3.67 (d, J=14.2 Hz, 1H), 3.60 (dd, J=14.9, 5.8 Hz, 1H), 3.28 (m, 6H), 3.08 (dd, J=15.3, 10.3 Hz, 1H), 2.98-2.68 (m, 4H), 2.46 (dd, J=14.4, 5.3 Hz, 1H), 2.32 (p, J=9.2 Hz, 1H), 2.19 (q, J=7.6 Hz, 1H), 2.12 (d, J=15.9 Hz, 2H), 2.01-1.86 (m, 1H), 1.86-1.65 (m, 7H), 1.52-1.28 (m, 2H), 1.14 (d, J=6.6 Hz, 3H). LCMS-ESI+: calc'd for $C_{39}H_{50}ClF_2N_4O_5S$: 759.31 (M+H); found: 759.33 (M+H).

Example 259

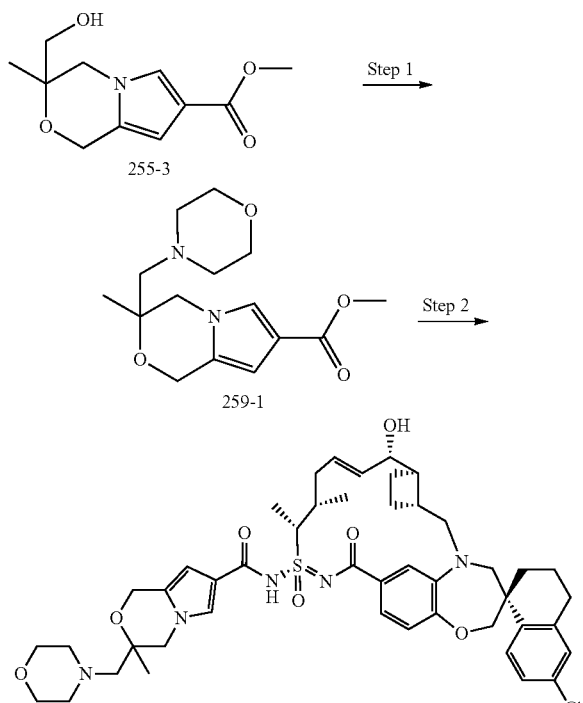

Step 1

Dess-Martin periodinane (85.4 mg, 201 μmol) was added to a stirred solution of 255-3 (32.4 mg, 144 μmol) in dichloromethane (1.0 mL) at room temperature. After 45 min, aqueous sodium thiosulfate solution (1.0 M, 1.0 mL), saturated sodium bicarbonate solution (5.0 mL), diethyl ether (60 mL), and ethyl acetate (60 mL) were added sequentially. The organic layer was washed sequentially with water (50 mL), a mixture of water and saturated aqueous sodium bicarbonate solution (1:1 v:v, 50 mL), and water (50 mL), dried over anhydrous magnesium sulfate, filtered, and concentrated under reduced pressure. The residue was dissolved in dichloromethane (2.0 mL) and stirred at room temperature. Morpholine (88.1 μL, 1.01 mmol) acetic acid (57.6 μL, 1.01 mmol), and sodium triacetoxyborohydride (213 mg, 1.01 mmol) were added sequentially, and the resulting mixture was heated to 45° C. After 45 min, the resulting mixture was cooled to room temperature, and saturated aqueous sodium carbonate solution (6.0 mL) and ethyl acetate (75 mL) were added sequentially. The organic layer was washed with a mixture of water and brine (3:1 v:v, 50 mL), dried over anhydrous magnesium sulfate, filtered, and concentrated under reduced pressure. The residue was purified by flash column chromatography on silica gel (0 to 9% methanol in dichloromethane) to give 259-1.

Step 2: Preparation of Example 259

Example 259 was synthesized in a manner similar to Example 229 using 259-1 instead of 229-3. 1H NMR (400 MHz, Acetone-d6) δ 7.79 (d, J=8.5 Hz, 1H), 7.44 (s, 1H), 7.28-7.16 (m, 3H), 7.15 (d, J=2.4 Hz, 1H), 7.00 (d, J=8.0 Hz, 1H), 6.33 (s, 1H), 5.95-5.82 (m, 1H), 5.74 (dd, J=15.3, 7.3 Hz, 1H), 4.90-4.76 (m, 2H), 4.48-3.59 (m, 16H), 3.40 (d, J=14.3 Hz, 1H), 3.19 (dd, J=15.2, 8.9 Hz, 1H), 3.10-1.42 (m, 15H), 1.56 (d, J=7.1 Hz, 3H), 1.32 (d, J=1.5 Hz, 3H), 1.05 (s, 3H). LCMS: 860.1.

Example 260

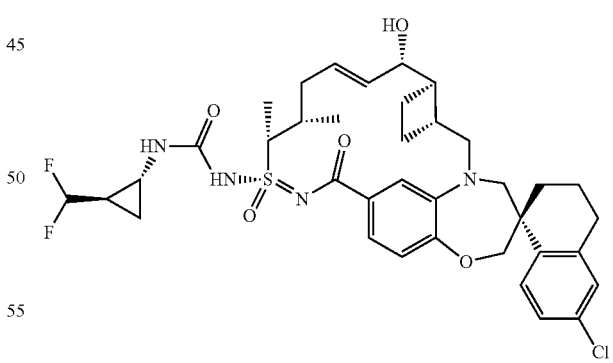

Example 260 was synthesized in the same manner as Example 75 using Example 359 and (1R,2R)-2-(difluoromethyl)cyclopropan-1-amine hydrochloride. $^1$H NMR (400 MHz, Methanol-d4) δ 7.75 (d, J=8.5 Hz, 1H), 7.19 (dd, J=8.5, 2.4 Hz, 1H), 7.15 (d, J=8.8 Hz, 1H), 7.12 (d, J=2.3 Hz, 1H), 6.99-6.92 (m, 2H), 5.99-5.79 (m, 2H), 5.79-5.65 (m, 1H), 4.42-4.26 (m, 1H), 4.20 (dd, J=8.5, 3.3 Hz, 1H), 4.10 (s, 2H), 3.84 (d, J=15.1 Hz, 1H), 3.66 (d, J=14.3 Hz, 1H), 3.29 (m, 1H), 3.15-3.06 (m, 1H), 2.96-2.68 (m, 3H), 2.50-2.35 (m, 1H), 2.31 (t, J=9.0 Hz, 1H), 2.17 (s, 2H), 2.11 (m, 2H), 2.03-1.91 (m, 2H), 1.91-1.81 (m, 2H), 1.75 (q, J=9.2 Hz, 1H), 1.66-1.42 (m, 5H), 1.23-1.00 (m, 4H), 1.00-0.88 (m, 1H). LCMS-ESI+: calc'd for $C_{37}H_{46}ClF_2N_4O_5S$: 731.28 (M+H); found: 731.11 (M+H).

Example 261

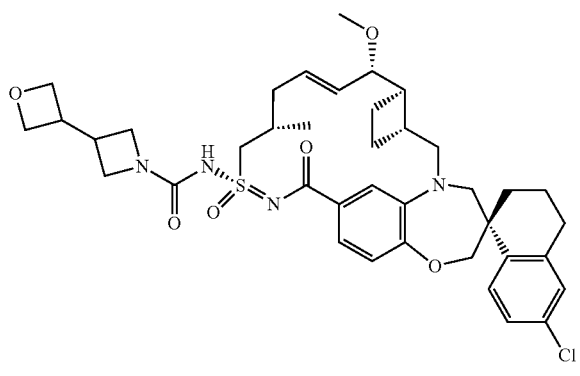 [SMILES: CO[C@H]1/C=C/C[C@H](C)C[S@@](=O)(NC(=O)N2CC(C3COC3)C2)=NC(=O)c2ccc3c(c2)N(C[C@@H]2CC[C@H]21)C[C@@]1(CCCc2cc(Cl)ccc21)CO3]

Example 261 was synthesized in the same manner as Example 182, using 3-(oxetan-3-yl)azetidine instead of rac-(1R,2R)-2-(1-methyl-1H-pyrazol-5-yl)cyclopropan-1-amine. 1H NMR (400 MHz, Methanol-d4) δ 7.75 (d, J=8.5 Hz, 1H), 7.19 (dd, J=8.5, 2.3 Hz, 1H), 7.12 (dt, J=4.3, 1.9 Hz, 2H), 7.00-6.86 (m, 2H), 5.98 (dt, J=14.2, 6.7 Hz, 1H), 5.58 (dd, J=15.2, 9.1 Hz, 1H), 4.45 (t, J=6.0 Hz, 2H), 4.37-4.12 (m, 3H), 4.08 (d, J=2.1 Hz, 2H), 3.92-3.71 (m, 3H), 3.71-3.55 (m, 2H), 3.26 (s, 3H), 3.08 (dd, J=15.2, 10.3 Hz, 2H), 3.01 (s, 2H), 2.91-2.66 (m, 3H), 2.47 (dd, J=12.2, 7.9 Hz, 2H), 2.38-2.29 (m, 1H), 2.26-2.05 (m, 3H), 1.97-1.88 (m, 2H), 1.78 (tt, J=17.1, 9.5 Hz, 3H), 1.45 (t, J=11.8 Hz, 2H), 1.31 (s, 2H), 1.15 (d, J=6.6 Hz, 3H). LCMS-ESI+ (m/z): [M+H]+ calcd for $C_{39}H_{49}ClN_4O_6S$: 737.31; found: 737.06.

Example 262

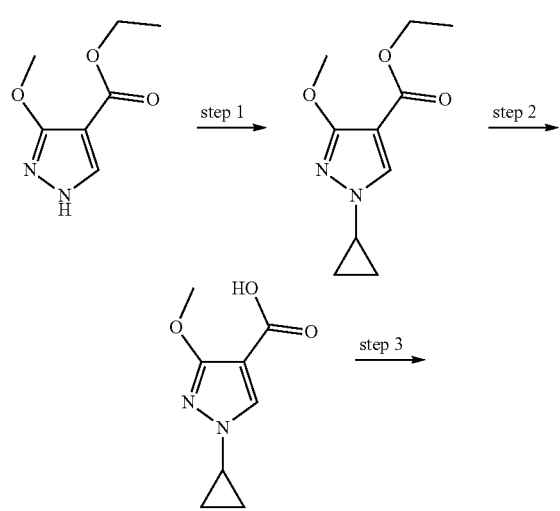

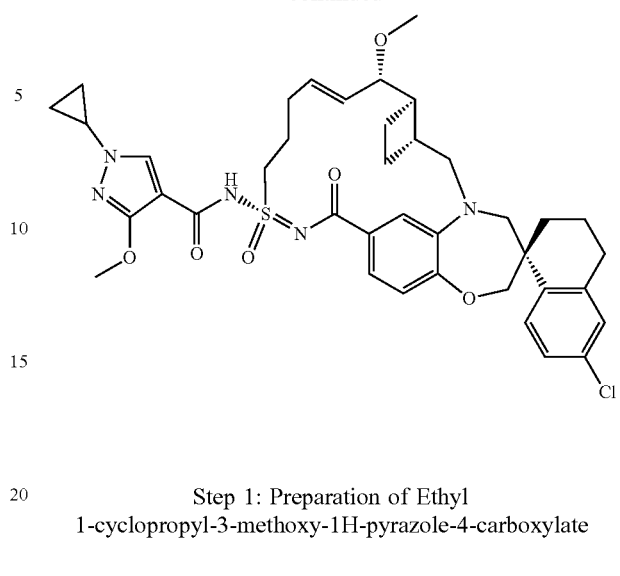

Step 1: Preparation of Ethyl 1-cyclopropyl-3-methoxy-1H-pyrazole-4-carboxylate The reaction mixture of ethyl 3-methoxy-1H-pyrazole-4-carboxylate (113 mg, 0.66 mmol), cyclopropylboronic acid (114 mg, 1.33 mmol), copper(II) acetate (120.61 mg, 0.66 mmol), 2,2'-bipyridyl (103.71 mg, 0.66 mmol) and sodium carbonate (140.76 mg, 1.33 mmol) in toluene (5 mL) was heated at 60° C. overnight with exposure to air. The reaction mixture was cooled down and filtered. The filtrate was concentrated down and purified by silica gel chromatograph (eluting with 0-100% EtOAc/hexane) to give the title compound (105 mg).

Step 2: Preparation of 1-cyclopropyl-3-methoxy-1H-pyrazole-4-carboxylic Acid The reaction mixture of ethyl 1-cyclopropyl-3-methoxy-pyrazole-4-carboxylate (12 mg, 0.057 mmol), 2 M NaOH (0.057 mL) in MeOH (1.0 mL) and water (0.5 mL) was stirred at 45° C. overnight. The reaction mixture was concentrated and used in the next step without purification.

Step 3

Example 262 was synthesized in the same manner as Example 18, using Example 109 instead of Example 5, and 2,3-dihydropyrazolo[5,1-b]oxazole-6-carboxylic acid was used instead of 3-methoxypropionic acid. 1H NMR (400 MHz, Methanol-d4) δ 8.14 (s, 1H), 7.77 (d, J=8.6 Hz, 1H), 7.37-7.30 (m, 1H), 7.23-7.09 (m, 3H), 6.92 (d, J=8.2 Hz, 1H), 6.11 (dt, J=14.1, 6.4 Hz, 1H), 5.62 (dd, J=15.3, 8.2 Hz, 1H), 4.19-3.95 (m, 6H), 3.87 (d, J=15.0 Hz, 1H), 3.79 (dd, J=8.1, 3.3 Hz, 1H), 3.71 (d, J=14.3 Hz, 1H), 3.63 (tt, J=7.4, 3.8 Hz, 1H), 3.38 (d, J=14.2 Hz, 1H), 3.29 (s, 3H), 3.08 (dd, J=15.0, 9.9 Hz, 1H), 2.92-2.71 (m, 3H), 2.51 (ddd, J=22.6, 9.8, 5.5 Hz, 3H), 2.30-2.19 (m, 2H), 2.12 (d, J=13.6 Hz, 1H), 1.94 (d, J=13.6 Hz, 3H), 1.78 (d, J=6.7 Hz, 3H), 1.51-1.40 (m, 1H), 1.17-1.07 (m, 5H), 1.07-1.00 (m, 2H). LCMS-ESI+ (m/z): [M+H]+ calcd for $C_{40}H_{48}ClN_5O_6S$: 762.30; found: 760.83.

Example 263

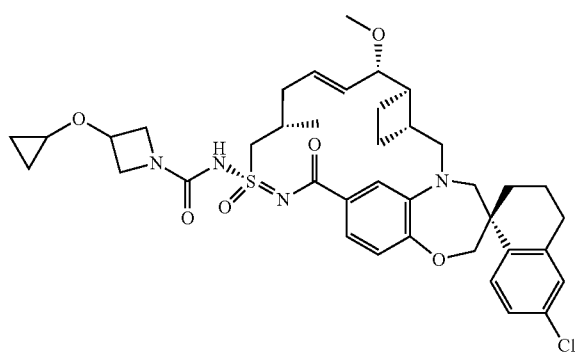 [SMILES: CO[C@H]1/C=C/C[C@H](C)C[S@@](=O)(NC(=O)N2CC(OC3CC3)C2)=NC(=O)c2ccc3c(c2)N(C[C@@H]2CC[C@H]21)C[C@@]1(CCCc2cc(Cl)ccc21)CO3]

Example 263 was synthesized in the same manner as Example 182, using 3-(cyclopropoxy)azetidine hydrochloride instead of rac-(1R,2R)-2-(1-methyl-1H-pyrazol-5-yl)cyclopropan-1-amine. 1H NMR (400 MHz, Methanol-d4) δ 7.75 (d, J=8.6 Hz, 1H), 7.19 (dd, J=8.6, 2.4 Hz, 1H), 7.12 (dt, J=4.3, 2.6 Hz, 2H), 6.93 (d, J=8.2 Hz, 2H), 5.97 (dt, J=14.2, 6.8 Hz, 1H), 5.58 (dd, J=15.2, 9.1 Hz, 1H), 4.48-4.39 (m, 1H), 4.38-4.15 (m, 3H), 4.08 (d, J=1.9 Hz, 2H), 4.01-3.80 (m, 3H), 3.76 (dd, J=9.1, 3.6 Hz, 1H), 3.67 (d, J=14.3 Hz, 2H), 3.36 (d, J=3.1 Hz, 1H), 3.26 (s, 3H), 3.08 (dd, J=15.3, 10.3 Hz, 1H), 2.88-2.70 (m, 2H), 2.52-2.42 (m, 2H), 2.35 (q, J=9.2 Hz, 1H), 2.25-2.04 (m, 3H), 2.01-1.69 (m, 5H), 1.44 (t, J=12.5 Hz, 1H), 1.31 (s, 3H), 1.15 (d, J=6.6 Hz, 2H), 0.96-0.88 (m, 1H), 0.68-0.58 (m, 2H), 0.58-0.46 (m, 2H). LCMS-ESI+ (m/z): [M+H]+ calcd for $C_{39}H_{49}ClN_4O_6S$: 737.31; found: 735.76.

Example 264

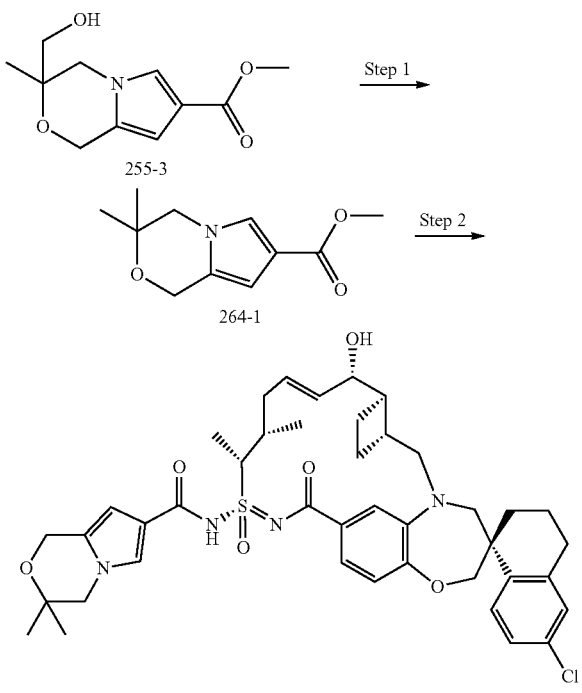

Step 1

Di(1H-imidazol-1-yl)methanethione (58.6 mg, 329 μmol) was added to a stirred mixture of 255-3 (37.0 mg, 164 μmol) and 4-(dimethylamino)pyridine (10 mg, 82 μmol) in tetrahydrofuran at room temperature. After 5 min, the resulting mixture was heated to 65° C. After 35 min, the resulting mixture was heated to 80° C. After 23 h, the resulting mixture was cooled to room temperature and was filtered through celite. The filter cake was extracted with ethyl acetate (20 mL), and the combined filtrates were concentrated under reduced pressure. The residue was redissolved in toluene (14 mL) and 1,4-dioxane (12 mL), tributylstannane (221 μL, 821 μmol) was added, and the resulting mixture was stirred and heated to 100° C. A solution of 2,2'-(diazene-1,2-diyl)bis(2-methylpropanenitrile) (8.1 mg, 49 μmol) in toluene (1.6 mL) was added via syringe pump over 30 min. After 20 min, the resulting mixture was cooled to room temperature and was concentrated under reduced pressure. The residue was purified by flash column chromatography on silica gel (0 to 27% ethyl acetate in hexanes) to give 264-1.

Step 2

Example 264 was synthesized in a manner similar to Example 255 using 264-1 instead of 255-4. 1H NMR (400 MHz, Acetone-d6) δ 7.78 (d, J=8.5 Hz, 1H), 7.39 (s, 1H), 7.29-7.10 (m, 4H), 6.99 (d, J=8.0 Hz, 1H), 6.31 (s, 1H), 5.95-5.82 (m, 1H), 5.74 (dd, J=15.3, 7.2 Hz, 1H), 4.91-3.81 (m, 12H), 3.74 (d, J=14.2 Hz, 1H), 3.40 (d, J=14.4 Hz, 1H), 3.19 (dd, J=15.3, 9.2 Hz, 1H), 3.09-1.13 (m, 24H), 1.05 (s, 3H). LCMS: 775.1.

Example 265

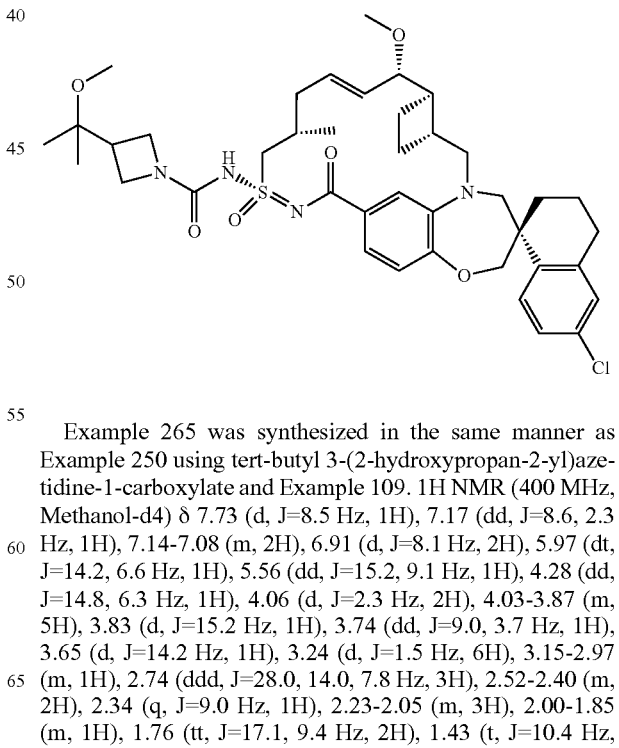

Example 265 was synthesized in the same manner as Example 250 using tert-butyl 3-(2-hydroxypropan-2-yl)azetidine-1-carboxylate and Example 109. 1H NMR (400 MHz, Methanol-d4) δ 7.73 (d, J=8.5 Hz, 1H), 7.17 (dd, J=8.6, 2.3 Hz, 1H), 7.14-7.08 (m, 2H), 6.91 (d, J=8.1 Hz, 2H), 5.97 (dt, J=14.2, 6.6 Hz, 1H), 5.56 (dd, J=15.2, 9.1 Hz, 1H), 4.28 (dd, J=14.8, 6.3 Hz, 1H), 4.06 (d, J=2.3 Hz, 2H), 4.03-3.87 (m, 5H), 3.83 (d, J=15.2 Hz, 1H), 3.74 (dd, J=9.0, 3.7 Hz, 1H), 3.65 (d, J=14.2 Hz, 1H), 3.24 (d, J=1.5 Hz, 6H), 3.15-2.97 (m, 1H), 2.74 (ddd, J=28.0, 14.0, 7.8 Hz, 3H), 2.52-2.40 (m, 2H), 2.34 (q, J=9.0 Hz, 1H), 2.23-2.05 (m, 3H), 2.00-1.85 (m, 1H), 1.76 (tt, J=17.1, 9.4 Hz, 2H), 1.43 (t, J=10.4 Hz, 1H), 1.29 (s, 2H), 1.13 (d, J=6.4 Hz, 9H). LCMS-ESI+ (m/z): [M+H]+ calculated for $C_{40}H_{53}ClN_4O_6S$: 753.34; found: 752.98.

Example 266

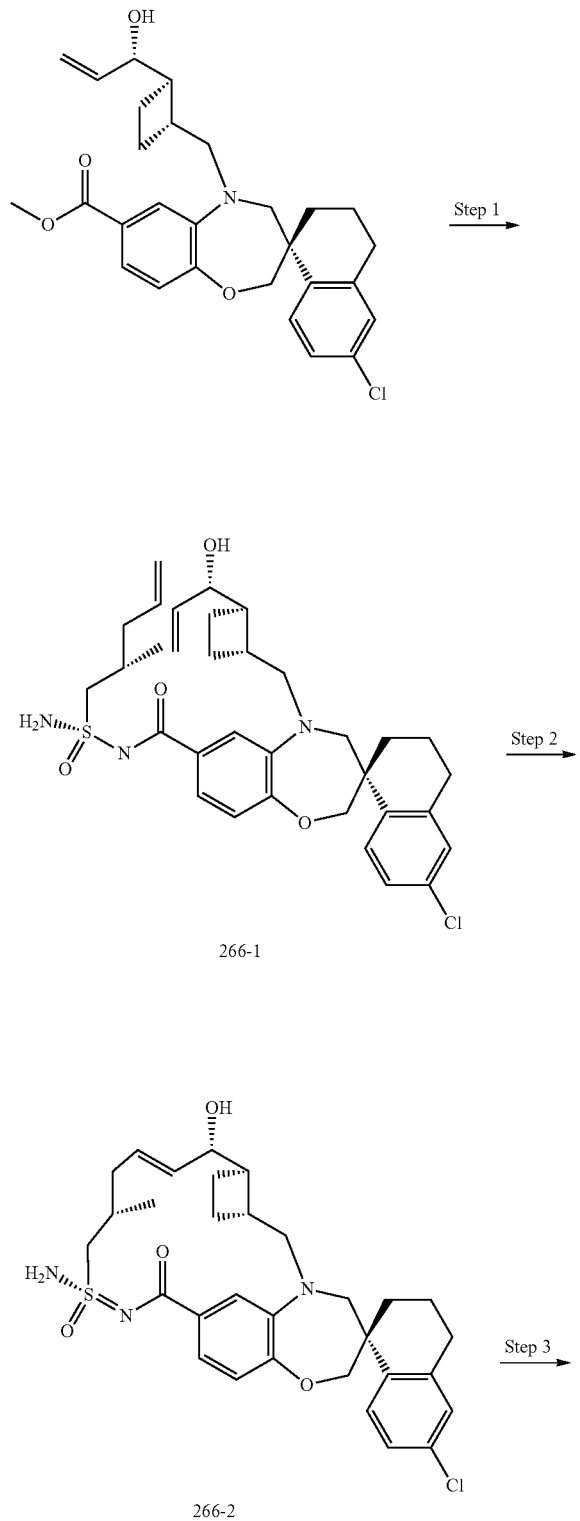

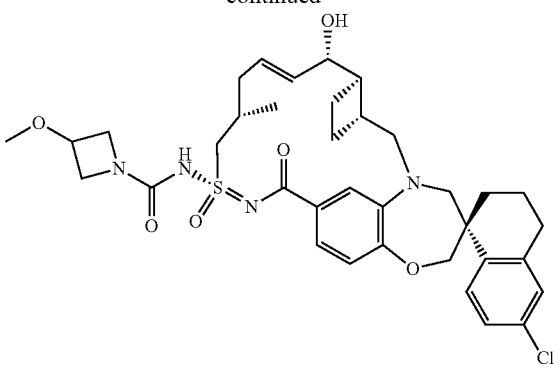

Example 266

Step 1

Aqueous sodium hydroxide solution (2.0 M, 3.1 mL, 6.2 mmol) was added via syringe to a stirred solution of methyl (S)-6'-chloro-5-(((1R,2R)-2-((S)-1-hydroxyallyl)cyclobutyl)methyl)-3',4,4',5-tetrahydro-2H,2'H-spiro[benzo[b][1,4] oxazepine-3,1'-naphthalene]-7-carboxylate (500 mg, 1.04 mmol) in methanol (14.8 mL) at room temperature, and the resulting mixture was heated to 60° C. After 27.5 h, the resulting mixture was allowed to cool to room temperature, acidified by addition of aqueous hydrogen chloride solution (1.0 M), and concentrated under reduced pressure. The residue was dissolved in dichloromethane, and the organic layer was washed with water, dried over anhydrous magnesium sulfate, and concentrated under reduced pressure. The residue was dissolved in dichloromethane (52 mL), 109-2-2 (536 mg, 2.08 mmol) and 4-(dimethylamino)pyridine (423 mg, 3.46 mmol) were added, and the resulting mixture was stirred at room temperature. 3-(((Ethylimino)methylene) amino)-N,N-dimethylpropan-1-amine hydrochloride (498 mg, 2.60 mmol) was added. After 18 h, ethyl acetate and aqueous hydrogen chloride solution (1.0 M) were added. The organic layer was washed sequentially with water and brine, dried over anhydrous magnesium sulfate, and concentrated under reduced pressure. The residue was dissolved in tetrahydrofuran (2.5 mL), methanol (29 mL), and water (0.16 mL) and the resulting mixture was stirred at room temperature. Potassium carbonate (2.39 g, 17.3 mmol) was added, and the resulting mixture was heated to 60° C. After stirring overnight, the resulting mixture was cooled to room temperature, and brine (8 mL) and a mixture of citric acid (1.0 g) in water (10 mL) were added. The aqueous layer was extracted sequentially with dichloromethane (30 mL) and ethyl acetate (30 mL). The combined organic layers were dried over anhydrous magnesium sulfate, filtered, and concentrated under reduced pressure. The residue was purified by flash column chromatography on silica gel (0 to 30% ethyl acetate in hexanes) to give intermediate 266-1.

Step 2

A stirred mixture of intermediate 266-1 (500 mg, 817 μmol) and (1,3-bis-(2,4,6-trimethylphenyl)-2-imidazolidinylidene)dichloro(o-isopropoxyphenyl methylene)ruthenium (102 mg, 163 μmol) in 1,2-dichloroethane (272 mL) was heated to 75° C. After 2.5 days, the resulting mixture was allowed to cool to room temperature and was concentrated under reduced pressure. The residue was purified by flash column chromatography on silica gel to give intermediate 266-2. ¹H NMR (400 MHz, Chloroform-d) δ 7.76 (d, J=8.5 Hz, 1H), 7.50-7.38 (m, 2H), 7.26-7.17 (m, 1H), 7.16-7.06 (m, 1H), 6.93 (d, J=8.1 Hz, 1H), 6.52-5.95 (m, 2H), 6.06 (dt, J=14.2, 6.6 Hz, 1H), 5.79-5.65 (m, 1H), 4.21 (t, J=5.8 Hz, 1H), 4.13-4.02 (m, 2H), 3.90-3.81 (m, 1H), 3.81-3.72 (m, 1H), 3.49-3.25 (m, 2H), 3.07 (dd, J=15.2, 9.1 Hz, 1H), 2.92-1.56 (m, 15H), 1.42 (t, J=13.0 Hz, 1H), 1.20 (d, J=6.5 Hz, 3H). LCMS: 584.2.

Step 3

A 4-dram vial was charged with intermediate 266-2 (1 equiv, 0.041 mmol, 24 mg), diphenyl carbonate (1.3 equiv, 0.053 mmol, 11 mg), N,N-dimethylaminopyridine (2.5 equiv, 0.103 mmol, 13 mg), CH₂Cl₂ (2 mL) and triethylamine (10 equiv, 0.411 mmol, 57 mL), then sealed and stirred at 50° C. for 15 hours. In a separate vial, 3-methoxyazetidine hydrochloride (10 equiv, 0.411 mmol, 51 mg) was treated with CH₂Cl₂ (0.5 mL) and triethylamine (20 equiv, 0.822 mmol, 115 mL). The reaction mixtures were then combined and heated to 60° C. overnight. The reaction mixture was concentrated and partially purified by preparative HPLC (10-100% MeCN in water, 0.1% TFA). The fractions containing desired product by LCMS were concentrated, dissolved in EtOAc and washed with water. The organic layer was back extracted with EtOAc and the combined organic layers were dried over sodium sulfate, filtered and concentrated. The crude material was purified by preparative TLC in 5:1 EtOAc:MeOH, filtered across Celite (eluted with 4:1 EtOAc:MeOH) then concentrated and purified again by preparative HPLC (10-100% MeCN in water, 0.1% TFA). The combined clean fractions were lyophilized to afford the desired product Example 266. LCMS-ESI+ (m/z): (M)⁺ calc'd for $C_{36}H_{45}ClN_4O_6S$: 696.2748; found: 695.92. ¹H NMR (400 MHz, Methanol-d4) δ 7.74 (d, J=8.5 Hz, 1H), 7.17 (dd, J=8.5, 2.3 Hz, 1H), 7.14-7.07 (m, 2H), 6.94 (s, 1H), 6.91 (d, J=8.1 Hz, 1H), 5.92 (dt, J=14.0, 6.7 Hz, 1H), 5.72 (dd, J=15.2, 8.5 Hz, 1H), 4.28-4.12 (m, 5H), 4.12-4.01 (m, 2H), 3.94-3.74 (m, 3H), 3.70-3.53 (m, 2H), 3.37-3.20 (m, 1H), 3.30 (s, 3H), 3.06 (dd, J=15.3, 10.0 Hz, 1H), 2.88-2.68 (m, 2H), 2.46-2.24 (m, 3H), 2.19-1.78 (m, 8H), 1.72 (q, J=9.0 Hz, 1H), 1.43 (t, J=12.8 Hz, 1H), 1.14 (d, J=6.6 Hz, 3H).

Example 267

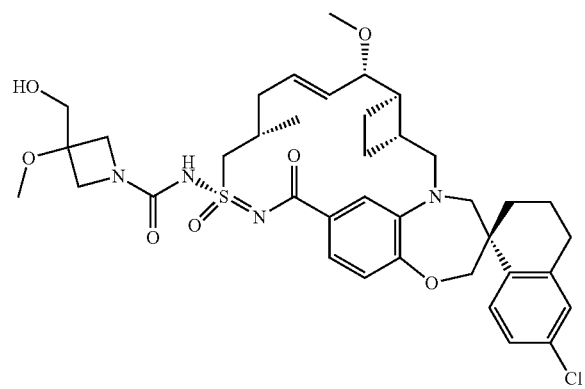 [SMILES: CO[C@H]1/C=C/C[C@H](C)C[S@@](=O)(NC(=O)N2CC(CO)(OC)C2)=NC(=O)c2ccc3c(c2)N(C[C@@H]2CC[C@H]21)C[C@@]1(CCCc2cc(Cl)ccc21)CO3]

Example 267 was prepared in the same manner as Example 362 with Example 109 and (3-methoxyazetidin-3-yl)methanol hydrochloride. LCMS-ESI+ (m/z): (M)⁺ calc'd for $C_{38}H_{49}ClN_4O_7S$: 740.3010; found: 739.79. ¹H NMR (400 MHz, Methanol-d4) δ 7.73 (d, J=8.5 Hz, 1H), 7.17 (dd, J=8.6, 2.3 Hz, 1H), 7.10 (q, J=3.8 Hz, 2H), 6.94-6.88 (m, 2H), 5.96 (dt, J=14.2, 6.7 Hz, 1H), 5.56 (dd, J=15.2, 9.1 Hz, 1H), 4.30 (dd, J=14.9, 6.2 Hz, 1H), 4.12-4.01 (m, 2H), 4.02-3.79 (m, 5H), 3.78-3.71 (m, 3H), 3.69-3.53 (m, 2H), 3.33 (s, 3H), 3.30-3.28 (m, 1H), 3.24 (s, 3H), 3.06 (dd, J=15.2, 10.3 Hz, 1H), 2.88-2.68 (m, 2H), 2.53-2.40 (m, 2H), 2.38-2.26 (m, 1H), 2.22-2.05 (m, 3H), 2.00-1.68 (m, 6H), 1.43 (t, J=12.9 Hz, 1H), 1.13 (d, J=6.6 Hz, 3H).

Example 268

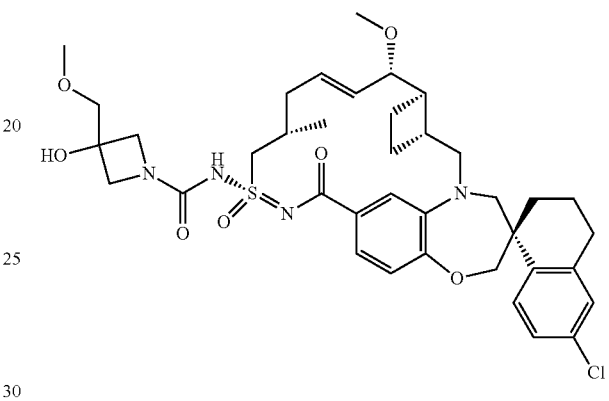

Example 268 was prepared in the same manner as Example 362 with Example 109 and 3-(methoxymethyl)azetidin-3-ol trifluoroacetic acid. LCMS-ESI+ (m/z): [M+H]⁺ calc'd for $C_{38}H_{49}ClN_4O_7S$: 741.3083; found: 740.83. ¹H NMR (400 MHz, Methanol-d4) δ 7.73 (d, J=8.5 Hz, 1H), 7.17 (dd, J=8.5, 2.4 Hz, 1H), 7.13-7.06 (m, 2H), 6.94-6.87 (m, 2H), 5.96 (dt, J=14.3, 6.7 Hz, 1H), 5.56 (dd, J=15.2, 9.1 Hz, 1H), 4.30 (dd, J=14.8, 6.4 Hz, 1H), 4.15-3.95 (m, 4H), 3.93-3.70 (m, 4H), 3.70-3.57 (m, 2H), 3.48-3.46 (m, 2H), 3.43 (s, 3H), 3.30-3.27 (m, 1H), 3.24 (s, 3H), 3.06 (dd, J=15.2, 10.3 Hz, 1H), 2.89-2.68 (m, 2H), 2.52-2.40 (m, 2H), 2.38-2.27 (m, 1H), 2.22-2.05 (m, 3H), 2.01-1.67 (m, 6H), 1.42 (t, J=12.9 Hz, 1H), 1.13 (d, J=6.7 Hz, 3H).

Example 269

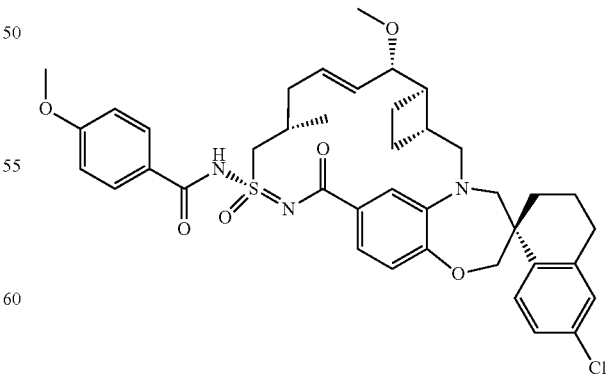

Example 269 was synthesized in the same manner as Example 18 using 4-methoxybenzoic acid and Example 109. ¹H NMR (400 MHz, Methanol-d₄) δ 8.18-7.99 (m, 2H), 7.75

(d, J=8.5 Hz, 1H), 7.18 (ddd, J=8.6, 3.6, 2.1 Hz, 2H), 7.12 (d, J=2.3 Hz, 1H), 7.04-6.99 (m, 3H), 6.97 (d, J=1.9 Hz, 1H), 6.94 (d, J=8.1 Hz, 1H), 6.03 (dt, J=14.3, 6.5 Hz, 1H), 5.60 (dd, J=15.2, 9.0 Hz, 1H), 4.43 (dd, J=14.8, 6.1 Hz, 1H), 4.08 (d, J=1.7 Hz, 2H), 3.89 (s, 3H), 3.87-3.82 (m, 2H), 3.78 (dd, J=9.0, 3.6 Hz, 1H), 3.68 (d, J=14.2 Hz, 1H), 3.30-3.25 (m, 2H), 3.27 (s, 3H), 3.08 (dd, J=15.3, 10.3 Hz, 1H), 2.91-2.70 (m, 2H), 2.48 (td, J=12.7, 5.0 Hz, 2H), 2.39 (q, J=9.0 Hz, 1H), 2.28-2.07 (m, 3H), 2.05-1.70 (m, 5H), 1.44 (t, J=12.7 Hz, 1H), 1.16 (d, J=6.4 Hz, 3H). LCMS-ESI+ (m/z): [M+H]+ calcd for $C_{40}H_{46}ClN_3O_6S$: 732.3; found: 732.2.

Example 270

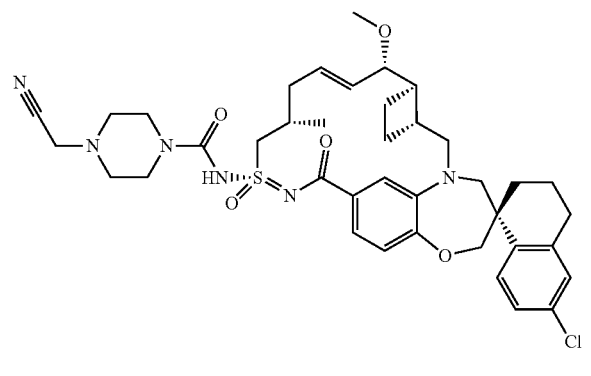 [SMILES: CO[C@H]1/C=C/C[C@H](C)C[S@@](=O)(NC(=O)N2CCN(CC#N)CC2)=NC(=O)c2ccc3c(c2)N(C[C@@H]2CC[C@H]21)C[C@@]1(CCCc2cc(Cl)ccc21)CO3]

Example 270 was synthesized in the same manner as Example 237 using Example 109 and 2-(piperazin-1-yl) acetonitrile. $^1$H NMR (400 MHz, Methanol-d4) δ 7.75 (d, J=8.5 Hz, 1H), 7.19 (dd, J=8.5, 2.4 Hz, 1H), 7.12 (d, J=2.4 Hz, 1H), 7.09 (dd, J=8.1, 1.9 Hz, 1H), 6.95 (d, J=8.1 Hz, 1H), 6.88 (d, J=2.0 Hz, 1H), 5.95 (dt, J=14.1, 6.7 Hz, 1H), 5.58 (dd, J=15.2, 9.3 Hz, 1H), 4.39 (dd, J=14.9, 6.4 Hz, 1H), 4.09 (s, 2H), 3.92-3.80 (m, 1H), 3.80-3.72 (m, 3H), 3.67 (d, J=14.1 Hz, 1H), 3.64-3.55 (m, 1H), 3.50 (m, 4H), 3.26 (m, 4H), 3.08 (dd, J=15.2, 10.4 Hz, 1H), 2.91-2.71 (m, 3H), 2.61 (s, 4H), 2.47 (dd, J=14.1, 5.3 Hz, 2H), 2.33 (q, J=9.2 Hz, 1H), 2.20 (q, J=7.6 Hz, 1H), 2.16-2.04 (m, 3H), 2.04-1.85 (m, 1H), 1.77 (m, 3H), 1.45 (t, J=12.8 Hz, 1H), 1.15 (d, J=6.6 Hz, 3H). LCMS-ESI+: calc'd for $C_{39}H_{50}ClN_6O_5S$: 749.32 (M+H); found: 749.26 (M+H).

Example 271

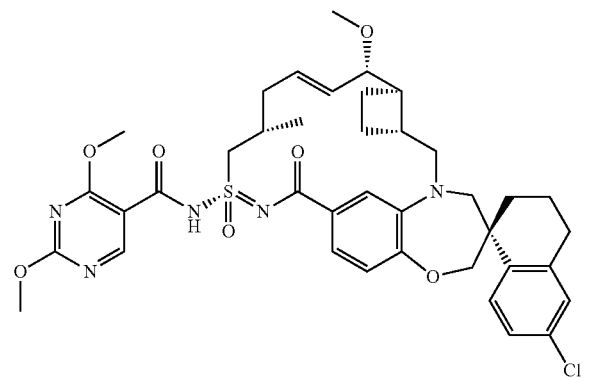 [SMILES: COc1ncc(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)c(OC)n1]

Example 271 was synthesized in a manner similar to Example 106 using 2,4-dimethoxypyrimidine-5-carboxylic acid instead of 2-((tetrahydro-2H-pyran-4-yl)oxy) acetic acid. 1H NMR (400 MHz, Acetone-d6) δ 9.00 (s, 1H), 7.79 (d, J=8.5 Hz, 1H), 7.54-7.47 (m, 1H), 7.34 (d, J=1.9 Hz, 1H), 7.25 (dd, J=8.5, 2.4 Hz, 1H), 7.14 (d, J=2.3 Hz, 1H), 6.94 (d, J=8.2 Hz, 1H), 6.18 (dt, J=14.2, 6.6 Hz, 1H), 5.67 (dd, J=15.6, 7.4 Hz, 1H), 4.27 (s, 3H), 4.13 (d, J=12.1 Hz, 1H), 4.09 (s, 3H), 4.04 (d, J=12.1 Hz, 1H), 4.02-3.72 (m, 4H), 3.49 (d, J=14.4 Hz, 1H), 3.26 (s, 3H), 3.16 (dd, J=15.1, 11.0 Hz, 1H), 2.97-1.37 (m, 16H), 1.14 (d, J=6.9 Hz, 3H). LCMS: 764.1.

Example 272

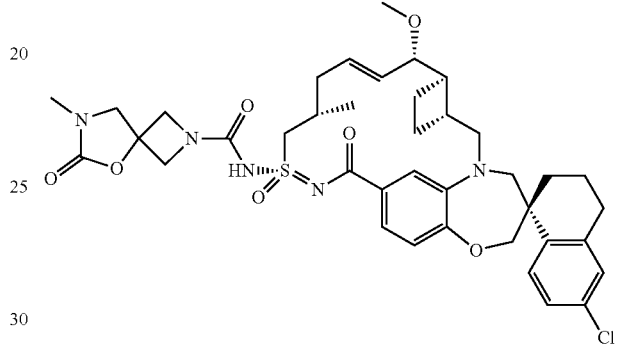

Example 272 was synthesized in the same manner as Example 237 using Example 109 and 7-methyl-5-oxa-2,7-diazaspiro[3.4]octan-6-one hydrochloride. $^1$H NMR (400 MHz, Methanol-d4) δ 7.75 (d, J=8.5 Hz, 1H), 7.19 (dd, J=8.5, 2.3 Hz, 1H), 7.14-7.07 (m, 2H), 6.94 (d, J=8.1 Hz, 1H), 6.90 (d, J=2.0 Hz, 1H), 5.96 (dt, J=14.3, 6.7 Hz, 1H), 5.58 (dd, J=15.1, 9.2 Hz, 1H), 4.43-4.15 (m, 6H), 4.09 (d, J=1.6 Hz, 2H), 3.84 (d, J=7.0 Hz, 3H), 3.76 (dd, J=9.2, 3.6 Hz, 1H), 3.67 (d, J=14.2 Hz, 1H), 3.26 (m, 4H), 3.08 (dd, J=15.3, 10.3 Hz, 1H), 2.88 (s, 3H), 2.84-2.72 (m, 2H), 2.55-2.42 (m, 3H), 2.33 (m, 1H), 2.27-2.06 (m, 3H), 1.94 (t, J=6.9 Hz, 2H), 1.78 (m, 3H), 1.45 (t, J=12.7 Hz, 1H), 1.15 (d, J=6.6 Hz, 3H). LCMS-ESI+: calc'd for $C_{39}H_{49}ClN_5O_7S$: 766.30 (M+H); found: 766.10 (M+H).

Example 273

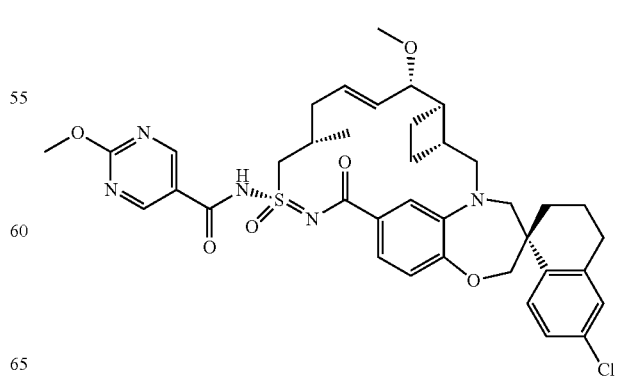

Example 273 was synthesized in the same manner as Example 18 using 2-methoxypyrimidine-5-carboxylic acid and Example 109. $^1$H NMR (400 MHz, Chloroform-d) δ 9.21 (d, J=5.1 Hz, 2H), 7.70 (d, J=8.5 Hz, 1H), 7.19 (dd, J=8.5, 2.4 Hz, 1H), 7.09 (s, 2H), 6.99 (dd, J=8.4, 3.8 Hz, 1H), 6.92 (d, J=9.4 Hz, 1H), 5.94-5.85 (m, 1H), 5.53 (dd, J=15.2, 9.1 Hz, 1H), 5.37 (s, 1H), 4.69 (d, J=14.9 Hz, 1H), 4.14 (d, J=1.5 Hz, 4H), 4.09 (s, 3H), 3.83 (d, J=15.3 Hz, 1H), 3.75-3.66 (m, 2H), 3.24 (s, 2H), 3.12 (s, 1H), 2.98 (dd, J=15.3, 10.3 Hz, 1H), 2.78 (dd, J=16.4, 11.7 Hz, 3H), 2.53-2.18 (m, 2H), 2.16-1.99 (m, 1H), 1.95 (d, J=10.5 Hz, 2H), 1.85-1.77 (m, 2H), 1.63 (t, J=9.5 Hz, 1H), 1.39 (t, J=12.7 Hz, 1H), 1.27-1.19 (m, 1H), 1.15 (d, J=6.1 Hz, 1H), 1.08 (d, J=6.1 Hz, 3H). LCMS-ESI+ (m/z): calcd for H+C$_{38}$H$_{44}$ClN$_5$O$_6$S: 733.27; found: 734.050 (M+H).

Example 274

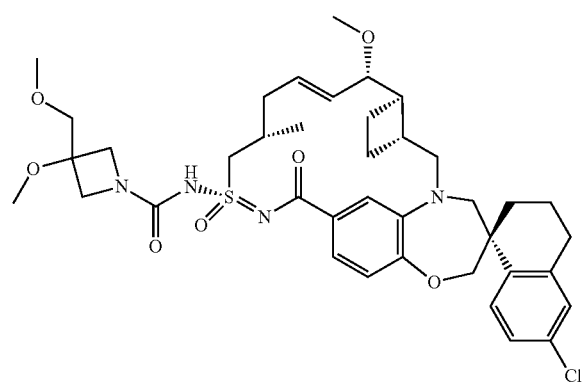 [SMILES: COCC1(OC)CN(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)C1]

A 2-dram vial was charged with Example 267 (1 equiv, 0.013 mmol, 10 mg) and THF (0.5 mL). Sodium hydride (60% dispersion in oil, 2 equiv, 0.027 mmol, 1.1 mg) was added and the reaction mixture stirred for 10 minutes. Iodomethane (5 equiv, 0.067 mmol, 4.2 mL) was then added and the reaction mixture was stirred for an additional 30 minutes at which point it was quenched with methanol, concentrated then re-dissolved in methanol, and purified by preparative HPLC (60-100% MeCN in water, 0.1% TFA). The combined clean fractions were lyophilized to afford the desired product Example 274. LCMS-ESI+ (m/z): (M)$^+$ calc'd for C$_{39}$H$_{51}$ClN$_4$O$_7$S: 754.3167; found: 754.07. $^1$H NMR (400 MHz, Methanol-d4) δ 7.73 (d, J=8.5 Hz, 1H), 7.17 (dd, J=8.5, 2.4 Hz, 1H), 7.10 (td, J=3.9, 1.9 Hz, 2H), 6.96-6.88 (m, 2H), 5.96 (dt, J=14.2, 6.7 Hz, 1H), 5.56 (dd, J=15.2, 9.1 Hz, 1H), 4.30 (dd, J=14.9, 6.3 Hz, 1H), 4.13-4.02 (m, 2H), 4.01-3.78 (m, 5H), 3.74 (dd, J=9.2, 3.7 Hz, 1H), 3.69-3.54 (m, 4H), 3.42 (s, 3H), 3.32 (s, 3H), 3.31-3.28 (m, 1H), 3.24 (s, 3H), 3.06 (dd, J=15.2, 10.3 Hz, 1H), 2.87-2.69 (m, 2H), 2.54-2.40 (m, 2H), 2.32 (p, J=9.0 Hz, 1H), 2.23-2.05 (m, 3H), 2.00-1.66 (m, 6H), 1.43 (t, J=12.8 Hz, 1H), 1.13 (d, J=6.7 Hz, 3H).

Example 275

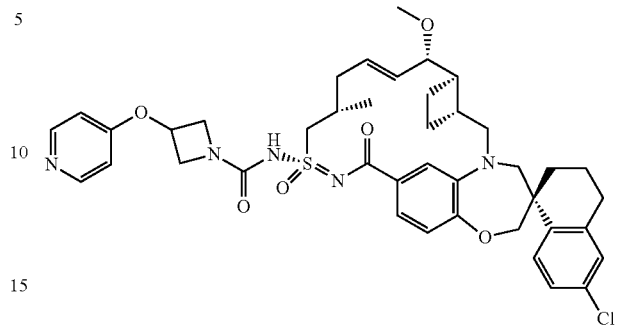

Example 275 was synthesized in the same manner as Example 362, using Example 109 and 4-(azetidin-3-yloxy) pyridine dihydrochloride. LCMS-ESI+ (m/z): [M+H]$^+$ calc'd for C$_{41}$H$_{48}$ClN$_5$O$_6$S: 774.3087; found: 773.81. $^1$H NMR (400 MHz, Methanol-d4) δ 8.69 (d, J=7.4 Hz, 2H), 7.72 (d, J=8.5 Hz, 1H), 7.53-7.43 (m, 2H), 7.17 (dd, J=8.5, 2.4 Hz, 1H), 7.13-7.05 (m, 2H), 6.96-6.86 (m, 2H), 5.96 (dt, J=14.3, 6.8 Hz, 1H), 5.56 (dd, J=15.2, 9.1 Hz, 1H), 5.39 (tt, J=6.6, 3.5 Hz, 1H), 4.56 (s, 2H), 4.32 (dd, J=14.9, 6.4 Hz, 1H), 4.26-3.96 (m, 4H), 3.83 (d, J=15.1 Hz, 1H), 3.74 (dd, J=9.2, 3.7 Hz, 1H), 3.70-3.55 (m, 2H), 3.30-3.27 (m, 1H), 3.24 (s, 3H), 3.06 (dd, J=15.3, 10.3 Hz, 1H), 2.89-2.69 (m, 2H), 2.53-2.39 (m, 2H), 2.32 (q, J=9.0 Hz, 1H), 2.23-2.06 (m, 3H), 2.01-1.66 (m, 6H), 1.43 (t, J=12.6 Hz, 1H), 1.13 (d, J=6.6 Hz, 3H).

Example 276

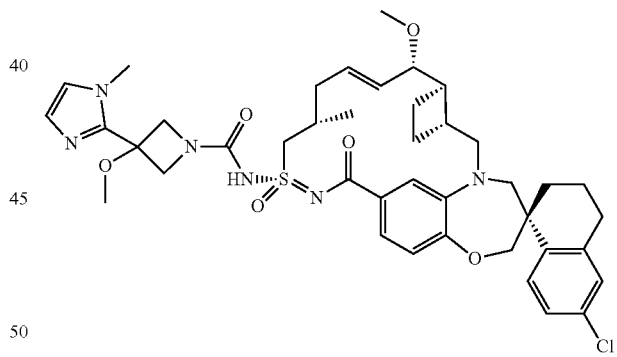

Example 276 was synthesized in the same manner as Example 237 using Example 109 and 2-(3-methoxyazetidin-3-yl)-1-methyl-1H-imidazole dihydrochloride. $^1$H NMR (400 MHz, Methanol-d4) δ 7.74 (d, J=8.5 Hz, 1H), 7.63 (d, J=1.9 Hz, 1H), 7.54 (d, J=1.9 Hz, 1H), 7.19 (dd, J=8.5, 2.3 Hz, 1H), 7.12 (d, J=2.3 Hz, 1H), 7.08 (dd, J=8.1, 1.8 Hz, 1H), 6.94 (d, J=8.1 Hz, 1H), 6.90 (d, J=2.0 Hz, 1H), 5.97 (dt, J=14.3, 6.6 Hz, 1H), 5.58 (dd, J=15.2, 9.2 Hz, 1H), 4.59 (s, 2H), 4.49-4.28 (m, 3H), 4.09 (d, J=1.7 Hz, 2H), 3.88 (s, 3H), 3.76 (dd, J=9.2, 3.7 Hz, 1H), 3.73-3.62 (m, 1H), 3.26 (m, 4H), 3.21 (s, 3H), 3.14-3.05 (m, 1H), 2.87-2.63 (m, 2H), 2.48 (m, 3H), 2.33 (t, J=9.1 Hz, 1H), 2.27-2.08 (m, 3H), 2.07-1.86 (m, 3H), 1.79 (tt, J=17.4, 9.5 Hz, 3H), 1.45 (t, J=12.7 Hz, 1H), 1.15 (d, J=6.5 Hz, 3H). LCMS-ESI+: calc'd for C$_{41}$H$_{52}$ClN$_6$O$_6$S: 791.33 (M+H); found: 791.43 (M+H).

Example 277

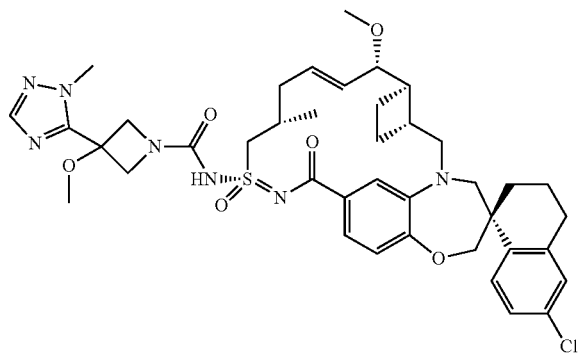 [SMILES: CO[C@H]1/C=C/C[C@H](C)C[S@@](=O)(NC(=O)N2CC(OC)(c3ncnn3C)C2)=NC(=O)c2ccc3c(c2)N(C[C@@H]2CC[C@H]21)C[C@@]1(CCCc2cc(Cl)ccc21)CO3]

Example 277 was synthesized in the same manner as Example 237 using Example 109 and 5-(3-methoxyazetidin-3-yl)-1-methyl-1H-1,2,4-triazole dihydrochloride. $^1$H NMR (400 MHz, Methanol-d4) δ 7.94 (s, 1H), 7.75 (d, J=8.5 Hz, 1H), 7.19 (dd, J=8.5, 2.3 Hz, 1H), 7.12 (d, J=2.3 Hz, 1H), 7.09 (d, J=8.4 Hz, 1H), 6.94 (d, J=8.1 Hz, 1H), 6.89 (d, J=2.0 Hz, 1H), 5.96 (dt, J=14.2, 6.6 Hz, 1H), 5.58 (dd, J=15.2, 9.2 Hz, 1H), 4.56 (m, 4H), 4.34 (dd, J=14.8, 6.3 Hz, 1H), 4.08 (d, J=1.5 Hz, 2H), 3.91 (s, 3H), 3.85 (d, J=15.1 Hz, 1H), 3.76 (dd, J=9.3, 3.7 Hz, 1H), 3.67 (d, J=14.2 Hz, 1H), 3.59 (d, J=14.0 Hz, 1H), 3.26 (m, 4H), 3.13 (s, 3H), 3.11-3.01 (m, 1H), 2.89-2.70 (m, 2H), 2.56-2.42 (m, 3H), 2.34 (q, J=9.2 Hz, 1H), 2.24-2.05 (m, 4H), 2.05-1.86 (m, 1H), 1.78 (m, 3H), 1.45 (t, J=12.6 Hz, 1H), 1.15 (d, J=6.3 Hz, 3H). LCMS-ESI+: calc'd for $C_{41}H_{52}ClN_6O_6S$: 792.32 (M+H); found: 792.25 (M+H).

Example 278

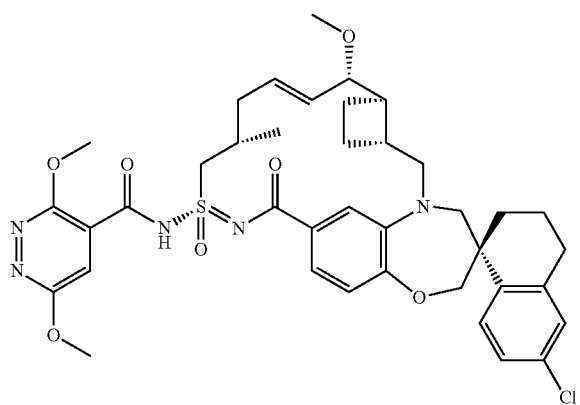 [SMILES: COc1cc(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)c(OC)nn1]

Example 278 was synthesized in a manner similar to Example 106 using 3,6-dimethoxypyridazine-4-carboxylic acid instead of 2-((tetrahydro-2H-pyran-4-yl)oxy) acetic acid. 1H NMR (400 MHz, Acetone-d6) δ 7.78 (d, J=8.5 Hz, 1H), 7.52 (s, 1H), 7.38 (d, J=8.0 Hz, 1H), 7.29-7.20 (m, 2H), 7.14 (d, J=2.4 Hz, 1H), 6.94 (d, J=8.2 Hz, 1H), 6.23-6.08 (m, 1H), 5.65 (dd, J=15.3, 7.9 Hz, 1H), 4.22 (s, 3H), 4.13 (d, J=12.1 Hz, 1H), 4.08 (s, 3H), 4.07-3.57 (m, 5H), 3.45 (d, J=14.4 Hz, 1H), 3.25 (s, 3H), 3.16 (dd, J=15.2, 10.5 Hz, 1H), 2.95-1.54 (m, 15H), 1.53-1.43 (m, 1H), 1.16 (d, J=6.8 Hz, 3H). LCMS: 764.2.

Example 279

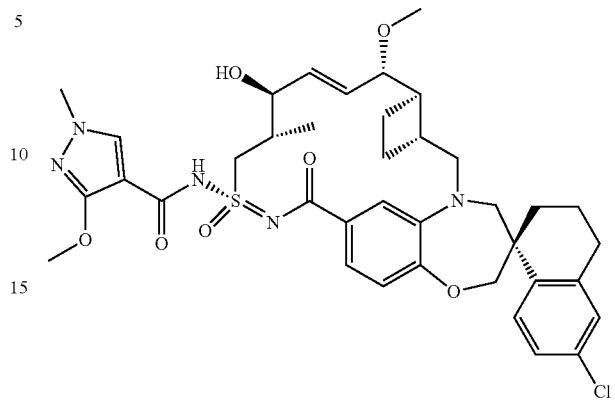

Example 154 (500 mg, 0.68 mmol) was combined with selenium dioxide (377 mg, 5 equiv.) and 1,4-dioxane (7 mL) was added. The reaction mixture was heated to reflux and the progress of the reaction was monitored by LCMS. After 4 hours (approximately 50% conversion), the reaction was cooled to room temperature and concentrated under reduced pressure. The residue was purified by Gilson reverse phase prep HPLC (50-100% ACN/H$_2$O with 0.1% TFA) to give Example 279. $^1$H NMR (400 MHz, Methanol-d$_4$) δ 8.15 (s, 1H), 7.72 (d, J=9A Hz, 1H), 7.37 (dd, J=8.3, 1.8 Hz, 1H), 7.19 (s, 1H), 7.16-7.07 (m, 2H), 6.89 (d, J=8.2 Hz, 1H), 6.15 (dd, J=15.5, 5.3 Hz, 1H), 5.83 (ddd, J=15.5, 8.0, 1.5 Hz, 1H), 4.54 (s, 1H), 4.05 (m, 7H), 3.90-3.82 (m, 3H), 3.81 (s, 3H), 3.69 (d, J=14.3 Hz, 1H), 3.41 (d, J=14.4 Hz, 1H), 3.29 (s, 3H), 3.18-3.04 (m, 1H), 2.92-2.69 (m, 2H), 2.51 (br, 2H), 2.44-2.25 (m, 1H), 2.16-2.03 (m, 1H), 2.02-1.92 (m, 3H), 1.88-1.74 (m, 3H), 1.43 (t, J=11.9 Hz, 1H), 1.15 (d, J=6.9 Hz, 3H). LCMS-ESI+ (m/z): [M+H]+ calcd for $C_{38}H_{46}ClN_5O_7S$: 752.3; found: 751.9.

Example 280

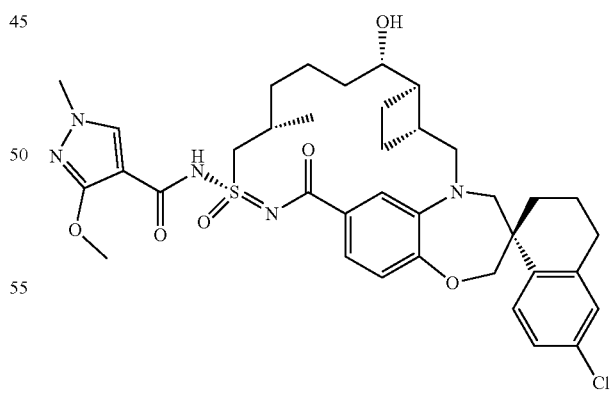

Example 223 (10 mg, 0.014 mmol) was combined with PtO$_2$ (15 mg, 0.028 mmol) and ethanol (0.5 mL) was added. A hydrogen balloon (1 atm) fitted to a glass adapter was attached to the round bottom flask. The reaction was stirred under atmospheric hydrogen for 5 hours and the progress of the reaction was monitored by LCMS. Upon completion, the reaction vessel was purged with a stream of argon. The solids were filtered away and washed with additional ethanol. The reaction mixture was then concentrated under reduced pressure and the residue was purified by Gilson reverse phase prep HPLC (50-100% ACN/H$_2$O with 0.1% TFA) to give Example 280. $^1$H NMR (400 MHz, Methanol-d$_4$) δ 8.08 (s, 1H), 7.77 (d, J=8.5 Hz, 1H), 7.39 (d, J=8.5 Hz, 1H), 7.28 (s, 1H), 7.18 (dd, J=8.5, 2.3 Hz, 1H), 7.12 (d, J=2.3 Hz, 1H), 6.94 (d, J=8.2 Hz, 1H), 4.15-4.01 (m, 5H), 4.01-3.84 (m, 3H), 3.81 (s, 3H), 3.78-3.68 (m, 2H), 3.19-3.07 (m, 1H), 2.89-2.76 (m, 2H), 2.58-2.21 (m, 3H), 2.12 (d, J=13.4 Hz, 1H), 2.01-1.92 (m, 4H), 1.88-1.41 (m, 11H), 1.10 (d, J=6.6 Hz, 3H). LCMS-ESI+ (m/z): [M+H]+ calcd for C$_{37}$H$_{46}$ClN$_5$O$_6$S: 724.3; found: 724.1.

Example 281 and Example 282

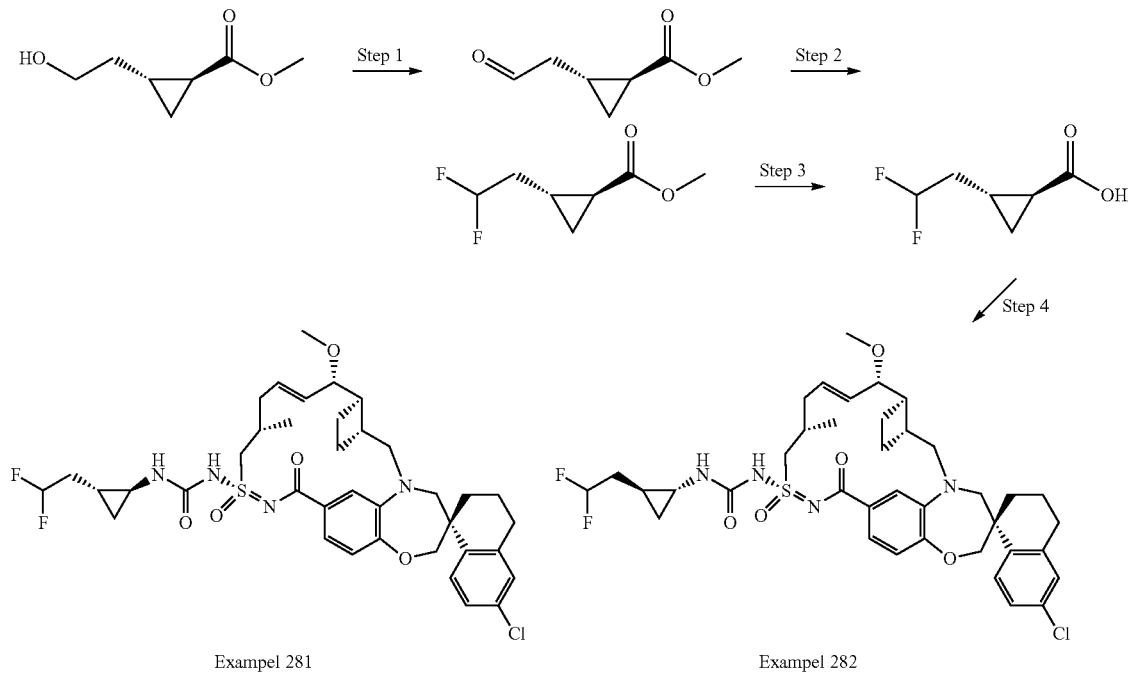

Exampel 281  Exampel 282

Step 1

To well stirred solution of methyl (1S,2R)-2-(2-hydroxyethyl) cyclopropane-1-carboxylate (0.5 g, 3.46 mmol) in DCM (23 mL) at 0° C. under argon was added Dess Martin periodinane (1.76 g, 4.16 mmol) at once, warmed to room temperature (20 min), and stirred for 2 h. The reaction was cooled to 0° C., and quenched with 1:1 mixture of 1 N aqueous solution of Na$_2$S$_2$O$_3$ and saturated NaHCO$_3$ (40 mL). The aqueous solution was extracted with DCM (2×20 mL). Combined DCM solution was added another 1:1 mixture of 1 N aqueous solution of Na$_2$S$_2$O$_3$ and saturated NaHCO$_3$ (20 mL). The DCM layers were combined and washed with brine solution once, dried over Na$_2$SO$_4$, concentrated and used for next step.

Step 2

To a solution of methyl (1S,2R)-2-(2-oxoethyl)cyclopropane-1-carboxylate in DCM (17.5 mL) at −78° C. was added diethylaminosulfur trifluoride (DAST) (1.7 g, 10.55 mmol) dropwise and cooling bath was removed. The mixture was stirred at room temperature overnight. The reaction was quenched with Na$_2$HCO$_3$, partitioned with water and DCM. The aqueous solution was extracted with DCM (2×20 mL). The combined DCM solution was dried over Na$_2$SO$_4$, filtered, concentrated and used for next step.

Step 3

To the crude methyl (1S,2R)-2-(2,2-difluoroethyl)cyclopropane-1-carboxylate (300 mg, 1.82 mmol) were added THF (15 mL), MeOH (3 mL) and 1 N LiOH (3 mL). This mixture was stirred at 65° C. for 90 min. The reaction was cooled to room temperature, and solvent was removed under reduced pressure. The crude residue was dissolved in water (20 mL), and acidified with 1.5 N HCl by drop wise addition to maintain pH 2-3 and stirred for 5 min. A precipitate was formed, filtered, washed with water, and dried to provide the crude product (1S,2R)-2-(2,2-difluoroethyl)cyclopropane-1-carboxylic acid used for next step. $^1$H NMR (400 MHz, DMSO-d$_6$) δ 12.15 (s, 1H), 6.09 (tt, J=56.5, 4.5 Hz, 1H), 1.84 (tdd, J=17.5, 7.2, 4.5 Hz, 2H), 1.43 (ddt, J=13.1, 9.8, 7.3 Hz, 2H), 0.97 (dt, J=8.8, 4.3 Hz, 1H), 0.77 (dddd, J=17.6, 8.1, 6.2, 3.9 Hz, 1H).

Step 4

To the mixture of trans-2-(2,2-difluoroethyl)cyclopropane-1-carboxylic acid (40 mg, 0.26 mmol) in acetonitrile (2 mL) were added triethylamine (118 uL, 0.84 mmol) and diphenyl phosphoryl azide (73.6 mg, 0.26 mmol). The mixture was then heated at 60° C. for 2 h. The reaction mixture was cooled to room temperature. To this mixture was added Example 109 at once and stirred at 60° C. 24 h. The reaction was concentrated, dissolved in MeOH (3 mL), filtered and purified by reverse phase prep HPLC, eluted with 60-100% ACN/H$_2$O with 0.1% TFA to afford two isomers Example 281 and Example 282 and the stereochemistry is arbitrarily assigned.

Example 281

¹H NMR (400 MHz, Methanol-d₄) δ 7.66 (d, J=8.5 Hz, 1H), 7.30 (d, J=8.1 Hz, 1H), 7.18 (d, J=8.3 Hz, 1H), 7.06 (d, J=2.2 Hz, 1H), 6.98-6.91 (m, 1H), 6.84 (dd, J=8.2, 4.9 Hz, 1H), 6.15-5.87 (m, 2H), 5.61 (dt, J=15.6, 8.8 Hz, 1H), 4.18 (td, J=16.0, 6.9 Hz, 2H), 3.99 (d, J=5.9 Hz, 2H), 3.87-3.70 (m, 4H), 3.63 (d, J=14.3 Hz, 1H), 3.27 (d, J=4.1 Hz, 4H), 3.05 (dd, J=15.2, 9.8 Hz, 1H), 2.90-2.64 (m, 2H), 2.49 (d, J=38.4 Hz, 4H), 2.31-1.63 (m, 5H), 1.52-1.22 (m, 3H), 1.12 (d, J=6.6 Hz, 4H), 0.96 (d, J=7.7 Hz, 1H), 0.83 (dt, J=9.5, 4.8 Hz, 1H), 0.70 (q, J=6.2 Hz, 1H). LCMS-ESI+ (m/z): [M+H]+ calcd for $C_{38}H_{47}ClF_2N_4O_5S$: 745.29; found: 744.75.

Example 282

¹H NMR (400 MHz, Methanol-d₄) δ 7.78-7.52 (m, 1H), 7.40-7.10 (m, 1H), 7.10-6.91 (m, 2H), 6.85 (d, J=8.0 Hz, 1H), 6.22-5.76 (m, 1H), 5.67-5.51 (m, 1H), 4.16 (ddd, J=25.1, 15.0, 8.3 Hz, 1H), 4.00 (s, 2H), 3.90-3.70 (m, 2H), 3.63 (d, J=14.2 Hz, 1H), 3.27 (d, J=3.1 Hz, 3H), 3.15-2.94 (m, 1H), 2.90-2.62 (m, 2H), 2.61-1.63 (m, 15H), 1.33 (d, J=39.5 Hz, 3H), 1.12 (t, J=6.3 Hz, 3H), 0.98 (d, J=6.8 Hz, 1H), 0.90-0.77 (m, 1H), 0.69 (q, J=6.3 Hz, 1H). LCMS-ESI+ (m/z): [M+H]+ calcd for $C_{38}H_{47}ClF_2N_4O_5S$: 745.29; found: 744.76.

Example 283

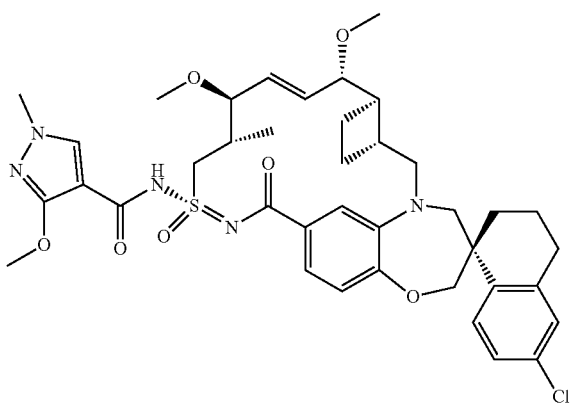 [SMILES: COc1nn(C)cc1C(=O)N[S@@]1(=O)=NC(=O)c2ccc3c(c2)N(C[C@@H]2CC[C@H]2[C@@H](OC)/C=C/[C@H](OC)[C@H](C)C1)C[C@@]1(CCCc2cc(Cl)ccc21)CO3]

Example 279 (200 mg, 0.27 mmol) was dissolved in DMF (2.7 mL) and sodium hydride (60% dispersion in oil, 22 mg, 0.53 mmol, 2 equiv.) was added in one portion. The mixture was stirred at room temperature for 5 min before iodomethane (76 mg, 0.53 mmol, 2 equiv.) was added. The reaction was then heated to 50° C. and the progress of the reaction was monitored by LCMS. Upon observing significant conversion (approx. 4:1 product: starting material), the reaction was cooled to 0° C. and water was added (ca. 5 drops). The residue was then purified directly by Gilson reverse phase prep HPLC (60-100% ACN/H₂O with 0.1% TFA) to give Example 283. ¹H NMR (400 MHz, Methanol-d₄) δ 8.08 (s, 1H), 7.76 (d, J=8.5 Hz, 1H), 7.36 (d, J=7.9 Hz, 1H), 7.24-7.15 (m, 2H), 7.12 (d, J=2.3 Hz, 1H), 6.92 (d, J=8.2 Hz, 1H), 6.01 (dd, J=15.4, 7.8 Hz, 1H), 5.83 (dd, J=15.3, 8.6 Hz, 1H), 4.06 (m, 6H), 3.9-3.8 (m, 7H), 3.73 (d, J=14.5 Hz, 1H), 3.41 (d, J=14.4 Hz, 1H), 3.31 (s, 3H), 3.30 (s, 3H), 3.19-3.06 (m, 1H), 2.92-2.70 (m, 2H), 2.52 (br, 2H), 2.24 (m, 1H), 2.05 (m, 2H), 1.96 (m, 3H), 1.83 (m, 3H), 1.46 (m, 1H), 1.19 (d, J=6.8 Hz, 3H). LCMS-ESI+ (m/z): [M+H]+ calcd for $C_{39}H_{48}ClN_5O_7S$: 766.3; found: 766.0.

Example 284

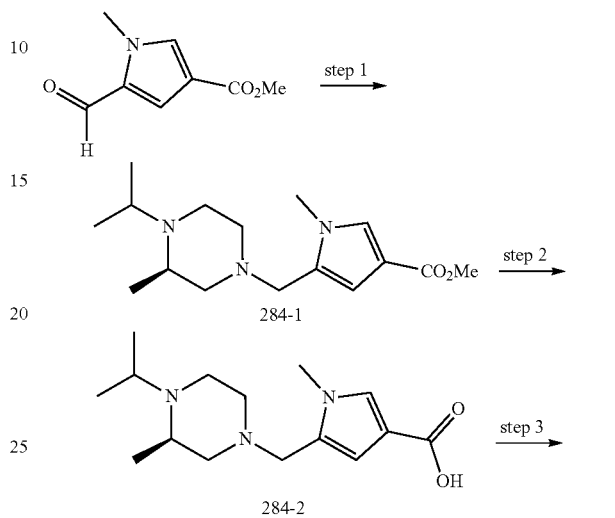

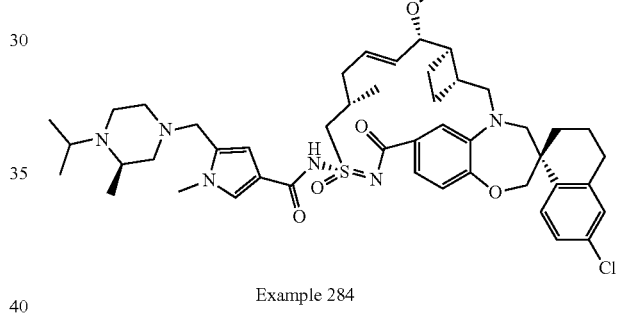

Example 284

Step 1

Synthesis of methyl 5-[[(3R)-4-isopropyl-3-methyl-piperazin-1-yl]methyl]-1-methyl-pyrrole-3-carboxylatebis TFA salt: The mixture of methyl 5-formyl-1-methyl-pyrrole-3-carboxylate (50.0 mg, 0.299 mmol) and (2R)-1-isopropyl-2-methyl-piperazine (42.5 mg, 0.299 mmol) in DCE (0.5 mL) was stirred at room temperature for 10 minutes before sodium triacetoxyborohydride (95.1 mg, 0.449 mmol) was added. The resulting mixture was stirred for overnight. The reaction was concentrated, redissolved in a mixture of water:DMF (5:1 V:V), filtered and purified by Gilson reverse phase prep HPLC, eluted with 2-50% ACN/H₂O with 0.1% TFA. The desired fractions were combined and frozen dried to give methyl 5-[[(3R)-4-isopropyl-3-methyl-piperazin-1-yl]methyl]-1-methyl-pyrrole-3-carboxylate; 2,2,2-trifluoroacetic acid (60.0 mg). LCMS-ESI+ (m/z): calcd H+ for $C_{16}H_{27}N_3O_2$:294.21; found: 293.99.

Step 2

Synthesis of 5-[[(3R)-4-isopropyl-3-methyl-piperazin-1-yl]methyl]-1-methyl-pyrrole-3-carboxylic acid; bis TFA salt: methyl 5-[[(3R)-4-isopropyl-3-methyl-piperazin-1-yl]methyl]-1-methyl-pyrrole-3-carboxylate; bis TFA salt (60.0 mg, 0.115 mmol) was dissolved in a mixture of MeOH (1.0 mL) and THF (1.0 mL) at rt. 1N NaOH (1.15 mL, 1.15 mmol) was added. The resulting mixture was then heated to 50° C. for 8 hrs. The reaction was concentrated, redissolved in a solution of 1N HCl (1.0 mL), filtered and purified by reverse phase prep HPLC, eluted with 2-50% ACN/H$_2$O with 0.1% TFA. Desired fractions were combined and frozen dried to give the title compound. LCMS-ESI+ (m/z): calcd H+ for C$_{15}$H25N$_3$O$_2$:280.19; found: 280.20.

Step 3: Synthesis of Example 284 the same procedure was followed as Example 18 using Example 109 and Intermediate 284-2. 1H NMR (400 MHz, Methanol-d4) δ 7.70 (d, J=8.4 Hz, 1H), 7.60 (d, J=1.8 Hz, 1H), 7.32 (dd, J=8.2, 1.8 Hz, 1H), 7.12-7.03 (m, 3H), 6.88 (d, J=8.3 Hz, 1H), 6.62-6.57 (m, 1H), 6.20-6.07 (m, 1H), 5.64 (dd, J=15.4, 8.4 Hz, 1H), 4.19 (dd, J=14.8, 6.4 Hz, 1H), 4.08-3.92 (m, 4H), 3.87-3.77 (m, 2H), 3.75 (s, 3H), 3.68 (d, J=14.3 Hz, 1H), 3.64-3.54 (m, 2H), 3.49-3.42 (m, 1H), 3.39 (d, J=14.3 Hz, 1H), 3.30 (s, 3H), 3.18-3.04 (m, 4H), 2.89-2.70 (m, 2H), 2.67-2.58 (m, 1H), 2.53-2.33 (m, 3H), 2.33-2.17 (m, 3H), 2.15-2.06 (m, 1H), 2.04-1.91 (m, 3H), 1.86-1.73 (m, 3H), 1.46-1.34 (m, 8H), 1.29 (d, J=6.6 Hz, 3H), 1.15 (d, J=6.4 Hz, 3H). LCMS-ESI+ (m/z): calcd H+ for C$_{47}$H$_{63}$ClN$_6$O$_5$S: 859.43; found: 859.13.

Example 285

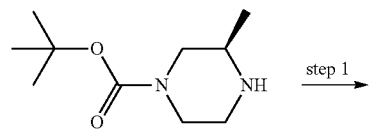

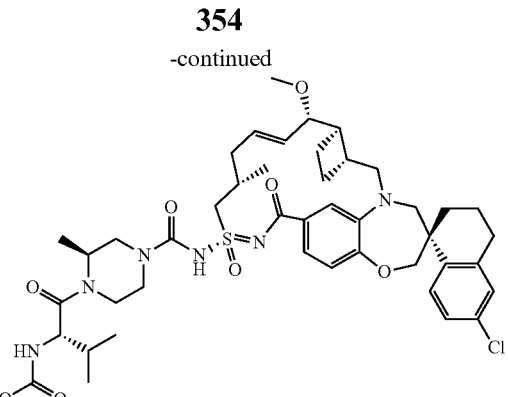

Example 285

Step 1

Synthesis of tert-butyl (3S)-4-[(2S)-2-(methoxycarbonylamino)-3-methyl-butanoyl]-3-methyl-piperazine-1-carboxylate: To the mixture of tert-butyl (3R)-3-methylpiperazine-1-carboxylate (250 mg, 1.25 mmol) and (2R)-2-(methoxycarbonyl amino)-3-methyl-butanoic acid (241 mg, 1.37 mmol) in DCM (6.0 mL) at room temperature was added EDCI.HCl (358 mg, 1.87 mmol) followed by DMAP (229 mg, 1.87 mmol). The resulting mixture was stirred at room temperature for overnight before it was diluted with DCM. The organic layer was washed sequentially with sat. NH$_4$Cl, sat. NaHCO$_3$ and brine, then it was dried over sodium sulfate, filtered and concentrated to give crude product which was purified by combiflash (0-100% EtOAc/hexanes). Desired fractions were combined and concentrated to give desired product (446 mg). LCMS-ESI+ (m/z): calcd H+ for C$_{17}$H$_{31}$N$_3$O$_5$: 358.23; found: 358.20.

Step 2

Synthesis of methyl N-[(1S)-2-methyl-1-[(2S)-2-methylpiperazine-1-carbonyl]propyl]carbamate; di HCl salt: tert-butyl (3S)-4-[(2S)-2-(methoxycarbonyl amino)-3-methyl-butanoyl]-3-methyl-piperazine-1-carboxylate (446 mg, 1.25 mmol) from step 1 was then dissolved in DCM (3.0 mL) and treated with 4 N HCl in 1,4-dioxane (1.25 mL) at room temperature for 3 hrs. The reaction was concentrated, coevaporated with EtOAc (3×4.0 mL) to give the title compound (270 mg). LCMS-ESI+ (m/z): calcd H+ for C$_{12}$H$_{23}$N$_3$O$_3$: 258.17; found: 258.17.

Step 3: Synthesis of Example 285

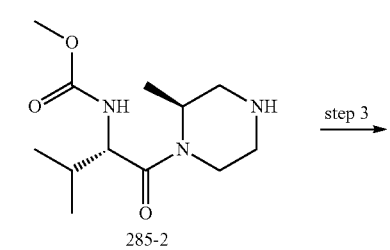

the same procedure was followed as the synthesis of Example 75 using Example 109, Intermediate 285-2 and DIEA. 1H NMR (400 MHz, Methanol-d4) δ 7.74 (d, J=8.5 Hz, 1H), 7.19 (dd, J=8.5, 2.4 Hz, 1H), 7.14-7.05 (m, 2H), 6.95 (d, J=8.1 Hz, 1H), 6.88 (d, J=1.9 Hz, 1H), 6.00-5.90 (m, 1H), 5.58 (dd, J=15.2, 9.3 Hz, 1H), 4.47-4.31 (m, 3H), 4.13-4.04 (m, 2H), 3.85 (d, J=15.1 Hz, 1H), 3.76 (dd, J=9.3, 3.7 Hz, 1H), 3.71-3.62 (m, 5H), 3.31-3.24 (m, 5H), 3.12-3.04 (m, 2H), 2.88-2.70 (m, 2H), 2.54-2.41 (m, 2H), 2.38-2.24 (m, 1H), 2.23-1.67 (m, 12H), 1.49-1.30 (m, 3H), 1.23-1.08 (m, 5H), 1.03-0.89 (m, 7H). LCMS-ESI+ (m/z): calcd H+ for C$_{45}$H$_{61}$ClN$_6$O$_8$S: 881.40; found: 880.97.

Example 286

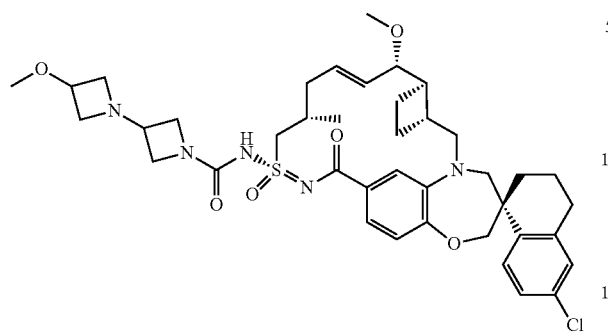

Example 286 was synthesized in the same manner as Example 182, using 1-(azetidin-3-yl)-3-methoxy-azetidine instead of rac-(1R,2R)-2-(1-methyl-1H-pyrazol-5-yl)cyclopropan-1-amine. 1H NMR (400 MHz, Methanol-d4) δ 7.74 (d, J=8.5 Hz, 1H), 7.17 (d, J=8.9 Hz, 1H), 7.11 (dd, J=9.6, 1.9 Hz, 2H), 6.96-6.87 (m, 2H), 6.02 (dt, J=14.2, 6.6 Hz, 1H), 5.56 (dd, J=15.2, 9.2 Hz, 1H), 4.45 (s, 1H), 4.34 (q, J=8.4, 7.5 Hz, 4H), 4.28 (s, 1H), 4.12 (d, J=13.1 Hz, 2H), 4.07 (d, J=1.9 Hz, 2H), 4.02 (d, J=15.2 Hz, 2H), 3.86 (d, J=15.2 Hz, 1H), 3.77 (dd, J=9.2, 3.7 Hz, 1H), 3.66 (d, J=14.0 Hz, 2H), 3.39 (s, 3H), 3.26 (s, 4H), 3.07 (dd, J=15.3, 10.2 Hz, 1H), 2.89-2.69 (m, 2H), 2.55-2.41 (m, 2H), 2.41-2.24 (m, 1H), 2.18 (t, J=7.5 Hz, 1H), 2.09 (t, J=14.3 Hz, 3H), 2.03-1.87 (m, 3H), 1.78 (tt, J=17.7, 9.5 Hz, 3H), 1.44 (t, J=12.8 Hz, 1H), 1.12 (d, J=6.5 Hz, 3H). LCMS-ESI+ (m/z): [M+H]+ calcd for $C_{40}H_{52}ClN_5O_6S$: 766.33; found: 766.11.

Example 287

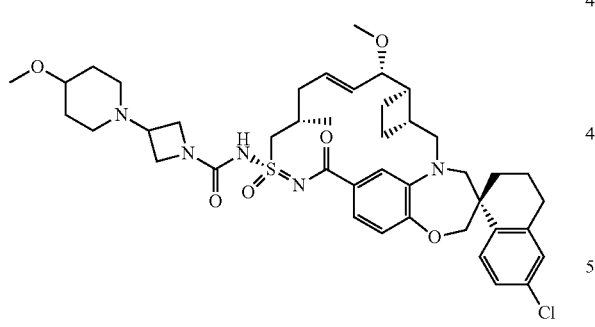

Example 286 was synthesized in the same manner as Example 182, using 1-(azetidin-3-yl)-4-methoxy-piperidine instead of rac-(1R,2R)-2-(1-methyl-1H-pyrazol-5-yl)cyclopropan-1-amine. 1H NMR (400 MHz, Methanol-d4) δ 7.73 (d, J=8.5 Hz, 1H), 7.24-7.06 (m, 3H), 6.90 (d, J=7.2 Hz, 2H), 6.00 (dd, J=14.7, 7.6 Hz, 1H), 5.57 (dd, J=15.2, 9.2 Hz, 1H), 4.34 (dd, J=14.6, 6.7 Hz, 3H), 4.21 (s, 2H), 4.07 (d, J=1.9 Hz, 3H), 3.93-3.55 (m, 6H), 3.40 (s, 3H), 3.26 (s, 3H), 3.08 (dd, J=15.3, 10.3 Hz, 3H), 2.90-2.70 (m, 3H), 2.58-2.42 (m, 3H), 2.34 (t, J=9.5 Hz, 2H), 2.15 (dd, J=25.4, 10.7 Hz, 4H), 2.04-1.60 (m, 8H), 1.44 (t, J=12.7 Hz, 1H), 1.13 (d, J=6.5 Hz, 3H). LCMS-ESI+ (m/z): [M+H]+ calcd for $C_{42}H_{56}ClN_5O_6S$: 794.36; found: 794.05.

Example 288

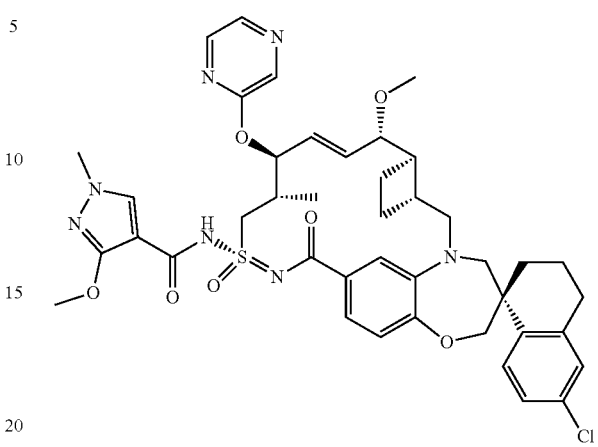

Example 288 was synthesized in the same manner as Example 283 using 2-fluoropyrazine and Example 279. 1H NMR (400 MHz, Methanol-d4) δ 8.25 (d, J=1.4 Hz, 1H), 8.12 (s, 1H), 8.08 (d, J=2.8 Hz, 1H), 7.95 (dd, J=2.8, 1.4 Hz, 1H), 7.75 (d, J=8.5 Hz, 1H), 7.43 (dd, J=8.3, 1.8 Hz, 1H), 7.25 (s, 1H), 7.15 (d, J=8.8 Hz, 1H), 7.11 (d, J=2.3 Hz, 1H), 6.91 (d, J=8.3 Hz, 1H), 6.24 (dd, J=15.6, 5.4 Hz, 1H), 6.15 (s, 1H), 5.88 (dd, J=15.5, 8.1 Hz, 1H), 4.24 (t, J=5.8 Hz, 2H), 4.06 (d, J=6.0 Hz, 5H), 3.81 (m, 6H), 3.72 (d, J=14.4 Hz, 1H), 3.40 (d, J=14.4 Hz, 1H), 3.16 (s, 3H), 3.08 (dd, J=15.2, 10.4 Hz, 1H), 2.91-2.61 (m, 3H), 2.49 (dd, J=27.4, 14.6 Hz, 2H), 2.10 (d, J=13.7 Hz, 1H), 2.03-1.81 (m, 2H), 1.73 (dq, J=15.0, 8.1, 7.7 Hz, 2H), 1.59-1.39 (m, 2H), 1.22 (d, J=6.9 Hz, 3H). LCMS-ESI+ (m/z): [M+H]+ calcd for $C_{42}H_{48}ClN_7O_7S$: 830.3; found: 829.7.

Example 289

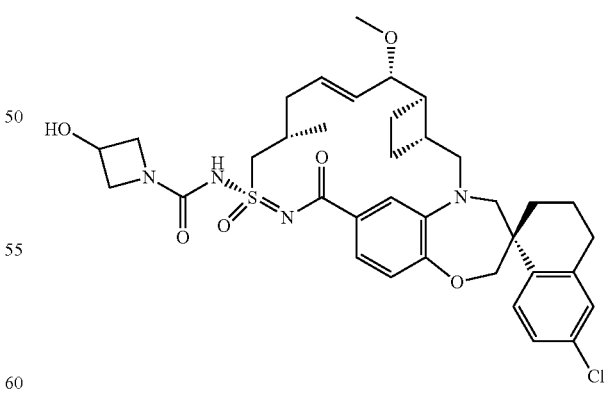

Example 289 was synthesized in the similar methods described herein. LCMS-ESI+(m/z): [M+H]+ calc'd for $C_{36}H_{45}ClN_4O_6S$: 697.2821; found: 696.81.

Example 290

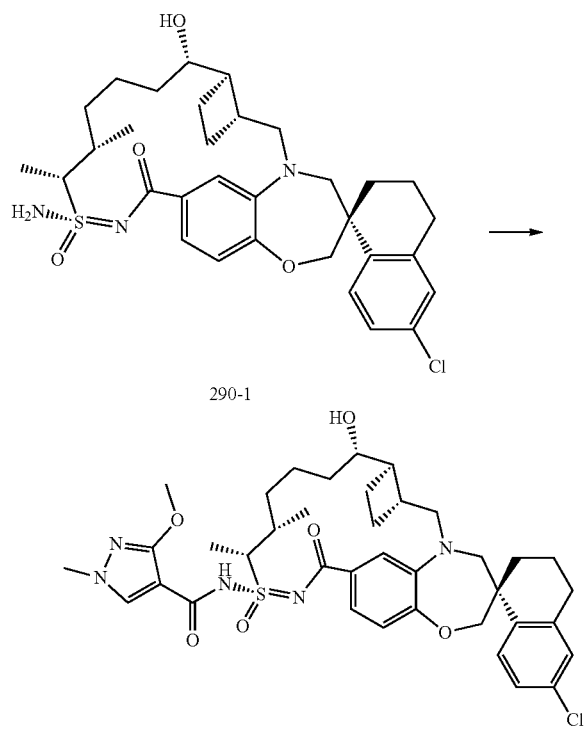

290-1

Synthesis of Intermediate 290-1: Intermediate 359-4 (35.0 mg, 0.0585 mmol) was dissolved in EtOH (10.0 mL) at room temperature, PtO$_2$ (16.0 mg) was added, the resulting mixture was degassed and hydrogenated under hydrogen balloon for 1 hr. The reaction was then filtered through 0.45 μm PTFE disc filter. The filtrate was concentrated, redissolved in DMF (1.2 mL), filtered, and purified by reverse phase prep HPLC. Desired fractions were combined and frozen dried to give 359-4. 1H NMR (400 MHz, Methanol-d4) δ 7.78 (d, J=8.5 Hz, 1H), 7.41 (dd, J=8.2, 1.9 Hz, 1H), 7.23-7.14 (m, 2H), 7.11 (d, J=2.3 Hz, 1H), 6.87 (d, J=8.2 Hz, 1H), 4.11-3.97 (m, 3H), 3.86 (d, J=15.0 Hz, 1H), 3.80-3.72 (m, 1H), 3.69-3.62 (m, 1H), 3.28 (d, J=14.1 Hz, 1H), 3.05 (dd, J=15.2, 9.2 Hz, 1H), 2.86-2.69 (m, 2H), 2.50-2.31 (m, 2H), 2.31-2.22 (m, 1H), 2.13-2.05 (m, 1H), 2.01-1.84 (m, 3H), 1.83-1.74 (m, 2H), 1.74-1.52 (m, 4H), 1.51-1.23 (m, 7H), 1.04 (d, J=6.8 Hz, 3H). LCMS-ESI+ (m/z): calcd H+ for C$_{32}$H$_{42}$ClN$_3$O$_4$: 600.26; found: 600.14.

Synthesis of Example 290

Intermediate 290-2 (10.0 mg, 0.0137 mmol) and 3-methoxy-1-methyl-pyrazole-4-carboxylic acid (2.79 mg, 0.0179 mmol) was mixed in DCM (1.0 mL) at room temperature. To this stirred mixture was added EDCI.HCl (3.41 mg, 0.0179 mmol) and DMAP (2.18 mg, 0.0179 mmol) followed by DIEA (5.32 mg, 0.041 mmol). The newly formed mixture was stirred at room temperature for 2 days and then it was concentrated, redissolved in DMF (1.2 mL), filtered and purified by reverse phase prep HPLC. 1H NMR (400 MHz, Methanol-d4) δ 7.95 (s, 1H), 7.77 (d, J=8.5 Hz, 1H), 7.31-7.24 (m, 1H), 7.19 (dd, J=8.5, 2.4 Hz, 1H), 7.16-7.10 (m, 2H), 6.95 (d, J=8.2 Hz, 1H), 4.19-4.06 (m, 3H), 3.99 (s, 3H), 3.85 (d, J=15.0 Hz, 1H), 3.79 (s, 3H), 3.74-3.65 (m, 2H), 3.18-3.08 (m, 1H), 2.88-2.71 (m, 2H), 2.51-2.20 (m, 3H), 2.15-2.06 (m, 1H), 2.04-1.87 (m, 3H), 1.87-1.77 (m, 2H), 1.77-1.33 (m, 12H), 1.14 (d, J=6.8 Hz, 3H). LCMS-ESI+ (m/z): calcd H+ for C$_{38}$H$_{48}$ClN$_5$O$_6$S: 738.30; found: 737.88.

Example 291

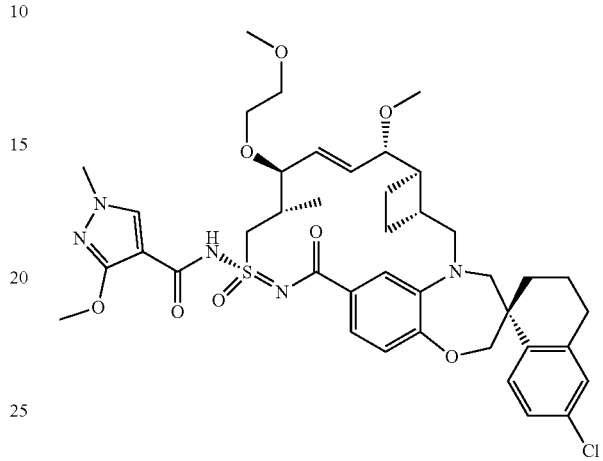

Example 291 was synthesized in the same manner as Example 283 using 1-iodo-2-methoxyethane and Example 279. $^1$H NMR (400 MHz, Methanol-d$_4$) δ 8.09 (s, 1H), 7.76 (d, J=8.6 Hz, 1H), 7.36 (d, J=8.8 Hz, 1H), 7.23-7.15 (m, 2H), 7.12 (d, J=2.3 Hz, 1H), 6.92 (d, J=8.2 Hz, 1H), 6.04 (dd, J=15.4, 7.2 Hz, 1H), 5.84 (dd, J=15.5, 8.5 Hz, 1H), 4.08 (m, 8H), 3.82 (m, 5H), 3.76-3.64 (m, 2H), 3.58-3.38 (m, 4H), 3.34 (s, 3H), 3.30 (s, 3H), 3.19-3.06 (m, 2H), 2.91-2.71 (m, 2H), 2.51 (m, 2H), 2.26 (m, 1H), 2.12 (m, 1H), 1.96 (m, 2H), 1.82 (d, J=6.3 Hz, 3H), 1.46 (t, J=13.1 Hz, 1H), 1.20 (d, J=6.8 Hz, 3H). LCMS-ESI+ (m/z): [M+H]+ calcd for C$_{41}$H$_{51}$ClFN$_5$O$_8$S: 810.3; found: 810.0.

Example 292

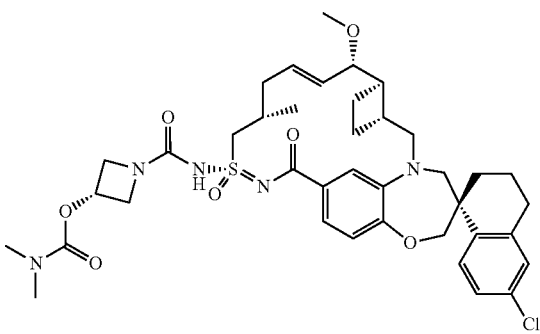

Example 292 was synthesized in the same manner as Example 75 using azetidin-3-yl-dimethylcarbamate bis-hydrochloric acid (prepared in same manner as trans-3-aminocyclobutyl dimethylcarbamate bis-hydrochloric acid (Example 360-step 1/2) starting from tert-butyl 3-hydroxyazetidine-1-carboxylate instead of trans-3-((tert-butoxycarbonyl)amino)cyclobutyl dimethylcarbamate) and Example 109. $^1$H NMR (400 MHz, Methanol-d4) δ 7.72 (d, J=8.5 Hz, 1H), 7.16 (d, J=8.8 Hz, 1H), 7.12-7.05 (m, 2H), 6.95-6.86 (m, 2H), 5.96 (dq, J=14.1, 7.2 Hz, 1H), 5.56 (dd, J=15.2, 9.1 Hz, 1H), 5.15-5.00 (m, 1H), 4.30 (dd, J=15.5, 6.9 Hz, 4H), 4.13-3.90 (m, 4H), 3.83 (d, J=15.2 Hz, 1H), 3.74 (dd, J=9.1, 3.6 Hz, 1H), 3.69-3.54 (m, 2H), 3.24 (s, 3H), 3.06 (dd, J=15.3, 10.3 Hz, 1H), 2.98 (s, 3H), 2.90 (s, 3H), 2.87-2.68 (m, 2H), 2.44 (dd, J=14.2, 6.7 Hz, 2H), 2.39-2.26 (m, 1H), 2.23-2.03 (m, 3H), 2.02-1.65 (m, 6H), 1.43 (t, J=12.9 Hz, 1H), 1.13 (d, J=6.6 Hz, 3H). LCMS-ESI+ (m/z): [M+H]+ calcd for $C_{39}H_{51}ClN_5O_7S$: 768.31; found: 767.73.

Example 293

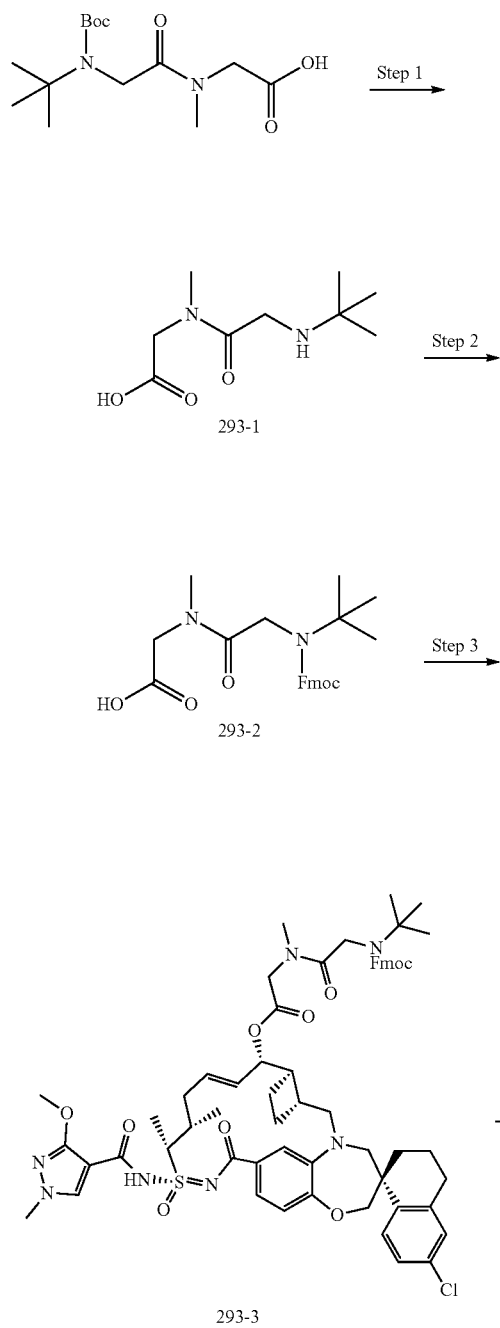

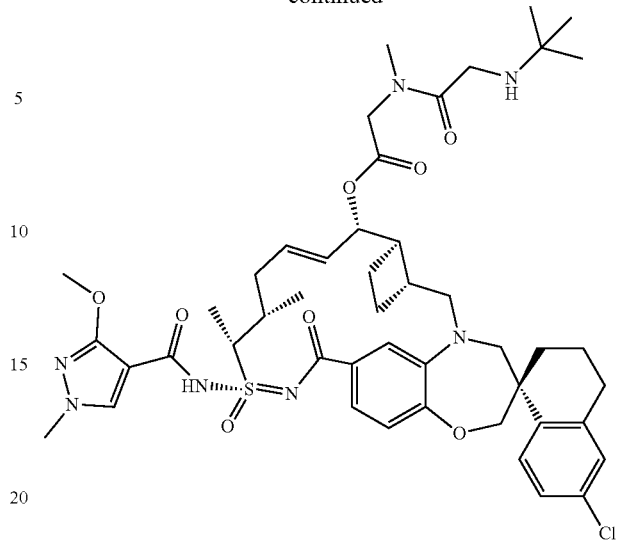

Example 293

Step 1: Preparation of A-(tert-butylglycyl)-A-methyl glycine (293-1)

To a solution of N—(N-(tert-butoxycarbonyl)-N-(tert-butyl)glycyl)-N-methylglycine (600 mg, 1.98 mmol) in DCM (10 mL) at 0° C. was added TFA (2 mL) slowly. The reaction mixture was warmed to room temperature and stirred for overnight. It was then concentrated to dryness and used in next step with no further purification. LCMS-ESI+: [M+H]$^+$ calc'd for $C_9H_{18}N_2O_3$: 203.14; found: 203.10.

Step 2

To the crude intermediate 293-1 (0.4 g, 1.98 mmol) was added 1.0 M $Na_2CO_3$ aqueous solution (6 mL). The reaction mixture was cooled to 0° C. and 9-fluorenylmethoxycarbonyl chloride (Fmoc-Cl) (1.03 g, 3.97 mmol) in dioxane (12 mL) was gradually added. The reaction mixture was stirred at room temperature for 14 hours and then was neutralized with 1.0 N HCl (13 mL) aqueous solution to a pH value of 2. It was then extracted with EtOAc (50 mL×2). The organic layers were combined, dried and concentrated. The crude residue was purified by column chromatography using 0-10% MeOH in DCM to afford intermediate 293-2. LCMS-ESI+: [M+H]$^+$ calc'd for $C_{24}H_{28}N_2O_5$: 425.21; found: 425.19.

Step 3

Intermediate 293-3 was synthesized in the same manner as Example 18 using intermediate 293-2 and Example 359. LCMS-ESI+: [M+H]$^+$ calc'd for $C_{62}H_{72}ClN_7O_{10}S$: 1142.48; found: 1142.08.

Step 4

To a solution of intermediate 293-3 (22 mg, 0.20 mmol) in DMF (1.2 mL) was added piperidine (0.3 mL). The reaction mixture was stirred for 20 min and LC/MS showed it went to completion. 0.5 ml of water was added to quench the reaction. The crude mixture was diluted with MeOH (2 mL) and purified by RP-HPLC (30-100% gradient, 0.1%

TFA) to afford Example 293. $^1$H NMR (400 MHz, Methanol-d4) δ 7.94 (d, J=4.3 Hz, 1H), 7.76 (t, J=8.1 Hz, 1H), 7.26-7.03 (m, 4H), 6.94 (t, J=1.1 Hz, 1H), 5.99 (d, J=15.0 Hz, 1H), 5.77 (td, J=16.8, 15.4, 8.2 Hz, 1H), 5.44 (ddd, J=37.1, 8.0, 3.8 Hz, 1H), 4.28 (d, J=28.4 Hz, 1H), 4.10 (t, J=4.4 Hz, 5H), 4.03-3.84 (m, 5H), 3.79 (d, J=1.5 Hz, 3H), 3.69 (t, J=12.5 Hz, 1H), 3.16 (t, J=5.5 Hz, 1H), 3.11 (s, 3H), 2.88-2.72 (m, 2H), 2.59-2.42 (m, 2H), 2.20 (s, 3H), 2.09 (d, J=13.7 Hz, 1H), 2.01-1.84 (m, 5H), 1.83-1.70 (m, 2H), 1.57 (d, J=7.0 Hz, 3H), 1.49 (d, J=12.7 Hz, 1H), 1.41 (d, J=9.4 Hz, 9H), 1.17 (q, J=3.1 Hz, 3H). LCMS-ESI+[M+H] calculated for $C_{47}H_{62}ClN_7O_8S$: 920.41; found: 920.20.

Example 294

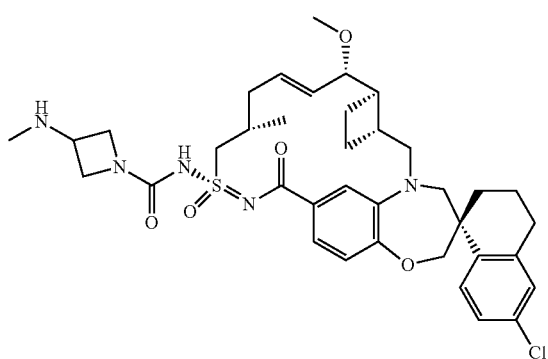 [SMILES: CNC1CN(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)C1]

Example 294 was synthesized in the similar method described herein. LCMS-ESI+(m/z): [M+H]$^+$ calc'd for $C_{37}H_{48}ClN_5O_5S$: 710.3137; found: 710.03.

Example 295

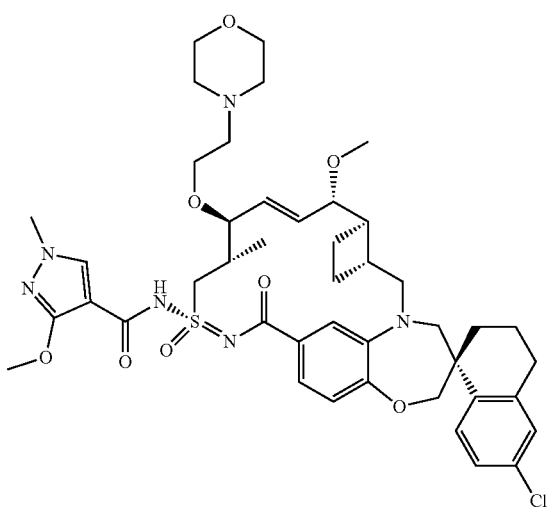 [SMILES: COc1nn(C)cc1C(=O)N[S@@]1(=O)=NC(=O)c2ccc3c(c2)N(C[C@@H]2CC[C@H]2[C@@H](OC)/C=C/[C@H](OCCN2CCOCC2)[C@H](C)C1)C[C@@]1(CCCc2cc(Cl)ccc21)CO3]

Example 291 was synthesized in the same manner as Example 283 using 4-(2-iodoethyl)morpholine and Example 279. $^1$H NMR (400 MHz, Methanol-d$_4$) δ 8.09 (s, 1H), 7.76 (d, J=8.5 Hz, 1H), 7.39 (dd, J=8.2, 1.9 Hz, 1H), 7.25 (s, 1H), 7.19 (dd, J=8.5, 2.3 Hz, 1H), 7.13 (d, J=2.3 Hz, 1H), 6.93 (d, J=8.2 Hz, 1H), 6.21 (dd, J=15.3, 8.7 Hz, 1H), 5.93 (dd, J=15.3, 8.8 Hz, 1H), 4.27 (dd, J=14.9, 5.5 Hz, 1H), 4.08 (m, 9H), 3.99-3.76 (m, 8H), 3.76-3.57 (m, 4H), 3.59-3.38 (m, 4H), 3.36-3.20 (m, 2H), 3.30 (s, 3H), 3.20-3.08 (m, 2H), 2.89-2.73 (m, 2H), 2.54 (m, 2H), 2.33 (m, 1H), 2.12 (d, J=13.2 Hz, 1H), 1.96 (m, 2H), 1.83 (m, 3H), 1.47 (t, J=12.4 Hz, 1H), 1.25 (d, J=6.9 Hz, 3H). LCMS-ESI+ (m/z): [M+H]+ calcd for $C_{44}H_{57}ClFN_6O_8S$: 865.4; found: 865.4.

Example 296

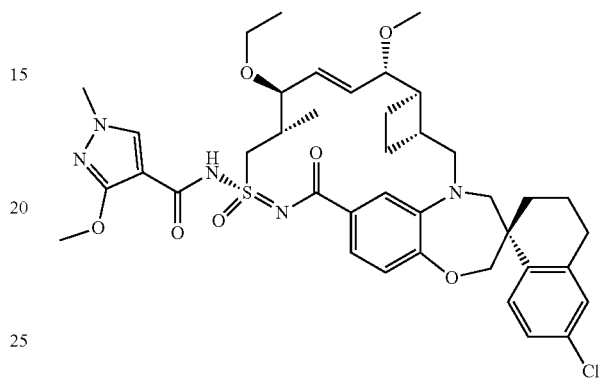

Example 296 was synthesized in the same manner as Example 283 using iodoethane and Example 279. $^1$H NMR (400 MHz, Methanol-d$_4$) δ 8.10 (s, 1H), 7.75 (d, J=8.5 Hz, 1H), 7.42-7.31 (m, 1H), 7.19 (s, 1H), 7.18-7.10 (m, 2H), 6.91 (d, J=8.2 Hz, 1H), 6.04 (dd, J=15.4, 7.6 Hz, 1H), 5.80 (dd, J=15.4, 8.6 Hz, 1H), 4.12-4.02 (m, 5H), 3.98 (d, J=7.5 Hz, 1H), 3.82 (m, 5H), 3.72 (d, J=14.4 Hz, 1H), 3.61 (dq, J=9.5, 7.0 Hz, 1H), 3.45-3.25 (m, 3H), 3.31 (m, 2H), 3.29 (s, 3H), 3.18-3.06 (m, 1H), 2.87-2.71 (m, 3H), 2.51 (s, 2H), 2.24 (d, J=7.7 Hz, 1H), 2.11 (d, J=13.7 Hz, 1H), 1.96 (m, 2H), 1.82 (d, J=7.2 Hz, 3H), 1.45 (t, J=11.8 Hz, 1H), 1.23-1.12 (m, 6H). LCMS-ESI+ (m/z): [M+H]+ calcd for $C_{40}H_{50}ClN_5O_7S$: 780.3; found: 780.1.

Example 297

Step 1

To the mixture of tert-butyl 3-oxoazetidine-1-carboxylate (50.0 mg, 0.292 mmol) and (9aS)-1,3,4,6,7,8,9,9a-octahydropyrazino[2,1-c][1,4]oxazine dihydrochloride (62.8 mg, 0.292 mmol) in DCE (1.0 mL) at room temperature was added Triethylamine (59.1 mg, 0.584 mmol). The resulting mixture was stirred at room temperature for 10 min and sodiumtriacetoxyborohydride (92.9 mg, 0.438 mmol) was added. The resulting mixture was stirred at room temperature for overnight. The reaction was then mixed with MeOH, the precipitate was filtered, the filtrate was purified by combiflash (4 g silica gel, 0-10% 2.0N MeOH/EtOAc). Desired fractions were combined and concentrated to give 297-1. 1H NMR (400 MHz, Chloroform-d) δ 3.94-3.75 (m, 5H), 3.73-3.62 (m, 2H), 3.24 (t, J=10.7 Hz, 1H), 3.11-3.02 (m, 1H), 2.82-2.71 (m, 2H), 2.68 (d, J=11.5 Hz, 1H), 2.54 (dt, J=10.8, 2.3 Hz, 1H), 2.44-2.30 (m, 3H), 2.20-2.10 (m, 1H), 1.68 (t, J=10.5 Hz, 1H), 1.41 (s, 9H). LCMS-ESI+ (m/z): calcd H+ for $C_{15}H_{27}N_3O_3$: 298.21; found: 297.98.

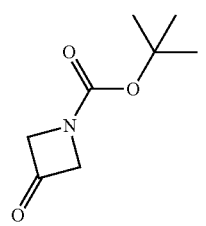

step1 →

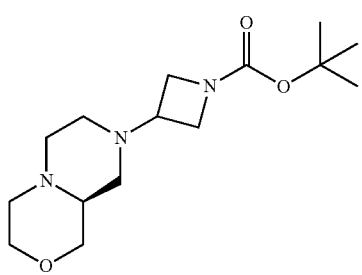

297-1 step2 →

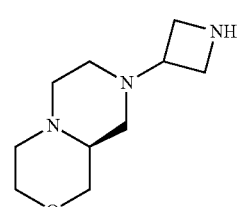

297-2 step3 →

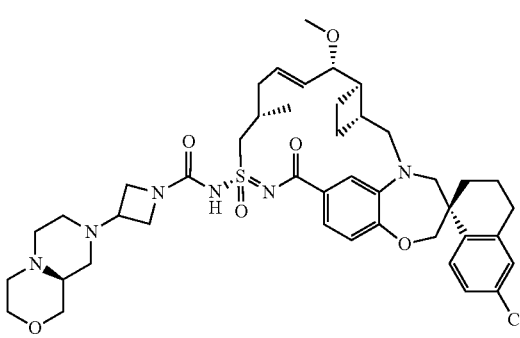

Example 297

Step 2

Intermediate 297-1 (53.2 mg, 0.179 mmol) was dissolved in DCM (1.0 mL) at room temperature. 4 N HCl in 1,4-dioxane (0.224 mL, 0.894 mmol) was added slowly. The resulting mixture was stirred at room temperature for 2 hrs. The reaction was concentrated, and coevaporated with EtOAc (3×2.0 mL) to give 297-2. 1H NMR (400 MHz, Methanol-d4) δ 4.22-4.00 (m, 7H), 3.94 (t, J=12.4 Hz, 1H), 3.71-3.50 (m, 5H), 3.46 (d, J=12.6 Hz, 1H), 3.18-3.02 (m, 2H), 2.60 (t, J=12.7 Hz, 1H), 2.24 (t, J=11.7 Hz, 1H). LCMS-ESI+ (m/z): calcd H+ for $C_{10}H_{19}N_3O$:198.15; found: 198.15.

Step 3: Synthesis of Example 297

To a solution of Example 109 (10.0 mg, 0.0167 mmol) in DCM (0.4 mL) was added acetonitrile (2.0 mL). To the mixture was added DMAP (10.2 mg, 0.084 mmol) and diphenyl carbonate (28.6 mg, 0.134 mmol). The reaction mixture was stirred at room temperature for 3 hrs. To the stirred mixture was added (9aS)-8-(azetidin-3-yl)-3,4,6,7,9,9a-hexahydro-1H-pyrazino[2,1-c][1,4]oxazine trihydrochloride (20.5 mg, 0.069 mmol) followed by DIEA (32.4 mg, 0.25 mmol). The reaction was then heated at 50° C. for 5 hrs before it was concentrated, redissolved in DMF (1.2 mL), filtered and purified by Gilson reverse phase prep HPLC. Desired fractions were combined and concentrated. The residue was diluted with water and frozen dried to give the title compound. 1H NMR (400 MHz, Methanol-d4) δ 7.74 (d, J=8.6 Hz, 1H), 7.18 (dd, J=8.4, 2.3 Hz, 1H), 7.14-7.07 (m, 2H), 6.96-6.89 (m, 2H), 6.02-5.92 (m, 1H), 5.58 (dd, J=15.3, 9.0 Hz, 1H), 4.31 (dd, J=14.9, 6.4 Hz, 1H), 4.21-3.97 (m, 5H), 3.89-3.81 (m, 1H), 3.76 (dd, J=9.1, 3.8 Hz, 1H), 3.71-3.63 (m, 1H), 3.54-3.46 (m, 1H), 3.45-3.36 (m, 1H), 3.32-3.17 (m, 13H), 3.13-3.04 (m, 2H), 2.87-2.73 (m, 2H), 2.55-2.41 (m, 3H), 2.40-2.29 (m, 1H), 2.25-2.04 (m, 4H), 2.00-1.68 (m, 7H), 1.50-1.34 (m, 2H), 1.14 (d, J=6.6 Hz, 3H). LCMS-ESI+ (m/z): calcd H+ for $C_{43}H_{57}N_6O_6S$: 821.37; found: 821.07.

Example 298

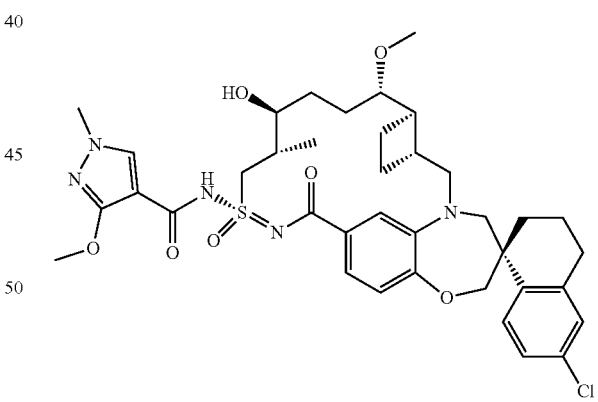

Example 298 was synthesized in the same manner as Example 280 using Example 279. ¹H NMR (400 MHz, Methanol-d₄) δ 8.08 (s, 1H), 8.00 (s, 1H), 7.77 (d, J=8.5 Hz, 1H), 7.39 (t, J=7.5 Hz, 1H), 7.29 (s, 1H), 7.18 (d, J=8.5 Hz, 1H), 7.12 (d, J=2.3 Hz, 1H), 6.93 (d, J=8.3 Hz, 1H), 4.09 (m, 6H), 3.82 (m, 5H), 3.71 (d, J=14.4 Hz, 1H), 3.61 (s, 1H), 3.37 (d, J=4.2 Hz, 2H), 3.18-3.04 (m, 1H), 3.02 (s, 3H), 2.88 (s, 3H), 2.80 (m, 2H), 2.56 (m, 2H), 2.26 (s, 1H), 2.11 (d, J=13.5 Hz, 1H), 2.01-1.9 (m, 2H), 1.76 (m, 4H), 1.67-1.39 (m, 4H), 1.19 (d, J=6.9 Hz, 3H). LCMS-ESI+ (m/z): [M+H]+ calcd for $C_{38}H_{48}ClN_5O_7S$: 754.3; found: 754.1.

Example 298

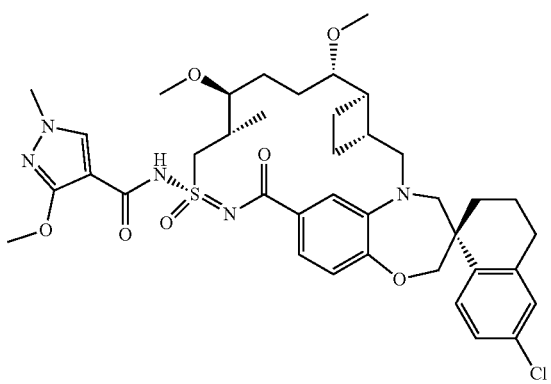 [SMILES: COc1nn(C)cc1C(=O)N[S@@]1(=O)=NC(=O)c2ccc3c(c2)N(C[C@@H]2CC[C@H]2[C@@H](OC)CC[C@H](OC)[C@H](C)C1)C[C@@]1(CCCc2cc(Cl)ccc21)CO3]

Example 299 was synthesized in the same manner as Example 280 using Example 279. $^1$H NMR (400 MHz, Methanol-$d_4$) δ 8.10 (s, 1H), 7.77 (d, J=8.5 Hz, 1H), 7.41 (dd, J=8.3, 1.8 Hz, 1H), 7.25 (s, 1H), 7.17 (dd, J=8.5, 2.3 Hz, 1H), 7.12 (d, J=2.3 Hz, 1H), 6.94 (d, J=8.2 Hz, 1H), 4.08 (m, 7H), 3.82 (m, 5H), 3.71 (d, J=14.2 Hz, 1H), 3.40 (m, 4H), 3.35 (m, 2H), 3.31 (s, 3H), 3.21 (d, J=7.2 Hz, 1H), 3.18-3.07 (m, 1H), 2.90-2.71 (m, 2H), 2.62 (m, 1H), 2.48 (m, 1H), 2.36 (m, 1H), 2.11 (d, J=13.5 Hz, 1H), 1.96 (m, 3H), 1.77 (d, J=7.4 Hz, 3H), 1.50 (q, J=11.3, 9.2 Hz, 4H), 1.16 (d, J=6.8 Hz, 3H). LCMS-ESI+ (m/z): [M+H]+ calcd for $C_{39}H_{50}ClN_5O_7S$: 768.3; found: 768.1.

Example 300

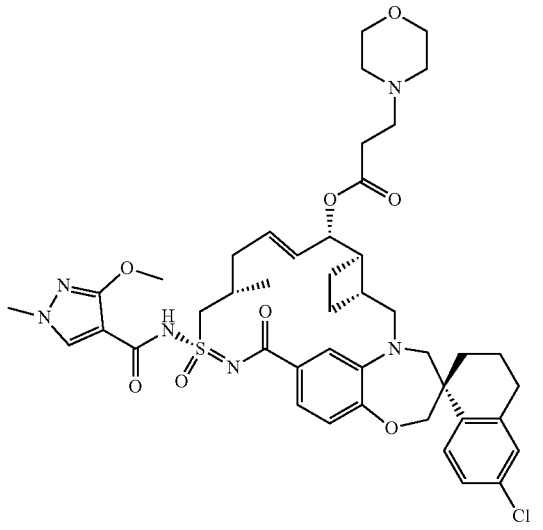 [SMILES: COc1nn(C)cc1C(=O)N[S@@]1(=O)=NC(=O)c2ccc3c(c2)N(C[C@@H]2CC[C@H]2[C@@H](OC(=O)CCN2CCOCC2)/C=C/C[C@H](C)C1)C[C@@]1(CCCc2cc(Cl)ccc21)CO3]

To a stirred solution of 3-methoxy-1-methyl-1H-pyrazole-4-carboxylic acid (6 mg, 0.038 mmol), 1-(3-dimethylaminopropyl)-3-ethylcarbodiimide HCl (10.75 mg, 0.069 mmol) and 4-(dimethylamino)pyridine (8.45 mg, 0.069 mmol) in DCM (5 mL) was added Example 223 (25 mg, 0.035 mmol). The reaction mixture was stirred at room temperature for 24 hr. Then the reaction mixture was diluted with DCM and water and extracted in DCM. The organic phase was dried over MgSO$_4$, filtered, concentrated down and purified on reversed phase chromatography 0.1% TFA 70-95% acetonitrile to give Example 300. 1H NMR (400 MHz, Chloroform-d) δ 11.16 (s, 1H), 7.97 (s, 1H), 7.75 (d, J=8.5 Hz, 1H), 7.50 (d, J=8.4 Hz, 1H), 7.28-7.17 (m, 2H), 7.10 (d, J=2.3 Hz, 1H), 6.94 (d, J=8.2 Hz, 1H), 6.11 (dd, J=14.9, 7.7 Hz, 1H), 5.74 (dd, J=15.6, 6.2 Hz, 1H), 5.33 (t, J=5.3 Hz, 1H), 4.11 (d, J=5.5 Hz, 3H), 4.07-3.88 (m, 3H), 3.82 (s, 2H), 3.76 (d, J=14.4 Hz, 1H), 3.57 (d, J=61.0 Hz, 2H), 3.42-3.18 (m, 3H), 3.13-2.58 (m, 6H), 2.48-2.21 (m, 3H), 2.07-1.47 (m, 13H), 1.40 (t, J=12.8 Hz, 1H), 1.28 (s, 2H), 1.19 (d, J=6.2 Hz, 2H), 0.96-0.70 (m, 2H). LCMS-ESI+ (m/z): [M+H]+ calcd for $C_{44}H_{55}ClN_6O_8S$: 862.35; found: 862.95.

Example 301

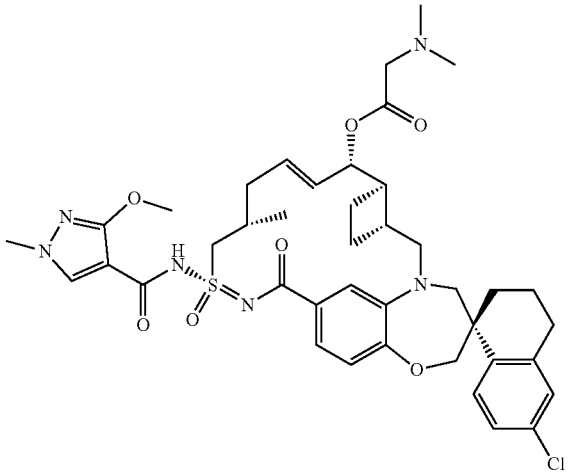 [SMILES: COc1nn(C)cc1C(=O)N[S@@]1(=O)=NC(=O)c2ccc3c(c2)N(C[C@@H]2CC[C@H]2[C@@H](OC(=O)CN(C)C)/C=C/C[C@H](C)C1)C[C@@]1(CCCc2cc(Cl)ccc21)CO3]

Example 301 was synthesized in the same manner as Example 404 using dimethylglycine and Example 223. 1H NMR (400 MHz, Chloroform-d) δ 8.10 (s, 1H), 7.76 (d, J=8.5 Hz, 1H), 7.48 (d, J=8.2 Hz, 1H), 7.25-7.12 (m, 2H), 7.10 (d, J=2.3 Hz, 1H), 6.93 (d, J=8.3 Hz, 1H), 6.37-6.21 (m, 1H), 5.85 (dd, J=15.7, 5.7 Hz, 1H), 5.33 (s, 1H), 4.55 (d, J=18.1 Hz, 1H), 4.35 (d, J=14.4 Hz, 1H), 4.15-3.87 (m, 5H), 3.90-3.66 (m, 4H), 3.29 (dd, J=28.4, 13.1 Hz, 3H), 3.04 (s, 5H), 2.78 (d, J=12.3 Hz, 5H), 2.49-2.15 (m, 5H), 2.11-1.91 (m, 3H), 1.89-1.62 (m, 4H), 1.38-1.13 (m, 4H). LCMS-ESI+ (m/z): [M+H]+ calcd for $C_{41}H_{51}ClN_6O_7S$: 807.32; found: 806.99.

Example 302

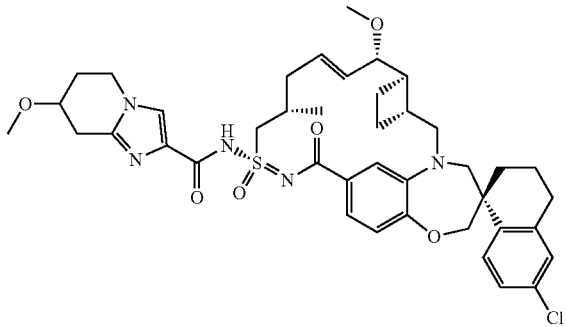 [SMILES: COC1CCn2cc(C(=O)N[S@@]3(=O)=NC(=O)c4ccc5c(c4)N(C[C@@H]4CC[C@H]4[C@@H](OC)/C=C/C[C@H](C)C3)C[C@@]3(CCCc4cc(Cl)ccc43)CO5)nc2C1]

Example 302 was synthesize in the same manner as Example 18, using Example 109 instead of Example 5, and 7-methoxy-5,6,7,8-tetrahydroimidazo[1,2-a]pyridine-2-carboxylic acid was used instead of 3-methoxypropionic acid. 1H NMR (400 MHz, Methanol-d4) δ 7.93 (s, 1H), 7.75 (d, J=8.5 Hz, 1H), 7.16 (ddd, J=19.0, 8.6, 2.3 Hz, 3H), 6.99-6.88 (m, 2H), 6.07 (dt, J=14.2, 6.5 Hz, 1H), 5.56 (dd, J=15.2, 9.3 Hz, 1H), 4.47 (dd, J=14.6, 6.2 Hz, 1H), 4.27 (dd, J=8.2, 4.3 Hz, 2H), 4.08 (d, J=1.8 Hz, 3H), 3.91-3.76 (m, 3H), 3.67 (d, J=14.2 Hz, 1H), 3.46 (s, 3H), 3.27 (s, 4H), 3.07 (dd, J=15.3, 10.3 Hz, 1H), 2.91-2.69 (m, 3H), 2.57-2.28 (m, 5H), 2.17 (dt, J=30.1, 13.2 Hz, 4H), 2.03-1.85 (m, 3H), 1.77 (dq, J=17.4, 9.1 Hz, 3H), 1.44 (t, J=12.2 Hz, 1H), 1.16-1.05 (m, 3H). LCMS-ESI+ (m/z): [M+H]+ calcd for $C_{41}H_{50}ClN_5O_6S$: 776.32; found: 776.29.

Example 303

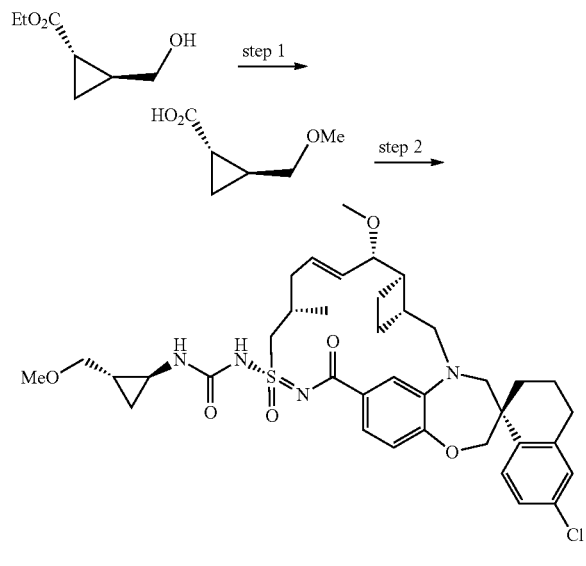

Step 1: Preparation of (1S,2S)-2-(methoxymethyl)cyclopropane-1-carboxylic Acid

A solution of ethyl (1S,2S)-2-(hydroxymethyl)cyclopropane-1-carboxylate (640 mg, 4.44 mmol) was suspended in THF (44 mL), cooled to 0° C. and treated with NaH (213 mg, 8.88 mmol). After 15 minutes, methyl iodide (1.38 mL, 22.2 mmol) was added and the reaction mixture was warmed to RT. After stirring for 1 h, EtOH (22 mL) was added carefully followed by 2M NaOH (22 mL, 44 mmol). The reaction mixture was then warmed to 65° C. and stirred at this temperature for 18 h. The mixture was then cooled to RT and poured into a separatory funnel containing 10% HCl. The aqueous layer was extracted 3× with DCM. The combined organics were dried over MgSO$_4$, then filtered and concentrated under reduced pressure to provide (1S,2S)-2-(methoxymethyl)cyclopropane-1-carboxylic acid (282 mg), which was carried on without further purification. $^1$H NMR (400 MHz, Chloroform-d) δ 3.43-3.30 (m, 4H), 3.26 (dd, J=10.4, 6.7 Hz, 1H), 1.76 (dddd, J=12.8, 10.4, 7.8, 5.2 Hz, 1H), 1.56 (dt, J=8.6, 4.4 Hz, 1H), 1.32-1.21 (m, 1H), 0.93 (ddd, J=8.2, 6.3, 4.3 Hz, 1H).

Step 2: Preparation of Example 303

(1S,2S)-2-(methoxymethyl) cyclopropane-1-carboxylic acid (112 mg, 0.861 mmol) was suspended in PhMe (1 mL), then treated with diphenyl phosphoryl azide (0.18 mL, 0.84 mmol) and trimethylamine (0.14 mL, 1.0 mmol). The stirred reaction mixture was heated to 80° C., then cooled to RT. Example 109 (50 mg, 0.084 mmol) was added and the stirred reaction mixture was heated to 50° C. for 4 h. Upon completion, the reaction mixture was diluted with EtOAc. The organic phase was washed with saturated NaHCO$_3$ solution, 5% citric acid and brine, then dried over MgSO$_4$, filtered, and concentrated under reduced pressure. The crude residue was purified by silica column chromatography (0% to 40% MeOH/EtOAc), then repurified by HPLC to afford Example 303. $^1$H NMR (400 MHz, Chloroform-d) δ 7.80-7.34 (m, 1H), 7.23-6.57 (m, 5H), 6.00 (dt, J=14.0, 6.7 Hz, 1H), 5.63 (ddd, J=41.7, 15.4, 8.5 Hz, 1H), 4.40-3.88 (m, 3H), 3.88-3.49 (m, 5H), 3.42 (s, 3H), 3.38-3.18 (m, 5H), 3.18-2.89 (m, 1H), 2.89-2.52 (m, 3H), 2.52-2.08 (m, 5H), 2.08-1.49 (m, 7H), 1.48-1.19 (m, 3H), 1.13 (d, J=6.3 Hz, 3H), 0.98 (dt, J=10.6, 5.4 Hz, 1H), 0.92-0.80 (m, 1H), 0.75 (q, J=6.6 Hz, 1H). LCMS-ESI+: calculated for $C_{38}H_{49}ClN_4O_6S$: 725.3 (M+H); found: 725.8 (M+H).

Example 304

Step 1

Sodium borohydride (494 mg, 13.1 mmol) was added to a solution of 5-formyl-1-methyl-pyrrole-3-carboxylic acid (500 mg, 3.27 mmol) in methanol (10 mL). After 2 hours, more sodium borohydride (494 mg, 13.1 mmol) was added. After 5 hours, the reaction was quenched with water (5 mL). The methanol was removed under reduced pressure. The aqueous phase was extracted with ethyl acetate (3×5 mL). The aqueous phases were diluted with ACN and subjected to lyophilization, providing 5-(hydroxymethyl)-1-methyl-1H-pyrrole-3-carboxylic acid sodium salt.

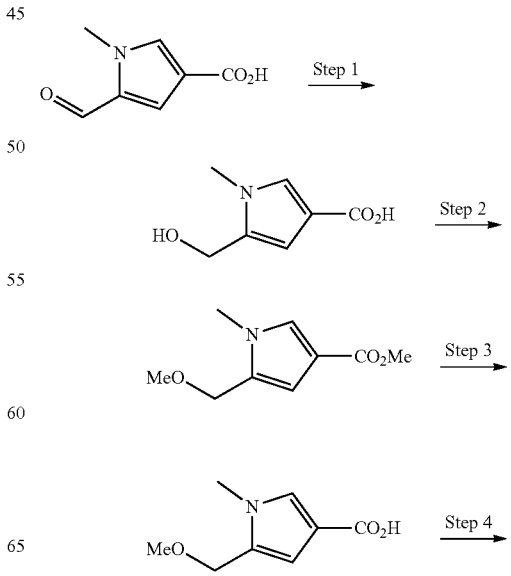

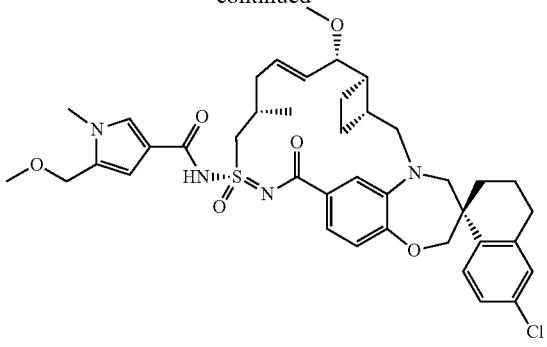

Step 2

5-(Hydroxymethyl)-1-methyl-1H-pyrrole-3-carboxylic acid sodium salt from above (507 mg, 3.27 mmol) was suspended in tetrahydrofuran (25 mL) and A-methyl-2-pyrrolidone (10 mL). Sodium hydride 60% suspension in mineral oil (250 mg, 6.54 mmol) was added. After 5 minutes, iodomethane (0.61 mL, 9.8 mmol) was added. After 16 h, sodium hydride 60% suspension in mineral oil (250 mg, 6.54 mmol) was added. After 5 minutes iodomethane (0.61 mL, 9.8 mmol) were added. After 4 days the reaction was diluted with ethyl acetate (100 mL) and washed with water (50 mL), 5% lithium chloride (2×) and brine (50 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure, providing methyl 5-(methoxymethyl)-1-methyl-1H-pyrrole-3-carboxylate. $^1$H NMR (400 MHz, DMSO-d6) δ 7.47 (d, J=1.9 Hz, 1H), 6.43 (d, J=1.8 Hz, 1H), 4.33 (s, 2H), 3.68 (s, 3H), 3.61 (s, 3H), 3.20 (s, 3H).

Step 3

A solution of 1 N lithium hydroxide (2.0 mL, 2.0 mmol) was added to a solution of methyl 5-(methoxymethyl)-1-methyl-1H-pyrrole-3-carboxylate (138 mg, 0.75 mmol) in methanol (10 mL). The solution was stirred at 40° C. for 18 hours. The reaction was cooled and the pH was adjusted to 2 with 1 N hydrochloric acid. The mixture was extracted with ethyl acetate (3×15 mL). The organic phases were combined and washed with brine, and dried over sodium sulfate. The solvent was removed under reduced pressure providing 5-(hydroxymethyl)-1-methyl-1H-pyrrole-3-carboxylic acid. $^1$H NMR (400 MHz, DMSO-d6) δ 11.68 (s, 1H), 7.38 (d, J=1.9 Hz, 1H), 6.38 (d, J=1.9 Hz, 1H), 4.32 (s, 2H), 3.60 (s, 3H), 3.20 (s, 3H).

Example 304 was synthesized in the same manner as Example 18 using 5-(methoxymethyl)-1-methyl-1H-pyrrole-3-carboxylic acid and Example 109. 1H NMR (400 MHz, Methanol-d4) δ 7.77 (d, J=8.5 Hz, 1H), 7.48 (s, 1H), 7.29 (d, J=8.2 Hz, 1H), 7.17 (dd, J=8.5, 2.3 Hz, 1H), 7.11 (d, J=2.3 Hz, 1H), 7.02 (s, 1H), 6.86 (d, J=8.0 Hz, 1H), 6.66-6.59 (m, 1H), 6.22-6.08 (m, 1H), 5.60-5.46 (m, 2H), 4.47-4.33 (m, 3H), 4.12-4.00 (m, 2H), 3.96 (d, J=11.9 Hz, 0H), 3.88 (d, J=15.1 Hz, 1H), 3.81 (dd, J=9.1, 3.2 Hz, 1H), 3.73-3.62 (m, 4H), 3.27 (m, 4H), 3.04 (dd, J=15.2, 9.6 Hz, 1H), 2.88-2.70 (m, 2H), 2.57 (m, 1H), 2.42 (m, 3H), 2.12 (m, 4H), 1.94 (m, 3H), 1.77 (m, 3H), 1.49-1.28 (m, 1H), 1.08 (d, J=5.9 Hz, 3H). LCMS-ESI+: calc'd for $C_{40}H_{49}ClN_4O_6S$: 749.31 (M+H); found: 749.85 (M+H).

Example 305

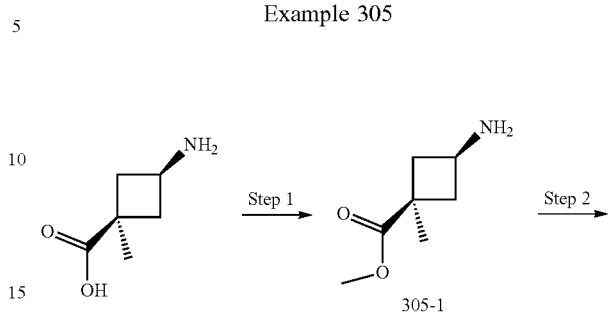

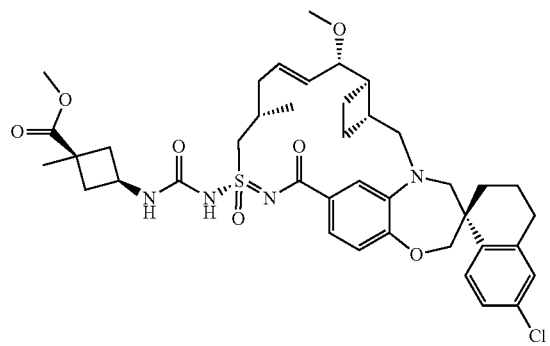

Step 1

Synthesis of 305-1: To the mixture of 3-amino-1-methyl-cyclobutanecarboxylic acid (250 mg, 1.94 mmol) in MeOH (1.0 mL) at room temperature was added 4 N HCl in 1,4-dioxane (1.94 mL, 7.74 mmol). The resulting mixture was stirred at room temperature for 2 days. The reaction was concentrated, co-evaporated with EtOAc (3×), and further dried over the vacuum line to give 305-1. 1H NMR (400 MHz, Methanol-d4) δ 3.95-3.80 (m, 1H), 3.74 (s, 3H), 2.65-2.52 (m, 2H), 2.40-2.25 (m, 2H), 1.46 (s, 3H).

Step 2

Example 305 was synthesized in the same manner as Example 75 using Example 109 and 305-1 and DIEA. 1H NMR (400 MHz, Methanol-d4) δ 7.74 (d, J=8.4 Hz, 1H), 7.23-7.09 (m, 3H), 6.99 (s, 1H), 6.91 (d, J=8.1 Hz, 1H), 6.10-5.98 (m, 1H), 5.65-5.54 (m, 1H), 4.37-4.22 (m, 2H), 4.11-4.01 (m, 2H), 3.89-3.74 (m, 3H), 3.73-3.65 (m, 4H), 3.27 (s, 3H), 3.12-3.02 (m, 1H), 2.89-2.71 (m, 2H), 2.53-2.35 (m, 5H), 2.32-2.23 (m, 2H), 2.23-2.16 (m, 1H), 2.16-2.08 (m, 2H), 2.00-1.71 (m, 7H), 1.48-1.40 (m, 4H), 1.13 (d, J=6.7 Hz, 3H). LCMS-ESI+ (m/z): calcd H+ for $C_{40}H_{51}ClN_4O_7S$: 767.32; found: 766.77.

Example 306

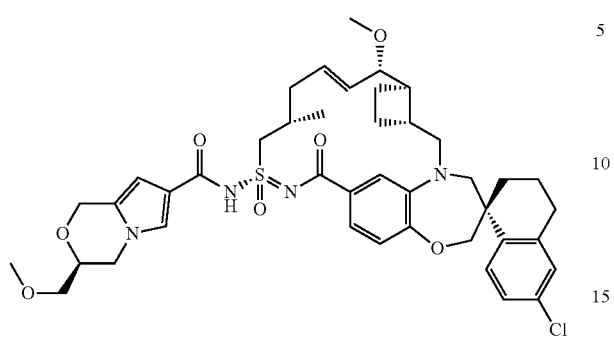

Example 306 was synthesized in a manner similar to Example 214 using (S)-2-(methoxymethyl)oxirane instead of (R)-2-(methoxymethyl)oxirane. 1H NMR (400 MHz, Acetone-d6) δ 7.78 (d, J=8.5 Hz, 1H), 7.50-7.38 (m, 1H), 7.34 (d, J=8.2 Hz, 1H), 7.27-7.21 (m, 2H), 7.14 (d, J=2.3 Hz, 1H), 6.91 (d, J=8.2 Hz, 1H), 6.31 (s, 1H), 6.23-6.10 (m, 1H), 5.62 (dd, J=15.5, 8.0 Hz, 1H), 4.93 (d, J=14.4 Hz, 1H), 4.74 (d, J=14.5 Hz, 1H), 4.26-3.94 (m, 5H), 3.94-3.81 (m, 2H), 3.81-3.71 (m, 2H), 3.64 (dd, J=10.4, 5.4 Hz, 1H), 3.55 (dd, J=10.4, 4.8 Hz, 1H), 3.43 (d, J=14.4 Hz, 1H), 3.39 (s, 3H), 3.24 (s, 3H), 3.14 (dd, J=15.1, 10.4 Hz, 1H), 2.96-1.39 (m, 16H), 1.13 (d, J=6.6 Hz, 3H). LCMS: 791.0.

Example 307

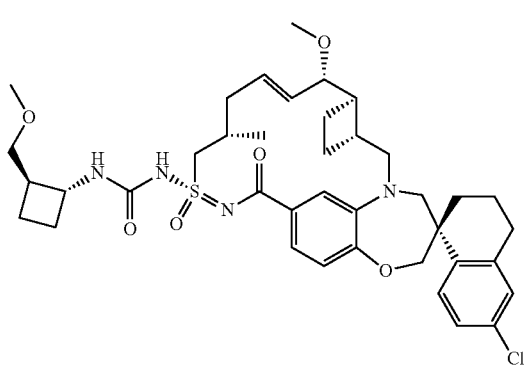 [SMILES: COC[C@@H]1CC[C@H]1NC(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Example 307 was synthesized in the same manner as Example 75 using (1R,2R)-2-(methoxymethyl)cyclobutan-1-amine and Example 109. 1H NMR (400 MHz, Methanol-d4) δ 7.76 (d, J=8.4 Hz, 1H), 7.20 (dd, J=20.9, 8.3 Hz, 2H), 7.13 (s, 1H), 7.03 (s, 1H), 6.90 (d, J=8.2 Hz, 1H), 6.08 (d, J=15.2 Hz, 1H), 5.59 (dd, J=15.4, 9.0 Hz, 1H), 4.25 (s, 1H), 4.04 (dd, J=19.9, 7.0 Hz, 3H), 3.91-3.63 (m, 4H), 3.46 (dd, J=11.2, 5.8 Hz, 2H), 3.36 (s, 3H), 3.27 (s, 3H), 3.09 (dd, J=15.1, 10.2 Hz, 1H), 2.89-2.73 (m, 2H), 2.44 (d, J=35.2 Hz, 4H), 2.20 (dd, J=23.2, 5.7 Hz, 2H), 1.96 (s, 3H), 1.89-1.70 (m, 4H), 1.56-1.40 (m, 3H), 1.13 (d, J=6.7 Hz, 3H), 0.91 (d, J=7.1 Hz, 1H), 0.61 (s, 1H), 0.12 (d, J=12.1 Hz, 1H). LCMS-ESI+[M+H]+ calc'd for $C_{39}H_{51}ClN_4O_6S$: 739.32; found:738.84.

Example 308

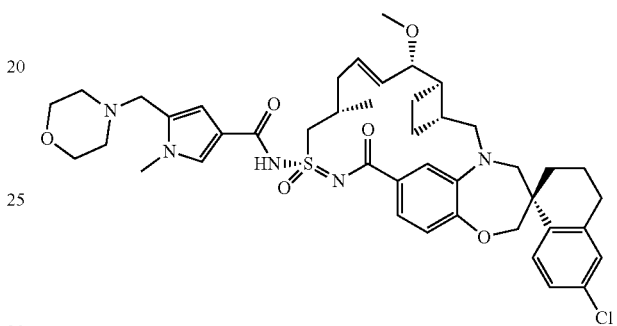

Example 308 was synthesized in the same manner as Example 18 using Example 109 and 1-methyl-5-(morpholinomethyl)-1H-pyrrole-3-carboxylic acid (prepared from 5-formyl-1-methyl-pyrrole-3-carboxylic acid and morpholine using similar procedure to Example 309-step 1). $^1$H NMR (400 MHz, Methanol-d4) δ 7.71 (d, J=1.9 Hz, 1H), 7.51 (d, J=8.5 Hz, 1H), 7.37 (dd, J=8.2 Hz, 1H), 7.28 (s, 1H), 7.01 (dd, J=12.9, 2.1 Hz, 2H), 6.77 (d, J=8.3 Hz, 1H), 6.70 (s, 1H), 6.20 (dd, J=15.1, 7.7 Hz, 1H), 5.73 (dd, J=15.4, 8.2 Hz, 1H), 4.44 (s, 2H), 4.15 (dd, J=14.7, 7.1 Hz, 1H), 4.02-3.85 (m, 3H), 3.80 (s, 4H), 3.78-3.71 (m, 1H), 3.61 (d, J=14.4 Hz, 1H), 3.50 (d, J=14.5 Hz, 1H), 3.14 (dd, J=15.2, 10.7 Hz, 1H), 3.02-2.82 (m, 2H), 2.82-2.65 (m, 1H), 2.65-2.44 (m, 1H), 2.34 (d, J=15.2 Hz, 3H), 2.12-1.96 (m, 1H), 1.96-1.79 (m, 3H), 1.32 (d, J=10.5 Hz, 2H), 1.19 (d, J=6.2 Hz, 3H). LCMS-ESI+: calc'd for $C_{43}H_{54}ClN_5O_6S$: 804.35 (M+H); found: 804.56 (M+H).

Example 309

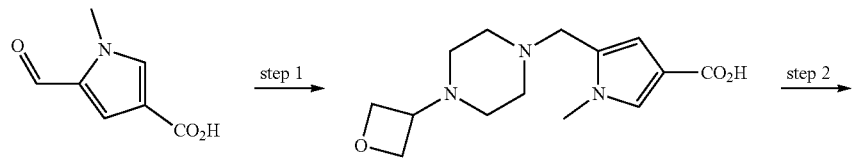

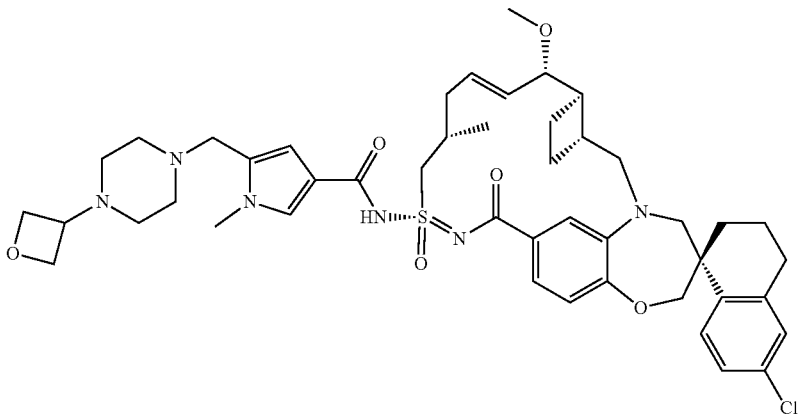

Step 1

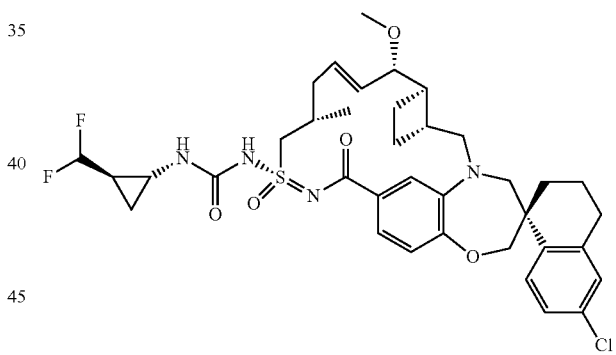

Example 310

1-(Oxetan-3-yl)piperazine was added to a solution of the 5-formyl-1-methyl-pyrrole-3-carboxylic acid (50 mg, 0.327 mmol) in tetrahydrofuran (3 mL). The solution was stirred at room temperature for 2 hours. Sodium borohydride (346 mg, 9 mmol) and methanol (0.5 mL) were added. After 2 h, the reaction was quenched with water (2 mL) and trifluoroacetic acid (0.3 mL). The solution was subjected to preparative HPLC. The fractions containing product were combined and subjected to lyophilization, providing 1-methyl-5-((4-(oxetan-3-yl)piperazin-1-yl)methyl)-1H-pyrrole-3-carboxylic acid. $^1$H NMR (400 MHz, Methanol-d4) δ 7.49 (d, J=1.8 Hz, 1H), 6.75 (d, J=1.8 Hz, 1H), 4.76 (t, J=6.9 Hz, 2H), 4.64 (dd, J=7.0, 5.6 Hz, 2H), 4.23 (s, 2H), 3.83 (t, J=6.1 Hz, 1H), 3.77 (s, 3H), 3.29-3.10 (m, 4H), 2.81 (s, 5H).

Step 2

Example 308 was synthesized in the same manner as Example 18 using Example 109 and 1-methyl-5-((4-(oxetan-3-yl)piperazin-1-yl)methyl)-1H-pyrrole-3-carboxylic acid. 1H NMR (400 MHz, Methanol-d4) δ 7.68 (d, J=1.8 Hz, 1H), 7.63 (d, J=8.6 Hz, 1H), 7.32 (d, J=8.3 Hz, 1H), 7.05 (dd, J=14.4, 2.1 Hz, 2H), 6.98 (s, 3H), 6.93 (s, 2H), 6.84 (d, J=8.2 Hz, 1H), 6.14 (dd, J=15.0, 7.6 Hz, 1H), 5.68 (dd, J=15.4, 8.3 Hz, 1H), 4.78 (t, J=6.9 Hz, 2H), 4.66 (t, J=6.3 Hz, 2H), 4.20 (d, J=14.2 Hz, 3H), 4.01 (s, 2H), 4.00-3.90 (m, 0H), 3.65 (d, J=14.5 Hz, 1H), 3.43 (d, J=14.4 Hz, 1H), 3.20-3.02 (m, 1H), 2.86 (d, J=16.7 Hz, 1H), 2.76 (dq, J=16.7, 8.7, 7.4 Hz, 2H), 2.49 (s, 2H), 2.30 (d, J=15.5 Hz, 2H), 2.22-2.05 (m, 1H), 1.97 (d, J=9.0 Hz, 1H), 1.84 (s, 0H), 1.40 (t, J=12.3 Hz, 1H), 1.17 (d, J=6.1 Hz, 3H). LCMS-ESI+: calc'd for $C_{46}H_{59}ClN_6O_6S$: 859.39 (M+H); found: 859.46 (M+H).

Example 310 was prepared in a similar manner to Example 75 using (1R,2R)-2-(difluoromethyl)cyclopropan-1-amine, triethylamine and Example 109. 1H NMR (400 MHz, Methanol-d4) δ 7.72 (d, J=8.4 Hz, 1H), 7.18 (d, J=8.3 Hz, 1H), 7.15-7.05 (m, 2H), 6.96 (s, 1H), 6.91 (d, J=8.1 Hz, 1H), 6.10-6.00 (m, 1H), 5.83 (td, J=57.3, 4.2 Hz, 1H), 5.61 (dd, J=15.3, 9.0 Hz, 1H), 4.27 (d, J=14.4 Hz, 1H), 4.06 (d, J=1.8 Hz, 2H), 3.84 (d, J=15.1 Hz, 1H), 3.77 (dd, J=9.0, 3.6 Hz, 1H), 3.67 (d, J=14.2 Hz, 1H), 3.30-3.23 (m, 4H), 3.08 (dd, J=15.2, 10.2 Hz, 1H), 2.78 (ddd, J=22.7, 18.6, 10.0 Hz, 3H), 2.45 (dt, J=34.4, 13.8 Hz, 3H), 2.21 (dd, J=14.9, 6.4 Hz, 1H), 2.15-2.04 (m, 1H), 2.04-1.87 (m, 2H), 1.82 (dt, J=21.0, 8.2 Hz, 2H), 1.59-1.48 (m, 1H), 1.43 (t, J=11.9 Hz, 1H), 1.31 (s, 2H), 1.14 (d, J=6.5 Hz, 3H), 1.09 (q, J=6.3 Hz, 1H), 1.04-0.85 (m, 1H). LCMS-ESI+: calc'd for $C_{37}H_{45}ClF_2N_4O_5S$: 731.28 (M+H); found: 731.13 (M+H).

Example 311

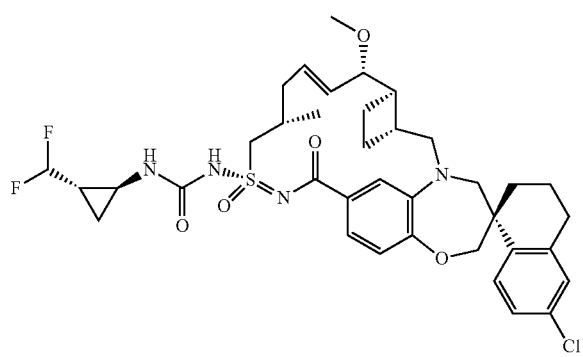 [SMILES: CO[C@H]1/C=C/C[C@H](C)C[S@@](=O)(NC(=O)N[C@H]2C[C@@H]2C(F)F)=NC(=O)c2ccc3c(c2)N(C[C@@H]2CC[C@H]21)C[C@@]1(CCCc2cc(Cl)ccc21)CO3]

Example 311 was prepared in a similar manner as Example 75 using (1S,2S)-2-(difluoromethyl)cyclopropan-1-amine, triethylamine and Example 109. 1H NMR (400 MHz, Methanol-d4) δ 7.78 (d, J=8.5 Hz, 1H), 7.18 (dt, J=9.2, 3.1 Hz, 2H), 7.10 (d, J=2.3 Hz, 1H), 6.93 (d, J=1.9 Hz, 1H), 6.82 (d, J=8.0 Hz, 1H), 6.17 (dd, J=14.9, 7.4 Hz, 1H), 5.84 (td, J=57.6, 4.0 Hz, 1H), 5.48 (dd, J=15.2, 9.3 Hz, 1H), 4.38 (dd, J=14.1, 6.9 Hz, 1H), 4.08-3.97 (m, 2H), 3.88 (d, J=15.0 Hz, 1H), 3.85-3.74 (m, 2H), 3.65 (d, J=14.1 Hz, 1H), 3.26 (m, 4H), 3.01 (dd, J=15.2, 10.0 Hz, 1H), 2.91-2.69 (m, 3H), 2.58 (dd, J=12.3, 6.2 Hz, 1H), 2.41 (dq, J=27.3, 9.2, 8.2 Hz, 2H), 2.18-2.01 (m, 3H), 1.99-1.85 (m, 2H), 1.76 (ddt, J=28.8, 18.5, 9.4 Hz, 2H), 1.55-1.30 (m, 3H), 1.06 (m, 4H), 0.92-0.79 (m, 1H). LCMS-ESI+: calc'd for $C_{37}H_{45}ClF_2N_4O_5S$: 731.28 (M+H); found: 731.02 (M+H).

Example 312

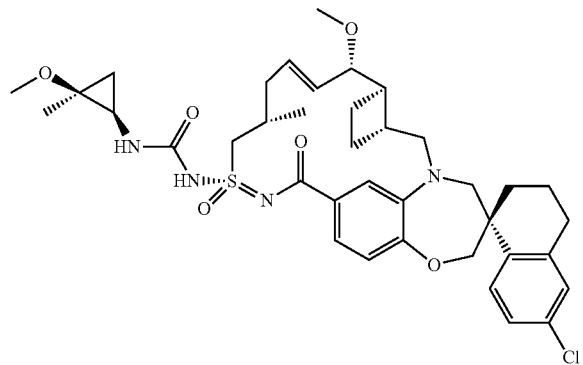 [SMILES: CO[C@H]1/C=C/C[C@H](C)C[S@@](=O)(NC(=O)N[C@@H]2C[C@]2(C)OC)=NC(=O)c2ccc3c(c2)N(C[C@@H]2CC[C@H]21)C[C@@]1(CCCc2cc(Cl)ccc21)CO3]

Example 312 was prepared in a similar manner to Example 75 using (1R,2S)-2-methoxy-2-methylcyclopropan-1-amine, triethylamine and Example 109. The stereochemistry is arbitrarily assigned but not absolute. 1H NMR (400 MHz, Methanol-d4) δ 7.76 (d, J=8.5 Hz, 1H), 7.23 (d, J=8.3 Hz, 1H), 7.18 (dd, J=8.5, 2.3 Hz, 1H), 7.12 (d, J=2.3 Hz, 1H), 7.02 (s, 1H), 6.90 (d, J=8.2 Hz, 1H), 6.06 (dt, J=14.3, 6.8 Hz, 1H), 5.58 (dd, J=15.3, 8.9 Hz, 1H), 4.28 (dd, J=14.9, 6.5 Hz, 1H), 4.13-4.00 (m, 2H), 3.86 (d, J=14.9 Hz, 1H), 3.78 (dd, J=8.9, 3.7 Hz, 1H), 3.68 (d, J=14.2 Hz, 1H), 3.38 (s, 3H), 3.30-3.25 (m, 4H), 3.07 (dd, J=15.2, 10.2 Hz, 1H), 2.90-2.74 (m, 2H), 2.70 (dd, J=8.0, 4.8 Hz, 1H), 2.54-2.43 (m, 1H), 2.38 (t, J=9.1 Hz, 1H), 2.20 (dt, J=14.6, 7.3 Hz, 1H), 2.12 (d, J=13.4 Hz, 2H), 2.01-1.87 (m, 2H), 1.87-1.69 (m, 3H), 1.45 (d, J=12.1 Hz, 1H), 1.39 (s, 3H), 1.31 (s, 1H), 1.13 (d, J=6.7 Hz, 3H), 0.93-0.84 (m, 1H), 0.72 (t, J=5.7 Hz, 1H). LCMS-ESI+: calc'd for $C_{38}H_{49}ClN_4O_6S$: 725.31 (M+H); found: 726.03 (M+H).

Example 313

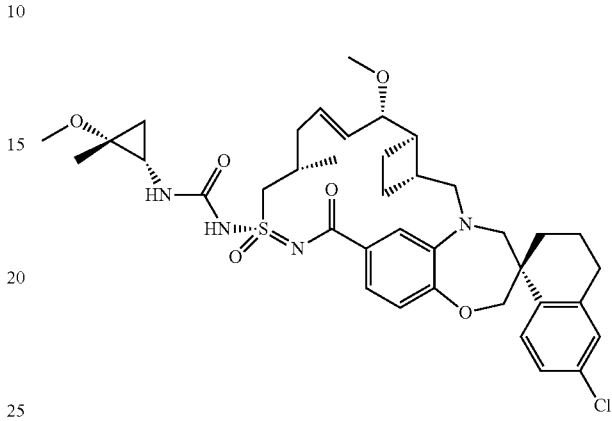

Example 313 was prepared in a similar manner to Example 312 using (1S,2R)-2-methoxy-2-methylcyclopropan-1-amine, triethylamine and Example 109. The stereochemistry is arbitrarily assigned but not absolute. LCMS-ESI+: calc'd for $C_{38}H_{49}ClN_4O_6S$: 725.31 (M+H); found: 726.20 (M+H).

Example 314

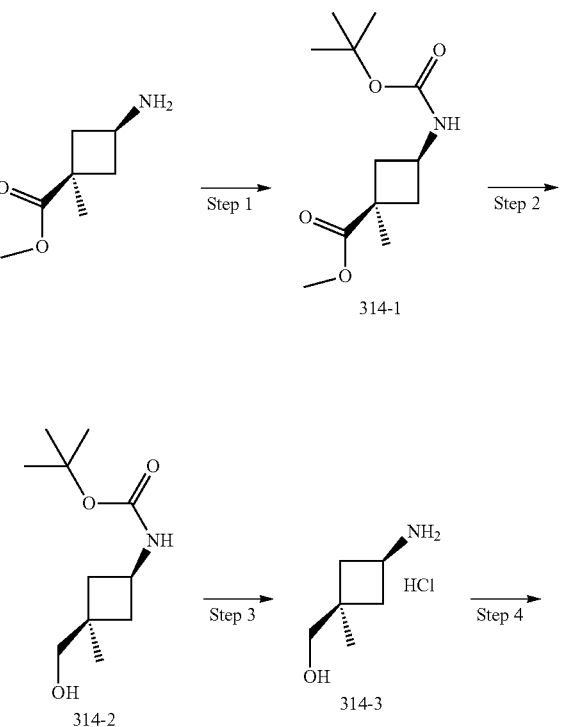

Example 314

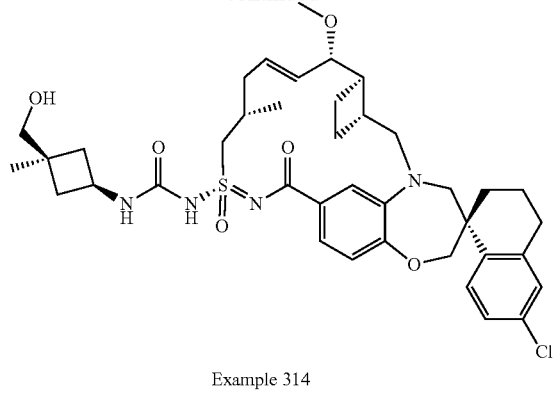

Step 1: Synthesis of 314-1

To the mixture of methyl 3-amino-1-methyl-cyclobutanecarboxylate HCl salt (248 mg, 1.38 mmol) in DCM (6.0 mL) at room temperature was added DIEA (537 mg, 4.15 mmol) followed by di-tert-butyl dicarbonate (362 mg, 1.66 mmol). The resulting mixture was stirred at rom temperature for overnight. The reaction was concentrated, redissolved in EtOAc, washed with 1N HCl, sat. NaHCO$_3$, brine, dried over sodium sulfate, filtered, and concentrated, further dried over the vacuum line to give 314-1. 1H NMR (400 MHz, Chloroform-d) δ 4.88-4.68 (m, 1H), 4.38-4.20 (m, 1H), 3.71 (s, 3H), 2.36-2.24 (m, 4H), 1.45 (s, 9H), 1.42 (s, 3H).

Step 2

Synthesis of 314-2: 314-1 (337 mg, 1.39 mmol) was dissolved in THF (7.0 mL), cooled to 0° C. 1.0 N superhydride in THF (2.77 mL, 2.77 mmol) was added. The reaction was allowed to warm up to room temperature as ice melted overnight. The reaction was slowly quenched with sat. NH$_4$Cl, and diluted with EtOAc. The organic layer was washed with brine, dried over sodium sulfate, filtered, and concentrated to give a crude product. The crude product was purified by combiflash (12 g silica gel, 0-100% EtOAc/Hexanes), detected by ELS detector. Desired fractions were combined and concentrated to give 314-2 (110.0 mg). 1H NMR (400 MHz, Chloroform-d) δ 4.18-4.08 (m, 1H), 3.54 (d, 1H), 3.36 (d, J=2.0 Hz, 1H), 2.09-1.99 (m, 2H), 1.92-1.78 (m, 2H), 1.43 (s, 9H), 1.15-1.09 (m, 3H).

Step 3: Synthesis of 314-3

314-2 (110 mg, 0.51 mmol) was treated with DCM (2.0 mL) and 4 N HCl in 1,4-dioxane (0.5 mL) at rt for 1 hr. The reaction was concentrated, coevaporated with EtOAc (3×3.0 mL) and further dried over the vacuum line to give 314-3.

Step 4

Example 314 was synthesized in the same manner as Example 75 using Example 109 and 314-3 and DIEA. 1H NMR (400 MHz, Methanol-d4) δ 7.70 (d, J=8.6 Hz, 1H), 7.26-7.18 (m, 1H), 7.12-7.03 (m, 2H), 7.00 (s, 1H), 6.88 (d, J=8.2 Hz, 1H), 6.12-6.00 (m, 1H), 5.68-5.56 (m, 1H), 4.32-4.18 (m, 2H), 4.08-3.98 (m, 2H), 3.87-3.74 (m, 3H), 3.66 (d, J=14.2 Hz, 1H), 3.35 (s, 2H), 3.29 (s, 3H), 3.08 (dd, J=15.2, 9.9 Hz, 1H), 2.89-2.70 (m, 2H), 2.59-2.39 (m, 3H), 2.25-2.01 (m, 6H), 1.98-1.74 (m, 8H), 1.46-1.35 (m, 1H), 1.18 (s, 3H), 1.14 (d, J=6.6 Hz, 3H). LCMS-ESI+ (m/z): calcd H+ for C$_{39}$H$_{51}$ClN$_4$O$_6$S: 739.32; found: 738.88.

Example 315

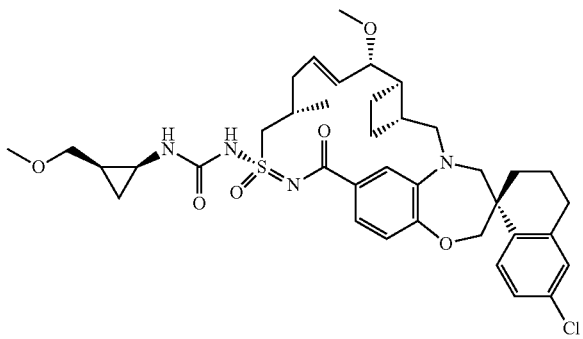 [SMILES: COC[C@@H]1C[C@@H]1NC(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3]

Example 315 was synthesized in the same manner as Example 316, using intermediate 316-3 and Example 109. The absolute configuration of the cis cyclopropane stereocenters has not been determined and is denoted arbitrarily. LCMS-ESI+ (m/z): [M+H]$^+$ calc'd for C$_{38}$H$_{49}$ClN$_4$O$_6$S: 725.3134; found: 724.89. $^1$H NMR (400 MHz, Methanol-t/4) δ 7.73 (d, J=8.5 Hz, 1H), 7.20 (d, J=8.2 Hz, 1H), 7.15 (d, J=8.6 Hz, 1H), 7.09 (d, J=2.2 Hz, 1H), 6.99 (s, 1H), 6.88 (d, J=8.1 Hz, 1H), 6.03 (dd, J=14.9, 7.5 Hz, 1H), 5.57 (dd, J=15.2, 8.9 Hz, 1H), 4.26 (dd, J=14.8, 6.6 Hz, 1H), 4.10-3.98 (m, 2H), 3.83 (d, J=15.0 Hz, 2H), 3.76 (dd, J=8.9, 3.7 Hz, 1H), 3.66 (d, J=14.2 Hz, 1H), 3.54-3.36 (m, 2H), 3.34 (s, 3H), 3.33-3.25 (m, 1H), 3.26 (s, 3H), 3.05 (dd, J=15.2, 10.2 Hz, 1H), 2.87-2.68 (m, 3H), 2.54-2.29 (m, 3H), 2.25-2.04 (m, 3H), 2.02-1.67 (m, 6H), 1.42 (t, J=12.6 Hz, 1H), 1.35-1.22 (m, 1H), 1.12 (d, J=6.4 Hz, 3H), 1.02 (ddd, J=9.0, 7.4, 5.7 Hz, 1H), 0.53 (td, J=6.0, 4.4 Hz, 1H).

Example 316

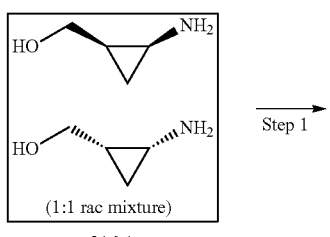

316-1

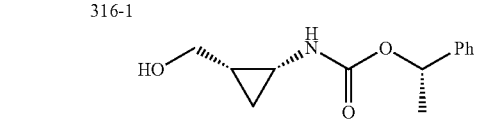

316-2

+  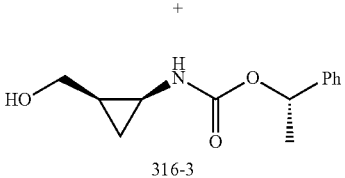

316-3

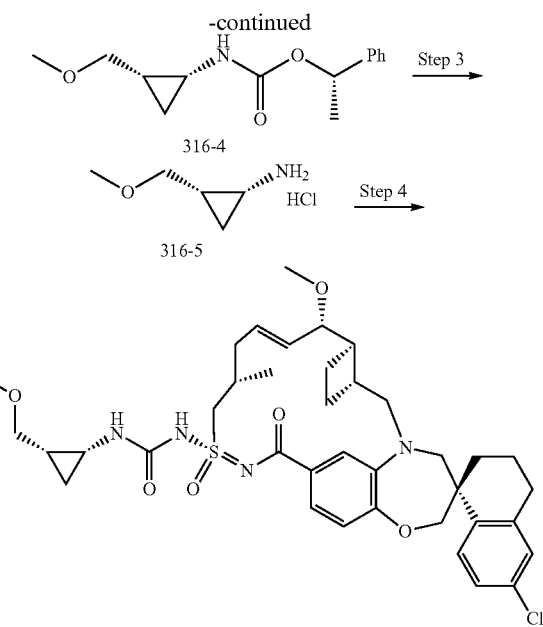

Example 316

Step 1

A solution of rac-[(1R*,2S*)-2-aminocyclopropyl]methanol (1 equiv, 3.44 mmol, 300 mg) in triethylamine (4 equiv, 13.8 mmol, 1.92 mL) and THF (15 mL) was treated with (4-nitrophenyl) [(1S)-1-phenylethyl] carbonate (1 equiv, 3.44 mmol, 989 mg). The reaction mixture was stirred overnight at room temperature, then concentrated and purified by silica gel chromatography (EtOAc/hexanes) to afford the desired product as a mixture of diastereomers 316-2/316-3 (375 mg). The diastereomeric mixture was purified by chiral SFC (IC column, 15% EtOH) to afford 316-2 (RT=1.52 min; 186 mg) and 316-3 (RT=1.14 min; 191 mg). The absolute stereochemistry of 316-2 and 316-3 has not been determined and is denoted arbitrarily.

Intermediate 316-2:

$^1$H NMR (400 MHz, Chloroform-d) δ 7.41-7.27 (m, 5H), 5.81 (q, J=6.6 Hz, 1H), 5.03 (s, 1H), 3.96 (d, J=11.8 Hz, 1H), 3.32 (s, 1H), 3.18 (t, J=11.2 Hz, 1H), 2.62 (q, J=6.9, 6.5 Hz, 1H), 1.53 (d, J=6.6 Hz, 3H), 1.39 (q, J=7.6 Hz, 1H), 0.93 (ddd, J=9.3, 7.2, 5.7 Hz, 1H), 0.28 (td, J=6.3, 4.2 Hz, 1H).

Intermediate 316-3:

$^1$H NMR (400 MHz, Chloroform-d) δ 7.43-7.29 (m, 5H), 5.82 (q, J=6.6 Hz, 1H), 5.02 (s, 1H), 3.87 (d, J=12.2 Hz, 1H), 3.20-2.94 (bs, 1H), 3.03 (t, J=11.2 Hz, 1H), 2.67 (d, J=5.4 Hz, 1H), 1.56 (d, J=6.6 Hz, 3H), 1.37 (ddp, J=13.6, 6.7, 4.0, 3.4 Hz, 1H), 0.93 (dt, J=9.4, 6.7 Hz, 1H), 0.25 (d, J=5.5 Hz, 1H).

Step 2

To a solution of intermediate 316-2 (1 equiv, 0.149 mmol, 35 mg) in CH$_2$Cl$_2$ (0.75 mL) was added sequentially powdered molecular sieves, 4 Å (1 wt equiv, 35 mg), 1,8-bis(dimethylamino)naphthalene (2.5 equiv, 0.372 mmol, 79.7 mg) and 1,8-bis(dimethylamino)naphthalene (2 equiv, 0.298 mmol, 44.0 mg). The reaction mixture was stirred at room temperature for 5 hours, filtered across Celite, and eluted with EtOAc. The filtrate was washed with 1 N HCl, water, and brine then dried with sodium sulfate, filtered and concentrated. The crude reaction mixture was purified by silica gel chromatography (EtOAc/hexanes) to afford the desired intermediate 316-4. $^1$H NMR (400 MHz, Chloroform-d) δ 7.42-7.26 (m, 5H), 5.82 (q, J=6.7 Hz, 1H), 5.26-4.88 (m, 1H), 3.60 (dd, J=10.4, 6.1 Hz, 1H), 3.38-3.22 (m, 1H), 3.35 (s, 3H), 2.72 (tdd, J=6.9, 4.1, 2.0 Hz, 1H), 1.54 (d, J=6.6 Hz, 3H), 1.28 (ddt, J=15.1, 8.6, 6.3 Hz, 1H), 1.00 (q, J=12 Hz, 1H), 0.50 (q, J=5.4 Hz, 1H).

Step 3

Intermediate 316-4 was treated with 4 N HCl/dioxane (1.5 mL), sealed and stirred at room temperature overnight. The reaction mixture was concentrated under a stream of argon, then further dried under high vacuum for 30 minutes to afford crude intermediate 316-5, which was carried on directly to Step 4.

Step 4

A 4-dram vial was charged with Example 109 (1 equiv, 0.017 mmol, 10 mg), diphenyl carbonate (6 equiv, 0.10 mmol, 21.5 mg), N,N-dimethylaminopyridine (4 equiv, 0.067 mmol, 8.2 mg) and MeCN (0.75 mL). The reaction vial was sealed and stirred at room temperature overnight. The reaction mixture was then treated with triethylamine (25 equiv, 0.42 mmol, 0.06 mL), combined with crude intermediate 316-5 from Step 3 and heated to 50° C. for 3 hours. The reaction mixture was cooled to room temperature, concentrated and purified by preparative HPLC (60-100% MeCN in water, 0.1% TFA) to afford Example 316. The absolute configuration of the cis cyclopropane stereocenters has not been determined and is denoted arbitrarily. LCMS-ESI+ (m/z): [M+H]$^+$ calc'd for C$_{38}$H$_{49}$ClN$_4$O$_6$S: 725.3134; found: 724.74. $^1$H NMR (400 MHz, Methanol-d$_4$) δ 7.73 (d, J=8.5 Hz, 1H), 7.25-7.12 (m, 2H), 7.10 (d, J=2.2 Hz, 1H), 6.99 (s, 1H), 6.89 (d, J=8.1 Hz, 1H), 6.09-5.96 (m, 1H), 5.57 (dd, J=15.3, 8.9 Hz, 1H), 4.26 (dd, J=14.8, 6.4 Hz, 1H), 4.11-3.99 (m, 2H), 3.89-3.78 (m, 2H), 3.76 (dd, J=8.9, 3.6 Hz, 1H), 3.66 (d, J=14.2 Hz, 1H), 3.60-3.45 (m, 1H), 3.46-3.37 (m, 1H), 3.35 (s, 3H), 3.30-3.25 (m, 1H), 3.25 (s, 3H), 3.05 (dd, J=15.2, 10.2 Hz, 1H), 2.88-2.67 (m, 3H), 2.54-2.29 (m, 3H), 2.26-2.04 (m, 3H), 2.01-1.66 (m, 6H), 1.42 (t, J=12.3 Hz, 1H), 1.29 (p, J=7.5 Hz, 1H), 1.12 (d, J=6.7 Hz, 3H), 1.02 (ddd, J=9.1, 7.5, 5.7 Hz, 1H), 0.50 (q, J=5.6 Hz, 1H).

Example 317

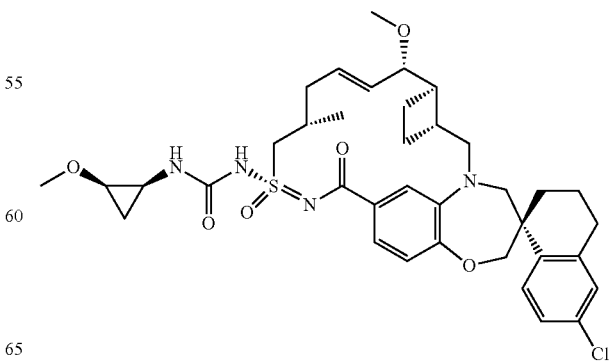

Example 317 was synthesized in the same manner as Example 75, using Example 109 and (1S,2R)-2-methoxycyclopropanamine hydrochloride. Triethylamine (40 equiv) was also added to the reaction mixture (Step 2). LCMS-ESI+ (m/z): [M+H]+ calc'd for $C_{37}H_{47}ClN_4O_6S$: 711.2978; found: 710.98. $^1$H NMR (400 MHz, Methanol-t/4) δ 7.74 (d, J=8.5 Hz, 1H), 7.20 (d, J=8.2 Hz, 1H), 7.16 (dd, J=8.5, 2.3 Hz, 1H), 7.10 (d, J=2.3 Hz, 1H), 7.00 (s, 1H), 6.88 (d, J=8.2 Hz, 1H), 6.03 (dd, J=14.9, 7.4 Hz, 1H), 5.57 (dd, J=15.3, 8.9 Hz, 1H), 4.26 (dd, J=14.8, 6.5 Hz, 1H), 4.12-3.97 (m, 2H), 3.84 (d, J=14.9 Hz, 2H), 3.76 (dd, J=8.9, 3.7 Hz, 1H), 3.66 (d, J=14.2 Hz, 1H), 3.42 (s, 3H), 3.30-3.26 (m, 2H), 3.25 (s, 3H), 3.05 (dd, J=15.2, 10.2 Hz, 1H), 2.87-2.69 (m, 3H), 2.55-2.29 (m, 3H), 2.25-2.04 (m, 3H), 2.02-1.64 (m, 6H), 1.42 (t, J=12.2 Hz, 1H), 1.12 (d, J=6.6 Hz, 3H), 0.96 (dt, J=8.2, 6.8 Hz, 1H), 0.55 (q, J=4.6 Hz, 1H).

Example 318

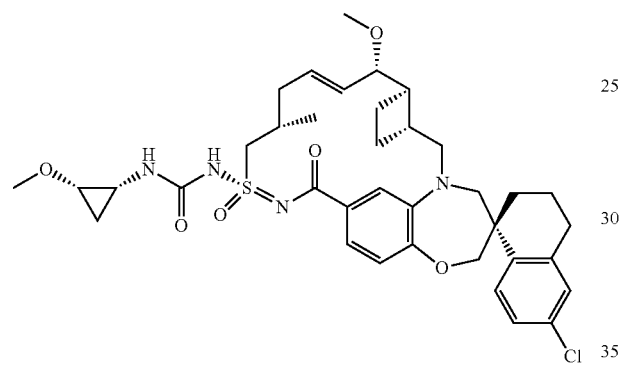

Example 318 was synthesized in the same manner as Example 75, using Example 109 and (1R,2S)-2-methoxycyclopropanamine hydrochloride. Triethylamine (40 equiv) was also added to the reaction mixture (Step 2). LCMS-ESI+ (m/z): [M+H]+ calc'd for $C_{37}H_{47}ClN_4O_6S$: 711.2978; found: 710.64. $^1$H NMR (400 MHz, Methanol-d$_4$) δ 7.73 (d, J=8.5 Hz, 1H), 7.20 (d, J=8.1 Hz, 1H), 7.15 (dd, J=8.5, 2.3 Hz, 1H), 7.09 (d, J=2.3 Hz, 1H), 6.99 (s, 1H), 6.88 (d, J=8.2 Hz, 1H), 6.03 (dd, J=14.9, 7.6 Hz, 1H), 5.57 (dd, J=15.3, 8.9 Hz, 1H), 4.26 (dd, J=14.8, 6.5 Hz, 1H), 4.11-3.97 (m, 2H), 3.83 (d, J=14.9 Hz, 2H), 3.76 (dd, J=8.9, 3.7 Hz, 1H), 3.66 (d, J=14.2 Hz, 1H), 3.41 (s, 3H), 3.29-3.26 (m, 2H), 3.25 (s, 3H), 3.05 (dd, J=15.2, 10.2 Hz, 1H), 2.87-2.66 (m, 3H), 2.56-2.29 (m, 3H), 2.25-2.04 (m, 3H), 2.01-1.66 (m, 6H), 1.41 (t, J=12.4 Hz, 1H), 1.11 (d, J=6.4 Hz, 3H), 0.97 (q, J=7.0 Hz, 1H), 0.59 (dd, J=7.5, 4.0 Hz, 1H).

Example 319

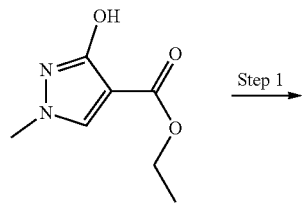 Step 1

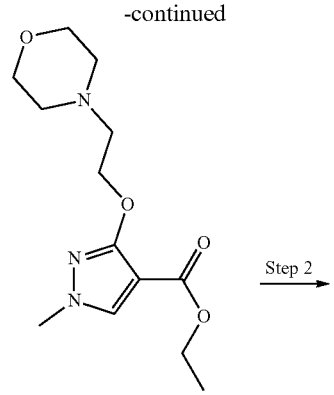 Step 2

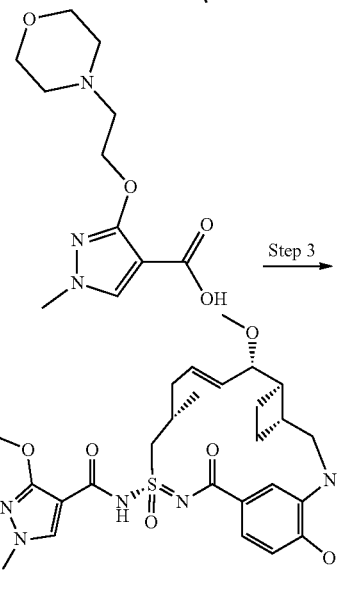

Step 3

Step 1

A round bottom flask was charged with starting ethyl 3-hydroxy-1-methyl-4-pyrazolecarboxylate (100 mg, 0.588 mmol). The flask was placed under high vacuum for 5 min, then backfilled with nitrogen atmosphere. DMF (3 mL) was added, followed by sodium hydride (60% dispersion in mineral oil, 27 mg, 1.2 equiv.) at 20° C. The flask was stirred at 20° C. for 60 min, then 4-(2-iodoethyl)morpholine (184 mg, 1.3 equiv.) was added. The reaction was stirred at 80° C. for 16 hr. The reaction was removed from heating and allowed to cool to 20° C., then the reaction was quenched with water and extracted five times into ethyl acetate. The combined organic phases were washed with brine, dried over magnesium sulfate, filtered and concentrated in vacuo to provide 120 mg crude product. Silica gel TLC (95:5 dichloromethane:methanol) of the crude product indicated complete consumption of starting aminopyrazole (Rf ~0.60) and one new UV-active product (Rf 0.50). The resulting residue was dissolved in dichloromethane and purified by flash column chromatography (silica gel, 12 g, 0 to 10% methanol in dichloromethane). The major UV-active product eluted at 5% dichloromethane. Fractions were assayed by silica gel TLC. The fractions containing the major UV-active product were collected and concentrated in vacuo to give ethyl 1-methyl-3-(2-morpholinoethoxy)-1H-pyrazole-4-carboxylate (120 mg). $^1$H NMR (400 MHz, Chloroform-d) δ 7.63 (s, 1H), 4.37 (t, J=5.7 Hz, 2H), 4.21 (q, J=7.1 Hz, 2H), 3.71 (s, 3H), 3.72-3.69 (m, 4H), 2.82 (t, J=5.7 Hz, 2H), 2.61 (t, J=4.7 Hz, 4H), 1.28 (t, J=7.1 Hz, 3H). LCMS-ESI+ (m/z): [M+H]$^+$ calculated for $C_{13}H_{21}N_3O_4$: 284.2; found: 284.1.

Step 2

To a glass screwtop vial charged with ethyl 1-methyl-3-(2-morpholinoethoxy)-1H-pyrazole-4-carboxylate (120 mg, 0.424 mmol) was added THF (4.2 mL), then sodium hydroxide (2 M in water, 0.96 mL). The resulting mixture was stirred vigorously in a metal heating block warmed to 60° C. for 12 hr, at which point silica gel TLC (95:5 dichloromethane:methanol) indicated nearly complete consumption of starting ethyl ester. The reaction was quenched with 1 N HCl (approx. 2 mL), added dropwise until pH 4-5 by pH paper. The resulting mixture was extracted three times with ethyl acetate. Then the aqueous phase was concentrated in vacuo to give 1-methyl-3-(2-morpholinoethoxy)-1H-pyrazole-4-carboxylic acid, in at least 95% purity by NMR, contaminated with an unidentified amount of sodium chloride (60 mg). $^1$H NMR (400 MHz, Methanol-$d_4$) δ 7.80 (s, 1H), 4.49 (t, J=4.9 Hz, 2H), 3.88 (t, J=4.6 Hz, 4H), 3.74 (s, 3H), 3.27 (t, J=5.0 Hz, 2H), 3.11 (t, J=4.5 Hz, 4H). LCMS-ESI+ (m/z): [M+H]$^+$ calculated for $C_{11}H_{17}N_3O_4$: 256.1; found: 256.1.

Step 3

Example 319 was prepared in a similar manner as Example 18 using 1-methyl-3-(2-morpholinoethoxy)-1H-pyrazole-4-carboxylic acid and Example 109. $^1$H NMR (400 MHz, Acetonitrile-$d_3$) δ 7.98 (s, 1H), 7.71 (d, J=8.5 Hz, 1H), 7.30 (dd, J=8.2, 1.9 Hz, 1H), 7.22 (d, J=2.0 Hz, 1H), 7.19 (dd, J=8.5, 2.4 Hz, 1H), 7.13 (d, J=2.3 Hz, 1H), 6.90 (d, J=8.3 Hz, 1H), 6.04 (dt, J=14.5, 6.9 Hz, 1H), 5.58 (dd, J=15.6, 7.6 Hz, 1H), 4.66 (dtt, J=13.0, 9.4, 4.6 Hz, 2H), 4.06 (d, J=12.2 Hz, 1H), 4.04-3.97 (m, 2H), 3.88 (dd, J=14.8, 7.3 Hz, 1H), 3.83-3.77 (m, 1H), 3.75 (s, 3H), 3.71 (d, J=14.3 Hz, 5H), 3.60 (s, 2H), 3.38 (d, J=14.4 Hz, 1H), 3.21 (s, 3H), 3.07 (dd, J=15.2, 10.8 Hz, 3H), 2.86-2.63 (m, 3H), 2.52 (dt, J=18.7, 7.6 Hz, 2H), 2.41 (td, J=9.0, 4.2 Hz, 1H), 2.34-2.21 (m, 1H), 2.16 (dt, J=15.0, 7.6 Hz, 1H), 2.09-2.00 (m, 1H), 1.90 (dd, J=9.1, 5.1 Hz, 3H), 1.84-1.60 (m, 5H), 1.41 (dt, J=14.8, 7.7 Hz, 1H), 1.06 (d, J=6.9 Hz, 3H). LCMS-ESI+ (m/z): [M+H]$^+$ calculated for $C_{43}H_{55}ClN_6O_7S$: 835.4; found: 835.3.

Example 320

Example 320 was synthesized in the same manner as Example 75 using Example 109 and 4-methoxypiperidine. 1H NMR (400 MHz, Methanol-d4) δ 7.75 (d, J=8.5 Hz, 1H), 7.19 (dd, J=8.5, 2.3 Hz, 1H), 7.14-7.07 (m, 2H), 6.94 (d, J=8.2 Hz, 1H), 6.88 (d, J=2.0 Hz, 1H), 5.96 (dt, J=14.2, 6.7 Hz, 1H), 5.58 (dd, J=15.2, 9.3 Hz, 1H), 4.38 (dd, J=14.9, 6.3 Hz, 1H), 4.13-4.04 (m, 2H), 4.04-3.89 (m, 2H), 3.85 (d, J=15.2 Hz, 1H), 3.76 (dd, J=9.3, 3.7 Hz, 1H), 3.67 (d, J=14.1 Hz, 1H), 3.63-3.54 (m, 1H), 3.52-3.43 (m, 1H), 3.39 (s, 3H), 3.31-3.30 (m, 1H), 3.28-3.24 (m, 4H), 3.08 (dd, J=15.3, 10.3 Hz, 1H), 2.87-2.71 (m, 2H), 2.54-2.42 (m, 2H), 2.38-2.27 (m, 1H), 2.22-2.06 (m, 3H), 1.99-1.69 (m, 9H), 1.58-1.39 (m, 3H), 1.14 (d, J=6.6 Hz, 3H). LCMS-ESI+ (m/z): calcd H+ for $C_{39}H_{51}ClN_4O_6S$: 739.32; found: 738.84.

Example 321

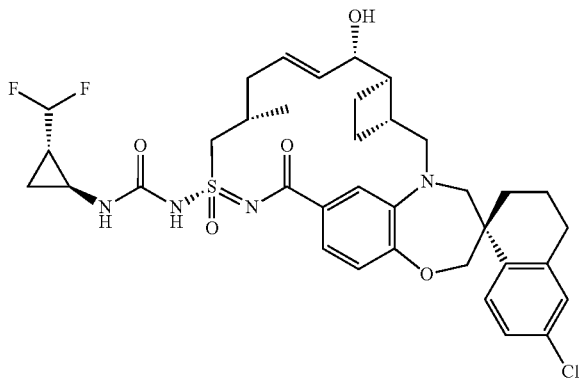 [SMILES: C[C@H]1C/C=C/[C@H](O)[C@@H]2CC[C@H]2CN2C[C@@]3(CCCc4cc(Cl)ccc43)COc3ccc(cc32)C(=O)N=[S@](=O)(NC(=O)N[C@H]2C[C@@H]2C(F)F)C1]

Example 321 was synthesized in the same manner as Example 75 using trans-2-(difluoromethyl)cyclopropan-1-amine hydrochloride and intermediate 266-2. 1H NMR (400 MHz, Methanol-d4) δ 7.72 (d, J=8.5 Hz, 1H), 7.15 (t, J=9.9 Hz, 2H), 7.09 (s, 1H), 6.99 (s, 1H), 6.89 (d, J=8.2 Hz, 1H), 5.94 (d, J=13.4 Hz, 1H), 5.81 (d, J=4.2 Hz, 1H), 5.78-5.64 (m, 1H), 4.18 (t, J=10.8 Hz, 2H), 4.10-3.99 (m, 2H), 3.74 (dd, J=66.1, 14.7 Hz, 3H), 3.17-2.97 (m, 1H), 2.77 (d, J=22.1 Hz, 4H), 2.36 (s, 4H), 2.21-2.02 (m, 3H), 1.96 (d, J=21.9 Hz, 3H), 1.86-1.65 (m, 1H), 1.59-1.36 (m, 2H), 1.13 (d, J=6.3 Hz, 4H), 1.06 (q, J=6.5 Hz, 1H), 0.92 (s, 1H). LCMS-ESI+ (m/z): [M+H]+ calcd for $C_{36}H_{43}ClF_2N_4O_5S$: 717.26; found: 716.77.

Example 322

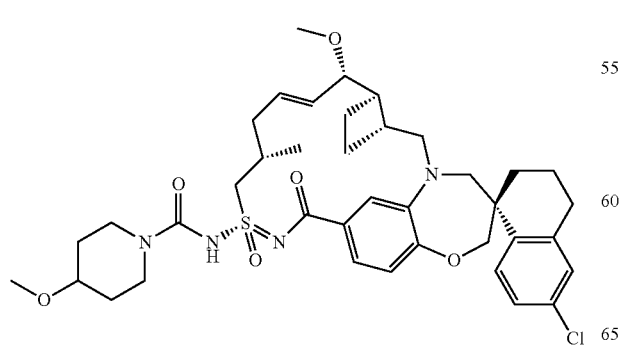

Example 322 was synthesized in the same manner as Example 75 using (1R,3R)-3-methoxycyclopentan-1-amine hydrochloride and Example 109. 1H NMR (400 MHz, DMSO-d6) δ 7.65 (d, J=8.5 Hz, 1H), 7.28 (dd, J=8.5, 2.4 Hz, 1H), 7.18 (d, J=2.3 Hz, 1H), 7.03 (dd, J=8.1, 1.8 Hz, 1H), 6.94 (d, J=8.1 Hz, 1H), 6.84 (d, J=2.0 Hz, 1H), 5.86 (dt, J=14.4, 6.8 Hz, 1H), 5.49 (dd, J=15.2, 8.9 Hz, 1H), 4.20-3.87 (m, 4H), 3.84-3.53 (m, 8H), 3.24 (s, 4H), 3.13 (s, 3H), 3.02 (dd, J=15.3, 10.4 Hz, 1H), 2.89-2.60 (m, 2H), 2.44-2.30 (m, 2H), 2.29-2.05 (m, 2H), 2.04-1.56 (m, 9H), 1.39 (td, J=17.2, 14.6, 9.7 Hz, 1H), 1.02 (d, J=6.8 Hz, 3H). LCMS-ESI+ (m/z): [M+H]+ calcd for C39H51ClN4O6S: 739.32; found: 738.81.

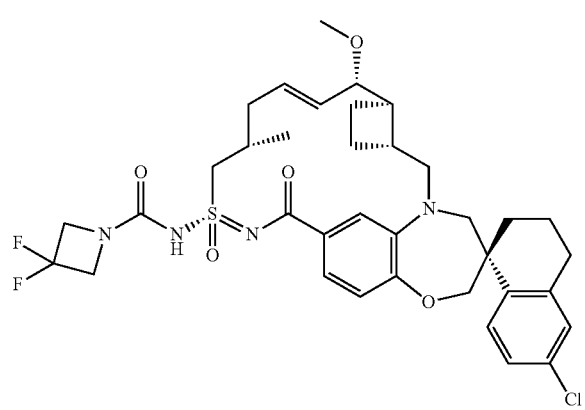 [SMILES: CO[C@H]1/C=C/C[C@H](C)C[S@@](=O)(NC(=O)N2CC(F)(F)C2)=NC(=O)c2ccc3c(c2)N(C[C@@H]2CC[C@H]21)C[C@@]1(CCCc2cc(Cl)ccc21)CO3]

Example 323 was synthesized in a manner similar to Example 244 using 106-4 instead of 240-1 and using 3,3-difluoroazetidin hydrochloride instead of 3-methoxyazetidine hydrochloride. 1H NMR (400 MHZ, Acetone-d6) δ 7.77 (d, J=8.6 Hz, 1H), 7.28-7.20 (m, 1H), 7.17-6.92 (m, 4H), 6.05-5.88 (m, 1H), 5.58 (dd, J=15.3, 9.0 Hz, 1H), 4.36 (t, J=12.5 Hz, 4H), 4.12 (d, J=12.1 Hz, 1H), 4.08 (d, J=12.0 Hz, 1H), 3.88 (d, J=15.1 Hz, 1H), 3.82-3.61 (m, 2H), 3.54 (d, J=13.5 Hz, 1H), 3.35 (d, J=14.2 Hz, 1H), 3.21 (s, 3H), 3.15 (dd, J=15.4, 10.3 Hz, 1H), 2.89-1.53 (m, 15H), 1.53-1.38 (m, 1H), 1.13 (d, J=6.6 Hz, 3H). LCMS: 717.5.

Example 324

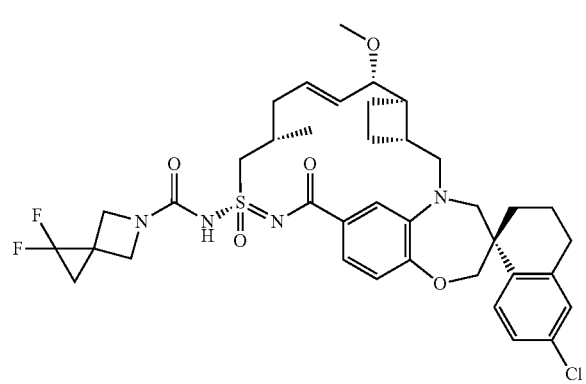 [SMILES: CO[C@H]1/C=C/C[C@H](C)C[S@@](=O)(NC(=O)N2CC3(C2)CC3(F)F)=NC(=O)c2ccc3c(c2)N(C[C@@H]2CC[C@H]21)C[C@@]1(CCCc2cc(Cl)ccc21)CO3]

Example 324 was synthesized in a manner similar to Example 244 using 106-4 instead of 240-1 and using 1,1-difluoro-5-azaspiro[2.3]hexane hydrochloride instead of 3-methoxyazetidine hydrochloride. 1H NMR (400 MHz, Acetone-d6) δ 7.77 (d, J=8.6 Hz, 1H), 7.25 (dd, J=8.5, 2.4 Hz, 1H), 7.14 (d, J=2.4 Hz, 1H), 7.10 (d, J=8.2 Hz, 1H), 7.01 (d, J=1.8 Hz, 1H), 6.97 (d, J=8.1 Hz, 1H), 5.98 (dt, J=14.1, 6.6 Hz, 1H), 5.58 (dd, J=15.3, 8.9 Hz, 1H), 4.45-3.94 (m, 6H), 3.89 (d, J=15.1 Hz, 1H), 3.80-3.67 (m, 2H), 3.58-3.40 (m, 1H), 3.35 (d, J=14.2 Hz, 1H), 3.21 (s, 3H), 3.15 (dd, J=15.4, 10.4 Hz, 1H), 2.96-0.77 (m, 18H), 1.14 (d, J=6.5 Hz, 3H). LCMS: 742.9.

Example 325

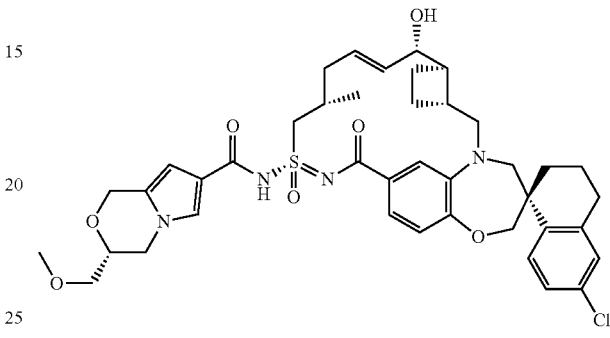

Example 325 was synthesized in a manner similar to Example 214 using Intermediate 359-4 instead of 106-4. 1H NMR (400 MHz, Acetone-d6) δ 7.79 (d, J=8.5 Hz, 1H), 7.51 (s, 1H), 7.41-7.32 (m, 2H), 7.25 (dd, J=8.5, 2.3 Hz, 1H), 7.15 (s, 1H), 6.94 (d, J=8.2 Hz, 1H), 6.35 (s, 1H), 6.09-5.97 (m, 1H), 5.87 (dd, J=15.8, 6.2 Hz, 1H), 4.96 (d, J=14.5 Hz, 1H), 4.75 (d, J=14.5 Hz, 1H), 4.32-3.42 (m, 12H), 3.39 (s, 3H), 3.15 (dd, J=15.2, 10.5 Hz, 1H), 2.88-1.39 (m, 16H), 1.15 (d, J=6.4 Hz, 3H). LCMS: 777.1.

Example 326

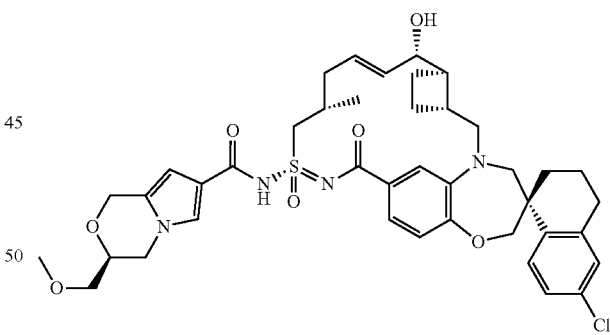

Example 326 was synthesized in a manner similar to Example 214 using Intermediate 359-4 instead of 106-4 and using (S)-2-(methoxymethyl)oxirane instead of (R)-2-(methoxymethyl)oxirane. 1H NMR (400 MHz, Acetone-d6) δ 7.79 (d, J=8.6 Hz, 1H), 7.55-7.47 (m, 1H), 7.39-7.32 (m, 2H), 7.25 (dd, J=8.5, 2.4 Hz, 1H), 7.14 (d, J=2.3 Hz, 1H), 6.94 (d, J=8.1 Hz, 1H), 6.35 (s, 1H), 6.10-5.95 (m, 1H), 5.87 (dd, J=15.7, 6.3 Hz, 1H), 4.96 (d, J=14.5 Hz, 1H), 4.75 (d, J=14.6 Hz, 1H), 4.35-3.85 (m, 8H), 3.75 (d, J=14.5 Hz, 1H), 3.65 (dd, J=10.4, 5.3 Hz, 1H), 3.56 (dd, J=10.4, 4.8 Hz, 1H), 3.45 (d, J=14.4 Hz, 1H), 3.39 (s, 3H), 3.15 (dd, J=15.2, 10.5 Hz, 1H), 2.84-1.65 (m, 15H), 1.53-1.42 (m, 1H), 1.15 (d, J=6.4 Hz, 3H). LCMS: 777.1.

Example 327

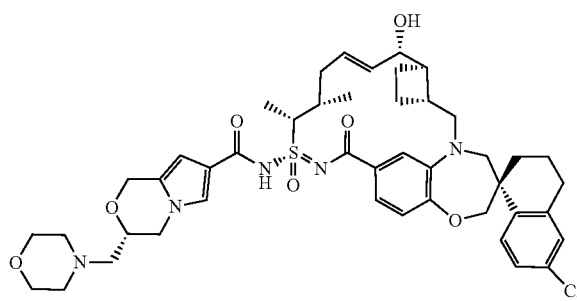

Example 327 was synthesized in a manner similar to Example 229 using morpholine instead of (R)-octahydropyrazino[2,1-c][1,4]oxazine dihydrochloride. 1H NMR (400 MHz, Acetone-d6) δ 7.78 (d, J=8.5 Hz, 1H), 7.44 (s, 1H), 7.29-7.17 (m, 3H), 7.15 (d, J=2.4 Hz, 1H), 7.00 (d, J=8.0 Hz, 1H), 6.32 (s, 1H), 5.95-5.80 (m, 1H), 5.74 (dd, J=15.4, 7.3 Hz, 1H), 4.94 (d, J=14.5 Hz, 1H), 4.84 (d, J=14.5 Hz, 1H), 4.67-1.71 (m, 35H), 1.55 (d, J=7.0 Hz, 3H), 1.54-1.42 (m, 1H), 1.08-1.00 (m, 3H). LCMS: 846.1.

Example 328

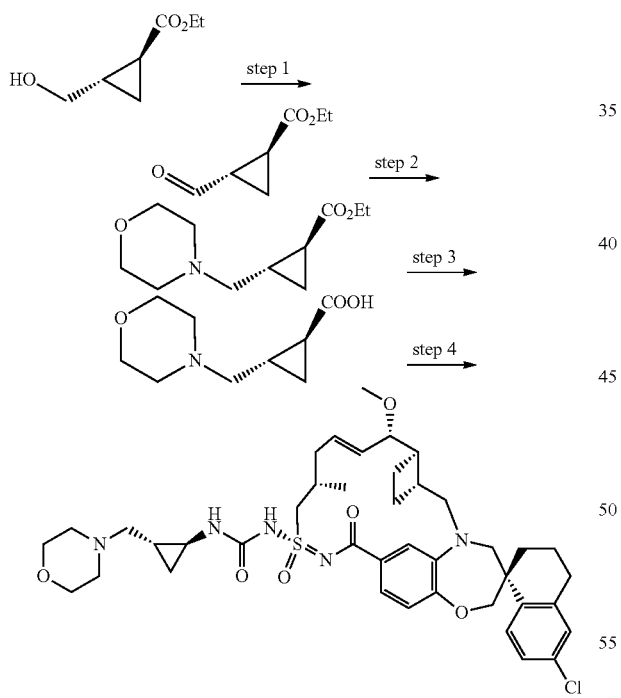

Step 1: Preparation of ethyl (1S,2S)-2-formylcyclopropane-1-carboxylate

The reaction mixture of ethyl rac-(1S,2S)-2-(hydroxymethyl)cyclopropanecarboxylate (110 mg, 0.76 mmol), Dess-Martin Periodinane (388.34 mg, 0.92 mmol) in DCM (4.0 mL) was stirred at rt overnight. The reaction mixture was washed with 1% $Na_2S_2O_4$, sat. $NaHCO_3$, extracted with DCM, dried over $MgSO_4$, filtered, concentrated, and the residue was purified by silica gel column (0-50% EtOAc/hexane) to give the product.

Step 2: Preparation of Ethyl (1S,2S)-2-(morpholinomethyl)cyclopropane-1-carboxylate To a solution of ethyl (1S,2S)-2-formylcyclopropane-1-carboxylate (100 mg, 0.7 mmol) in DCM (3.0 mL) was added morpholine (0.08 mL, 0.93 mmol) at 0° C. Then to the mixture was added sodium triacetoxyborohydride (0.22 g, 1.06 mmol). The reaction mixture was stirred at rt overnight. The reaction mixture was purified by silica gel chromatography (0-100% EtOAc/hexane, then 0-15% DCM/MeOH) to give the product.

Step 3: Preparation of (1S,2S)-2-(morpholinomethyl)cyclopropane-1-carboxylic Acid The reaction mixture of ethyl (1S,2S)-2-(morpholinomethyl) cyclopropanecarboxylate (80 mg, 0.375 mol), 2 M NaOH (0.38 mL) in MeOH (2 mL) and $H_2O$ (0.5 mL) was heated at 45° C. overnight. The reaction mixture was concentrated, azeotroped with toluene (×3) to remove moisture and go to next step without purification.

Step 4: Preparation of Example 328

The reaction mixture of (1S,2S)-2-(morpholinomethyl) cyclopropane-1-carboxylic acid (60 mg, 0.32 mmol), diphenyl phosphoryl azide (94 mg, 0.341 mmol), trimethylamine (35 mg, 0.352 mmol) in toluene (1.0 mL) was stirred at 100° C. for 2 h. Then the reaction mixture was cooled down to rt. To the mixture was added Example 109 and the reaction mixture was stirred at 45° C. overnight. The reaction mixture was concentrated, the residue was purified by reserve phase HPLC (10-100% acetonitrile/$H_2O$, containing 0.1% TFA) to give the product. 1H NMR (400 MHz, Methanol-d4) δ 7.74 (d, J=8.5 Hz, 1H), 7.18 (dd, J=8.5, 2.4 Hz, 1H), 7.12 (q, J=2.9, 2.2 Hz, 2H), 6.97 (d, J=2.0 Hz, 1H), 6.92 (d, J=8.1 Hz, 1H), 6.01 (dt, J=14.4, 6.8 Hz, 1H), 5.59 (dd, J=15.3, 9.0 Hz, 1H), 4.30 (dd, J=14.9, 6.5 Hz, 1H), 4.18-3.99 (m, 4H), 3.84 (dd, J=14.0, 8.7 Hz, 3H), 3.80-3.61 (m, 4H), 3.53-3.41 (m, 2H), 3.27 (s, 4H), 3.08 (dd, J=15.2, 10.3 Hz, 1H), 2.95-2.61 (m, 4H), 2.58-2.29 (m, 4H), 2.28-2.06 (m, 3H), 2.04-1.69 (m, 6H), 1.45 (t, J=12.1 Hz, 1H), 1.39-1.23 (m, 2H), 1.12 (dd, J=15.0, 5.6 Hz, 3H), 0.92 (dt, J=7.9, 5.8 Hz, 1H). LCMS-ESI+ (m/z): [M+H]+ calcd for $C_{41}H_{54}ClN_5O_6S$: 780.35; found: 780.39.

Example 329

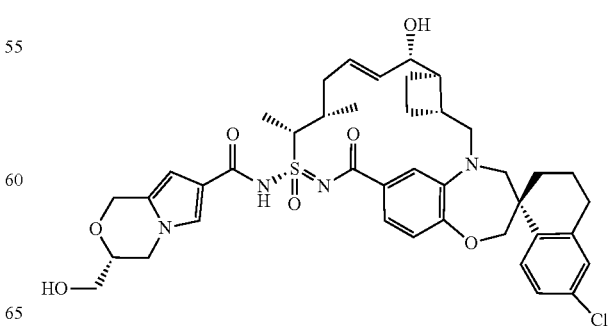

389

Example 329 was synthesized in a manner similar to Example 167 using 229-2 instead of 167-2 and using Intermediate 359-4 instead of 106-4. 1H NMR (400 MHz, Acetone-d6) δ 7.77 (d, J=8.6 Hz, 1H), 7.50-6.85 (m, 6H), 6.28 (s, 1H), 6.06-5.56 (m, 2H), 4.91 (d, J=14.5 Hz, 1H), 4.71 (d, J=14.5 Hz, 1H), 4.49-2.97 (m, 13H), 2.81-1.13 (m, 19H), 1.13-0.96 (m, 3H). LCMS: 777.4.

Example 330

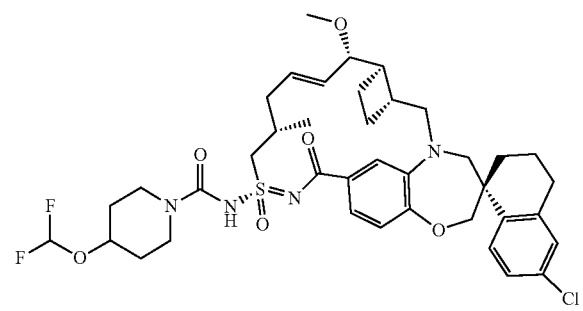 [SMILES: CO[C@H]1/C=C/C[C@H](C)C[S@@](=O)(NC(=O)N2CCC(OC(F)F)CC2)=NC(=O)c2ccc3c(c2)N(C[C@@H]2CC[C@H]21)C[C@@]1(CCCc2cc(Cl)ccc21)CO3]

Example 330 was synthesized in the same manner as Example 75 using Example 109 and 4-(difluoromethoxy)piperidine. 1H NMR (400 MHz, Methanol-d4) δ 7.75 (d, J=8.5 Hz, 1H), 7.19 (dd, J=8.5, 2.4 Hz, 1H), 7.15-7.06 (m, 2H), 6.94 (d, J=8.1 Hz, 1H), 6.88 (d, J=2.0 Hz, 1H), 5.97 (dt, J=14.2, 6.7 Hz, 1H), 5.58 (dd, J=15.2, 9.2 Hz, 1H), 4.44-4.33 (m, 2H), 4.12-4.03 (m, 2H), 4.00-3.81 (m, 3H), 3.76 (dd, J=9.3, 3.7 Hz, 1H), 3.70-3.55 (m, 2H), 3.28-3.24 (m, 4H), 3.08 (dd, J=15.3, 10.3 Hz, 1H), 2.89-2.71 (m, 2H), 2.54-2.42 (m, 2H), 2.39-2.27 (m, 1H), 2.22-2.06 (m, 3H), 1.97-1.87 (m, 5H), 1.86-1.62 (m, 6H), 1.51-1.38 (m, 1H), 1.14 (d, J=6.6 Hz, 3H). LCMS-ESI+ (m/z): calcd H+ for $C_{39}H_{49}ClF_2N_4O_6S$: 775.30; found: 774.79.

Example 331

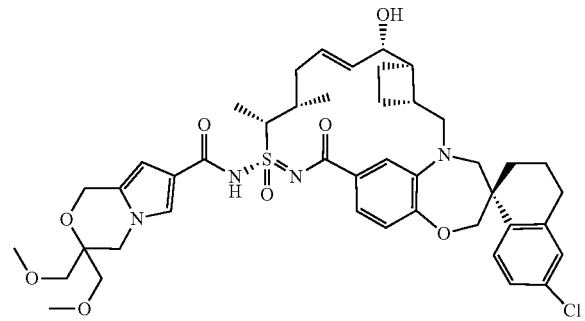 [SMILES: COCC1(COC)Cn2cc(C(=O)N[S@@]3(=O)=NC(=O)c4ccc5c(c4)N(C[C@@H]4CC[C@H]4[C@@H](O)/C=C/C[C@H](C)[C@H]3C)C[C@@]3(CCCc4cc(Cl)ccc43)CO5)cc2CO1]

Example 331 was synthesized in a manner similar to Example 255 using 239-3 instead of 255-3. 1H NMR (400 MHz, Acetone-d6) δ 7.79 (d, J=8.5 Hz, 1H), 7.61-6.91 (m, 8H), 6.34 (s, 1H), 6.17-5.58 (m, 2H), 4.79 (s, 2H), 4.24-2.88 (m, 12H), 4.05 (s, 4H), 3.35 (s, 6H), 2.82-1.25 (m, 18H), 1.11-1.03 (m, 3H). LCMS: 835.3.

390

Example 332

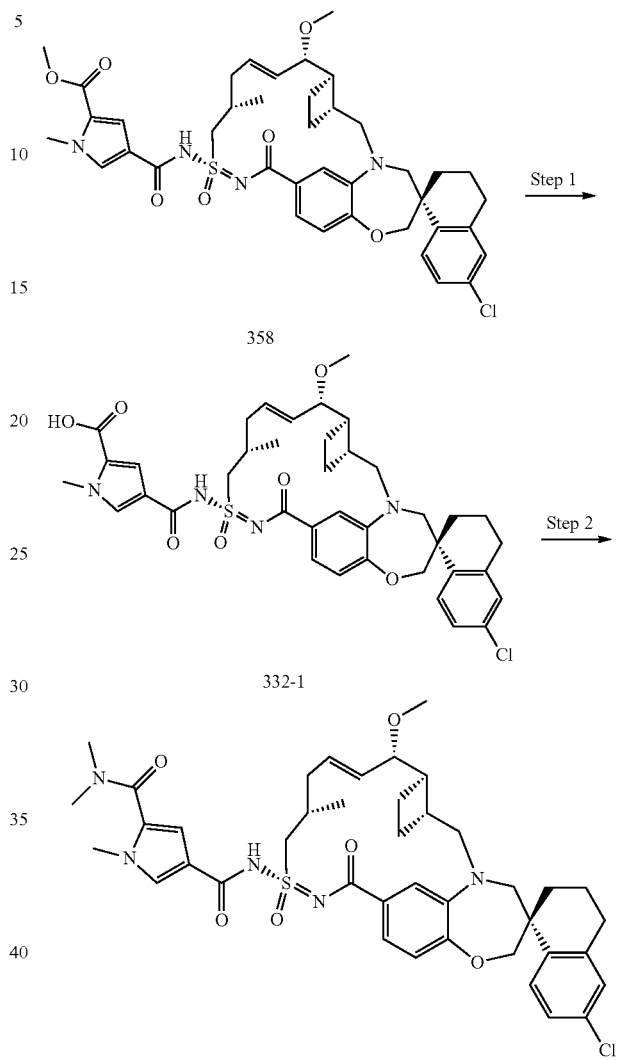

Step 1

To a stirred solution of Example 358 (25 mg, 0.033 mmol) in methanol (5 mL) was added 1N of NaOH (1 mL) and stirred at rt for 24 h. 1 N HCl (1 mL) was added to the reaction mixture and the reaction mixture was concentrated under reduced pressure. Water was added and the mixture was extracted with dichloromethane. The organic phase was dried over anhydrous magnesium sulfate and the solvent was removed under reduced pressure to give intermediate 332-1.

Step 2

Example 332 was synthesized by coupling intermediate 332-1 with dimethyl amine using EDCI/DMAP in DCM. 1H NMR (400 MHz, Chloroform-d) δ 7.75 (d, J=8.5 Hz, 1H), 7.44 (d, J=1.8 Hz, 1H), 7.21 (dd, J=8.4, 2.3 Hz, 1H), 7.11 (d, J=2.4 Hz, 1H), 6.97 (d, J=8.2 Hz, 1H), 6.87 (d, J=1.8 Hz, 1H), 5.96 (dt, J=13.8, 6.4 Hz, 1H), 5.59 (dd, J=15.4, 8.1 Hz, 1H), 4.37-4.00 (m, 2H), 3.86 (s, 2H), 3.75 (d, J=12.3 Hz, 1H), 3.38-2.90 (m, 5H), 2.87-2.66 (m, 1H), 2.45 (s, 2H), 2.29-1.47 (m, 9H), 1.28 (s, 14H), 1.11 (d, J=6.7 Hz, 2H), 0.90 (t, J=6.7 Hz, 3H). LCMS-ESI+ (m/z): [M+H]+ calc'd for C$_{41}$H$_{50}$ClN$_5$O$_6$S: 776.32; found: 776.12.

Example 333

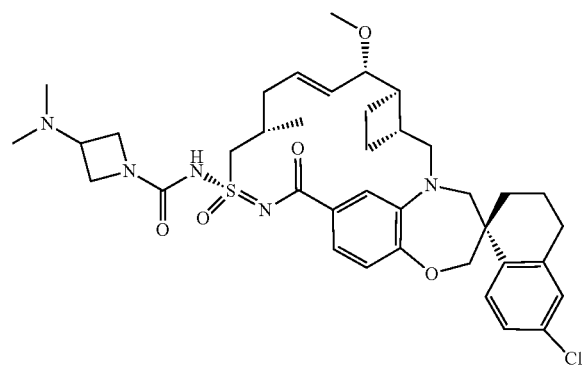 [SMILES: CO[C@H]1/C=C/C[C@H](C)C[S@@](=O)(NC(=O)N2CC(N(C)C)C2)=NC(=O)c2ccc3c(c2)N(C[C@@H]2CC[C@H]21)C[C@@]1(CCCc2cc(Cl)ccc21)CO3]

Example 333 was synthesized in the same manner as Example 362, using Example 109 and N,N-dimethylazetidin-3-amine dihydrochloride. LCMS-ESI+ (m/z): [M+H]$^+$ calc'd for C$_{38}$H$_{50}$ClN$_5$O$_5$S: 724.3294; found: 724.08. $^1$H NMR (400 MHz, Methanol-d$_4$) δ 7.71 (d, J=8.5 Hz, 1H), 7.14 (d, J=8.6 Hz, 1H), 7.10 (d, J=2.2 Hz, 1H), 7.07 (dd, J=8.2, 1.9 Hz, 1H), 6.93-6.86 (m, 2H), 5.97 (dt, J=14.3, 6.7 Hz, 1H), 5.56 (dd, J=15.2, 9.2 Hz, 1H), 4.39-4.24 (m, 3H), 4.24-4.13 (m, 2H), 4.13-3.99 (m, 3H), 3.83 (d, J=15.1 Hz, 1H), 3.74 (dd, J=9.2, 3.7 Hz, 1H), 3.69-3.54 (m, 2H), 3.28-3.25 (m, 1H), 3.24 (s, 3H), 3.06 (dd, J=15.3, 10.3 Hz, 1H), 2.91 (s, 6H), 2.87-2.69 (m, 2H), 2.46 (dd, J=13.0, 7.5 Hz, 2H), 2.32 (p, J=8.9 Hz, 1H), 2.23-2.03 (m, 3H), 2.01-1.65 (m, 6H), 1.42 (t, J=12.3 Hz, 1H), 1.12 (d, J=6.5 Hz, 3H).

Example 334

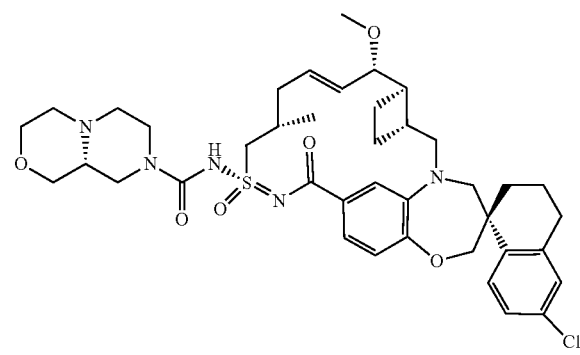 [SMILES: CO[C@H]1/C=C/C[C@H](C)C[S@@](=O)(NC(=O)N2CCN3CCOC[C@H]3C2)=NC(=O)c2ccc3c(c2)N(C[C@@H]2CC[C@H]21)C[C@@]1(CCCc2cc(Cl)ccc21)CO3]

Example 334 was synthesized in the same manner as Example 362, using Example 109 and (R)-octahydropyrazino[2,1-c][1,4]oxazine dihydrochloride. LCMS-ESI+ (m/z): [M+H]$^+$ calc'd for C$_{40}$H$_{52}$ClN$_5$O$_6$S: 766.3400; found: 766.10. $^1$H NMR (400 MHz, Methanol-d4) δ 7.72 (d, J=8.5 Hz, 1H), 7.17 (dd, J=8.5, 2.4 Hz, 1H), 7.11 (d, J=2.3 Hz, 1H), 7.05 (dd, J=8.1, 1.9 Hz, 1H), 6.93 (d, J=8.1 Hz, 1H), 6.86 (d, J=2.0 Hz, 1H), 5.94 (dt, J=14.3, 6.7 Hz, 1H), 5.56 (dd, J=15.2, 9.3 Hz, 1H), 4.57 (s, 2H), 4.39 (dd, J=14.9, 6.7 Hz, 1H), 4.20-3.94 (m, 4H), 3.84 (d, J=15.0 Hz, 2H), 3.75 (dd, J=9.4, 3.7 Hz, 1H), 3.70-3.60 (m, 2H), 3.61-3.36 (m, 4H), 3.30-3.25 (m, 3H), 3.24 (s, 3H), 3.21-3.12 (m, 1H), 3.07 (dd, J=15.4, 10.2 Hz, 1H), 2.87-2.69 (m, 3H), 2.54-2.38 (m, 2H), 2.29 (p, J=8.9, 8.4 Hz, 1H), 2.23-2.02 (m, 3H), 2.01-1.66 (m, 6H), 1.43 (t, J=12.6 Hz, 1H), 1.11 (d, J=6.5 Hz, 3H).

Example 335

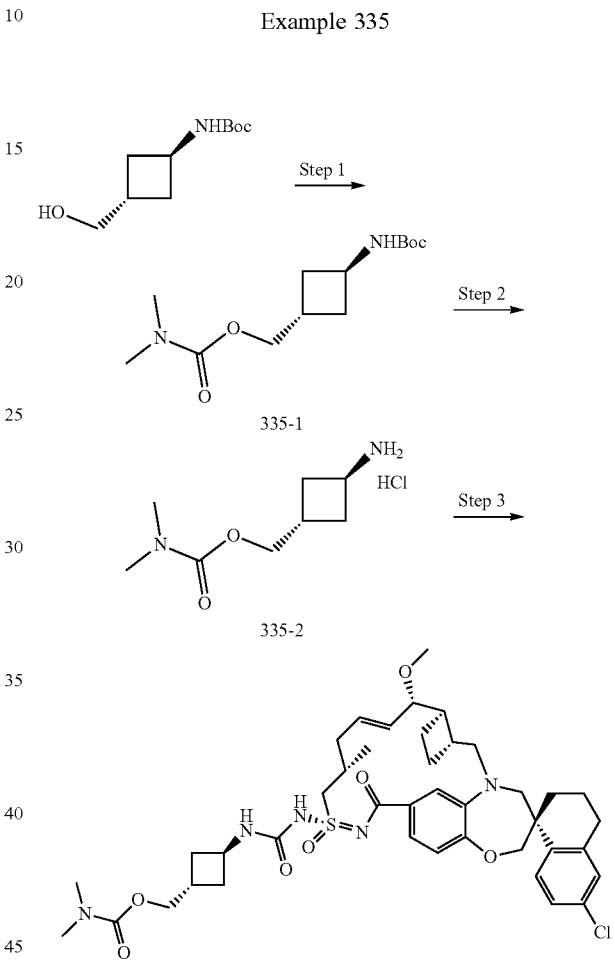

Step 1

The reaction mixture of tert-butyl (trans-3-(hydroxymethyl) cyclobutyl)carbamate (368 mg, 1.83 mmol) and N,N-dimethylcarbamoyl chloride (0.20 mL, 2.19 mmol) in pyridine was heated at 90° C. overnight. Upon cooling to room temperature, 5 mL of iced water was added and the reaction mixture was diluted with EtOAc (70 mL), washed with water (30 mL), brine, dried and concentrated, and purified by column chromatography using 0-60% EtOAc in hexane to afford intermediate 335-1. $^1$H NMR (400 MHz, Acetone-d$_6$) δ 6.27 (s, 1H), 4.21 (m, 1H), 4.12-4.00 (m, 2H), 2.92 (s, 3H), 2.86 (s, 3H), 2.54-2.38 (m, 1H), 2.21-2.10 (m, 4H), 1.40 (s, 9H).

Step 2

Intermediate 335-2 (130 mg, 0.48 mmol) was dissolved in EtOAc (1 mL) and then 4 N HCl in dioxane (4 mL) was added. The reaction mixture was stirred at room temperature for 4 hrs. Nitrogen was bubbled through to drive out the HCl and the solvent was removed to get 335-2. It was used without further purification in next step.

Step 3

Example 335 was synthesized in the same manner as Example 75 using intermediate 335-2 and Example 109. $^1$H NMR (400 MHz, Methanol-$d_4$) δ 7.67 (d, J=9.0 Hz, 1H), 7.31 (d, J=6.9 Hz, 1H), 7.21 (d, J=8.1 Hz, 1H), 7.06 (s, 1H), 6.97 (s, 1H), 6.86 (d, J=8.1 Hz, 1H), 6.03 (d, J=15.4 Hz, 1H), 5.57 (dd, J=15.3, 8.7 Hz, 1H), 4.34-4.27 (m, 1H), 4.20 (d, J=13.9 Hz, 1H), 4.11 (d, J=6.8 Hz, 2H), 4.03 (s, 2H), 3.79 (dd, J=23.6, 12.1 Hz, 3H), 3.68 (d, J=14.1 Hz, 1H), 3.27 (s, 3H), 3.06-3.00 (m, 1H), 2.94 (s, 3H), 2.92 (s, 3H), 2.77 (d, J=18.8 Hz, 2H), 2.56 (s, 2H), 2.45 (d, J=18.0 Hz, 2H), 2.29-2.21 (m, 3H), 2.15 (q, J=11.8, 10.2 Hz, 4H), 2.03 (d, J=7.4 Hz, 2H), 1.95 (d, J=11.5 Hz, 2H), 1.79 (d, J=5.1 Hz, 2H), 1.39 (d, J=13.8 Hz, 2H), 1.11 (d, J=6.2 Hz, 3H). LCMS-ESI$^+$[M+H]$^+$ calc'd for $C_{41}H_{54}ClN_5O_7S$: 796.34; found: 795.87.

Example 336

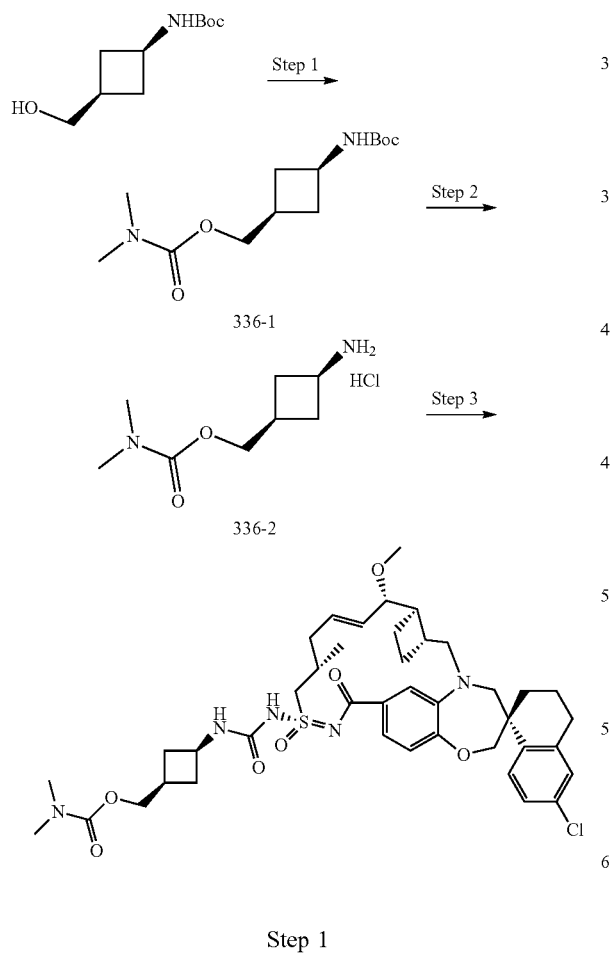

Step 1

The reaction mixture of tert-butyl (cis-3-(hydroxymethyl) cyclobutyl) carbamate (515 mg, 2.56 mmol) and ACV-dimethylcarbamoyl chloride (0.31 mL, 3.33 mmol) in pyridine was heated at 90° C. overnight. Upon cooling to room temperature, 5 mL of iced water was added and the reaction mixture was diluted with ethyl ether (70 mL), washed with water (30 mL), brine, dried and concentrated, and purified by column chromatography using 30-80% EtOAc in hexane to afford intermediate 336-1. $^1$H NMR (400 MHz, Acetone-$d_6$) δ 6.24 (s, 1H), 3.98 (m, 3H), 2.90 (s, 3H), 2.87 (s, 3H), 2.34 (m, 2H), 2.29-2.19 (m, 1H), 1.78 (m, 2H), 1.39 (s, 9H).

Step 2: Preparation of Intermediate 336-2

Intermediate 336-1 (165 mg, 0.61 mmol) was dissolved in EtOAc (1 mL) and then 4 N HCl in dioxane (4 mL) was added. The reaction mixture was stirred at room temperature for 4 hrs. Nitrogen was bubbled through to drive out the HCl and the solvent was removed to get 336-2. It was used with no further purification in next step.

Step 3

Example 336 was synthesized in the same manner as Example 75 using intermediate 336-2 and Example 109. $^1$H NMR (400 MHz, Methanol-$d_4$/Chloroform-d (3/1)) δ 7.66 (d, 1H), 7.21 (d, J=8.1 Hz, 1H), 7.05 (d, J=2.1 Hz, 1H), 7.02 (d, J=8.5 Hz, 1H), 6.97 (s, 1H), 6.85 (d, J=8.2 Hz, 1H), 6.03 (dd, J=14.6, 7.6 Hz, 1H), 5.59 (dd, J=15.4, 8.7 Hz, 1H), 4.20-4.09 (m, 2H), 4.05-3.99 (m, 4H), 3.79 (dd, J=19.0, 12.5 Hz, 3H), 3.71-3.63 (m, 1H), 3.28 (s, 3H), 3.03 (dd, J=15.1, 9.7 Hz, 1H), 2.93 (s, 3H), 2.91 (s, 3H), 2.85-2.73 (m, 2H), 2.55-2.39 (m, 5H), 2.35-2.28 (m, 1H), 2.21 (d, J=17.3 Hz, 2H), 2.07 (d, J=13.7 Hz, 2H), 1.96 (d, J=5.2 Hz, 1H), 1.77 (dd, J=19.6, 9.7 Hz, 6H), 1.41-1.32 (m, 2H), 1.12 (d, J=6.3 Hz, 3H). LCMS-ESI+[M+H]$^+$ calc'd for $C_{41}H_{54}ClN_5O_7S$: 796.34; found:795.84.

Example 337

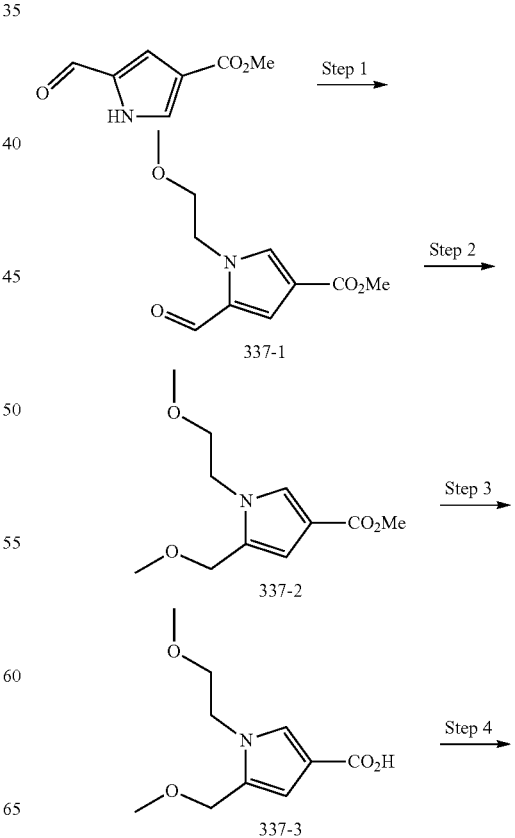

395
-continued

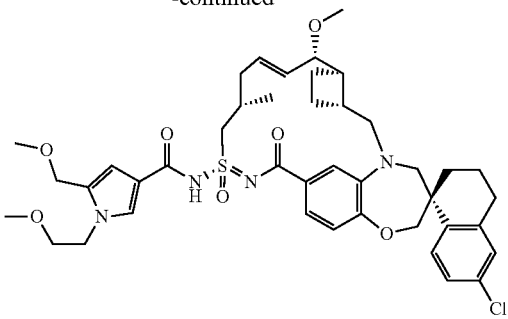

Step 1

A vigorously stirred mixture of methyl 5-formyl-1H-pyrrole-3-carboxylate (400 mg, 2.61 mmol), 1-bromo-2-methoxy ethane (982 μL, 10.5 mmol), and potassium carbonate (722 mg, 5.22 mmol) in acetonitrile (8.0 mL) 80° C. After 210 min, the reaction mixture was allowed to cool to room temperature, was filtered through celite, and was concentrated under reduced pressure. The residue was purified by flash column chromatography on silica gel (0 to 45% ethyl acetate in hexanes) to give 337-1.

Step 2

Sodium borohydride (274 mg, 7.24 mmol) was added to a stirred solution of 337-1 (510 mg, 2.41 mmol) in methanol (10 mL) and tetrahydrofuran (5.0 mL) at 0° C., and the resulting mixture was warmed to room temperature. After 20 min, ethyl acetate (125 mL) was added. The organic layer was washed with a mixture of water and brine (1:1 v:v, 2×80 mL), dried over anhydrous magnesium sulfate, filtered, and concentrated under reduced pressure. The residue was dissolved in N,N-dimethylformamide (6.0 mL), and the resulting mixture was stirred and cooled to −20° C. Potassium bis(trimethylsilyl)amide solution (1.0 M in tetrahydrofuran, 4.11 mL, 4.1 mmol) was added via syringe. After 10 min, iodomethane (342 μL, 5.48 mmol) was added via syringe, and the resulting mixture was warmed to room temperature. After 60 min, saturated aqueous ammonium chloride solution (5 mL), diethyl ether (65 mL), and ethyl acetate (65 mL) were added sequentially. The organic layer was washed sequentially with a mixture of water and brine (2:1 v:v, 100 mL) and water (100 mL), dried over anhydrous magnesium sulfate, filtered, and concentrated under reduced pressure. The residue was purified by flash column chromatography on silica gel (0 to 45% ethyl acetate in hexanes) to give 337-2.

Step 3

Aqueous sodium hydroxide solution (2.0 M, 3.18 mL, 6.4 mmol) was added via syringe to a stirred solution of 337-3 (248 mg, 1.09 mmol) in tetrahydrofuran (1.0 mL) and methanol (3.0 mL) at room temperature, and the resulting mixture was heated to 70° C. After 2 h, the resulting mixture was allowed to cool to room temperature, and aqueous hydrogen chloride solution (2.0 M, 3.5 mL), water (5 mL), and brine (20 mL) were added sequentially. The aqueous layer was extracted sequentially with dichloromethane (2×) and ethyl acetate (30 mL), and the combined organic layers were dried over anhydrous magnesium sulfate, filtered, and concentrated under reduced pressure to give 337-3.

396

Step 4

3-(((Ethylimino)methylene)amino)-N,N-dimethylpropan-1-amine hydrochloride (6.7 mg, 35 μmol) was added to a stirred mixture of 106-4 (7.0 mg, 12 μmol), X-3 (5.0 mg, 23 μmol), and 4-(dimethylamino)pyridine (4.3 mg, 35 μmol) in dichloromethane (1.0 mL) at room temperature, and the resulting mixture was heated to 45° C. After 60 min, ethyl acetate (30 mL) was added. The organic layer was washed sequentially with aqueous citric acid solution (5% wt., 30 mL) and water (30 mL), dried over magnesium sulfate, filtered, and concentrated under reduced pressure. The residue was purified by flash column chromatography on silica gel (0 to 10% methanol in dichloromethane) to give impure Example 337. The impure product was purified on C18-reverse phase silica gel (0 to 100% acetonitrile in water) to give Example 337. 1H NMR (400 MHz, Acetone-d6) δ 7.79 (d, J=8.6 Hz, 1H), 7.33 (d, J=8.2 Hz, 1H), 7.27-7.21 (m, 2H), 7.14 (s, 1H), 7.02-6.79 (m, 1H), 6.57 (s, 1H), 6.32-6.06 (m, 1H), 5.75-5.44 (m, 1H), 4.72-3.02 (m, 14H), 3.32 (s, 3H), 3.27 (s, 3H), 3.24 (s, 3H), 2.86-1.18 (m, 16H), 1.13 (d, J=6.6 Hz, 3H). LCMS: 815.1 (M+Na)+.

Example 338

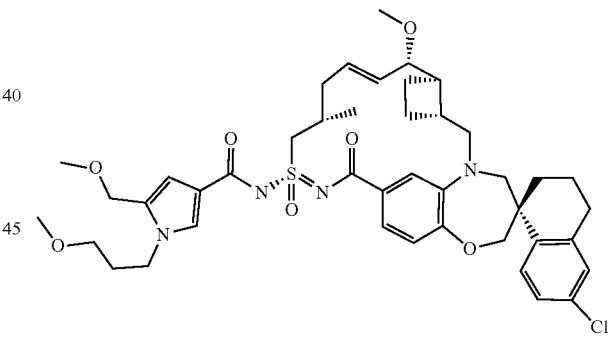

Example 338 was synthesized in a manner similar to Example 337 using 1-bromo-3-methoxypropane instead of 1-bromo-2-m ethoxy ethane. 1H NMR (400 MHz, Acetone-d6) δ 7.79 (d, J=8.6 Hz, 1H), 7.33 (d, J=8.3 Hz, 1H), 7.30-7.18 (m, 2H), 7.13 (d, J=2.3 Hz, 1H), 7.01-6.76 (m, 1H), 6.52 (s, 1H), 6.37-6.06 (m, 1H), 5.69-5.46 (m, 1H), 4.57-2.97 (m, 14H), 3.31 (s, 3H), 3.26 (s, 3H), 3.24 (s, 3H), 2.96-1.18 (m, 18H), 1.12 (d, J=6.6 Hz, 3H). LCMS: 829.1 (M+Na)+.

Example 339

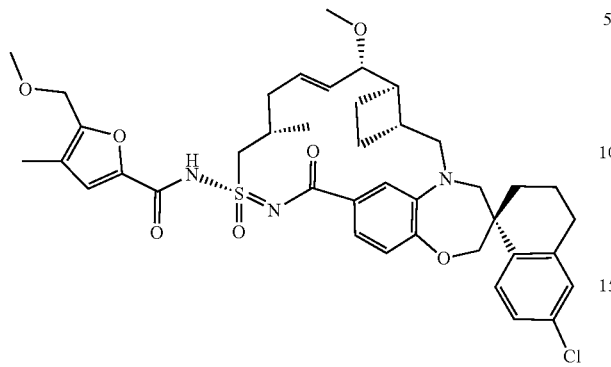

Example 339 was prepared in a similar manner to Example 106 using 5-(methoxymethyl)-4-methylfuran-2-carboxylic acid and Example 109. $^1$H NMR (400 MHz, Acetone-d$_6$) δ 7.76 (d, J=8.5 Hz, 1H), 7.28-7.18 (m, 2H), 7.11 (d, J=8.8 Hz, 3H), 6.93 (d, J=8.1 Hz, 1H), 6.08 (br s, 1H), 5.61 (dd, J=15.4, 8.5 Hz, 1H), 4.43 (s, 2H), 4.16-3.99 (m, 2H), 3.88 (d, J=14.9 Hz, 1H), 3.73 (d, J=13.1 Hz, 2H), 3.38 (d, J=14.6 Hz, 2H), 3.33 (s, 3H), 3.22 (s, 3H), 3.20-3.10 (m, 2H) 2.87-2.69 (m, 2H), 2.47 (s, 4H), 2.25 (d, J=14.5 Hz, 4H), 2.11 (s, 3H), 2.00-1.66 (m, 5H), 1.14 (d, J=6.2 Hz, 3H). LCMS-ESI+ (m/z): [M+H]+ calcd for C$_{40}$H$_{49}$ClN$_3$O$_7$S: 750.29; found: 749.94.

Example 340

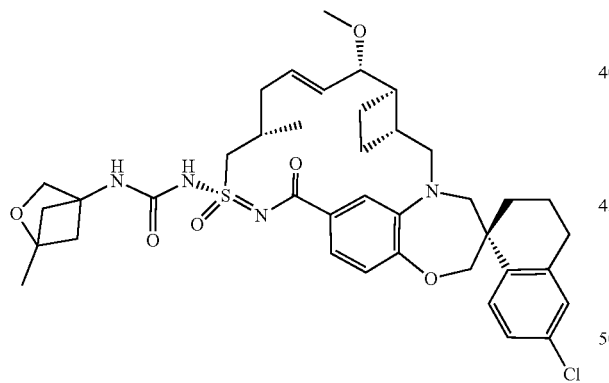

Example 340 was synthesized in the same manner as Example 281 using 1-methyl-2-oxabicyclo[2.1.1]hexane-4-carboxylic acid and Example 109. 1H NMR (400 MHz, DMSO-d6) δ 7.66 (d, J=8.5 Hz, 1H), 7.60 (s, 1H), 7.27 (dd, J=8.5, 2.4 Hz, 1H), 7.18 (d, J=2.3 Hz, 1H), 7.13 (d, J=8.2 Hz, 1H), 6.95 (s, 1H), 6.90 (d, J=8.1 Hz, 1H), 5.96 (dt, J=14.4, 6.8 Hz, 1H), 5.49 (dd, J=15.2, 8.7 Hz, 1H), 4.15-3.88 (m, 3H), 3.78 (t, J=16.6 Hz, 2H), 3.70-3.52 (m, 8H), 3.22 (d, J=14.2 Hz, 1H), 3.14 (s, 3H), 3.01 (dd, J=15.2, 10.5 Hz, 1H), 2.88-2.60 (m, 2H), 2.46-2.20 (m, 3H), 2.18-2.07 (m, 1H), 2.05-1.91 (m, 4H), 1.90-1.78 (m, 2H), 1.77-1.55 (m, 4H), 1.35 (s, 3H), 1.01 (d, J=6.8 Hz, 3H). LCMS-ESI+ (m/z): [M+H]+ calcd for C$_{39}$H$_{49}$ClN$_4$O$_6$S: 737.31; found: 736.75.

Example 341

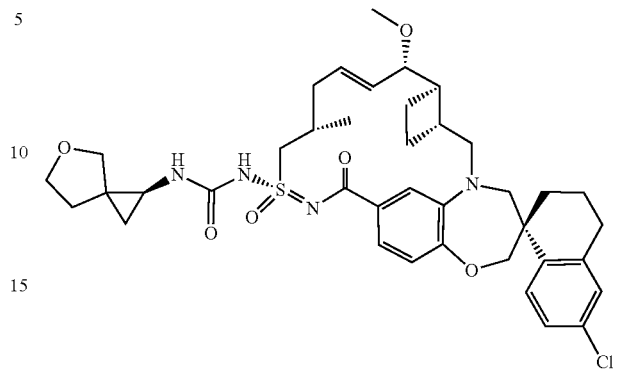

Example 341 was synthesized in the same manner as Example 281 using 5-oxaspiro[2.4]heptane-1-carboxylic acid and Example 109. Mixture of two isomers separated and stereo chemistry arbitrarily assigned but not absolute. 1H NMR (400 MHz, DMSO-d6) δ 7.66 (d, J=8.5 Hz, 1H), 7.27 (dd, J=8.5, 2.4 Hz, 1H), 7.16 (dd, J=14.5, 5.3 Hz, 2H), 6.97 (d, J=12.0 Hz, 2H), 6.89 (d, J=8.2 Hz, 1H), 6.55 (s, 1H), 6.07-5.85 (m, 1H), 5.49 (dd, J=15.3, 8.7 Hz, 1H), 4.17-4.01 (m, 2H), 3.95 (d, J=12.2 Hz, 1H), 3.91-3.72 (m, 3H), 3.69-3.47 (m, 3H), 3.27-3.17 (m, 6H), 3.14 (d, J=1.8 Hz, 3H), 3.01 (dd, J=15.2, 10.5 Hz, 1H), 2.87-2.58 (m, 3H), 2.44-2.31 (m, 2H), 2.31-2.06 (m, 1H), 2.00 (d, J=14.3 Hz, 1H), 1.74 (ddt, J=55.6, 20.6, 8.8 Hz, 6H), 1.36 (d, J=10.0 Hz, 1H), 1.08 (t, J=6.9 Hz, 1H), 1.00 (dd, J=6.8, 4.2 Hz, 3H), 0.70 (dt, J=21.3, 5.1 Hz, 1H. LCMS-ESI+ (m/z): [M+H]+ calcd for C$_{39}$H$_{49}$ClN$_4$O$_6$S: 737.31; found: 736.87.

Example 342

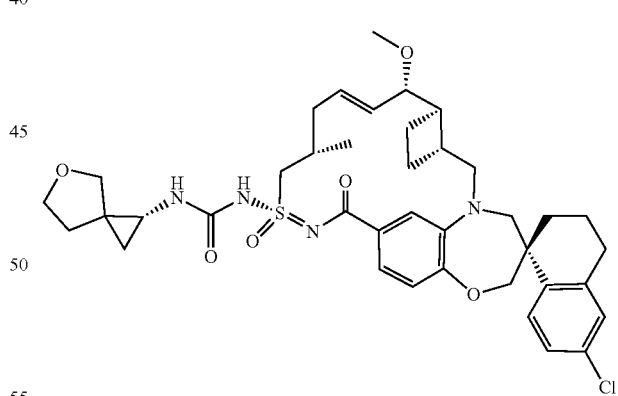

Example 342 was synthesized in the same manner as Example 281 using 5-oxaspiro[2.4]heptane-1-carboxylic acid and Example 109. Stereo chemistry arbitrarily assigned but not absolute. 1H NMR (400 MHz, DMSO-d6) δ 7.66 (d, J=8.5 Hz, 1H), 7.27 (dd, J=8.5, 2.4 Hz, 1H), 7.16 (dd, J=13.4, 5.2 Hz, 2H), 6.98 (d, J=16.0 Hz, 2H), 6.89 (dd, J=8.2, 2.5 Hz, 1H), 6.55 (s, 1H), 5.96 (s, 1H), 5.50 (dd, J=15.3, 8.6 Hz, 1H), 4.04 (d, J=12.3 Hz, 2H), 3.95 (d, J=12.3 Hz, 1H), 3.90-3.71 (m, 3H), 3.71-3.60 (m, 2H), 3.59-3.46 (m, 2H), 3.22 (d, J=14.5 Hz, 4H), 3.14 (d, J=1.8 Hz, 3H), 3.01 (dd, J=15.2, 10.5 Hz, 1H), 2.87-2.58 (m, 4H), 2.44-2.32

(m, 2H), 2.20 (d, J=54.6 Hz, 1H), 1.99 (d, J=14.0 Hz, 2H), 1.91-1.57 (m, 5H), 1.40 (d, J=13.8 Hz, 1H), 1.12-0.93 (m, 4H), 0.70 (dt, J=20.0, 5.1 Hz, 1H). LCMS-ESI+(m/z): [M+H]+ calcd for $C_{39}H_{49}ClN_4O_6S$: 737.31; found: 736.87.

Example 343

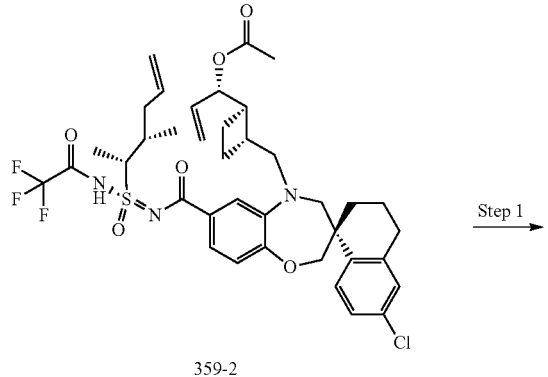

359-2

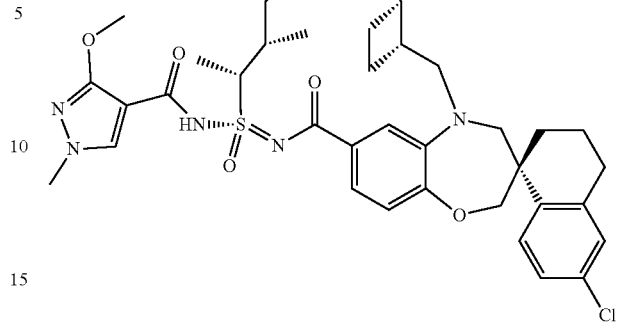

Example 343

Step 1: Preparation of Intermediate 343-1

To a stirred solution of intermediate 359-2 (1.4 g, 1.83 mmol) in methanol (20 mL) was added water (2 mL), $K_2CO_3$ (1.7 g, 18.3 mmol) and stirred at 60° C. for 24 hrs. More water was added and the mixture was extracted with dichloromethane. The organic phase was dried over anhydrous magnesium sulfate and the solvent was removed under reduced pressure.

Step 2

To a stirred solution of Intermediate 184-1 (0.72 g, 1.1 mmol) in DCM (5 mL) was added 3-methoxy-1-methyl-1H-pyrazole-4-carboxylic acid (200 mg, 1.2 mmol), 1-(3-dimethylaminopropyl)-3-ethylcarbodiimide HCl (397 mg, 2.5 mmol) and 4-(dimethylamino)pyridine (312 mg, 2.5 mmol). The reaction mixture was stirred at room temperature for 24 hr. Then the reaction mixture was diluted with DCM, and washed with 1 N HCl and brine. The organic phase was dried over $MgSO_4$, filtered, concentrated, and purified on normal phase chromatography 0-10% DCM/MeOH to yield intermediate 343-2.

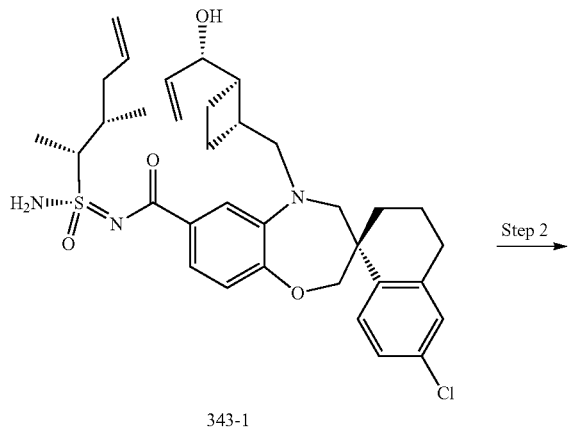

343-1

Step 3

To a stirred solution of intermediate 343-2 (100 mg, 0.13 mmol), Hoveyda-Grubbs II (33 mg, 0.039 mmol) and TFA (44 mg, 0.39 mmol) in 1,2-dichloroethane (38 mL) was degassed with argon. The reaction mixture was stirred at 60° C. overnight. The reaction mixture was concentrated and purified on reversed phase chromatography 0.1% TFA 70-95% acetonitrile to give Example 343. 1H NMR (400 MHz, Chloroform-d) δ7.84-7.70 (m, 2H), 7.52 (dd, J=8.2, 1.9 Hz, 1H), 7.39 (d, J=1.9 Hz, 1H), 7.20 (dd, J=8.5, 2.3 Hz, 1H), 7.11 (d, J=2.3 Hz, 1H), 6.95 (d, J=8.3 Hz, 1H), 5.64 (t, J=10.0 Hz, 1H), 5.49 (td, J=10.8, 4.1 Hz, 1H), 4.75 (d, J=8.4 Hz, 1H), 4.48 (dt, J=7.7, 3.9 Hz, 1H), 4.11 (d, J=18.9 Hz, 4H), 3.92 (d, J=15.1 Hz, 1H), 3.83 (s, 3H), 3.49 (d, J=14.7 Hz, 1H), 3.28 (dd, J=15.3, 10.1 Hz, 2H), 2.93-2.53 (m, 4H), 2.39 (s, 2H), 2.18-1.72 (m, 10H), 1.48 (d, J=6.9 Hz, 2H), 1.40 (d, J=7.2 Hz, 3H), 1.28 (s, 2H), 0.93-0.72 (m, 2H). LCMS-ESI+ (m/z): [M+H]+ calcd for $C_{38}H_{46}ClN_5O_6S$: 736.29; found: 736.16.

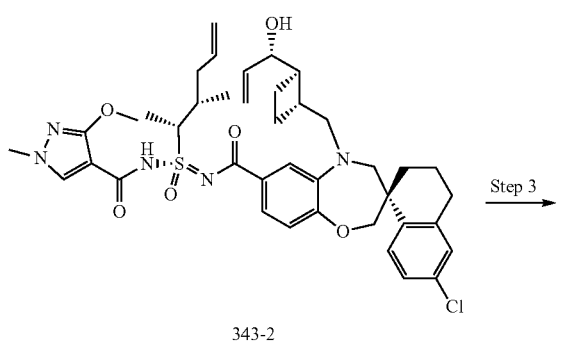

343-2

Example 344

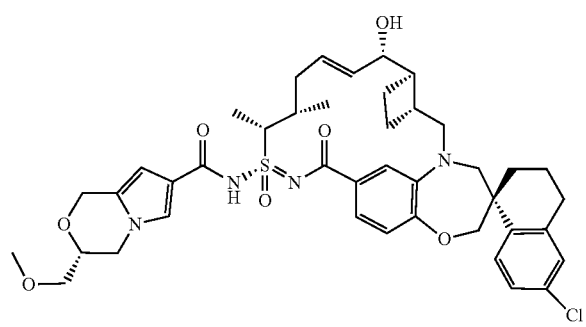 [SMILES: COC[C@H]1Cn2cc(C(=O)N[S@@]3(=O)=NC(=O)c4ccc5c(c4)N(C[C@@H]4CC[C@H]4[C@@H](O)/C=C/C[C@H](C)[C@H]3C)C[C@@]3(CCCc4cc(Cl)ccc43)CO5)cc2CO1]

Example 344 was synthesized in a manner similar to Example 344 using Intermediate 359-4 instead of 106-4. 1H NMR (400 MHz, Acetone-d6) δ 7.79 (d, J=8.5 Hz, 1H), 7.43 (s, 1H), 7.30-7.17 (m, 3H), 7.15 (d, J=2.3 Hz, 1H), 7.00 (d, J=8.0 Hz, 1H), 6.30 (s, 1H), 5.95-5.81 (m, 1H), 5.74 (dd, J=15.1, 7.2 Hz, 1H), 4.92 (d, J=14.5 Hz, 1H), 4.80-4.67 (m, 1H), 4.44-3.31 (m, 12H), 3.39 (s, 3H), 3.19 (dd, J=15.2, 8.7 Hz, 1H), 3.13-1.40 (m, 15H), 1.55 (d, J=7.2 Hz, 3H), 1.11-0.99 (m, 3H). LCMS: 791.0.

Example 345

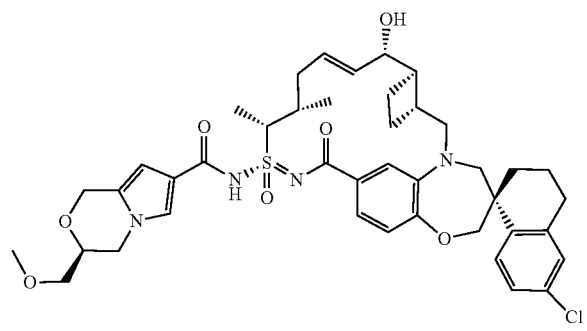 [SMILES: COC[C@@H]1Cn2cc(C(=O)N[S@@]3(=O)=NC(=O)c4ccc5c(c4)N(C[C@@H]4CC[C@H]4[C@@H](O)/C=C/C[C@H](C)[C@H]3C)C[C@@]3(CCCc4cc(Cl)ccc43)CO5)cc2CO1]

Example 345 was synthesized in a manner similar to Example 214 using Intermediate 359-4 instead of 106-4 and using (S)-2-(methoxymethyl)oxirane instead of (R)-2-(methoxymethyl)oxirane. 1H NMR (400 MHz, Acetone-d6) δ 7.79 (d, J=8.5 Hz, 1H), 7.44 (s, 1H), 7.29-7.17 (m, 3H), 7.15 (d, J=2.3 Hz, 1H), 7.00 (d, J=8.0 Hz, 1H), 6.31 (s, 1H), 5.96-5.82 (m, 1H), 5.74 (dd, J=15.2, 7.3 Hz, 1H), 4.92 (d, J=14.4 Hz, 1H), 4.73 (d, J=14.4 Hz, 1H), 4.47-3.33 (m, 12H), 3.39 (s, 3H), 3.19 (dd, J=15.1, 8.7 Hz, 1H), 3.05-1.41 (m, 15H), 1.56 (d, J=7.1 Hz, 2H), 1.11-0.98 (m, 3H). LCMS: 791.0.

Example 346

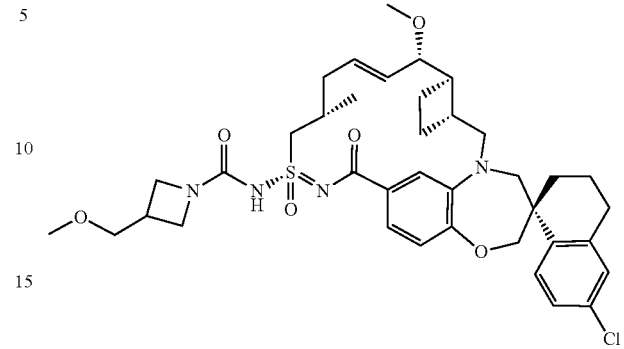

Example 346 was prepared in a similar manner as Example 75 using 3-(methoxymethyl)azetidine hydrochloride, triethylamine and Example 109. 1H NMR (400 MHz, DMSO-d6) δ 7.65 (d, J=8.5 Hz, 1H), 7.28 (dd, J=8.5, 2.4 Hz, 1H), 7.18 (d, J=2.3 Hz, 1H), 7.07 (dd, J=8.2, 1.8 Hz, 1H), 6.91 (d, J=8.1 Hz, 1H), 6.87 (d, J=2.0 Hz, 1H), 5.90 (dt, J=14.4, 6.8 Hz, 1H), 5.49 (dd, J=15.2, 8.8 Hz, 1H), 4.17-3.87 (m, 4H), 3.83-3.68 (m, 2H), 3.68-3.53 (m, 2H), 3.51 (s, 6H), 3.28 (s, 3H), 3.20 (d, J=14.1 Hz, 1H), 3.13 (s, 4H), 3.01 (dd, J=15.3, 10.4 Hz, 1H), 2.87-2.59 (m, 4H), 2.45-2.31 (m, 2H), 2.29-2.06 (m, 2H), 2.04-1.57 (m, 7H), 1.45-1.32 (m, 1H), 1.01 (d, J=6.8 Hz, 3H). LCMS-ESI+ (m/z): LCMS-ESI+ (m/z): [M+H]+ calcd for $C_{38}H_{49}ClN_4O_6S$: 725.31; found: 725.06.

Example 347

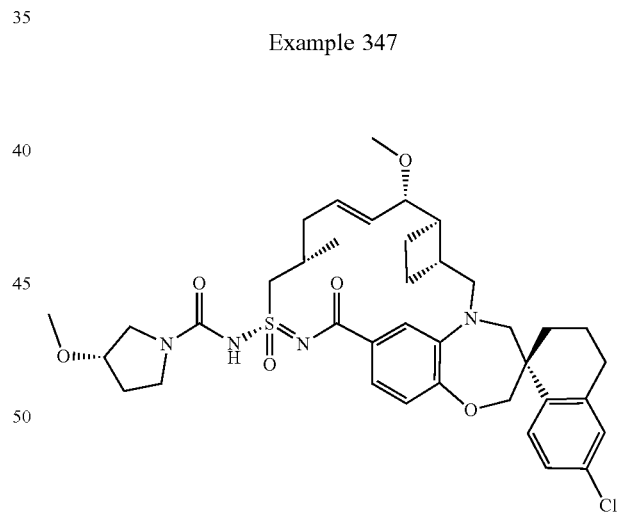

Example 347 was prepared in a similar manner to Example 75 using (S)-3-methoxypyrrolidine, triethylamine and Example 109. 1H NMR (400 MHz, DMSO-d6) δ 7.65 (d, J=8.5 Hz, 1H), 7.28 (dd, J=8.5, 2.4 Hz, 1H), 7.18 (d, J=2.3 Hz, 1H), 7.03 (dd, J=8.1, 1.8 Hz, 1H), 6.94 (d, J=8.1 Hz, 1H), 6.84 (d, J=2.0 Hz, 1H), 5.86 (dt, J=14.4, 6.8 Hz, 1H), 5.49 (dd, J=15.2, 8.9 Hz, 1H), 4.20-3.87 (m, 4H), 3.84-3.53 (m, 8H), 3.24 (s, 4H), 3.13 (s, 3H), 3.02 (dd, J=15.3, 10.4 Hz, 1H), 2.89-2.60 (m, 2H), 2.44-2.30 (m, 2H), 2.29-2.05 (m, 2H), 2.04-1.56 (m, 8H), 1.39 (td, J=17.2, 14.6, 9.7 Hz, 1H), 1.02 (d, J=6.8 Hz, 3H). LCMS-ESI+(m/z): [M+H]+ calcd for $C_{38}H_{49}ClN_4O_6S$: 725.31; found: 725.00.

Example 348

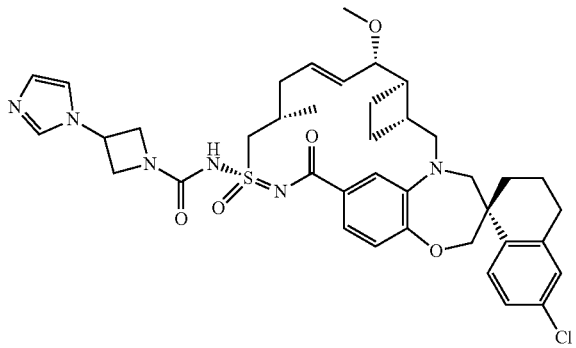 [SMILES: CO[C@H]1/C=C/C[C@H](C)C[S@@](=O)(NC(=O)N2CC(n3ccnc3)C2)=NC(=O)c2ccc3c(c2)N(C[C@@H]2CC[C@H]21)C[C@@]1(CCCc2cc(Cl)ccc21)CO3]

Example 348 was synthesized in the same manner as Example 362, using Example 109 and 1-(azetidin-3-yl) imidazole dihydrochloride. LCMS-ESI+ (m/z): [M+H]+ calc'd for $C_{39}H_{47}ClN_6O_5S$: 747.3090; found: 747.13. $^1$H NMR (400 MHz, Methanol-$d_4$) δ 9.16 (s, 1H), 7.94 (t, J=1.8 Hz, 1H), 7.72 (d, J=8.5 Hz, 1H), 7.68 (t, J=1.8 Hz, 1H), 7.16 (dd, J=8.4, 2.3 Hz, 1H), 7.12-7.05 (m, 2H), 6.96-6.87 (m, 2H), 5.97 (dt, J=14.3, 6.5 Hz, 1H), 5.57 (dd, J=15.2, 9.1 Hz, 1H), 5.35 (td, J=8.0, 4.0 Hz, 1H), 4.68-4.51 (m, 2H), 4.43-4.20 (m, 3H), 4.13-4.00 (m, 2H), 3.84 (d, J=15.1 Hz, 1H), 3.75 (dd, J=9.2, 3.6 Hz, 1H), 3.70-3.57 (m, 2H), 3.28-3.26 (m, 1H), 3.24 (s, 3H), 3.07 (dd, J=15.2, 10.3 Hz, 1H), 2.88-2.68 (m, 2H), 2.52-2.40 (m, 2H), 2.32 (p, J=8.6 Hz, 1H), 2.24-2.03 (m, 3H), 2.00-1.67 (m, 6H), 1.43 (t, J=12.7 Hz, 1H), 1.14 (d, J=6.5 Hz, 3H).

Example 350

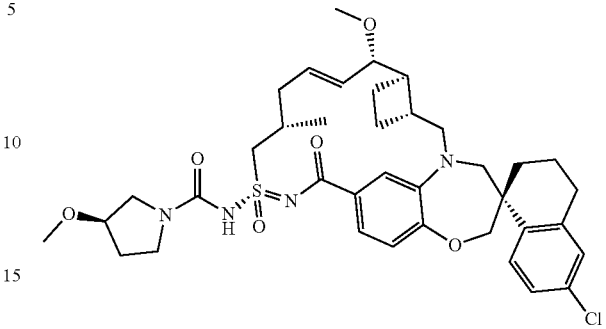

Example 350 was synthesized in the same manner as Example 75 using Example 109 and (3R)-3-methoxypyrrolidine; hydrochloride and DIEA. 1H NMR (400 MHz, Methanol-d4) δ 7.75 (d, J=8.5 Hz, 1H), 7.19 (dd, J=8.5, 2.3 Hz, 1H), 7.14-7.08 (m, 2H), 6.94 (d, J=8.1 Hz, 1H), 6.90 (s, 1H), 6.01-5.91 (m, 1H), 5.58 (dd, J=15.2, 9.2 Hz, 1H), 4.39-4.29 (m, 1H), 4.13-4.05 (m, 2H), 4.05-4.00 (m, 1H), 3.85 (d, J=15.4 Hz, 1H), 3.76 (dd, J=9.3, 3.6 Hz, 1H), 3.71-3.49 (m, 5H), 3.48-3.39 (m, 1H), 3.36 (s, 3H), 3.26 (s, 3H), 3.13-3.03 (m, 1H), 2.88-2.71 (m, 2H), 2.54-2.43 (m, 2H), 2.39-2.28 (m, 1H), 2.24-1.67 (m, 12H), 1.50-1.39 (m, 1H), 1.18-1.11 (m, 3H). LCMS-ESI+ (m/z): calcd H+ for $C_{38}H_{49}ClN_4O_6S$: 725.31; found: 724.95.

Example 351

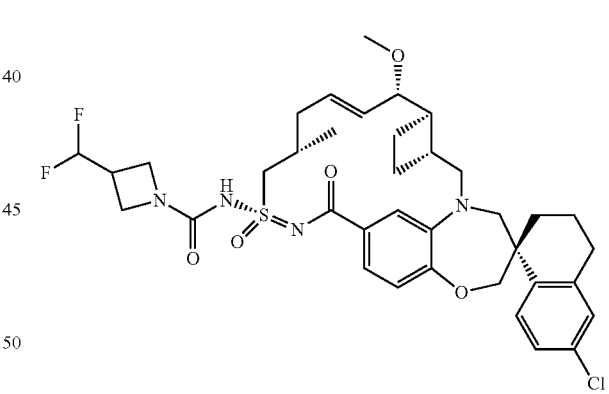 [SMILES: CO[C@H]1/C=C/C[C@H](C)C[S@@](=O)(NC(=O)N2CC(CC(F)F)C2)=NC(=O)c2ccc3c(c2)N(C[C@@H]2CC[C@H]21)C[C@@]1(CCCc2cc(Cl)ccc21)CO3]

Example 351 was synthesized in the same manner as Example 75 using 3-(difluoromethyl)azetidine and Example 109. $^1$H NMR (400 MHz, Methanol-$d_4$) δ 7.75 (d, J=8.5 Hz, 1H), 7.19 (dd, J=8.5, 2.4 Hz, 1H), 7.11 (dd, J=8.4, 2.0 Hz, 2H), 6.96-6.89 (m, 2H), 6.32-5.87 (m, 2H), 5.58 (dd, J=15.2, 9.1 Hz, 1H), 4.33 (dd, J=14.9, 6.4 Hz, 1H), 4.24-3.93 (m, 5H), 3.85 (d, J=15.2 Hz, 1H), 3.76 (dd, J=9.2, 3.6 Hz, 1H), 3.65 (m, 2H), 3.27 (m, 2H), 3.26 (s, 3H), 3.18-3.00 (m, 2H), 2.92-2.71 (m, 2H), 2.55-2.29 (m, 3H), 2.25-2.07 (m, 3H), 1.97-1.70 (m, 5H), 1.44 (t, J=12.2 Hz, 1H), 1.15 (d, J=6.6 Hz, 3H). LCMS-ESI+ (m/z): [M+H]+ calcd for $C_{37}H_{45}ClF_2N_4O_5S$: 731.3; found: 730.8.

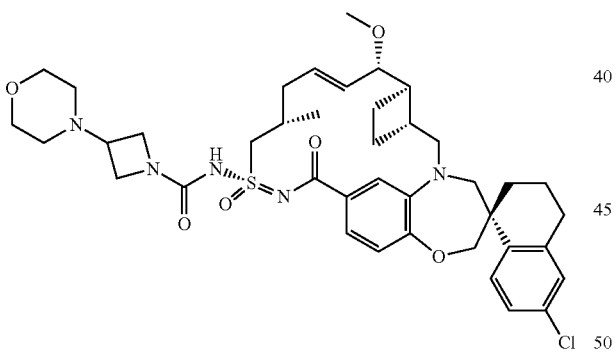

Example 349 was synthesized in the same manner as Example 362, using Example 109 and 4-(azetidin-3-yl) morpholine dihydrochloride. LCMS-ESI+ (m/z): [M+H]+ calc'd for $C_{40}H_{52}ClN_5O_6S$: 766.3400; found: 765.95. $^1$H NMR (400 MHz, Methanol-d4) δ 7.70 (d, J=8.5 Hz, 1H), 7.18-7.03 (m, 3H), 6.97-6.82 (m, 2H), 5.96 (dt, J=14.1, 6.6 Hz, 1H), 5.57 (dd, J=15.2, 9.1 Hz, 1H), 4.39-4.15 (m, 5H), 4.11-3.99 (m, 4H), 3.93 (s, 3H), 3.83 (d, J=15.2 Hz, 1H), 3.74 (dd, J=9.2, 3.6 Hz, 1H), 3.69-3.59 (m, 2H), 3.31-3.25 (m, 5H), 3.24 (s, 3H), 3.07 (dd, J=15.3, 10.3 Hz, 1H), 2.87-2.68 (m, 2H), 2.53-2.40 (m, 2H), 2.33 (p, J=8.3, 7.4 Hz, 1H), 2.23-2.04 (m, 3H), 2.01-1.67 (m, 6H), 1.42 (t, J=12.6 Hz, 1H), 1.13 (d, J=6.5 Hz, 3H).

Example 352

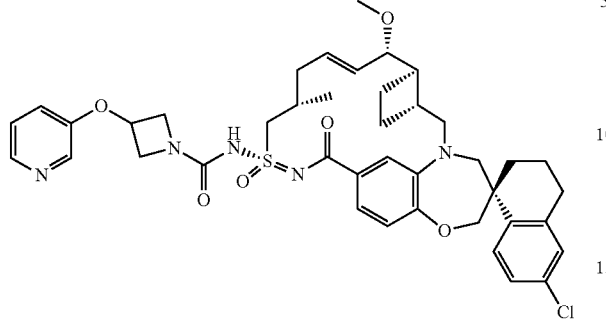

Example 352 was synthesized in the same manner as Example 362, using Example 109 and 3-(azetidin-3-yloxy) pyridine dihydrochloride. LCMS-ESI+ (m/z): [M+H]+ calc'd for $C_{41}H_{48}ClN_5O_6S$: 774.3087; found: 773.82. $^1$H NMR (400 MHz, Methanol-$d_4$) δ 8.41 (d, J=16.0 Hz, 2H), 7.76 (dd, J=27A, 11.3 Hz, 3H), 7.16 (dd, J=8.5, 2.3 Hz, 1H), 7.13-7.03 (m, 2H), 6.95-6.86 (m, 2H), 5.95 (dt, J=14.3, 6.7 Hz, 1H), 5.56 (dd, J=15.2, 9.1 Hz, 1H), 5.20 (s, 1H), 4.51 (s, 2H), 4.32 (dd, J=14.9, 6.3 Hz, 1H), 4.14-4.01 (m, 4H), 3.83 (d, J=15.1 Hz, 1H), 3.74 (dd, J=9.2, 3.7 Hz, 1H), 3.68-3.55 (m, 2H), 3.29-3.25 (m, 1H), 3.24 (s, 3H), 3.06 (dd, J=15.2, 10.3 Hz, 1H), 2.87-2.66 (m, 2H), 2.54-2.38 (m, 2H), 2.32 (q, J=9.0 Hz, 1H), 2.23-2.04 (m, 3H), 2.00-1.65 (m, 6H), 1.42 (t, J=12.7 Hz, 1H), 1.13 (d, J=6.5 Hz, 3H).

Example 353

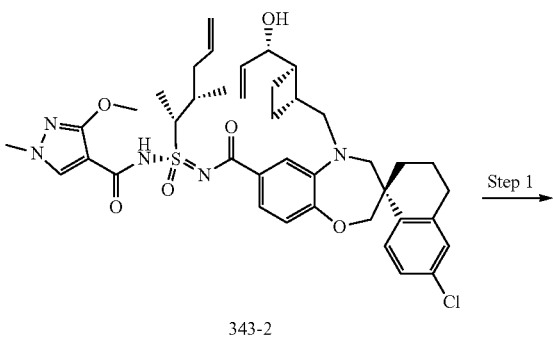

343-2

Step 1

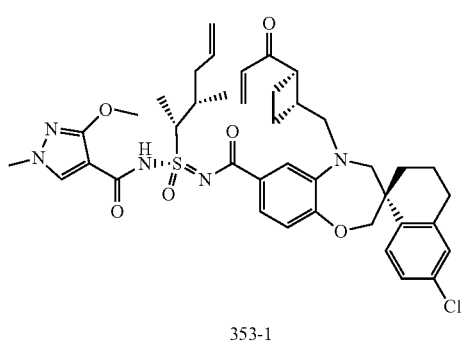

353-1

Step 2

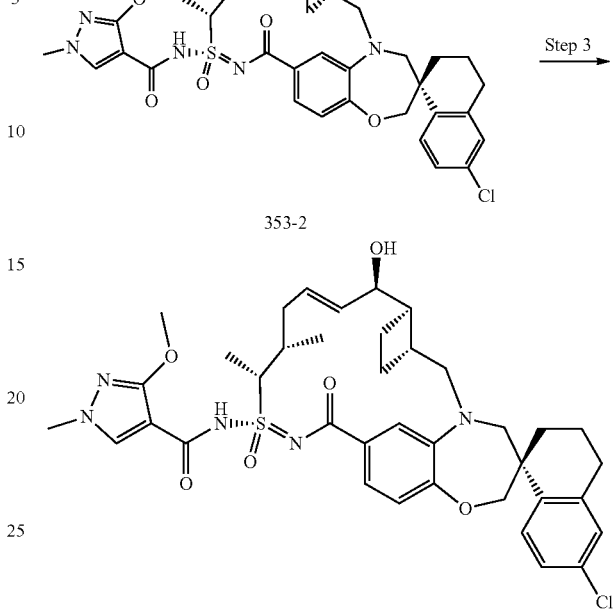

353-2

Step 3

Example 353

Step 1

To a stirred solution of Intermediate 343-2 (145 mg, 0.19 mmol) in DCM (5 mL) in ice-water bath was added Dess-Martin periodinane (241 mg, 0.56 mmol) in one portion. The reaction was warmed at room temperature and stirred for 30 min. Reaction mixture was diluted with DCM, and washed with 1 N HCl and brine. The organic phase was dried over MgSO$_4$, filtered, concentrated and purified on reversed phase chromatography 0.1% TFA 70-95% acetonitrile to give intermediate 353-1.

Step 2

To a stirred solution of intermediate 353-1 (50 mg, 0.06 mmol), Hoveyda-Grubbs II (16.6 mg, 0.020 mmol) and TFA (22 mg, 0.19 mmol) in 1,2-dichloroethane (19 mL) was degassed with argon. The reaction mixture was stirred at 60° C. overnight. The reaction mixture was concentrated and purified on normal phase chromatography 0-10% DCM/MeOH to yield intermediate 353-2.

Step 3

To a stirred solution of intermediate 174-2 (16 mg, 0.022 mmol) in methanol (2 mL) and CeCl$_3$ (16 mg, 0.065 mmol) at 0° C. was added in small portions NaBH$_4$ (1.2 mg, 0.033 mmol), and stirred at 0° C. for 1 h. The mixture was diluted with a 10% aqueous ammonium chloride solution. The organic solvent was removed using an evaporator. The remaining aqueous solution was subjected to two extractions with ethyl acetate. The organic layer was washed with saturated brine, then dried over sodium sulfate and then concentrated. The residue was purified on reversed phase chromatography 0.1% TFA 70-95% acetonitrile to give Example 353. ¹H NMR (400 MHz, Chloroform-d) δ 7.84-7.72 (m, 2H), 7.63 (s, 1H), 7.33 (d, J=7.7 Hz, 2H), 7.21 (dd, J=8.5, 2.4 Hz, 1H), 7.10 (d, J=2.3 Hz, 1H), 6.95 (d, J=8.2 Hz, 1H), 5.58 (dd, J=15.5, 7.5 Hz, 1H), 5.51-5.40 (m, 1H), 4.11 (d, J=15.5 Hz, 4H), 3.96 (d, J=16.1 Hz, 1H), 3.84-3.68 (m, 3H), 3.26 (d, J=14.3 Hz, 1H), 3.08-2.90 (m, 1H), 2.85-2.72 (m, 2H), 2.59 (s, 2H), 2.09 (d, J=15.0 Hz, 5H), 1.98-1.67 (m, 4H), 1.56 (d, J=7.3 Hz, 3H), 1.28 (m, 2H), 1.02 (d, J=6.9 Hz, 2H), 0.92-0.78 (m, 3H), 0.72-0.45 (m, 2H). LCMS-ESI+(m/z): [M+H]+ calcd for $C_{38}H_{46}ClN_5O_6S$: 736.29; found: 736.16.

Example 354

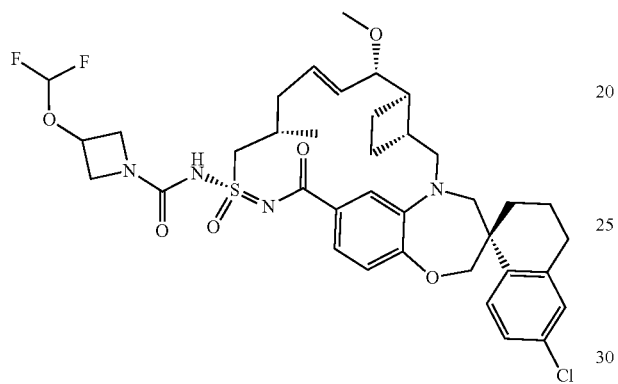

Example 354 was synthesize in the same manner as Example 182, using 3-(difluoromethoxy)azetidine instead of rac-(1R,2R)-2-(1-methyl-1H-pyrazol-5-yl)cyclopropan-1-amine. 1H NMR (400 MHz, Methanol-d4) δ 7.75 (d, J=8.5 Hz, 1H), 7.19 (dd, J=8.6, 2.4 Hz, 1H), 7.11 (dd, J=8.2, 2.0 Hz, 2H), 7.00-6.88 (m, 2H), 6.49 (t, J=74.0 Hz, 1H), 5.97 (dt, J=14.4, 6.8 Hz, 1H), 5.58 (dd, J=15.2, 9.2 Hz, 1H), 4.32 (dd, J=14.7, 6.6 Hz, 2H), 4.09 (d, J=1.8 Hz, 3H), 3.85 (d, J=15.2 Hz, 1H), 3.76 (dd, J=9.2, 3.6 Hz, 1H), 3.72-3.54 (m, 3H), 3.26 (s, 3H), 3.08 (dd, J=15.2, 10.3 Hz, 2H), 2.88-2.67 (m, 3H), 2.55-2.43 (m, 2H), 2.35 (q, J=8.9 Hz, 2H), 2.25-2.08 (m, 3H), 1.96 (s, 3H), 1.79 (tt, J=17.5, 9.5 Hz, 3H), 1.45 (t, J=12.5 Hz, 1H), 1.15 (d, J=6.6 Hz, 3H). LCMS-ESI+ (m/z): [M+H]+ calcd for $C_{37}H_{45}ClF_2N_4O_6S$: 747.27; found: 746.28.

Example 355

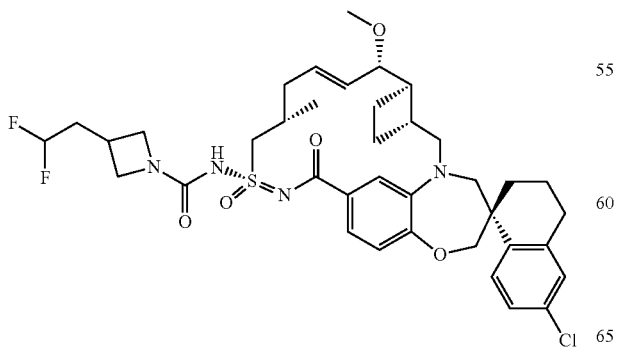

Example 355 was synthesized in the same manner as Example 75 using 3-(2,2-difluoroethyl)azetidine and Example 109. ¹H NMR (400 MHz, Methanol-d₄) δ 7.75 (d, J=8.5 Hz, 1H), 7.19 (dd, J=8.5, 2.4 Hz, 1H), 7.12 (d, J=2.3 Hz, 2H), 6.92 (d, J=2.6 Hz, 2H), 6.02-5.93 (m, 1H), 5.58 (dd, J=15.2, 9.0 Hz, 1H), 4.30 (dd, J=14.8, 6.4 Hz, 1H), 4.21 (br, 3H), 4.08 (d, J=2.5 Hz, 2H), 3.97-3.70 (m, 2H), 3.73-3.57 (m, 2H), 3.3-3.26 (m, 2H), 3.26 (s, 2H), 3.17-3.02 (m, 1H), 2.97-2.75 (m, 4H), 2.56-2.43 (m, 1H), 2.35 (q, J=9.3, 8.2 Hz, 1H), 2.28-2.07 (m, 3H), 2.01-1.78 (m, 4H), 1.45 (t, J=12.7 Hz, 1H), 1.15 (d, J=6.6 Hz, 3H). LCMS-ESI+ (m/z): [M+H]+ calcd for $C_{38}H_{47}ClF_2N_4O_5S$: 745.3; found: 744.8.

Example 356

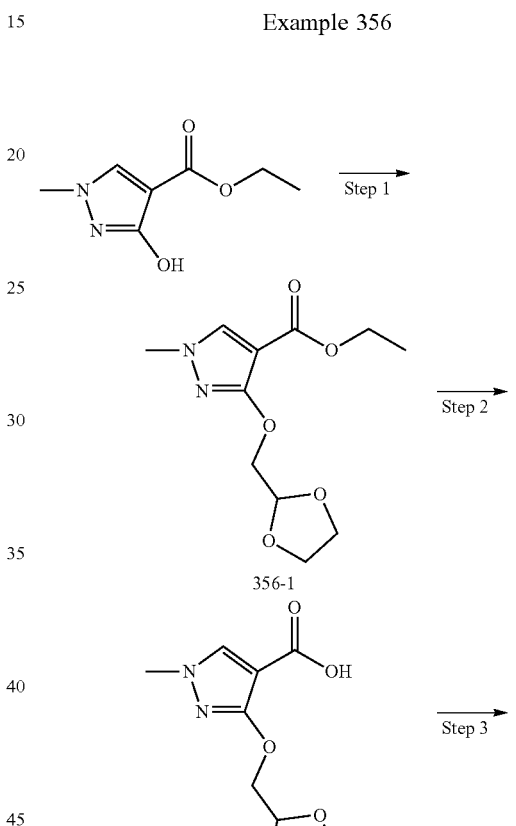

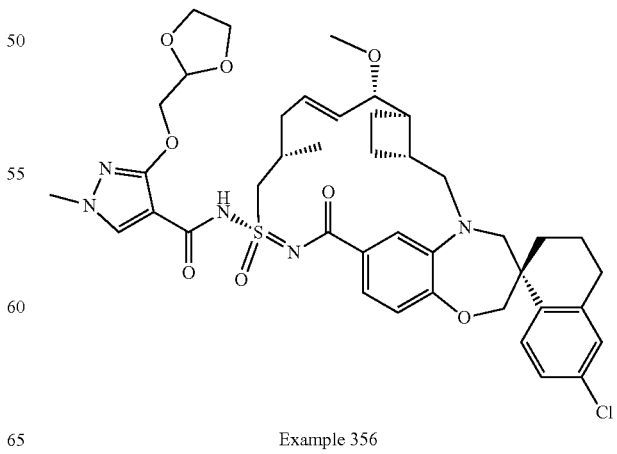

Example 356

Step 1: Synthesis of 356-1

To the mixture of ethyl 3-hydroxy-1-methyl-pyrazole-4-carboxylate (200.0 mg, 1.18 mmol) and 1,3-dioxolan-2-ylmethanol (159 mg, 1.53 mmol) in THF (5.0 mL) at room temperature was added tri-N-butylphosphine (309 mg, 1.53 mmol) followed by diisopropyl azodicarboxylate (309 mg, 1.53 mmol) dropwise. The resulting mixture was stirred at room temperature for 3 hours and then heated at 70° C. for overnight. The reaction was cooled to room temperature, concentrated, purified by combiflash (12 g silica gel, 0-50% EtOAc/Hexanes). The desired fractions were concentrated to give the title compound. 1H NMR (400 MHz, Chloroform-d) δ 7.80 (s, 1H), 5.24 (t, J=3.9 Hz, 1H), 4.51 (d, J=3.9 Hz, 2H), 4.30 (q, J=7.1 Hz, 2H), 4.07-3.99 (m, 2H), 3.99-3.93 (m, 2H), 3.76 (s, 3H), 1.37 (t, J=7.1 Hz, 3H).

Step 2: Synthesis of 356-2

Intermediate 356-1 (44.0 mg, 0.172 mmol) in EtOH and treated with 1N NaOH (0.21 mL, 0.21 mmol) at 60° C. for 1 hr. Additional 1 N NaOH (1.72 mL, 1.72 mmol) was added, the reaction mixture was heated continuously for 5 hrs. The reaction was cooled to room temperature, concentrated, diluted with EtOAc, washed with 1 N HCl, brine, dried over sodium sulfate, filtered and concentrated to give 356-2. 1H NMR (400 MHz, Chloroform-d) δ 7.85 (s, 1H), 5.24 (t, J=3.9 Hz, 1H), 4.51 (d, J=3.9 Hz, 2H), 4.08-3.91 (m, 4H), 3.75 (s, 3H).

Step 3

Example 356 was synthesized in the same manner as Example 18 using Example 109 and 356-2. 1H NMR (400 MHz, Methanol-d4) δ 7.87 (s, 1H), 7.76 (d, J=8.5 Hz, 1H), 7.23-7.15 (m, 2H), 7.12 (d, J=2.3 Hz, 1H), 6.99 (s, 1H), 6.94 (d, J=8.2 Hz, 1H), 6.11-5.99 (m, 1H), 5.61 (dd, J=15.2, 8.9 Hz, 1H), 5.23 (t, J=3.7 Hz, 1H), 4.56-4.45 (m, 2H), 4.37 (dd, J=14.8, 6.4 Hz, 1H), 4.13-4.04 (m, 2H), 4.02-3.96 (m, 2H), 3.96-3.83 (m, 4H), 3.78 (dd, J=8.9, 3.6 Hz, 1H), 3.73-3.66 (m, 4H), 3.28 (s, 3H), 3.09 (dd, J=15.3, 10.2 Hz, 1H), 2.89-2.75 (m, 2H), 2.54-2.36 (m, 3H), 2.29-2.09 (m, 4H), 1.97-1.71 (m, 6H), 1.50-1.40 (m, 1H), 1.16 (d, J=6.6 Hz, 3H). LCMS-ESI+ (m/z): calcd H+ for $C_{41}H_{50}ClN_5O_8S$: 808.31; found: 807.99.

Example 357

Example 357 was synthesized in the same manner as Example 75 using (1r,3r)-3-fluorocyclobutan-1-amine hydrochloride and Example 109. ${}^1$H NMR (400 MHz, Methanol-d$_4$) δ 7.69 (d, J=8.5 Hz, 1H), 7.21 (d, J=8.2 Hz, 1H), 7.09 (d, J=2.1 Hz, 1H), 7.05 (d, J=8.4 Hz, 1H), 6.97 (s, 1H), 6.87 (d, J=8.2 Hz, 1H), 6.06 (d, J=15.4 Hz, 1H), 5.62 (dd, J=15.4, 8.9 Hz, 1H), 4.41 (s, 1H), 4.23 (d, J=12.7 Hz, 1H), 4.03 (s, 2H), 3.89-3.71 (m, 3H), 3.66 (d, J=14.2 Hz, 1H), 3.36 (s, 1H), 3.29 (s, 4H), 3.07 (dd, J=15.2, 9.9 Hz, 1H), 2.89-2.70 (m, 3H), 2.64-2.50 (m, 3H), 2.50-2.31 (m, 5H), 2.20 (s, 2H), 2.10 (d, J=13.6 Hz, 1H), 1.96 (s, 2H), 1.80 (d, J=6.9 Hz, 2H), 1.41 (t, J=13.1 Hz, 1H), 1.14 (d, J=6.4 Hz, 3H). LCMS-ESI+[M+H] calc'd for $C_{37}H_{46}ClFN_4O_5S$: 713.29; found: 712.75.

Example 358

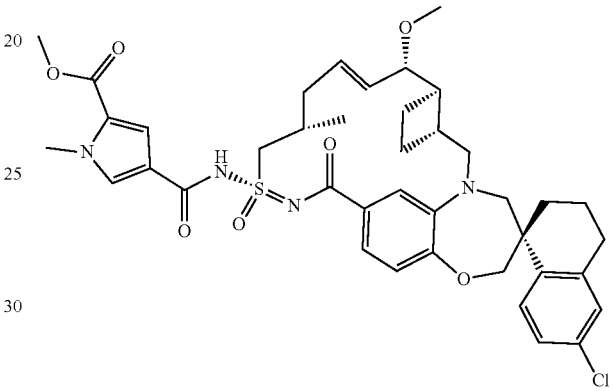

Example 358 was synthesized in the same manner as Example 18 using 5-(methoxycarbonyl)-1-methyl-1H-pyrrole-3-carboxylic acid and Example 109. ${}^1$H NMR (400 MHz, Chloroform-d) δ 7.74 (d, J=8.5 Hz, 1H), 7.51 (d, J=1.9 Hz, 1H), 7.41 (dd, J=6.4, 1.8 Hz, 1H), 7.20 (dd, J=8.5, 2.3 Hz, 1H), 7.11 (d, J=2.4 Hz, 2H), 6.97 (d, J=8.2 Hz, 2H), 5.96 (dt, J=14.6, 6.6 Hz, 1H), 5.59 (dd, J=15.5, 8.2 Hz, 1H), 4.17-4.03 (m, 2H), 4.00 (s, 2H), 3.91-3.69 (m, 7H), 3.29 (d, J=5.6 Hz, 4H), 3.06-2.90 (m, 2H), 2.88-2.68 (m, 3H), 2.45 (d, J=10.3 Hz, 2H), 2.32-1.57 (m, 8H), 1.48-1.23 (m, 3H), 1.11 (d, J=6.6 Hz, 3H). LCMS-ESI+ (m/z): [M+H]+ calcd for $C_{40}H_{47}ClN_4O_7S$: 763.29 found: 763.12.

Example 359

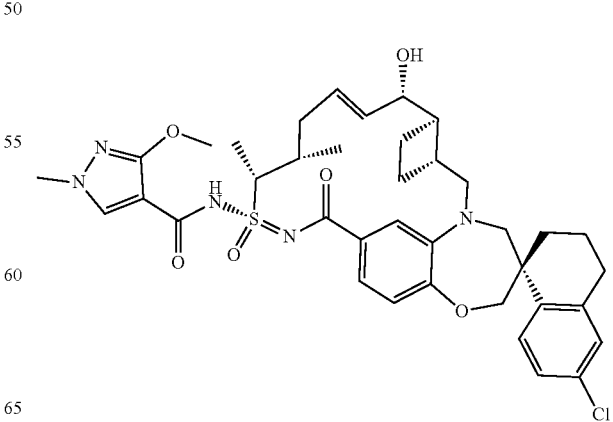

Method 1

Step 1

To a stirred solution of (S)-6'-chloro-5-(((1R,2R)-2-((S)-1-hydroxyallyl)cyclobutyl)methyl)-3',4,4',5-tetrahydro-2H,2'H-spiro[benzo[b] [1,4]oxazepine-3,1'-naphthalene]-7-carboxylic acid (500 mg, 1.068 mmol) in tetrahydrofuran was added pyridine (337 mg, 4.24 mmol) and acetic anhydride (545 mg, 5.34 mmol). The mixture was stirred at 60° C. overnight followed by evaporation of the solvents. The residue was dissolved in ethyl acetate and washed with water. The organic layer was concentrated. Solids were dissolved in $CH_2Cl_2$ and cooled down to 0° C. To this mixture, $SOCl_2$ (2 mL) was added dropwise under vigorous stirring. The mixture was stirred at 0° C. and let it warm slowly to room temperature. After reaction was completed, water was added to the mixture and vigorously stirred overnight. Desired product was extracted in DCM. Organic phase was dried over $Mg_2SO_4$ and evaporated under reduced pressure to give intermediate 359-1.

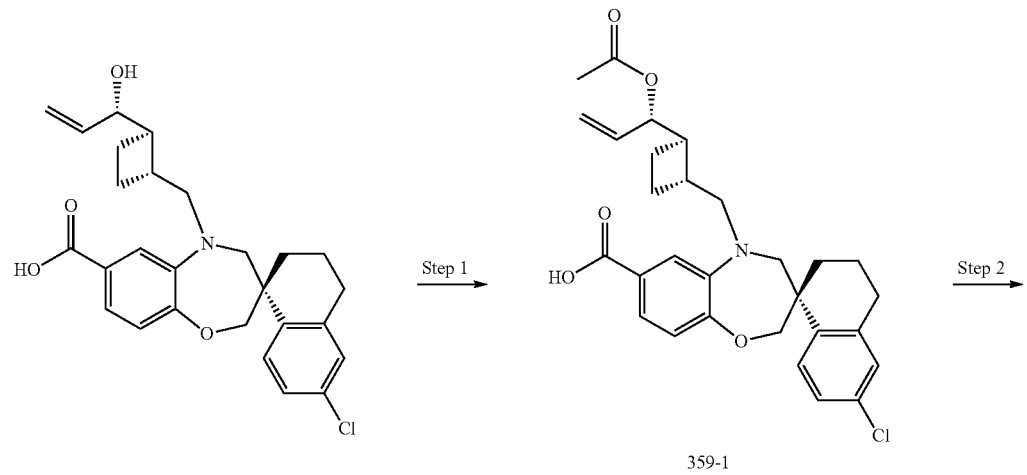

359-1

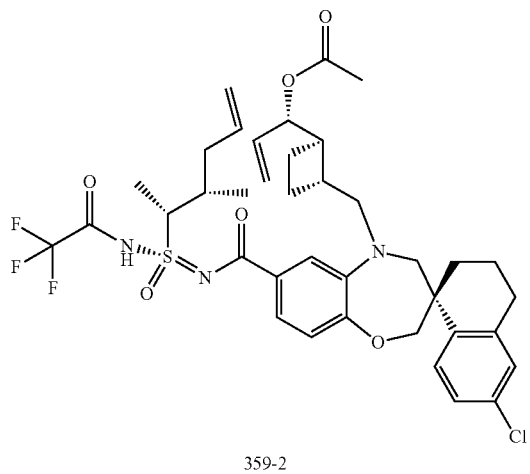

359-2

Step 3

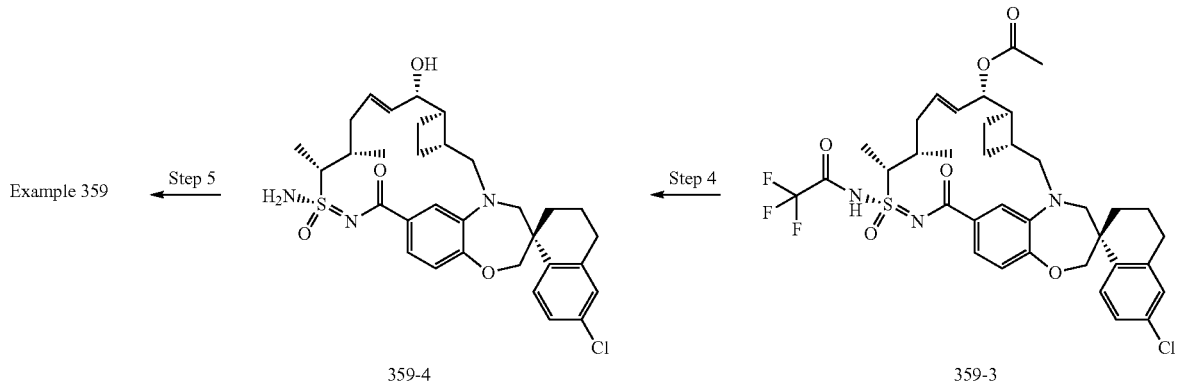

Step 2

To a stirred solution of 359-1 (200 mg, 0.39 mmol) in DCM (10 mL) was added N—((S)-amino((2R,3S)-3-methylhex-5-en-2-yl)(oxo)-16-sulfanylidene)-2,2,2-trifluoroacetamide (110-2-2) (110 mg, 0.41 mmol), 1-(3-dimethylaminopropyl)-3-ethylcarbodiimide HCl (122 mg, 0.78 mmol) and 4-(dimethylamino)pyridine (96 mg, 0.78 mmol). The reaction mixture was stirred at room temperature for 4 hr. Then the reaction mixture was diluted with DCM, washed with 1 N HCl, and brine. The organic phase was dried over MgSO$_4$, filtered, concentrated down and purified by normal phase chromatography 20-80% EtOAc/hexanes to yield intermediate 359-2.

Step 3

Synthesis of Intermediate 359-3: To a stirred solution of intermediate 359-2 (250 mg, 0.33 mmol), Hoveyda-Grubbs II (61 mg, 0.098 mmol) in 1,2-dichloroethane (90 mL) was degassed with argon. The reaction mixture was stirred at 60° C. overnight. The reaction mixture was concentrated and the residue was used on next step.

Step 4: Preparation of Intermediate 359-4

To a stirred solution of intermediate 359-3 (58 mg, 0.079 mmol) in methanol (10 mL) was added water (1 mL) and K$_2$CO$_3$ (38 mg, 0.39 mmol) and stirred at 60° C. for 24 hrs. Water was added and the mixture extracted with dichloromethane. The organic phase was dried over anhydrous magnesium sulfate and the solvent removed under reduced pressure.

Step 5

Example 359 was synthesized in the same manner as Example 18 using 3-methoxy-1-methyl-1H-pyrazole-4-carboxylic acid and intermediate 359-4. 1H NMR (400 MHz, Chloroform-d) δ 7.83-7.66 (m, 3H), δ 7.33 (s, 1H), 7.21 (dd, J=8.5, 2.3 Hz, 1H), 7.10 (d, J=2.3 Hz, 1H), 6.95 (d, J=8.3 Hz, 1H), 5.85-5.74 (m, 1H), 5.70-5.62 (m, 1H), 4.19-4.00 (m, 3H), 3.80 (s, 3H), 3.31 (d, J=14.2 Hz, 2H), 3.07 (d, J=15.7 Hz, 2H), 2.89-2.69 (m, 3H), 2.61-2.35 (m, 3H), 2.25-1.67 (m, 10H), 1.58 (d, J=7.2 Hz, 3H), 1.44 (t, J=12.5 Hz, 2H), 1.28 (s, 2H), 1.02 (d, J=6.7 Hz, 3H). LCMS-ESI+ (m/z): [M+H]+ calcd for C$_{38}$H$_{46}$ClN$_5$O$_6$S: 736.29; found: 736.10.

Method 2

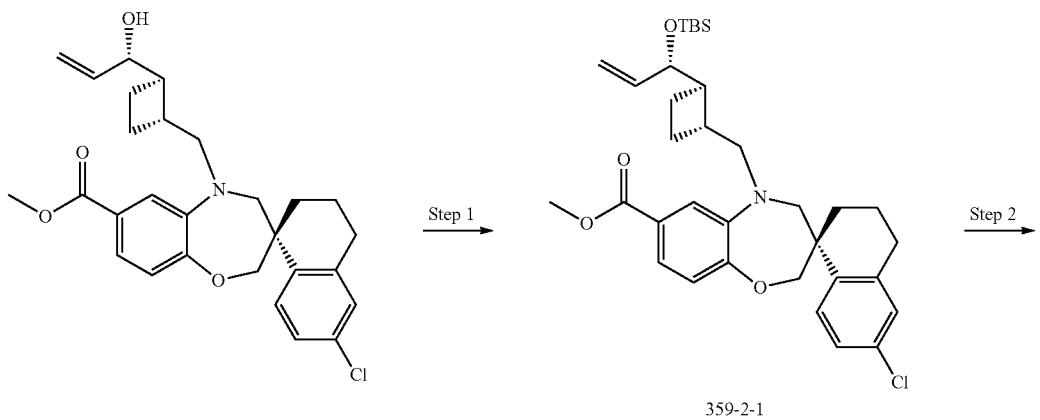

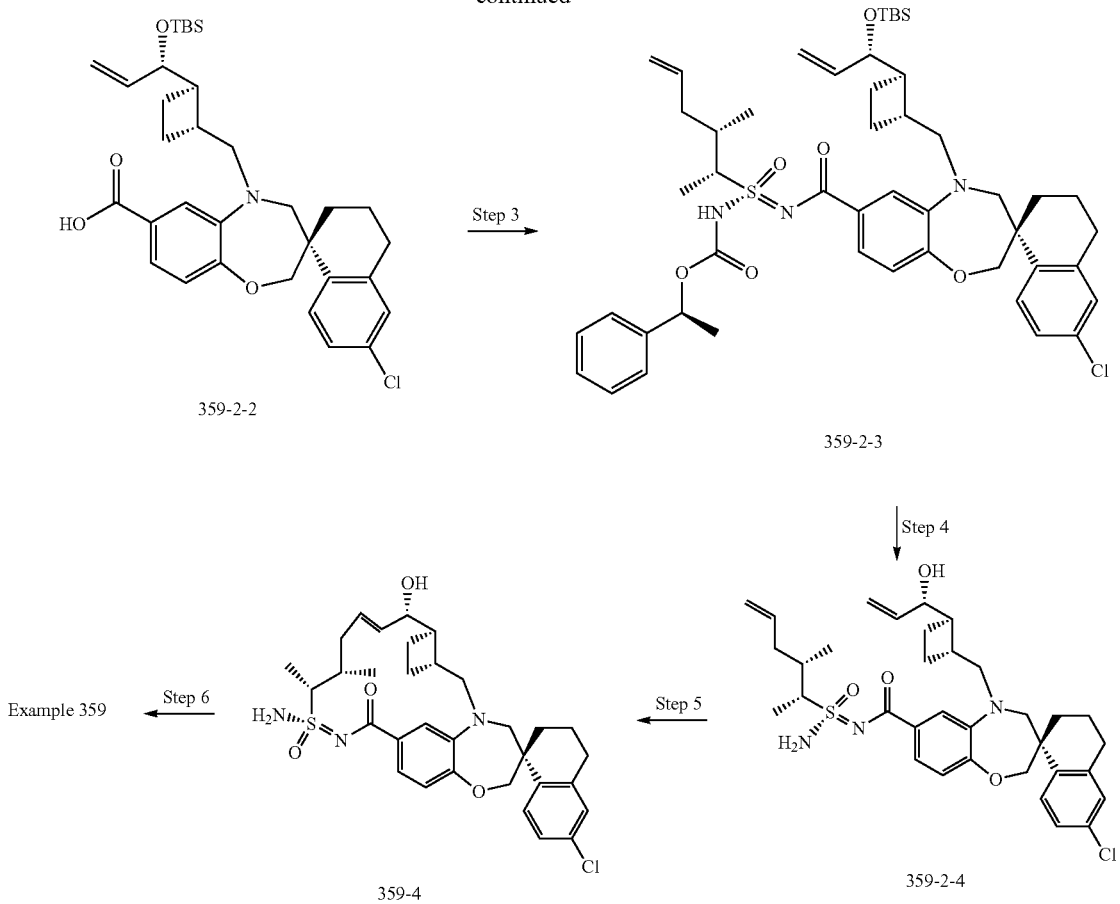

-continued

Step 1 tert-Butyl chlorodimethylsilane (4.5 g, 1.2 equiv) was added to a solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (12 g, 24.9 mmol) and imidazole (2.2 g, 1.3 equiv) in DMF (60 mL). After 2 hr, the reaction was diluted with EtOAc and washed with water, 5% aqueous LiCl and brine. The organic phase was dried over sodium sulfate and the solvent was removed under reduced pressure. The residue was subjected to flash column chromatography (silica gel, 0-100% EtOAc/hexanes). The fractions containing product were combined and the solvent was removed under reduced pressure, providing 359-2-1 (14.5 g, 97%). $^1$H NMR (400 MHz, Chloroform-d) δ 7.69 (d, J=8.5 Hz, 1H), 7.46-7.38 (m, 2H), 7.18 (dd, J=8.5, 2.4 Hz, 1H), 7.11 (d, J=2.3 Hz, 1H), 6.97-6.90 (m, 1H), 5.82 (ddd, J=16.7, 10.4, 6.0 Hz, 1H), 5.23 (dt, J=17.1, 1.6 Hz, 1H), 5.05 (dt, J=10.5, 1.5 Hz, 1H), 4.20-4.03 (m, 4H), 3.90 (s, 3H), 3.59 (d, J=14.2 Hz, 1H), 3.48 (dd, J=14.5, 4.0 Hz, 1H), 3.38-3.21 (m, 2H), 2.79 (q, J=5.3 Hz, 2H), 2.69 (td, J=8.7, 3.9 Hz, 1H), 2.22-2.10 (m, 1H), 2.10-1.86 (m, 2H), 1.77-1.68 (m, 2H), 1.65-1.49 (m, J=9.3 Hz, 3H), 0.91 (s, 9H), 0.05 (s, 3H), 0.05 (s, 3H). LCMS-ESI+ (m/z): [M+H]+ calcd for $C_{34}H_{46}ClNO_4Si$: 596.3; found: 596.2.

Step 2

Intermediate 359-2-1 (14.5 g, 24.3 mmol) was combined with lithium hydroxide (2.3 g, 4 equiv), water (97 mL), methanol (100 mL) and tetrahydrofuran (150 mL). The mixture was heated at 60° C. for 5 hr. The reaction was concentrated in vacuo, then the remaining solution was acidified with 1 N aqueous HCl (120 mL). The mixture was extracted with EtOAc, and the combined organic phases were dried over sodium sulfate and concentrated under reduced pressure, providing intermediate 359-2-2. $^1$H NMR (400 MHz, Chloroform-d) δ 7.70 (d, J=8.5 Hz, 1H), 7.52-7.46 (m, 2H), 7.19 (dd, J=8.5, 2.4 Hz, 1H), 7.11 (d, J=2.3 Hz, 1H), 6.96 (d, J=8.7 Hz, 1H), 5.80 (ddd, J=16.8, 10.4, 6.0 Hz, 1H), 5.24 (dt, J=17.2, 1.6 Hz, 1H), 5.05 (dt, J=10.6, 1.5 Hz, 1H), 4.19-4.04 (m, 4H), 3.61 (d, J=14.3 Hz, 1H), 3.51 (dd, J=14.5, 4.0 Hz, 1H), 3.36 (d, J=14.3 Hz, 1H), 3.28 (dd, J=14.5, 9.5 Hz, 1H), 2.79 (d, J=4.5 Hz, 2H), 2.71 (td, J=8.7, 4.0 Hz, 1H), 2.20-2.11 (m, 1H), 2.06-1.83 (m, 1H), 1.77 (q, J=8.4, 7.8 Hz, 2H), 1.65 (q, J=9.3 Hz, 2H), 1.55 (q, J=12.9, 12.2 Hz, 2H), 0.91 (s, 9H), 0.05 (d, J=4.5 Hz, 6H). LCMS-ESI+ (m/z): [M+H]+ calcd for $C_{33}H_{44}ClNO_4Si$: 582.3; found: 582.5.

Step 3

Intermediate 359-2-2 (13.2 g, 22.7 mmol) was combined with Intermediate 110-1-2 (7.72 g, 1.05 equiv), 1-ethyl-3-(3-dimethylaminopropyl) carbodiimide hydrochloride (3.87 g, 1.10 equiv), 4-dimethylaminopyridine, (3.05 g, 1.10 equiv), and DCM (160 mL) were combined and stirred at room temperature for 2 hr. The reaction was diluted with DCM (200 mL) and washed with water (150 mL), saturated NaHCO₃ (150 mL) and saturated NH₄Cl (150 mL). The organic phase was dried over sodium sulfate and the solvent was removed under reduced pressure. The residue was subjected to flash column chromatography (silica gel, 0-100% EtOAc/hexanes). The fractions containing product were combined and the solvent was removed under reduced pressure, providing intermediate 359-2-3. LCMS-ESI+ (m/z): [M+H]⁺ calcd for $C_{49}H_{66}ClN_3O_6SSi$: 888.4; found: 889.6.

Step 4

Intermediate 359-2-3 (16.2 g, 18.2 mmol) was combined with DCM (300 mL) and trifluoroacetic acid (100 mL) and stirred at room temperature for 16 hr. The above reagents were combined and stirred at RT for 16 h. The majority of the volatiles were removed under reduced pressure. The residue was diluted with DCM (100 mL). This solution was washed with sat NaHCO₃ (2×300 mL). The aqueous was washed with DCM (50 mL). The combined organic phases were washed with brine and dried over sodium sulfate and the solvent was removed under reduced pressure. The residue was subjected to flash chromatography (0-100% EtOAc/hexanes). The fractions containing product were combined and the solvent was removed under reduced pressure providing intermediate 359-2-4. ¹H NMR (400 MHz, Chloroform-d) δ 7.83 (d, J=2.0 Hz, 1H), 7.75 (d, J=8.5 Hz, 1H), 7.51 (dd, J=8.2, 1.9 Hz, 1H), 7.19 (dd, J=8.5, 2.2 Hz, 1H), 7.10 (d, J=2.3 Hz, 1H), 6.93 (d, J=8.3 Hz, 1H), 5.85 (ddt, J=16.2, 11.4, 5.7 Hz, 1H), 5.75 (dt, J=10.4, 7.3 Hz, 1H), 5.33-5.23 (m, 1H), 5.15-5.06 (m, 3H), 4.21-4.03 (m, 1H), 3.94 (d, J=14.8 Hz, 1H), 3.66 (d, J=14.2 Hz, 1H), 3.60-3.48 (m, 1H), 3.26 (d, J=14.2 Hz, 1H), 3.12 (dd, J=14.8, 8.9 Hz, 1H), 2.81-2.71 (m, 3H), 2.58 (dt, J=18.8, 8.5 Hz, 2H), 2.18 (dd, J=13.9, 6.6 Hz, 1H), 2.11-1.99 (m, 5H), 1.99-1.89 (m, 1H), 1.85 (q, J=9.2, 8.6 Hz, 2H), 1.74-1.43 (m, 3H), 1.37 (d, J=7.0 Hz, 3H), 1.12 (d, J=6.8 Hz, 3H). LCMS-ESI⁺ (m/z): [M+H]⁺ calcd for $C_{34}H_{44}ClN_3O_4S$: 626.3; found: 626.8.

Step 5

A solution of intermediate 359-2-4 (300 mg, 0.48 mmol) in DCE (20 mL) was degassed with argon for 5 min. MgO (60 mg, 3.0 equiv) and Hoveyda-Grubbs II catalyst (60 mg, 0.20 equiv) were added. The mixture was stirred and degassed for 10 min. The mixture was heated at 70° C. for 2 hr. The reaction was cooled and ACN was added. The solvent was removed under reduced pressure. The residue was subjected to flash column chromatography (silica gel, 20-100% (20% MeOH/EtOAc)/hexanes). The fractions containing product were combined and the solvent was removed under reduced pressure, providing intermediate 359-4. ¹H NMR (400 MHz, Chloroform-d) δ 7.77 (d, J=8.5 Hz, 1H), 7.50-7.43 (m, 2H), 7.20 (dd, J=8.5, 2.3 Hz, 1H), 7.10 (d, J=2.3 Hz, 1H), 6.94 (d, J=8.1 Hz, 1H), 6.42 (s, 2H), 5.81 (dd, J=16.1, 4.2 Hz, 1H), 5.77-5.65 (m, 1H), 4.20 (s, 1H), 4.10 (d, J=6.5 Hz, 2H), 3.83 (dd, J=15.3, 5.8 Hz, 1H), 3.77 (d, J=14.5 Hz, 1H), 3.57 (t, J=7.2 Hz, 1H), 3.37 (d, 1H), 3.15-3.07 (m, 1H), 2.83-2.73 (m, 3H), 2.73-2.60 (m, 1H), 2.51 (dt, J=17.1, 9.6 Hz, 2H), 2.16 (t, J=14.5 Hz, 1H), 2.08-2.02 (m, 1H), 2.01-1.77 (m, 4H), 1.72-1.47 (dd, J=18.1, 9.2 Hz, 4H), 1.41 (m, 4H), 1.11 (d, J=6.9 Hz, 3H). LCMS-ESI⁺ (m/z): [M+H]⁺ calcd for $C_{32}H_{40}ClN_3O_4S$: 598.3; found: 598.5.

Step 6

Example 359 was prepared in a manner similar to Example 18, using intermediate 359-4 and 1-methyl-1H-pyrazole-4-carboxylic acid.

Example 360

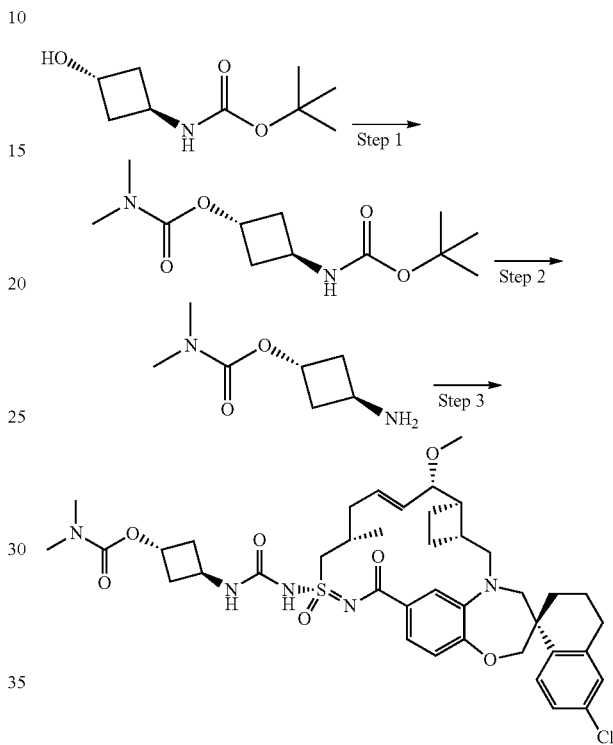

Step 1: Preparation of trans-3-((tert-butoxycarbonyl)amino)cyclobutyl Dimethylcarbamate tert-butyl trans-(3-hydroxycyclobutyl)carbamate (1000.0 mg, 5.341 mmol) was treated with dimethylcarbamic chloride (1723.0 mg, 16.02 mmol, 3.0 equiv.) in the presence of DMAP (1957.5 mg, 16.02 mmol, 3 equiv.) and DIPEA (3451.4 mg, 26.70 mmol, 5 equiv.) in DCE (20 mL) at 60° C. for 15 h. The reaction mixture was quenched with water (30 mL) and the whole was extracted with EtOAc (30 mL×3). Obtained organic layer was washed with brine (30 mL) and dried over Na₂SO₄. The solvent was removed under a reduced pressure. Obtained crude mixture was purified by a silica-gel column chromatography (13-50% EtOAc/hexane) to give trans-3-((tert-butoxycarbonyl)amino)cyclobutyl dimethylcarbamate.

Step 2: Preparation of trans-3-aminocyclobutyl dimethylcarbamate bis-hydrochloric Acid trans-3-((tert-butoxycarbonyl)amino)cyclobutyl dimethylcarbamate (114.2 mg, 0.442 mmol) was treated with 4 N—HCl (6 mL) at rt. After 2 h, the solvent was removed under a reduced pressure to give trans-3-aminocyclobutyl dimethylcarbamate bis-hydrochloric acid.

Step 3

Example 360 was synthesized in the same manner as Example 75 using trans-3-aminocyclobutyl dimethylcarbamate bis-hydrochloric acid and Example 109. $^1$H NMR (400 MHz, Acetone-d$_6$) δ 7.70 (d, J=8.5 Hz, 1H), 7.56 (s, 1H), 7.28 (s, 1H), 7.12 (dd, J=8.5, 2.3 Hz, 1H), 7.04 (d, J=2.2 Hz, 1H), 6.77 (d, J=8.2 Hz, 1H), 6.10 (br s, 1H), 5.48 (br s, 1H), 4.96 (brs, 1H), 4.30 (br s, 1H), 4.00 (s, 2H), 3.94-3.55 (m, 3H), 3.51-3.16 (m, 7H), 2.89 (d, J=13.0 Hz, 6H), 2.75 (d, J=16.5 Hz, 2H), 2.64-1.55 (m, 16H), 1.38 (t, J=12.6 Hz, 1H), 1.02 (d, J=6.7 Hz, 3H). LCMS-ESI+ (m/z): [M+H]+ calcd for C$_{40}$H$_{53}$ClN$_5$O$_7$S: 782.33; found: 781.74.

Example 361

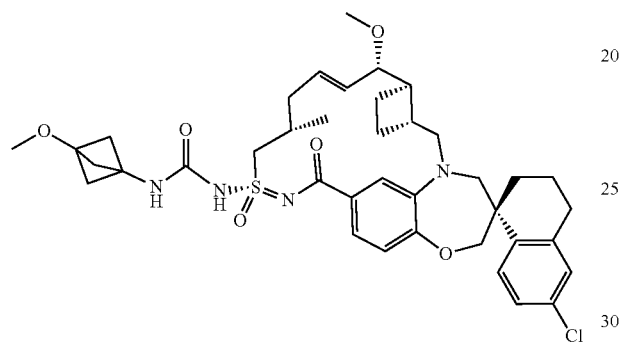

Example 361 was synthesized in the same manner as Example 75 using 3-methoxybicyclo[1.1.1]pentan-1-amine hydrochloric acid and Example 109. $^1$H NMR (400 MHz, Methanol-d$_4$) 7.69 (d, J=8.5 Hz, 1H), 7.56 (s, 1H), 7.25 (br s, 1H), 7.11 (d, J=8.4 Hz, 1H), 7.07-6.96 (m, 2H), 6.80 (d, J=8.2 Hz, 1H), 6.08 (m, 1H), 5.50 (m, 1H), 4.05-3.92 (m, 3H), 3.89-3.62 (m, 3H), 3.42 (d, J=10.2 Hz, 1H), 3.29 (s, 3H), 3.25 (s, 3H), 3.13 (dd, J=15.2, 10.2 Hz, 1H), 2.79-2.06 (m, 11H), 1.99 (s, 6H), 1.97-1.67 (m, 3H), 1.48-1.33 (m, 1H), 1.05 (d, J=6.6 Hz, 3H). LCMS-ESI+ (m/z): [M+H]+ calcd for C$_{39}$H$_{50}$ClN$_4$O$_6$S: 737.31; found: 736.72.

Example 362

A 4-dram vial was charged with Example 109 (1 equiv, 0.025 mmol, 15 mg), diphenyl carbonate (8 equiv, 0.201 mmol, 43.0 mg), N,N-dimethylaminopyridine (5 equiv, 0.125 mmol, 15.3 mg) and MeCN (0.75 mL). The reaction vial was sealed and stirred at room temperature overnight. In a separate vial, 3-methoxyazetidine hydrochloride (10 equiv, 0.251 mmol, 31.0 mg) was treated with MeCN (0.5 mL) and triethylamine (40 equiv, 1.0 mmol, 0.14 mL) then combined with the reaction mixture, sealed and heated to 50° C. for 3 hours. The reaction mixture was concentrated and purified by preparative HPLC (60-100% MeCN in water, 0.1% TFA) and lyophilized to afford the desired product Example 362. LCMS-ESI+ (m/z): [M+H]+ calc'd for C$_{37}$H$_{47}$ClN$_4$O$_6$S: 711.2978; found: 710.79. $^1$H NMR (400 MHz, Methanol-d$_4$) δ 7.73 (d, J=8.5 Hz, 1H), 7.17 (dd, J=8.5, 2.4 Hz, 1H), 7.14-7.02 (m, 2H), 6.96-6.85 (m, 2H), 5.96 (dt, J=14.2, 6.7 Hz, 1H), 5.56 (dd, J=15.2, 9.1 Hz, 1H), 4.29 (dd, J=14.9, 6.3 Hz, 1H), 4.20 (s, 3H), 4.06 (d, J=2.2 Hz, 2H), 3.83 (d, J=15.2 Hz, 3H), 3.74 (dd, J=9.2, 3.7 Hz, 1H), 3.63 (t, J=17.6 Hz, 2H), 3.30 (s, 3H), 3.30-3.25 (m, 1H), 3.24 (s, 3H), 3.06 (dd, J=15.2, 10.3 Hz, 1H), 2.87-2.66 (m, 2H), 2.45 (dd, J=12.6, 7.9 Hz, 2H), 2.32 (p, J=9.1 Hz, 1H), 2.14 (ddd, J=27.8, 14.4, 8.6 Hz, 3H), 2.01-1.63 (m, 6H), 1.42 (dd, J=14.2, 10.8 Hz, 1H), 1.13 (d, J=6.6 Hz, 3H).

Example 363

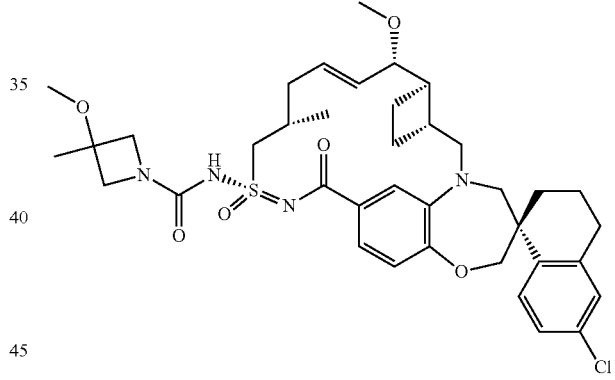

Example 363 was synthesized in the same manner as Example 362, using Example 109 and 3-methoxy-3-methylazetidine hydrochloride. LCMS-ESI+ (m/z): [M+H]+ calc'd for C$_{38}$H$_{49}$ClN$_4$O$_6$S: 725.3134; found: 724.90. $^1$H NMR (400 MHz, Methanol-d$_4$) δ 7.73 (d, J=8.5 Hz, 1H), 7.17 (dd, J=8.5, 2.3 Hz, 1H), 7.13-7.05 (m, 2H), 6.95-6.86 (m, 2H), 5.96 (dt, J=14.2, 6.7 Hz, 1H), 5.56 (dd, J=15.2, 9.1 Hz, 1H), 4.29 (dd, J=14.9, 6.3 Hz, 1H), 4.11-4.02 (m, 2H), 3.97 (s, 2H), 3.88-3.54 (m, 6H), 3.31-3.29 (m, 1H), 3.26 (s, 3H), 3.24 (s, 3H), 3.06 (dd, J=15.3, 10.3 Hz, 1H), 2.87-2.69 (m, 2H), 2.52-2.40 (m, 2H), 2.33 (q, J=9.0 Hz, 1H), 2.23-2.03 (m, 3H), 1.98-1.66 (m, 6H), 1.48 (s, 3H), 1.45-1.36 (m, 1H), 1.13 (d, J=6.6 Hz, 3H).

Example 364

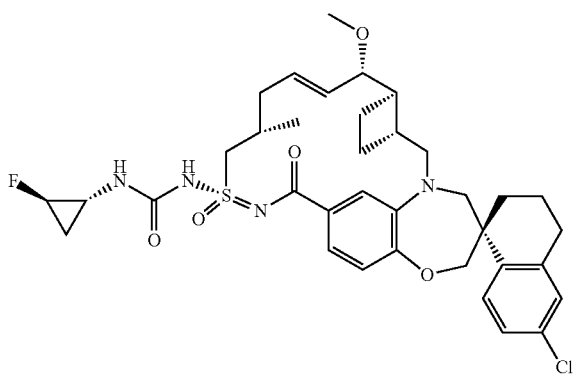 [SMILES: CO[C@H]1/C=C/C[C@H](C)C[S@@](=O)(NC(=O)N[C@@H]2C[C@H]2F)=NC(=O)c2ccc3c(c2)N(C[C@@H]2CC[C@H]21)C[C@@]1(CCCc2cc(Cl)ccc21)CO3]

An oven-dried 4-dram vial was charged with (1S,2R)-2-fluorocyclo propanecarboxylic acid (15 equiv, 0.376 mmol, 39.2 mg), toluene (0.75 mL), triethylamine (16.5 equiv, 0.414 mmol, 0.058 mL) and diphenylphosphoryl azide (15 equiv, 0.376 mmol, 0.081 mL). The vial was sealed and heated to 85° C. in a pre-heated sand bath for 2 hours. The reaction mixture was then cooled to room temperature, treated with Example 109 (1 equiv, 0.025 mmol, 15 mg), sealed and heated to 45° C. for 3 hours. The reaction mixture was cooled to room temperature, diluted with EtOAc, washed with half-saturated aqueous NaHCO$_3$, neutralized with 1 N HCl, and washed with brine. The organic layer was dried over sodium sulfate, filtered and concentrated. The crude reaction mixture was purified by preparative HPLC (60-100% MeCN in water, 0.1% TFA) and lyophilized to afford the desired product Example 364. LCMS-ESI+(m/z): [M+H]$^+$ calc'd for C$_{36}$H$_{44}$ClFN$_4$O$_5$S: 699.2778; found: 698.72. $^1$H NMR (400 MHz, Methanol-<74) δ 7.71 (d, J=8.5 Hz, 1H), 7.19-7.05 (m, 3H), 6.98-6.84 (m, 2H), 5.99 (dd, J=14.6, 7.5 Hz, 1H), 5.58 (dd, J=15.2, 9.0 Hz, 1H), 4.69-4.46 (m, 1H), 4.26 (dd, J=14.9, 6.4 Hz, 1H), 4.11-3.98 (m, 2H), 3.86-3.61 (m, 4H), 3.30-3.26 (m, 1H), 3.25 (s, 3H), 3.05 (dd, J=15.2, 10.3 Hz, 1H), 2.95 (ddd, J=20.9, 10.0, 5.1 Hz, 1H), 2.87-2.68 (m, 2H), 2.55-2.41 (m, 2H), 2.41-2.29 (m, 1H), 2.25-2.04 (m, 3H), 2.01-1.67 (m, 6H), 1.41 (t, J=12.2 Hz, 1H), 1.37-1.22 (m, 1H), 1.12 (d, J=6.4 Hz, 3H), 0.96 (dddd, J=11.9, 7.8, 6.7, 5.3 Hz, 1H).

Example 365

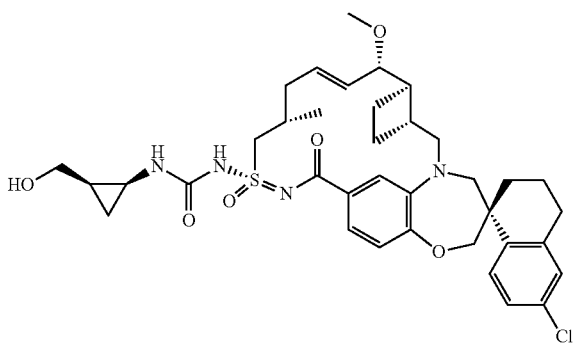 [SMILES: CO[C@H]1/C=C/C[C@H](C)C[S@@](=O)(NC(=O)N[C@H]2C[C@H]2CO)=NC(=O)c2ccc3c(c2)N(C[C@@H]2CC[C@H]21)C[C@@]1(CCCc2cc(Cl)ccc21)CO3]

Example 365 was synthesized in the same manner as Example 316, using intermediate 316-3 (directly in Step 3) and Example 109. The absolute configuration of the cis cyclopropane stereocenters has not been determined and is denoted arbitrarily. LCMS-ESI+(m/z): [M+H]$^+$ calc'd for C$_{37}$H$_{47}$ClN$_4$O$_6$S: 711.2978; found: 710.84. $^1$H NMR (400 MHz, Methanol-d$_4$) δ 7.73 (d, J=8.5 Hz, 1H), 7.19-7.12 (m, 2H), 7.10 (d, J=2.2 Hz, 1H), 6.95 (s, 1H), 6.90 (d, J=8.1 Hz, 1H), 6.01 (dt, J=14.3, 6.8 Hz, 1H), 5.57 (dd, J=15.3, 8.9 Hz, 1H), 4.26 (td, J=15.5, 6.5 Hz, 1H), 4.11-3.98 (m, 2H), 3.89-3.60 (m, 5H), 3.44-3.36 (m, 1H), 3.31-3.26 (m, 1H), 3.25 (s, 3H), 3.05 (dd, J=15.2, 10.4 Hz, 1H), 2.87-2.63 (m, 3H), 2.54-2.41 (m, 2H), 2.35 (dt, J=17.7, 9.6 Hz, 1H), 2.25-2.03 (m, 3H), 2.01-1.66 (m, 6H), 1.42 (t, J=13.8 Hz, 1H), 1.35-1.21 (m, 1H), 1.12 (d, J=6.3 Hz, 3H), 0.99 (q, J=7.4 Hz, 1H), 0.44 (q, J=5.6 Hz, 1H).

Example 366

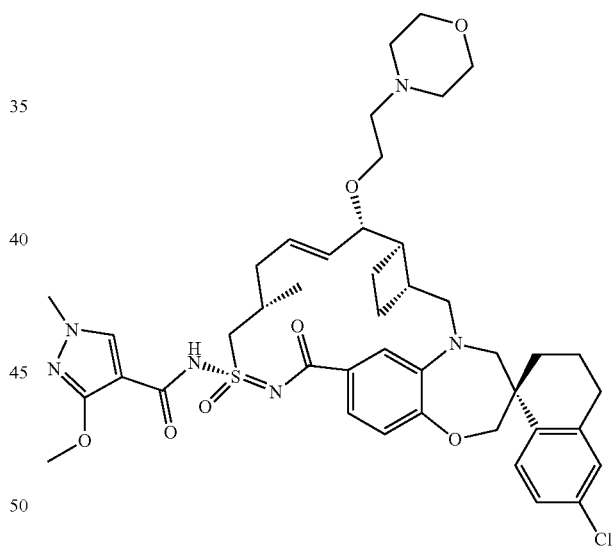

Example 366 was synthesized in the same manner as Example 367 using Example 223 and 4-(2-iodoethyl)morpholine instead of iodoethane. LCMS-ESI+ (m/z): [M+H]+ calcd for C$_{43}$H$_{55}$ClN$_6$O$_7$S: 835.4; found: 835.0.

Example 367

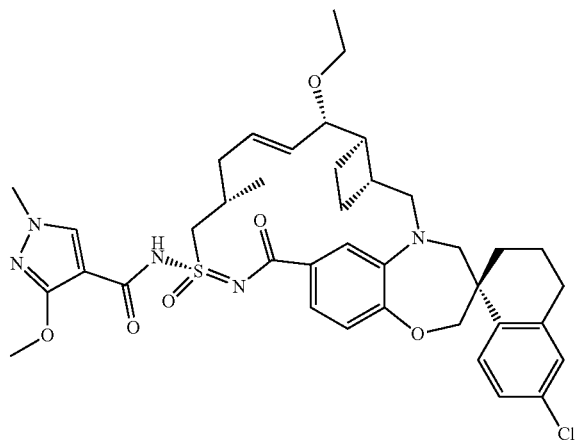 [SMILES: CCO[C@H]1/C=C/C[C@H](C)C[S@@](=O)(NC(=O)c2cn(C)nc2OC)=NC(=O)c2ccc3c(c2)N(C[C@@H]2CC[C@H]21)C[C@@]1(CCCc2cc(Cl)ccc21)CO3]

Example 223 (10 mg, 0.014 mmol) was dissolved in DMF (0.1 mL). NaH was added at room temperature followed by iodoethane (10 equiv.). The reaction mixture was heated to 80° C. via a metal heating block. The progress of the reaction was monitored by LCMS. Upon observing the full consumption of the starting material, the residue was directly purified Gilson reverse phase HPLC (60:40→100 MeCN/H$_2$O, 0.1% TFA) to afford Example 367. LCMS-ESI+ (m/z): [M+H]+ calcd for C$_{39}$H$_{48}$ClN$_5$O$_6$S: 750.3; found: 750.0.

Example 368

Step 1

To a stirred solution of (S)-6'-chloro-5-(((1R,2R)-2-((S)-1-methoxy allyl)cyclobutyl)methyl)-3',4,4',5-tetrahydro-2H, 2'H-spiro[benzo[b][1,4]oxazepine-3,1'-naphthalene]-7-carbonyl chloride (600 mg, 1.19 mmol) in acetonitrile (12 mL) was added pyridazine (105 mg, 1.31 mmol) at room temperature and stirred for 10 min. A solution of a mixture of diastereomers (3R)—N'-(tert-butyldimethylsilyl)hept-6-ene-3-sulfonimidamide (383 mg, 1.31 mmol) in acetonitrile was added and stirred at room temperature overnight. Then the reaction mixture was diluted with DCM, washed with water and brine. The organic phase was dried over MgSO$_4$, filtered, and concentrated down to yield 368-1.

Step 2

To a stirred solution of 368-1 (700 g, 1.09 mmol) in DCM (14 mL) was added di-tert-butyl dicarbonate (334 mg, 1.53 mmol), trimethylamine (132 mg, 1.3 mmol) and 4-(dimethylamino)pyridine (13 mg, 0.10 mmol). The reaction mixture was stirred at room temperature for 1 hr. Then the reaction mixture was diluted with DCM, washed with 1N HCl, brine, and then a saturated aqueous solution of NaHCO$_3$. The organic phase was dried over MgSO$_4$, filtered, and concentrated to yield 368-2.

Step 3

To a stirred solution of 368-2 (600 mg, 0.81 mmol) and Hoveyda-Grubbs II (50.6 mg, 0.08 mmol) in 1,2-dichloroethane (270 mL) was degassed with argon. The reaction mixture was stirred at 60° C. overnight. The reaction mixture

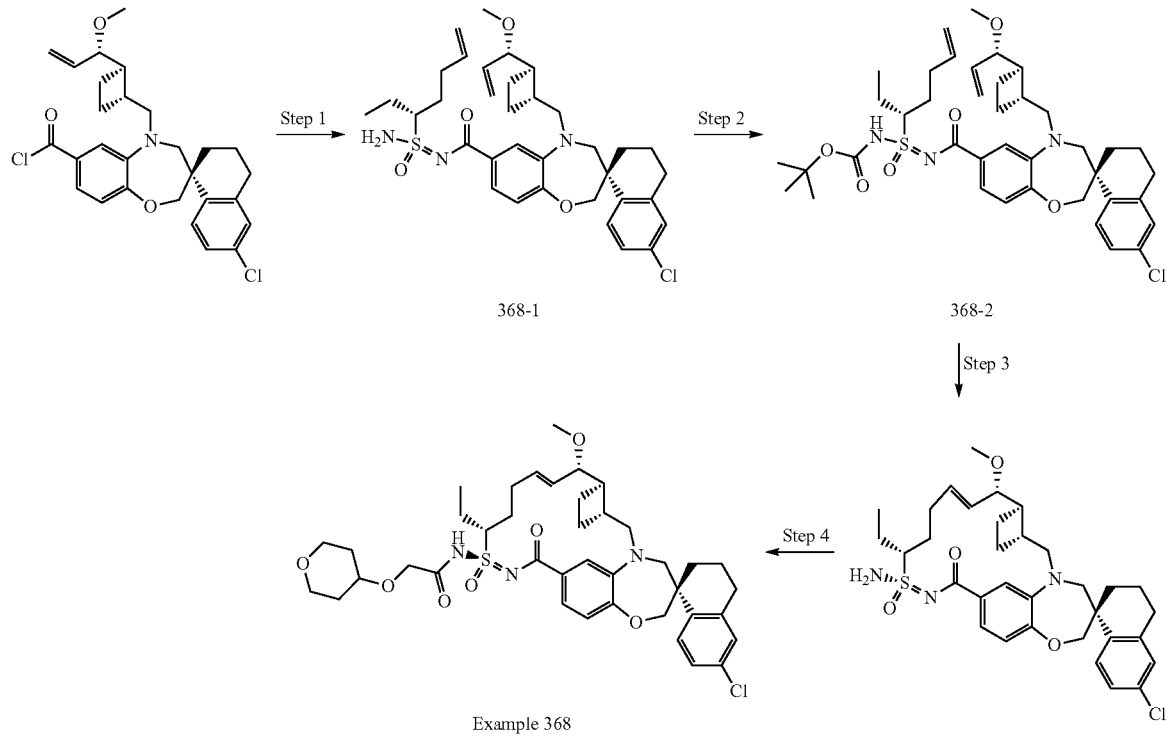

was concentrated and purified on reversed phase chromatography 0.1% TFA 65-95% acetonitrile to give 368-3.

Step 4

To a stirred solution of 368-3 (80 mg, 0.13 mmol) in DCM (5 mL) was added 2-((tetrahydro-2H-pyran-4-yl)oxy)acetic acid (31 mg, 0.196 mmol), 1-(3-dimethylaminopropyl)-3-ethylcarbodiimide HCl (40 mg, 0.26 mmol), and 4-(dimethylamino)pyridine (31.9 mg, 0.26 mmol). The reaction mixture was stirred at room temperature for 24 hr. Then the reaction mixture was diluted with DCM, and washed with 1N HCl and brine. The organic phase was dried over MgSO$_4$, filtered, concentrated, and purified on reversed phase chromatography 0.1% TFA 70-95% acetonitrile to give Example 368. 1H NMR (400 MHz, Chloroform-d) δ 7.71 (d, J=8.5 Hz, 1H), 7.45 (dd, J=8.3, 1.9 Hz, 1H), 7.37 (d, J=2.0 Hz, 1H), 7.16 (dd, J=8.5, 2.3 Hz, 1H), 7.07 (d, J=2.3 Hz, 1H), 6.91 (d, J=8.2 Hz, 1H), 5.75 (td, J=11.0, 5.2 Hz, 1H), 5.38 (t, J=10.3 Hz, 1H), 4.16 (s, 3H), 4.11-3.92 (m, 5H), 3.84 (d, J=15.3 Hz, 1H), 3.78-3.67 (m, 2H), 3.55 (ddd, J=11.8, 8.7, 4.1 Hz, 3H), 3.41 (d, J=14.7 Hz, 2H), 3.31 (s, 5H), 2.96-2.64 (m, 3H), 2.39 (q, J=8.8 Hz, 1H), 2.28 (t, J=13.7 Hz, 2H), 2.19-1.58 (m, 15H), 1.42 (t, J=12.8 Hz, 1H), 1.25 (s, 2H), 1.02 (t, J=7.4 Hz, 3H). LCMS-ESI+ (m/z): [M+H]+ calcd for $C_{40}H_{52}ClN_3O_7S$: 754.32; found: 754.15.

Example 369

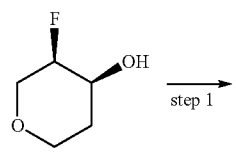

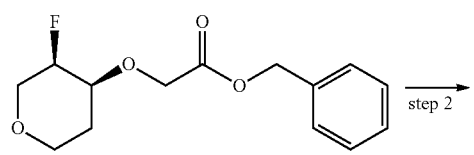

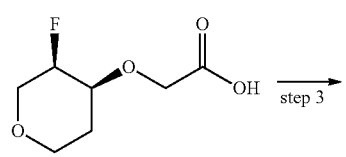

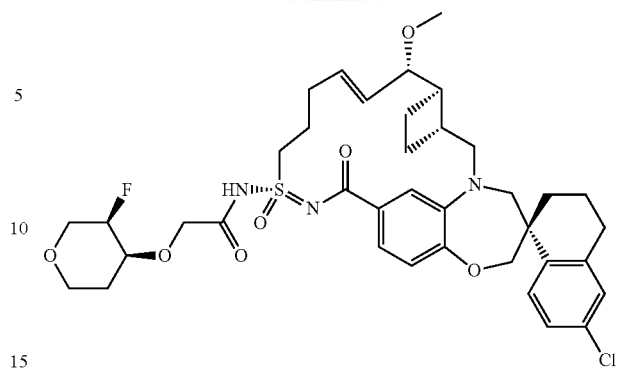

Example 369

Step 1

(3R,4S)-3-Fluorotetrahydro-2H-pyran-4-ol (500 mg, 4.162 mmol) and benzyl 2-bromoacetate (1.049 g, 4.579 mmol, 1.1 equiv) were treated with KHMDS (1.0 M in THF, 4.16 mL, 4.16 mmol) in THF (15 mL) at −78° C. for 2 h. The resulting mixture was concentrated by removing THF and the residue was suspended into CH$_2$Cl$_2$. The suspension was filtered and the filtrate was concentrated to give a crude product. The crude product was purified by a silica-gel column chromatography (0-40% EtOAc/hexane) to give benzyl 2-(((3R,4S)-3-fluorotetrahydro-2H-pyran-4-yl)oxy) acetate. 1H NMR (400 MHz, Methanol-d4) δ 7.41-7.29 (m, 5H), 5.21 (s, 2H), 4.30 (s, 2H), 4.03-3.96 (m, 1H), 3.92-3.87 (m, 1H), 3.81-3.70 (m, 1H), 3.61-3.41 (m, 3H), 2.02-1.92 (m, 1H), 1.86-1.80 (m, 1H).

Step 2

Benzyl 2-(((3R,4S)-3-fluorotetrahydro-2H-pyran-4-yl) oxy)acetate (50.0 mg, 1.983 mg) was treated with 10% Pd/C (1.9 mg) in EtOAc (5 mL) under atmospheric pressure of a hydrogen atmosphere for 2 h. The catalyst was filtered off through Celite and obtained filtrate was concentrated. Crude 2-(((3R,4S)-3-fluorotetrahydro-2H-pyran-4-yl)oxy)acetic acid was immediately used for the subsequent step without further purification and characterizations.

Step 3

Example 369 was synthesized in the same manner as Example 21 using 2-(((3R,4S)-3-fluorotetrahydro-2H-pyran-4-yl)oxy)acetic acid. 1H NMR (400 MHz, Chloroform-d) δ 7.74 (d, J=8.5 Hz, 1H), 7.39 (dd, J=8.2, 1.8 Hz, 1H), 7.30 (s, 1H), 7.18 (dd, J=8.5, 2.3 Hz, 1H), 7.07 (d, J=2.3 Hz, 1H), 6.91 (d, J=8.2 Hz, 1H), 5.93-5.64 (m, 2H), 4.98-4.77 (m, 1H), 4.35-4.20 (m, 2H), 4.15-3.97 (m, 4H), 3.88 (p, J=9.4 Hz, 3H), 3.81-3.51 (m, 5H), 3.29 (s, 3H), 3.06-2.96 (m, 1H), 2.81-2.69 (m, 3H), 2.47-2.21 (m, 4H), 2.14-2.02 (m, 4H), 1.92 (p, J=8.6 Hz, 3H), 1.77-1.69 (m, 3H), 1.38 (t, J=12.9 Hz, 2H). LCMS-ESI+ (m/z): [M+H]+ calcd for $C_{38}H_{47}ClFN_3O_7S$: 744.28; found: 744.28.

Example 370

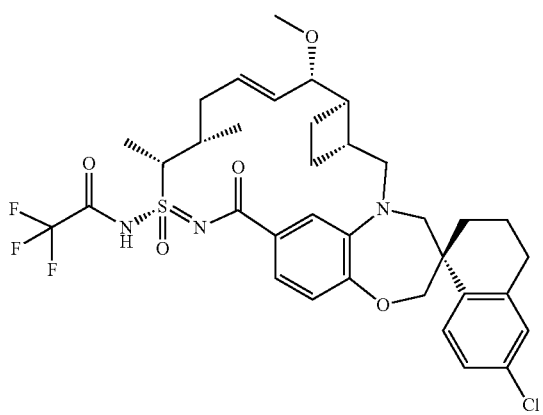 [SMILES: CO[C@H]1/C=C/C[C@H](C)[C@@H](C)[S@@](=O)(NC(=O)C(F)(F)F)=NC(=O)c2ccc3c(c2)N(C[C@@H]2CC[C@H]21)C[C@@]1(CCCc2cc(Cl)ccc21)CO3]

¹H NMR (400 MHz, Methanol-d₄) δ 7.75 (d, J=8.4 Hz, 1H), 7.19 (dd, J=8.4, 2.4 Hz, 1H), 7.12 (d, J=2.4 Hz, 1H), 7.09 (dd, J=8.2, 1.8 Hz, 1H), 6.95-6.93 (m, 2H), 5.99-5.92 (m, 1H), 5.59 (dd, J=15.2, 9.2 Hz, 1H), 4.54-4.49 (m, 1H), 4.13-4.07 (m, 2H), 3.84 (d, J=15.2 Hz, 1H), 3.73 (dd, J=9.4, 3.4 Hz, 1H), 3.65 (d, J=14.0 Hz, 1H), 3.37-3.29 (m, 2H), 3.24 (s, 3H), 3.16-3.06 (m, 1H), 2.88-2.73 (m, 3H), 2.50-1.72 (m, 10H), 1.57 (d, J=7.2 Hz, 3H), 1.45 (t, J=13.0 Hz, 1H), 1.16 (d, J=6.8 Hz, 3H). LCMS-ESC (m/z): [M+H]⁺ calculated for $C_{35}H_{41}ClF_3N_3O_5S$: 708.25; found: 708.2.

Example 371

The mixture of 3-hydroxy-3-methyl-cyclobutanecarboxylic acid (2.6 mg, 0.0196 mmol) and Example 110 (8.0 mg, 0.0131 mmol) in DCM (1.0 mL) was cooled to 0° C. 1-(3-Dimethylaminopropyl)-3-ethylcarbodiimide HCl salt (5.0 mg, 0.0261 mmol) was added followed by DMAP (3.2 mg, 0.0261 mmol). The reaction was removed from the cooling bath and stirred at room temperature for overnight. The reaction was concentrated to remove DCM, diluted with DMF (1 mL), filtered and purified by Gilson reverse phase prep HPLC (60-100% ACN/H₂O with 0.1% TFA). Desired fractions were pooled and frozen dried to give Example 371. LCMS-ESI+ (m/z): calcd H+ for $C_{39}H_{50}ClN_3O_6S$: 724.31; found: 723.99.

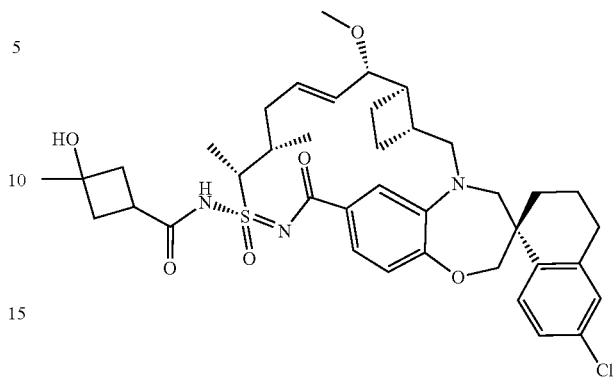

Example 372

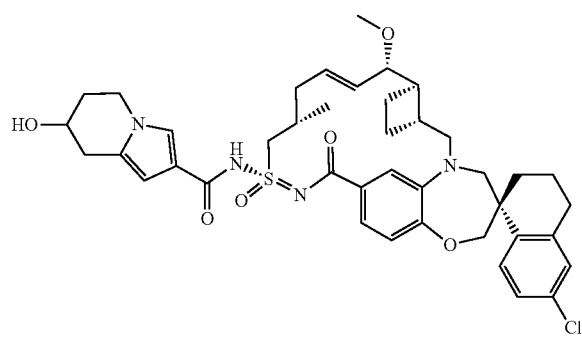 [SMILES: CO[C@H]1/C=C/C[C@H](C)C[S@@](=O)(NC(=O)c2cc3n(c2)CCC(O)C3)=NC(=O)c2ccc3c(c2)N(C[C@@H]2CC[C@H]21)C[C@@]1(CCCc2cc(Cl)ccc21)CO3]

Example 306 was synthesized in the same manner as Example 18 using 7-hydroxy-5,6,7,8-tetrahydroindolizine-2-carboxylic acid and Example 109. LCMS-ESI+ (m/z): [M+H]+ calcd for $C_{41}H_{49}ClN_4O_6$: 761.3; found: 761.0.

Example 373

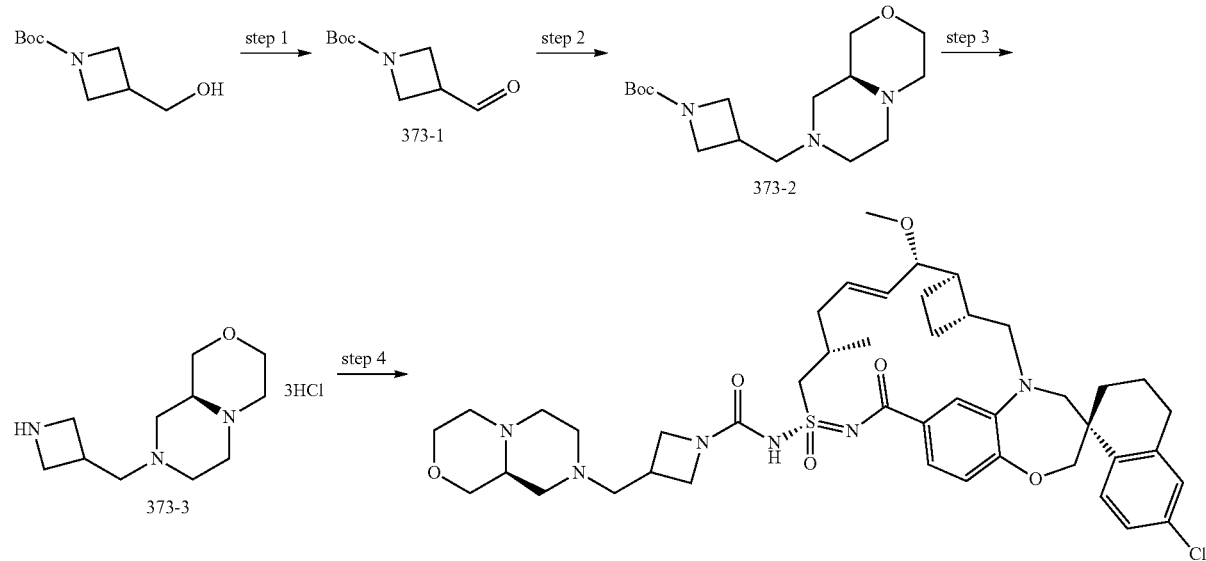

Example 373

Step 1: Synthesis of 373-1 tert-butyl 3-(hydroxymethyl)azetidine-1-carboxylate (139 mg, 0.742 mmol) was dissolved in DCM (5.0 mL) and cooled to 0° C., Dess-Martin Periodinane (409 mg, 0.965 mmol) was added. The reaction was removed from the cooling bath and stirred at room temperature for 1 hr. The reaction was then treated with 1N sodium thiosulfate (10.0 mL) and sat. NaHCO$_3$ (10.0 mL), stirred vigorously for 15 min. The mixture was then diluted with DCM (20.0 mL), the layers were separated, and the organic layer was washed with brine, dried over sodium sulfate, filtered, and concentrated to give 373-1.

Step 2: Synthesis of 373-2

(9aS)-1,3,4,6,7,8,9,9a-octahydropyrazino[2,1-c][1,4]oxazine; dihydrochloride (713 mg, 3.31 mmol) was suspended in DCM (10.0 mL) at room temperature, 25 wt % NaOMe in MeOH (1.55 mL) was added dropwise. The resulting milky suspension was stirred at rt for 2 hrs. The reaction was concentrated, treated with EtOAc at rt for 1 hr, then filtered. The filtrate was concentrated, and dried over the vacuum line for overnight. The free based material (57.6 mg, 0.405 mmol) was dissolved in DCM (4.0 mL) at room temperature. 373-1 (50.0 mg, 0.27 mmol) was added. The mixture was stirred for 2 hrs before STAB (85.8 mg, 0.405 mmol) was added. The newly formed mixture was stirred for 1 h. The reaction was concentrated by removing DCM, redissolved in EtOAc, and treated with 1N NaOH, layers were separated. The aqueous layer was extracted with EtOAc twice. Combined organic layer was dried over sodium sulfate, filtered, and concentrated to give 373-2. LCMS-ESI+ (m/z): calcd H+ for $C_{16}H_{29}N_3O_3$: 312.22; found: 312.23.

Step 3: Synthesis of 373-3

373-2 (84.0 mg, 0.27 mmol) was dissolved in DCM (1.0 mL) at room temperature, 4 N HCl in 1,4-dioxane (0.27 mL, 1.08 mmol) was added. The reaction was stirred at room temperature for 1 hr. The reaction was concentrated, coevaporated with EtOAc three times, further dried over the vacuum line to give 373-3.

Step 4

Example 373 was synthesized in the same manner as Example 75 using Example 109 and 373-3 and DIEA. LCMS-ESI+ (m/z): calcd H+ for $C_{44}H_{59}ClN_6O_6S$: 835.39; found: 835.26.

Example 374

Example 374 was synthesized in the same manner as Example 279 using Example 188 and selenium dioxide (40 eq). 1H NMR (400 MHz, Methanol-d4) δ 7.97 (s, 1H), 7.75 (d, J=8.5 Hz, 1H), 7.25-7.16 (m, 2H), 7.12 (d, J=2.3 Hz, 2H), 6.92 (dd, J=8.2, 2.1 Hz, 1H), 6.18-6.06 (m, 1H), 5.82-5.74 (m, 1H), 4.43-4.26 (m, 2H), 4.10 (s, 2H), 3.99 (s, 3H), 3.86-3.76 (m, 6H), 3.70-3.61 (m, 1H), 3.27 (s, 3H), 3.18- 3.08 (m, 1H), 2.91-2.72 (m, 2H), 2.57-2.27 (m, 3H), 2.14-2.05 (m, 1H), 1.99-1.79 (m, 6H), 1.71 (d, J=7.0 Hz, 3H), 1.53-1.41 (m, 1H), 1.27 (d, J=8.8, 7.0 Hz, 3H). LCMS-ESI+ (m/z): calcd H+ for $C_{39}H_{48}ClN_5O_7S$: 766.30; found: 765.05.

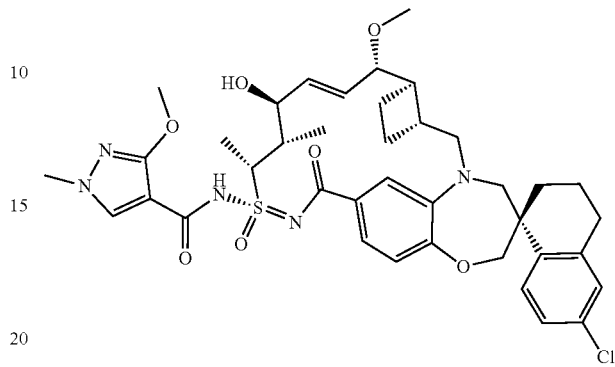

Example 375

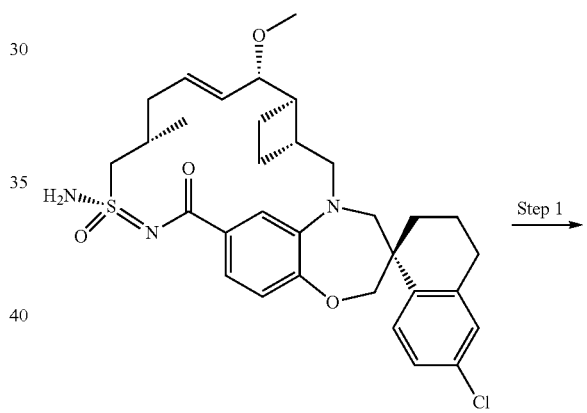

Example 109

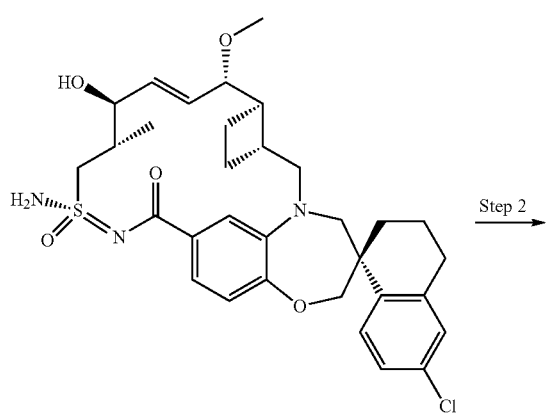

375-1

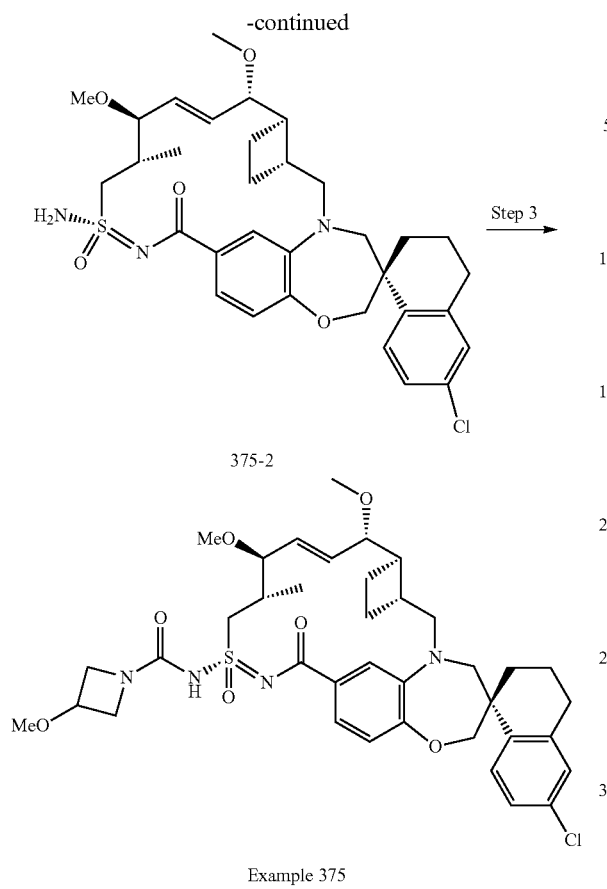

375-2

Example 375

Step 1

Example 109 (445 mg, 0.744 mmol) was dissolved in dioxane (7 mL). Selenium dioxide (330 mg, 4 equiv.) was added in one portion. The mixture was heated to reflux until LCMS indicated approximately 50% conversion to the corresponding allylic alcohol. The reaction mixture was then cooled to room temperature and the residue was purified by Gilson reverse phase prep HPLC (40-90% ACN/H$_2$O with 0.1% TFA) to give intermediate 375-1. $^1$H NMR (400 MHz, Methanol-d$_4$) δ 7.76 (d, J=8.6 Hz, 1H), 7.29 (dd, J=8.2, 1.9 Hz, 1H), 7.18 (dd, J=8.6, 2.3 Hz, 1H), 7.11 (d, J=2.4 Hz, 1H), 7.07 (d, J=1.9 Hz, 1H), 6.84 (d, J=8.2 Hz, 1H), 6.25 (dd, J=15.3, 6.1 Hz, 1H), 5.76 (dd, J=15.5, 9.0 Hz, 1H), 4.38 (d, J=6.0 Hz, 1H), 4.26 (dd, J=15.0, 6.1 Hz, 1H), 4.09-4.00 (m, 2H), 3.93-3.81 (m, 2H), 3.65 (d, J=14.1 Hz, 1H), 3.30 (m, 6H), 3.10-3.03 (m, 1H), 2.87-2.70 (m, 3H), 2.57-2.30 (m, 2H), 2.25-2.09 (m, 2H), 2.01-1.66 (m, 7H), 1.43 (t, J=12.7 Hz, 1H), 1.21 (d, J=6.9 Hz, 3H). LCMS-ESI+(m/z): [M+H]+ calcd for C$_{32}$H$_{40}$ClN$_3$O$_5$S: 614.3; found: 614.1.

Step 2

Di-tert-butyl dicarbonate (16.9 mg, 77.4 μmol) was added to a stirred mixture of Intermediate 375-1 (31.7 mg, 51.6 μmol), triethylamine (21.6 μL, 155 μmol), 4-(dimethylamino)pyridine (18.9 mg, 155 μmol), and water (4.6 μL, 260 μmol) in tetrahydrofuran (3.0 mL) at 0° C., and the resulting mixture was warmed to room temperature. After 40 min, a solution of citric acid (200 mg) in water (5 mL) was added. Ethyl acetate (60 mL) was added. The organic layer was washed sequentially with water (30 mL) and a mixture of water and brine (1:1 v:v, 30 mL), then dried over anhydrous magnesium sulfate, filtered, and concentrated under reduced pressure. The residue was dissolved in tetrahydrofuran (1.0 mL), stirred, and cooled to −40° C. Iodomethane (32.2 μL, 516 μmol) was added via syringe. After 1 min, potassium bis(trimethylsilyl)amide solution (1.0 M in tetrahydrofuran) was added over 1 min via syringe. After 1 min, the resulting mixture was warmed to room temperature. After 30 min, a solution of phosphoric acid (260 mg) and sodium dihydrogen phosphate dehydrate (90 mg) in water (10 mL) was added. Ethyl acetate (60 mL) was added. The organic layer was washed sequentially with a mixture of water and brine (1:1 v:v, 30 mL) and brine (2×30 mL), dried over anhydrous magnesium sulfate, filtered, and concentrated under reduced pressure. The residue was dissolved in dichloromethane (10 mL), and the resulting mixture was stirred at room temperature. Trifluoroacetic acid (1.0 mL) was added. After 20 min, trifluoroacetic acid (0.55 mL) was added. After 30 min, a solution of sodium dihydrogen phosphate dehydrate (6.3 g) in water (15 mL) was added. Brine (10 mL) was added, and the aqueous layer was extracted with dichloromethane (2×30 mL). The combined organic layers were dried over anhydrous magnesium sulfate, filtered, and concentrated under reduced pressure. The residue was purified by flash column chromatography on silica gel (0 to 70% ethyl acetate in dichloromethane) to give 375-2.

Step 2

Example 375 was synthesized in a manner similar to Example 244 using 375-2 instead of 240-1. 1H NMR (400 MHz, Acetone-d6) δ 7.77 (d, J=8.4 Hz, 1H), 7.25 (dd, J=8.5, 2.4 Hz, 1H), 7.18-7.03 (m, 3H), 6.96 (d, J=8.1 Hz, 1H), 5.94 (dd, J=15.3, 8.1 Hz, 1H), 5.80 (dd, J=15.3, 9.0 Hz, 1H), 4.35-4.16 (m, 4H), 4.13 (d, J=12.2 Hz, 1H), 4.08 (d, J=12.1 Hz, 1H), 3.97-3.44 (m, 6H), 3.39 (d, J=14.2 Hz, 1H), 3.30 (s, 3H), 3.28 (s, 3H), 3.25 (s, 3H), 3.18 (dd, J=15.3, 10.4 Hz, 1H), 3.05-1.38 (m, 14H), 1.23 (d, J=6.8 Hz, 3H). LCMS: 741.2.

Example 376

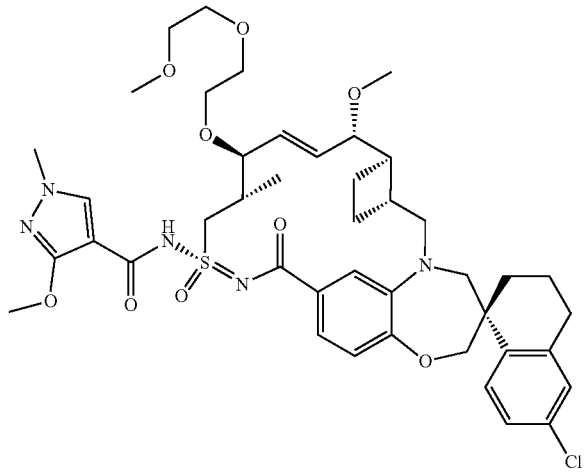 [SMILES: COCCOCCO[C@H]1/C=C/[C@H](OC)[C@@H]2CC[C@H]2CN2C[C@@]3(CCCc4cc(Cl)ccc43)COc3ccc(cc32)C(=O)N=[S@](=O)(NC(=O)c2cn(C)nc2OC)C[C@H]1C]

Example 376 was synthesized in the same manner as Example 283 using 1-iodo-2-(2-methoxyethoxy)ethane and Example 279. $^1$H NMR (400 MHz, Methanol-d$_4$) δ 8.09 (s, 1H), 7.75 (d, J=8.6 Hz, 1H), 7.41-7.31 (m, 1H), 7.23-7.14 (m, 2H), 7.12 (m, 1H), 6.92 (d, J=8.2 Hz, 1H), 6.05 (dd, J=15.4, 7.3 Hz, 1H), 5.85 (dd, J=15.4, 8.5 Hz, 1H), 4.15-4.01 (m, 9H), 3.82 (m, 5H), 3.76-3.58 (m, 6H), 3.54-3.44 (m, 4H), 3.41 (d, J=14.4 Hz, 1H), 3.35 (s, 3H), 3.30 (s, 3H), 3.19-3.06 (m, 1H), 2.89-2.73 (m, 2H), 2.51 (br, 2H), 2.27 (m, 1H), 2.11 (m, 1H), 2.0-1.89 (m, 2H), 1.82 (m, 3H), 1.46 (t, J=11.7 Hz, 1H), 1.20 (d, J=6.8 Hz, 3H). LCMS-ESI+ (m/z): [M+H]+ calcd for $C_{43}H_{56}ClN_5O_9S$: 854.3; found: 854.1.

Example 377 and Example 378

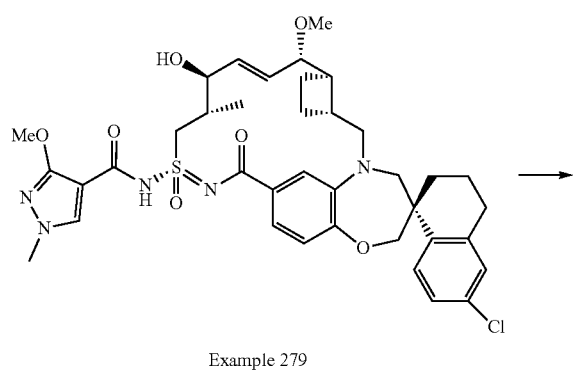

Example 279

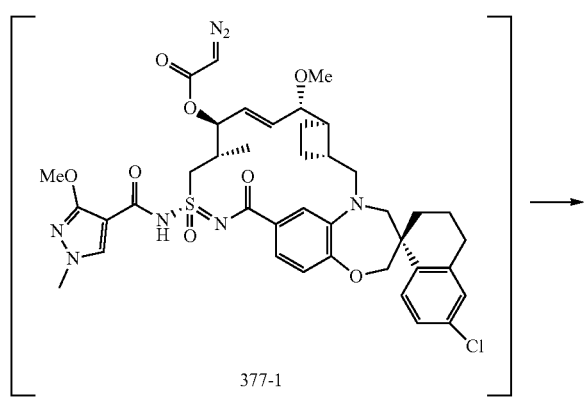

377-1

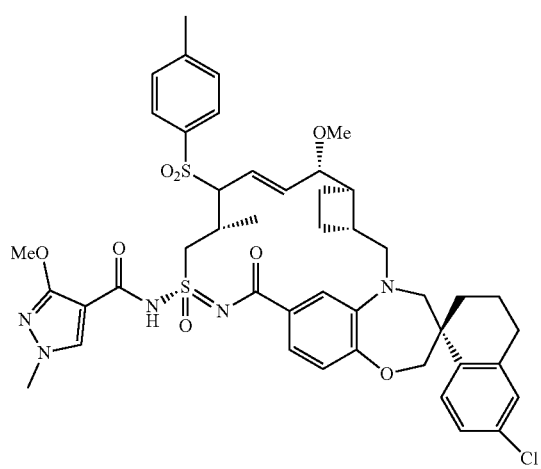

Example 377

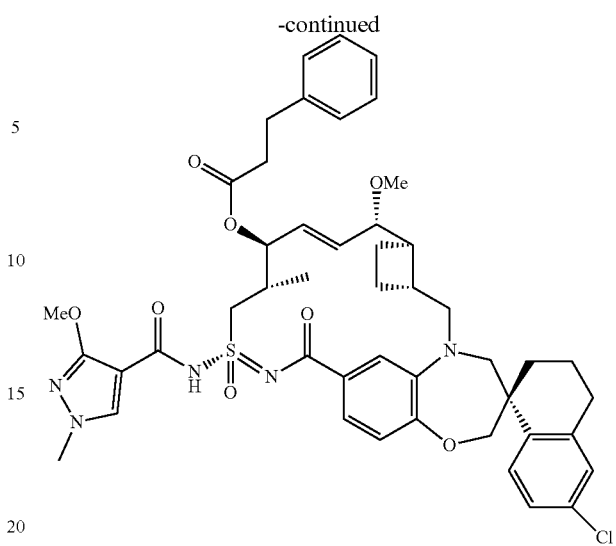

Example 378

2-(2-Tosylhydrazono)acetyl chloride (34.4 mg, 132 μmol) and N,N-dimethylaniline (33.5 μL, 264 μmol) were added sequentially to a stirred solution of Example 279 (33.1 mg, 44.0 μmol) in dichloromethane (0.9 mL) at 0° C. After 7 min, the resulting mixture was warmed to room temperature. After 55 min, 2-(2-tosylhydrazono)acetyl chloride (80.0 mg, 307 μmol) and ACV-dimethylaniline (80.0 μL, 630 μmol) were added sequentially. After 13 min, the resulting mixture was cooled to 0° C., and triethylamine (163 μL, 1.17 mmol) was added via syringe. After 20 min, toluene (60 mL) and a mixture of sodium dihydrogen phosphate monohydrate (160 mg) and sodium hydrogen phosphate heptahydrate (1.04 g) in water (100 mL) were added sequentially. The biphasic mixture was agitated, and the layers were separated. The organic layer was washed sequentially with a mixture of sodium dihydrogen phosphate monohydrate (80 mg) and sodium hydrogen phosphate heptahydrate (502 mg) in water (50 mL), a solution of citric acid (100 mg) in water (50 mL), and water (50 mL); dried over anhydrous sodium sulfate; filtered; and concentrated under reduced pressure to a volume of 8.5 mL. The resulting mixture containing crude 377-1 was added over 90 min via syringe pump to a vigorously stirred mixture of copper(I) trifluoromethanesulfonate toluene complex (6.7 mg, 22 μmol) and toluene (5.0 mL) at 100° C. After 15 min, the resulting mixture was cooled to room temperature, was filtered through celite, and was concentrated under reduced pressure. The residue was purified by reverse phase preparative hplc (0.1% trifluoroacetic acid in acetonitrile/water) to give Example 377 as a 1:1 mixture of diastereomers. 1H NMR (400 MHz, Acetone-d6) δ 8.21-6.64 (m, 11H), 6.20-5.79 (m, 1H), 5.74-5.14 (m, 2H), 4.25-2.99 (m, 17H), 2.99-1.17 (m, 17H), 1.13 (d, J=6.9 Hz, 1.5H), 1.06 (d, J=6.9 Hz, 1.5H). LCMS: 890.1. Further elution gave Example 378. 1H NMR (400 MHz, Acetone-d6) δ 8.10 (s, 1H), 7.79 (d, J=8.5 Hz, 1H), 7.53-6.32 (m, 10H), 6.32-5.21 (m, 3H), 4.29-2.84 (m, 8H), 4.08 (s, 3H), 3.85 (s, 3H), 3.23 (s, 3H), 2.83-1.21 (m, 18H), 1.15 (d, J=6.8 Hz, 3H). LCMS: 884.2.

Example 379

Step 1: Preparation of Ethyl 3-(3-methoxyazetidin-1-yl)-1-methyl-1H-pyrazole-4-carboxylate The reaction mixture of ethyl 3-bromo-1-methyl-pyrazole-4-carboxylate (150 mg, 0.64 mmol), 3-methoxyazetidine hydrochloride (119.3 mg, 0.97 mmol), Cs$_2$CO$_3$ (629.09 mg, 1.93 mmol) and XanTphos Pd G3 (122.07 mg, 0.13 mmol) in N-Methyl-2-pyrrolidone (3 mL) was heated at 120° C. overnight. The reaction mixture was cooled down, washed with water, extracted with EtOAc, dried over MgSO$_4$, filtered, concentrated, and purified by silica gel column (eluting with 0-100% EtOAc/hexane) to give the product.

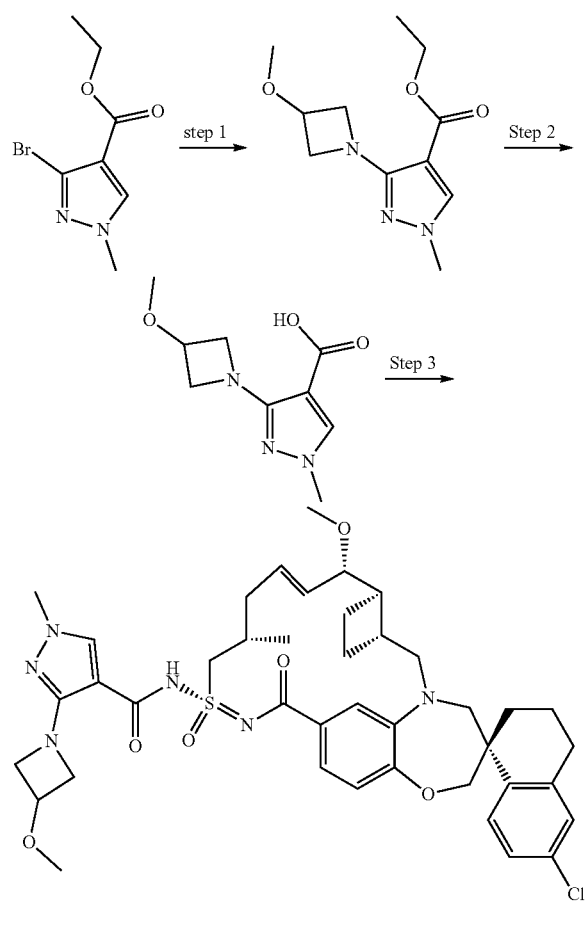

Step 2: Preparation of 3-(3-methoxyazetidin-1-yl)-1-methyl-1H-pyrazole-4-carboxylic Acid the reaction mixture of ethyl 3-(3-methoxyazetidin-1-yl)-1-methyl-pyrazole-4-carboxylate (14 mg, 0.06 mmol), 2M NaOH (0.06 mL) in EtOH (1.0 mL) and water (0.5 mL) was stirred at 45° C. overnight. The reaction mixture was cooled down, concentrated, co-evaporated with toluene to remove moisture and go to the next step without purification.

Step 3

Example 379 was synthesized in the same manner as Example 18, using Example 109 instead of Example 5, and 3-(3-methoxyazetidin-1-yl)-1-methyl-1H-pyrazole-4-carboxylic acid was used instead of 3-methoxypropionic acid. 1H NMR (400 MHz, Methanol-d4) δ 7.82-7.70 (m, 2H), 7.29 (d, J=8.3 Hz, 1H), 7.19 (dd, J=8.6, 2.3 Hz, 1H), 7.14-7.04 (m, 2H), 6.91 (d, J=8.2 Hz, 1H), 6.10 (dt, J=14.2, 6.7 Hz, 1H), 5.61 (dd, J=15.4, 8.6 Hz, 1H), 4.56 (dd, J=8.8, 6.3 Hz, 1H), 4.51-4.45 (m, 1H), 4.33-4.23 (m, 2H), 4.19 (dd, J=8.7, 4.4 Hz, 1H), 4.13-4.02 (m, 3H), 4.02-3.91 (m, 2H), 3.86 (d, J=15.1 Hz, 1H), 3.78 (dd, J=8.5, 2.8 Hz, 1H), 3.74 (s, 2H), 3.69 (d, J=14.3 Hz, 1H), 3.29 (s, 3H), 3.08 (dd, J=14.9, 9.3 Hz, 2H), 2.92-2.70 (m, 3H), 2.49 (d, J=26.9 Hz, 4H), 2.33-2.19 (m, 2H), 2.19-2.05 (m, 2H), 2.02-1.73 (m, 6H), 1.46 (d, J=11.8 Hz, 1H), 1.16 (d, J=6.8 Hz, 3H). LCMS-ESI+ (m/z): [M+H]+ calcd for C$_{41}$H$_{51}$ClN$_6$O$_6$S: 791.33; found: 791.13.

Example 380

Step 1: Preparation of Ethyl 3-(4-methoxy-1-piperidyl)-1-methyl-pyrazole-4-carboxylate The reaction mixture of ethyl 3-bromo-1-methyl-pyrazole-4-carboxylate (200 mg, 0.86 mmol), 4-methoxypiperidine (197.67 mg, 1.72 mmol), Cs$_2$CO$_3$ (838.79 mg, 2.57 mmol) and XanTphos Pd G3 (162.76 mg, 0.17 mmol) in dimethylacetamide (5 mL) was heated at 120° C. overnight. The reaction mixture was cooled down, washed with water, extracted with EtOAc, dried over MgSO$_4$, filtered, concentrated, and purified by silica gel chromatography (0-100% EtOAc/hexane) to give the product (14 mg).

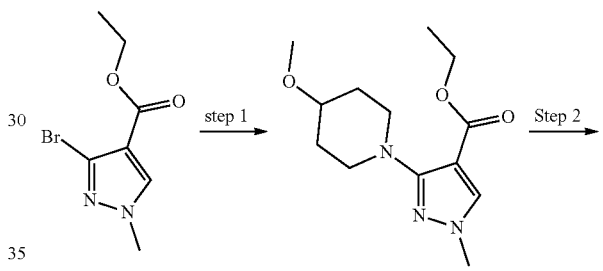

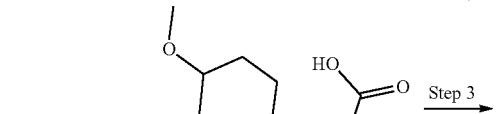

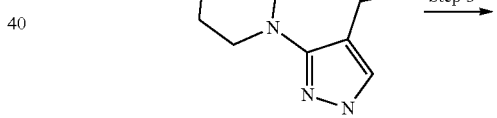

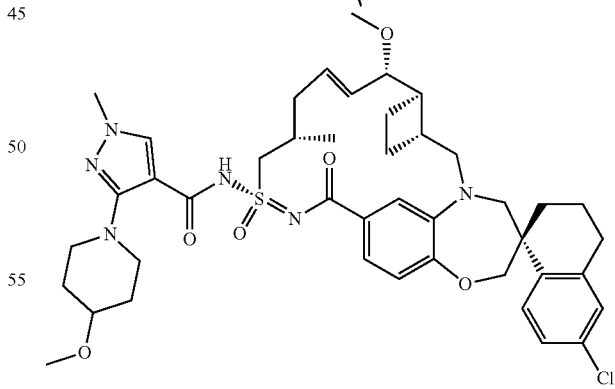

Step 2: Preparation of 3-(4-methoxy-1-piperidyl)-1-methyl-pyrazole-4-carboxylic Acid The reaction mixture of ethyl 3-(4-methoxy-1-piperidyl)-1-methyl-pyrazole-4-carboxylate (14 mg, 0.05 mmol), 2M NaOH (0.05 ml) in EtOH (1 mL) and water (0.5 mL) was heated at 45° C. overnight. The reaction mixture was then cooled down, concentrated, co-evaporated with toluene to remove moisture and go to next step without purification.

Step 3

Example 380 was synthesized in the same manner as Example 18, using Example 109 instead of Example 5, and 3-(4-methoxy-1-piperidyl)-1-methyl-pyrazole-4-carboxylic acid was used instead of 3-methoxypropionic acid. 1H NMR (400 MHz, Methanol-d4) δ 7.92 (s, 1H), 7.76 (d, J=8.5 Hz, 1H), 7.27 (dd, J=8.2, 1.9 Hz, 1H), 7.19 (dd, J=8.5, 2.3 Hz, 1H), 7.12 (d, J=2.4 Hz, 1H), 7.07 (s, 1H), 6.91 (d, J=8.2 Hz, 1H), 6.11 (dt, J=14.5, 6.9 Hz, 1H), 5.62 (dd, J=15.3, 8.7 Hz, 1H), 4.32 (dd, J=14.8, 6.4 Hz, 1H), 4.14-3.97 (m, 3H), 3.91-3.74 (m, 5H), 3.70 (d, J=14.3 Hz, 1H), 3.52-3.45 (m, 1H), 3.42 (s, 2H), 3.29 (s, 3H), 3.27-3.22 (m, 3H), 3.13-3.00 (m, 2H), 2.90-2.69 (m, 3H), 2.46 (s, 3H), 2.36-2.20 (m, 2H), 2.10 (t, J=17.1 Hz, 4H), 1.94 (d, J=5.1 Hz, 2H), 1.91-1.65 (m, 6H), 1.45 (t, J=11.8 Hz, 1H), 1.15 (d, J=6.8 Hz, 3H). LCMS-ESI+ (m/z): [M+H]+ calcd for $C_{43}H_{55}ClN_6O_6S$: 819.36; found: 819.20.

Example 381

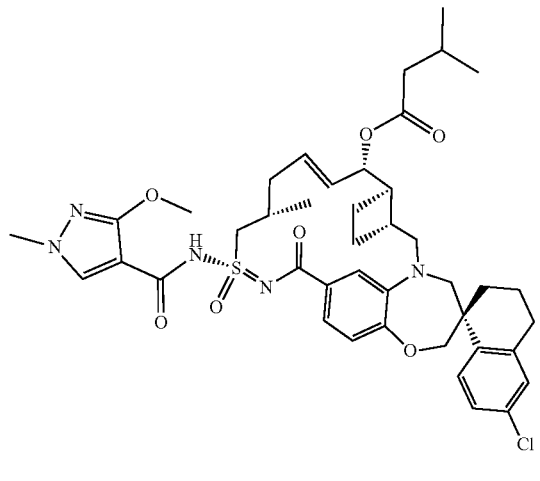 [SMILES: CC[C@H]1CN2C[C@@]3(CCCc4cc(Cl)ccc43)COc3ccc(cc32)C(=O)N=[S@](=O)(NC(=O)c2cn(C)nc2OC)C[C@@H](C)C/C=C/[C@H](OC(=O)CC(C)C)[C@@H]1C]

Example 381 was synthesized in the same manner as Example 223 using 3-methylbutanoic acid and intermediate 266-2. 1H NMR (400 MHz, Chloroform-d) δ 7.84 (s, 1H), 7.76 (d, J=8.5 Hz, 1H), 7.50 (dd, J=8.3, 1.9 Hz, 1H), 7.36 (d, J=2.0 Hz, 1H), 7.20 (dd, J=8.5, 2.3 Hz, 1H), 7.10 (d, J=2.3 Hz, 1H), 6.94 (d, J=8.3 Hz, 1H), 5.93 (dt, J=13.6, 6.6 Hz, 1H), 5.73 (dd, J=15.7, 6.1 Hz, 1H), 5.33 (t, J=5.7 Hz, 1H), 4.21-3.97 (m, 6H), 3.96-3.62 (m, 6H), 3.32 (d, J=14.4 Hz, 1H), 3.04 (dd, J=15.2, 9.6 Hz, 1H), 2.88-2.70 (m, 2H), 2.61 (d, J=18.4 Hz, 1H), 2.55-2.23 (m, 3H), 2.20-1.99 (m, 4H), 1.97-1.60 (m, 5H), 1.34 (d, J=52.1 Hz, 3H), 1.12 (d, J=6.8 Hz, 3H), 0.94 (dd, J=6.4, 5.2 Hz, 6H). LCMS-ESI+ (m/z): [M+H]+ calcd for $C_{42}H_{52}ClN_5O_7S$: 807.42; found: 807.17.

Example 382

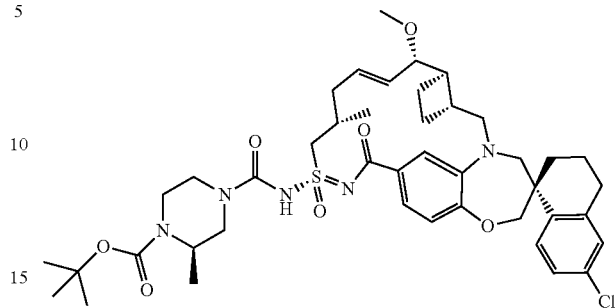

Example 382 was synthesized in the same manner as Example 75 using Example 109 and tert-butyl (2R)-2-methylpiperazine-1-carboxylate. 1H NMR (400 MHz, Methanol-d4) δ 7.74 (d, J=8.6 Hz, 1H), 7.18 (dd, J=8.5, 2.4 Hz, 1H), 7.14-7.07 (m, 2H), 6.95 (dd, J=8.1, 1.7 Hz, 1H), 6.88 (d, J=2.0 Hz, 1H), 6.01-5.90 (m, 1H), 5.58 (dd, J=15.2, 9.3 Hz, 1H), 4.40 (dd, J=14.8, 6.3 Hz, 1H), 4.35-4.23 (m, 1H), 4.18-4.02 (m, 3H), 3.85 (d, J=14.6 Hz, 2H), 3.76 (dd, J=9.3, 3.7 Hz, 1H), 3.71-3.56 (m, 2H), 3.27-3.24 (m, 4H), 3.17-2.98 (m, 3H), 2.89-2.70 (m, 2H), 2.55-2.41 (m, 2H), 2.38-2.23 (m, 1H), 2.23-2.06 (m, 4H), 2.01-1.68 (m, 7H), 1.49 (s, 9H), 1.46-1.38 (m, 1H), 1.24-1.09 (m, 6H). LCMS-ESI+ (m/z): calcd H+ for $C_{43}H_{58}ClN_5O_7S$: 824.37; found: 823.89.

Example 383

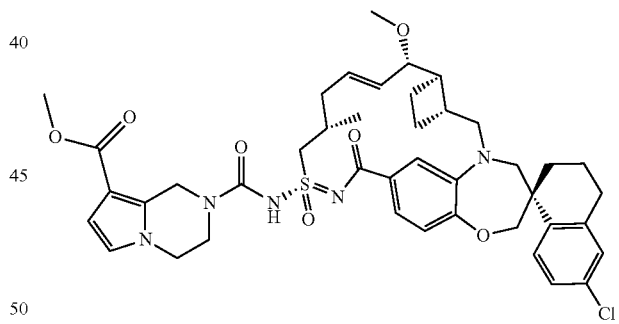

Example 383 was synthesized in the same manner as Example 75 using Example 109 and methyl 1,2,3,4-tetra-hydropyrrolo[1,2-a]pyrazine-8-carboxylate. 1H NMR (400 MHz, Methanol-d4) δ 7.74 (d, J=8.5 Hz, 1H), 7.18 (dd, J=8.5, 2.4 Hz, 1H), 7.14-7.06 (m, 2H), 6.94 (d, J=8.1 Hz, 1H), 6.90-6.84 (m, 1H), 6.68 (d, J=3.0 Hz, 1H), 6.54 (d, J=3.0 Hz, 1H), 6.02-5.89 (m, 1H), 5.58 (dd, J=15.2, 9.3 Hz, 1H), 4.44-4.29 (m, 1H), 4.12-4.00 (m, 5H), 3.88-3.53 (m, 8H), 3.28-3.23 (m, 4H), 3.13-3.02 (m, 1H), 2.88-2.71 (m, 2H), 2.55-2.40 (m, 2H), 2.37-2.24 (m, 1H), 2.24-2.06 (m, 4H), 2.01-1.66 (m, 7H), 1.50-1.37 (m, 1H), 1.20-1.14 (m, 3H). LCMS-ESI+ (m/z): calcd H+ for $C_{42}H_{50}ClN_5O_7S$: 804.31; found: 803.76.

Example 384

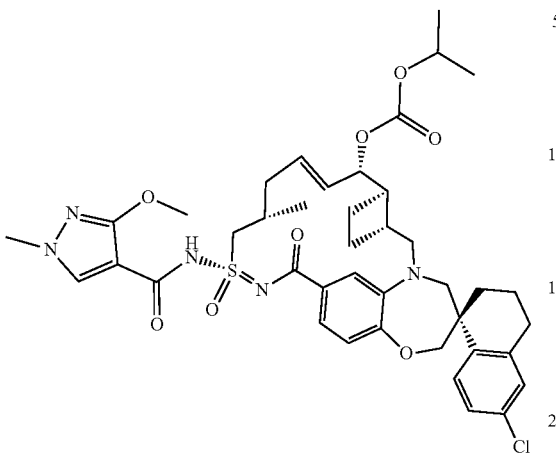

To a stirred solution of Example 223 (10 mg, 0.014 mmol) in DCM (5 mL) was added isopropyl carbonochloridate (16.97 mg, 0.138 mmol) at 0° C. and stirred for 30 min and then to room temperature overnight. The reaction mixture was evaporated and purified on reversed phase chromatography 0.1% TFA 70-95% acetonitrile to give Example 384. 1H NMR (400 MHz, Chloroform-d) δ 7.84 (s, 1H), 7.77 (d, J=8.5 Hz, 1H), 7.50 (dd, J=8.3, 1.8 Hz, 1H), 7.20 (dd, J=8.5, 2.5 Hz, 1H), 7.10 (d, J=2.4 Hz, 1H), 6.94 (d, J=8.3 Hz, 1H), 6.04 (dt, J=14.3, 6.5 Hz, 1H), 5.74 (dd, J=15.8, 6.8 Hz, 1H), 5.17 (t, J=5.8 Hz, 1H), 4.86 (p, J=6.3 Hz, 1H), 4.21-3.96 (m, 5H), 3.82 (s, 6H), 3.32 (d, J=14.5 Hz, 1H), 3.04 (dd, J=15.2, 10.0 Hz, 1H), 2.86-2.24 (m, 9H), 2.20-1.58 (m, 8H), 1.42 (t, J=10.3 Hz, 1H), 1.30 (dd, J=7.3, 6.2 Hz, 6H), 1.11 (d, J=6.8 Hz, 2H). LCMS-ESI+ (m/z): [M+H]+ calcd for $C_{41}H_{50}ClN_5O_8S$: 808.31; found: 808.60.

Example 385

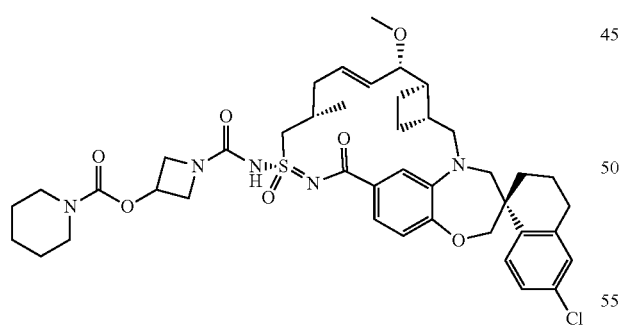

Example 385 was synthesized in the same manner as Example 75 using trans-azetidin-3-yl piperidine-1-carboxylate bis-trifluoroacetic acid and Example 109. 1H NMR (400 MHz, Methanol-d4) δ 7.72 (d, J=8.5 Hz, 1H), 7.16 (d, J=9.2 Hz, 1H), 7.09 (d, J=6.2 Hz, 2H), 6.91 (d, J=8.4 Hz, 2H), 5.95 (dt, J=14.2, 6.7 Hz, 1H), 5.56 (dd, J=15.2, 9.1 Hz, 1H), 5.14-5.02 (m, 1H), 4.38-4.25 (m, 3H), 4.14-4.01 (m, 2H), 3.97 (s, 1H), 3.83 (d, J=15.1 Hz, 1H), 3.74 (dd, J=9.3, 3.6 Hz, 1H), 3.65 (d, J=14.2 Hz, 1H), 3.59 (dd, J=15.0, 5.7 Hz, 1H), 3.55-3.35 (m, 4H), 3.27 (d, J=14.4 Hz, 1H), 3.24 (s, 3H), 3.06 (dd, J=15.3, 10.3 Hz, 1H), 2.85-2.65 (d, J=18.2 Hz, 2H), 2.54-2.39 (m, 2H), 2.39-2.25 (m, 1H), 2.24-2.05 (m, 3H), 1.99-1.49 (m, 8H), 1.44 (d, J=12.8 Hz, 1H), 1.13 (d, J=6.6 Hz, 3H). LCMS-ESI+ (m/z): [M+H]+ calcd for $C_{42}H_{55}ClN_5O_7S$: 808.34; found: 807.90.

Example 386

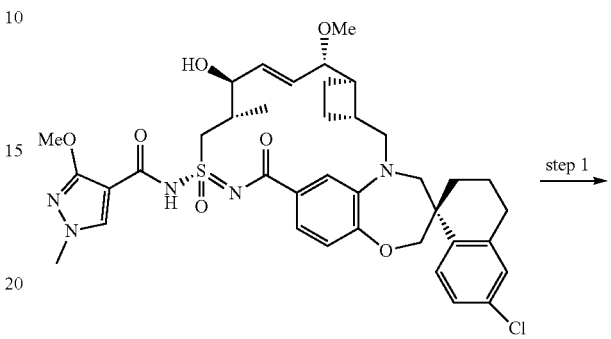

Example 279

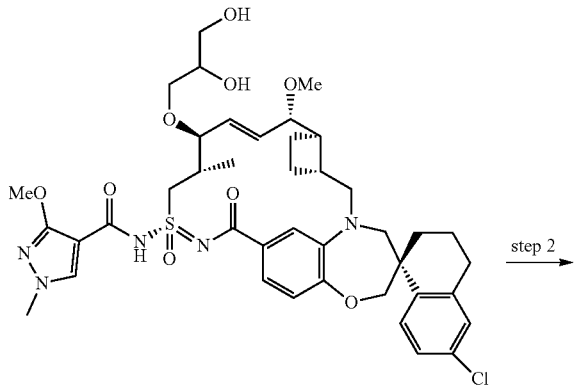

386-1

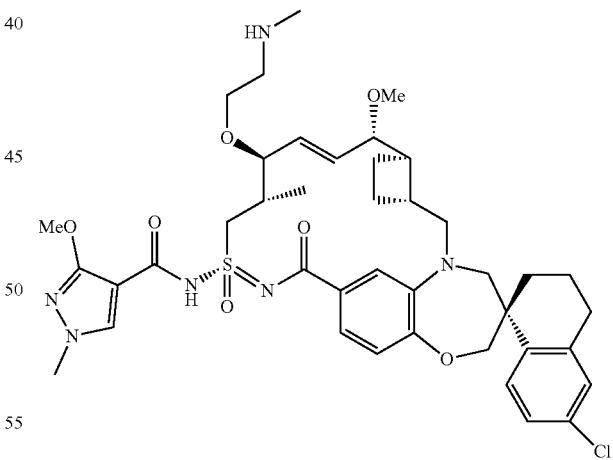

Example 386

Step 1

Potassium bis(trimethylsilyl)amide solution (1.0 M in tetrahydrofuran, 199 μL, 199 μmol) was added over 1 min via syringe to a stirred mixture of Example 279 (30 mg, 40 μmol) and allyl bromide (20.7 μL, 239 μmol) in tetrahydrofuran (2.0 mL) at −40° C. After 2 min, the resulting mixture was warmed to room temperature. After 40 min, a solution of citric acid (100 mg) in water (10 mL) was added. Ethyl acetate (35 mL) was added, and the organic layer was washed sequentially with water (10 mL) and a mixture of water and brine (1:1 v:v, 20 mL), dried over anhydrous magnesium sulfate, filtered, and concentrated under reduced pressure. The residue was dissolved in tert-butyl alcohol (1.0 mL), water (0.5 mL), and tetrahydrofuran (0.3 mL). The resulting mixture was stirred at room temperature, and 4-methylmorpholine-N-oxide (9.9 mg, 85 µmol) and osmium tetroxide solution (2.5% wt. in tert-butyl alcohol, 50 µL, 4 µmol) were added sequentially. After 90 min, sodium sulfite (83.2 mg, 808 µmol) was added, and the resulting mixture was stirred vigorously. After 10 min, the resulting mixture was filtered through celite, and the filter cake was extracted with ethyl acetate (25 mL) and dichloromethane (10 mL). The combined filtrates were washed sequentially with a mixture of citric acid (100 mg) in water (10 mL) and brine (10 mL) and a mixture of water and brine (1:1 v:v, 10 mL), dried over anhydrous magnesium sulfate, filtered through celite, and concentrated under reduced pressure to give 386-1.

Step 2

Sodium periodate (23.3 mg, 109 µmol) was added to a vigorously stirred mixture of 386-1 (12 mg, 15 µmol), tetrahydrofuran (1.0 mL), and water (0.5 mL) at room temperature. After 45 min, ethyl acetate (30 mL) and a solution of citric acid (100 mg) in water (10 mL) were added sequentially. The organic layer was washed with a mixture of water and brine (1:1 v:v, 2×15 mL), dried over anhydrous magnesium sulfate, filtered, and concentrated under reduced pressure. The residue was dissolved in toluene (3.0 mL), finely ground sarcosine (25.9 mg, 290 µmol) was added, and the resulting mixture was stirred vigorously and was heated to 120° C. After 45 min, the resulting mixture was cooled to room temperature and was concentrated under reduced pressure. The residue was purified by reverse phase preparative HPLC (0.1% trifluoroacetic acid in acetonitrile/water) to give Example 386. 1H NMR (400 MHz, Methanol-d4) δ 8.07 (s, 1H), 7.76 (d, J=8.5 Hz, 1H), 7.37 (dd, J=8.3, 1.8 Hz, 1H), 7.26-7.16 (m, 2H), 7.13 (d, J=2.3 Hz, 1H), 6.93 (d, J=8.2 Hz, 1H), 6.12 (dd, J=15.4, 8.3 Hz, 1H), 5.92 (dd, J=15.4, 8.6 Hz, 1H), 4.37-4.00 (m, 5H), 4.07 (s, 3H), 3.95-3.77 (m, 2H), 3.83 (s, 3H), 3.72 (d, J=14.4 Hz, 1H), 3.56 (ddd, J=10.2, 6.0, 3.8 Hz, 1H), 3.42 (d, J=14.4 Hz, 1H), 3.38-3.19 (m, 2H), 3.18-3.07 (m, 1H), 2.93-1.59 (m, 13H), 2.77 (s, 3H), 1.55-1.41 (m, 1H), 1.25 (d, J=6.9 Hz, 3H). LCMS: 809.3.

Example 387

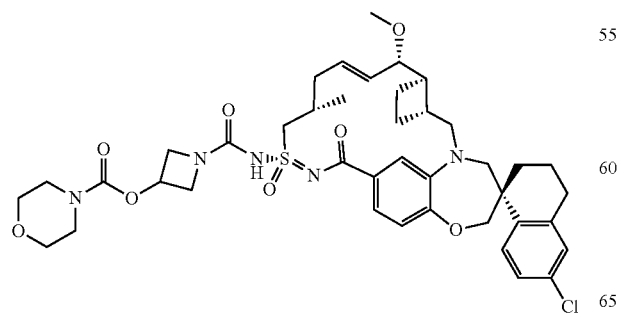

Example 387 was synthesized in the same manner as Example 75 using trans-azetidin-3-yl morpholine-4-carboxylate bis-trifluoroacetic acid and Example 109. 1H NMR (400 MHz, MeOH-d4) δ 7.72 (d, J=8.5 Hz, 1H), 7.16 (dd, J=8.5, 2.4 Hz, 1H), 7.09 (dt, J=5.0, 2.1 Hz, 2H), 6.94-6.86 (m, 2H), 5.95 (dt, J=14.3, 6.7 Hz, 1H), 5.56 (dd, J=15.3, 9.1 Hz, 1H), 5.12 (tt, J=6.9, 4.0 Hz, 1H), 4.30 (m, 3H), 4.03 (dd, J=25.5, 6.3 Hz, 4H), 3.83 (d, J=15.0 Hz, 1H), 3.74 (dd, J=9.2, 3.6 Hz, 1H), 3.71-3.56 (m, 6H), 3.48 (d, J=24.7 Hz, 4H), 3.27 (d, J=14.4 Hz, 1H), 3.24 (s, 3H), 3.05 (dd, J=15.3, 10.3 Hz, 1H), 2.89-2.67 (m, 2H), 2.55-2.39 (m, 2H), 2.33 (q, J=9.0 Hz, 1H), 2.23-2.05 (m, 3H), 1.99-1.65 (m, 5H), 1.42 (t, J=13.8 Hz, 1H), 1.13 (d, J=6.6 Hz, 3H). LCMS-ESI+ (m/z): [M+H]+ calcd for $C_{41}H_{53}ClN_5O_8S$: 810.32; found: 809.82.

Example 388

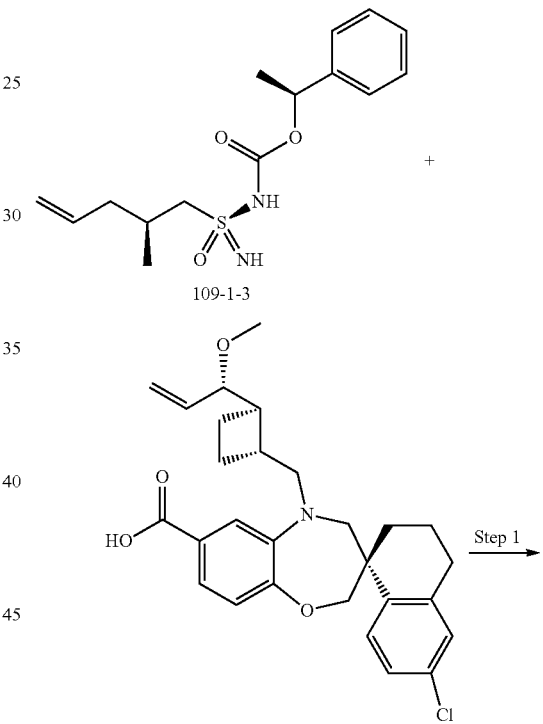

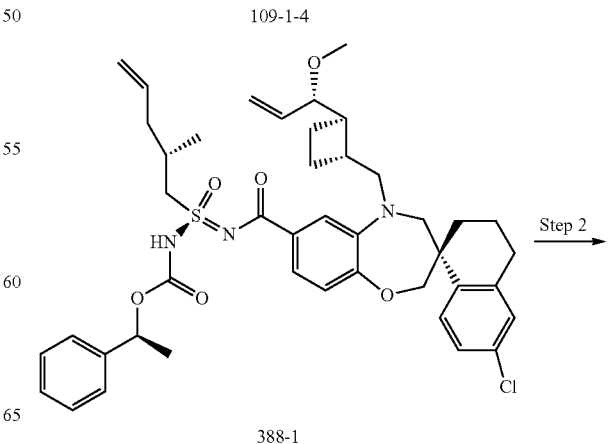

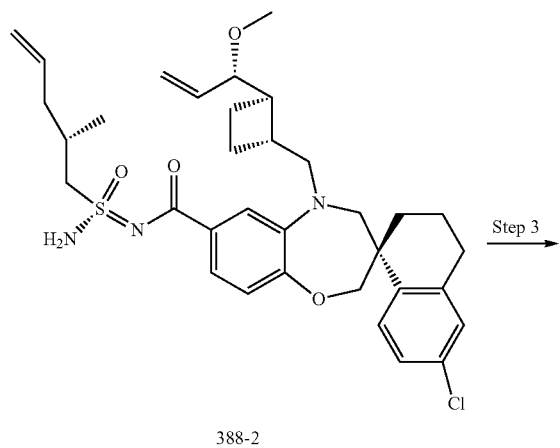

388-2

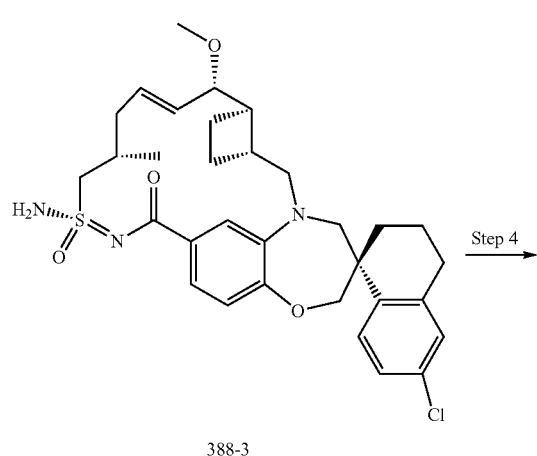

388-3

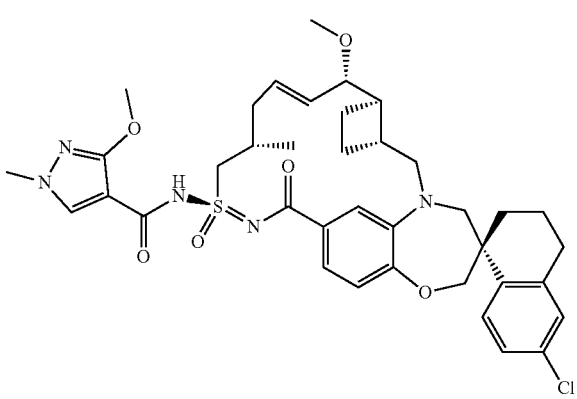

Example 388

Step 1: Synthesis of Intermediate 388-1

The mixture of 109-1-3 (155.0 mg, 0.498 mmol) and 109-1-4 (200 mg, 0.415 mmol) in DCM (3.0 mL) at room temperature was treated with EDCI.HCl (159 mg, 0.830 mmol) followed by DMAP (101 mg, 0.83 mmol). After stirred at room temperature for overnight and reaction mixture was concentrated. The residue was dissolved in EtOAc (100.0 mL), washed with sat'd $NH_4Cl$, sat. $NaHCO_3$, brine, dried over sodium sulfate, filtered and concentrated to give 388-1. LCMS-ESI+ (m/z): calcd H+ for $C_{43}H_{52}ClN_3O_6S$: 774.33; found: 774.02.

Step 2: Synthesis of 388-2

388-1 was treated with a mixture of TFA (2.0 mL) and DCM (4.0 mL) at room temperature for 1 hr. The reaction was then diluted with EtOAc, neutralized with sat. $NaHCO_3$ till pH~7, washed with brine, dried over sodium sulfate, filtered and concentrated to give crude 388-2, purified by combiflash (12 g silica gel, 0-50% EtOAc/Hexanes). Desired fractions were combined and concentrated, and treated with MeOH to give 388-2. 1H NMR (400 MHz, Methanol-d4) δ 7.67 (d, J=8.5 Hz, 1H), 7.55 (d, J=2.0 Hz, 1H), 7.44 (dd, J=8.2, 1.9 Hz, 1H), 7.17-7.05 (m, 2H), 6.84 (d, J=8.2 Hz, 1H), 5.78 (ddt, J=16.1, 10.8, 6.9 Hz, 1H), 5.57 (ddd, J=17.1, 10.5, 7.9 Hz, 1H), 5.21-5.02 (m, 4H), 4.10-3.96 (m, 2H), 3.62 (dd, J=14.3, 4.4 Hz, 1H), 3.58-3.48 (m, 3H), 3.37-3.34 (m, 1H), 3.31 (s, 1H), 2.84-2.66 (m, 2H), 2.53 (pd, J=8.0, 4.0 Hz, 1H), 2.35-2.21 (m, 2H), 2.21-2.09 (m, 2H), 2.08-1.92 (m, 3H), 1.91-1.81 (m, 2H), 1.81-1.47 (m, 4H), 1.13 (d, J=6.3 Hz, 3H).

Step 3: Synthesis of 388-3

The solution of 388-2 (173 mg, 0.277 mmol) in DCE (35.0 mL) was degassed with nitrogen. Hoveryda=Grubbs II catalyst (26.0 mg, 0.0415 mmol) was added, the resulting mixture was sparged with nitrogen for 3 more minutes, and then it was capped and heated at 80° C. overnight under nitrogen balloon. The reaction was cooled to room temperature, mixed with silica gel, concentrated to dryness, and purified by combiflash (12 g silica gel, 0-60% EtOAc/Hexanes, dry loading). Desired fractions were combined and concentrated to give 388-3. 1H NMR (400 MHz, Methanol-d4) δ 7.77 (d, J=8.5 Hz, 1H), 7.26 (dd, J=8.2, 1.9 Hz, 1H), 7.19 (dd, J=8.5, 2.4 Hz, 1H), 7.12 (d, J=2.3 Hz, 1H), 7.06 (d, J=1.9 Hz, 1H), 6.86 (d, J=8.2 Hz, 1H), 6.02 (dt, J=14.1, 6.7 Hz, 1H), 5.56 (dd, J=15.4, 8.7 Hz, 1H), 4.21 (dd, J=14.1, 6.8 Hz, 1H), 4.11-3.98 (m, 2H), 3.85 (d, J=14.9 Hz, 1H), 3.77 (dd, J=8.8, 3.3 Hz, 1H), 3.69 (d, J=14.2 Hz, 1H), 3.27 (s, 3H), 3.19-3.11 (m, 1H), 3.11-3.03 (m, 1H), 2.89-2.71 (m, 2H), 2.58-2.37 (m, 3H), 2.29-2.20 (m, 1H), 2.17-2.08 (m, 2H), 2.00-1.87 (m, 4H), 1.84-1.70 (m, 3H), 1.50-1.39 (m, 1H), 1.14 (d, J=6.8 Hz, 3H). LCMS-ESI+ (m/z): calcd H+ for $C_{32}H_{40}ClN_3O_4S$:598.24; found: 598.03.

Step 4

To the mixture of 388-3 (70.0 mg, 0.117 mmol) and 3-methoxy-1-methyl-pyrazole-4-carboxylic acid (36.5 mg, 0.234 mmol) in DCM (2.0 mL) at room temperature was added EDCI.HCl (44.7 mg, 0.234 mmol) followed by DMAP (28.6 mg, 0.234 mmol). The resulting mixture was stirred at room temperature for overnight. The reaction was then concentrated, redissolved in DMF (3.6 mL), filtered and purified by Gilson reverse phase prep HPLC. Desired fractions were combined and concentrated, frozen dried, triturated with acetonitrile, and filtered to give Example 388. 1H NMR (400 MHz, Methanol-d4) δ 8.04 (s, 1H), 7.76 (d, J=8.5 Hz, 1H), 7.33 (d, J=8.5 Hz, 1H), 7.19 (d, J=8.8 Hz, 2H), 7.13 (s, 1H), 6.90 (d, J=8.2 Hz, 1H), 6.16-6.04 (m, 1H), 5.64 (dd, J=15.5, 8.1 Hz, 1H), 4.25-4.13 (m, 1H), 4.11-3.99 (m, 6H), 3.83-3.74 (m, 6H), 3.30 (s, 3H), 3.17-3.13 (m, 1H), 2.91-2.76 (m, 2H), 2.66-2.40 (m, 5H), 2.30-2.21 (m, 1H), 2.17-2.08 (m, 1H), 1.99-1.91 (m, 3H), 1.84-1.73 (m, 3H), 1.53-1.41 (m, 1H), 1.20 (d, J=6.9 Hz, 3H). LCMS-ESI+ (m/z): calcd H+ for $C_{38}H_{46}ClN_5O_6S$: 736.29; found: 735.97.

Example 389

Example 389 was synthesized in a manner similar to Example 106 using 3-methoxy-1-methyl-1H-pyrazole-4-carboxylic acid instead of 2-((tetrahydro-2H-pyran-4-yl)oxy)acetic acid and using Example 5 instead of 106-4. 1H NMR (400 MHz, Acetone-d6) δ 8.11 (s, 1H), 7.79 (d, J=8.5 Hz, 1H), 7.48 (d, J=2.0 Hz, 1H), 7.42 (dd, J=8.2, 1.9 Hz, 1H), 7.26 (dd, J=8.5, 2.4 Hz, 1H), 7.14 (d, J=2.3 Hz, 1H), 6.93 (d, J=8.2 Hz, 1H), 5.97 (dt, J=15.7, 5.1 Hz, 1H), 5.85 (dd, J=15.9, 8.0 Hz, 1H), 4.13 (d, J=12.1 Hz, 1H), 4.07 (s, 3H), 4.05-3.93 (m, 2H), 3.89 (d, J=13.5 Hz, 1H), 3.85 (s, 3H), 3.80 (d, J=14.3 Hz, 1H), 3.59 (dd, J=7.9, 3.2 Hz, 1H), 3.49 (d, J=14.3 Hz, 1H), 3.27 (s, 3H), 3.23-3.14 (m, 1H), 3.01-1.55 (m, 16H), 1.54-1.41 (m, 1H). LCMS: 722.1.

Example 390

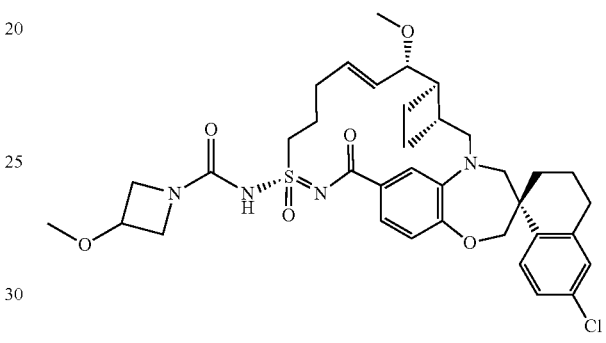

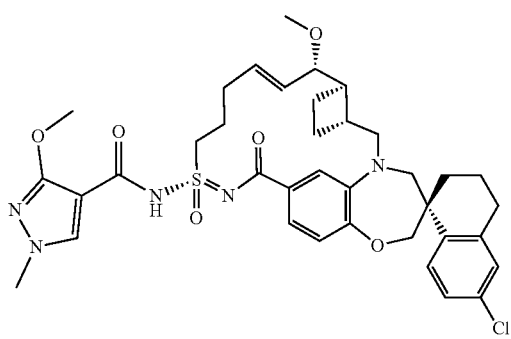 [SMILES: COc1nn(C)cc1C(=O)N[S@@]1(=O)=NC(=O)c2ccc3c(c2)N(C[C@@H]2CC[C@H]2[C@@H](OC)/C=C/CCC1)C[C@@]1(CCCc2cc(Cl)ccc21)CO3]

Example 390 was synthesized in a manner similar to Example 244 using Example 5 instead of 240-1. 1H NMR (400 MHz, Acetone-d6) δ 7.78 (d, J=8.5 Hz, 1H), 7.32-7.21 (m, 3H), 7.14 (d, J=2.4 Hz, 1H), 6.94 (d, J=8.1 Hz, 1H), 5.98-5.87 (m, 1H), 5.79-5.69 (m, 1H), 4.36-4.16 (m, 3H), 4.12 (d, J=12.1 Hz, 1H), 4.03 (d, J=12.1 Hz, 1H), 3.99-3.22 (m, 7H), 3.30 (s, 3H), 3.24 (s, 3H), 3.17 (dd, J=15.2, 10.8 Hz, 1H), 2.95-1.55 (m, 16H), 1.52-1.41 (m, 1H). LCMS: 697.1.

Example 391

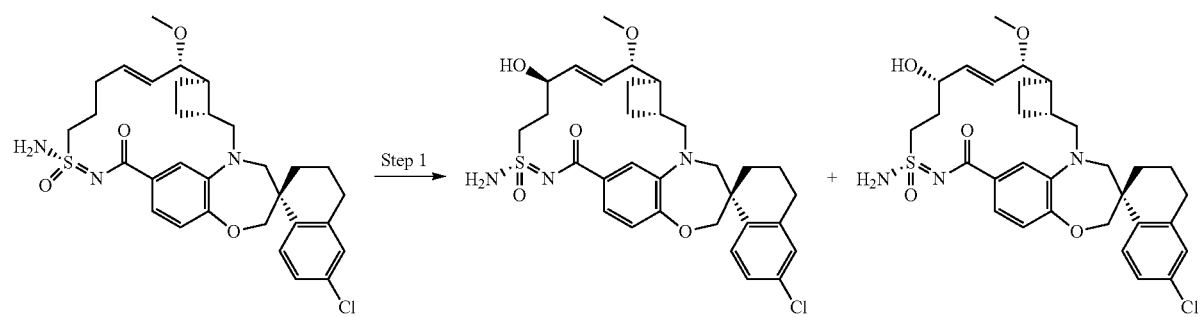

Example 5      391-1      391-2

Step 2

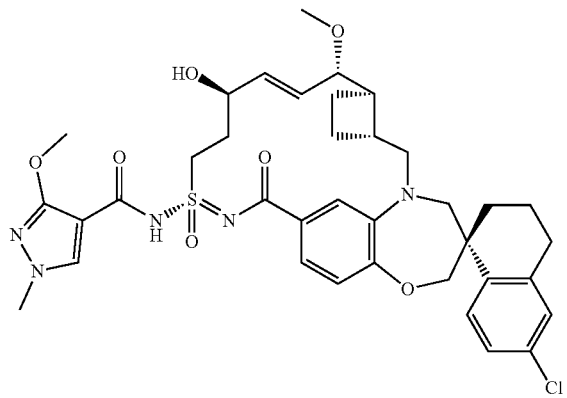

391-3

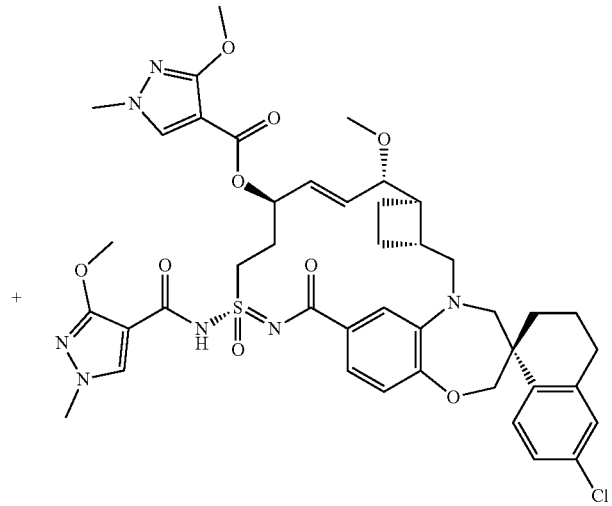

Example 391

Step 1

Selenium dioxide (261 mg, 2.36 mmol) was added to a vigorously stirred solution of Example 5 (393 mg, 673 µmol) in 1,4-dioxane (6.7 mL) at room temperature, and the resulting mixture was heated to 80° C. After 10 min, the resulting mixture was heated to 100° C. After 60 min, the resulting mixture was cooled to room temperature and was filtered through celite. The filter cake was extracted with dichloromethane (10 mL), and the combined filtrates were concentrated under reduced pressure. The residue was purified by reverse phase preparative HPLC (0.1% trifluoroacetic acid in acetonitrile/water) to give 391-1 and 391-2.

Step 2

Example 391 was synthesized in a manner similar to Example 106 using 3-methoxy-1-methyl-1H-pyrazole-4-carboxylic acid instead of 2-((tetrahydro-2H-pyran-4-yl)oxy)acetic acid and using 391-1 instead of 106-4. 1H NMR (400 MHz, Acetone-d6) δ 8.11 (s, 1H), 7.94 (s, 1H), 7.79 (d, J=8.6 Hz, 1H), 7.51-7.43 (m, 2H), 7.25 (dd, J=8.5, 2.4 Hz, 1H), 7.14 (d, J=2.3 Hz, 1H), 6.94 (d, J=8.7 Hz, 1H), 6.17-6.01 (m, 2H), 5.72 (d, J=4.8 Hz, 1H), 4.26 (dd, J=14.2, 7.0 Hz, 1H), 4.13 (d, J=12.1 Hz, 1H), 4.10-3.70 (m, 4H), 4.08 (s, 3H), 3.91 (s, 3H), 3.85 (s, 3H), 3.69 (s, 3H), 3.48 (d, J=14.4 Hz, 1H), 3.27 (s, 3H), 3.15 (dd, J=15.0, 10.9 Hz, 1H), 2.93-1.54 (m, 14H), 1.54-1.43 (m, 1H). LCMS: 898.0 (M+Na)+.

Example 392

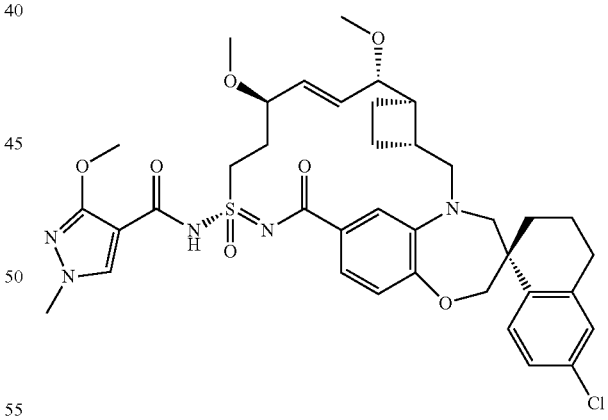

Potassium bis(trimethylsilyl)amide solution (1.0 M in tetrahydrofuran, 27 µL, 27 µmol) was added over 1 min via syringe to a stirred mixture of Intermediate 391-3 (4.0 mg, 5.4 µmol) and iodomethane (3.4 µL, 54 µmol) in tetrahydrofuran (1.0 mL) at −40° C. After 2 min, the resulting mixture was warmed to room temperature. After 7 min, trifluoroacetic acid (50 µL) was added, and the resulting mixture was concentrated under reduced pressure. The residue was purified by reverse phase preparative HPLC (0.1% trifluoroacetic acid in acetonitrile/water) to give Example 392. 1H NMR (400 MHz, Acetone-d6) δ 8.11 (s, 1H), 7.77

(d, J=8.5 Hz, 1H), 7.48 (s, 1H), 7.42 (d, J=8.3 Hz, 1H), 7.23 (d, J=8.7 Hz, 1H), 7.14 (d, J=1.3 Hz, 1H), 6.91 (d, J=8.2 Hz, 1H), 6.00 (dd, J=15.7, 7.2 Hz, 1H), 5.89 (dd, J=15.7, 8.0 Hz, 1H), 4.14 (d, J=11.9 Hz, 1H), 4.11-4.04 (m, 1H), 4.06 (s, 3H), 4.01 (d, J=12.1 Hz, 1H), 3.94-3.43 (m, 5H), 3.30 (s, 3H), 3.26 (s, 3H), 3.16 (dd, J=14.8, 10.9 Hz, 1H), 2.96-1.63 (m, 14H), 1.56-1.46 (m, 1H). LCMS: 752.2.

Example 393

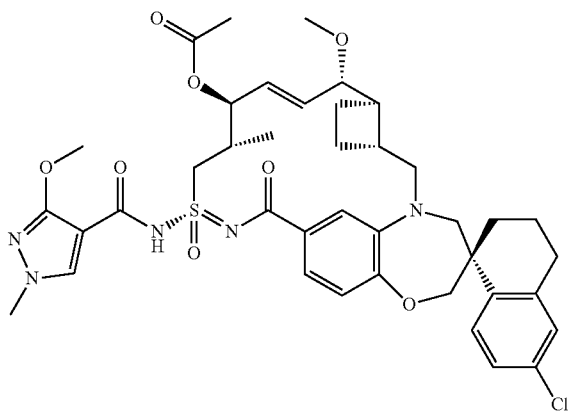 [SMILES: COc1nn(C)cc1C(=O)N[S@@]1(=O)=NC(=O)c2ccc3c(c2)N(C[C@@H]2CC[C@H]2[C@@H](OC)/C=C/[C@H](OC(C)=O)[C@H](C)C1)C[C@@]1(CCCc2cc(Cl)ccc21)CO3]

Acetic anhydride (5.0 µL, 53 µmol) was added via syringe to a stirred mixture of Example 279 (4 mg, 5 µmol) and 4-(dimethylamino)pyridine (7.8 mg, 64 µmol) in dichloromethane (0.6 mL) at room temperature, and the resulting mixture was heated to 45° C. After 30 min, the resulting mixture was cooled to room temperature and was concentrated under reduced pressure. The residue was purified by reverse phase preparative HPLC (0.1% trifluoroacetic acid in acetonitrile/water) to give Example 393. 1H NMR (400 MHz, Acetone-d6) δ 8.14 (s, 1H), 7.79 (d, J=8.5 Hz, 1H), 7.48 (dd, J=8.3, 1.9 Hz, 1H), 7.36 (d, J=2.0 Hz, 1H), 7.25 (dd, J=8.4, 2.4 Hz, 1H), 7.14 (d, J=2.4 Hz, 1H), 6.93 (d, J=8.2 Hz, 1H), 6.13 (dd, J=15.8, 5.4 Hz, 1H), 5.90 (dd, J=15.7, 7.4 Hz, 1H), 5.72 (s, 1H), 4.18 (dd, J=15.2, 6.8 Hz, 1H), 4.11-4.03 (m, 2H), 4.09 (s, 3H), 4.01-3.88 (m, 2H), 3.87 (s, 3H), 3.77 (d, J=14.4 Hz, 1H), 3.49 (d, J=14.3 Hz, 1H), 3.23 (s, 2H), 3.18 (dd, J=15.2, 10.4 Hz, 1H), 2.96-1.18 (m, 17H), 1.12 (d, J=6.9 Hz, 3H). LCMS: 794.1.

Example 394

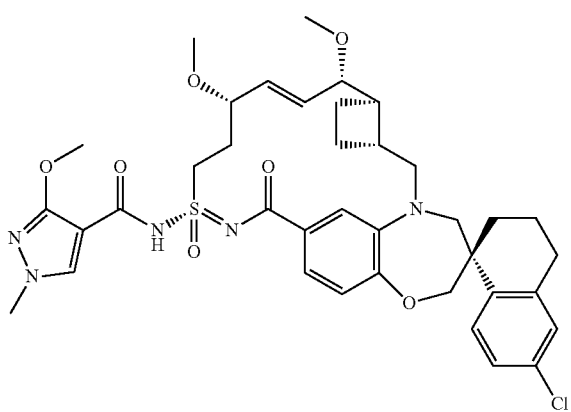 [SMILES: COc1nn(C)cc1C(=O)N[S@@]1(=O)=NC(=O)c2ccc3c(c2)N(C[C@@H]2CC[C@H]2[C@@H](OC)/C=C/[C@@H](OC)CC1)C[C@@]1(CCCc2cc(Cl)ccc21)CO3]

Example 394 was synthesized in a manner similar to Example 106 using 3-methoxy-1-methyl-1H-pyrazole-4-carboxylic acid instead of 2-((tetrahydro-2H-pyran-4-yl)oxy)acetic acid and using 391-2 instead of 106-4. 1H NMR (400 MHz, Acetone-d6) δ 8.09 (s, 1H), 7.78 (d, J=8.5 Hz, 1H), 7.45-7.39 (m, 2H), 7.24 (dd, J=8.6, 2.4 Hz, 1H), 7.12 (d, J=2.4 Hz, 1H), 6.91 (d, J=8.1 Hz, 1H), 6.05 (dd, J=16.3, 7.9 Hz, 1H), 5.83 (dd, J=15.9, 5.0 Hz, 1H), 4.31-3.68 (m, 6H), 4.05 (s, 3H), 3.83 (s, 3H), 3.58 (dd, J=8.3, 3.0 Hz, 1H), 3.45 (d, J=14.4 Hz, 1H), 3.36 (s, 3H), 3.28 (s, 3H), 3.23-3.14 (m, 1H), 2.85-1.54 (m, 14H), 1.53-1.39 (m, 1H). LCMS: 752.1.

Example 395 and Example 396

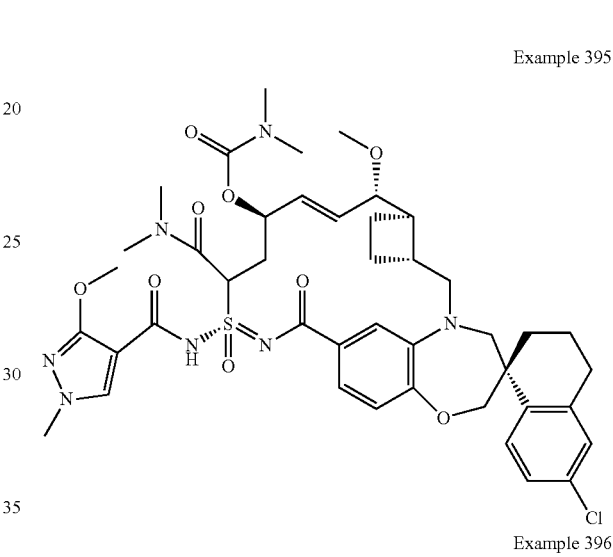

Example 395

Example 396

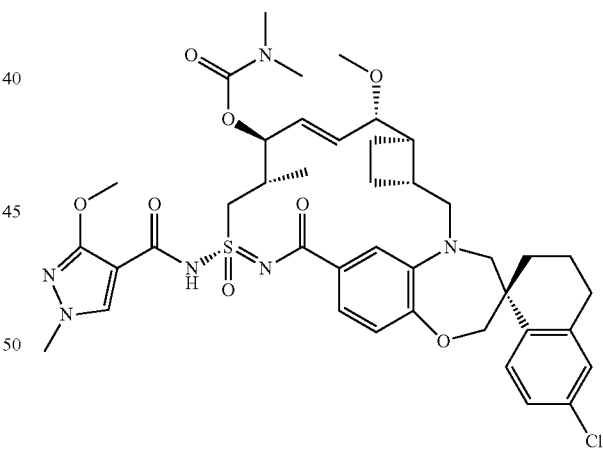

Preparation of Example 395 and Example 396: Potassium bis(trimethylsilyl)amide solution (1.0 M in tetrahydrofuran, 66.5 µL, 66.5 µmol) was added over 1 min via syringe to a stirred solution of Example 279 (5.0 mg, 6.6 µmol) in tetrahydrofuran (0.6 mL) at −40° C. After 1 min, ACV-dimethylcarbamyl chloride (12.2 µL, 133 µmol) was added via syringe. After 2 min, the resulting mixture was warmed to room temperature. After 40 min, acetic acid (50 µL) and methanol (100 µL) were added sequentially, and the resulting mixture was concentrated under reduced pressure. The residue was purified by reverse phase preparative hplc (0.1% trifluoroacetic acid in acetonitrile/water) to give Example 395. 1H NMR (400 MHz, Acetone-d6) δ 8.43-7.66 (m, 2H), 7.48-7.05 (m, 4H), 7.04-6.82 (m, 1H), 6.13-5.42 (m, 2H), 5.38-5.15 (m, 1H), 4.34-3.10 (m, 17H), 3.10-1.18 (m, 28H). LCMS: 894.6. Further elution gave Example 396. 1H NMR (400 MHz, Acetone-d6) δ 8.20-6.65 (m, 7H), 6.34-5.38 (m, 3H), 4.51-3.22 (m, 17H), 3.22-1.12 (m, 20H), 1.05 (d, J=7.1 Hz, 3H). LCMS: 823.0.

Example 397

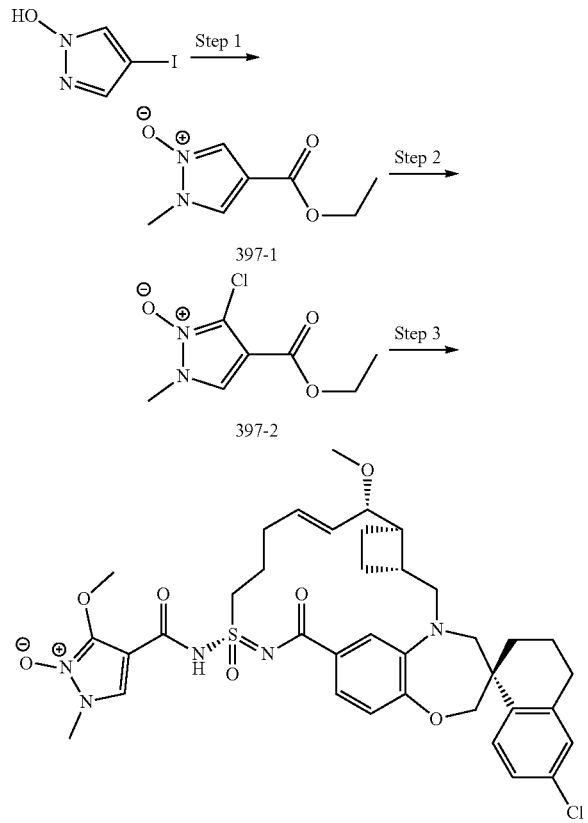

Example 397

Step 1

Dimethyl sulfate (8.54 mL, 90.2 mmol) was added via syringe to a stirred solution of 4-iodo-1H-pyrazol-1-ol (3.79 g, 18.0 mmol) in chloroform (20 mL) at room temperature. After 16 h, the resulting mixture was poured into diethyl ether (150 mL), and the resulting inhomogenous mixture was swirled vigorously. The supernatant was decanted, and the residual gel was dissolved in ethanol (19 mL) and stirred at room temperature. Triethylamine (8.33 mL, 59.8 mmol) and [1,1'-bis(diphenylphosphino) ferrocene]dichloropalladium(II) (375 mg, 512 µmol) were added sequentially. The resulting mixture was placed under an atmosphere of carbon monoxide (1 atm) and was heated to 90° C. After 28 h, the resulting mixture was cooled to room temperature and was filtered through celite. The filter cake was extracted with a mixture of methanol (25 mL) and dichloromethane (50 mL). Potassium phosphate (14.5 g, 68.3 mmol) was added to the combined filtrates, and the resulting inhomogeneous mixture was stirred vigorously. After 15 min, the resulting mixture was filtered through celite and was concentrated under reduced pressure. The residue was dissolved in a mixture of dichloromethane (50 mL) and toluene (25 mL), basic alumina (30 g) was added, and the resulting slurry was concentrated under reduced pressure. The residue was purified by flash column chromatography on silica gel (0 to 6% methanol in dichloromethane) to give 397-1.

Step 2

2,2,6,6-Tetramethylpiperidinylmagnesium chloride lithium chloride complex solution (1.0 M in tetrahydrofuran/toluene, 3.85 mL, 3.85 mmol) was added via syringe to a stirred solution of 397-1 (131 mg, 770 µmol) in tetrahydrofuran (40 mL) at −40° C. After 3 h, a solution of hexachloroethane (1.28 g, 5.39 mmol) in tetrahydrofuran (15 mL) was added via cannula. After 3 min, the resulting mixture was warmed to room temperature. After 4.5 h, silica gel (12 g) was added, and the resulting slurry was concentrated under reduced pressure. The residue was purified by flash column chromatography on silica gel (0 to 5% methanol in dichloromethane) to give impure 397-2. The impure material was purified by reverse phase preparative HPLC (0.1% trifluoroacetic acid in acetonitrile/water) to give 397-2.

Step 3

Sodium methoxide solution (25% wt. in methanol, 121 µL, 528 µmol) was added via syringe to a stirred solution of 397-2 (21.6 mg, 106 µmol) in methanol (0.5 mL) at room temperature, and the resulting mixture was heated to 70° C. After 22 min, aqueous sodium hydroxide solution (2.0 M, 158 µL, 317 µmol) was added via syringe. After 15 min, the resulting mixture was cooled to room temperature, and hydrogen chloride solution (4.0 M in 1,4-dioxane, 211 µL, 844 µmol) was added via syringe. The resulting mixture was concentrated under reduced pressure. The residue was dissolved in dichloromethane (1.0 mL) and was stirred at room temperature. 106-4 (10.0 mg, 16.7 µmol), 4-(dimethylamino)pyridine (20.4 mg, 167 µmol), and 3-(((ethylimino)methylene)amino)-N,N-dimethylpropan-1-amine hydrochloride (12.8 mg, 66.9 µmol) were added sequentially, and the resulting mixture was heated to 45° C. After 1 h, the resulting mixture was cooled to room temperature and was concentrated under reduced pressure. The residue was purified by reverse phase preparative hplc (0.1% trifluoroacetic acid in acetonitrile/water) to give Example 397. 1H NMR (400 MHz, Acetone-d6) δ 7.96-7.61 (m, 2H), 7.42-6.87 (m, 5H), 6.15-6.00 (m, 1H), 5.69-5.50 (m, 1H), 4.27 (s, 3H), 4.25-3.24 (m, 7H), 3.23 (s, 3H), 3.21-3.10 (m, 1H), 2.94-1.19 (m, 16H), 1.14 (d, J=6.1 Hz, 3H). LCMS: 752.2.

Example 398

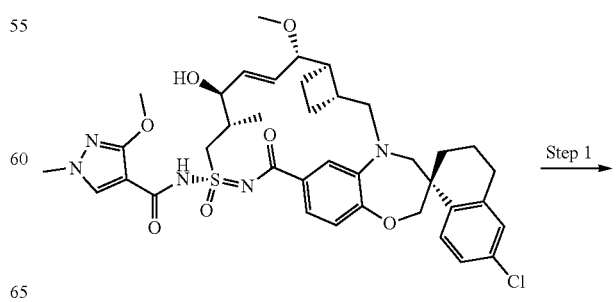

Example 279

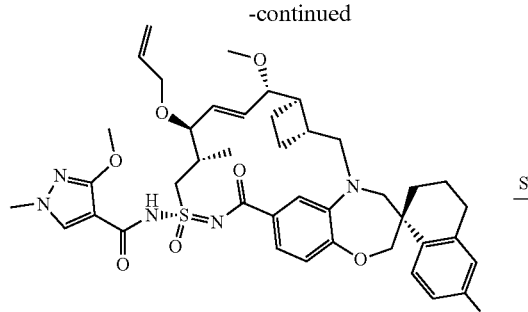

398-1

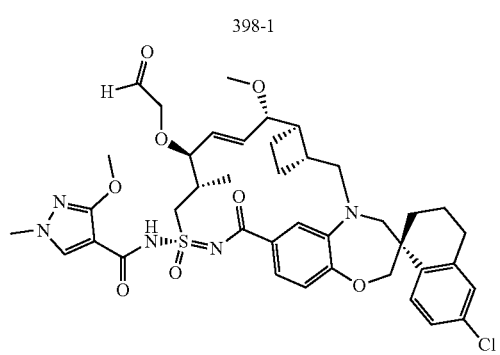

398-2

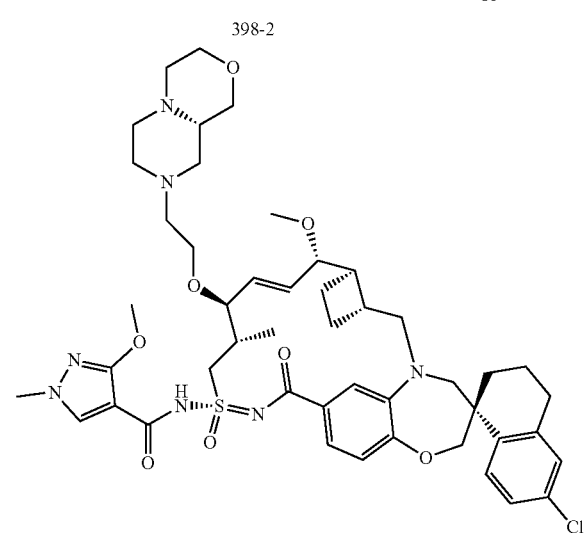

Example 398

Step 1: Synthesis of 398-1

To a solution of Example 279 (20.0 mg, 0.0266 mmol) in DMF (1.0 mL) at room temperature was added allyl bromide (19.3 mg, 0.16 mmol) followed by 60% NaH dispersion in mineral oil (6.38 mg, 0.16 mmol). The reaction was heated at 50° C. for 90 min. LCMS showed about –50% conversion. Additional allyl bromide (19.3 mg, 0.16 mmol) and 60% NaH dispersion in mineral oil (6.38 mg, 0.16 mmol) were added, heated at 50° C. for another 90 min. The reaction was quenched with sat. NH$_4$Cl, washed with brine, dried over sodium sulfate, filtered, and concentrated to give 398-1. LCMS-ESI+ (m/z): calcd H+ for $C_{41}H_{50}ClN_5O_7S$: 792.31; found: 792.03.

Step 2: Synthesis of 398-2

398-1 (21.0 mg, 0.0265 mmol) was dissolved in a mixture of tBuOH (1.0 mL), THF (0.3 mL) and water (0.5 mL) at room temperature. NaIO4 (42.5 mg, 0.199 mmol) was added followed by 2.5% OsO4 in tBuOH (33.2 uL, 0.0027 mmol). The resulting mixture was stirred at room temperature for 90 minutes. The reaction was quenched with 1 N sodium thiosulfate, stirred vigorously at room temperature for 10 min, extracted with EtOAc (2×20 mL). Combined organic layer was washed with brine, dried over sodium sulfate, filtered, and concentrated to give 398-2. LCMS-ESI+ (m/z): calcd H+ for $C_{40}H_{48}ClN_5O_8S$: 794.29; found: 793.96.

Step 3: Synthesis of Example 398

To the mixture of 398-2 and (9aS)-1,3,4,6,7,8,9,9a-octahydropyrazino[2,1-c][1,4]oxazine; dihydrochloride (11.4 mg, 0.053 mmol) in DCE (1.0 mL) at room temperature was added DIEA (6.83 mg, 0.053 mmol). The resulting mixture was stirred for 5 minutes, STAB (11.2 mg, 0.053 mmol) was added, and the reaction was stirred for overnight. The reaction was concentrated, re-dissolved in DMF (1.2 mL) and water (0.6 mL), filtered and purified by reverse phase prep HPLC (40-90% ACN/H2O with 0.1% TFA). The desired fractions were combined and frozen dried to give Example 398. 1H NMR (400 MHz, Methanol-d4) δ 8.08 (s, 1H), 7.76 (d, J=8.5 Hz, 1H), 7.38 (dd, J=8.2, 1.9 Hz, 1H), 7.24 (d, J=2.0 Hz, 1H), 7.19 (dd, J=8.5, 2.4 Hz, 1H), 7.13 (d, J=2.3 Hz, 1H), 6.93 (d, J=8.2 Hz, 1H), 6.18 (dd, J=15.4, 8.5 Hz, 1H), 5.92 (dd, J=15.4, 8.8 Hz, 1H), 4.26 (dd, J=15.0, 5.1 Hz, 1H), 4.13-4.04 (m, 7H), 3.94-3.78 (m, 9H), 3.75-3.59 (m, 4H), 3.46-3.36 (m, 4H), 3.31 (s, 3H), 3.23-3.09 (m, 3H), 2.90-2.76 (m, 4H), 2.70-2.47 (m, 5H), 2.36-2.25 (m, 1H), 2.12 (d, J=13.6 Hz, 1H), 2.02-1.88 (m, 3H), 1.83 (d, J=7.4 Hz, 3H), 1.53-1.41 (m, 1H), 1.24 (d, J=6.9 Hz, 3H). LCMS-ESI+ (m/z): calcd H+ for $C_{47}H_{62}ClN_7O_8S$: 920.41; found: 920.45.

Example 399

Step 1: Synthesis of 399-1

Intermediate 399-1 (22.0 mg, 0.0358 mmol) and 5-formyl-1-methyl-pyrrole-3-carboxylic acid (11.0 mg, 0.0716 mmol) were dissolved in DCM (2.0 mL) at room temperature, EDCI.HCl (13.7 mg, 0.0716 mmol) was added followed by DMAP (8.75 mg, 0.0716 mmol). The resulting mixture was stirred for 1 hr. The reaction was concentrated, re-dissolved in EtOAc, the organic layer was washed sequentially with sat. NH$_4$Cl, sat. NaHCO$_3$, and brine, dried over sodium sulfate, filtered, and concentrated to give 399-1. LCMS-ESI+ (m/z): calcd H+ for $C_{39}H_{45}ClN_4O_7S$: 749.27; found: 748.96.

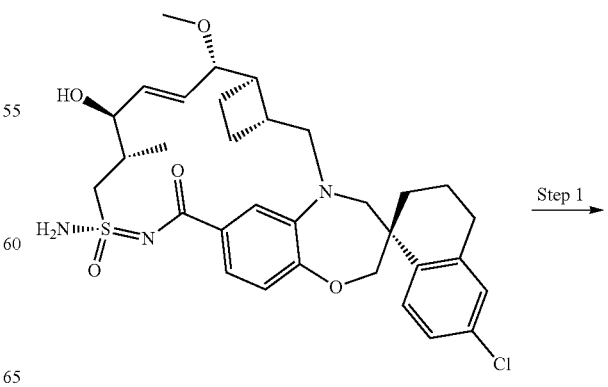

375-1

455

-continued

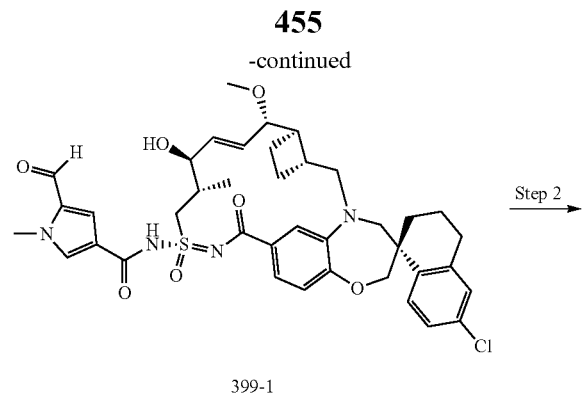

399-1

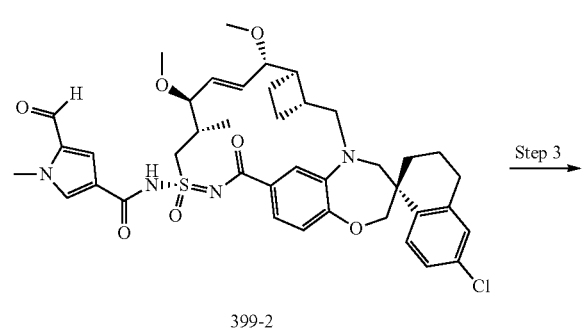

399-2

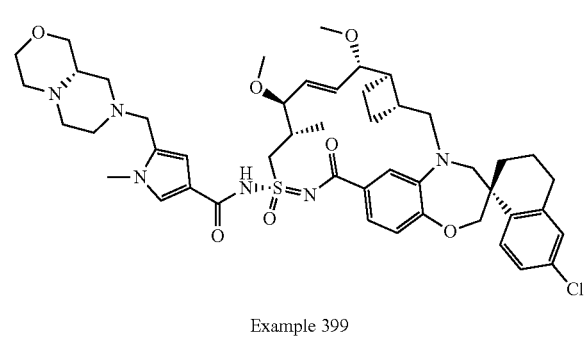

Example 399

Step 2: Synthesis of 399-2

399-1 was dissolved in DMF (1.0 mL) at room temperature; MeI (21.4 mg, 0.151 mmol) was added followed by 60% NaH dispersion in mineral oil (6.02 mg, 0.151 mmol). The resulting mixture was heated at 50° C. for 30 min, and the reaction was then cooled to room temperature, diluted with DMF (0.5 mL), filtered, and purified by reverse phase prep HPLC. Desired fractions were combined and frozen dried to give 399-2. LCMS-ESI+ (m/z): calcd H+ for $C_{40}H_{47}ClN_4O_7S$ 763.29; found: 762.98.

456

Step 3

To the stirred mixture of 399-2 (28 mg, 0.037 mmol) and (9aS)-1,3,4,6,7,8,9,9a-octahydropyrazino[2,1-c][1,4] oxazine; dihydrochloride (11.8 mg, 0.055 mmol) in DCE (1.0 mL) at room temperature was added DIEA (16.6 mg, 0.128 mmol). The resulting mixture was stirred for 5 minutes before STAB (11.7 mg, 0.055 mmol) was added. The newly formed mixture was then stirred at room temperature for overnight, and then concentrated, re-dissolved in DMF (1.2 mL), filtered, and purified by reverse phase prep HPLC. Desired fractions were combined and frozen dried to give Example 399. LCMS-ESI+ (m/z): calcd H+ for $C_{47}H_{61}ClN_6O_7S$: 889.40; found: 889.19. 1H NMR (400 MHz, Methanol-d4) δ 7.69 (d, J=1.9 Hz, 1H), 7.60 (d, J=8.5 Hz, 1H), 7.34 (dd, J=8.3, 1.8 Hz, 1H), 7.05 (dd, J=9.9, 2.1 Hz, 2H), 6.91-6.78 (m, 3H), 6.21-6.11 (m, 1H), 5.68 (dd, J=15.3, 8.3 Hz, 1H), 4.14 (dd, J=14.7, 6.7 Hz, 1H), 4.06-3.88 (m, 7H), 3.84-3.72 (m, 7H), 3.64 (d, J=14.5 Hz, 1H), 3.47-3.42 (m, 1H), 3.25-3.09 (m, 5H), 3.06-2.65 (m, 8H), 2.58-2.34 (m, 3H), 2.34-2.14 (m, 4H), 2.08 (d, J=13.6 Hz, 1H), 2.02-1.78 (m, 6H), 1.42-1.35 (m, 1H), 1.16 (d, J=6.2 Hz, 3H).

Example 400

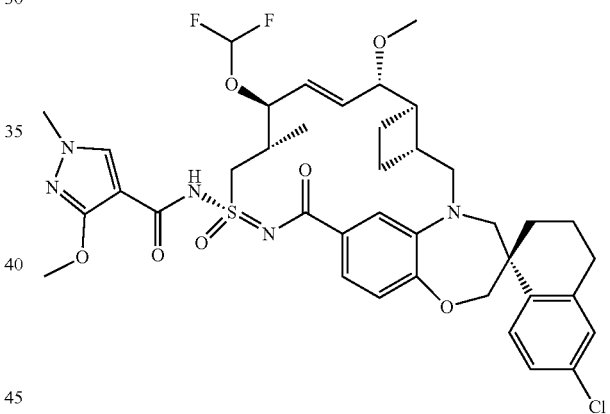

Example 279 (10 mg, 0.014 mmol) was dissolved in a 1:1 mixture of dichlormethane and H₂O (0.15 mL: 0.15 mL). Potassium bifluoride (15 mg) was added as a solid. The reaction was stirred at room temperature for 2 min before (bromodifluoromethyl)trimethylsilane was added (50 μL). The reaction was heated to 50° C. for 8 hours before it was cooled to room temperature. The reaction mixture was purified directly by Gilson reverse phase prep HPLC (60-100% ACN/H₂O with 0.1% TFA) to give Example 400. ¹H NMR (400 MHz, Methanol-d₄) δ 8.09 (s, 1H), 7.77 (d, J=8.4 Hz, 1H), 7.43-7.37 (m, 1H), 7.24 (s, 1H), 7.21-7.14 (m, 1H), 7.12 (d, J=2.2 Hz, 2H), 6.92 (t, J=ID Hz, 1H), 6.44 (s, 1H), 6.18 (dd, J=15.5, 6.1 Hz, 1H), 5.93 (dd, J=15.2, 8.2 Hz, 1H), 4.16-3.99 (m, 8H), 3.89 (m, 2H), 3.82 (m, 4H), 3.73 (d, J=13.9 Hz, 1H), 3.41 (d, J=14.3 Hz, 1H), 3.28 (s, 3H), 3.15 (m, 1H), 2.83 (m, 2H), 2.52 (m, 1H), 2.40 (m, 1H), 2.08 (m, 1H), 1.92 (m, 2H), 1.79 (m, 3H), 1.33 (m, 1H), 1.19 (d, J=6.8 Hz, 3H). LCMS-ESI+ (m/z): [M+H]+ calcd for $C_{39}H_{45}ClF_2N_5O_7S$: 802.3; found: 802.5.

Example 401

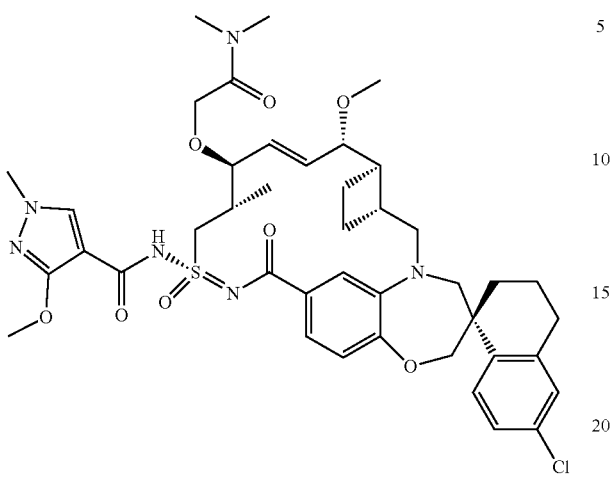

Example 401 was synthesized in the same manner as Example 283 using 2-bromo-N,N-dimethylacetamide and Example 279. $^1$H NMR (400 MHz, Methanol-$d_4$) δ 8.11 (s, 1H), 7.75 (d, J=8.5 Hz, 1H), 7.36 (dd, J=8.2, 1.9 Hz, 1H), 7.23-7.08 (m, 3H), 6.91 (d, J=8.2 Hz, 1H), 6.06 (dd, J=15.5, 7.6 Hz, 1H), 5.89 (dd, J=15.5, 8.5 Hz, 1H), 4.26 (d, J=13.9 Hz, 1H), 4.19-4.00 (m, 9H), 3.92-3.84 (m, 2H), 3.82 (s, 3H), 3.72 (d, J=14.3 Hz, 1H), 3.41 (d, J=14.4 Hz, 1H), 3.35 (m, 2H), 3.31 (s, 3H), 3.17-3.07 (m, 1H), 2.99 (s, 3H), 2.88 (s, 3H), 2.86-2.71 (m, 1H), 2.52 (m, 2H), 2.36 (m, 1H), 2.11 (d, J=13.6 Hz, 1H), 1.96 (m, 2H), 1.82 (d, J=7.0 Hz, 3H), 1.47 (d, J=13.6 Hz, 1H), 1.23 (d, J=6.9 Hz, 3H). LCMS-ESI+ (m/z): [M+H]+ calcd for $C_{42}H_{53}ClN_6O_8S$: 837.3; found: 837.9.

Example 402

Example 402 was synthesized in the same manner as Example 283 using 2-(chloromethyl)pyridine and Example 279. $^1$H NMR (400 MHz, Methanol-$d_4$) δ 8.71 (d, J=5.7 Hz, 1H), 8.37 (t, J=8.4 Hz, 1H), 8.08 (s, 1H), 7.94 (d, J=7.9 Hz, 1H), 7.85-7.80 (m, 1H), 7.77 (d, J=8.5 Hz, 1H), 7.40-7.35 (m, 1H), 7.23-7.11 (m, 4H), 6.94 (d, J=8.2 Hz, 1H), 6.15 (dd, J=15.6, 7.6 Hz, 1H), 5.99 (dd, J=15.5, 8.3 Hz, 1H), 4.82-4.69 (m, 1H), 4.32-4.10 (m, 4H), 4.07 (s, 3H), 3.92-3.84 (m, 3H), 3.83 (s, 3H), 3.79-3.68 (m, 2H), 3.41 (d, J=14.3 Hz, 1H), 3.28 (s, 3H), 3.21-3.01 (m, 2H), 2.87-2.75 (m, 2H), 2.66-2.34 (m, 3H), 2.11 (m, 1H), 1.96 (m, 2H), 1.83 (m, 3H), 1.47 (s, 1H), 1.26 (d, J=6.9 Hz, 3H). LCMS-ESI+ (m/z): [M+H]+ calcd for $C_{44}H_{51}ClN_6O_7S$: 843.3; found: 843.2.

Example 403

Example 279 (10 mg, 0.014 mmol) was dissolved in DMF (0.15 mL). Sodium hydroxide (excess, 1 pellet) was added as a solid. The reaction was heated to 50° C. for 8 hours before it was cooled to room temperature. The reaction mixture was purified directly by Gilson reverse phase prep HPLC (40-90% ACN/H$_2$O with 0.1% TFA) to give Example 403. $^1$H NMR (400 MHz, Methanol-$d_4$) δ 8.08 (s, 1H), 7.76 (d, J=8.6 Hz, 1H), 7.37 (dd, J=8.2, 1.8 Hz, 1H), 7.25-7.17 (m, 2H), 7.13 (d, J=2.3 Hz, 1H), 6.93 (d, J=8.3 Hz, 1H), 6.15 (dd, J=15.4, 8.7 Hz, 1H), 5.94 (dd, J=15.3, 8.7 Hz, 1H), 4.23 (dd, J=14.9, 4.3 Hz, 1H), 4.16-4.02 (m, 8H), 3.86 (d, J=9.8 Hz, 6H), 3.82 (s, 3H), 3.75-3.61 (m, 2H), 3.46-3.38 (m, 2H), 3.33-3.28 (m, 2H), 3.20-3.09 (m, 1H), 2.96 (m, 6H), 2.89-2.75 (m, 2H), 2.62-2.46 (m, 2H), 2.29 (m, 1H), 2.12 (d, J=13.7 Hz, 1H), 1.96 (m, 2H), 1.84 (m, 3H), 1.46 (d, J=10.5 Hz, 1H), 1.26 (d, J=6.9 Hz, 3H). LCMS-ESI+ (m/z): [M+H]+ calcd for $C_{42}H_{55}ClN_6O_7S$: 823.4; found: 823.4.

Example 404

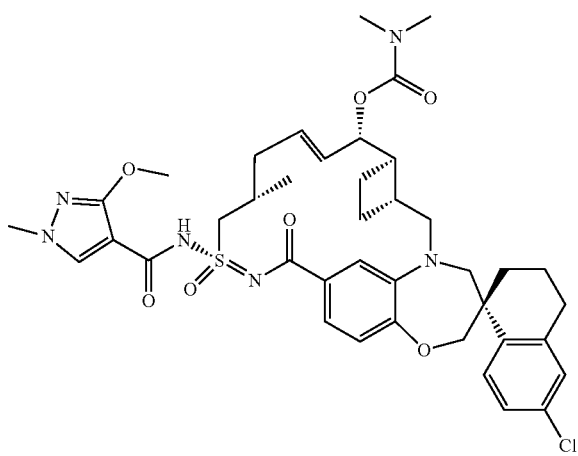 [SMILES: COc1nn(C)cc1C(=O)N[S@@]1(=O)=NC(=O)c2ccc3c(c2)N(C[C@@H]2CC[C@H]2[C@@H](OC(=O)N(C)C)/C=C/C[C@H](C)C1)C[C@@]1(CCCc2cc(Cl)ccc21)CO3]

To a stirred solution of Example 223 (10 mg, 0.014 mmol) in dimethylcarbamic chloride (2 mL) was added DMAP (16 mg, 0.138 mmol) and stirred for at 80° C. overnight. The solvent was evaporated, and the reaction mixture was purified on reversed phase chromatography 0.1% TFA 70-95% acetonitrile to give Example 404 $^1$H NMR (400 MHz, Chloroform-d) δ 7.83 (s, 1H), 7.75 (d, J=8.6 Hz, 1H), 7.49 (dd, J=8.2, 1.9 Hz, 1H), 7.43 (d, J=2.0 Hz, 1H), 7.19 (dd, J=8.5, 2.3 Hz, 1H), 7.10 (d, J=2.3 Hz, 1H), 6.93 (d, J=8.2 Hz, 1H), 5.89 (dt, J=13.3, 6.4 Hz, 1H), 5.73 (dd, J=15.7, 5.4 Hz, 1H), 5.26 (t, J=5.6 Hz, 1H), 4.18-3.97 (m, 5H), 3.82 (s, 3H), 3.71 (d, J=14.5 Hz, 2H), 3.33 (d, J=14.6 Hz, 1H), 3.06 (dd, J=15.3, 9.0 Hz, 1H), 2.93-2.63 (m, 7H), 2.61-2.47 (m, 2H), 2.43-1.55 (m, 11H), 1.41 (dd, J=23.1, 10.6 Hz, 2H), 1.28 (s, 1H), 1.14 (d, J=6.8 Hz, 3H). LCMS-ESI+ (m/z): [M+H]+ calcd for $C_{40}H_{49}ClN_6O_7S$: 793.31; found: 792.58.

Examples 405-464 were synthesized by the methods described herein.

| Example | Structure | LCMS-ESI+ (m/z): [M + H]+ calcd | LCMS-ESI+ (m/z): [M + H]+ found |
|---|---|---|---|
| 405 | 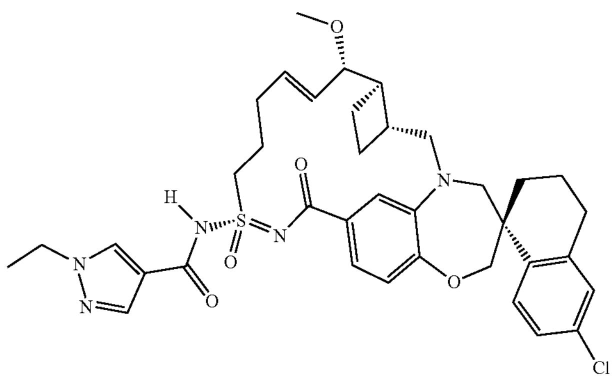 [SMILES: CCn1cc(C(=O)N[S@@]2(=O)=NC(=O)c3ccc4c(c3)N(C[C@@H]3CC[C@H]3[C@@H](OC)/C=C/CCC2)C[C@@]2(CCCc3cc(Cl)ccc32)CO4)cn1] | 706.28 | 706.19 |
| 406 | 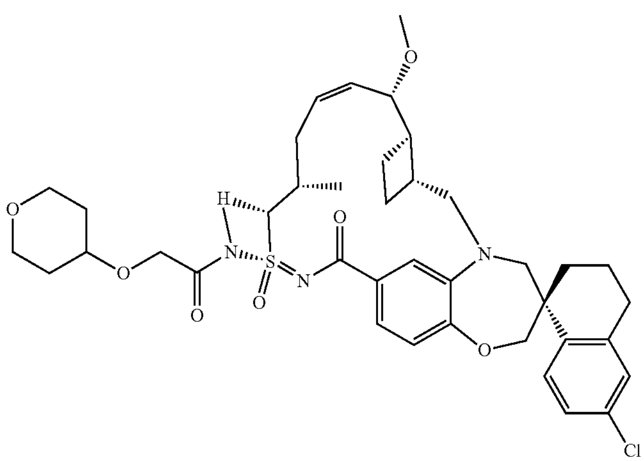 | 754.3 | 754.3 |

-continued
| Example | Structure | LCMS-ESI+ (m/z): [M + H]+ calcd | LCMS-ESI+ (m/z): [M + H]+ found |
|---|---|---|---|
| 407 | 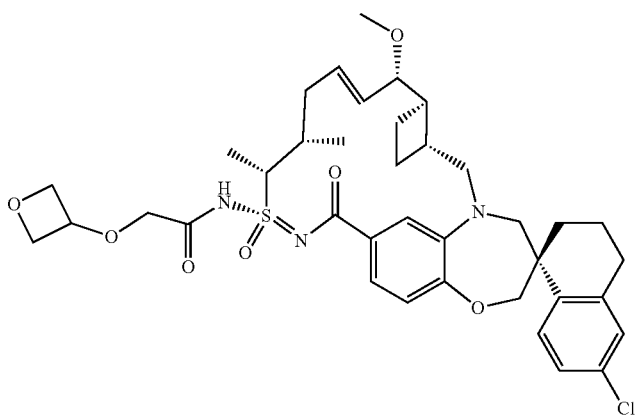 [SMILES: CO[C@H]1/C=C/C[C@H](C)[C@@H](C)[S@@](=O)(NC(=O)COC2COC2)=NC(=O)c2ccc3c(c2)N(C[C@@H]2CC[C@H]21)C[C@@]1(CCCc2cc(Cl)ccc21)CO3] | 726.3 | 726.1 |
| 408 | 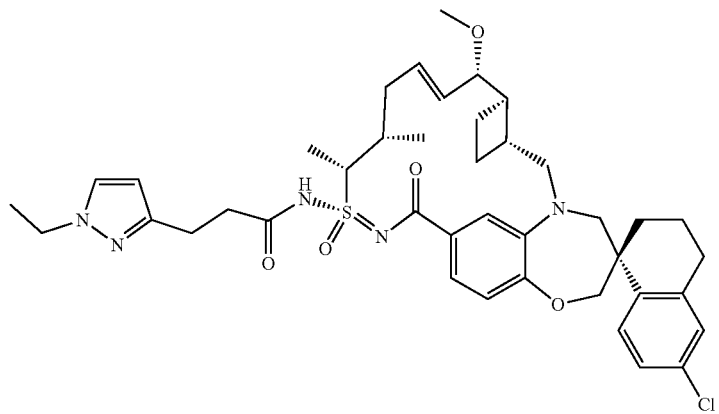 [SMILES: CCn1ccc(CCC(=O)N[S@@]2(=O)=NC(=O)c3ccc4c(c3)N(C[C@@H]3CC[C@H]3[C@@H](OC)/C=C/C[C@H](C)[C@H]2C)C[C@@]2(CCCc3cc(Cl)ccc32)CO4)n1] | 762.3 | 762.1 |
| 409 | 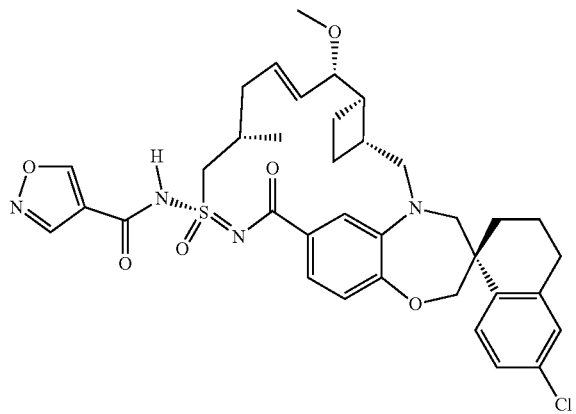 | 693.24 | 692.92 |

-continued
| Example | Structure | LCMS-ESI+ (m/z): [M + H]+ calcd | LCMS-ESI+ (m/z): [M + H]+ found |
| --- | --- | --- | --- |
| 410 | 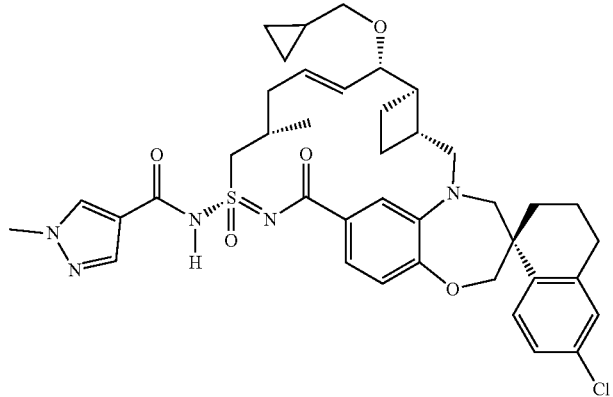 [SMILES: C[C@H]1C/C=C/[C@H](OCC2CC2)[C@@H]2CC[C@H]2CN2C[C@@]3(CCCc4cc(Cl)ccc43)COc3ccc(cc32)C(=O)N=[S@](=O)(NC(=O)c2cnn(C)c2)C1] | 746.3 | 746.1 |
| 411 | 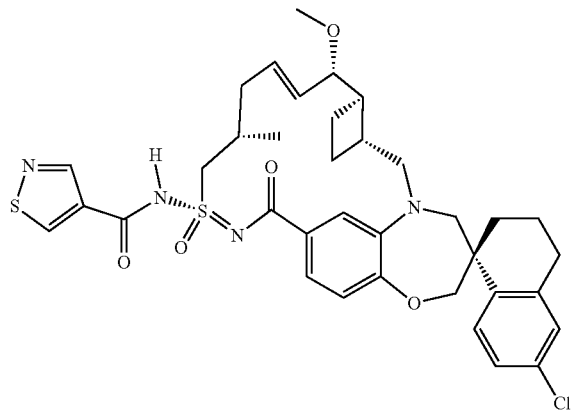 | 709.22 | 708.96 |
| 412 | 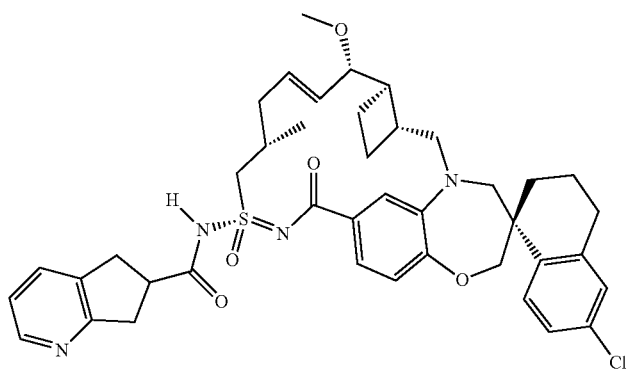 [SMILES: CO[C@H]1/C=C/C[C@H](C)C[S@@](=O)(NC(=O)C2Cc3cccnc3C2)=NC(=O)c2ccc3c(c2)N(C[C@@H]2CC[C@H]21)C[C@@]1(CCCc2cc(Cl)ccc21)CO3] | 743.3 | 743.15 |

-continued
| Example | Structure | LCMS-ESI+ (m/z): [M + H]+ calcd | LCMS-ESI+ (m/z): [M + H]+ found |
|---|---|---|---|
| 413 | 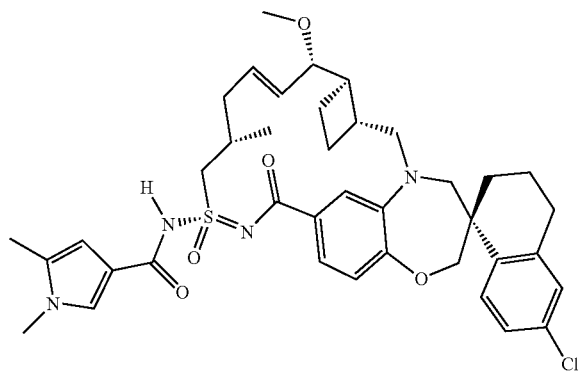 [SMILES: CO[C@H]1/C=C/C[C@H](C)C[S@@](=O)(NC(=O)c2cc(C)n(C)c2)=NC(=O)c2ccc3c(c2)N(C[C@@H]2CC[C@H]21)C[C@@]1(CCCc2cc(Cl)ccc21)CO3] | 719.3 | 719 |
| 414 | 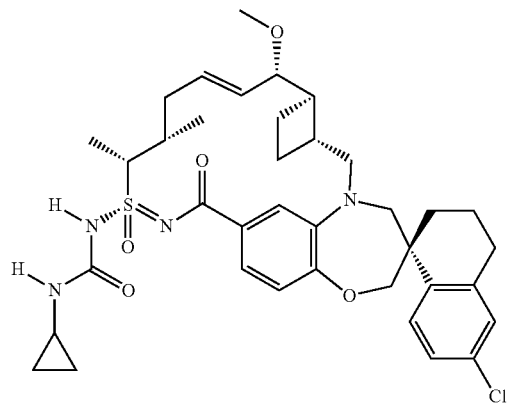 [SMILES: CO[C@H]1/C=C/C[C@H](C)[C@@H](C)[S@@](=O)(NC(=O)NC2CC2)=NC(=O)c2ccc3c(c2)N(C[C@@H]2CC[C@H]21)C[C@@]1(CCCc2cc(Cl)ccc21)CO3] | 695.3 | 694.7 |
| 415 | 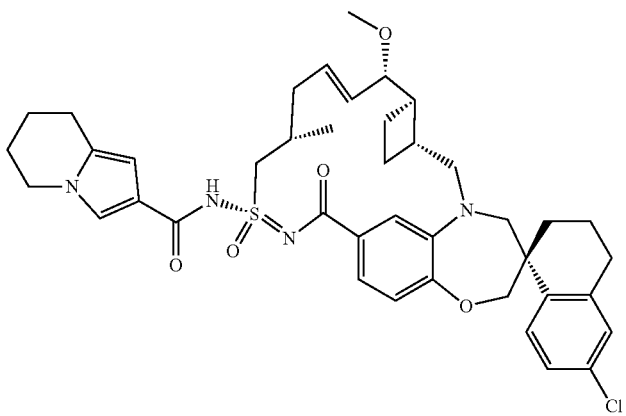 [SMILES: CO[C@H]1/C=C/C[C@H](C)C[S@@](=O)(NC(=O)c2cc3n(c2)CCCC3)=NC(=O)c2ccc3c(c2)N(C[C@@H]2CC[C@H]21)C[C@@]1(CCCc2cc(Cl)ccc21)CO3] | 745.31 | 745.31 |

| Example | Structure | LCMS-ESI+ (m/z): [M + H]+ calcd | LCMS-ESI+ (m/z): [M + H]+ found |
|---|---|---|---|
| 416 | 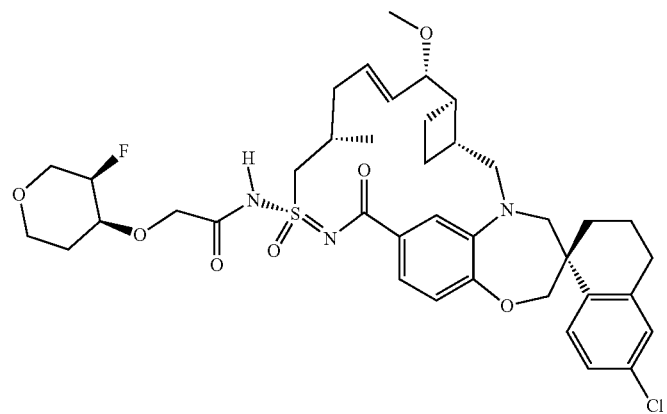 [SMILES: CO[C@H]1/C=C/C[C@H](C)C[S@@](=O)(NC(=O)CO[C@H]2CCOC[C@H]2F)=NC(=O)c2ccc3c(c2)N(C[C@@H]2CC[C@H]21)C[C@@]1(CCCc2cc(Cl)ccc21)CO3] | 758.34 | 758.82 |
| 417 | 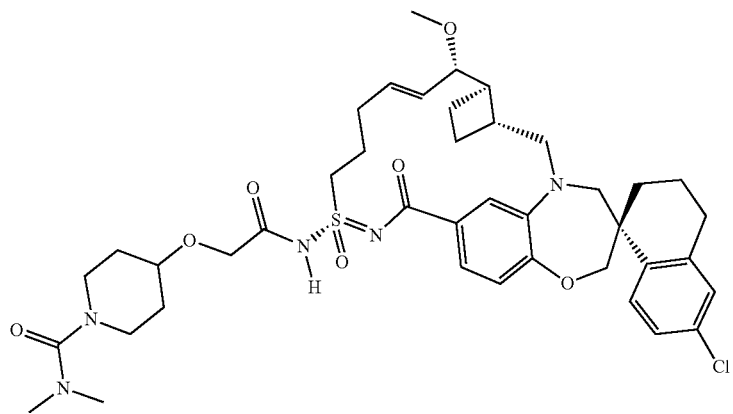 | 796.34 | 796.2 |
| 418 | 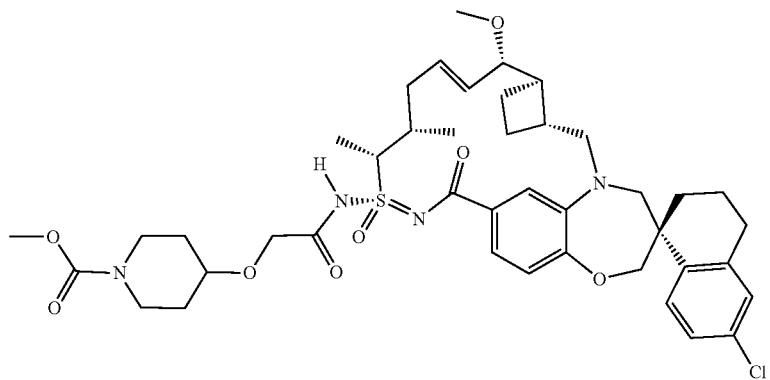 [SMILES: COC(=O)N1CCC(OCC(=O)N[S@@]2(=O)=NC(=O)c3ccc4c(c3)N(C[C@@H]3CC[C@H]3[C@@H](OC)/C=C/C[C@H](C)[C@H]2C)C[C@@]2(CCCc3cc(Cl)ccc32)CO4)CC1] | 811.34 | 811.05 |

-continued

| Example | Structure | LCMS-ESI+ (m/z): [M + H]+ calcd | LCMS-ESI+ (m/z): [M + H]+ found |
|---|---|---|---|
| 419 | 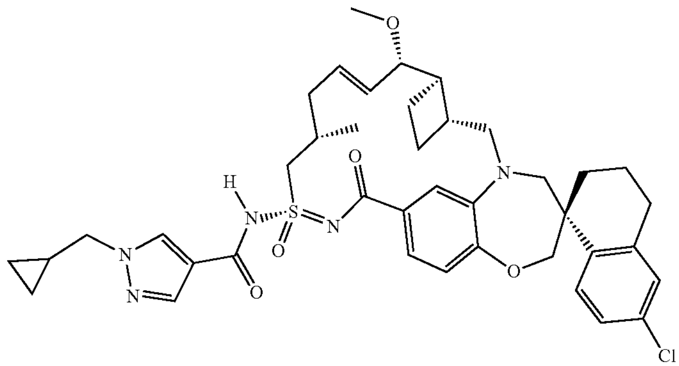 [SMILES: CO[C@H]1/C=C/C[C@H](C)C[S@@](=O)(NC(=O)c2cnn(CC3CC3)c2)=NC(=O)c2ccc3c(c2)N(C[C@@H]2CC[C@H]21)C[C@@]1(CCCc2cc(Cl)ccc21)CO3] | 746.3 | 746.1 |
| 420 | 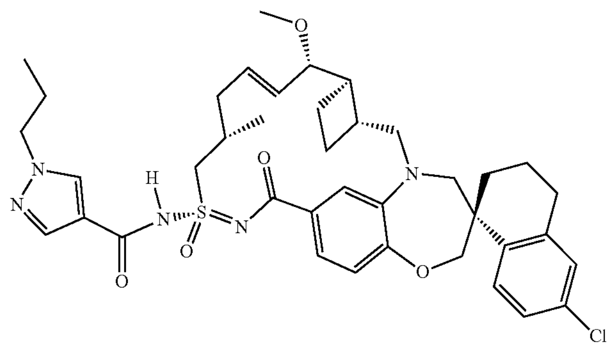 [SMILES: CCCn1cc(C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)cn1] | 733.31 | 734.33 |
| 421 | 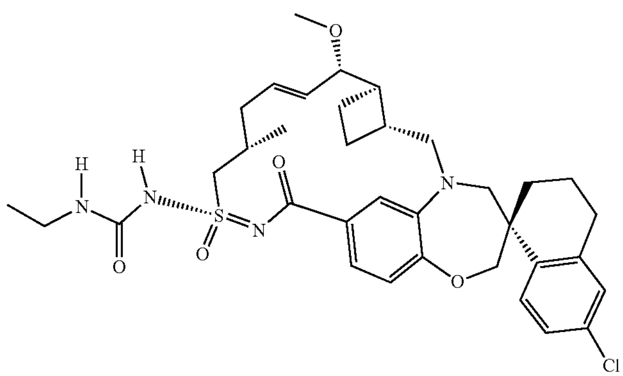 | 669.28 | 668.76 |
| 422 | 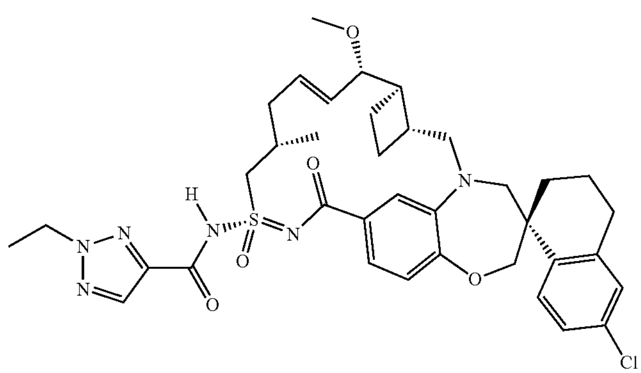 | 721.3 | 720.98 |

US 11,643,400 B2
471                                                                 472
-continued
| Example | Structure | LCMS-ESI+ (m/z): [M + H]+ calcd | LCMS-ESI+ (m/z): [M + H]+ found |
|---|---|---|---|
| 423 | 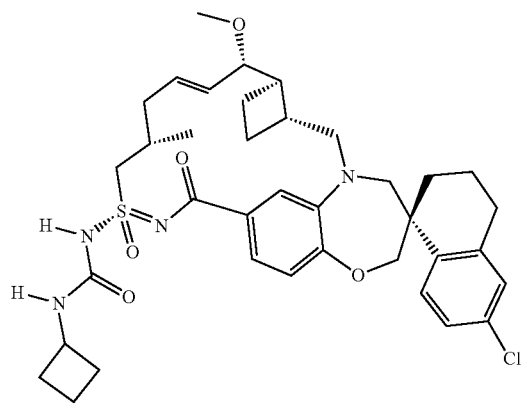 | 695.3 | 694.78 |
| 424 | 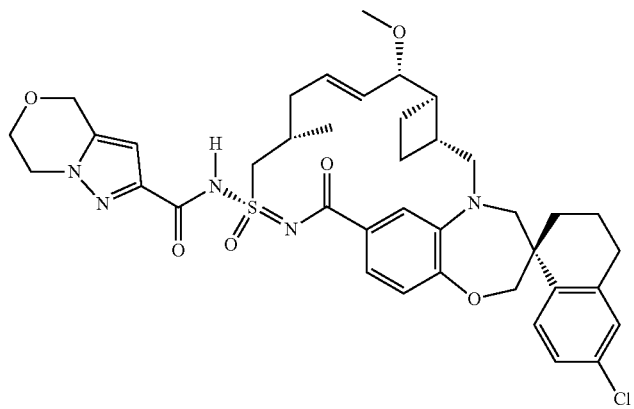 [SMILES: CO[C@H]1/C=C/C[C@H](C)C[S@@](=O)(NC(=O)c2cc3n(n2)CCOC3)=NC(=O)c2ccc3c(c2)N(C[C@@H]2CC[C@H]21)C[C@@]1(CCCc2cc(Cl)ccc21)CO3] | 748.293 | 747.68 |
| 425 | 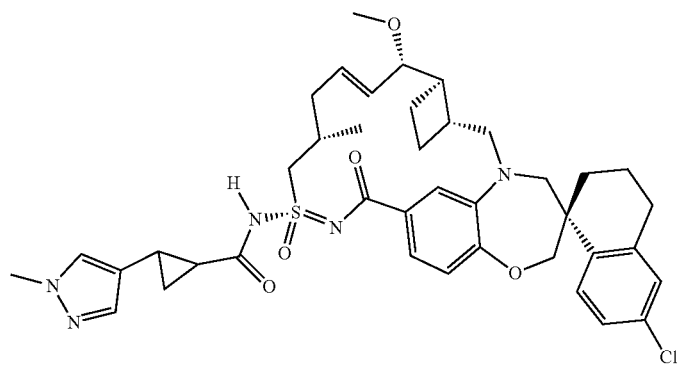 [SMILES: CO[C@H]1/C=C/C[C@H](C)C[S@@](=O)(NC(=O)C2CC2c2cnn(C)c2)=NC(=O)c2ccc3c(c2)N(C[C@@H]2CC[C@H]21)C[C@@]1(CCCc2cc(Cl)ccc21)CO3] | 746.31 | 746.03 |

-continued
| Example | Structure | LCMS-ESI+ (m/z): [M + H]+ calcd | LCMS-ESI+ (m/z): [M + H]+ found |
|---|---|---|---|
| 426 | 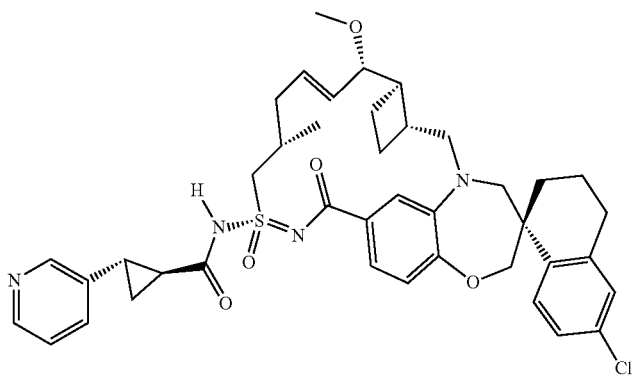 [SMILES: CO[C@H]1/C=C/C[C@H](C)C[S@@](=O)(NC(=O)[C@H]2C[C@@H]2c2cccnc2)=NC(=O)c2ccc3c(c2)N(C[C@@H]2CC[C@H]21)C[C@@]1(CCCc2cc(Cl)ccc21)CO3] | 743.3 | 743.11 |
| 427 | 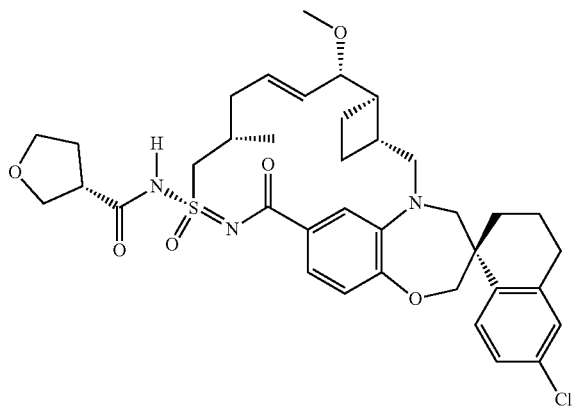 [SMILES: CO[C@H]1/C=C/C[C@H](C)C[S@@](=O)(NC(=O)[C@H]2CCOC2)=NC(=O)c2ccc3c(c2)N(C[C@@H]2CC[C@H]21)C[C@@]1(CCCc2cc(Cl)ccc21)CO3] | 696.2869 | 695.95 |
| 428 | 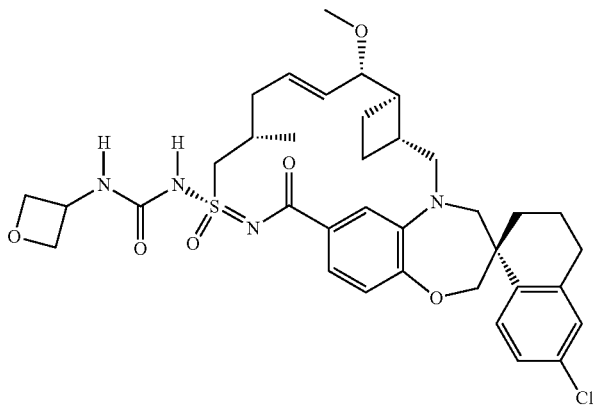 [SMILES: CO[C@H]1/C=C/C[C@H](C)C[S@@](=O)(NC(=O)NC2COC2)=NC(=O)c2ccc3c(c2)N(C[C@@H]2CC[C@H]21)C[C@@]1(CCCc2cc(Cl)ccc21)CO3] | 697.2821 | 696.92 |

-continued
| Example | Structure | LCMS-ESI+ (m/z): [M + H]+ calcd | LCMS-ESI+ (m/z): [M + H]+ found |
|---|---|---|---|
| 429 | 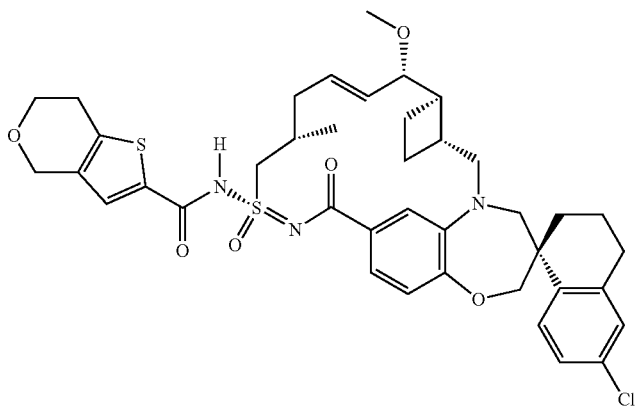 [SMILES: CO[C@H]1/C=C/C[C@H](C)C[S@@](=O)(NC(=O)c2cc3c(s2)CCOC3)=NC(=O)c2ccc3c(c2)N(C[C@@H]2CC[C@H]21)C[C@@]1(CCCc2cc(Cl)ccc21)CO3] | 764.25 | 763.93 |
| 430 | 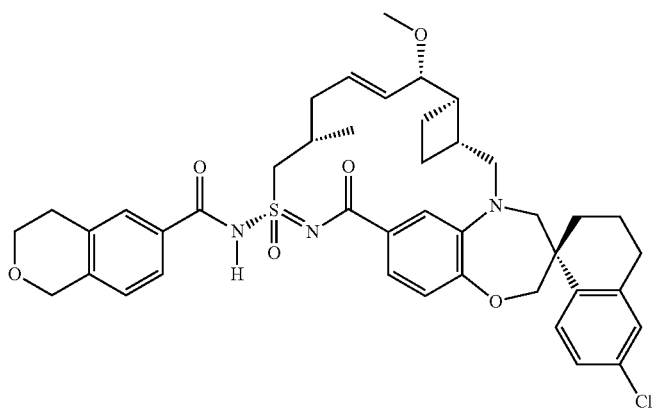 [SMILES: CO[C@H]1/C=C/C[C@H](C)C[S@@](=O)(NC(=O)c2ccc3c(c2)CCOC3)=NC(=O)c2ccc3c(c2)N(C[C@@H]2CC[C@H]21)C[C@@]1(CCCc2cc(Cl)ccc21)CO3] | 758.3 | 758.2 |
| 431 | 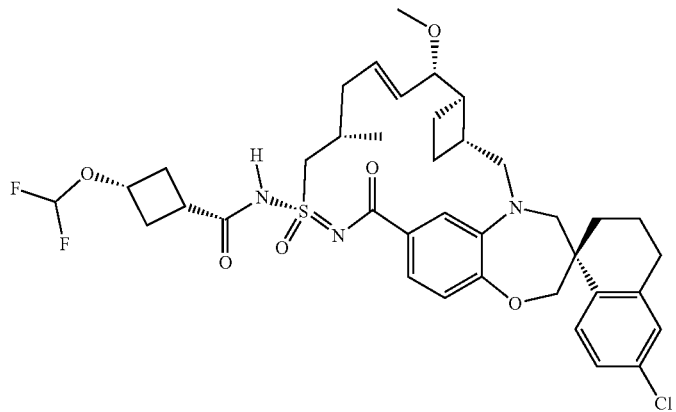 | 746.28 | 745.97 |

-continued
| Example | Structure | LCMS-ESI+ (m/z): [M + H]+ calcd | LCMS-ESI+ (m/z): [M + H]+ found |
|---|---|---|---|
| 432 | 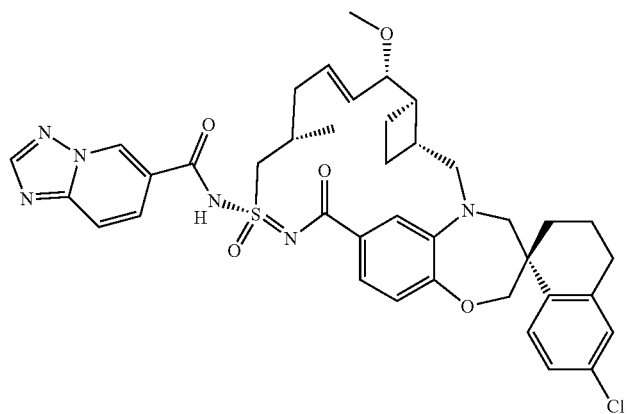 | 743.29 | 743.24 |
| 433 | 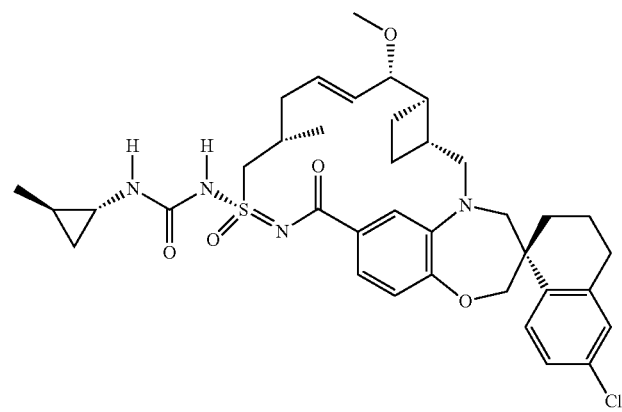 [SMILES: CO[C@H]1/C=C/C[C@H](C)C[S@@](=O)(NC(=O)N[C@@H]2C[C@H]2C)=NC(=O)c2ccc3c(c2)N(C[C@@H]2CC[C@H]21)C[C@@]1(CCCc2cc(Cl)ccc21)CO3] | 695.3 | 695.2 |
| 434 | 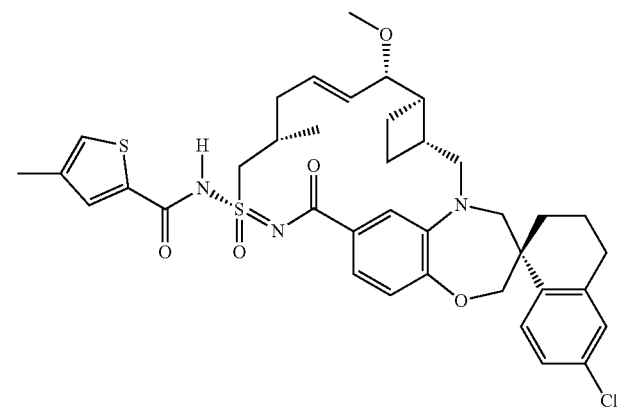 [SMILES: CO[C@H]1/C=C/C[C@H](C)C[S@@](=O)(NC(=O)c2cc(C)cs2)=NC(=O)c2ccc3c(c2)N(C[C@@H]2CC[C@H]21)C[C@@]1(CCCc2cc(Cl)ccc21)CO3] | 722.24 | 721.86 |

-continued

| Example | Structure | LCMS-ESI+ (m/z): [M + H]+ calcd | LCMS-ESI+ (m/z): [M + H]+ found |
|---|---|---|---|
| 435 | 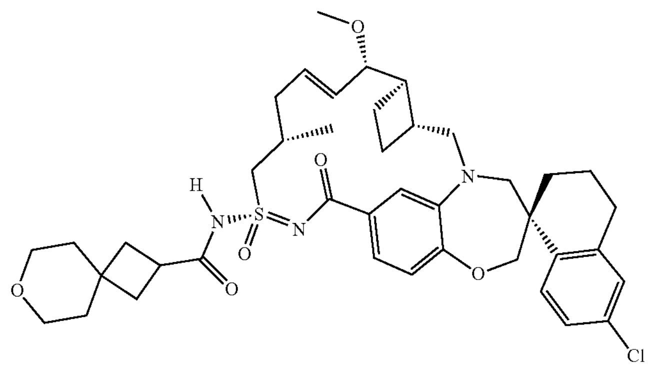 [SMILES: CO[C@H]1/C=C/C[C@H](C)C[S@@](=O)(NC(=O)C2CC3(CCOCC3)C2)=NC(=O)c2ccc3c(c2)N(C[C@@H]2CC[C@H]21)C[C@@]1(CCCc2cc(Cl)ccc21)CO3] | 750.33 | 750.14 |
| 436 | 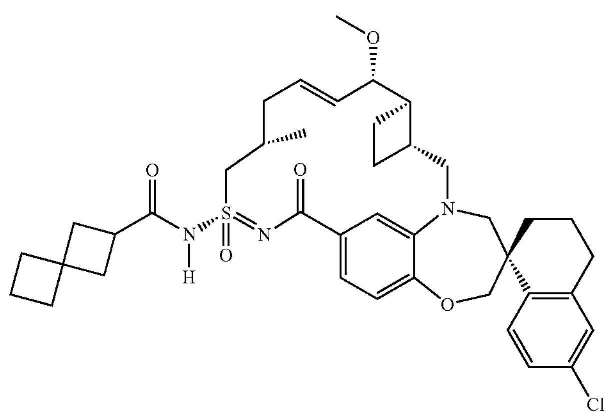 [SMILES: CO[C@H]1/C=C/C[C@H](C)C[S@@](=O)(NC(=O)C2CC3(CCC3)C2)=NC(=O)c2ccc3c(c2)N(C[C@@H]2CC[C@H]21)C[C@@]1(CCCc2cc(Cl)ccc21)CO3] | 720.3 | 720.4 |
| 437 | 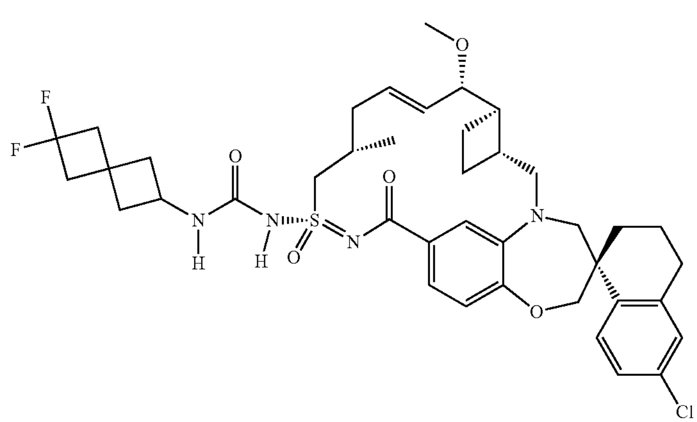 [SMILES: CO[C@H]1/C=C/C[C@H](C)C[S@@](=O)(NC(=O)NC2CC3(C2)CC(F)(F)C3)=NC(=O)c2ccc3c(c2)N(C[C@@H]2CC[C@H]21)C[C@@]1(CCCc2cc(Cl)ccc21)CO3] | 771.31 | 770.75 |

-continued

| Example | Structure | LCMS-ESI+ (m/z): [M + H]+ calcd | LCMS-ESI+ (m/z): [M + H]+ found |
| --- | --- | --- | --- |
| 438 | 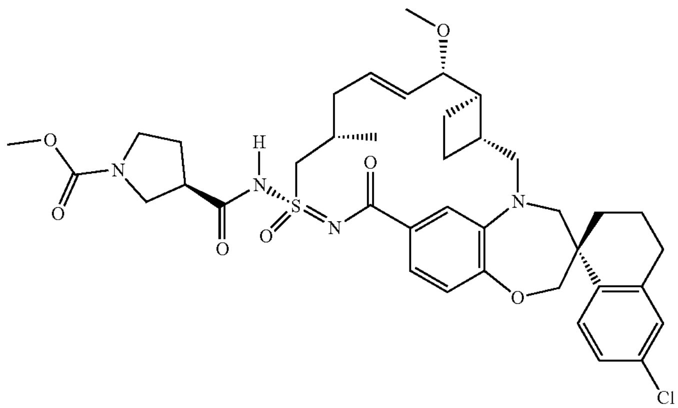 [SMILES: COC(=O)N1CC[C@@H](C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)C1] | 753.3083 | 753.02 |
| 439 | 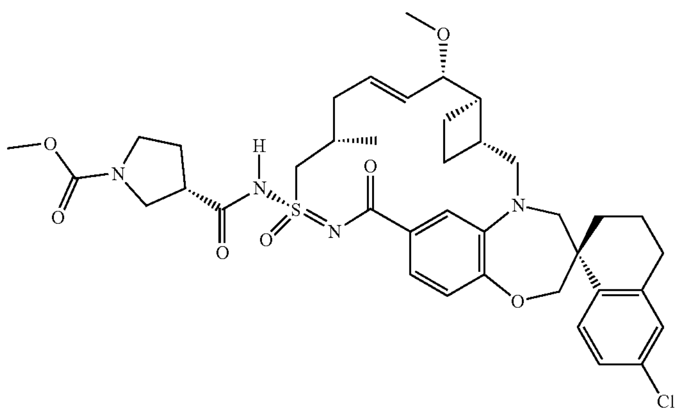 [SMILES: COC(=O)N1CC[C@H](C(=O)N[S@@]2(=O)=NC(=O)c3ccc4c(c3)N(C[C@@H]3CC[C@H]3[C@@H](OC)/C=C/C[C@H](C)C2)C[C@@]2(CCCc3cc(Cl)ccc32)CO4)C1] | 753.3083 | 753.07 |
| 440 | 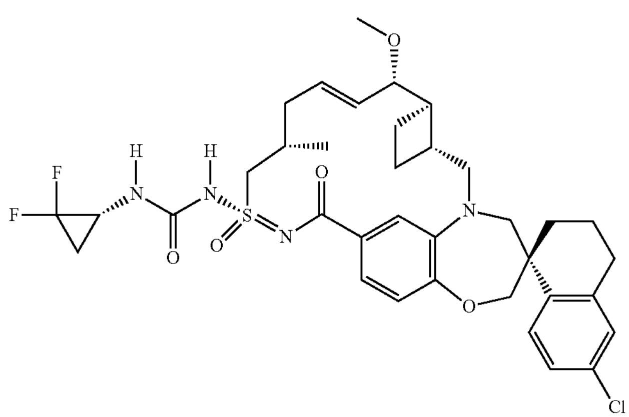 [SMILES: CO[C@H]1/C=C/C[C@H](C)C[S@@](=O)(NC(=O)N[C@@H]2CC2(F)F)=NC(=O)c2ccc3c(c2)N(C[C@@H]2CC[C@H]21)C[C@@]1(CCCc2cc(Cl)ccc21)CO3] | 717.2684 | 716.71 |

-continued
| Example | Structure | LCMS-ESI+ (m/z): [M + H]+ calcd | LCMS-ESI+ (m/z): [M + H]+ found |
|---|---|---|---|
| 441 | 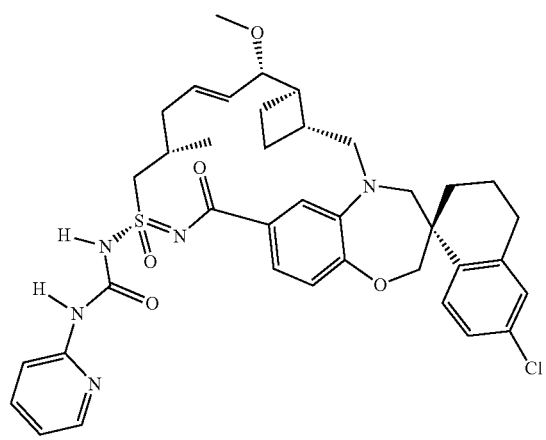 | 718.28 | 718.01 |
| 442 | 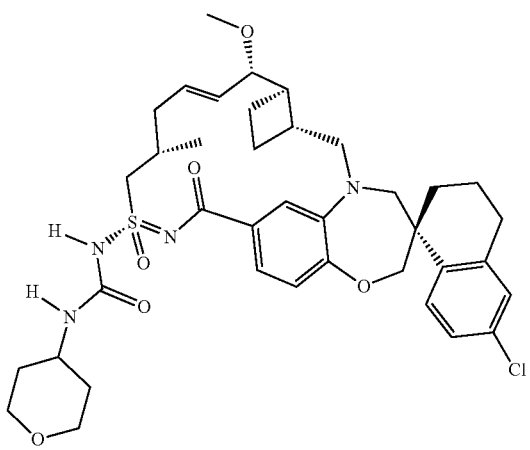 | 725.31 | 724.69 |
| 443 | 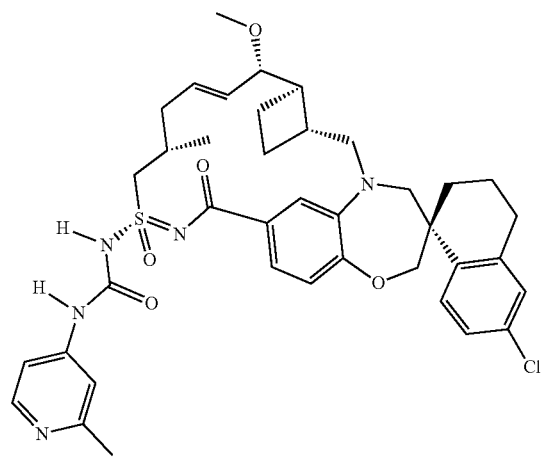 | 732.29 | 732.21 |

-continued

| Example | Structure | LCMS-ESI+ (m/z): [M + H]+ calcd | LCMS-ESI+ (m/z): [M + H]+ found |
|---|---|---|---|
| 444 | 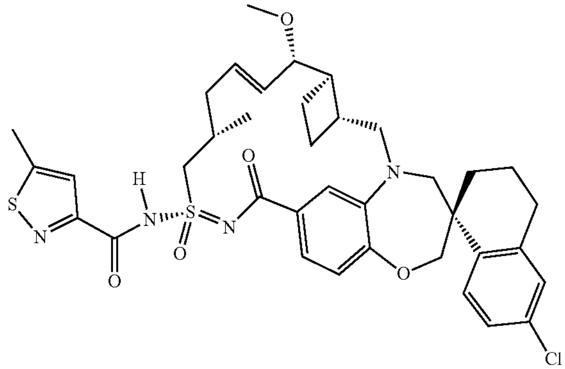 [SMILES: CO[C@H]1/C=C/C[C@H](C)C[S@@](=O)(NC(=O)c2cc(C)sn2)=NC(=O)c2ccc3c(c2)N(C[C@@H]2CC[C@H]21)C[C@@]1(CCCc2cc(Cl)ccc21)CO3] | 722.24 | 723.209 |
| 445 | 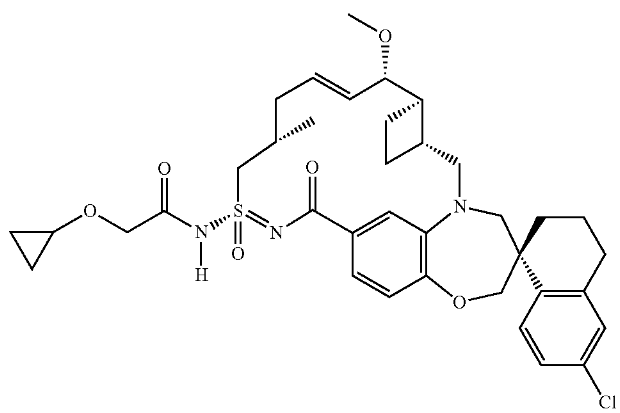 [SMILES: CO[C@H]1/C=C/C[C@H](C)C[S@@](=O)(NC(=O)COC2CC2)=NC(=O)c2ccc3c(c2)N(C[C@@H]2CC[C@H]21)C[C@@]1(CCCc2cc(Cl)ccc21)CO3] | 696.3 | 695.9 |
| 446 | 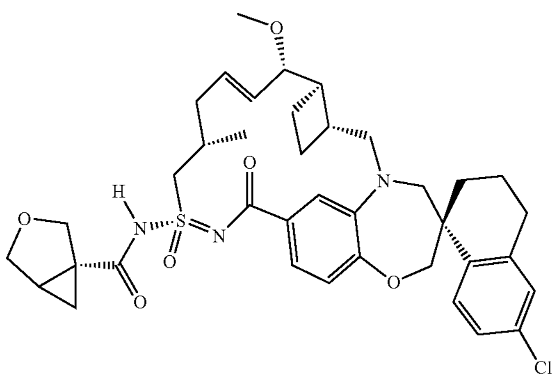 [SMILES: CO[C@H]1/C=C/C[C@H](C)C[S@@](=O)(NC(=O)[C@@]23COCC2C3)=NC(=O)c2ccc3c(c2)N(C[C@@H]2CC[C@H]21)C[C@@]1(CCCc2cc(Cl)ccc21)CO3] | 708.28 | 708.23 |
| 447 | 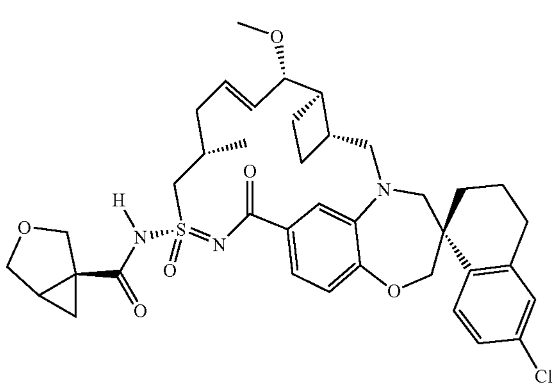 [SMILES: CO[C@H]1/C=C/C[C@H](C)C[S@@](=O)(NC(=O)[C@]23COCC2C3)=NC(=O)c2ccc3c(c2)N(C[C@@H]2CC[C@H]21)C[C@@]1(CCCc2cc(Cl)ccc21)CO3] | 708.28 | 708.23 |

| Example | Structure | LCMS-ESI+ (m/z): [M + H]+ calcd | LCMS-ESI+ (m/z): [M + H]+ found |
|---|---|---|---|
| 448 | 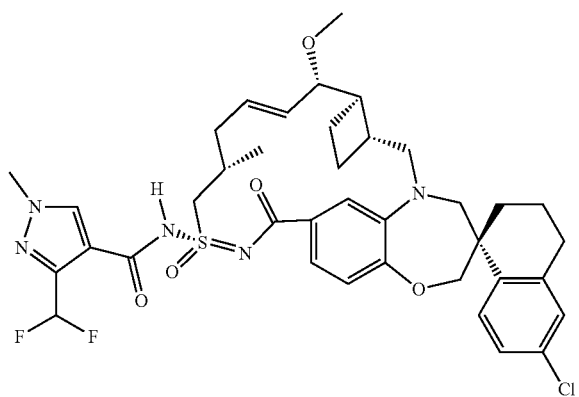 | 756.3 | 756.9 |
| 449 | 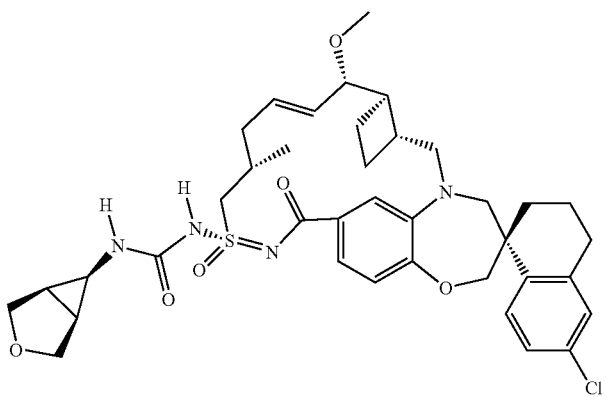 | 723.3 | 723.6 |
| 450 | 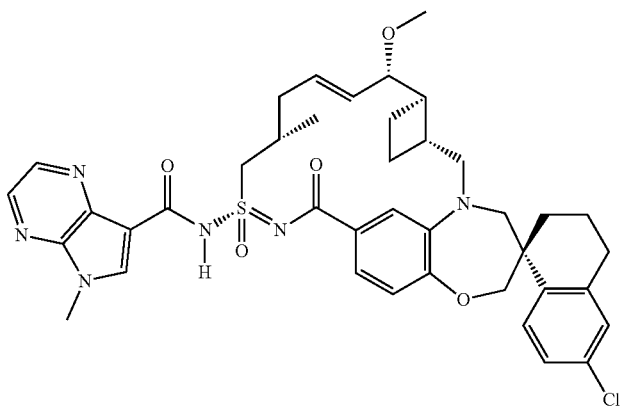 [SMILES: CO[C@H]1/C=C/C[C@H](C)C[S@@](=O)(NC(=O)c2cn(C)c3nccnc23)=NC(=O)c2ccc3c(c2)N(C[C@@H]2CC[C@H]21)C[C@@]1(CCCc2cc(Cl)ccc21)CO3] | 757.2933 | 757.1 |

| Example | Structure | LCMS-ESI+ (m/z): [M + H]+ calcd | LCMS-ESI+ (m/z): [M + H]+ found |
|---------|-----------|---------------------------------|---------------------------------|
| 451 | 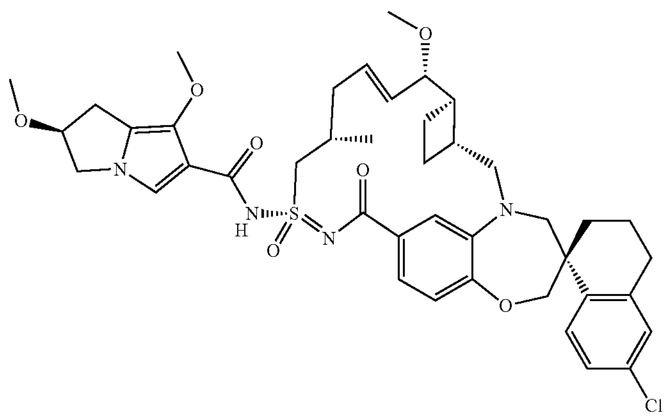 | 791.32 | 791.2 |
| 452 | 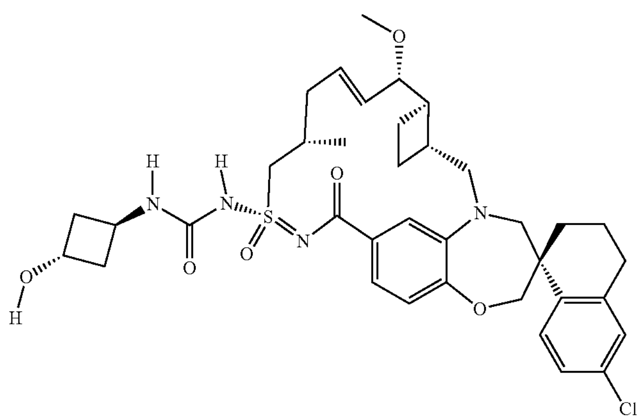 [SMILES: CO[C@H]1/C=C/C[C@H](C)C[S@@](=O)(NC(=O)N[C@H]2C[C@H](O)C2)=NC(=O)c2ccc3c(c2)N(C[C@@H]2CC[C@H]21)C[C@@]1(CCCc2cc(Cl)ccc21)CO3] | 711.3 | 710.66 |
| 453 | 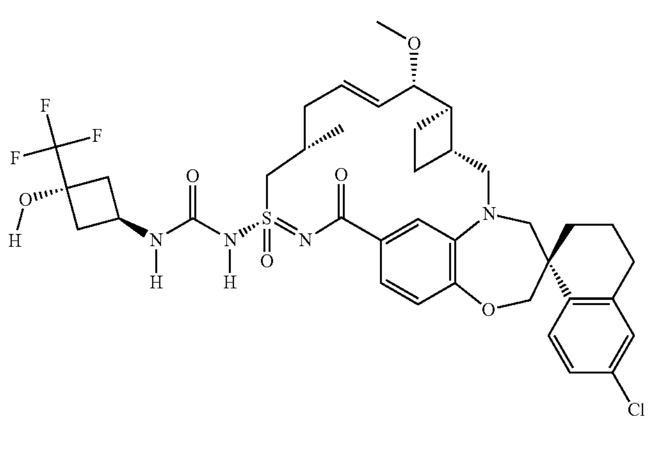 [SMILES: CO[C@H]1/C=C/C[C@H](C)C[S@@](=O)(NC(=O)N[C@H]2C[C@@](O)(C(F)(F)F)C2)=NC(=O)c2ccc3c(c2)N(C[C@@H]2CC[C@H]21)C[C@@]1(CCCc2cc(Cl)ccc21)CO3] | 779.28 | 778.68 |

-continued

| Example | Structure | LCMS-ESI+ (m/z): [M + H]+ calcd | LCMS-ESI+ (m/z): [M + H]+ found |
|---|---|---|---|
| 454 | 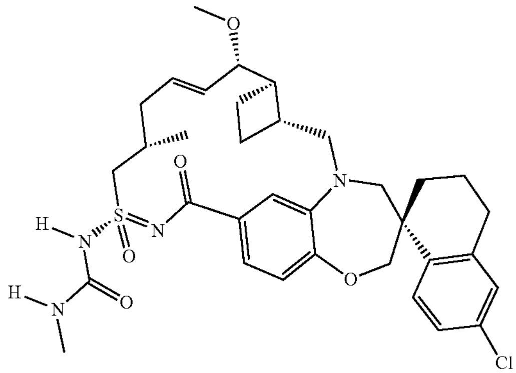 | 655.26 | 655.79 |
| 455 | 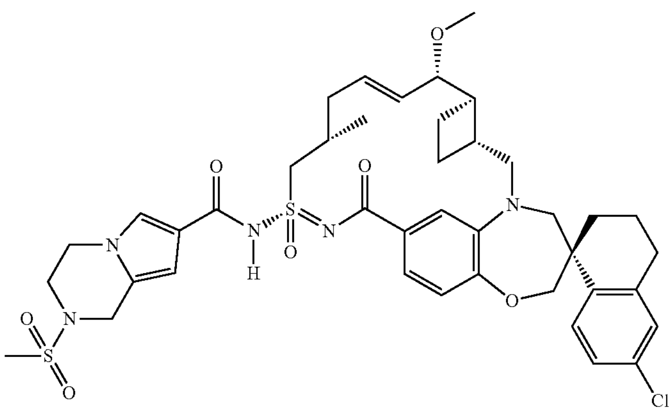 [SMILES: CO[C@H]1/C=C/C[C@H](C)C[S@@](=O)(NC(=O)c2cc3n(c2)CCN(S(C)(=O)=O)C3)=NC(=O)c2ccc3c(c2)N(C[C@@H]2CC[C@H]21)C[C@@]1(CCCc2cc(Cl)ccc21)CO3] | 846.2732 | 846.1 |
| 456 | 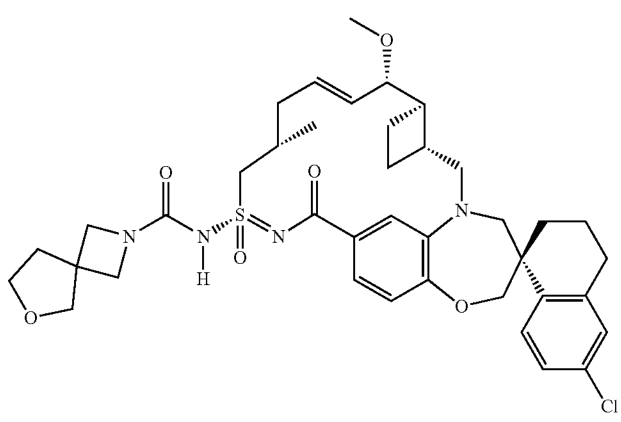 [SMILES: CO[C@H]1/C=C/C[C@H](C)C[S@@](=O)(NC(=O)N2CC3(CCOC3)C2)=NC(=O)c2ccc3c(c2)N(C[C@@H]2CC[C@H]21)C[C@@]1(CCCc2cc(Cl)ccc21)CO3] | 737.31 | 736.79 |

| Example | Structure | LCMS-ESI+ (m/z): [M + H]+ calcd | LCMS-ESI+ (m/z): [M + H]+ found |
|---|---|---|---|
| 457 | 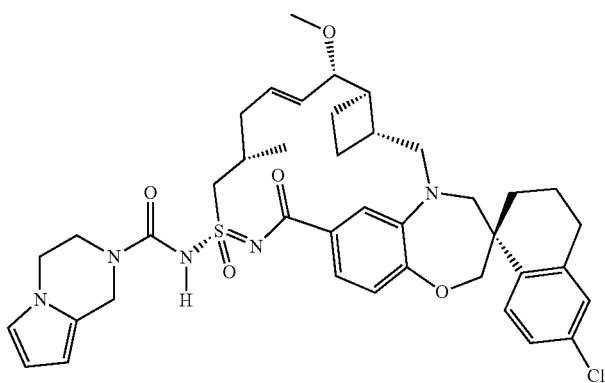 | 746.31 | 745.82 |
| 458 | 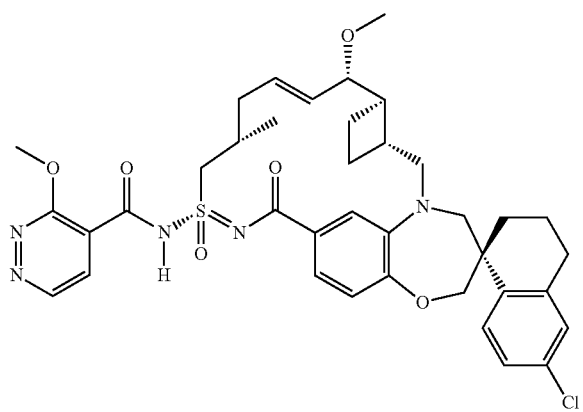 [SMILES: COc1nnccc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3] | 734.2774 | 734.1 |
| 459 | 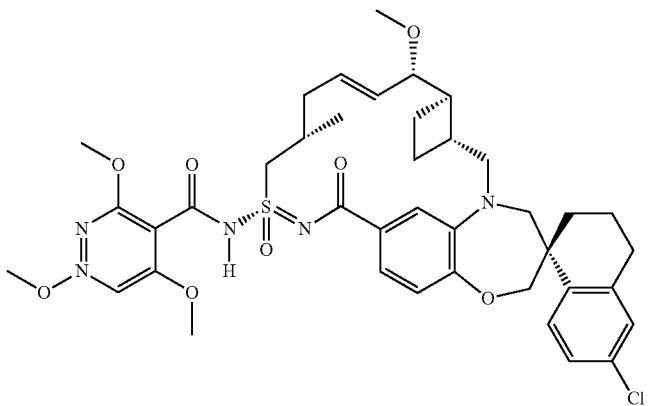 | 794.2985 | 794.1 |

| Example | Structure | LCMS-ESI+ (m/z): [M + H]+ calcd | LCMS-ESI+ (m/z): [M + H]+ found |
|---|---|---|---|
| 460 | 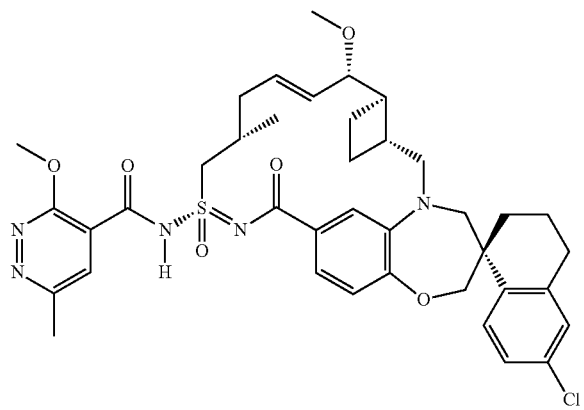 [SMILES: COc1nnc(C)cc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3] | 748.293 | 748.2 |
| 461 | 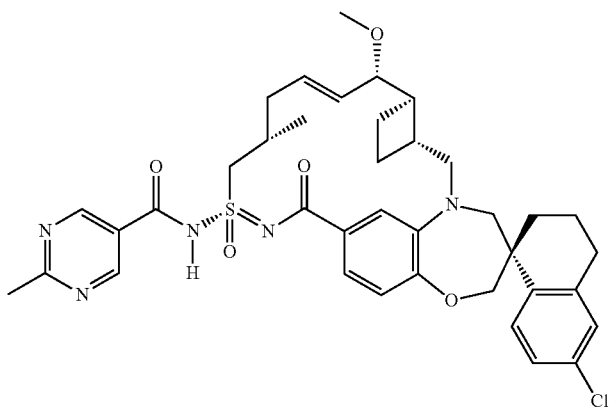 [SMILES: CO[C@H]1/C=C/C[C@H](C)C[S@@](=O)(NC(=O)c2cnc(C)nc2)=NC(=O)c2ccc3c(c2)N(C[C@@H]2CC[C@H]21)C[C@@]1(CCCc2cc(Cl)ccc21)CO3] | 718.2824 | 718.1 |
| 462 | 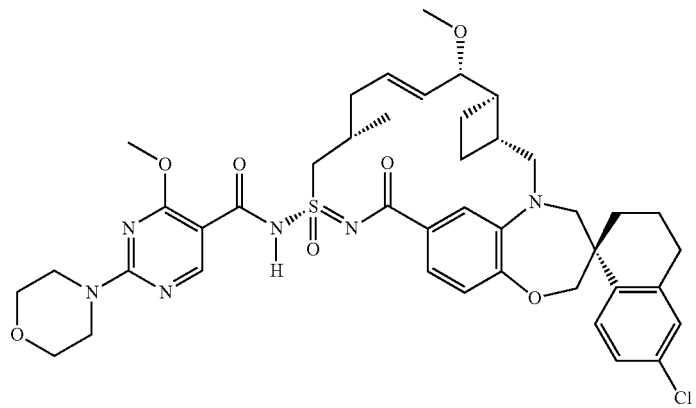 [SMILES: COc1nc(N2CCOCC2)ncc1C(=O)N[S@@]1(=O)=NC(=O)c2ccc3c(c2)N(C[C@@H]2CC[C@H]2[C@@H](OC)/C=C/C[C@H](C)C1)C[C@@]1(CCCc2cc(Cl)ccc21)CO3] | 819.3301 | 819.1 |

| Example | Structure | LCMS-ESI+ (m/z): [M + H]+ calcd | LCMS-ESI+ (m/z): [M + H]+ found |
|---|---|---|---|
| 463 | 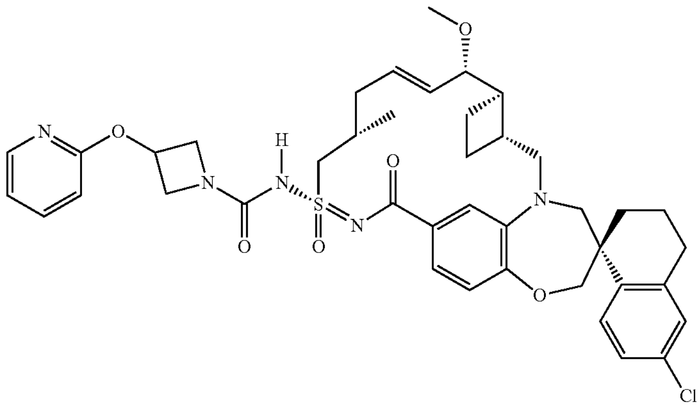 [SMILES: CO[C@H]1/C=C/C[C@H](C)C[S@@](=O)(NC(=O)N2CC(Oc3ccccn3)C2)=NC(=O)c2ccc3c(c2)N(C[C@@H]2CC[C@H]21)C[C@@]1(CCCc2cc(Cl)ccc21)CO3] | 774.3087 | 774.61 |
| 464 | 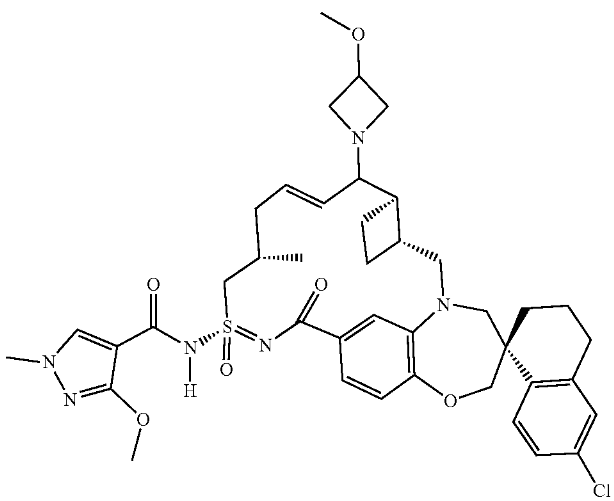 [SMILES: COc1nn(C)cc1C(=O)N[S@@]1(=O)=NC(=O)c2ccc3c(c2)N(C[C@@H]2CC[C@H]2C(N2CC(OC)C2)/C=C/C[C@H](C)C1)C[C@@]1(CCCc2cc(Cl)ccc21)CO3] | 791.33 | 791.28 |

MCL-1/Bim Binding AlphaLISA Assay.

Inhibition of the MCL-1 and Bim interaction was measured in the following AlphaLISA assay.

Materials

Recombinant human MCL-1 protein (C-terminal 6×His Tagged Mcl-1 containing residues 171-327) was generated at Gilead Sciences, Inc. (Foster City, Calif.). A biotinylated peptide derived from human Bim (residues 51-76) was purchased from CPC Scientific (Sunnyvale, Calif.). (CPC 834113). AlphaLISA anti-6His-acceptor beads (AL128R), AlphaScreen Streptavidin donor beads (6760002B), and Proxiplate-384 Plus (6008289) were purchased from PerkinElmer.

Methods

The AlphaLISA assay was performed in a 384-well Proxiplate in a total volume of 40 μL. The reaction mixture contained 0.0625 nM 6×His-Mcl-1 (171-327), 0.0625 nM biotinylated-Bim peptide, 10 μg/mL AlphaLISA anti-6×His-AlphaLISA acceptor beads, 40 μg/mL AlphaScreen streptavidin donor beads, and serially diluted test compounds in the binding buffer (20 mM Hepes, pH 7.5 (Teknova H1035); 150 mM NaCl (Promega V4221); 0.002% Brij 35 (Thermo Scientific 20150); 1 mM Dithiothreitol (DTT) Solution (Affymetrix 70726); 0.01% BSA (BioLabs B9000S)). 1,000× test compounds were pre-spotted onto 384-well Proxiplate (Labcyte Echo) by Echo 555 Liquid Handler (Labcyte Inc., San Jose, Calif.) followed by incubation of 5 μl Mcl-1 (171-327) for 1 hour. Then 5 μL Bim (51-76) was added and incubated for 2 hours. Five μL AlphaLISA anti-6His-AlphaLISA acceptor beads were then added for 1 hour followed by addition of 5 μL AlphaScreen streptavidin donor beads for 1 hour. The reaction plates were then read on an Envision multimode reader (PerkinElmer) using AlphaScreen settings. IC$_{50}$ values were calculated and reported in Table 1. Comparative Example 1 is Example 4 from International Publication No. WO 2016/033486). Percent inhibition was calculated as shown below:

% Inhibition=100%*(Well−Neg)/(Pos−Neg)

Neg: negative control, DMSO
Pos: positive control, no Mcl-1 protein, no biotinylated-Bim peptide

TABLE 1

| MCL-1/Bim IC$_{50}$ (nM) | |
|---|---|
| Example | IC$_{50}$ (nM) |
| 1 | 0.9 |
| 2 | 1.5 |
| 3 | 4.1 |
| 4 | 0.7 |
| 5 | 60.2 |
| 6 | 27.3 |
| 7 | 1.2 |
| 8 | 0.7 |
| 9 | 6.6 |
| 10 | 3.6 |
| 11 | 6.5 |
| 12 | 1.7 |
| 13 | 1.8 |
| 14 | 0.3 |
| 15 | 7.4 |
| 16 | 4.2 |
| 17 | 11.3 |
| 18 | 0.3 |
| 19 | 1.1 |
| 20 | 0.5 |
| 21 | 0.8 |
| 22 | 0.1 |
| 23 | 0.8 |
| 24 | 0.2 |
| 25 | 0.6 |
| 26 | 1.8 |
| 27 | 1.6 |
| 28 | 0.2 |
| 29 | 0.6 |
| 30 | 0.6 |
| 31 | 3.1 |
| 32 | 1.4 |
| 33 | 2.9 |
| 34 | 2.0 |
| 35 | 0.2 |
| 36 | 8.1 |
| 37 | 1.4 |
| 38 | 0.2 |
| 39 | 0.1 |
| 40 | 0.1 |
| 41 | 0.1 |
| 42 | 0.1 |
| 43 | 1.6 |
| 44 | 0.1 |
| 45 | 0.1 |
| 46 | 0.1 |
| 47 | 0.1 |
| 48 | 3.7 |
| 49 | 0.1 |
| 50 | 1.4 |
| 51 | 0.1 |
| 52 | 0.9 |
| 53 | 0.2 |
| 54 | 0.2 |
| 55 | 0.2 |
| 56 | 0.6 |
| 57 | 0.2 |
| 58 | 0.2 |
| 59 | 0.1 |
| 60 | 0.2 |
| 61 | 0.1 |
| 62 | 0.4 |
| 63 | 1.4 |
| 64 | 5.2 |
| 65 | 1.8 |
| 66 | 2.7 |
| 67 | 1.2 |
| 68 | 46.9 |
| 69 | 4.0 |
| 70 | 0.2 |
| 71 | 0.7 |
| 72 | 0.1 |
| 73 | 0.3 |
| 74 | 7.3 |
| 75 | 0.3 |
| 76 | 10.5 |

TABLE 1-continued

| MCL-1/Bim IC$_{50}$ (nM) | |
|---|---|
| Example | IC$_{50}$ (nM) |
| 77 | 5.3 |
| 78 | 0.8 |
| 79 | 0.4 |
| 80 | 0.3 |
| 81 | 0.5 |
| 82 | 1.1 |
| 83 | 0.1 |
| 84 | 0.1 |
| 85 | 0.6 |
| 86 | 1.8 |
| 87 | 3.2 |
| 88 | 1.5 |
| 89 | 0.5 |
| 90 | 0.5 |
| 91 | 0.1 |
| 92 | 0.1 |
| 93 | 51.0 |
| 94 | 0.9 |
| 95 | 1.1 |
| 96 | 0.4 |
| 97 | 0.6 |
| 98 | 0.3 |
| 99 | 0.2 |
| 100 | 0.2 |
| 101 | 1.4 |
| 102 | 0.3 |
| 103 | 1.0 |
| 104 | 0.1 |
| 105 | 0.1 |
| 106 | 0.1 |
| 107 | 0.1 |
| 108 | 0.1 |
| 109 | 10.643 |
| 110 | 2.634 |
| 111 | 0.093 |
| 112 | 0.047 |
| 113 | 0.046 |
| 114 | 0.043 |
| 115 | 0.068 |
| 116 | 0.08 |
| 117 | 0.113 |
| 118 | 0.103 |
| 119 | 0.145 |
| 120 | 0.167 |
| 121 | 0.163 |
| 122 | 0.161 |
| 123 | 0.071 |
| 124 | 0.066 |
| 125 | 0.074 |
| 126 | 0.099 |
| 127 | 0.085 |
| 128 | 0.068 |
| 129 | 0.077 |
| 130 | 0.18 |
| 131 | 0.046 |
| 132 | 0.038 |
| 133 | 0.051 |
| 134 | 0.072 |
| 135 | 0.213 |
| 136 | 0.183 |
| 137 | 0.491 |
| 138 | 0.112 |
| 139 | 0.116 |
| 140 | 0.043 |
| 141 | 0.086 |
| 142 | 0.097 |
| 143 | 0.173 |
| 144 | 0.05 |
| 145 | 0.037 |
| 146 | 0.062 |
| 147 | 0.051 |
| 148 | 0.043 |
| 149 | 0.109 |
| 150 | 0.071 |
| 151 | 0.036 |
| 152 | 0.057 |

TABLE 1-continued

MCL-1/Bim IC$_{50}$ (nM)

| Example | IC$_{50}$ (nM) |
|---|---|
| 153 | 0.086 |
| 154 | 0.05 |
| 155 | 0.060 |
| 156 | 0.111 |
| 157 | 0.234 |
| 158 | 0.135 |
| 159 | 0.087 |
| 160 | 0.031 |
| 161 | 0.025 |
| 162 | 0.180 |
| 163 | 0.263 |
| 164 | 0.141 |
| 165 | 0.035 |
| 166 | 0.067 |
| 167 | 0.141 |
| 168 | 0.222 |
| 169 | 0.048 |
| 170 | 0.060 |
| 171 | 0.033 |
| 172 | 0.022 |
| 173 | 0.087 |
| 174 | 0.153 |
| 175 | 0.140 |
| 176 | 0.138 |
| 177 | 0.129 |
| 178 | 0.141 |
| 179 | 0.102 |
| 180 | 0.092 |
| 181 | 0.146 |
| 182 | 0.144 |
| 183 | 0.132 |
| 184 | 0.108 |
| 185 | 0.041 |
| 186 | 0.066 |
| 187 | 0.107 |
| 188 | 0.069 |
| 189 | 0.033 |
| 190 | 0.055 |
| 191 | 0.103 |
| 192 | 0.054 |
| 193 | 0.046 |
| 194 | 0.030 |
| 195 | 0.036 |
| 196 | 0.040 |
| 197 | 0.041 |
| 198 | 0.043 |
| 199 | 0.117 |
| 200 | 0.064 |
| 201 | 0.042 |
| 202 | 0.082 |
| 203 | 0.073 |
| 204 | 0.048 |
| 205 | 0.075 |
| 206 | 0.047 |
| 207 | 0.162 |
| 208 | 0.136 |
| 209 | 0.202 |
| 210 | 0.071 |
| 211 | 0.082 |
| 212 | 0.040 |
| 213 | 0.076 |
| 214 | 0.185 |
| 215 | 0.203 |
| 216 | 0.196 |
| 217 | 0.065 |
| 218 | 0.345 |
| 219 | 0.099 |
| 220 | 0.122 |
| 221 | 0.046 |
| 222 | 0.044 |
| 223 | 0.039 |
| 224 | 0.195 |
| 225 | 0.043 |
| 226 | 0.095 |
| 227 | 0.076 |
| 228 | 0.069 |
| 229 | 0.030 |
| 230 | 0.027 |
| 231 | 0.051 |
| 232 | 0.052 |
| 233 | 0.016 |
| 234 | 0.053 |
| 235 | 0.035 |
| 236 | 0.055 |
| 237 | 0.044 |
| 238 | 0.033 |
| 239 | 0.042 |
| 240 | 0.018 |
| 241 | 0.087 |
| 242 | 0.074 |
| 243 | 0.059 |
| 244 | 0.032 |
| 245 | 0.066 |
| 246 | 0.096 |
| 247 | 0.042 |
| 248 | 0.042 |
| 249 | 0.140 |
| 250 | 0.029 |
| 251 | 0.037 |
| 252 | 0.043 |
| 253 | 0.037 |
| 254 | 0.126 |
| 255 | 0.096 |
| 256 | 0.162 |
| 257 | 0.083 |
| 258 | 0.117 |
| 259 | 0.098 |
| 260 | 0.061 |
| 261 | 0.053 |
| 262 | 0.056 |
| 263 | 0.073 |
| 264 | 0.263 |
| 265 | 0.046 |
| 266 | 0.085 |
| 267 | 0.030 |
| 268 | 0.058 |
| 269 | 0.081 |
| 270 | 0.041 |
| 271 | 0.100 |
| 272 | 0.018 |
| 273 | 0.077 |
| 274 | 0.043 |
| 275 | 0.053 |
| 276 | 0.068 |
| 277 | 0.061 |
| 278 | 0.089 |
| 279 | 0.041 |
| 280 | 0.044 |
| 281 | 0.154 |
| 282 | 0.086 |
| 283 | 0.029 |
| 284 | 0.061 |
| 285 | 0.131 |
| 286 | 0.037 |
| 287 | 0.029 |
| 288 | 0.144 |
| 289 | 0.053 |
| 290 | 0.030 |
| 291 | 0.039 |
| 292 | 0.020 |
| 293 | 0.058 |
| 294 | 0.129 |
| 295 | 0.040 |
| 296 | 0.053 |
| 297 | 0.033 |
| 298 | 0.016 |
| 299 | 0.039 |
| 300 | 0.026 |
| 301 | 0.040 |
| 302 | 0.091 |
| 303 | 0.045 |
| 304 | 0.129 |

TABLE 1-continued

MCL-1/Bim IC$_{50}$ (nM)

| Example | IC$_{50}$ (nM) |
|---|---|
| 305 | 0.088 |
| 306 | 0.057 |
| 307 | 0.120 |
| 308 | 0.031 |
| 309 | 0.029 |
| 310 | 0.074 |
| 311 | 0.024 |
| 312 | 0.039 |
| 313 | 0.064 |
| 314 | 0.054 |
| 315 | 0.127 |
| 316 | 0.056 |
| 317 | 0.034 |
| 318 | 0.066 |
| 319 | 0.038 |
| 320 | 0.035 |
| 321 | 0.037 |
| 322 | 0.057 |
| 323 | 0.158 |
| 324 | 0.058 |
| 325 | 0.100 |
| 326 | 0.076 |
| 327 | 0.051 |
| 328 | 0.049 |
| 329 | 0.087 |
| 330 | 0.030 |
| 331 | 0.075 |
| 332 | 0.071 |
| 333 | 0.039 |
| 334 | 0.041 |
| 335 | 0.235 |
| 336 | 0.100 |
| 337 | 0.050 |
| 338 | 0.090 |
| 339 | 0.070 |
| 340 | 0.031 |
| 341 | 0.032 |
| 342 | 0.029 |
| 343 | 0.019 |
| 344 | 0.049 |
| 345 | 0.037 |
| 346 | 0.031 |
| 347 | 0.084 |
| 348 | 0.041 |
| 349 | 0.026 |
| 350 | 0.055 |
| 351 | 0.035 |
| 352 | 0.046 |
| 353 | 0.103 |
| 354 | 0.039 |
| 355 | 0.062 |
| 356 | 0.081 |
| 357 | 0.113 |
| 358 | 0.114 |
| 359 | 0.038 |
| 360 | 0.052 |
| 361 | 0.055 |
| 362 | 0.024 |
| 363 | 0.042 |
| 364 | 0.064 |
| 365 | 0.040 |
| 366 | 0.086 |
| 367 | 0.063 |
| 368 | |
| 369 | |
| 370 | |
| 371 | |
| 372 | |
| 373 | |
| 374 | 0.058 |
| 375 | 0.046 |
| 376 | 0.031 |
| 377 | 0.106 |
| 378 | 1.152 |
| 379 | 0.834 |
| 380 | 4.539 |
| 381 | 0.769 |
| 382 | 1.400 |
| 383 | 0.659 |
| 384 | 0.340 |
| 385 | 0.128 |
| 386 | 0.048 |
| 387 | 0.102 |
| 388 | 1.065 |
| 389 | 0.075 |
| 390 | 0.061 |
| 391 | 0.702 |
| 392 | 0.070 |
| 393 | 0.062 |
| 394 | 1.718 |
| 395 | 5.267 |
| 396 | |
| 397 | 0.045 |
| 398 | |
| 399 | 0.070 |
| 400 | 0.058 |
| 401 | 0.044 |
| 402 | 0.098 |
| 403 | 0.059 |
| 404 | 0.092 |
| 405 | 0.113 |
| 406 | 0.103 |
| 407 | 0.113 |
| 408 | 0.054 |
| 409 | 0.147 |
| 410 | 0.194 |
| 411 | 0.178 |
| 412 | 0.072 |
| 413 | 0.478 |
| 414 | 0.217 |
| 415 | 0.526 |
| 416 | 0.047 |
| 417 | 0.092 |
| 418 | 0.197 |
| 419 | 0.186 |
| 420 | 0.237 |
| 421 | 0.081 |
| 422 | 0.035 |
| 423 | 0.056 |
| 424 | 0.037 |
| 425 | 0.078 |
| 426 | 0.091 |
| 427 | 0.104 |
| 428 | 0.069 |
| 429 | 0.129 |
| 430 | 0.170 |
| 431 | 0.121 |
| 432 | 0.070 |
| 433 | 0.133 |
| 434 | 0.446 |
| 435 | 0.114 |
| 436 | 0.886 |
| 437 | 0.301 |
| 438 | 0.187 |
| 439 | 0.138 |
| 440 | 0.051 |
| 441 | 0.223 |
| 442 | 0.134 |
| 443 | 0.187 |
| 444 | 0.101 |
| 445 | 0.091 |
| 446 | 0.149 |
| 447 | 0.132 |
| 448 | 0.117 |
| 449 | 0.131 |
| 450 | 0.234 |
| 451 | 0.520 |
| 452 | 0.045 |
| 453 | 0.092 |
| 454 | 0.098 |
| 455 | 0.147 |
| 456 | 0.099 |

TABLE 1-continued

MCL-1/Bim IC$_{50}$ (nM)

| Example | IC$_{50}$ (nM) |
|---|---|
| 457 | 0.085 |
| 458 | 0.079 |
| 459 | 0.085 |
| 460 | 0.089 |
| 461 | 0.087 |
| 462 | 0.251 |
| 463 | 0.219 |
| 464 | 0.209 |
| Comparative Example 1 | 0.5 |

SKBR3 Cell Viability Assay

Materials

SKBR3 Cells (ATCC HTB-30) were obtained from ATCC (Manassas, Va.) and cultured in McCoy 5A's medium (ATCC 30-2007)+10% fetal bovine serum (SH30071.03, HyClone, Pittsburgh, Pa.) plus 1× Penicillin-Streptomycin L-glutamine (Corning 30-009-C1, Corning, N.Y.)).

Methods

The cell viability assay was conducted in a 384-well tissue culture plate (Grenier 781086, Monroe, N.C.) in a total volume of 70 μL. Test compounds were prepared in 1,000×, serially diluted, and pre-spotted into 384-well tissue culture plate by Echo 555 Liquid Handler (Labcyte Inc., San Jose, Calif.). Seventy pi of 6,000 SKBR3 cells were dispensed into each well of the plate and incubated at 37° C. with 5% CO$_2$ for 72 hours. At the end of incubation, 2× CellTiter Glo (CTG) reagents (1 part buffer with 2 parts substrate) (Promega, Madison, Wis.) were prepared, and the plate and the reagent were equilibrated to room temperature for 30 minutes. CTG reagent was added to each plate by Biomek FX at 20 μL/well with 5 times pipetting and mixing to induce cell lysis. Luminescence was read by Envision multimode reader (PerkinElmer). EC$_{50}$ values were calculated and reported in Table 2. Comparative Example 1 is Example 4 from International Publication No. WO 2016/033486). Percent inhibition was calculated as followed:

% Inhibition=100%*(Well−Neg)/(Pos−Neg)

Neg, negative control, DMSO
Pos, positive control, 10 μM Puromycin

TABLE 2

MCL-1 CV SKBR3 EC$_{50}$ (nM)

| Example | EC$_{50}$ (nM) |
|---|---|
| 1 | 1701.8 |
| 2 | 792.2 |
| 3 | N.D. |
| 4 | 899.1 |
| 5 | 10000.0 |
| 6 | 8731.8 |
| 7 | 4800.1 |
| 8 | N.D. |
| 9 | 7776.1 |
| 10 | N.D. |
| 11 | 10000.0 |
| 12 | 4464.8 |
| 13 | 3274.3 |
| 14 | 356.3 |
| 15 | 7734.0 |
| 16 | 10000.0 |
| 17 | 10000.0 |
| 18 | 894.5 |
| 19 | 1084.8 |
| 20 | 2060.5 |
| 21 | 1303.0 |
| 22 | 259.4 |
| 23 | 1451.0 |
| 24 | 891.2 |
| 25 | 2005.9 |
| 26 | 1685.9 |
| 27 | 2080.3 |
| 28 | 8407.1 |
| 29 | 1838.6 |
| 30 | 1835.7 |
| 31 | 2585.3 |
| 32 | 1478.8 |
| 33 | 7436.2 |
| 34 | 3354.6 |
| 35 | 265.7 |
| 36 | 10000.0 |
| 37 | 1612.6 |
| 38 | 280.0 |
| 39 | 261.6 |
| 40 | 328.0 |
| 41 | 255.5 |
| 42 | 3338.7 |
| 43 | 2410.8 |
| 44 | 375.6 |
| 45 | 191.2 |
| 46 | 512.3 |
| 47 | 758.2 |
| 48 | 8453.2 |
| 49 | 207.2 |
| 50 | 3320.5 |
| 51 | 705.4 |
| 52 | 1951.8 |
| 53 | 388.1 |
| 54 | 3809.1 |
| 55 | 685.2 |
| 56 | 1180.4 |
| 57 | 596.5 |
| 58 | 663.5 |
| 59 | 873.9 |
| 60 | 1090.8 |
| 61 | 774.8 |
| 62 | 2427.2 |
| 63 | 9713.3 |
| 64 | 5825.9 |
| 65 | 1971.3 |
| 66 | 5828.7 |
| 67 | 1040.8 |
| 68 | 6299.0 |
| 69 | 7800.5 |
| 70 | 373.6 |
| 71 | 1385.7 |
| 72 | 262.0 |
| 73 | 2449.3 |
| 74 | 10000.0 |
| 75 | 691.7 |
| 76 | 6330.5 |
| 77 | 6036.1 |
| 78 | 4068.4 |
| 79 | 3031.6 |
| 80 | 1059.2 |
| 81 | 612.3 |
| 82 | 2315.0 |
| 83 | 460.5 |
| 84 | 783.2 |
| 85 | 3092.7 |
| 86 | 4913.7 |
| 87 | 10000.0 |
| 88 | 2571.9 |
| 89 | 854.8 |
| 90 | 4557.9 |
| 91 | 616.1 |
| 92 | 245.0 |
| 93 | 4822.2 |
| 94 | 901.6 |
| 95 | 1103.0 |
| 96 | 603.6 |

TABLE 2-continued

MCL-1 CV SKBR3 EC$_{50}$ (nM)

| Example | EC$_{50}$ (nM) |
|---|---|
| 97 | 787.7 |
| 98 | 2188.5 |
| 99 | 2091.9 |
| 100 | 2260.5 |
| 101 | 2586.5 |
| 102 | 891.3 |
| 103 | 10000.0 |
| 104 | N.D. |
| 105 | 351.4 |
| 106 | N.D. |
| 107 | N.D. |
| 108 | N.D. |
| 109 | |
| 110 | |
| 111 | 721.43 |
| 112 | 73.25 |
| 113 | |
| 114 | 154.23 |
| 115 | |
| 116 | 141.46 |
| 117 | 82.89 |
| 118 | 184.35 |
| 119 | 93.75 |
| 120 | 106.06 |
| 121 | 71.54 |
| 122 | 112.69 |
| 123 | 114.49 |
| 124 | 95.85 |
| 125 | 88.65 |
| 126 | 122.98 |
| 127 | 157.55 |
| 128 | 96.44 |
| 129 | 64.66 |
| 130 | 152.35 |
| 131 | 161.74 |
| 132 | 71.99 |
| 133 | 130.07 |
| 134 | 59.56 |
| 135 | 131.91 |
| 136 | 76.42 |
| 137 | 103.58 |
| 138 | 60.54 |
| 139 | 94.07 |
| 140 | 38.59 |
| 141 | 65.32 |
| 142 | 416.33 |
| 143 | 218.95 |
| 144 | 50.76 |
| 145 | 147.42 |
| 146 | 184.91 |
| 147 | 110.61 |
| 148 | 37.17 |
| 149 | 95.28 |
| 150 | 39.26 |
| 151 | |
| 152 | 55.70 |
| 153 | 69.50 |
| 154 | 24.1 |
| 155 | 43.01 |
| 156 | 145.374 |
| 157 | 64.776 |
| 158 | 47.436 |
| 159 | 144.479 |
| 160 | 35.036 |
| 161 | 168.251 |
| 162 | 136.473 |
| 163 | 98.741 |
| 164 | 106.452 |
| 165 | 45.503 |
| 166 | 79.778 |
| 167 | 58.568 |
| 168 | 74.154 |
| 169 | 60.981 |
| 170 | 209.553 |
| 171 | 129.805 |
| 172 | 125.128 |

TABLE 2-continued

MCL-1 CV SKBR3 EC$_{50}$ (nM)

| Example | EC$_{50}$ (nM) |
|---|---|
| 173 | 67.868 |
| 174 | 102.675 |
| 175 | 33.867 |
| 176 | 79.254 |
| 177 | 46.373 |
| 178 | 143.607 |
| 179 | 82.519 |
| 180 | 134.333 |
| 181 | 37.915 |
| 182 | 136.147 |
| 183 | 195.116 |
| 184 | 47.24 |
| 185 | 99.209 |
| 186 | 167.95 |
| 187 | 43.096 |
| 188 | 78.259 |
| 189 | 64.255 |
| 190 | |
| 191 | 123.213 |
| 192 | 39.714 |
| 193 | |
| 194 | |
| 195 | 29.64 |
| 196 | 99.186 |
| 197 | 129.808 |
| 198 | 103.987 |
| 199 | 58.219 |
| 200 | |
| 201 | 103.304 |
| 202 | 90.982 |
| 203 | 76.148 |
| 204 | 136.301 |
| 205 | 58.879 |
| 206 | |
| 207 | 43.957 |
| 208 | 45.025 |
| 209 | |
| 210 | 43.444 |
| 211 | 54.2 |
| 212 | 37.619 |
| 213 | 56.973 |
| 214 | 55.876 |
| 215 | |
| 216 | |
| 217 | 83.199 |
| 218 | 85.531 |
| 219 | 145.684 |
| 220 | 97.761 |
| 221 | 103.725 |
| 222 | 80.097 |
| 223 | 37.34 |
| 224 | 83.461 |
| 225 | 51.277 |
| 226 | 71.326 |
| 227 | 21.252 |
| 228 | 69.861 |
| 229 | |
| 230 | 47.091 |
| 231 | 39.981 |
| 232 | 242.625 |
| 233 | 47.175 |
| 234 | 73.857 |
| 235 | 39.785 |
| 236 | 151.512 |
| 237 | 120.97 |
| 238 | 23.352 |
| 239 | |
| 240 | 91.536 |
| 241 | |
| 242 | 83.993 |
| 243 | 41.72 |
| 244 | 116.254 |
| 245 | 60.739 |
| 246 | 176.397 |
| 247 | 84.985 |
| 248 | 55.287 |

TABLE 2-continued

MCL-1 CV SKBR3 EC$_{50}$ (nM)

| Example | EC$_{50}$ (nM) |
| --- | --- |
| 249 | 221.575 |
| 250 | 44.38 |
| 251 | 39.574 |
| 252 | 82.721 |
| 253 | 39.167 |
| 254 | 154.781 |
| 255 | |
| 256 | 160.518 |
| 257 | 89.674 |
| 258 | 194.681 |
| 259 | |
| 260 | |
| 261 | 72.01 |
| 262 | 85.774 |
| 263 | 62.236 |
| 264 | |
| 265 | 96.236 |
| 266 | 53.788 |
| 267 | 184.308 |
| 268 | 88.772 |
| 269 | 264.075 |
| 270 | 61.679 |
| 271 | 175.649 |
| 272 | 47.923 |
| 273 | 81.006 |
| 274 | 82.551 |
| 275 | 90.367 |
| 276 | 64.262 |
| 277 | 60.866 |
| 278 | 80.523 |
| 279 | |
| 280 | 50 |
| 281 | 183.521 |
| 282 | 28.657 |
| 283 | 84.797 |
| 284 | 54.672 |
| 285 | 79.68 |
| 286 | 65.07 |
| 287 | 25.014 |
| 288 | 169.57 |
| 289 | 588.134 |
| 290 | 26.375 |
| 291 | |
| 292 | 45.095 |
| 293 | 69.205 |
| 294 | 260.141 |
| 295 | 21.969 |
| 296 | 64.086 |
| 297 | 68.966 |
| 298 | 71.896 |
| 299 | 59.742 |
| 300 | 26.776 |
| 301 | 41.854 |
| 302 | 301.941 |
| 303 | 22.84 |
| 304 | 21.302 |
| 305 | 139.57 |
| 306 | 43.594 |
| 307 | 96.799 |
| 308 | 16.109 |
| 309 | 10.548 |
| 310 | 230.419 |
| 311 | 13.432 |
| 312 | 43.55 |
| 313 | 94.474 |
| 314 | 32.934 |
| 315 | 164.107 |
| 316 | 115.522 |
| 317 | 48.506 |
| 318 | 74.379 |
| 319 | 19.879 |
| 320 | 36.615 |
| 321 | 47.093 |
| 322 | 64.447 |
| 323 | 169.714 |
| 324 | 37.906 |
| 325 | 50.295 |
| 326 | 52.579 |
| 327 | 28.609 |
| 328 | 72.183 |
| 329 | 56.983 |
| 330 | 56.423 |
| 331 | 68.944 |
| 332 | 51.133 |
| 333 | 38.306 |
| 334 | 48.609 |
| 335 | 66.239 |
| 336 | 60.424 |
| 337 | 86.397 |
| 338 | 123.754 |
| 339 | 53.182 |
| 340 | 37.086 |
| 341 | 39.429 |
| 342 | 33.638 |
| 343 | 17.328 |
| 344 | 18.544 |
| 345 | 22.56 |
| 346 | 30.944 |
| 347 | 79.756 |
| 348 | 84.676 |
| 349 | 33.724 |
| 350 | 75.591 |
| 351 | 58.806 |
| 352 | 54.429 |
| 353 | 256.743 |
| 354 | 36.948 |
| 355 | 67.355 |
| 356 | 233.261 |
| 357 | 206.237 |
| 358 | 95.129 |
| 359 | 19.022 |
| 360 | 139.487 |
| 361 | 44 |
| 362 | 17.259 |
| 363 | 46.531 |
| 364 | 258.689 |
| 365 | 145.67 |
| 366 | 53.129 |
| 367 | 100.501 |
| 368 | |
| 369 | |
| 370 | 5795.45 |
| 371 | |
| 372 | |
| 373 | |
| 374 | 47.482 |
| 375 | 22.367 |
| 376 | 26.706 |
| 377 | 33.992 |
| 378 | 1182.46 |
| 379 | 1663.07 |
| 380 | 3401.06 |
| 381 | 534.464 |
| 382 | 562.153 |
| 383 | 1195.62 |
| 384 | 153.799 |
| 385 | 221.972 |
| 386 | 83.761 |
| 387 | 161.643 |
| 388 | 1395.31 |
| 389 | 303.742 |
| 390 | 86.369 |
| 391 | 4557.45 |
| 392 | 142.343 |
| 393 | 33.351 |
| 394 | 4745.65 |
| 395 | 6177.74 |
| 396 | |
| 397 | |
| 398 | |
| 399 | 19.98 |
| 400 | 530.34 |

TABLE 2-continued

MCL-1 CV SKBR3 EC$_{50}$ (nM)

| Example | EC$_{50}$ (nM) |
|---|---|
| 401 | 117.941 |
| 402 | 90.153 |
| 403 | 13.758 |
| 404 | 196.712 |
| 405 | 195.953 |
| 406 | 332.427 |
| 407 | |
| 408 | 240.875 |
| 409 | 297.308 |
| 410 | 145.606 |
| 411 | 174.67 |
| 412 | 179.346 |
| 413 | 129.529 |
| 414 | 153.743 |
| 415 | 104.739 |
| 416 | 130.943 |
| 417 | 403.335 |
| 418 | 335.297 |
| 419 | 135.182 |
| 420 | 124.328 |
| 421 | 152.44 |
| 422 | 187.244 |
| 423 | 168.533 |
| 424 | 147.23 |
| 425 | 170.703 |
| 426 | 316.412 |
| 427 | 331.872 |
| 428 | 164.693 |
| 429 | 260.617 |
| 430 | 139.281 |
| 431 | 233.147 |
| 432 | 171.684 |
| 433 | 394.987 |
| 434 | 402.832 |
| 435 | 167.159 |
| 436 | 752.744 |
| 437 | 122.588 |
| 438 | 278.341 |
| 439 | 789.246 |
| 440 | 284.088 |
| 441 | 373.917 |
| 442 | 122.053 |
| 443 | 161.763 |
| 444 | 171.572 |
| 445 | 209.764 |
| 446 | 175.783 |
| 447 | 161.434 |
| 448 | 250.704 |
| 449 | 146.579 |
| 450 | 167.379 |
| 451 | 160.647 |
| 452 | 282.052 |
| 453 | 96.749 |
| 454 | 146.083 |
| 455 | 145.824 |
| 456 | 174.228 |
| 457 | 391.672 |
| 458 | 376.136 |
| 459 | 194.159 |
| 460 | |
| 461 | 151.118 |
| 462 | 344.509 |
| 463 | |
| 464 | 222.449 |
| Comparative Example 1 | 2190.4 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

The invention claimed is:

1. A compound according to Formula (Ia):

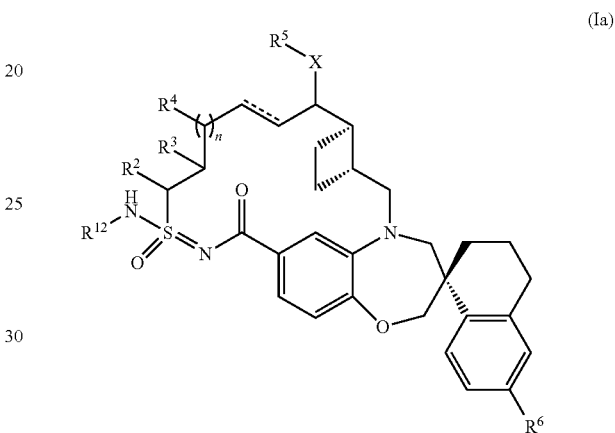

(Ia)

or a pharmaceutically acceptable salt thereof;

wherein:

═ is a single or double bond;

X is O or NR$^7$;

R$^{12}$ is hydrogen or —C(O)R$^1$;

R$^1$ is C$_{1-6}$alkyl, C$_{1-6}$haloalkyl, C$_{2-6}$alkenyl, C$_{2-6}$alkynyl, C$_{3-10}$cycloalkyl, C$_{6-10}$aryl, 3-12 membered heterocyclyl, 5-10 membered heteroaryl, —OR$^7$, or —NR$^8$R$^9$, wherein said C$_{1-6}$alkyl, C$_{2-6}$alkynyl, C$_{3-10}$cycloalkyl, C$_{6-10}$aryl, 3-12 membered heterocyclyl, and 5-10 membered heteroaryl are optionally substituted with 1-5 R$^{10}$ groups;

R$^2$ is hydrogen, C$_{1-6}$alkyl, C$_{1-6}$heteroalkyl, C$_{3-10}$cycloalkyl, or 3-12 membered heterocyclyl, wherein said C$_{1-6}$alkyl, C$_{1-6}$heteroalkyl, C$_{3-10}$cycloalkyl, and 3-12 membered heterocyclyl are optionally substituted with 1-5 R$^{10}$ groups;

R$^3$ and R$^4$ are independently hydrogen, C$_{1-6}$alkyl, C$_{1-6}$heteroalkyl, —NR$^8$R$^9$, NR$^8$C(O)R$^9$, —NR$^8$C(O)OR$^9$, C$_{6-10}$aryl, C$_{3-10}$cycloalkyl, 5-10 membered heteroaryl, 3-12 membered heterocyclyl, —C(O)R$^7$, —C(O)OR$^7$, —C(O)NR$^8$R$^9$, —OC(O)NR$^8$R$^9$, —CN, or —SO$_2$R$^7$, wherein said C$_{1-6}$alkyl, C$_{1-6}$heteroalkyl, C$_{6-10}$aryl, C$_{3-10}$cycloalkyl, 5-10 membered heteroaryl, and 3-12 membered heterocyclyl are optionally substituted with 1-5 R$^{10}$ groups;

$R^5$ is hydrogen, $C_{1-6}$alkyl, —(CH$_2$CH$_2$O)$_p$R$^7$, $C_{1-6}$heteroalkyl, $C_{6-10}$aryl, $C_{3-10}$cycloalkyl, 5-10 membered heteroaryl, or 3-12 membered heterocyclyl, wherein
said $C_{1-6}$alkyl, $C_{1-6}$heteroalkyl, $C_{6-10}$aryl, $C_{3-10}$cycloalkyl, 5-10 membered heteroaryl, and 3-12 membered heterocyclyl are optionally substituted with 1-5 $R^{10}$ groups;

$R^6$ is hydrogen or halo;

each $R^7$ is independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, wherein
said $C_{1-6}$ alkyl, $C_{3-10}$cycloalkyl, $C_{1-6}$heteroalkyl, 3-12 membered heterocyclyl, $C_{6-10}$ aryl, and 5-10 membered heteroaryl are optionally substituted with from 1-5 $R^{10}$;

each $R^8$ and $R^9$ are independently hydrogen, $C_{1-6}$alkyl, $C_{3-10}$cycloalkyl, $C_{1-6}$heteroalkyl, 3-12 membered heterocyclyl, $C_{6-10}$aryl, or 5-10 membered heteroaryl, or $R^8$ and $R^9$ together with the atoms to which they are attached form a 3-12 membered heterocycle, wherein
said $C_{1-6}$alkyl, $C_{3-10}$cycloalkyl, $C_{1-6}$heteroalkyl, 3-12 membered heterocyclyl, $C_{6-10}$aryl, and 5-10 membered heteroaryl are optionally substituted with 1-5 $R^{10}$;

each $R^{10}$ is independently $C_{1-6}$alkyl, $C_{3-10}$cycloalkyl, $C_{1-6}$heteroalkyl, 3-12 membered heterocyclyl, $C_{6-10}$aryl, 5-10 membered heteroaryl, halo, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_q$R$^a$, —S(O)$_2$NR$^a$R$^b$, —NR$^a$S(O)$_2$R$^b$, —N$_3$, —CN, or —NO$_2$, or two $R^{10}$ groups form a fused, spiro, or bridged $C_{3-10}$ cycloalkyl or 3-12 membered heterocyclyl, wherein
each $C_{1-6}$alkyl, $O_{1-6}$ heteroalkyl, $C_{2-6}$alkynyl, $C_{3-10}$cycloalkyl, $C_{6-10}$aryl, 3-12 membered heterocycle, and 5-10 membered heteroaryl is optionally substituted with 1-5 $R^{20}$ groups;

each $R^a$ and $R^b$ is independently hydrogen, $C_{1-6}$alkyl, $C_{2-6}$ alkenyl, $C_{3-10}$cycloalkyl, $C_{1-6}$heteroalkyl, 3-12 membered heterocyclyl, $C_{6-10}$aryl, 5-10 membered heteroaryl, or $R^a$ and $R^b$ together with the atoms to which they are attached form a 3-12 membered heterocyclyl, wherein
said $C_{1-6}$alkyl, $C_{2-6}$ alkenyl, $C_{3-10}$cycloalkyl, $C_{1-6}$heteroalkyl, 3-12 membered heterocyclyl, $C_{6-10}$aryl, 5-10 membered heteroaryl is optionally substituted with 1-5 $R^{20}$ groups;

each $R^{20}$ is independently $C_{1-6}$ alkyl, $C_{3-10}$ cycloalkyl, $C_{1-6}$ heteroalkyl, 3-12 membered heterocyclyl, $C_6$-$C_{10}$ aryl, 5-10 membered heteroaryl, hydroxyl, $O_{1-6}$ alkoxy, amino, —CN, —C(O)H, —C(O)NH$_2$, —C(O)NH(C$_{1-6}$ alkyl), —C(O)N(C$_{1-6}$ alkyl)$_2$, —COOH, —C(O)C$_{1-6}$ alkyl, —C(O)OC$_{1-6}$ alkyl, or halogen;

n is 0, 1, or 2;
p is 0, 1, or 2;
q is 0, 1, or 2;

the $C_{1-6}$heteroalkyl is an alkyl group in which one to three of the carbon atoms are each independently replaced with the same or different heteroatomic group; wherein $C_{1-6}$heteroalkyl has 1-6 carbon atoms; and wherein the heteroatomic group is independently selected from nitrogen, sulfur, phosphorus, oxygen, —N(O)—, —S(O)—, and —S(O)$_2$—;

the 3-12 membered heterocyclyl is a non-aromatic group having a single ring or multiple rings; wherein the 3-12 membered heterocyclyl has one to three heteroatoms independently selected from nitrogen, sulfur, phosphorus, —N(O)—, —S(O)—, and —S(O)$_2$—; wherein the multiple rings may be fused, bridged, or spiro; and the 5-10 membered heteroaryl is an aromatic group having a single ring or multiple rings;
wherein the 5-10 membered heteroaryl contains one to three ring heteroatoms independently selected from nitrogen, oxygen, sulfur, —N(O)—, —S(O)—, and —S(O)$_2$.

2. The compound of claim 1, according to Formula (IIa):

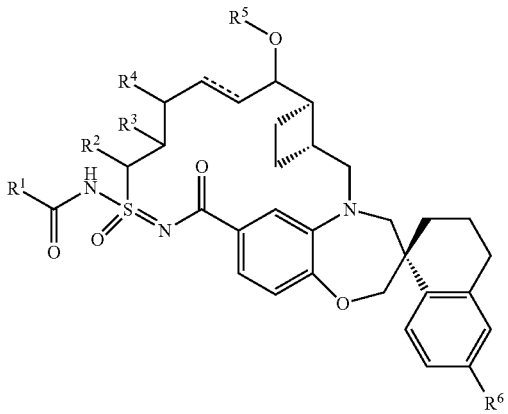

(IIa)

or a pharmaceutically acceptable salt thereof.

3. The compound of claim 1, wherein:
$R^2$ is hydrogen or $C_{1-3}$alkyl;
$R^3$ is hydrogen or $C_{1-3}$alkyl;
$R^4$ is hydrogen;
$R^5$ is $C_{1-3}$alkyl, wherein
said $C_{1-3}$alkyl is optionally substituted with a 5-6 membered heterocyclyl;
or a pharmaceutically acceptable salt thereof.

4. The compound of claim 1, wherein:
$R^2$ is hydrogen, methyl, or ethyl;
$R^3$ is hydrogen or methyl;
$R^4$ is hydrogen; and
$R^5$ is hydrogen, methyl,

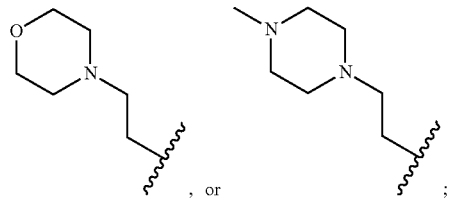

, or ;

or a pharmaceutically acceptable salt thereof.

5. The compound of claim 1, wherein:
$R^2$ is hydrogen; and
$R^3$ is $C_{1-3}$alkyl;
or a pharmaceutically acceptable salt thereof.

6. The compound of claim 1, or a pharmaceutically acceptable salt thereof, wherein $R^2$ is hydrogen.

7. The compound of claim 1, or a pharmaceutically acceptable salt thereof, wherein $R^3$ is methyl.

8. The compound of claim 1, or a pharmaceutically acceptable salt thereof, wherein $R^4$ is hydrogen.

9. The compound of claim 1, or a pharmaceutically acceptable salt thereof, wherein $R^5$ is methyl.

10. The compound of claim 1, or a pharmaceutically acceptable salt thereof, wherein $R^6$ is Cl.

11. The compound of claim 1, or a pharmaceutically acceptable salt thereof, wherein $R^1$ is 3-12 membered heterocyclyl, or 5-10 membered heteroaryl; and wherein 3-12 membered heterocyclyl, or 5-10 membered heteroaryl is optionally substituted with 1-2 $R^{10}$.

12. The compound of claim 1, or a pharmaceutically acceptable salt thereof, wherein $R^1$ is

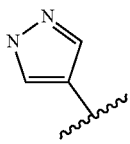

substituted with 1-2 $R^{10}$.

13. The compound of claim 1, or a pharmaceutically acceptable salt thereof, wherein $R^1$ is

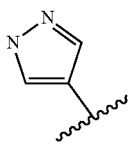

substituted with two groups selected from $C_{1-4}$alkyl and $C_{1-4}$alkoxyl.

14. The compound of claim 1, or a pharmaceutically acceptable salt thereof, wherein $R^1$ is

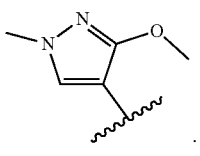

15. The compound of claim 1, or a pharmaceutically acceptable salt thereof, wherein $R^1$ is selected from:

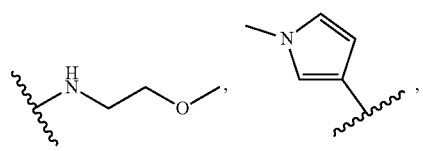

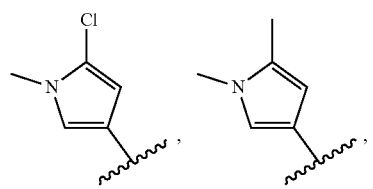

-continued

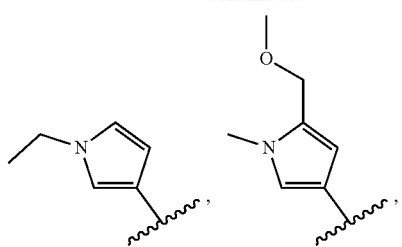

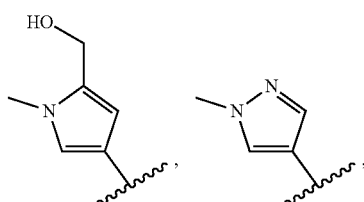

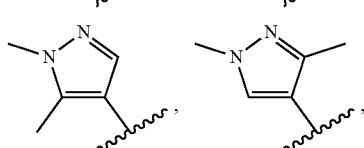

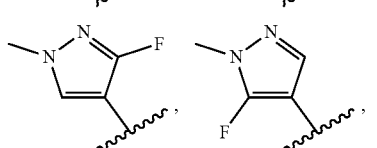

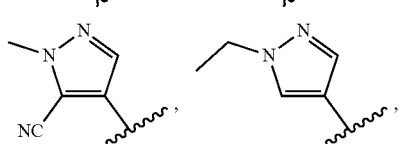

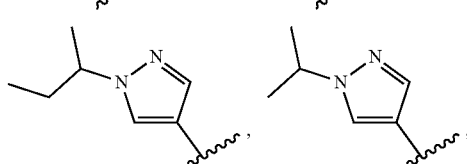

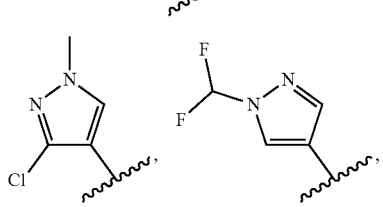

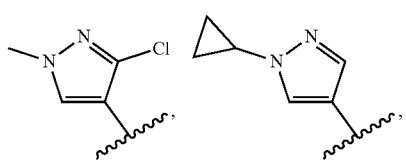

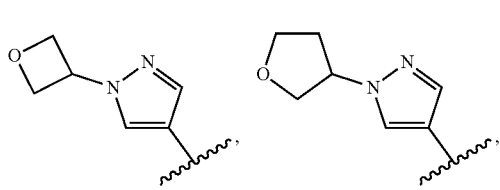

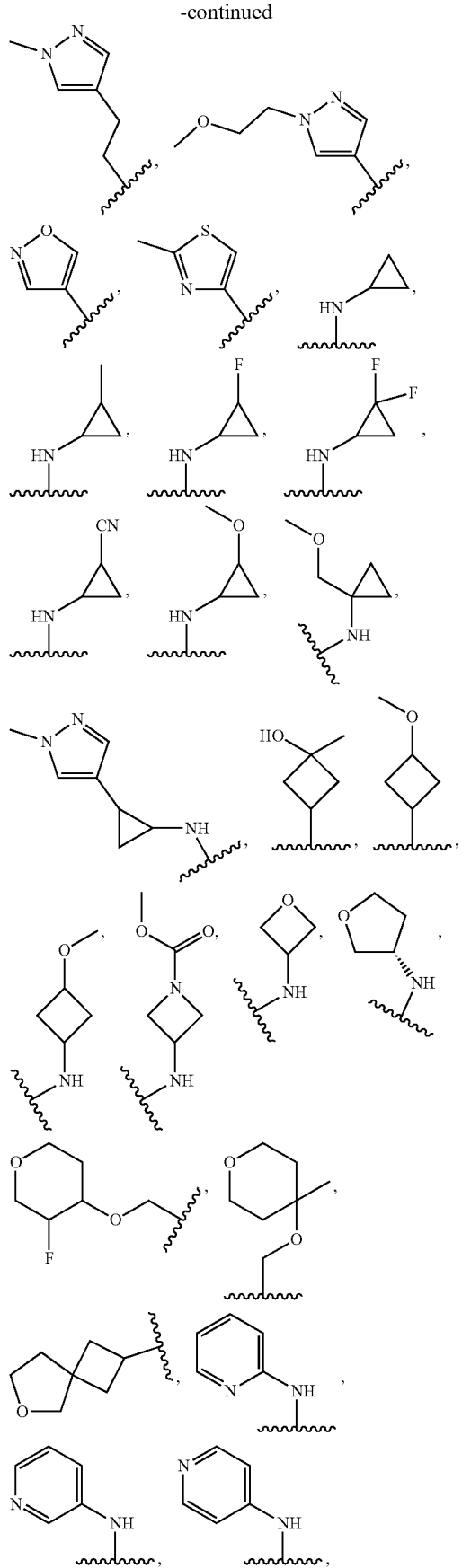
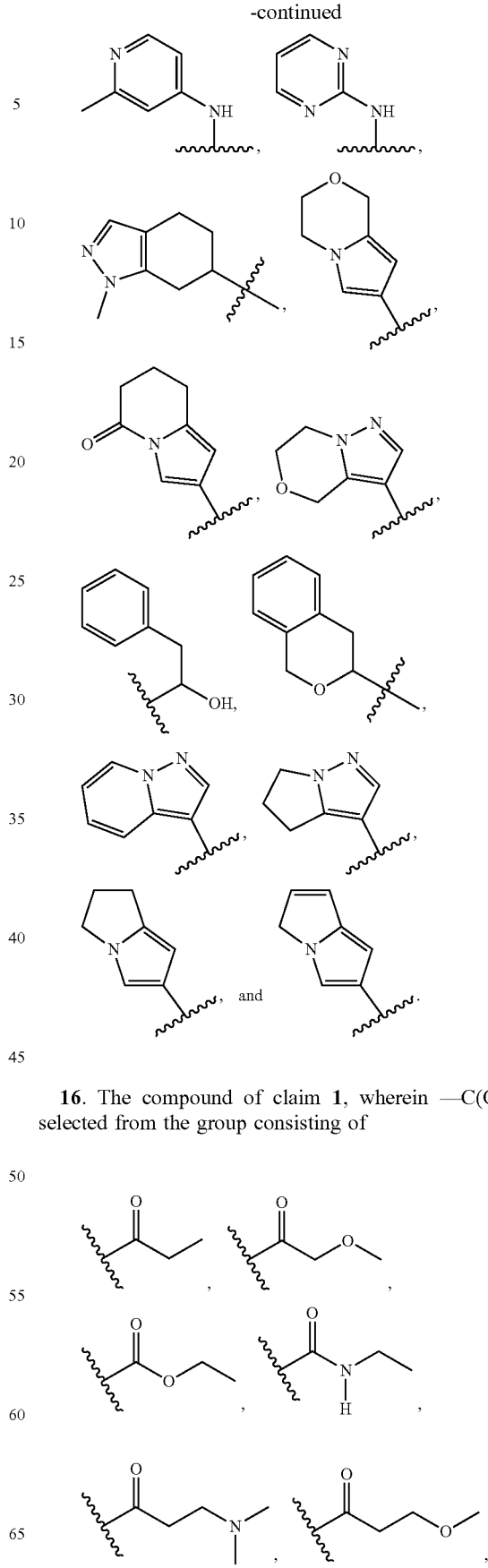
16. The compound of claim 1, wherein —C(O)R[1] is selected from the group consisting of 519
-continued
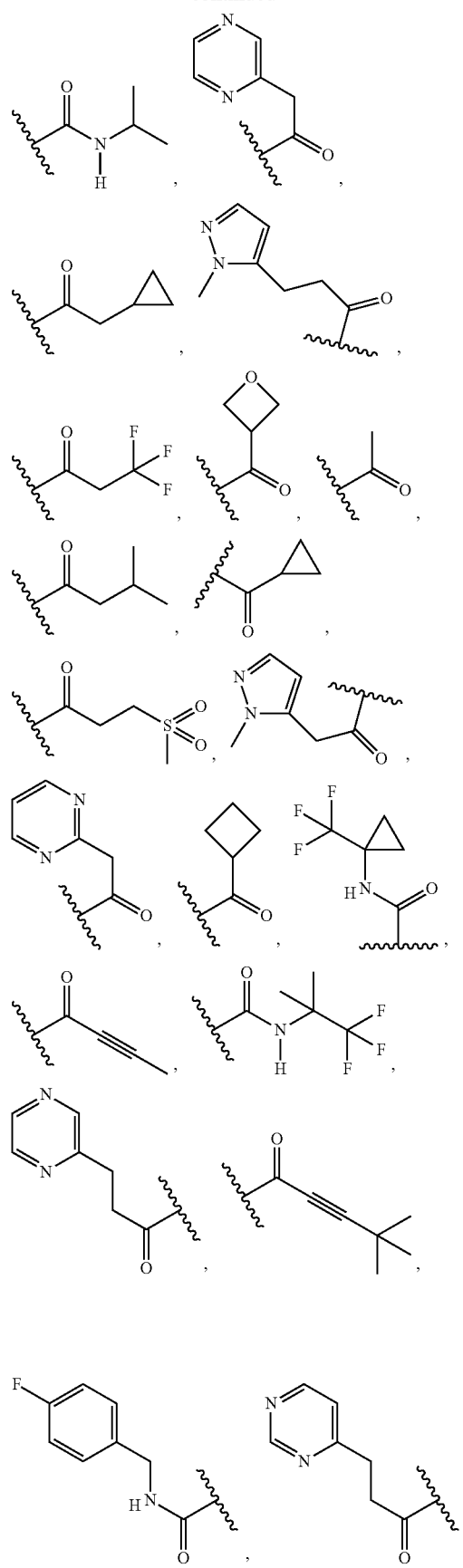
520
-continued
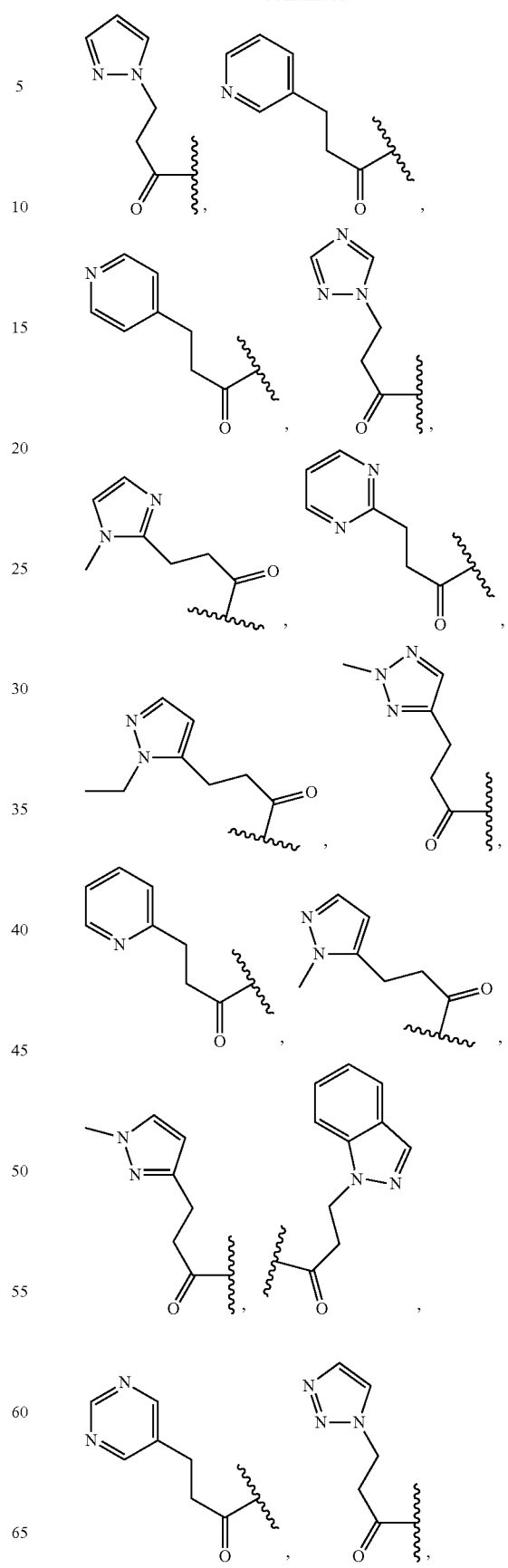

521
-continued
522
-continued
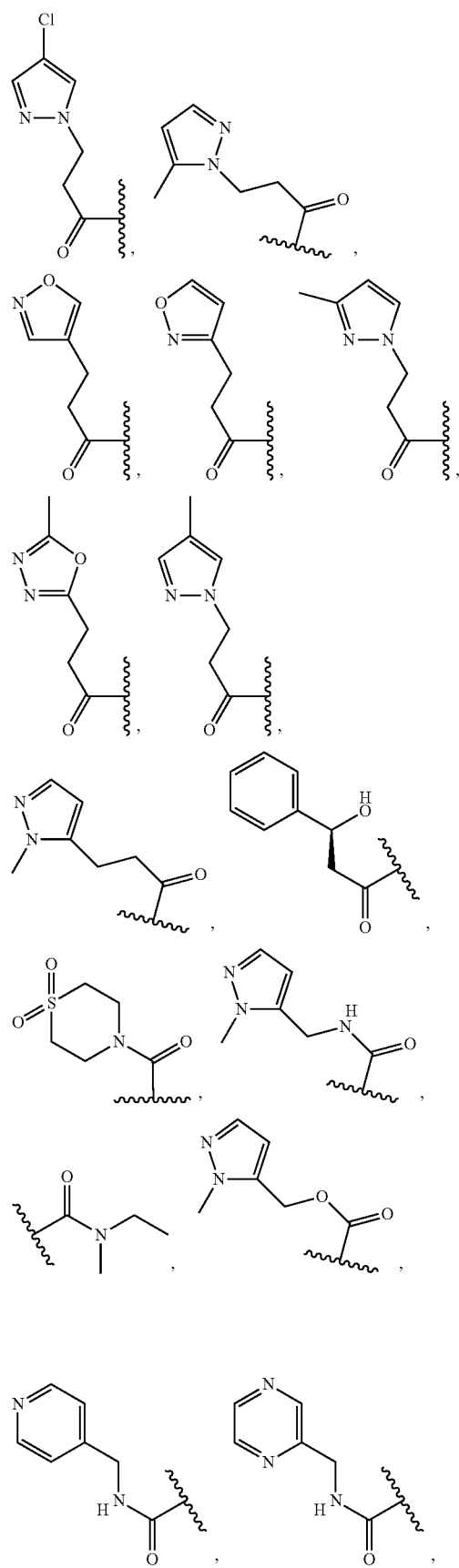
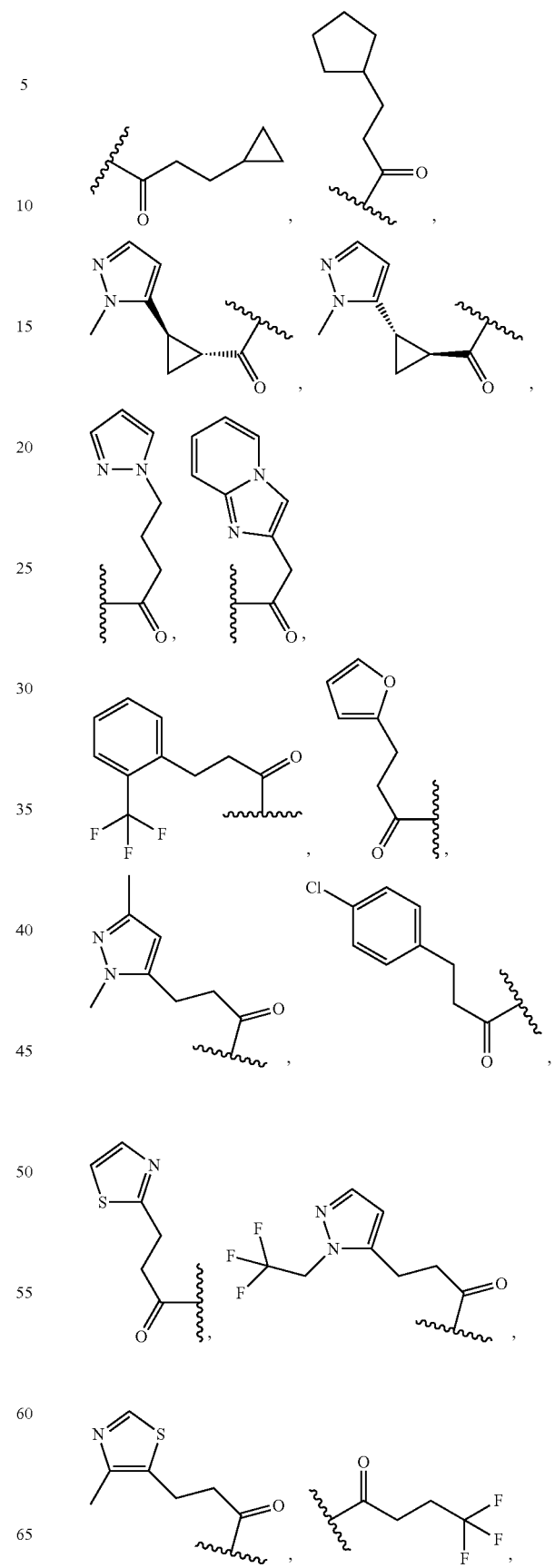

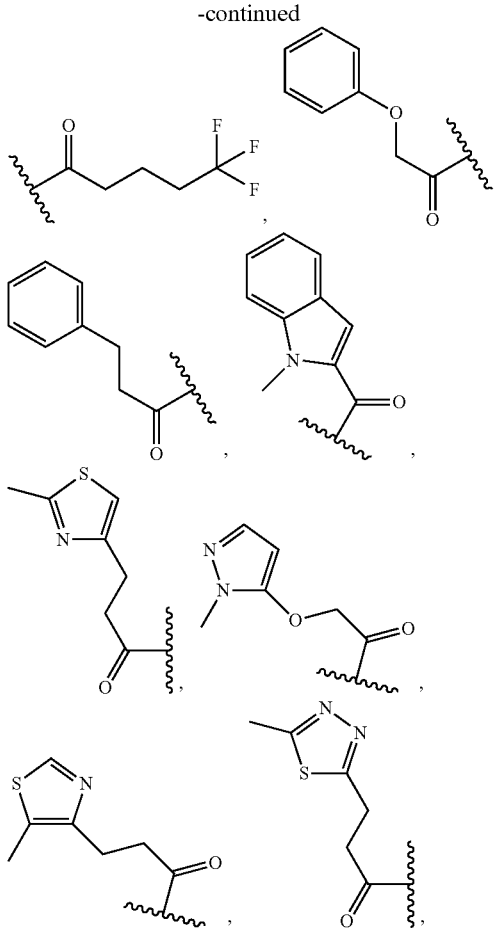

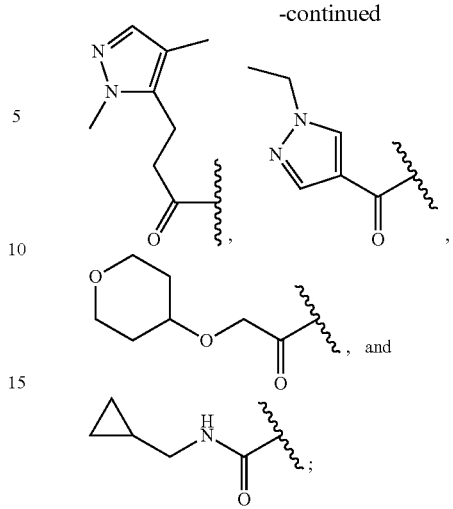

or a pharmaceutically acceptable salt thereof.

17. A pharmaceutical composition comprising the compound of claim 1, or a pharmaceutically acceptable salt thereof, and a pharmaceutically acceptable excipient.

18. The pharmaceutical composition of claim 17, further comprising one or more additional therapeutic agents.

19. The pharmaceutical composition of claim 18, wherein the additional therapeutic agent is a chemotherapeutic drug.

20. The pharmaceutical composition of claim 18, wherein the additional therapeutic agent is an immune checkpoint inhibitor, wherein the immune checkpoint inhibitor is selected from anti-PD-1 antibody, anti-PD-L1 antibody, and anti PD-1/PD-L1 interaction inhibitor.

\* \* \* \* \*